(12) United States Patent
Marshall et al.

(10) Patent No.: US 11,987,789 B2
(45) Date of Patent: May 21, 2024

(54) SYSTEMS, DEVICES, AND METHODS FOR ISOTACHOPHORESIS

(71) Applicant: Purigen Biosystems, Inc., Pleasanton, CA (US)

(72) Inventors: Lewis A. Marshall, Oakland, CA (US); Amy L. Hiddessen, Pleasanton, CA (US); Nathan P. Hoverter, Pleasanton, CA (US); Klint A. Rose, Oakland, CA (US); Juan G. Santiago, Stanford, CA (US); Matthew S. Munson, Evanston, IL (US); Janine Mok, Palo Alto, CA (US); Sean Arin, Oakland, CA (US); Yatian Qu, Sunnyvale, CA (US); Andrew Lee, Hayward, CA (US); Michael Christopher De Renzi, Pleasanton, CA (US)

(73) Assignee: Purigen Biosystems, Inc., Pleasanton, CA (US)

(*) Notice: Subject to any disclaimer, the term of this patent is extended or adjusted under 35 U.S.C. 154(b) by 0 days.

(21) Appl. No.: 17/230,582

(22) Filed: Apr. 14, 2021

(65) Prior Publication Data

US 2021/0230576 A1    Jul. 29, 2021

Related U.S. Application Data

(62) Division of application No. 16/052,565, filed on Aug. 1, 2018, now Pat. No. 11,041,150.

(Continued)

(51) Int. Cl.
*B01L 3/00*    (2006.01)
*B01L 9/00*    (2006.01)
(Continued)

(52) U.S. Cl.
CPC ...... *C12N 15/101* (2013.01); *B01L 3/502738* (2013.01); *B01L 3/502746* (2013.01);
(Continued)

(58) Field of Classification Search
CPC ........ B01L 3/502746; G01N 27/44717; G01N 27/44791
See application file for complete search history.

(56) References Cited

U.S. PATENT DOCUMENTS

| 863,583 A | 8/1907 | Blankmeister |
| 3,799,742 A | 3/1974 | Coleman |

(Continued)

FOREIGN PATENT DOCUMENTS

| CA | 2304641 A1 | 4/1999 |
| CN | 1326549 A | 12/2001 |

(Continued)

OTHER PUBLICATIONS

L.A. Marshall, Designing Automated Systems for Sample Preparation of Nucleic Acids using Isotachophoresis, Dissertation for the Degree of Doctor of Philosophy, 2013. (Year: 2013).*

(Continued)

*Primary Examiner* — Caitlyn Mingyun Sun
(74) *Attorney, Agent, or Firm* — Bret E. Field; Bozicevic, Field & Francis LLP

(57) ABSTRACT

The present disclosure relates to fluidic systems and devices for processing, extracting, or purifying one or more analytes. These systems and devices can be used for processing samples and extracting nucleic acids, for example by isotachophoresis. In particular, the systems and related methods can allow for extraction of nucleic acids, including non-crosslinked nucleic acids, from samples such as tissue or cells. The systems and devices can also be used for multiplex parallel sample processing.

27 Claims, 150 Drawing Sheets

Related U.S. Application Data

(60) Provisional application No. 62/541,086, filed on Aug. 3, 2017, provisional application No. 62/541,089, filed on Aug. 3, 2017, provisional application No. 62/540,515, filed on Aug. 2, 2017.

(51) Int. Cl.
  *C12N 15/10* (2006.01)
  *G01N 27/447* (2006.01)

(52) U.S. Cl.
  CPC ... *B01L 3/502761* (2013.01); *B01L 3/502776* (2013.01); *B01L 3/5085* (2013.01); *G01N 27/44717* (2013.01); *B01L 9/527* (2013.01); *B01L 2200/0621* (2013.01); *B01L 2200/0642* (2013.01); *B01L 2400/0421* (2013.01); *B01L 2400/0688* (2013.01); *G01N 27/44704* (2013.01); *G01N 27/44743* (2013.01); *G01N 27/44791* (2013.01)

(56) References Cited

U.S. PATENT DOCUMENTS

| | | |
|---|---|---|
| 3,811,326 A | 5/1974 | Sokol |
| 3,869,365 A | 3/1975 | Sunden |
| 3,912,609 A | 10/1975 | Arlinger |
| 3,948,753 A | 4/1976 | Arlinger |
| 3,992,150 A | 11/1976 | Retzer |
| 4,061,560 A | 12/1977 | Hannig et al. |
| 4,233,029 A | 11/1980 | Columbus |
| 4,416,762 A | 11/1983 | Akiyama et al. |
| 4,426,451 A | 1/1984 | Columbus |
| 4,454,235 A | 6/1984 | Johnson |
| 4,537,747 A | 8/1985 | Castaneda |
| 4,596,780 A | 6/1986 | Castaneda |
| 4,618,476 A | 10/1986 | Columbus |
| 4,790,919 A | 12/1988 | Baylor, Jr. et al. |
| 4,868,129 A | 9/1989 | Gibbons et al. |
| 4,897,169 A | 1/1990 | Bier et al. |
| 4,900,677 A | 2/1990 | Hewitt et al. |
| 5,322,608 A | 6/1994 | Karger et al. |
| 5,447,612 A | 9/1995 | Bier et al. |
| 5,464,515 A | 11/1995 | Bellon et al. |
| 5,580,523 A | 12/1996 | Bard |
| 5,629,414 A | 5/1997 | Boothroyd et al. |
| 5,631,128 A | 5/1997 | Kozal et al. |
| 5,650,268 A | 7/1997 | Kozal et al. |
| 5,800,692 A | 9/1998 | Naylor et al. |
| 5,817,225 A | 10/1998 | Hinton et al. |
| 5,827,415 A | 10/1998 | Guer et al. |
| 5,856,086 A | 1/1999 | Kozal et al. |
| 5,859,196 A | 1/1999 | Boothroyd et al. |
| 5,939,291 A | 8/1999 | Loewy et al. |
| 5,981,235 A | 11/1999 | Shultz et al. |
| 5,992,820 A | 11/1999 | Fare et al. |
| 6,090,251 A | 7/2000 | Sundberg et al. |
| 6,107,038 A | 8/2000 | Choudhary et al. |
| 6,130,098 A | 10/2000 | Handique et al. |
| 6,132,579 A | 10/2000 | Edwards et al. |
| 6,143,248 A | 11/2000 | Kellogg et al. |
| 6,296,020 B1 | 10/2001 | McNeely et al. |
| 6,352,838 B1 | 3/2002 | Krulevitch et al. |
| 6,561,224 B1 | 5/2003 | Cho |
| 6,581,899 B2 | 6/2003 | Williams |
| 6,626,417 B2 | 9/2003 | Winger et al. |
| RE38,352 E | 12/2003 | Kozal et al. |
| 6,669,831 B2 | 12/2003 | Chow et al. |
| 6,685,813 B2 | 2/2004 | Williams et al. |
| 6,695,009 B2 | 2/2004 | Chien et al. |
| 6,730,204 B2 | 5/2004 | Mariella, Jr. et al. |
| 6,761,811 B2 | 7/2004 | Mariella, Jr. et al. |
| 6,770,182 B1 | 8/2004 | Griffiths et al. |
| 6,780,584 B1 | 8/2004 | Edman et al. |
| 6,818,113 B2 | 11/2004 | Williams et al. |
| 6,905,583 B2 | 6/2005 | Wainright et al. |
| 6,908,593 B1 | 6/2005 | Shartle |
| 6,934,836 B2 | 8/2005 | Strand et al. |
| 6,935,772 B2 | 8/2005 | Karp et al. |
| 6,939,454 B2 | 9/2005 | Kaji |
| 7,005,050 B2 | 2/2006 | Burns et al. |
| 7,204,263 B2 | 4/2007 | Tsukita et al. |
| 7,214,299 B2 | 5/2007 | Armstrong et al. |
| 7,223,325 B2 | 5/2007 | Landers et al. |
| 7,316,771 B2 | 1/2008 | Weber et al. |
| 7,364,916 B2 | 4/2008 | Sundberg et al. |
| 7,371,533 B2 | 5/2008 | Slater et al. |
| 7,399,394 B2 | 7/2008 | Weber et al. |
| 7,429,354 B2 | 9/2008 | Andersson et al. |
| 7,473,551 B2 | 1/2009 | Warthoe et al. |
| 7,494,577 B2 | 2/2009 | Williams et al. |
| 7,517,442 B1 | 4/2009 | Champagne et al. |
| 7,591,936 B2 | 9/2009 | Sarrut et al. |
| 7,635,563 B2 | 12/2009 | Horvitz et al. |
| 7,694,694 B2 | 4/2010 | Welle et al. |
| 7,875,160 B2 | 1/2011 | Jary et al. |
| 7,926,514 B2 | 4/2011 | Park et al. |
| 7,951,278 B2 | 5/2011 | Santiago et al. |
| 8,017,408 B2 | 9/2011 | Meinhart et al. |
| 8,021,531 B2 | 9/2011 | Park et al. |
| 8,037,903 B2 | 10/2011 | Wang et al. |
| 8,105,471 B1 | 1/2012 | Han et al. |
| 8,133,371 B2 | 3/2012 | Marziali et al. |
| 8,277,628 B2 | 10/2012 | Ronaghi et al. |
| 8,394,251 B2 | 3/2013 | Santiago et al. |
| 8,414,754 B1 | 4/2013 | Santiago et al. |
| 8,524,061 B2 | 9/2013 | Utz et al. |
| 8,562,804 B2 | 10/2013 | Santiago et al. |
| 8,580,097 B2 | 11/2013 | Kurosawa et al. |
| 8,585,883 B2 | 11/2013 | Schoch |
| 8,597,590 B2 | 12/2013 | Yue et al. |
| 8,721,858 B2 | 5/2014 | Chambers et al. |
| 8,821,704 B2 | 9/2014 | Santiago et al. |
| 8,846,314 B2 | 9/2014 | Chambers et al. |
| 8,894,946 B2 | 11/2014 | Nielsen et al. |
| 8,986,529 B2 | 3/2015 | Santiago et al. |
| 8,999,129 B2 | 4/2015 | Jung et al. |
| 9,057,673 B2 | 6/2015 | Rogacs et al. |
| 9,144,799 B2 | 9/2015 | Rose et al. |
| 9,151,732 B2 | 10/2015 | Santiago et al. |
| 9,285,340 B2 | 3/2016 | Jung et al. |
| 9,297,039 B2 | 3/2016 | Santiago et al. |
| 9,599,590 B2 | 3/2017 | Sabin et al. |
| 9,753,007 B1 | 9/2017 | Chambers et al. |
| 10,073,054 B2 | 9/2018 | Santiago et al. |
| 10,132,775 B2 | 11/2018 | Santiago et al. |
| 10,233,441 B2 | 3/2019 | Santiago et al. |
| 10,415,030 B2 | 9/2019 | Marshall et al. |
| 10,787,660 B2 | 9/2020 | Santiago et al. |
| 10,822,603 B2 | 11/2020 | Marshall et al. |
| 11,041,150 B2 | 6/2021 | Marshall et al. |
| 2001/0055812 A1 | 12/2001 | Mian et al. |
| 2002/0008029 A1 | 1/2002 | Williams et al. |
| 2002/0036018 A1 | 3/2002 | McNeely et al. |
| 2002/0079223 A1 | 6/2002 | Williams et al. |
| 2002/0139674 A1 | 10/2002 | Mariella et al. |
| 2002/0189946 A1 | 12/2002 | Wainright et al. |
| 2003/0224436 A1 | 12/2003 | Nelson et al. |
| 2003/0230486 A1 | 12/2003 | Chien et al. |
| 2004/0031683 A1 | 2/2004 | Eipel et al. |
| 2004/0050698 A1 | 3/2004 | Eckerskorn et al. |
| 2004/0058349 A1 | 3/2004 | Van et al. |
| 2004/0063217 A1 | 4/2004 | Webster et al. |
| 2004/0108207 A1 | 6/2004 | Kurnik et al. |
| 2004/0120856 A1 | 6/2004 | Andersson et al. |
| 2004/0241656 A1 | 12/2004 | Jan et al. |
| 2004/0256230 A1 | 12/2004 | Yager et al. |
| 2004/0265172 A1* | 12/2004 | Pugia ............ B01L 3/502746 436/180 |
| 2005/0014134 A1 | 1/2005 | West et al. |
| 2005/0079519 A1 | 4/2005 | Boles et al. |
| 2005/0115837 A1 | 6/2005 | Burgi et al. |
| 2005/0121324 A1 | 6/2005 | Park et al. |
| 2005/0133370 A1 | 6/2005 | Park et al. |

(56) References Cited

U.S. PATENT DOCUMENTS

| | | |
|---|---|---|
| 2005/0142570 A1 | 6/2005 | Parthasarathy et al. |
| 2005/0167269 A1 | 8/2005 | Updyke et al. |
| 2005/0170362 A1 | 8/2005 | Wada et al. |
| 2006/0002817 A1 | 1/2006 | Bohm et al. |
| 2006/0019286 A1 | 1/2006 | Horvitz et al. |
| 2006/0042948 A1 | 3/2006 | Santiago et al. |
| 2006/0065528 A1 | 3/2006 | Lopez et al. |
| 2006/0078998 A1 | 4/2006 | Puskas et al. |
| 2006/0094119 A1 | 5/2006 | Ismagilov et al. |
| 2006/0254915 A1 | 11/2006 | Hirokawa et al. |
| 2007/0026439 A1 | 2/2007 | Faulstich et al. |
| 2007/0229631 A1 | 10/2007 | Yano |
| 2007/0284250 A1 | 12/2007 | Magnant et al. |
| 2008/0000774 A1 | 1/2008 | Park et al. |
| 2008/0020386 A1 | 1/2008 | Chen et al. |
| 2008/0021674 A1 | 1/2008 | Puskas et al. |
| 2008/0156080 A1 | 7/2008 | Balgley et al. |
| 2008/0166770 A1 | 7/2008 | Morita et al. |
| 2008/0197019 A1 | 8/2008 | Santiago et al. |
| 2008/0227185 A1 | 9/2008 | Schonfeld et al. |
| 2008/0233402 A1 | 9/2008 | Carlson et al. |
| 2009/0095057 A1* | 4/2009 | Staats .................. G01N 30/56 250/281 |
| 2009/0134031 A1 | 5/2009 | Ogle et al. |
| 2009/0178929 A1 | 7/2009 | Broer et al. |
| 2009/0194420 A1 | 8/2009 | Mariella, Jr. et al. |
| 2009/0220948 A1 | 9/2009 | Oviso et al. |
| 2009/0250345 A1 | 10/2009 | Powell et al. |
| 2009/0269745 A1 | 10/2009 | Tonoike et al. |
| 2009/0282978 A1 | 11/2009 | Jensen et al. |
| 2009/0317894 A1 | 12/2009 | Diges et al. |
| 2010/0084271 A1 | 4/2010 | Santiago et al. |
| 2010/0089529 A1* | 4/2010 | Barholm-Hansen .......................... B01L 3/502746 156/247 |
| 2010/0116657 A1 | 5/2010 | Fiering et al. |
| 2010/0120130 A1 | 5/2010 | Srinivasan et al. |
| 2010/0209927 A1 | 8/2010 | Menon et al. |
| 2010/0224494 A1 | 9/2010 | Chambers et al. |
| 2010/0261612 A1 | 10/2010 | Young et al. |
| 2010/0270157 A1 | 10/2010 | Kurosawa et al. |
| 2010/0294663 A1 | 11/2010 | Weber |
| 2010/0323913 A1 | 12/2010 | Young et al. |
| 2011/0024296 A1 | 2/2011 | Park et al. |
| 2011/0036718 A1 | 2/2011 | Jung et al. |
| 2011/0104816 A1 | 5/2011 | Pollack et al. |
| 2011/0174624 A1 | 7/2011 | Weber et al. |
| 2011/0220499 A1 | 9/2011 | Chambers et al. |
| 2011/0290648 A1 | 12/2011 | Majlof et al. |
| 2011/0297546 A1 | 12/2011 | Schoch |
| 2012/0061242 A1 | 3/2012 | Santiago et al. |
| 2012/0097272 A1 | 4/2012 | Vulto et al. |
| 2012/0152746 A1 | 6/2012 | Santiago et al. |
| 2012/0160689 A1 | 6/2012 | Utz et al. |
| 2012/0175258 A1 | 7/2012 | Mariella, Jr. et al. |
| 2013/0175173 A1 | 7/2013 | Ivory et al. |
| 2014/0014515 A1 | 1/2014 | Santiago et al. |
| 2014/0332389 A1 | 11/2014 | Young et al. |
| 2015/0037784 A1 | 2/2015 | Rogacs et al. |
| 2015/0191717 A1 | 7/2015 | Santiago et al. |
| 2015/0219594 A1 | 8/2015 | Vulto et al. |
| 2016/0139078 A1 | 5/2016 | Henry et al. |
| 2016/0153934 A1 | 6/2016 | Santiago et al. |
| 2016/0160208 A1 | 6/2016 | Santiago et al. |
| 2016/0209360 A1 | 7/2016 | Santiago et al. |
| 2016/0320286 A1 | 11/2016 | Miki et al. |
| 2017/0021350 A1 | 1/2017 | Goodwin, Jr. |
| 2017/0153202 A1 | 6/2017 | Dolnik |
| 2018/0237767 A1 | 8/2018 | Santiago et al. |

FOREIGN PATENT DOCUMENTS

| | | |
|---|---|---|
| CN | 1422180 A | 6/2003 |
| CN | 1548957 A | 11/2004 |
| CN | 1715929 A | 1/2006 |
| CN | 102395421 A | 3/2012 |
| CN | 103402641 A | 11/2013 |
| CN | 104419764 A | 3/2015 |
| CN | 105190280 A | 12/2015 |
| DE | 3328964 C1 | 2/1985 |
| DE | 102012219156 A1 | 4/2014 |
| EP | 0305210 A2 | 3/1989 |
| EP | 1742057 A1 | 1/2007 |
| EP | 1932593 A1 | 6/2008 |
| EP | 2213364 A1 | 8/2010 |
| EP | 2340122 A1 | 7/2011 |
| EP | 2541239 A2 | 1/2013 |
| EP | 2972185 A1 | 1/2016 |
| JP | H0387648 A | 4/1991 |
| JP | 2002527250 A | 8/2002 |
| JP | 2004521315 A | 7/2004 |
| JP | 2008539443 A | 11/2008 |
| JP | 2012516414 A | 7/2012 |
| JP | 2015530240 A | 10/2015 |
| JP | 2016024021 A | 2/2016 |
| JP | 2016512886 A | 5/2016 |
| JP | 2016212090 A | 12/2016 |
| WO | WO-0022436 A1 | 4/2000 |
| WO | WO-03015901 A1 | 2/2003 |
| WO | WO-2005033283 A2 | 4/2005 |
| WO | WO-2008053047 A2 | 5/2008 |
| WO | WO-2008105308 A1 | 9/2008 |
| WO | WO-2008124064 A1 | 10/2008 |
| WO | WO-2009079028 A1 | 6/2009 |
| WO | WO-2009137415 A2 | 11/2009 |
| WO | WO-2010026222 A1 | 3/2010 |
| WO | WO-2012120101 A1 | 9/2012 |
| WO | WO-2014060998 A1 | 4/2014 |
| WO | WO-2014153092 A1 | 9/2014 |
| WO | WO-2017132630 A1 | 8/2017 |
| WO | WO-2019028197 A1 | 2/2019 |

OTHER PUBLICATIONS

Bahga, et al., Coupled Isotachophoretic Preconcentration and Electrophoretic Separation Using Bidirectional Isotachophoresis, Anal. Chem. 2011,83, 6154-6162.

Bahga, et al., Integration of rapid DNA hybridization and capillary zone electrophoresis using bidirectional isotachophoresis†. Analyst, 2013;138:87-90.

Beard N.R. et al., In-Column Field-Amplified Sample Stacking of Biogenic Amines on Microfabricated Electrophoresis Devices. Electrophoresis, 24.4 (2003): 732-739.

Bercovici, et al., Rapid Detection of Urinary Tract Infections Using Isotachophoresis and Molecular Beacons. Anal. Chem. 2011, 83, 4110-4117.

Birnboim et al. A rapid alkaline extraction procedure for screening recombinant plasmid DNA. Nucl. Acids Res 7:1513-1526 (1979).

Blidner, R. et al., "Choice of FFPE DNA isolation method affects both yield and functional quality and impacts variant calling by targeted NGS", published online Nov. 5, 2015 [retrieved from Internet Apr. 13, 2017] < url: http:="" asuragen.com="" wp-content="" uploads="" 2016="" 06="" blidner_choice-of-ffpe-dna-isolation-method-affects-both-yield-and-functional-quality...pdf="" ></url: > .

Bocek, Petr, et al., "Effect of a Concentration Cascade of the Leading Electrolyte on the Separation Capacity in isotachophresis", Journal of Chromatography, 1978, pp. 323-326, vol. 156, Publisher: Elsevier Scientific Publishing Company, Published in: Amsterdam, Netherlands.

Breadmore, M.C., Unlimited-volume stacking of ions in capillary electrophoresis. Part 1: Stationary isotachophoretic stacking of anions. Electrophoresis 2008, 29, 1082-1091.

Chambers R.D. et al., Imaging and Quantification of Isotachophoresis Zones Using Nonfocusing Fluorescent Tracers. Analytical Chemistry, 81.8 (2009): 3022-3028.

Chen, et al., Determination of Binding Constants by Affinity Capillary Electrophoresis, Electrospray Ionization Mass Spectrometry and Phase-distribution Methods, Trends Analyt Chem., Oct. 2008, 27(9); 738-748 D.

(56) References Cited

OTHER PUBLICATIONS

CIPO. Search Report for related Chinese Patent Application No. 201480021876.2 dated Jun. 2, 2017, 15 Pages.
Co-pending U.S. Appl. No. 15/668,557, inventors Chambers; Robert D et al., filed on Aug. 3, 2017.
Desjardin et al. (1996) Alkaline decontamination of sputum specimens adversely affects stability of mycobacterial mRNA. J. Clin. Microbial. 34(10):2435-2439.
Devolder et al., "Pneumatic and hydraulic microactuators: a review", 2010, pp. 1-18, J.Micromech. Microeng. v20.
Dossil., et al., Microchip Free-Flow Electrophoresis on Glass Substrate Using Laser-Printing Toner as Structural Material. Electrophoresis, 27 (2006): 4935-4942.
Eddington et al., "Flow control with hydrogels", 2004, pp. 199-210, Advanced Drug DeliveryReviews v56.
Eisenbarth G.S., Application of Monoclonal Antibody Techniques to Biochemical Research. Analytical Biochemistry, 111.1 (1981): 1-16.
EP17745057.4 Extended European Search Report dated May 15, 2019.
EP18841854.5 Extended European Search Report dated Mar. 18, 2021.
Erlich, et al. Recent advances in the polymerase chain reaction. Science. Jun. 21, 1991;252(5013):1643-51.
European search report dated Jan. 25, 2017 for EP Application No. 14769958.1.
Foret et al., Indirect Photometric Detection in Capillary Zone Electrophoresis. Journal of Chromatography, 470 (1989): 299-308.
Friend, J. et al. Fabrication of microfluidic devices using polydimethylsiloxane, 2010, Biomicrofluidics, vol. 4, pp. 026502 (1-5).
Fu J. et al., A Patterned Anisotropic Nanofluidic Sieving Structure for Continuous-flow Separation of DNA and Proteins. Nature, 2.2 (2007): 121-128.
Fung, et al., Application of Capillary electrophoresis fortrace ion analysis in rain water, J, Microcolumn separations, 2000; 12(6):337-344.
Garcia-Schwarz, G., et al. On-chip Isotachophoresis for Separation of Ions and Purification of Nucleic Acids, Journal of VisualizedExperiments, vol. 61, pp. 1-8 (Year: 2012).
Goet et al., Micro Contact Based on Isotachophoretic Sample Transport. Lab Chip, 9 (2009): 3586-3593.
Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.
Gross L. et al., Indirect Fluorometric Detection of Cations in Capillary Zone Electrophoresis. American Chemical Society, (1990): 427-431.
Hilber, W., Stimulus-active polymer actuators for next-generation microfluidic devices. Applied Physics A, Aug. 2016; 122:75, 39 Pages.
Hinckley, J. O. N., Transphoresis and Isotachophoresis- Automatable Fast Analysis of Electrolytes, Proteins, and Cells, with Supression of Gravitational Effects, Clinical Chemistry, vol. 20, No. 8, 1974, 973-991 D.
Hosokawa et al.. "Power-free poly(dimethylsiloxane) microfluidic devices for gold nanoparticle-based DNA analysis", Lab Chip, vol. 4, pp. 181-185, May 12, 2004. http://pubs.rsc.org/en/Content/Articlelanding/2004/LC/b403930k#! divAbstract.entire document.
International Search Report dated Jul. 29, 2014 for International PCT Patent Application No. PCT/US2014/029017.
Jacob et al., Micro Free-Flow IEF Enhanced by Active Cooling and Functionalized Gels. Electrophoresis, 27 (2006): 4960-4969.
Jacobson S. et al., Microchip Electrophoresis With Sample Stacking. Electrophoresis, 16.4 (1995): 481-486.
Janasek D. et al., Isotachophoresis in Free-Flow Using a Miniaturized Device. Analytical Chemistry, 78.11 (2006): 3815-3819.
Juan S.G. et al., Stanford Microfluidics Laboratory. Stanford University, May 2016, http://microfluidics.stanford.edu.
Jung, et al., On-Chip Millionfold Sample Stacking Using Transient Isotachophoresis, Anal. Chem., Apr. 2006, 78:2319-27.
Karsenty, et al., Current Monitoring in a Microchannel with Repeated Constrictions for Accurate Detection of Sample Location in Isotachophoresis. Anal. Chem. 2015, 87, 388-393.
Khurana, et al., Effects of Carbon Dioxide on Peak Mode Isotachophoresis: Simultaneous Preconcentration and Separation, Lab Chip, 2009, 9, 1377-1384.
Khurana, et al., Preconcentration, Separation, and Indirect Detection of Nonfluorescent Analytes Using Fluorescent Mobility Markers, Analytical Chemistry, vol. 80, No. 1, Jan. 1, 2008, 279-286 D.
Khurana, et al., Sample Zone Dynamics in Peak Mode Isotachophoresis, Analytical Chemistry, Published on Web, Jul. 22, 2008, pp. A-H.
Kitagawa et al., High-speed Analysis of Proteins by Microchip Isoelectric Focusing with Linear-imaging UV Detection, Analytical Sciences, Aug. 2009, vol. 25, 979-984.
KřivánkováL., et al., Synergism of Capillary Isotachophoresis and Capillary Zone Electrophoresis. Journal of Chromatography B: Biomedical Sciences and Applications, 689 (1997): 13-34.
Kondratova, et al., Concentration and isolation of DNA from biological fluids by agarose gel isotachophoresis. BioTechniques, Nov. 2005; 39:695-699.
Krivankova et al., Isotachophoresis 17. Methods in Enzymology, 270 (1996): 375-401.
Lee, G-8, et al. Microfluidic Chips for DNA Amplification, Electrophoresis Separation and On-Line Optical Detection, 2003, IEEE pp. 423-426.
Liao et al. (2007) Development of an advanced electrochemical DNA biosensor for bacterial pathogen detection. J. Mol. Diagn. 9 (2):158-168.
Liu, et al., Isotachophoresis preconcentration integrated microfluidic chip for highly sensitive genotyping of the hepatitis B virus. Journal of Chromatography B, 844 (2006) 32-38.
Mariella R. Jr., Sample Preparation: The Weak Link in Microfluidics-Based Biodetection. Biomed Microdevices, 10 (2008): 777-784.
Marshall, et al., An injection molded microchip for nucleic acid purification from 25 microliter samples using isotachophoresis. Journal of Chromatography A, 1331 (2014) 139-142.
Marshall, et al. An Injection Molded Microchip for Nucleic Acid Purification from 25 Microliter Samples Using Isotachophoresis, Supporting Information, 2014. 5 pages.
Marshall, et al., Integrated Printed Circuit Board Device for Cell Lysis and Nucleic Acid Extraction. | Anal. Chem. 2012, 84, 9640-9645.
Marshall L. A. et al. "An Injection-Molded Device for Purification of Nucleic Acids From Whole Blood Using Isotachophoresis." 2013 Annual Meeting of the AES, 8 pgs. (Nov. 2013).
Marshall L.A. and Santiago, J. G. "A Novel Device for Highly-Efficient Extraction of Nucleic Acids from 100 Microliter Whole Blood Samples." 2012 Annual Meeting of the AES, 4 pgs. (Oct. 31, 2012).
Morio, et al. Quantitative analysis of trifluoroacetate in the urine and blood by isotachophoresis. Anesthesiology. Jul. 1980;53(l):56-9.
Mowio., "Mowio- History/Manufacture/Structure, p. A 1- no date available.".
Nagoyova I. et al., Discrete Spacers for Photometric Characterization of Humic Acids Separated by Capillary Isotachophoresis. Journal of Chromatography A, (2001): 191-200.
Notice of Allowance dated May 29, 2014 for U.S. Appl. No. 12/716,142.
Notice of Allowance dated May 30, 2017 for U.S. Appl. No. 14/497,050.
Notice of Allowance dated Jun. 6, 2014 for U.S. Appl. No. 12/716,142.
Oerlemans, F. et al., Isotachophoresis of Urinary Purines and Pyrimidines: The Use of Spacers and Enzymes for Identification. Journal of Chromatography, 225 (1981): 369-379.
Office Action dated Mar. 10, 2017 for U.S. Appl. No. 14/213,832.
Office Action dated Mar. 17, 2016 for U.S. Appl. No. 14/497,050.
Office Action dated May 16, 2012 for U.S. Appl. No. 12/716,142.
Office Action dated Aug. 24, 2017 for U.S. Appl. No. 14/213,832.
Office Action dated Sep. 16, 2016 for U.S. Appl. No. 14/497,050.
Office Action dated Oct. 19, 2011 for U.S. Appl. No. 12/716,142.

(56) References Cited

OTHER PUBLICATIONS

Oh et al., "A review of microvalves", 2006, pp. R13-R39, J. Micromech. Microeng. v16.
Oshurkova et al., Coulophoretic Titration. Translated from Doklady Akademii Nauk SSSR v227n6, (1975): 316-319.
Oshurkova et al., Russian Chemical Reviews, 62.8 (1993): 729-742.
Oshurkova et al., Russian Journal of Electrochemistry, 40.5 (2004): 583-587.
Park et al., Controlling Data Quality and Reproducibility of a High-Sensitivity Immuniassay Using Isotachophoresis in a Microchip. Analytical Chemistry, 80 (2008): 808-814.
PCT/US2017/015519 International Search Report and Written Opinion dated Apr. 27, 2017.
PCT/US2018/044898 International Search Report and Written Opinion dated Dec. 11, 2018.
Pei, et al., Isotachophoretic detemincaoint of Urea-Ammonium in Plasma: A candidate reference method, J. Clin. Chem. Clin. Biochem, 1990; 28:447-451.
Persat, A. and Santiago, J.G., Electrokinetic control of sample splitting at a channel bifurcation using isotachophoresis. New Journal of Physics, 2009: 15 Pages.
Persat, A. and Santiago, J.G., On-Chip Isothermal Polymerase Chain Reaction. IMECE 2007; 2 Pages.
Persat, A. et al., "Quantification of Global MicroRNA Abundance by Selective Isotachophoresis", Analytical Chemistry, 2010, vol. 82, pp. 9631-9635.
Persat et al., MicroRNA Profiling by Simultaneous Selective Isotachophoresis and Hybridization With Molecular Beacons. Analytical Chemistry, 83 (2011): 2310-2316.
Persat, et al., Purification of Nucleic Acids from Whole Blood Using Isotachophoresis, Analytical Chemistry, 81.22 (Nov. 15, 2009): 9507-9511, supporting materials.
Persat, et al., Purification of Nucleic Acids from Whole Blood Using Isotachophoresis, Analytical Chemistry, vol. 81, No. 22, Nov. 15, 2009,9507-9511 D.
Persat, et al., Supporting information: Quantification of global microRNA abundance by selective isotachophoresis. Department of mechanical engineering, 2010.
Petr et al., Capillary Isotachophoresis From the Student Point of View-Images and the Reality. Journal of Separation Science, 29 (2006): 2705-2715.
Prest et al., Bidirectional Isotachophoresis on a Planar Chip With Integrated Conductivity Detection. Analyst, 127 (2002): 1413-1419.
Prest et al. "Miniaturised isotachophoresis of Dna" J. of Chromatography A, 2007, 1156: 154-159.
Quirino J.P. et al., Sample Stacking of Fast-Moving Anions in Capillary Zone Electrophoresis With pH-Suppressed Electroosmotic Flow. Journal of Chromatography, 850.1-2 (1999): 339-344.
Rogacs, A. et al., "Purification of nucleic acids using isotachophoresis", Journal of Chromatography A, 2014, vol. 1335, pp. 105-120.
Ross, et al., Microfluidic Temperature Gradient Focusing, Anal. Chem., Jun. 2002, 74:2556-64.
Ryan et al., Micro Free-Flow Electrophoresis: Theory and Applications. Anal Bioanal Chem, 394 (2009): 187-198.
Schafer-Neilsen et al., Separation of Macromolecules in Isotachophoresis Systems Involving Single or Multiple Counterions. Journal of Biochemical and Biophysical Methods, 3 (1980): 97-128.
Schoch, et al., Rapid and Selective Extraction, Isolation, Preconcentration, and Quantitation of Small RNAs from Cell Lysate Using On-chip Isotachophoresis, Lab Chip, 2009, 9, 2145-2152 D.
Singh et al. (2006) An alkaline solution simplifies nucleic acid preparation for RT-PCR and infectivity assays of viroids from crude sap and spotted membrane. J. Viral. Methods 132(1-2):204-211.
Stover, Fredericks., "Enhancing Isotachophoresis Sensitivity by Low-Concentration Electrolyte Cascading", Journal of Chromatography, 1985, pp. 45-48, vol. 320, Publisher: Elsevier Science Publishers BV., Published in: Amsterdam, Netherlands.
Thormann, et al., Impact of electoosmosis on isotachophoresis in open-tubular fused-silica capillaries: Analysis of the evolution of a stationary steady-state zone structure by computer simulation and experimental validation. Electrophoresis, 1995; 16:2016-2026.
U.S. Appl. No. 14/828,487 Notice of Allowance dated Jul. 17, 2018.
U.S. Appl. No. 15/081,415 Notice of Allowance dated May 10, 2018.
US 7,247,224, Jul. 2007, Weber (withdrawn).
U.S. Appl. No. 16/998,839 Final Office Action dated Jan. 6, 2023.
U.S. Appl. No. 11/755,449 Notice of Allowance dated Dec. 3, 2012.
U.S. Appl. No. 11/755,449 Office Action dated Apr. 23, 2012.
U.S. Appl. No. 11/755,449 Office Action dated Dec. 30, 2011.
U.S. Appl. No. 11/755,449 Office Action dated Jan. 5, 2011.
U.S. Appl. No. 11/755,449 Office Action dated Jul. 26, 2011.
U.S. Appl. No. 11/755,449 Office Action dated Jul. 7, 2010.
U.S. Appl. No. 11/880,479 Notice of Allowance dated Aug. 4, 2010.
U.S. Appl. No. 11/880,479 Notice of Allowance dated Mar. 23, 2011.
U.S. Appl. No. 12/542,215 Notice of Allowance dated Dec. 18, 2015.
U.S. Appl. No. 12/542,215 Office Action dated Aug. 27, 2014.
U.S. Appl. No. 12/542,215 Office Action dated Jul. 9, 2015.
U.S. Appl. No. 12/542,215 Office Action dated May 29, 2012.
U.S. Appl. No. 12/542,215 Office Action dated Sep. 28, 2011.
U.S. Appl. No. 12/587,537 Notice of Allowance dated Nov. 13, 2012.
U.S. Appl. No. 12/587,537 Office Action dated Feb. 23, 2012.
U.S. Appl. No. 12/943,677 Notice of Allowance dated Jun. 10, 2015.
U.S. Appl. No. 12/943,677 Office Action dated Mar. 26, 2015.
U.S. Appl. No. 12/943,677 Office Action dated May 6, 2013.
U.S. Appl. No. 12/943,677 Office Action dated Oct. 19, 2012.
U.S. Appl. No. 13/065,168 Notice of Allowance dated Mar. 6, 2014.
U.S. Appl. No. 13/065,168 Office Action dated Apr. 26, 2013.
U.S. Appl. No. 13/065,168 Office Action dated Aug. 22, 2013.
U.S. Appl. No. 13/134,165 Notice of Allowance dated Jun. 12, 2013.
U.S. Appl. No. 13/134,165 Office Action dated Feb. 21, 2013.
U.S. Appl. No. 13/199,895 Notice of Allowance dated Dec. 17, 2014.
U.S. Appl. No. 13/199,895 Office Action dated Jul. 30, 2013.
U.S. Appl. No. 13/199,895 Office Action dated May 8, 2014.
U.S. Appl. No. 13/199,895 Office Action dated Nov. 6, 2012.
U.S. Appl. No. 13/252,138 Notice of Allowance dated May 18, 2015.
U.S. Appl. No. 13/252,138 Office Action dated Feb. 5, 2014.
U.S. Appl. No. 13/252,138 Office Action dated Jun. 18, 2014.
U.S. Appl. No. 13/252,138 Office Action dated Oct. 22, 2014.
U.S. Appl. No. 13/373,773 Notice of Allowance dated Jul. 18, 2013.
U.S. Appl. No. 13/413,161 Notice of Allowance dated Dec. 19, 2014.
U.S. Appl. No. 13/413,161 Office Action dated May 8, 2014.
U.S. Appl. No. 13/764,376 Notice of Allowance dated Apr. 25, 2014.
U.S. Appl. No. 13/764,376 Office Action dated Oct. 15, 2013.
U.S. Appl. No. 13/972,655 Notice of Allowance dated May 6, 2015.
U.S. Appl. No. 13/972,655 Office Action dated Feb. 20, 2015.
U.S. Appl. No. 13/972,655 Office Action dated Jul. 29, 2014.
U.S. Appl. No. 13/972,655 Office Action dated Oct. 29, 2014.
U.S. Appl. No. 14/450,069 Office Action dated Dec. 6, 2017.
U.S. Appl. No. 14/450,069 Office Action dated Jan. 10, 2020.
U.S. Appl. No. 14/450,069 Office Action dated Oct. 1, 2018.
U.S. Appl. No. 14/450,069 Office Action dated Oct. 6, 2020.
U.S. Appl. No. 14/450,069 Office Action dated Jun. 14, 2019.
U.S. Appl. No. 14/465,138 Notice of Allowance dated Nov. 19, 2015.
U.S. Appl. No. 14/465,138 Office Action dated Apr. 30, 2015.
U.S. Appl. No. 14/828,487 Office Action dated Apr. 9, 2018.
U.S. Appl. No. 14/828,487 Office Action dated Nov. 1, 2017.
U.S. Appl. No. 15/081,415 Office Action dated Jan. 16, 2018.
U.S. Appl. No. 15/668,557 Office Action dated Apr. 1, 2019.
U.S. Appl. No. 15/668,557 Office Action dated Jan. 11, 2021.
U.S. Appl. No. 15/668,557 Office Action dated May 1, 2020.
U.S. Appl. No. 15/668,557 Office Action dated Nov. 19, 2019.
U.S. Appl. No. 15/668,557 Office Action dated Oct. 19, 2018.

(56) References Cited

OTHER PUBLICATIONS

U.S. Appl. No. 16/046,560 Notice of Allowance dated Jul. 29, 2020.
U.S. Appl. No. 16/046,560 Office Action dated Apr. 24, 2020.
U.S. Appl. No. 16/052,565 Notice of Allowance dated Apr. 1, 2021.
U.S. Appl. No. 16/052,565 Office Action dated Nov. 16, 2020.
U.S. Appl. No. 16/121,219 Notice of Allowance dated Sep. 17, 2020.
U.S. Appl. No. 16/121,219 Office Action dated Jun. 2, 2020.
U.S. Appl. No. 16/121,219 Office Action dated Mar. 20, 2020.
U.S. Appl. No. 16/121,219 Office Action dated Sep. 11, 2019.
U.S. Appl. No. 16/175,500 Notice of Allowance dated Jun. 17, 2019.
U.S. Appl. No. 16/175,500 Office Action dated Feb. 4, 2019.
U.S. Appl. No. 16/192,034 Notice of Allowance dated Jul. 20, 2020.
U.S. Appl. No. 16/192,034 Office Action dated Feb. 7, 2020.
U.S. Appl. No. 16/192,034 Office Action dated Jan. 18, 2019.
U.S. Appl. No. 16/192,034 Office Action dated May 13, 2019.
U.S. Appl. No. 16/192,034 Office Action dated May 14, 2020.
U.S. Appl. No. 16/997,614 Notice of Allowance dated Oct. 3, 2022.
U.S. Appl. No. 16/997,614 Office Action dated Aug. 17, 2022.
U.S. Appl. No. 16/998,839 Office Action dated Sep. 16, 2022.
U.S. Appl. No. 15/853,370 Notice of Allowance dated Nov. 9, 2018.
Wagner H., Free-Flow Electrophoresis. Nature, 341 (1989): 669-670.
Wainright A. et al., Preconcentration and Separation of Double-stranded DNA Fragments by Electrophoresis in Plastic Microfluidic Devices. Electrophoresis, 24.21 (2003): 3784-3792.
Wainright A. et al., Sample Pre-Concentration by Isotachophoresis in Microfluidic Devices. Journal of Chromatography, 979.1-2 (2002): 69-80.
Wang et al., Million-fold Preconcentration of Proteins and Peptides by Nanofluidic Filter, Anal. Chem., Jul. 15, 2005, 77:4293-99.
Woolley et al., Ultra-High-Speed DNA Fragment Separations Using Microfabricated Capillary Array Electrophoresis Chips. Proceedings of the National Academy of Sciences of the United States of America, 99 (1994): 11348-11352.
Xu et al., Electrokinetic Supercharging Preconcentration and Microchip Gel Electrophoretic Separation of Sodium Dodecyl Sulfate-Protein Complexes. Electrophoresis, 24 (2003): 3821-3827.
Xu et al., High-Sensitivity Capillary Gel Electrophoretic Analysis of DNA Fragments on an Electrophoresis Microchip Using Electrokinetic Injection With Transient Isotachophoretic Preconcentration. Journal of Chromatography A, 990 (2003): 53-61.
Xu et al., Optimization of the Electrokinetic Supercharging Preconcentration for High-Sensitivity Microchip Gel Electrophoresis on a Cross-Geometry Microchip. Electrophoresis, 25 (2004): 2357-2362.
Xu et al., Performance of Electrokinetic Supercharging for High-sensitivity Detection of DNA Fragments in Chip Gel Electrophoresis. Electrophoresis, 24 (2004): 3875-3881.
Yang, et al., Sample Stacking in Laboratory-on-a-Chip Devices, J. Chromatogr., A, Jul. 2001, 924:155-63.
Zhang C.X. et al., Head-Column-Field-Amplified Sample Stacking in Binary System Capillary Electrophoresis: A Robust Approach Providing Over 1000-Fold Sensitivity Enhancement. Analytical Chemistry, 68.15 (1996): 2523-2532.
Zhang, W., B.A. Direct PCT sequencing with denaturants in:Rapley R. (eds.) PCR sequencing protocols methods in molecular biology, 1996; 65.
Zhong, et al., Automatic Extraction and Processing of Small RNAs on a Multi-well/Multi-channel (M&M) Chip. Analyst. Dec. 7, 2012;137(23):5546-52. doi: 10.1039/c2an35883b. Epub Sep. 21, 2012.

\* cited by examiner

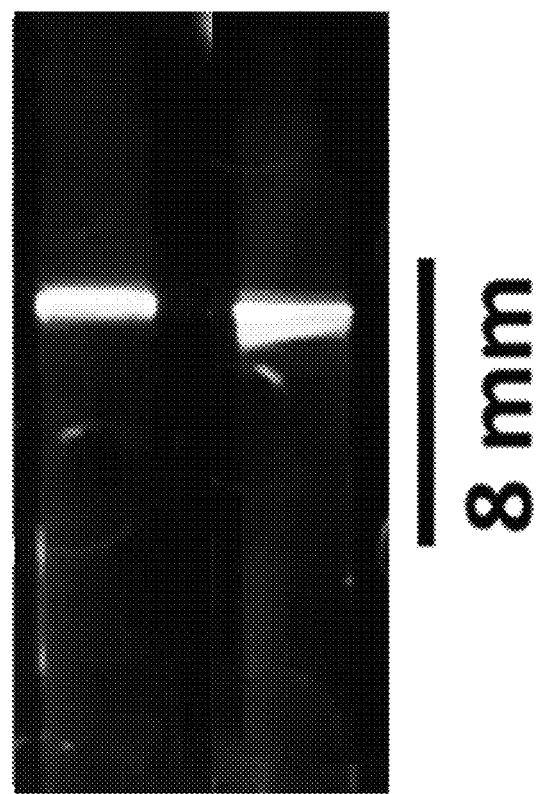
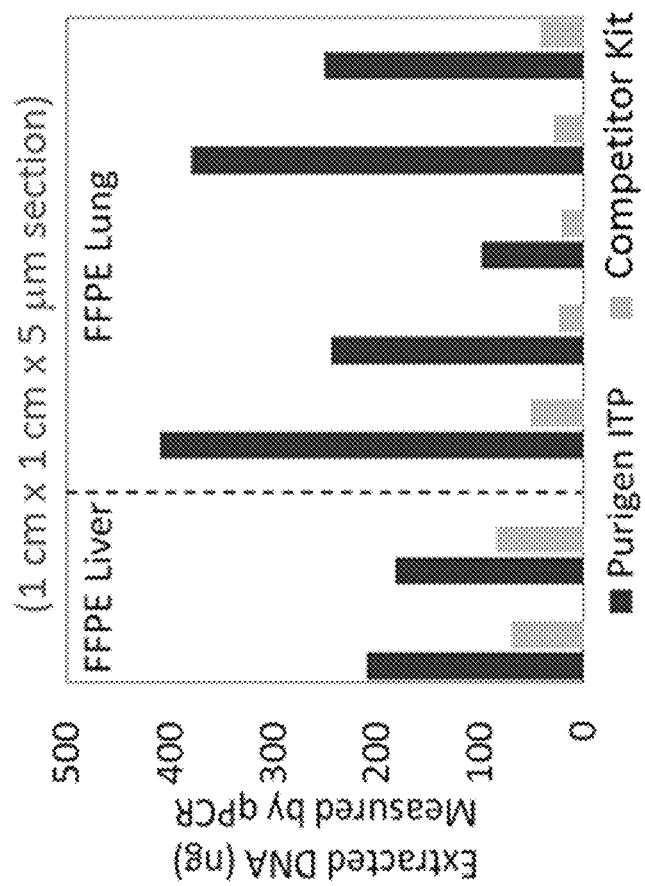
FIG. 24A
FIG. 24B

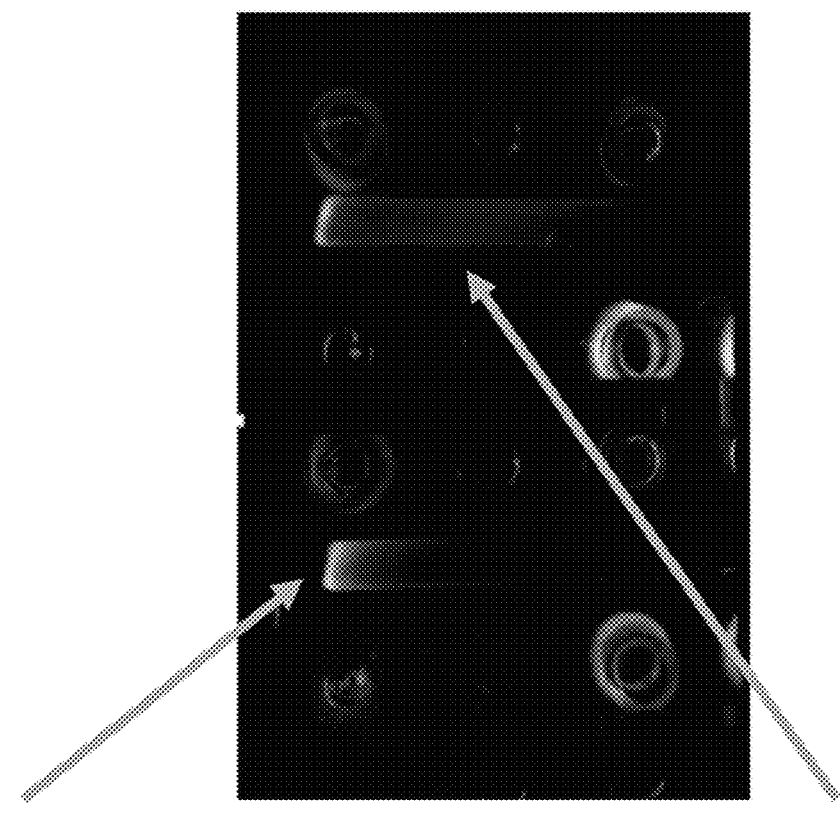
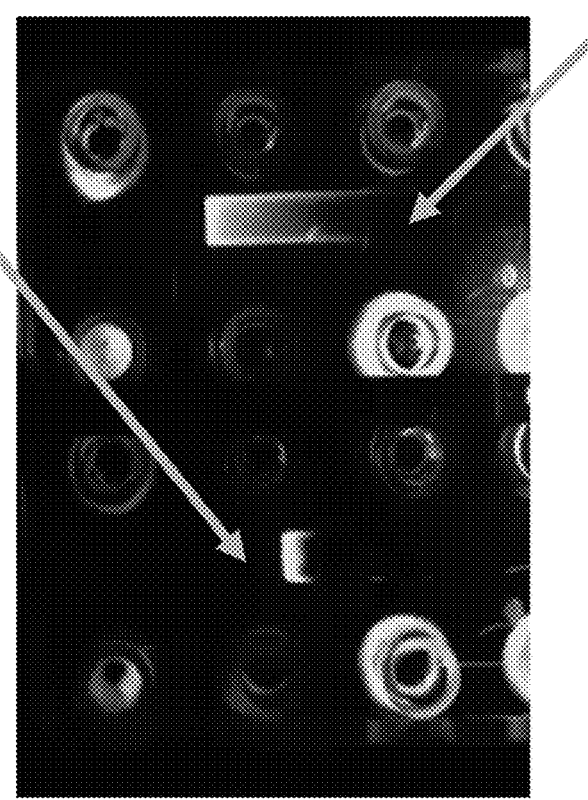
2501　　2502
FIG. 25B
FIG. 25A

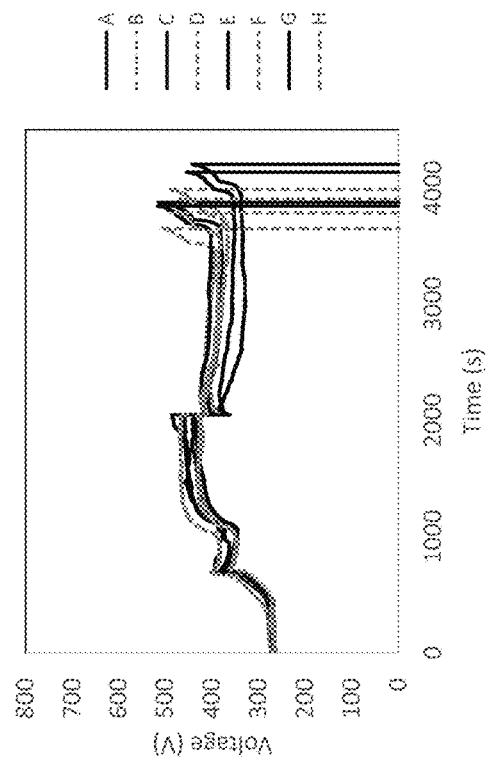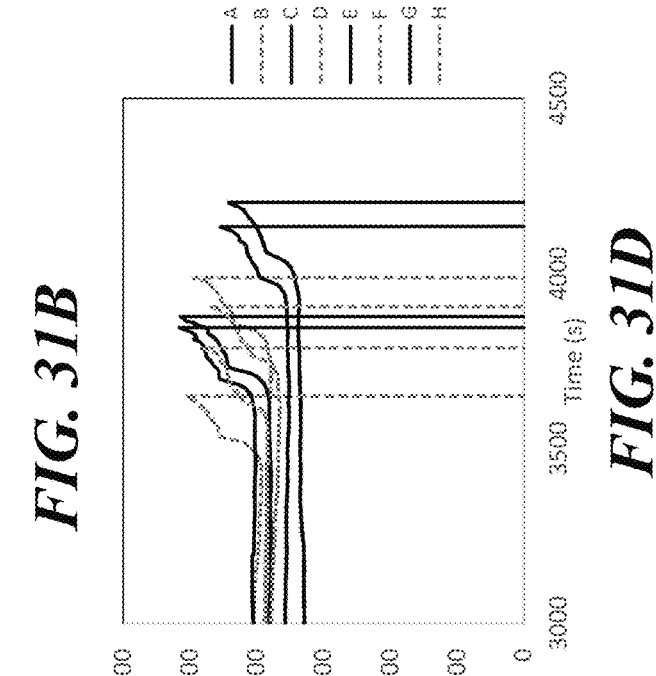
FIG. 31A  FIG. 31B  FIG. 31C  FIG. 31D

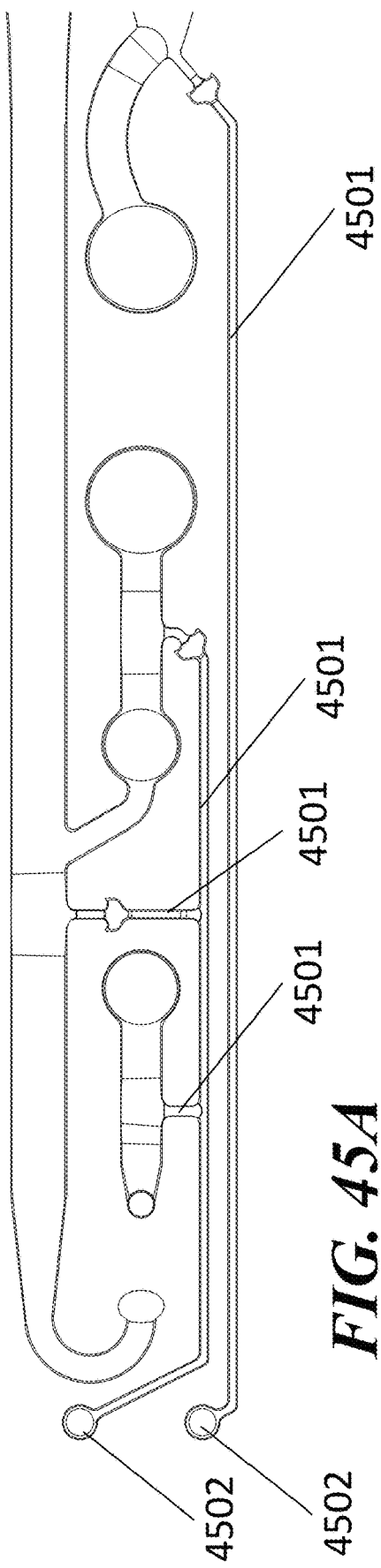
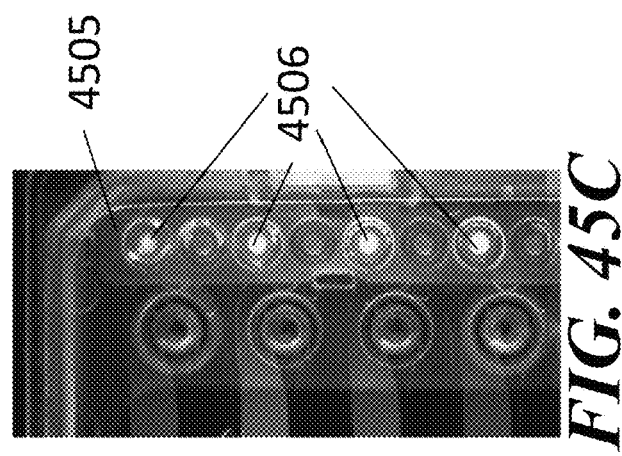
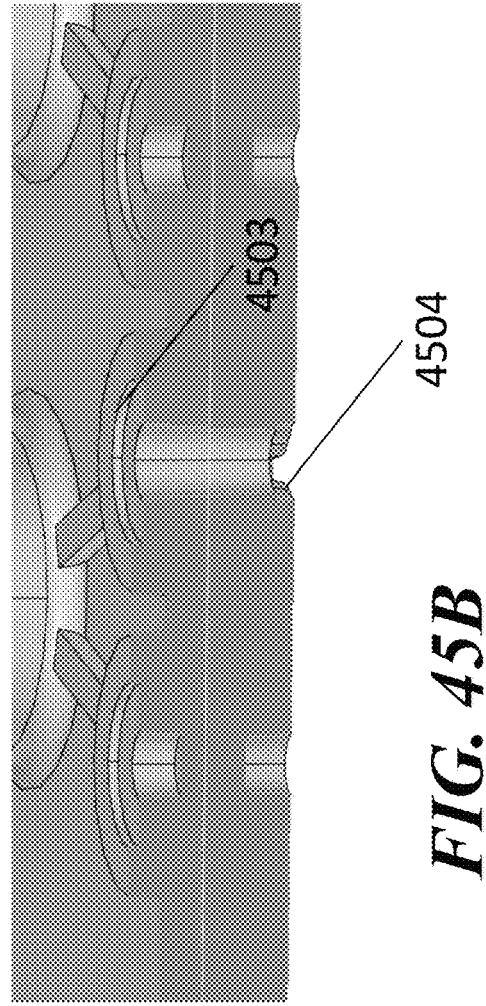
FIG. 45A
FIG. 45B
FIG. 45C

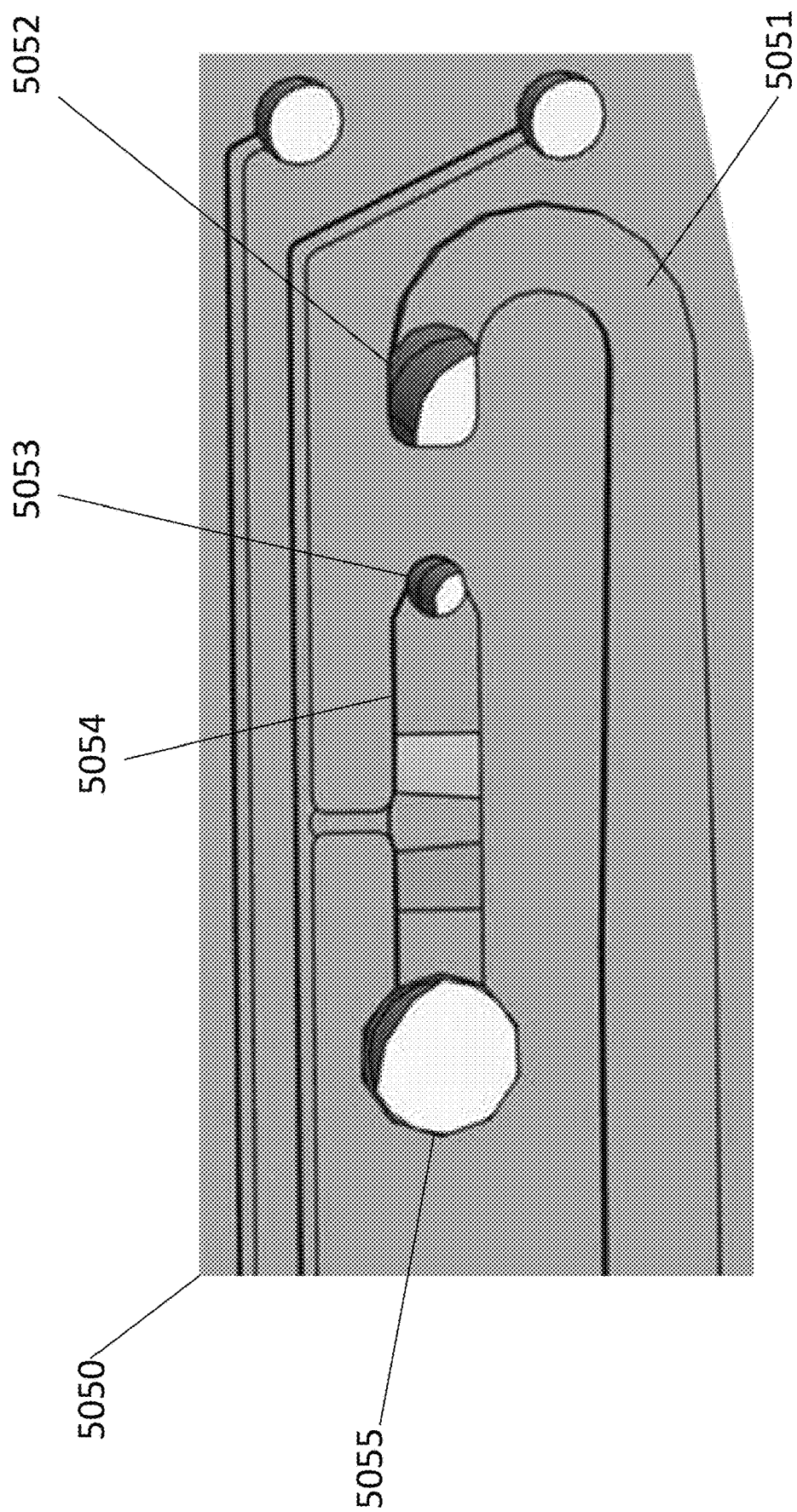
FIG. 50A1

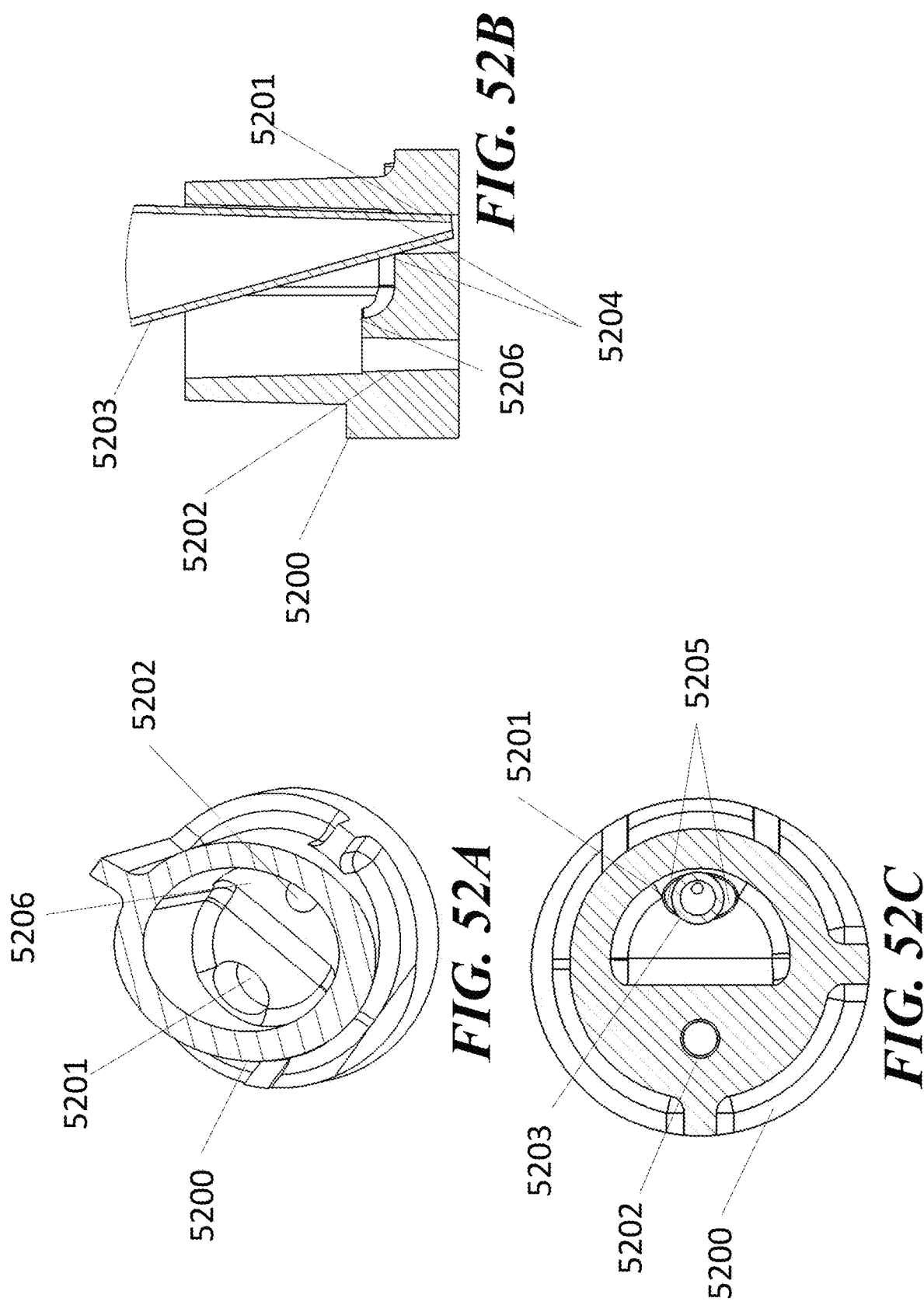

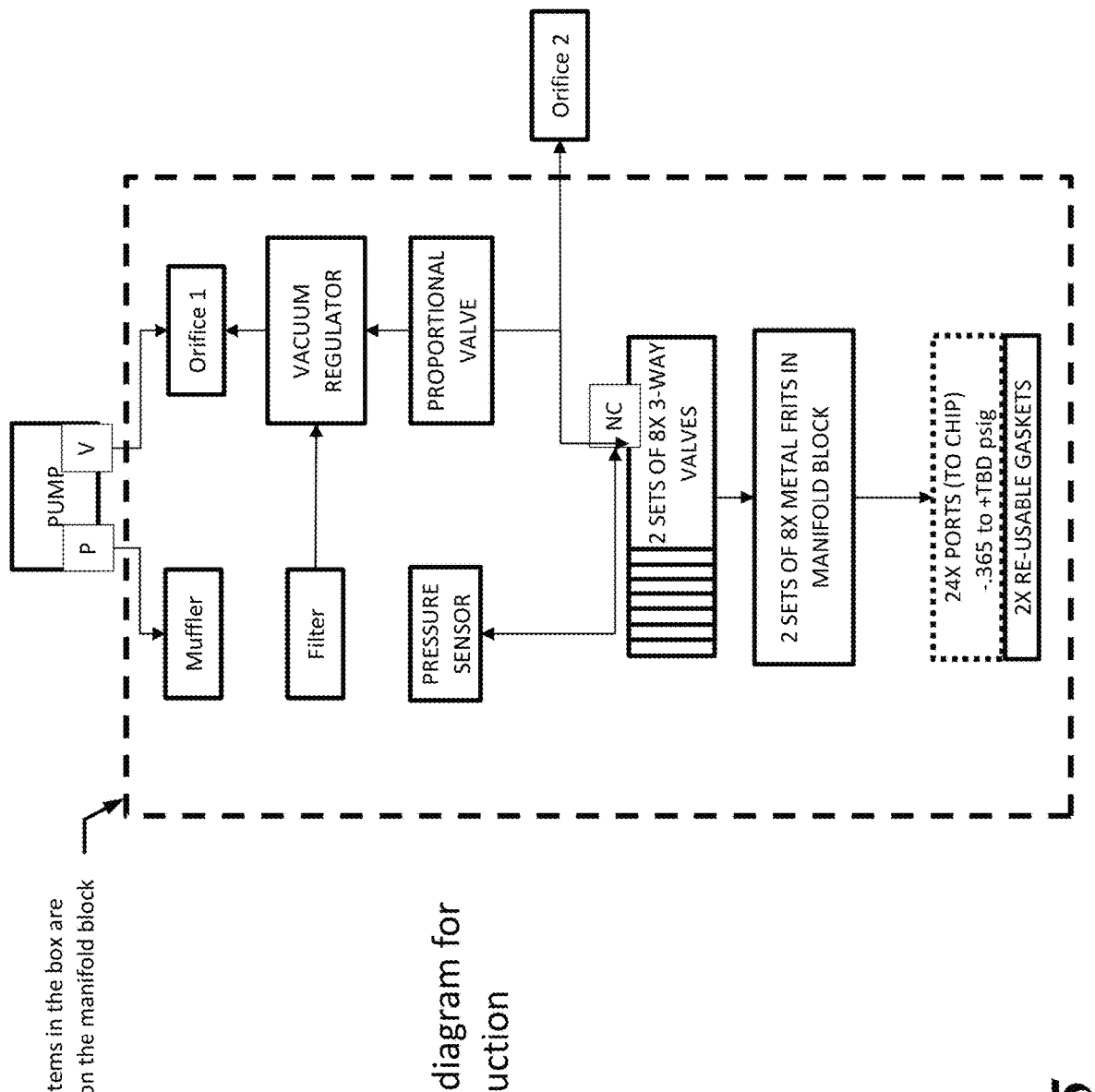
FIG. 55 Pneumatic control block diagram for beta prototype and production instrument

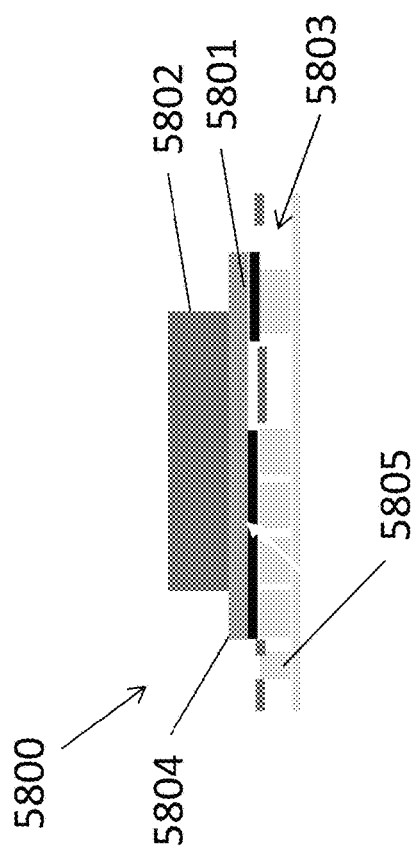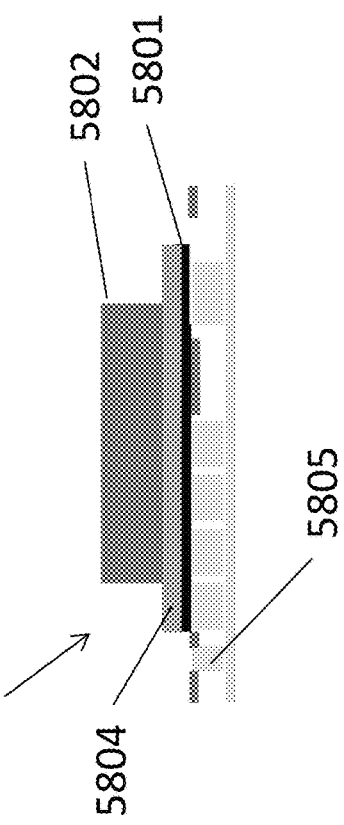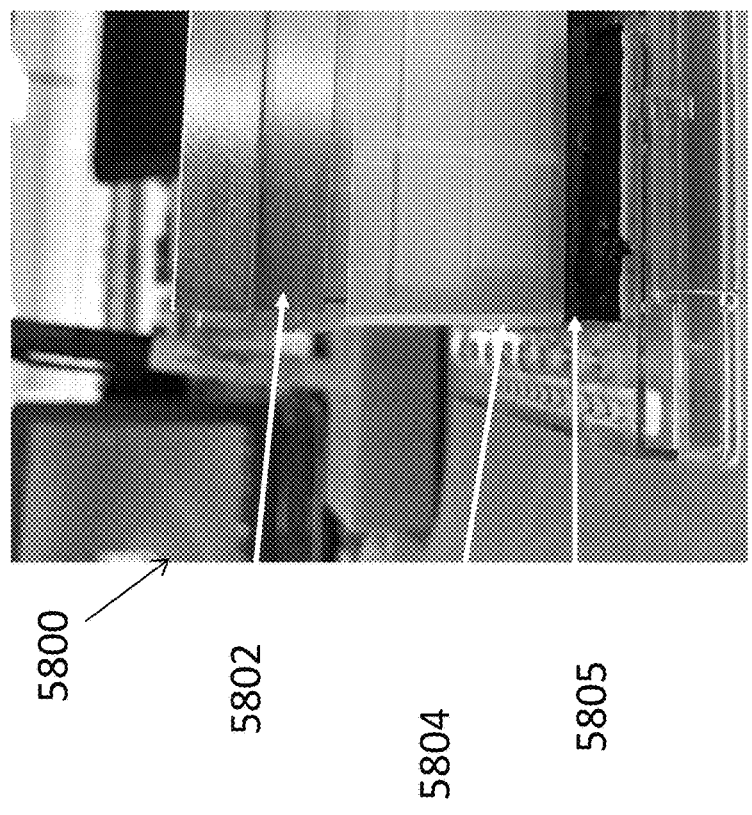
FIG. 58B
FIG. 58C
FIG. 58A

A) KAPA hgDNA Quant & QC

| | A | | | | | B | | | | | C | | | | |
|---|---|---|---|---|---|---|---|---|---|---|---|---|---|---|---|
| Pico Green Content (x) | 28.4x | 5.7x | 0.57x | 0.057x | 0.005x | 28.4x | 5.7x | 0.57x | 0.057x | 0.005x | 28.4x | 5.7x | 0.57x | 0.057x | 0.005x |
| Ct | 24 | 23.58 | 23.62 | 23.47 | 23.48 | 28.43 | 26.73 | 26.57 | 26.85 | 26.61 | 32.6 | 30.87 | 30.43 | 30.49 | 30.59 |

FIG. 72A

B) BioRad RPP30 FAM

| | A | | | | | B | | | | | C | | | | |
|---|---|---|---|---|---|---|---|---|---|---|---|---|---|---|---|
| Pico Green Content (x) | 57x | 5.7x | 0.57x | 0.057x | 0.005x | 57.X | 5.7x | 0.57x | 0.057x | 0.005x | 57x | 5.7x | 0.57x | 0.057x | 0.005x |
| Ct | 40* | 27.91 | 28.55 | 28.36 | 28.66 | N/A | 33.32 | 32.27 | 32.7 | 32.14 | N/A | 35.33 | 35.9 | 35.2 | 35.36 |

FIG. 72B

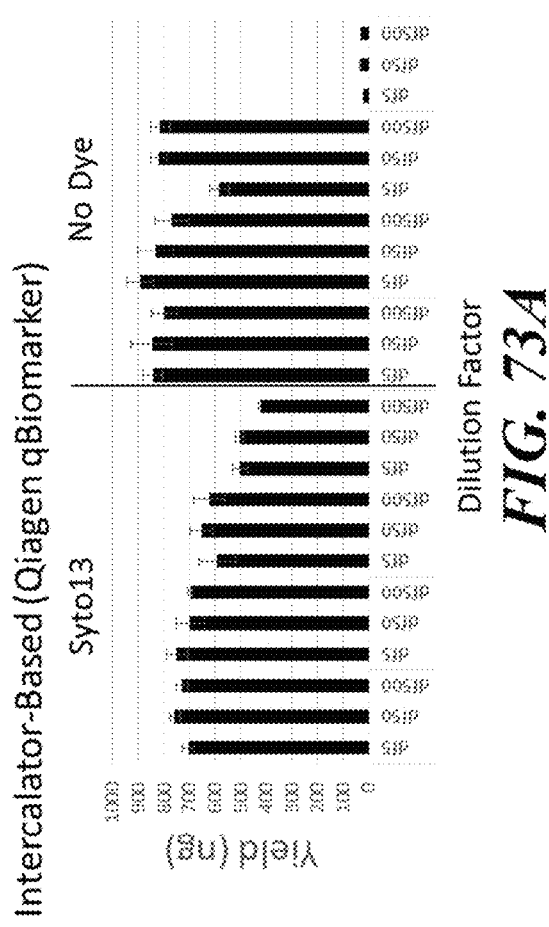
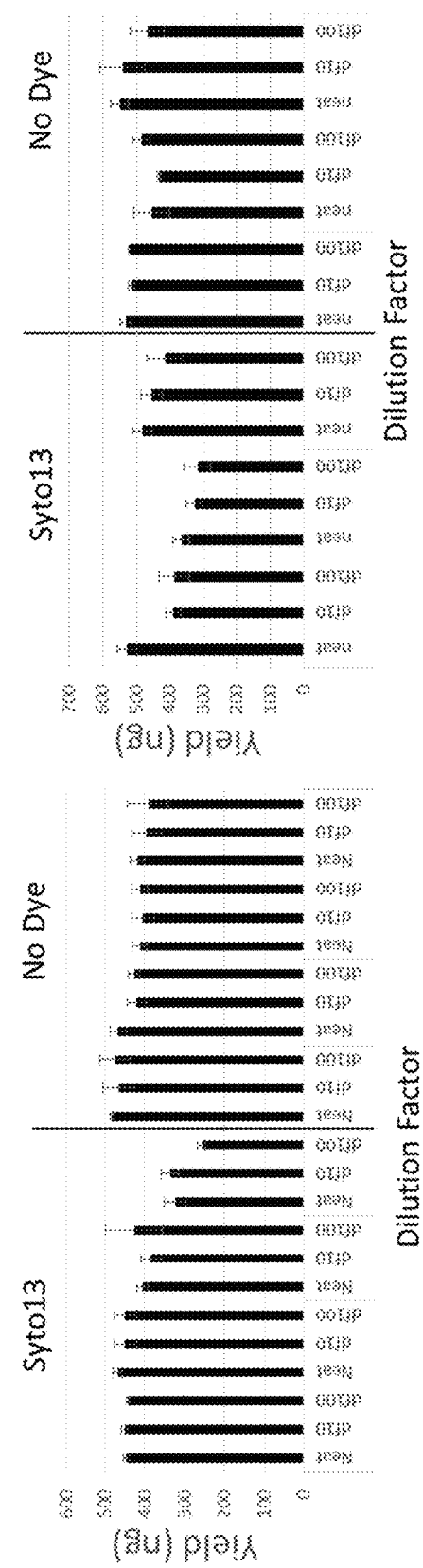
FIG. 73A
FIG. 73B
FIG. 73C

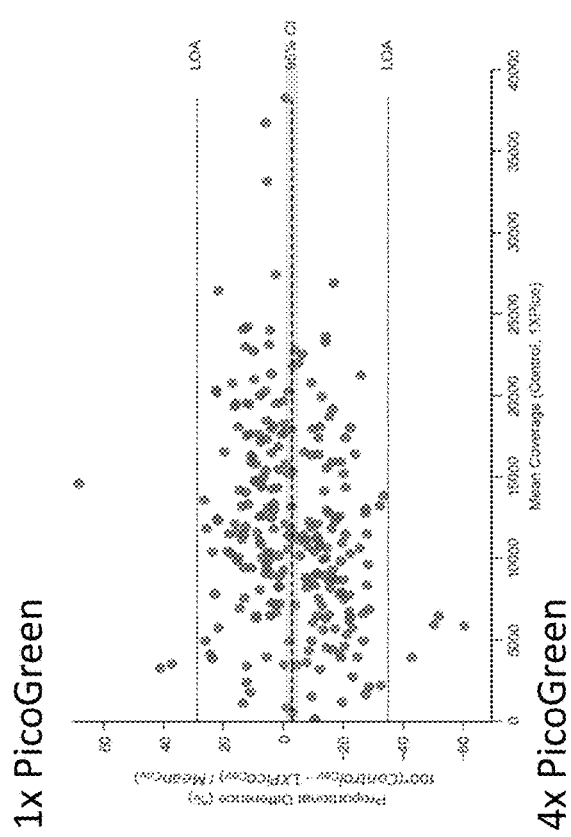
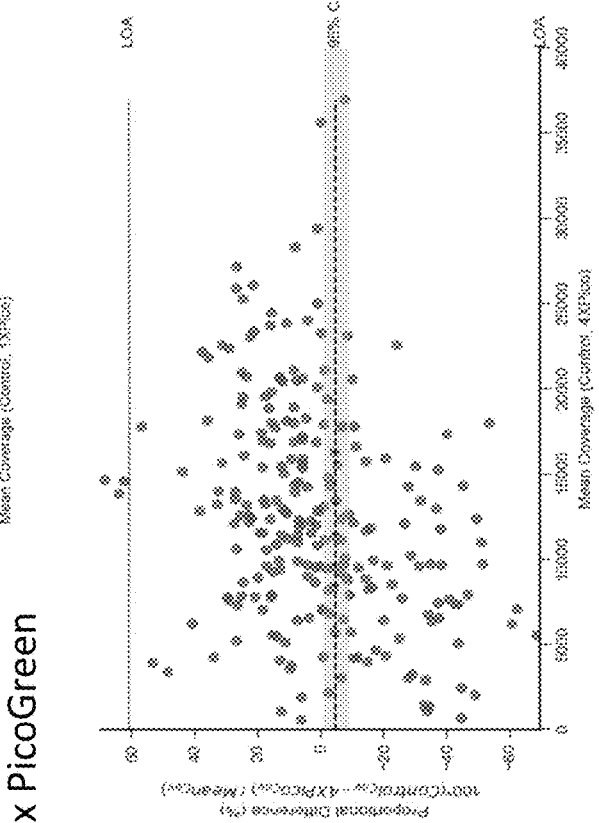
FIG. 74

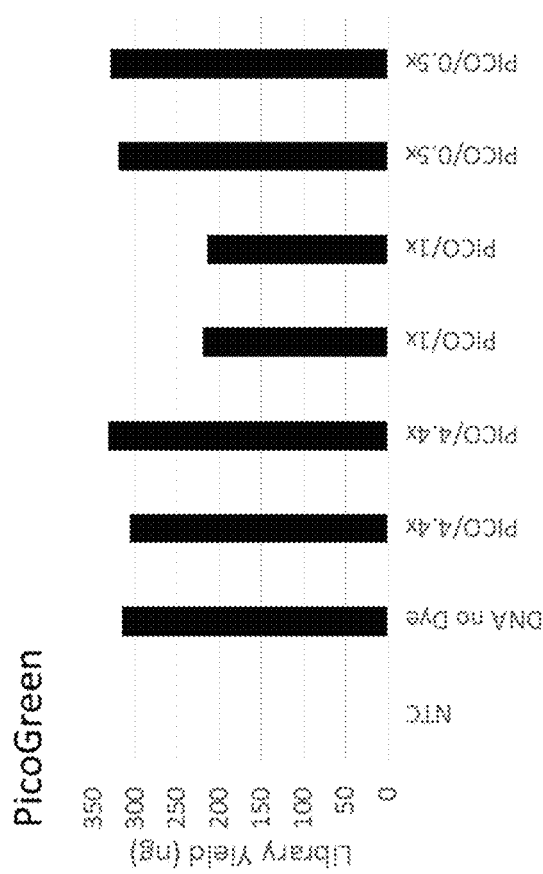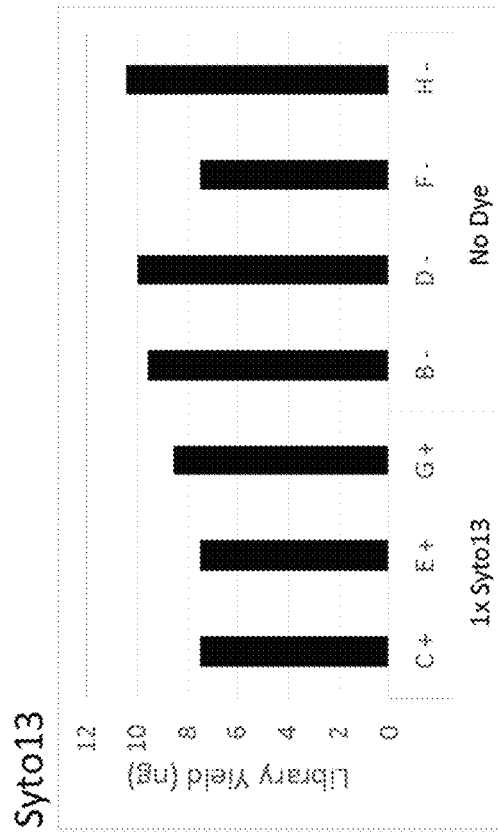

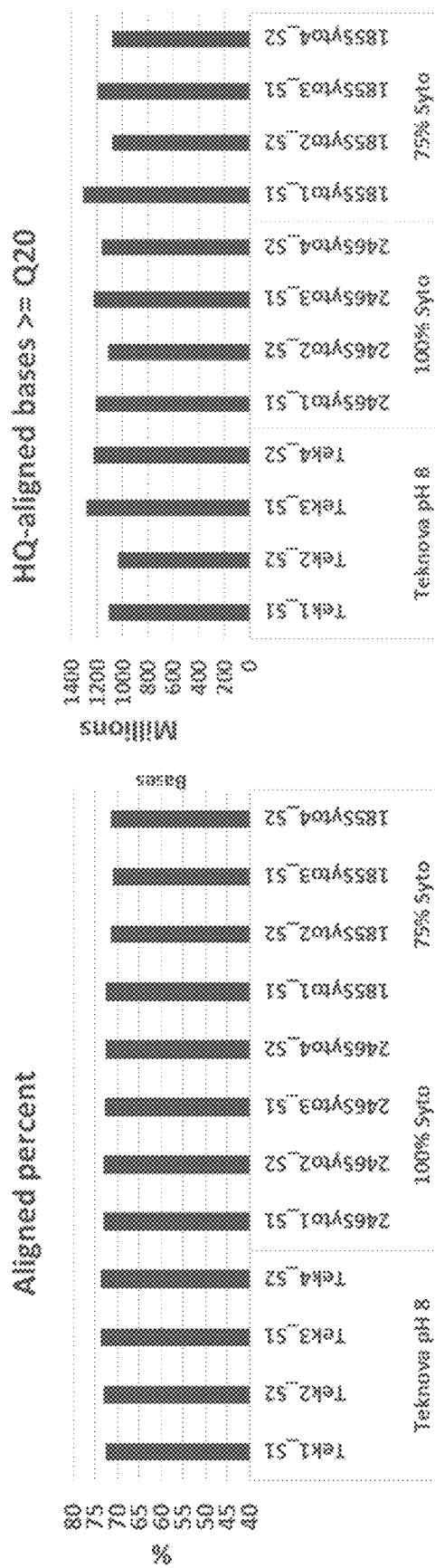
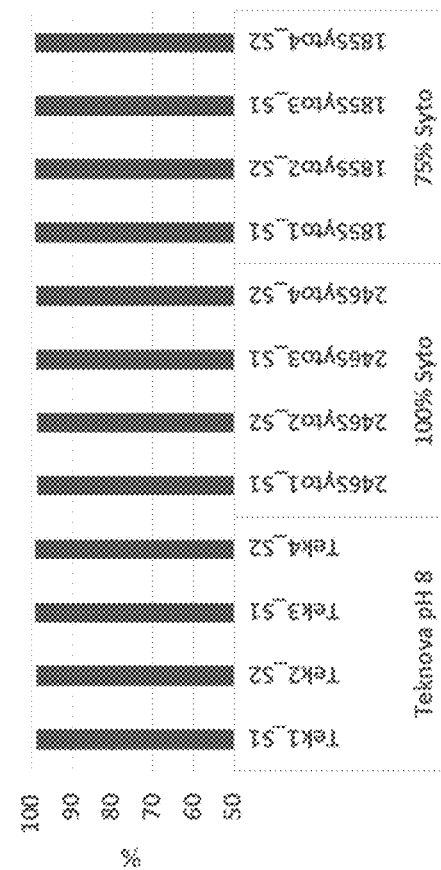
FIG. 80A
FIG. 80B
FIG. 80C

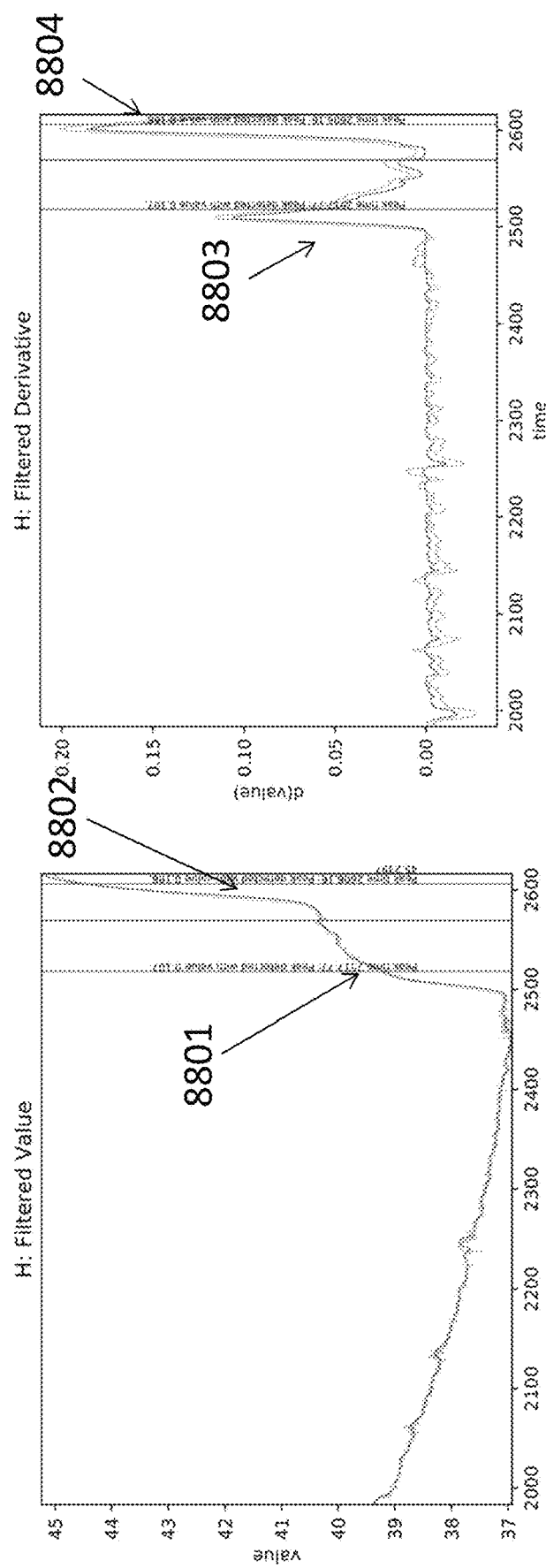

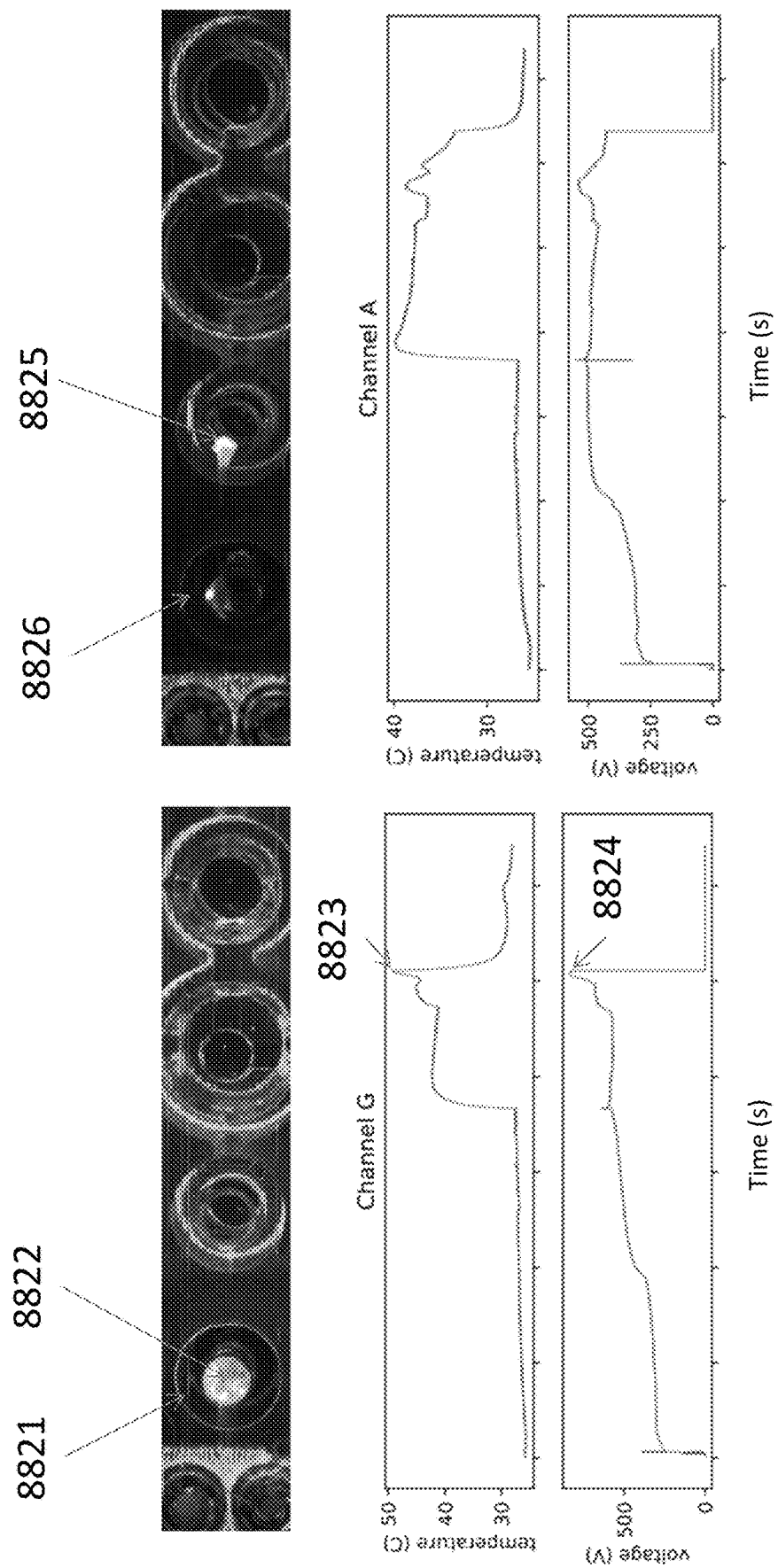

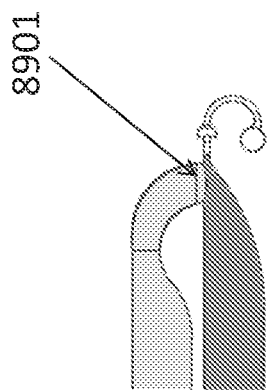
FIG. 89A
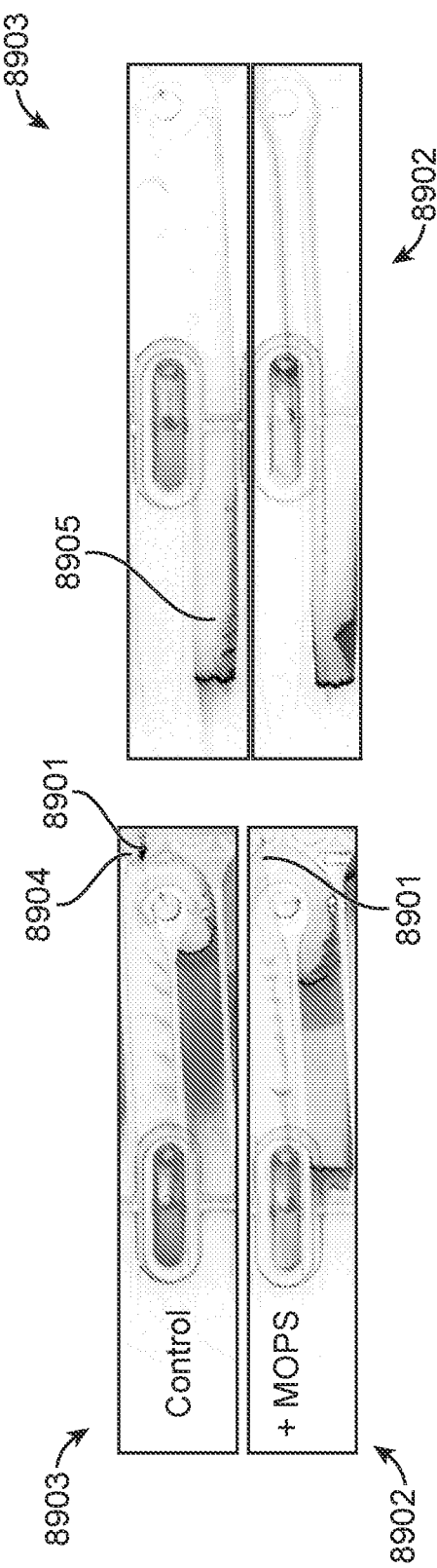
FIG. 89B
FIG. 89C

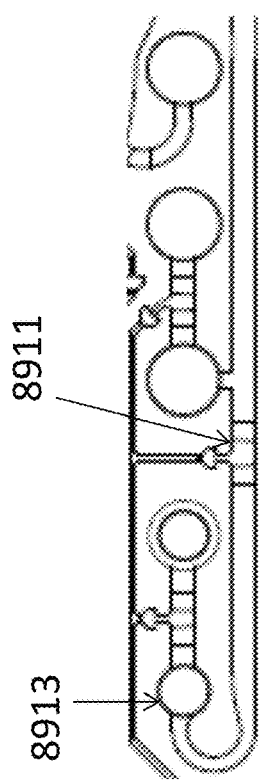
FIG. 89D
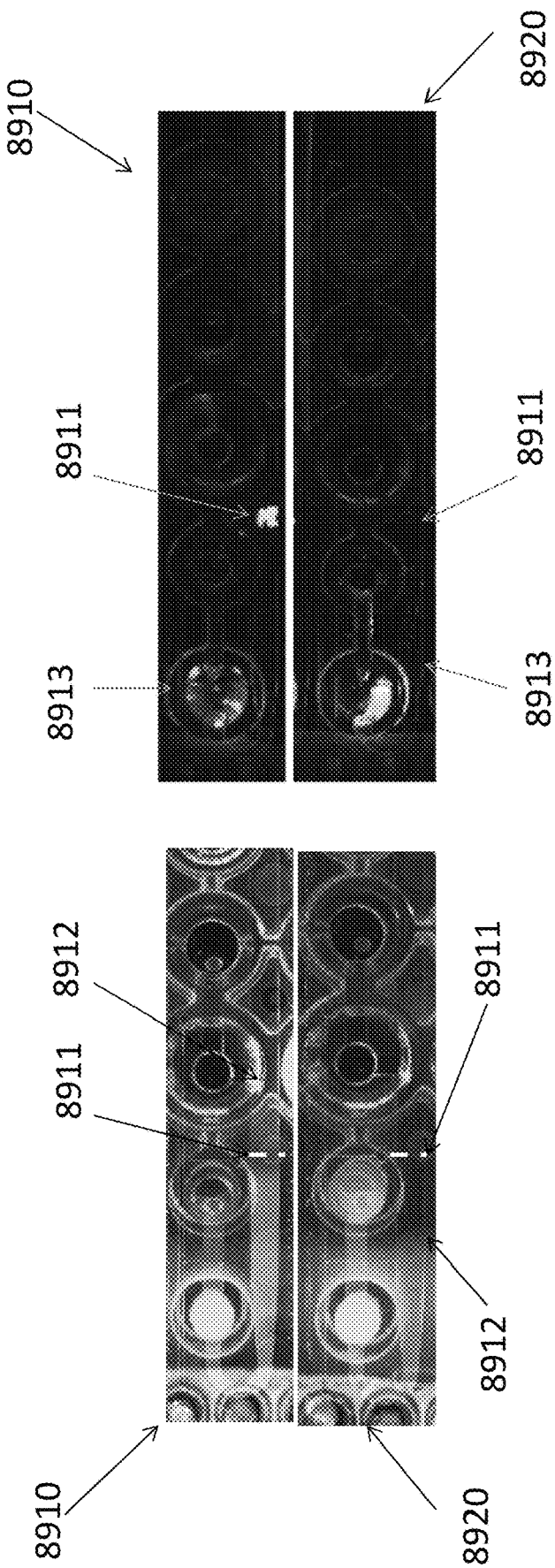
FIG. 89F
FIG. 89E

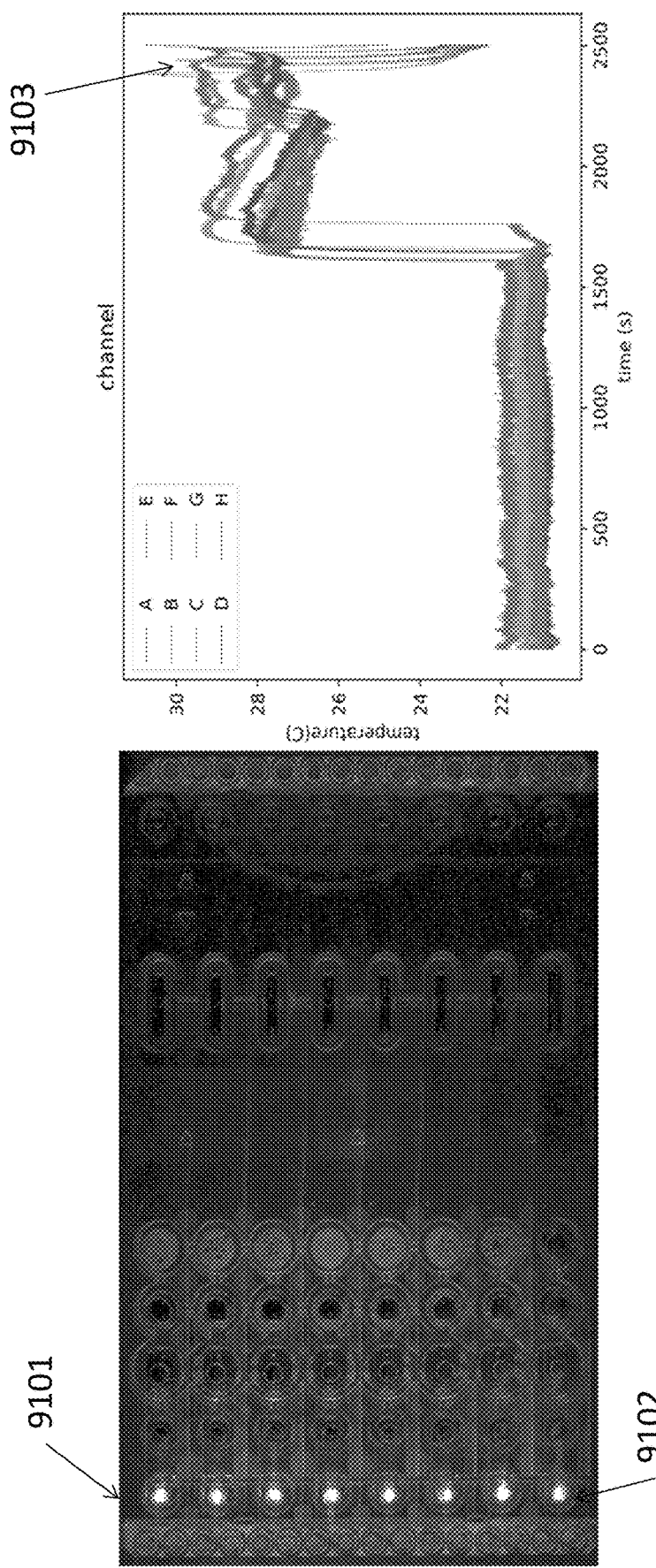

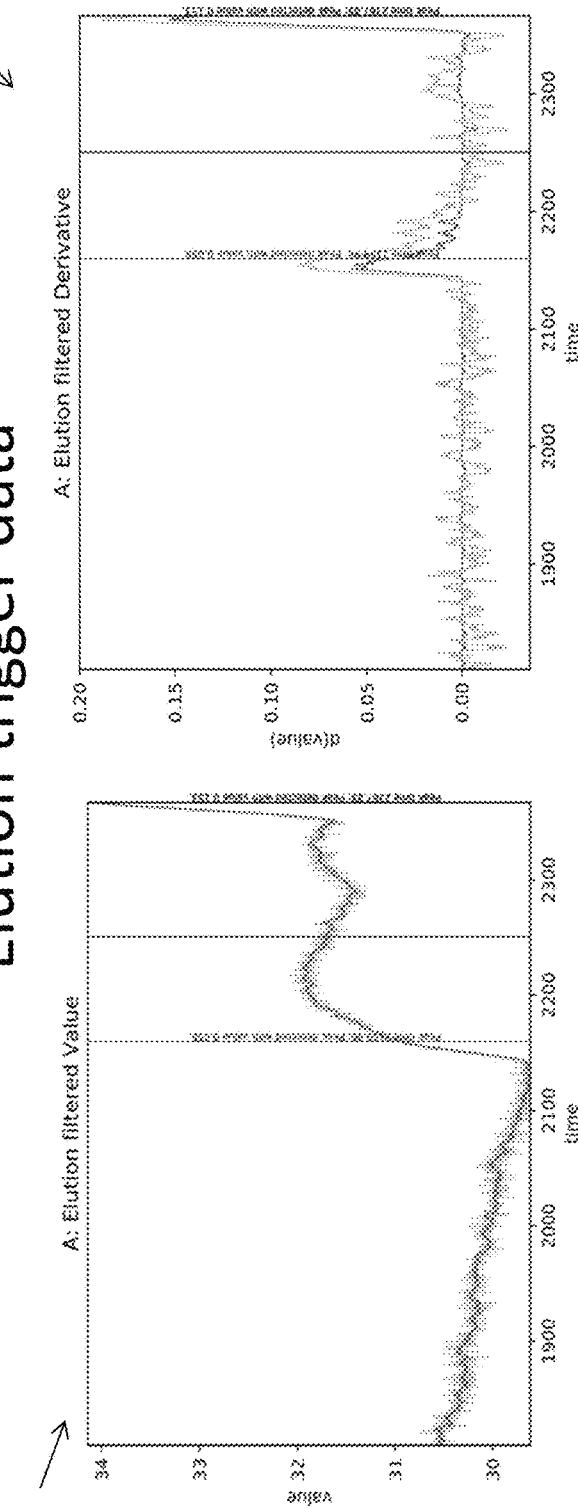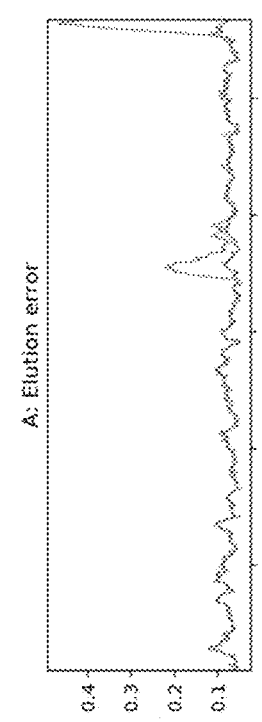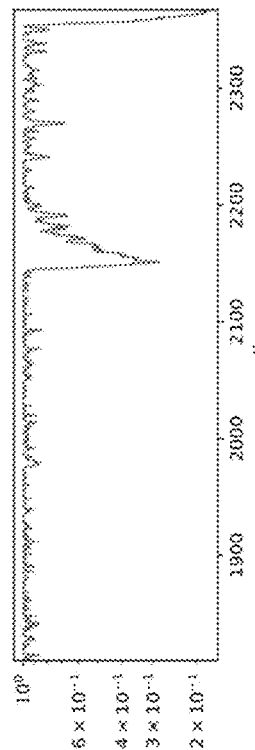
FIG. 92F

SYSTEMS, DEVICES, AND METHODS FOR ISOTACHOPHORESIS

CROSS-REFERENCE

This is a divisional application of U.S. patent application Ser. No. 16/052,565, filed on Aug. 1, 2018, entitled "Systems, Devices, And Methods For Isotachophoresis", which claims the benefit of U.S. Provisional Application No. 62/540,515, filed Aug. 2, 2017, entitled "Isotachophoresis for Purification of Nucleic Acids"; U.S. Provisional Application No. 62/541,086, filed Aug. 3, 2017, entitled "Isotachophoresis Devices for Purification of Nucleic Acids"; and U.S. Provisional Application No. 62/541,089, filed Aug. 3, 2017, entitled "Nucleic Acid Analysis Using Isotachophoresis and Intercalating Dye", the entire contents of which are herein incorporated by reference.

This application is related to co-pending PCT Application No. PCT/US2017/015519, filed Jan. 28, 2017, entitled "Isotachophoresis for Purification of Nucleic Acids", the entire contents of which are herein incorporated by reference.

STATEMENT AS TO FEDERALLY SPONSORED RESEARCH

This invention was made with the support of the United States government under contract number 1R43HG007620-01 awarded by the National Institutes of Health. The government has certain rights in the invention.

BACKGROUND

Formalin-fixed paraffin-embedded (FFPE) samples have been collected, prepared, stored, and archived in large tissue banks for more than a century. As of 2008, there were over 400 million FFPE samples stored in biobanks worldwide, and this number is growing. These samples are often accompanied by clinical information such as primary diagnosis, therapeutic regimen, and follow-up data, making them an important resource for the development of therapeutics and the discovery of genome and transcriptome biomarkers.

Sample preparation methods to extract and purify nucleic acids from FFPE samples remain manually intensive and laborious. Approaches for FFPE extraction and purification vary widely but often include difficult-to-automate and difficult-to-accelerate steps of wax removal, centrifugation, buffer exchanges, temperature control, cross-link reduction and enzyme treatment. FFPE generally refers to cross-linking proteins in a sample using formalin and embedding the sample in paraffin (wax). FFPE treatment of a sample often enables the sample to be preserved over time and can be especially useful for long-term storage. The cross-linked proteins may bind up the DNA and RNA in the sample, thereby generally making it unusable for downstream applications such as amplification, library preparation, or sequencing.

Removal of paraffin and protein crosslinks in FFPE samples may be a challenging process. Deparaffinization is traditionally performed using highly flammable xylenes. Alternately or in series, the sample can be treated with other solvents, mineral oil and alkaline chemistry and/or elevated temperature. After deparaffinization, proteins in the sample can be treated with different agents or subjected to conditions that may require additional time and effort.

At the end of digestion and denaturation, a mix of crosslinked and non-crosslinked nucleic acids may remain. Removal of the non-crosslinked material may be important for high quality results from assays such as amplification or sequencing; in some cases, if the fraction of non-crosslinked material is too low, the downstream assay may fail to perform resulting in a loss of not only the sample itself, but also labor, time and resources.

SUMMARY

Isotachophoresis (ITP) is an electrophoretic technique which can use a discontinuous buffer containing a leading electrolyte (LE) with a higher effective mobility magnitude and a trailing electrolyte (TE) with a lower effective mobility magnitude (e.g., relative to the LE) to focus sample species that have a greater effective mobility magnitude than the trailing electrolyte but a lower effective mobility magnitude than the leading electrolyte. ITP can selectively focus nucleic acids from samples by more than 10,000-fold in less than five minutes. The present disclosure provides methods and devices employing and automating ITP for sample preparation, including extraction, purification, enrichment, and highly sensitive quantitation, and is particularly useful for preparing and purifying nucleic acids from FFPE samples and other biological samples.

Sample preparation is important to genomic analysis, yet it remains a primary source of analysis variability and can require significant manual labor. The present disclosure includes techniques and devices to address this challenge, such as by using on-chip isotachophoresis (ITP) for extraction and purification of nucleic acids. These techniques include methods to enrich (concentrate) non-crosslinked nucleic acids to enable higher yield and higher quality nucleic acid sample preparation and produce more useable samples (e.g., fewer quality-check rejections) from FFPE and other preserved or fresh samples.

The present disclosure includes techniques and devices for automation of nucleic acid sample preparation from samples, including solid tissue, lysed solid tissue, preserved or fixed tissue samples (e.g., FFPE), whole blood, plasma and serum, buccal swabs, dried blood spots and other forensic samples, fresh or fresh frozen (FF) tissues, biopsy tissue, organ tissue, solid organ tissue, samples comprising connections (e.g. gap junctions, tight junctions, adherent junctions) between cells, cultured or harvested cells from blood or tissues, stool, and bodily fluids (e.g., saliva, urine), or any combination thereof. Samples can include cellular and cell-free nucleic acids, for both eukaryotic and prokaryotic organisms, or any combination thereof. The techniques of the present disclosure, compared to existing approaches, can be faster, less manually intensive, more suited for both small and large starting amounts of tissue, and can achieve higher yield from samples and higher quality analyses of samples.

An aspect of the present disclosure provides a fluidic device comprising an isotachophoresis (ITP) circuit comprising: (a) a first channel comprising first and second capillary barriers that are spaced apart; and (b) a first loading reservoir in fluid communication with said first channel via a first aperture in said first channel, wherein said first aperture is positioned between said first and second capillary barriers to permit a liquid entering said first channel via said first aperture to flow in one direction along said first channel and arrest at said first capillary barrier and to flow in another direction along said first channel and arrest at said second capillary barrier.

In some embodiments of aspects provided herein, said liquid entering said first channel via said first aperture flows along a path to said first capillary barrier that is longer than a width of said first channel. In some embodiments of aspects provided herein, said liquid entering said first channel via said first aperture flows along a path to said second capillary barrier that is longer than a width of said first channel. In some embodiments of aspects provided herein, said liquid entering said first channel via said first aperture flows such that a meniscus of said first liquid arrests at said first capillary barrier or at said second capillary barrier. In some embodiments of aspects provided herein, said first capillary barrier is configured and arranged to be breached by a liquid when a first burst pressure is applied to said one or more branched fluidic circuits and said second capillary barrier is configured and arranged to be breached by said liquid when a second burst pressure is applied to said one or more branched fluidic circuits. In some embodiments of aspects provided herein, said first and second burst pressures are about equal. In some embodiments of aspects provided herein, said first burst pressure is higher than said second burst pressure. In some embodiments of aspects provided herein, one or both of said first and second capillary barriers is a cliff capillary barrier. In some embodiments of aspects provided herein, said ITP circuit comprises a second channel in fluid communication with said first channel and said first capillary barrier is configured and arranged to arrest flow of a second liquid as it flows along said second channel such that a liquid-liquid interface is formed between said first and second liquids at said first capillary barrier. In some embodiments of aspects provided herein, one or both of said first and second capillary barriers is a plateau capillary barrier. In some embodiments of aspects provided herein, said plateau capillary barrier is configured and arranged so that an air gap forms between said first liquid after said first liquid arrests at said plateau capillary barrier and a second liquid after said second liquid flows toward said plateau capillary barrier in another direction and arrests at said plateau capillary barrier opposite to said first liquid. In some embodiments of aspects provided herein, one or both of said first and second capillary barriers comprises a plateau. In some embodiments of aspects provided herein, one or both of said first and second capillary barriers comprises a ramp without a plateau. In some embodiments of aspects provided herein, said first capillary barrier is a cliff capillary barrier and said second capillary barrier is a plateau capillary barrier. In some embodiments of aspects provided herein, said at least one ITP branch further comprises a third capillary barrier that is a plateau capillary barrier. In some embodiments of aspects provided herein, said first minimum pressure is at least two times higher than said second minimum pressure. In some embodiments of aspects provided herein, said fluidic device further comprises a substrate having a first face and a second face, wherein said first face comprises a plurality of reservoirs including said first loading reservoir and said second face comprises a plurality of channels including said first channel, wherein said plurality of reservoirs communicate with said plurality of channels via through holes in said substrate. In some embodiments of aspects provided herein, said ITP circuit further comprises a second loading reservoir and a second channel, wherein said second loading reservoir is in fluid communication with said second channel via a second aperture and said second channel comprises a third capillary barrier wherein said third capillary barrier is configured and arranged to use capillary forces to arrest a meniscus of a liquid flowing along said second channel at said third capillary barrier In some embodiments of aspects provided herein, said second channel is adjacent to said second capillary barrier within said first channel, and said second capillary barrier is configured and arranged to use capillary forces to arrest a meniscus of said liquid flowing along said second channel at said second capillary barrier. In some embodiments of aspects provided herein, said ITP circuit further comprises a third loading reservoir fluidly connected to a third channel via a third aperture, wherein said third channel is fluidly connected to said second reservoir, wherein said third channel comprises a fourth capillary barrier positioned between said second aperture and said third aperture. In some embodiments of aspects provided herein, said first channel or first loading reservoir comprises sample buffer. In some embodiments of aspects provided herein, said second channel or second loading reservoir comprises a first leading electrolyte buffer. In some embodiments of aspects provided herein, said third channel or third loading reservoir comprises a second leading electrolyte buffer. In some embodiments of aspects provided herein, the fluidic device further comprises a fourth channel or reservoir in fluidic communication with said first channel and adjacent to said first capillary barrier. In some embodiments of aspects provided herein, said fourth channel or loading reservoir comprises trailing electrolyte buffer. In some embodiments of aspects provided herein, said ITP circuit comprises an elution channel connected to a first elution reservoir at an elution junction. In some embodiments of aspects provided herein, said elution channel, said first elution reservoir, or both, comprise a first elution buffer. In some embodiments of aspects provided herein, said first aperture, said second aperture, said third aperture, said elution junction, or combination thereof, is a through-hole. In some embodiments of aspects provided herein, said ITP circuit comprises a second elution reservoir that is separated from said first elution reservoir by said elution channel and wherein said elution channel comprises a fifth capillary barrier. In some embodiments of aspects provided herein, said third, fourth or fifth capillary barrier, in any combination, is a plateau capillary barrier. In some embodiments of aspects provided herein, said second elution reservoir comprises a second elution buffer with a higher ion concentration than said first elution buffer. In some embodiments of aspects provided herein, said ITP circuit comprises a first leading electrolyte buffer reservoir connected to a second leading electrolyte buffer reservoir by a buffering channel, wherein said buffering channel comprises first and second leading electrolyte buffer that meets at an interface at which a plateau capillary barrier is situated. In some embodiments of aspects provided herein, said first capillary barrier, said second capillary barrier, said third capillary barrier, said fourth capillary barrier or said fifth capillary barrier, in any combination, is adjacent to an air channel comprising a constriction. In some embodiments of aspects provided herein, the fluidic device further comprises at least two additional ITP circuits, each comprising a first loading reservoir and a first channel, wherein said first loading reservoir is in fluid communication with said first channel via a first aperture and said first channel comprises first and second capillary barriers that are spaced apart and positioned at either side of said first aperture to permit a liquid entering said first channel via said first aperture to flow in one direction along said first channel and arrest at said first capillary barrier and to flow in another direction along said first channel and arrest at said second capillary barrier. In some embodiments of aspects provided herein, the fluidic device further comprises at least five additional ITP circuits, each comprising a first loading reservoir and a first channel, wherein said first loading reservoir is in fluid communication with said first channel via a first aperture and said first channel comprises first and second capillary barriers that are spaced apart and positioned at either side of said first aperture to permit a liquid entering said first channel via said first aperture to flow in one direction along said first channel and arrest at said first capillary barrier and to flow in another direction along said first channel and arrest at said second capillary barrier. In some embodiments of aspects provided herein, said sample reservoir is connected to said sample channel through a through hole. In some embodiments of aspects provided herein, said sample reservoir is closed by a removable material. In some embodiments of aspects provided herein, said removable material is a film. In some embodiments of aspects provided herein, said removable material is a heat-seal material or adhesive material. In some embodiments of aspects provided herein, said removable material is a film comprising a plastic or a polymer. In some embodiments of aspects provided herein, the fluidic device further comprises one or more pneumatic channels opening at one or more pneumatic ports and in communication with each of said capillary barriers. In some embodiments of aspects provided herein, the fluidic device further comprises: (a) a substrate having a first face and a second face, wherein said first face comprises a plurality of reservoirs including said first loading reservoir and said second face comprises a plurality of channels including said first channel, wherein said plurality of reservoirs communicate with said plurality of channels via through holes in said substrate; (b) a layer of material covering said second face, thereby forming closed channels; and (c) a cover covering at least part of said first face and comprising through holes that communicate with ports in said first face through gaskets. In some embodiments of aspects provided herein, said first face further comprises said one or more pneumatic ports. In some embodiments of aspects provided herein, said one or more pneumatic ports have a head height that is shorter than said first loading reservoir. In some embodiments of aspects provided herein, said one or more pneumatic ports have a head height that is shorter than at least one reservoir of said plurality of reservoirs. In some embodiments of aspects provided herein, said cover layer is attached to said second face through a solvent heat bond, pressure, adhesive bond, laser weld, or combination thereof. In some embodiments of aspects provided herein, said cover further comprises a porous, air-permeable, hydrophobic material positioned between the through holes in the ports. In some embodiments of aspects provided herein, said first channel is a sample channel with a depth less than 2 mm. In some embodiments of aspects provided herein, said first channel is a sample channel that has a depth greater than about 10 µm. In some embodiments of aspects provided herein, said sample channel has a depth that is between about 400 µm and about 1.2 mm. In some embodiments of aspects provided herein, said second channel is a leading electrolyte buffer channel with a depth of less than about 1 mm. In some embodiments of aspects provided herein, said leading electrolyte buffer channel has a depth that is between about 10 µm and about 600 µm. In some embodiments of aspects provided herein, said elution channel has a depth of less than about 1 mm. In some embodiments of aspects provided herein, said elution channel has a depth that is between about 10 µm and about 600 µm. In some embodiments of aspects provided herein, said first, second, or elution channels, or a combination thereof, has a depth of greater than about 40 µm, or a depth greater than about 10 µm. In some embodiments of aspects provided herein, said sample channel has a volume of about 10 µL to about 1 ml. In some embodiments of aspects provided herein, said sample channel, said leading electrolyte buffer channel, said elution channel, or combination thereof, has a volume of less than about 1 ml. In some embodiments of aspects provided herein, at least one loading reservoir comprises (a) a conical-shaped section in a region of said at least one reservoir bordering said substrate and (b) a cylindrical through-hole or aperture that penetrates through said substrate. In some embodiments of aspects provided herein, said fluidic device comprises at least one loading reservoir comprising (a) an entryway for ambient air at one end and (b) an aperture that penetrates said substrate at another end of said loading reservoir, wherein said at least one loading reservoir has a frustoconical shape with a wider region of said frustoconical shape positioned at said entryway for ambient air and a narrower region positioned at said aperture that penetrates said substrate. In some embodiments of aspects provided herein, said frustoconical shape comprises a guide wall that is positioned at an angle relative to said surface of said substrate within a range of about 60 degrees to about 90 degrees. In some embodiments of aspects provided herein, said substrate comprises pneumatic ports configured to have a height or depth to minimize sample loss. In some embodiments of aspects provided herein, said pneumatic ports have a height relative to a surface of said substrate that is shorter than a height of said sample loading reservoir. In some embodiments of aspects provided herein, said pneumatic ports on said substrate are inset into a surface of said first face of said substrate with a depth of from about 1 µm to about 1 mm or are protruding from a surface of said first face of said substrate at a height of about 0 µm to about 2 mm. In some embodiments of aspects provided herein, said pneumatic ports on said substrate are inset into a surface of said first face of said substrate with a depth of from about 1 µm to about 500 µm or are protruding from a surface of said first face of said substrate at a height of about 0 µm to about 1 mm. In some embodiments of aspects provided herein, said first loading reservoir is a sample loading reservoir, said second loading reservoir is a leading electrolyte buffer reservoir, said third loading reservoir is a second leading electrolyte buffer reservoir, said fourth loading reservoir is a trailing electrolyte buffer reservoir, said fifth loading reservoir is an elution reservoir buffer, and said sixth loading reservoir is a elution buffer high reservoir.

An aspect of the present disclosure provides a method of loading said fluidic device, comprising loading a buffer into said first, second, third, fourth, fifth, or sixth loading reservoirs.

An aspect of the present disclosure provides a method of loading said fluidic device, comprising loading a buffer into said first, second, third, fourth, fifth, or sixth channels.

In some embodiments of aspects provided herein, said fluidic device comprises a first channel comprising a plateau capillary barrier adjacent to a second channel and said loading of said buffer comprises loading a first buffer into said first channel or reservoir and a second buffer into said second channel or reservoir. In some embodiments of aspects provided herein, said method further comprises applying a first positive or negative pneumatic pressure to said fluidic device such that a first and second buffer arrest at a base of a ramp within said plateau capillary barrier. In some embodiments of aspects provided herein, said applying of said first positive or negative pneumatic pressure comprises increasing or decreasing said first positive or negative pressure at fixed increments. In some embodiments of aspects provided herein, said method further comprises applying a second positive or negative pneumatic pressure to said fluidic device such that said first and second buffers flow long a ramp at either side of said plateau capillary barrier. In some embodiments of aspects provided herein, said applying of second positive or negative pneumatic pressure comprises increasing or decreasing said second positive or negative pressure at fixed increments. In some embodiments of aspects provided herein, said first and second buffers arrest at a plateau of said plateau capillary barrier with an air gap between them, said air gap situated above or below said plateau of said plateau capillary barrier. In some embodiments of aspects provided herein, said method further comprises applying a third positive or negative pneumatic pressure to said fluidic device such that said first and second liquid enter said air gap such that a liquid-liquid interface forms between said first and second buffer above or below said plateau of said plateau capillary barrier.

An aspect of the present disclosure provides a fluidic device comprising a fluidic channel and disposed in said fluidic channel a capillary barrier that restricts flow of a liquid in said fluidic channel, wherein said capillary barrier comprises: (a) a ramp protruding from a surface of said fluidic channel at a first angle; (b) a plateau area, and (c) a cliff area extending from said plateau area to said surface of said fluidic channel and wherein said cliff area intersects with said surface at a second angle that is substantially steeper than said first angle.

In some embodiments of aspects provided herein, said second angle is at least about 10 degrees, at least about 15 degrees, or at least about 20 degrees steeper than said first angle. In some embodiments of aspects provided herein, said ramp declines or inclines along a length of said fluidic channel. In some embodiments of aspects provided herein, said first angle is less than 60 degrees. In some embodiments of aspects provided herein, said second angle is greater than 60 degrees. In some embodiments of aspects provided herein, said plateau area is substantially parallel to said surface of said fluidic channel. In some embodiments of aspects provided herein, said plateau area is slanted no more than about 10 degrees relative to said surface of said fluidic channel. In some embodiments of aspects provided herein, said ramp, plateau area or cliff area, in any combination, has a substantially flat surface. In some embodiments of aspects provided herein, said ramp, plateau area or cliff area, in any combination, has a curved surface. In some embodiments of aspects provided herein, said ramp, plateau area or cliff area, in any combination, has a surface that comprises one or more grooves, ridges, indentations, steps, etchings, or protrusions. In some embodiments of aspects provided herein, said ramp, plateau area or cliff area, in any combination, has a surface that comprises regions with faces at different angles. In some embodiments of aspects provided herein, a width of said ramp, plateau area, or cliff area, substantially occupies a width of said fluidic channel.

An aspect of the present disclosure provides a fluidic device comprising a fluidic channel and disposed in said fluidic channel a capillary barrier that restricts flow of a liquid in said fluidic channel, wherein said capillary barrier comprises: (a) a first ramp protruding from a surface of said fluidic channel at a first angle that is less than 80 degrees; (b) a plateau area; and (c) a second ramp extending from said plateau area to said surface of said fluidic channel and wherein said second ramp intersects with said surface at a second angle that is less than 80 degrees.

In some embodiments of aspects provided herein, said first and second angles are identical or substantially identical. In some embodiments of aspects provided herein, said first and second angles are different. In some embodiments of aspects provided herein, said first ramp, said second ramp, or said plateau area, in any combination, has a surface that comprises one or more grooves, ridges, indentations, steps, etchings, or protrusions.

An aspect of the present disclosure provides a fluidic device, comprising a capillary barrier that (a) comprises a cross-sectional area with a trapezoidal shape; (b) protrudes from an interior surface of said fluidic channel; (c) has a plateau surface that is substantially parallel to said interior surface of said fluidic channel; (d) has a ramp surface connecting said plateau surface to said interior surface of said fluidic channel, wherein said ramp surface inclines or declines along a length of said fluidic channel; and (e) is configured and arranged to arrest and position a meniscus of a liquid flowing along a length of said fluidic channel.

In some embodiments of aspects provided herein, said capillary barrier extends substantially across a width of said fluidic channel. In some embodiments of aspects provided herein, said capillary barrier is further configured and arranged to create a liquid-liquid interface. In some embodiments of aspects provided herein, said trapezoidal shape is an isosceles trapezoid. In some embodiments of aspects provided herein, said trapezoidal shape is a right trapezoid comprising two angles that are substantially right angles. In some embodiments of aspects provided herein, said trapezoidal shape is a scalene trapezoid.

In some embodiments of aspects provided herein, said capillary barrier is a "plateau capillary barrier." In some embodiments of aspects provided herein, said capillary barrier is a "cliff capillary barrier." In some embodiments of aspects provided herein, said fluidic device comprises both a cliff capillary barrier and a plateau capillary barrier in the same fluidic circuit. In some embodiments of aspects provided herein, the fluidic device further comprises a sample channel comprising a cliff capillary barrier. In some embodiments of aspects provided herein, the fluidic device further comprises a plateau capillary barrier situated between buffer channels.

An aspect of the present disclosure provides an isotachophoresis (ITP) system comprising: (a) an interface configured to engage a fluidic device, wherein said fluidic device comprises one or more branched fluidic circuits, each of said branched fluidic circuits comprising a plurality of loading reservoirs including a trailing electrolyte reservoir, a first leading electrolyte reservoir and a first elution buffer reservoir and wherein said interface comprises: (i) a pneumatic manifold comprising a plurality of manifold pneumatic channels opening onto one or more manifold ports and communicating with a source of positive or negative pneumatic pressure, each manifold port configured to engage one or more pneumatic ports of said fluidic device when said fluidic device is engaged with said interface; and (ii) a plurality of electrodes, each communicating with a voltage or current source, including a first, second and third electrode, wherein said plurality of electrodes are configured to be positioned in said trailing electrolyte reservoir, said first leading electrolyte reservoir and said first elution buffer reservoir, respectively, when said fluidic device is engaged with said interface; (b) a source of positive or negative pneumatic pressure communicating with said pneumatic manifold; and (c) a voltage or current source communicating with said electrodes.

In some embodiments of aspects provided herein, the isotachophoresis system comprises a motor to engage the interface with an engaged fluidic device. In some embodiments of aspects provided herein, said fluidic device is engaged with said interface. In some embodiments of aspects provided herein, said pneumatic manifold further comprises valves for controlling pneumatic pressure to pneumatic channels in at least one of said branched fluidic circuits. In some embodiments of aspects provided herein, the isotachophoresis system further comprises: (d) a ridge having a long, narrow tip, a heating element configured to heat said tip, and an actuator configured to press said ridge tip against a fluidic device engaged with said interface to close a plurality of fluidic channels in said microfluidic device. In some embodiments of aspects provided herein, system is configured such that a plurality of fluidic channels may be closed with a heat-sealable material, PCR film, parafilm, plastic wrap, adhesive layer, or a material that is not secured by a seal.

In some embodiments of aspects provided herein, said system is configured such that a plurality of fluidic channels within said fluidic device may be closed by a load bearing block. In some embodiments of aspects provided herein, said system is configured such that a plurality of fluidic channels within said fluidic device may be closed by a mechanical actuator block with rubber sealing member.

In some embodiments of aspects provided herein, the system further comprises a temperature measuring device. In some embodiments of aspects provided herein, the system further comprises a display to display operating parameters of the system. In some embodiments of aspects provided herein, said display displays temperature.

In some embodiments of aspects provided herein, said display displays a measure of light detected by a light sensor. In some embodiments of aspects provided herein, said display displays voltage or current across fluidic circuits. In some embodiments of aspects provided herein, said system further comprises a voltage or current measuring device. In some embodiments of aspects provided herein, the system further comprises an optical assembly comprising one or more light sources configured to direct light to a fluidic channel of said fluidic circuit and one or more light sensors to detect light emitted from a fluidic channel of said fluidic circuit. In some embodiments of aspects provided herein, said interface further comprises one or more alignment marks for aligning said fluidic device in a particular orientation. In some embodiments of aspects provided herein, the system further comprises software which regulates the electrodes in response to temperature, current or voltage. In some embodiments of aspects provided herein, said fluidic device further comprises a plurality of branched fluidic circuits, each of which comprises independent electrical circuitry. In some embodiments of aspects provided herein, each of said branched fluidic circuits is coupled to a same voltage or current source or to different voltage or current sources.

An aspect of the present disclosure provides a method of creating a fluidic circuit comprising: (a) providing a fluidic device, wherein said fluidic device comprises at least one branched fluidic circuit that comprises a trailing electrolyte buffer reservoir, a first channel, a first leading electrolyte buffer reservoir, a sample loading reservoir, a second leading electrolyte buffer reservoir, and a first elution buffer reservoir, all in fluidic communication with another, wherein: (i) said trailing electrolyte buffer reservoir comprises a trailing electrolyte buffer; (ii) said first leading electrolyte buffer reservoir comprises a first leading electrolyte buffer; (iii) said second leading electrolyte buffer reservoir comprises a second electrolyte buffer different from said first electrolyte buffer; and (iv) said first elution buffer reservoir comprises a first elution buffer; (b) applying pneumatic pressure to said trailing electrolyte buffer reservoir and said leading electrolyte buffer reservoir such that said trailing electrolyte buffer and said leading electrolyte buffer each enter said first channel and arrest within said first channel with an air gap between said trailing electrolyte buffer and said leading electrolyte buffer; (c) loading a sample into said air gap between said trailing electrolyte buffer and said leading electrolyte buffer within said first channel; and (d) applying pneumatic pressure to said second leading electrolyte buffer reservoir and said first elution buffer reservoir such that said second leading electrolyte buffer and said first elution buffer each enter said fluidic circuit virtually simultaneously.

In some embodiments of aspects provided herein, said pneumatic pressure is positive or negative pneumatic pressure. In some embodiments of aspects provided herein, said applying pneumatic pressure in operation (b) results in said trailing electrolyte buffer being arrested at a first capillary barrier within said first channel and said leading electrolyte buffer being arrested at a second capillary barrier within said first channel. In some embodiments of aspects provided herein, said applying pneumatic pressure in operation (d) results in said second leading electrolyte buffer being arrested at a third capillary barrier within said fluidic circuit and said first elution buffer being arrested at a fourth capillary barrier within said fluidic channel.

In some embodiments of aspects provided herein, said first and second capillary barriers are cliff capillary barriers or ramp capillary barriers. In some embodiments of aspects provided herein, said third and fourth capillary barriers are plateau capillary barriers. In some embodiments of aspects provided herein, said third and fourth capillary barriers each have a burst pressure that is lower than a burst pressure of said first capillary barrier or of said second capillary barrier. In some embodiments of aspects provided herein, said sample comprises a wetting agent.

An aspect of the present disclosure provides a fluidic device comprising one or more branched fluidic circuits, wherein each of said branched fluidic circuits comprises an isotachophoresis ("ITP") branch and an elution branch in communication with said ITP branch, wherein: (a) said ITP branch comprises a trailing electrolyte buffer reservoir, a sample channel, a leading electrolyte buffer channel, a first leading buffer electrolyte reservoir and a second leading electrolyte buffer reservoir, all in communication with each other, wherein: (i) said sample channel is separated from said trailing electrolyte reservoir by a first cliff capillary barrier and from said leading electrolyte buffer channel by a second cliff capillary barrier, (ii) said leading electrolyte reservoir is separated from said second leading electrolyte reservoir by a first plateau capillary barrier; and (b) said elution branch comprises an elution channel, a first elution buffer reservoir and a second elution buffer reservoir, all in communication with each other, wherein: (i) said first elution buffer reservoir is separated from said second elution buffer reservoir a second plateau capillary barrier, and (ii) said leading electrolyte buffer channel is separated from at least part of said elution channel by a third plateau capillary barrier.

An aspect of the present disclosure provides a method of creating a fluidic circuit comprising: (a) providing a fluidic device of the an aspect provided herein wherein: (i) said trailing electrolyte buffer reservoir comprises trailing electrolyte buffer; (ii) said first leading electrolyte buffer reservoir comprises first leading electrolyte buffer; (iii) said second leading electrolyte buffer reservoir comprises second leading electrolyte buffer; (iv) said first elution buffer reservoir comprises first elution buffer; and (v) said second elution buffer reservoir comprises second elution buffer; (b) applying negative pneumatic pressure to said first and second cliff capillary barriers to prime trailing electrolyte buffer and first leading electrolyte buffer at said cliff capillary barriers; (c) loading sample into said sample channel, wherein said sample comprises a wetting agent sufficient to create fluidic connections across said first and second cliff capillary barriers; and (d) applying negative pneumatic pressure to said first, second, and third plateau capillary barriers to create fluidic connections across said first, second, and third plateau capillary barriers.

In some embodiments of aspects provided herein, the method further comprises: (e) inserting a first electrode into trailing electrolyte buffer in said trailing electrolyte buffer reservoir; (f) inserting a second electrode into second leading electrolyte buffer in said second leading electrolyte buffer reservoir; and (g) applying a voltage or current across said first electrode and second electrode.

In some embodiments of aspects provided herein, the method further comprises: (h) inserting a third electrode into second elution buffer in said second elution buffer reservoir; and (i) after operation (g), applying a voltage or current across said first and third electrode, and, optionally, reducing current of said second electrode.

In some embodiments of aspects provided herein, the method further comprises adding a topper liquid to said sample reservoir. In some embodiments of aspects provided herein, the method further comprises spiking said sample with trailing electrolyte buffer. In some embodiments of aspects provided herein, the method further comprises applying a voltage or current in response to a triggering event. In some embodiments of aspects provided herein, said voltage is within a range of about 0 V to about 1500 V. In some embodiments of aspects provided herein, the method further comprises applying negative pneumatic pressure of between about 0 mpsi and about 200 mpsi. In some embodiments of aspects provided herein, aid applied negative pneumatic pressure is between about 10 mpsi and about 80 mpsi.

An aspect of the present disclosure provides a fluidic device comprising a fluidic channel, said fluidic channel comprising: (a) a first wall substantially parallel to a third wall and a second wall substantially parallel to a fourth wall; and (b) a capillary barrier, wherein said capillary barrier comprises: (i) a side that is disposed on or integrated into an interior surface of said second wall and that extends substantially between said first wall and said third wall; (ii) first and second lateral side walls that are connected to, integrated into, or adjacent to said first and third walls respectively, wherein said first and second lateral side walls each comprise a cross-sectional area with a trapezoidal shape; (iii) a plateau surface that is substantially parallel to said second wall and situated between said second and fourth walls; and (iv) a ramp connecting said second wall to said plateau surface, wherein said ramp inclines or declines along a length of said fluidic channel.

In some embodiments of aspects provided herein, said trapezoidal shape is an isosceles trapezoid. In some embodiments of aspects provided herein, said trapezoidal shape is a right trapezoid comprising two angles that are substantially right angles. In some embodiments of aspects provided herein, said trapezoidal shape is a scalene trapezoid. In some embodiments of aspects provided herein, said capillary barrier is a "plateau capillary barrier." In some embodiments of aspects provided herein, said capillary barrier is a "cliff capillary barrier." In some embodiments of aspects provided herein, said fluidic device comprises both a cliff capillary barrier and a plateau capillary barrier in the same fluidic circuit. In some embodiments of aspects provided herein, the device further comprises a sample channel comprising a cliff capillary barrier. In some embodiments of aspects provided herein, the device further comprises a plateau capillary barrier situated between buffer channels.

An aspect of the present disclosure provides a fluidic device comprising a fluidic channel, said fluidic channel comprising a capillary barrier protruding from a first wall of said fluidic channel into said fluidic channel, wherein said capillary barrier comprises (i) two lateral sides, each having a cross-sectional area with a trapezoidal shape; (ii) a plateau side substantially parallel to said first wall of said channel; and (iii) a ramp with one edge intersecting said plateau side to form an interior obtuse angle of said capillary barrier and with an opposing edge intersecting said first wall of said channel to form an interior acute angle of said capillary barrier.

In some embodiments of aspects provided herein, said capillary barrier further comprises a side connecting said plateau side to said first wall. In some embodiments of aspects provided herein, said side connecting said plateau side to said first wall is about perpendicular to said first wall. In some embodiments of aspects provided herein, said side connecting said plateau side to said first wall intersects said first wall at an acute angle. In some embodiments of aspects provided herein, at least one of said lateral sides is substantially parallel to, or integrated into, a second wall of said fluidic channel.

An aspect of the present disclosure provides a fluidic system comprising: (a) a first isotachophoresis circuit in a microfluidic chip comprising: (i) a first sample reservoir; (ii) a trailing electrolyte buffer reservoir comprising trailing electrolyte buffer in fluid communication with said sample reservoir; and (iii) a leading electrolyte buffer channel comprising leading electrolyte buffer in fluid communication with said sample reservoir; (b) a sensor configured to detect a temperature change in said leading electrolyte buffer channel; and (c) an apparatus configured to monitor voltage or current in said first isotachophoresis circuit and supply a constant electrical current within said first isotachophoresis circuit.

In some embodiments of aspects provided herein, said leading electrolyte channel comprises an elution channel. In some embodiments of aspects provided herein, said sensor is configured and arranged to detect a temperature change in said elution channel. In some embodiments of aspects provided herein, said fluidic system further comprises an elution well. In some embodiments of aspects provided herein, said first isotachophoresis circuit further comprises an elution channel comprising elution buffer.

An aspect of the present disclosure provides a fluidic system comprising: (a) a first isotachophoresis circuit in a microfluidic chip comprising: (i) a first sample reservoir in fluid communication with a first fluidic channel; (ii) a first, a second, and a third buffer reservoir in fluid communication with said first fluidic channel, wherein said first and second buffer reservoirs are separated by a first capillary barrier; and (iii) an elution reservoir in fluid communication with said first fluidic channel; (b) a sensor configured to detect a temperature change in said first fluidic channel within said first isotachophoresis region; and (c) an apparatus configured to monitor voltage or current and supply a constant electrical current within said first isotachophoresis circuit.

In some embodiments of aspects provided herein, said first fluidic channel comprising a second capillary barrier adjacent to said first sample reservoir. In some embodiments of aspects provided herein, said first capillary barrier is a plateau capillary barrier and said second capillary barrier is a cliff capillary barrier. In some embodiments of aspects provided herein, said first capillary barrier is a cliff capillary barrier, a plateau capillary barrier, or a ramp capillary barrier. In some embodiments of aspects provided herein, said first fluidic channel comprises a cliff capillary barrier and a constriction downstream of said cliff barrier. In some embodiments of aspects provided herein, the system further comprises a temperature sensor configured downstream of said constriction.

An aspect of the present disclosure provides a fluidic system, said fluidic system comprising: a fluidic chip comprising a plurality of circuits, wherein each of said circuits comprises an elution channel in fluid communication with an elution reservoir; and a mechanical member comprising a ridge, wherein said mechanical member is configured to simultaneously apply mechanical pressure to a plurality of said elution channels via said ridge in order to at least partially close said elution channels by plastic deformation of at least one wall of said elution channels.

In some embodiments of aspects provided herein, the system further comprises a bottom film bonded to a substrate layer, said bottom layer forming a wall of each of said elution channels, wherein the bottom film and the substrate layer each comprise materials with the same melting point. In some embodiments of aspects provided herein, each elution channel comprises a bend and wherein the ridge at least partially closes each elution channel in two places across the bend. In some embodiments of aspects provided herein, said ridge completely closes said channels.

An aspect of the present disclosure provides a method of retrieving analyte from an assay comprising: introducing said analyte into one of said circuits in said fluidic system of an aspect provided herein; allowing said analyte to migrate to said elution channel in said one of said circuits; and engaging said mechanical member in order to apply mechanical pressure to said plurality of elution channels via said ridge in order to at least partially close said elution channels by plastic deformation of at least one wall of said elution channels.

An aspect of the present disclosure provides a fluidic device comprising: a first liquid channel; a gas channel in fluid communication with said first liquid channel; a pneumatic port in fluid communication with said gas channel; and an air-permeable hydrophobic membrane disposed across said pneumatic port, wherein said hydrophobic membrane is not liquid permeable and is configured to inhibit liquid from exiting said pneumatic port when a negative pressure is applied to said gas channel via said pneumatic port.

In some embodiments of aspects provided herein, the device further comprises a gasket disposed over said pneumatic port. In some embodiments of aspects provided herein, the device further comprises a constriction between liquid and gas channel to inhibit liquid from exiting said gas channel. In some embodiments of aspects provided herein, said gasket is secured in place by a cover layer comprising a channel communicating with said gas channel through said port. In some embodiments of aspects provided herein, said cover layer comprises an interference fit configured to maintain a compressive force on said gasket.

An aspect of the present disclosure provides a method comprising: (a) providing a fluidic circuit comprising: (i) an elution well adjacent to an elution channel that contains elution buffer wherein said elution channel is connected to a leading electrolyte channel that contains leading electrolyte buffer, and (ii) a capillary barrier situated at an interface between said elution buffer and said leading electrolyte buffer; (b) flowing said interface between said leading electrolyte buffer and said elution buffer towards said elution well; and (c) arresting flow of said interface between said leading electrolyte buffer and said elution buffer such that said capillary barrier is fully engulfed by said leading electrolyte buffer.

In some embodiments of aspects provided herein, the fluidic circuit further comprises a sample well in fluidic communication with said elution well. In some embodiments of aspects provided herein, the method further comprises introducing a nucleic acid sample into said sample well and applying an electrical current to said fluidic circuit in order to move said nucleic acid sample over said capillary barrier.

An aspect of the present disclosure provides a method comprising: (a) providing a fluidic device comprising a fluidic circuit having a trailing electrolyte buffer reservoir, a sample channel, a leading electrolyte buffer channel and an elution reservoir, all in communication with each other, wherein: (i) said leading electrolyte buffer channel is fluidly connected to said elution reservoir via an aperture in said leading electrolyte buffer channel situated below said elution reservoir; (ii) said trailing electrolyte buffer reservoir comprises trailing electrolyte buffer, (ii) said sample channel comprises an analyte, (iii) said leading electrolyte buffer channel comprises leading electrolyte buffer, (iv) said elution reservoir comprises elution buffer; and (b) applying a current across said fluidic circuit to move said analyte to said elution reservoir, wherein said current is configured and arranged to generate a first temperature at an interface between said analyte and said trailing electrolyte buffer and a second temperature at an interface between said sample and said leading electrolyte buffer, wherein a temperature difference exists between said first temperature and said second temperature; and wherein, when said analyte reaches said aperture in said leading electrolyte buffer channel situated below said elution reservoir, said analyte enters into said elution reservoir facilitated by said temperature difference.

In some embodiments of aspects provided herein, the method further comprises pipetting said analyte from said elution reservoir.

An aspect of the present disclosure provides a method of quantifying a nucleic acid sample, the method comprising: providing a fluidic device comprising an isotachophoresis (ITP) channel comprising a nucleic acid sample, wherein said nucleic acid sample comprises nucleic acids complexed with an intercalating dye; performing ITP in said fluidic channel in order to focus said nucleic acids complexed with said intercalating dye; and quantifying said nucleic acids complexed with said intercalating dye within said channel by measuring intensity of said intercalating dye after ITP has been performed, wherein said intercalating dye comprises one or more of SYTO™ 13, PicoGreen®, EvaGreen®, or Quantifluor®.

In some embodiments of aspects provided herein, said dye comprises SYTO™ 13. In some embodiments of aspects provided herein, said dye comprises PicoGreen®. In some embodiments of aspects provided herein, said dye comprises EvaGreen®. In some embodiments of aspects provided herein, said dye comprises Quantifluor®. In some embodiments of aspects provided herein, said nucleic acids complexed with said intercalating dye are situated in a region of said ITP channel that comprise leading electrolyte buffer or elution buffer. In some embodiments of aspects provided herein, said nucleic acids complexed with said intercalating dye comprise RNA or DNA, or combination thereof. In some embodiments of aspects provided herein, said nucleic acid sample further comprises a contaminant. In some embodiments of aspects provided herein, said contaminant comprises protein, cellular debris, lipids, plasma membranes, small molecules, or combination thereof. In some embodiments of aspects provided herein, said performing ITP in said fluidic channel cause said nucleic acids complexed with said intercalating dye to separate from said contaminant.

An aspect of the present disclosure provides a fluidic device comprising one or more branched fluidic circuits, wherein each of said branched fluidic circuits comprises an isotachophoresis ("ITP") branch and an elution branch in communication with said ITP branch, wherein: said ITP branch comprises a trailing electrolyte buffer reservoir, a sample channel, a leading electrolyte buffer channel, a first leading buffer electrolyte reservoir and a second leading electrolyte buffer reservoir, all in communication with each other; and said elution branch comprises an elution channel and an elution well, said elution well comprising a first and second through-hole in communication with said elution channel.

In some embodiments of aspects provided herein, said first and second through-holes are circular. In some embodiments of aspects provided herein, said first through-hole has an elliptical shape. In some embodiments of aspects provided herein, said first through-hole has a maximum dimension across of less than 1.5 mm, or a maximum dimension across of less than 1 mm. In some embodiments of aspects provided herein, said second through-hole has a maximum dimension across of less than 1.5 mm. In some embodiments of aspects provided herein, said second through-hole has a maximum dimension across of less than 1 mm. In some embodiments of aspects provided herein, said first through-hole and said second through-hole are on a same vertical plane within the elution well. In some embodiments of aspects provided herein, said first through-hole and said second through-hole are on a different vertical plane within the elution well. In some embodiments of aspects provided herein, said first through-hole and said second through-hole are aligned with a longitudinal axis of the elution channel. In some embodiments of aspects provided herein, said first through-hole is configured to constrain a pipette tip at a predetermined coupling position. In some embodiments of aspects provided herein, said first through-hole comprises a circular cross-section. In some embodiments of aspects provided herein, said first through-hole comprises an elliptical cross-section. In some embodiments of aspects provided herein, said first through-hole comprises a D-shaped cross-section. In some embodiments of aspects provided herein, said first through-hole comprises a guide wall disposed at an angle within a range of about 60 degrees to about 90 degrees relative to the channel. In some embodiments of aspects provided herein, said elution well comprises a one or more vertical gates separating the first through-hole and the second through-hole. In some embodiments of aspects provided herein, said elution well comprises a circular cross-section. In some embodiments of aspects provided herein, said elution well comprises an elongate cross-section.

An aspect of the present disclosure provides a fluidic device comprising: a first channel terminating at an end in a first through hole; a second channel terminating at an end in a second through hole; and a fluid reservoir defined by a wall having a height of no more than 25 mm, no more than 15 mm, no more than 10 mm, or greater than 10 mm; wherein the reservoir is in fluidic communication with each of two fluidic channels through the first and second through holes, and wherein the first through hole enters the reservoir at a position lower in the reservoir than the second through hole.

In some embodiments of aspects provided herein, the first channel communicates with a first electrode; and the second channel communicates with a second electrode; wherein the channels and reservoir comprise an electrically conductive fluid and wherein application of a voltage across the first and second electrodes produces a current that travels through the reservoir. In some embodiments of aspects provided herein, said wall has a height within a range of about 8 mm to about 10 mm. In some embodiments of aspects provided herein, said first and second through holes have areas of about 0.2 mm2 to 7 mm2 and about 0.2 mm2 and 7 mm2, respectively. In some embodiments of aspects provided herein, said first and second through holes have areas of about 0.8 mm2 to 1.5 mm2 and about 1 mm2 and 2.75 mm2, respectively. In some embodiments of aspects provided herein, said second through hole enters the reservoir though a platform in the reservoir positioned about 1 mm to about 6 mm above a point of entry into said reservoir of said first through hole. In some embodiments of aspects provided herein, said volume of said reservoir between said first and second through holes is no more than about 2.5 ml, 1 ml, or 0.5 ml. In some embodiments of aspects provided herein, said volume of the reservoir between the first and second through holes is 0.1 mL.

An aspect of the present disclosure provides a method comprising: providing any of the fluidic devices described herein, wherein the channels and reservoir comprise an electrically conductive fluid and the first channel further comprises an ionic analyte; applying a voltage across the first and second electrodes to produce a current that travels through the reservoir; and moving the analyte through the first through hole into the reservoir.

In some embodiments of aspects provided herein, said analyte comprises nucleic acid, e.g., RNA or DNA. In some embodiments of aspects provided herein, the method further comprises performing isotachoelectrophoresis in the first channel, whereby the analyte moves into the reservoir.

An aspect of the present disclosure provides a fluidic device comprising: a fluidic channel having length and width; a reservoir positioned above said fluidic channel and fluidically connected to said fluidic channel through one or a plurality of through holes; wherein at least part of each through hole is substantially co-extensive with said fluidic channel across said width of said fluidic channel and has a shape wherein, when said fluidic channel and said reservoir comprise an electrically conductive fluid and an electric current is passed through said fluidic channel, at least 5%, at least 6%, at least 7%, at least 10%, or at least 20% of said electric current passes through said reservoir.

In some embodiments of aspects provided herein, said reservoir comprises one through hole. In some embodiments of aspects provided herein, said reservoir comprises two through holes arranged along a longitudinal axis of the channel. In some embodiments of aspects provided herein, said one or two through holes have a shape of a square, a rectangle, an oval or have an elongated dimension in a direction of width. In some embodiments of aspects provided herein, said one or two through holes comprise one or two sides that span said width of said fluidic channel, or a width of said reservoir, wherein said sides are each at least 75% linear.

An aspect of the present disclosure provides a method comprising: providing any of the devices described herein, wherein the channel and the reservoir comprise an electrically conductive fluid and the reservoir comprises an ionic analyte; and passing an electric current is passed through the channel; wherein the electric current moves at least some of the analyte from the reservoir into the channel.

An aspect of the present disclosure provides a fluidic device comprising one or more branched fluidic circuits, wherein each of said branched fluidic circuits comprises an isotachophoresis ("ITP") branch, wherein: said ITP branch comprises a trailing electrolyte buffer reservoir, a sample channel, a leading electrolyte buffer channel, a first leading buffer electrolyte reservoir and a second leading electrolyte buffer reservoir, all in communication with each other, a sample reservoir comprising a first through-hole in communication with said sample channel.

In some embodiments of aspects provided herein, said first through-hole has a square or rectangular shape. In some embodiments of aspects provided herein, said first through-hole has a maximum dimension within a range of about 0.5 mm to about 5 mm. In some embodiments of aspects provided herein, said first through-hole has a maximum dimension of about 1.5 mm In some embodiments of aspects provided herein, said first through-hole has a maximum dimension of about 1 mm In some embodiments of aspects provided herein, said first through-hole has a volume of less than about 15 ul. In some embodiments of aspects provided herein, said first through-hole has a volume of about 7 ul. In some embodiments of aspects provided herein, said first through-hole has a width within a range of about 80% to about 120% of a width of said sample channel. In some embodiments of aspects provided herein, said first through-hole has a width of about 100% of the width of said sample channel. In some embodiments of aspects provided herein, the sample reservoir further comprises a second through-hole in communication with said sample channel. In some embodiments of aspects provided herein, the first and second through-holes are separated by filler block. In some embodiments of aspects provided herein, the filler block has a height within the channel within a range of about 0.2 mm to about 2 mm. In some embodiments of aspects provided herein, the filler block has a height within the channel of about 1.2 mm. In some embodiments of aspects provided herein, said second through-hole has a square or rectangular shape. In some embodiments of aspects provided herein, said second through-hole has a maximum dimension within a range of about 0.5 mm to about 5 mm. In some embodiments of aspects provided herein, said second through-hole has a maximum dimension of about 1.5 mm. In some embodiments of aspects provided herein, said second through-hole has a maximum dimension of about 1 mm. In some embodiments of aspects provided herein, said second through-hole has a volume of less than about 15 ul. In some embodiments of aspects provided herein, said second through-hole has a volume of about 7 ul. In some embodiments of aspects provided herein, said second through-hole has a width within a range of about 80% to about 120% of a width of said sample channel. In some embodiments of aspects provided herein, said second through-hole has a width within a range of about 80% to about 120% of a width of said sample channel. In some embodiments of aspects provided herein, when an electric field is applied to the ITP branch, greater than 10% of an electric current applied travels above a top surface of said sample channel across a length of said sample reservoir. In some embodiments of aspects provided herein, said sample reservoir has a conical shape with a narrower portion having a diameter within a range of about 0.1 mm to about 4 mm. In some embodiments of aspects provided herein, said sample reservoir has a conical shape with a narrower portion having a diameter within a range of about 1 mm to about 4 mm. In some embodiments of aspects provided herein, said sample reservoir has an oval shape.

An aspect of the present disclosure provides a device for performing vertical isotachophoresis, the device comprising: one or more cylindrical columns comprising an interior channel defined by an inner wall of the cylindrical column, each cylindrical column comprising: a first stage comprising a first gel plug disposed at a first location within the interior channel and a first space disposed within the interior channel between the first gel plug and an upper end of the cylindrical column; a second stage comprising a second gel plug disposed at a second location within the interior channel, the second location being located below the first location and oriented in line with gravity, and a second space disposed within the interior channel between the first gel plug and the second gel plug; and a third stage comprising a third gel plug disposed at a third location within the interior channel, the third location being located below the second location and oriented in line with gravity, and a third space disposed within the interior channel between the second gel plug and the third gel plug.

In some embodiments of aspects provided herein, the one or more cylindrical columns comprises a plurality of cylindrical columns, the plurality of cylindrical columns being arranged to conform to a standard microtiter plate dimensions. In some embodiments of aspects provided herein, the one or more cylindrical columns has a cross-sectional column area of about 9 mm×9 mm. In some embodiments of aspects provided herein, the first space comprises a trailing electrolyte buffer, the second space comprises an analyte, and the third space comprises a first leading electrolyte buffer. In some embodiments of aspects provided herein, the device further comprises a fourth stage comprising a fourth gel plug disposed at a fourth location within the interior channel, the fourth location being located below the third location and oriented in line with gravity, and a fourth space disposed within the interior channel between the third gel plug and the fourth gel plug. In some embodiments of aspects provided herein, the fourth space comprises an elution buffer. In some embodiments of aspects provided herein, the device further comprises a fifth stage comprising a fifth gel plug disposed at a fifth location within the interior channel, the fifth location being located below the fourth location and oriented in line with gravity, and a fifth space disposed within the interior channel between the fourth gel plug and the fifth gel plug. In some embodiments of aspects provided herein, the fifth space comprises a second leading electrolyte buffer.

An aspect of the present disclosure provides a method for focusing an analyte, the method comprising: introducing said analyte into said second space of said second stage above said second gel plug of any of the vertical or column ITP devices described herein; and applying a current across said device to move said analyte in the direction of gravity from the second space, through the second gel plug, and into said third space.

A method further comprising applying said current across said device to move said analyte in the direction of gravity from the third space, through the third gel plug, and into said fourth space.

In some embodiments of aspects provided herein, the method further comprises removing said analyte from said fourth space.

An aspect of the present disclosure provides a method for sample purification, comprising: (a) loading into a fluidic device (i) a tissue sample comprising lysed solid tissue, wherein said lysed solid tissue comprises nucleic acids and a contaminant, (ii) a trailing electrolyte buffer comprising first trailing electrolyte ions with an effective mobility having a magnitude lower than a magnitude of an effective mobility of said nucleic acids, and (iii) a leading electrolyte buffer comprising first leading electrolyte ions, with a second effective mobility, wherein said second effective mobility has a magnitude greater than said magnitude of said effective mobility of said nucleic acids; and (b) applying an electric field within said fluidic device to conduct isotachophoresis with said first trailing electrolyte ions, said nucleic acids, and said first leading electrolyte ions, thereby purifying said nucleic acids from said contaminant in said tissue sample.

In some embodiments of aspects provided herein, said effective mobility of said first trailing electrolyte ions has a magnitude greater than a magnitude of an effective mobility of said contaminant. In some embodiments of aspects provided herein, said fluidic device is a microfluidic chip and said tissue sample, said trailing electrolyte buffer and said leading electrolyte buffer are loaded into a first zone of said microfluidic chip. Some embodiments of aspects provided herein may further comprise, in said first zone of said microfluidic chip, conducting on said tissue sample at least one sample preparation procedure selected from the group consisting of (1) removing embedding material, (2) disrupting tissue, (3) lysing cells, (4) de-crosslinking said nucleic acids, (5) digesting proteins, and (6) digesting said nucleic acids. In some embodiments of aspects provided herein, said isotachophoresis is conducted in a second zone of said microfluidic chip, wherein said second zone is separate from and fluidically connected to said first zone. In some embodiments of aspects provided herein, said solid tissue is derived from a solid organ. In some embodiments of aspects provided herein, said lysed solid tissue comprises a chemical fixative. In some embodiments of aspects provided herein, said chemical fixative is formalin. In some embodiments of aspects provided herein, said solid tissue is formalin fixed paraffin embedded tissue (FFPE). In some embodiments of aspects provided herein, said lysed solid tissue comprises urea or thiourea. Some embodiments of aspects provided herein further comprise disrupting cell-cell junctions, extracellular matrix, or connective tissue in order to obtain said lysed solid tissue. In some embodiments of aspects provided herein, said lysed solid tissue comprises solid particles. In some embodiments of aspects provided herein, said nucleic acids comprise dispersed or solvated nucleic acids. In some embodiments of aspects provided herein, said contaminant is selected from the group consisting of crosslinked nucleic acids, embedding material, tissue debris, fixation chemicals, proteins, inhibitors, and combinations thereof. In some embodiments of aspects provided herein, said contaminant comprises crosslinked nucleic acids. In some embodiments of aspects provided herein, said tissue sample is combined with said trailing electrolyte buffer prior to said loading. In some embodiments of aspects provided herein, said tissue sample is combined with said leading electrolyte buffer prior to said loading. In some embodiments of aspects provided herein, said loading of said leading electrolyte buffer is conducted prior to said loading of said tissue sample. In some embodiments of aspects provided herein, said solid tissue is lysed in said leading electrolyte buffer prior to said loading of said tissue sample. In some embodiments of aspects provided herein, said solid tissue is lysed in said trailing electrolyte buffer prior to said loading of said tissue sample. In some embodiments of aspects provided herein, said sample preparation procedure comprises, prior to said applying of said electric field, removing embedding material by incubating said tissue sample in said fluidic device at a temperature of at least about 37° C. for a duration of at least about 1 minute. In some embodiments of aspects provided herein, said temperature is from about 40° C. to about 80° C. In some embodiments of aspects provided herein, said duration is from about 1 minute to about 120 minutes. In some embodiments of aspects provided herein, said sample preparation procedure comprises disrupting tissue or lysing cells by applying mechanical stress to said tissue sample. In some embodiments of aspects provided herein, said sample preparation procedure comprises disrupting tissue or lysing cells by applying heat to said tissue sample. In some embodiments of aspects provided herein, said applying heat results in a temperature of said tissue sample from about 30° C. to about 80° C. In some embodiments of aspects provided herein, said sample preparation procedure comprises disrupting tissue or lysing cells by contacting said tissue sample with a solution with pH of at least 10 or by proteolytically digesting said tissue sample. In some embodiments of aspects provided herein, said proteolytic digestion is conducted at a temperature greater than about 25° C. In some embodiments of aspects provided herein, said sample preparation procedure comprises disrupting tissue or lysing cells by applying at least one surfactant to said tissue sample. In some embodiments of aspects provided herein, said sample preparation procedure comprises disrupting tissue or lysing cells by applying a solution comprising urea to said tissue or cell sample. In some embodiments of aspects provided herein, said solution further comprises thiourea. In some embodiments of aspects provided herein, a concentration of said urea in said solution is within a range of from about 4 M to about 9 M and a concentration of said thiourea in said solution is in a range of from about 0.5 M to about 3.5 M. In some embodiments of aspects provided herein, a concentration of said urea in said solution is from about 6.5 M to about 7.5 M and a concentration of said thiourea in said solution is from about 1.5 M to about 2.5 M. In some embodiments of aspects provided herein, said sample preparation procedure comprises de-crosslinking said nucleic acids by digesting crosslinking proteins with proteinase K. In some embodiments of aspects provided herein, said sample preparation procedure comprises digesting said nucleic acids with DNase or RNase. Some embodiments of aspects provided herein further comprise eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, said tissue sample and said purified nucleic acids in said output solution comprise crosslinked nucleic acids and a concentration of said crosslinked nucleic acids in said output solution is at least about two-fold lower than a concentration of said crosslinked nucleic acids in said tissue sample. In some embodiments of aspects provided herein, said contaminant is present in said output solution at a concentration that is at least two-fold less than a concentration of said contaminant in said tissue sample. In some embodiments of aspects provided herein, said first trailing electrolyte ions comprise caproic acid. In some embodiments of aspects provided herein, said first leading electrolyte ions comprise chloride. In some embodiments of aspects provided herein, said trailing electrolyte buffer comprises second trailing electrolyte ions having a different effective mobility than said first trailing electrolyte ions. In some embodiments of aspects provided herein, said second trailing electrolyte ions comprise HEPES (4-(2-hydroxyethyl)-1-piperazineethanesulfonic acid) or MOPS (3-(N-morpholino)propanesulfonic acid). In some embodiments of aspects provided herein, said second trailing electrolyte ions comprise HEPES (4-(2-hydroxyethyl)-1-piperazineethanesulfonic acid) and said first trailing electrolyte ions comprise caproic acid. In some embodiments of aspects provided herein, said second trailing electrolyte ions comprise MOPS (3-(N-morpholino)propanesulfonic acid) and said first trailing electrolyte ions comprise caproic acid. In some embodiments of aspects provided herein, said second trailing electrolyte ions comprise HEPES (4-(2-hydroxyethyl)-1-piperazineethanesulfonic acid) and said first trailing electrolyte ions comprise MOPS. In some embodiments of aspects provided herein, said trailing electrolyte buffer comprises second trailing electrolyte ions with a second effective mobility, wherein said second effective mobility has a magnitude about the same as or lower than said magnitude of said effective mobility of said contaminant. In some embodiments of aspects provided herein, said tissue sample loaded into said fluidic device has a volume of at least 50 μl. Some embodiments of aspects provided herein further comprise, in said first zone of said microfluidic chip, conducting on said tissue sample a first sample processing procedure, and in a second zone of said microfluidic chip, conducting on said tissue sample an enzymatic reaction. In some embodiments of aspects provided herein, said first sample processing procedure comprises removal of embedding material, disruption of tissue, or cell lysis, and said enzymatic reaction comprises de-crosslinking said nucleic acids, digesting proteins, or digesting nucleic acids. In some embodiments of aspects provided herein, said first zone and said second zone each are each heated to a temperature above 37° C. In some embodiments of aspects provided herein, said first zone is heated to a temperature of about 60° C. to 100° C. during said first sample processing procedure and wherein said second zone is heated to a temperature of 40° C. to 60° C.

An aspect of the present disclosure provides a method for simultaneously purifying nucleic acids from at least two different samples comprising: (a) loading into a first channel of a microfluidic chip (i) a first sample comprising first nucleic acids and a first contaminant, (ii) a first trailing electrolyte buffer comprising first trailing ions, wherein a magnitude of an effective mobility of said first trailing ions is less than a magnitude of an effective mobility of said first nucleic acids, and (iii) a first leading electrolyte buffer comprising first leading ions, wherein a magnitude of an effective mobility of said first leading ions is greater than said magnitude of said effective mobility of said first nucleic acids; (b) loading into a second channel of said microfluidic chip (i) a second sample comprising second nucleic acids and a second contaminant, (ii) a second trailing electrolyte buffer comprising second trailing ions, wherein a magnitude of said second trailing ions is less than a magnitude of an effective mobility of said second nucleic acids, and (iii) a second leading electrolyte buffer comprising second leading ions, wherein a magnitude of an effective mobility of said second leading ions is greater than said magnitude of said effective mobility of said second nucleic acids; and (c) applying a first electric field within said microfluidic chip to conduct isotachophoresis in said first channel with said first trailing ions, said first nucleic acids, and said first leading ions, and applying a second electric field to conduct isotachophoresis in said second channel with said second trailing ions, said second nucleic acids, and said second leading ions, thereby simultaneously purifying said first nucleic acids from said first contaminant and said second nucleic acids from said second contaminant.

In some embodiments of aspects provided herein, said first sample and said second sample are different sample types. In some embodiments of aspects provided herein, said first nucleic acids and said second nucleic acids are different types or lengths of nucleic acids. In some embodiments of aspects provided herein, said first trailing electrolyte buffer or said first leading electrolyte buffer further comprises a lysis agent or a tissue disruption agent. In some embodiments of aspects provided herein, said lysis agent or said tissue disruption agent comprises one or more agents selected from the group consisting of a solution with pH greater than about 12, a proteinase, urea, thiourea, and a surfactant. In some embodiments of aspects provided herein, said first sample comprises lysed solid tissue. In some embodiments of aspects provided herein, said second sample comprises lysed cells. In some embodiments of aspects provided herein, said first sample does not contact said second sample during said conducting of isotachophoresis. Some embodiments of aspects provided herein further comprise loading into a third channel of said microfluidic chip (i) a third sample comprising third nucleic acids and a third contaminant, (ii) a third trailing electrolyte buffer comprising third trailing ions, wherein a magnitude of an effective mobility of said third trailing ions is less than a magnitude of an effective mobility of said third nucleic acids, and (iii) a third leading electrolyte buffer comprising third leading ions, wherein a magnitude of an effective mobility of said third leading ions is greater than said magnitude of said effective mobility of said third nucleic acids, wherein said electric field is applied within said microfluidic chip to conduct said isotachophoresis in said third channel with said third trailing ions, said third nucleic acids, and said third leading ions, thereby simultaneously purifying said first nucleic acids from said first contaminant, said second nucleic acids from said second contaminant and said third nucleic acids from said third contaminant. In some embodiments of aspects provided herein, said first and second electric fields are generated from a single electrode pair. In some embodiments of aspects provided herein, said first and second electric fields are generated from different electrode pairs. In some embodiments of aspects provided herein, said first and second channels are coupled to independent sensors. In some embodiments of aspects provided herein, feedback from said independent sensors is used to independently control said first and second electric fields. In some embodiments of aspects provided herein, said independent sensors sense voltage and said feedback is used to control current (or resistance) within said first and second channels. In some embodiments of aspects provided herein, said nucleic acids comprise DNA. In some embodiments of aspects provided herein, said nucleic acids comprise RNA.

As aspect of the present disclosure provides a method for sample purification, comprising: (a) loading onto a fluidic device (i) a sample comprising fixed cells, fixed tissue, or embedded tissue, wherein said sample comprise nucleic acids, (ii) a trailing electrolyte buffer comprising trailing electrolytes, wherein said trailing electrolytes have a lower effective mobility than said nucleic acids, and (iii) a leading electrolyte buffer comprising leading electrolytes, wherein said leading electrolytes have a higher effective mobility than said nucleic acids; and (b) applying an electric field on said fluidic device to conduct isotachophoresis with said trailing electrolytes, said nucleic acids, and said leading electrolytes, thereby purifying said nucleic acids from a contaminant in said sample.

In some embodiments of aspects provided herein, said contaminant is selected from the group consisting of crosslinked nucleic acids, embedding material, fixation chemicals, enzymes, and inhibitors. In some embodiments of aspects provided herein, said sample comprises said fixed cells, said fixed tissue, or both said fixed cells and said fixed tissue. In some embodiments of aspects provided herein, said sample is formalin-fixed. In some embodiments of aspects provided herein, said sample comprises said embedded tissue. In some embodiments of aspects provided herein, said sample comprises said tissue embedded in paraffin. In some embodiments of aspects provided herein, said sample is a formalin-fixed paraffin-embedded (FFPE) tissue sample. In some embodiments of aspects provided herein, said sample comprises a tissue biopsy. In some embodiments of aspects provided herein, said sample is a dissected formalin-fixed paraffin-embedded (FFPE) sample. Some embodiments of aspects provided herein further comprise comparing a characteristic of said nucleic acids to nucleic acids from other samples, wherein said characteristic is an expression level, a nucleic acid sequence, a molecular weight, nucleic acid integrity, nucleic-acid stranded-ness (e.g. double- versus single-stranded), or nucleic acid purity. In some embodiments of aspects provided herein, said sample is a tumor sample. In some embodiments of aspects provided herein, said trailing electrolyte buffer has a pH of greater than about 7. Some embodiments of aspects provided herein further comprises, prior to said applying said electric field, incubating said tissue sample in said fluidic device at a temperature of at least about 37° C. for a duration of at least about 1 minute. In some embodiments of aspects provided herein, said temperature is from about 40° C. to about 80° C. In some embodiments of aspects provided herein, said duration is from about 1 minute to about 120 minutes. In some embodiments of aspects provided herein, said leading electrolyte buffer comprises proteinase K. Some embodiments of aspects provided herein further comprise removing protein crosslinks from said nucleic acids using said proteinase K. Some embodiments of aspects provided herein further comprise, after said applying said electric field, removing protein crosslinks from said nucleic acids using heat. Some embodiments of aspects provided herein further comprise eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, a concentration of said crosslinked nucleic acids in said output solution is at least about two-fold lower than a concentration of said crosslinked nucleic acids in said tissue sample. In some embodiments of aspects provided herein, said output solution has a volume equal to or less than about 50 µL. In some embodiments of aspects provided herein, said tissue sample has a mass of at least about 1 ng. In some embodiments of aspects provided herein, said tissue sample has a volume greater than 25 µL. In some embodiments of aspects provided herein, said trailing electrolytes have a higher effective mobility than said contaminant. In some embodiments of aspects provided herein, said trailing electrolytes comprise (i) first ions, wherein said first ions have a higher effective mobility magnitude than said contaminant, and (ii) second ions, wherein said second ions have an effective mobility magnitude about the same as or lower than said contaminant. In some embodiments of aspects provided herein, said conducting isotachophoresis quenches a pH of said tissue sample to about 7.5. Some embodiments of aspects provided herein further comprise, prior to said loading, conducting de-paraffinization on said sample. Some embodiments of aspects provided herein further comprise detecting a concentration of said nucleic acids. In some embodiments of aspects provided herein, said concentration is less than or equal to about 1 picogram per microliter (pg/µL).

An aspect of the present disclosure provides a method for sample purification, comprising: (a) loading into a fluidic device (i) a tissue sample comprising lysed solid tissue and nucleic acids, (ii) a trailing electrolyte buffer, said trailing electrolyte buffer comprising trailing electrolyte ions with a first effective mobility, wherein said first effective mobility has a magnitude lower than a magnitude of an effective mobility of said nucleic acids, (iii) a first leading electrolyte buffer in a first leading electrolyte reservoir, said first leading electrolyte buffer comprising first leading electrolyte ions with a second effective mobility, wherein said second effective mobility has a magnitude greater than said magnitude of said effective mobility of said nucleic acids, and (iv) a second leading electrolyte buffer in a second leading electrolyte reservoir, said second leading electrolyte buffer comprising second leading electrolyte ions with a third effective mobility, wherein said third effective mobility has a magnitude greater than said magnitude of said effective mobility of said nucleic acids, wherein said first leading electrolyte buffer is different from said second leading electrolyte buffer; (b) first conducting isotachophoresis with said trailing electrolyte ions, said nucleic acids, and said first leading electrolyte ions, thereby purifying said nucleic acids from said contaminant in said tissue sample; and (c) second conducting isotachophoresis with said trailing electrolyte ions, said nucleic acids, and said second leading electrolyte ions.

In some embodiments of aspects provided herein, said second conducting isotachophoresis comprises changing an applied current from a first channel to a second channel. In some embodiments of aspects provided herein, said first leading electrolyte ions are the same as said second leading electrolyte ions, and wherein a concentration of said first leading electrolyte ions in said first leading electrolyte buffer is different from a concentration of said second leading electrolyte ions in said second leading electrolyte buffer. In some embodiments of aspects provided herein, said second effective mobility has a magnitude greater than said magnitude of said third effective mobility. In some embodiments of aspects provided herein, said first leading electrolyte ions are different from said second leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said first leading electrolyte buffer comprises third leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said second leading electrolyte buffer comprises third leading electrolyte ions. Some embodiments of aspects provided herein further comprise collecting said nucleic acids in said second leading electrolyte reservoir and removing said nucleic acids from said second leading electrolyte reservoir. In some embodiments of aspects provided herein, said first conducting isotachophoresis and said second conducting isotachophoresis are performed by applying a single electric field. In some embodiments of aspects provided herein, said first conducting isotachophoresis and said second conducting isotachophoresis are performed by applying more than one electric field. In some embodiments of aspects provided herein, the concentration of said second leading electrolyte ions in said second leading electrolyte buffer is less than 50 mM. In some embodiments of aspects provided herein, said second leading electrolyte buffer comprises 50 mM Tris HCl.

An aspect of the present disclosure provides a microfluidic device comprising: (a) a first isotachophoresis region in a microfluidic chip comprising: (i) a first sample reservoir in fluid communication with a first fluidic channel, (ii) a first buffer reservoir in fluid communication with said first fluidic channel, and (iii) a second buffer reservoir in fluid communication with said first channel; and (b) a second isotachophoresis region in said microfluidic chip comprising: (i) a second sample reservoir in fluid communication with a second fluidic channel, (ii) a third buffer reservoir in fluid communication with said second fluidic channel, and (iii) a fourth buffer reservoir in fluid communication with said second channel, wherein said first isotachophoresis region is not in fluid communication with said second isotachophoresis region and wherein said microfluidic device is configured to independently control a first electric circuit that applies current to said first isotachophoresis region and a second electric circuit that applies current to said second isotachophoresis region.

In some embodiments of aspects provided herein, a leakage rate between said first and second isotachophoresis regions is less than 1 μl per hour. In some embodiments of aspects provided herein, current leakage between said first and second isotachophoresis regions is less than 1 μA. In some embodiments of aspects provided herein, an impedance is greater than 1 megaOhm. In some embodiments of aspects provided herein, said first fluidic channel holds a liquid volume greater than 100 μl. In some embodiments of aspects provided herein, said first fluidic channel is separated from said second fluidic channel by a distance that is at least 5-fold less than a width of said first channel. In some embodiments of aspects provided herein, said microfluidic device is configured to control said first electric circuit simultaneously with said second electric circuit. Some embodiments of aspects provided herein further comprise an elution reservoir in fluid communication to said first channel, wherein a temperature sensor is situated within 5 mm of said elution reservoir.

An aspect of the present disclosure provides a method, comprising: (a) providing an electrokinetic fluidic device comprising a sample input reservoir in fluid communication with a channel; (b) loading a sample volume into said sample input reservoir; (c) moving at least 50% of said sample volume from said sample input reservoir to said channel, without adding additional volume to said sample input reservoir; and (d) applying an ionic current through said channel.

In some embodiments of aspects provided herein, said moving is conducted with aid of gravity. In some embodiments of aspects provided herein, said ionic current does not substantially pass through said channel. In some embodiments of aspects provided herein, said at least 50% of said sample volume comprises at least 80% of said sample volume. In some embodiments of aspects provided herein, said sample volume comprises nucleic acids. In some embodiments of aspects provided herein, said sample volume comprises a tissue sample or a formalin-fixed paraffin-embedded (FFPE) sample. In some embodiments of aspects provided herein, said applying an ionic current comprises conducting isotachophoresis. In some embodiments of aspects provided herein, a total sample volume loaded into said sample input reservoir is less than or equal to an internal volume of said input reservoir. In some embodiments of aspects provided herein, said sample input reservoir comprises a top region connected to a bottom region via a tapered region, wherein said top region has a first diameter and said bottom region has a second diameter, wherein said first diameter is at least two-fold longer than said second diameter in order to facilitate said moving at least 50% of said sample volume from said sample input reservoir to said channel. In some embodiments of aspects provided herein, said sample volume is at least 25 μl. In some embodiments of aspects provided herein, said sample volume is at least 50 μl. In some embodiments of aspects provided herein, said sample volume is at least 100 μl.

An aspect of the present disclosure provides a microfluidic chip comprising: a first sample input reservoir, wherein said first sample input reservoir comprises a top region connected to a bottom region via a tapered region, wherein said top region has a first inner hydraulic diameter and said bottom region has a second inner hydraulic diameter, wherein said first inner hydraulic diameter is at least 2-fold longer than said second inner hydraulic diameter and wherein said first sample input reservoir is in fluid communication with a first channel; a first buffer reservoir in fluid communication with said first channel, wherein said first sample reservoir is configured so that a free surface of a liquid in said first sample reservoir has a negligible buffer head height difference relative to a liquid in said first buffer reservoir; and a second buffer reservoir in fluid communication with said first channel.

In some embodiments of aspects provided herein, said first inner hydraulic diameter is a range of about 1 mm to about 15 mm. In some embodiments of aspects provided herein, said second inner hydraulic diameter is a range of about 0.5 mm to about 5 mm. In some embodiments of aspects provided herein, said first sample reservoir is configured to hold a sample volume of at least 100 μl. In some embodiments of aspects provided herein, said microfluidic chip is configured to move at least 50% of said sample volume from said first sample reservoir to said first channel when a vacuum is applied thereto. In some embodiments of aspects provided herein, said microfluidic chip is configured to conduct isotachophoresis on a sample that enters said first channel.

An aspect of the present disclosure provides a method of extracting nucleic acids, comprising: (a) exposing a biological sample comprising cells or tissue to a solution comprising urea or thiourea, thereby lysing said cells or tissue within said biological sample and producing a cellular lysate; (b) introducing said cellular lysate into a device; and (c) performing isotachophoresis with said device in order to isolate nucleic acids from said cellular lysate.

Some embodiments of aspects provided herein further comprise digesting said sample with proteinase K. In some embodiments of aspects provided herein, said solution comprises urea and thiourea. In some embodiments of aspects provided herein, said solution comprises a ratio of urea to thiourea of about 2 to 1. In some embodiments of aspects provided herein, a concentration of said urea in said solution is from about 4 M to about 9 M and a concentration of said thiourea in said solution is from about 0.5 M to about 3.5 M. In some embodiments of aspects provided herein, a concentration of said urea in said solution is from about 6.5 M to about 7.5 M and a concentration of said thiourea in said solution is from about 1.5 M to about 2.5 M. In some embodiments of aspects provided herein, said solution comprises trailing electrolyte ions or leading electrolyte ions or both trailing electrolyte ions and leading electrolyte ions.

An aspect of the present disclosure provides a method of purifying high molecular weight nucleic acids from a tissue sample, comprising: (a) loading into a fluidic device: (i) a cellular sample comprising genomic DNA and a contaminant, wherein said cellular sample is contacted with a lysis buffer prior to or after said loading of said cellular sample into said fluidic device, (ii) a trailing electrolyte buffer, said trailing electrolyte buffer comprising trailing electrolyte ions with a first effective mobility, wherein said first effective mobility has a magnitude lower than a magnitude of an effective mobility of said high molecular weight nucleic acids and a magnitude greater than a magnitude of said contaminant, and (iii) a first leading electrolyte buffer, said first leading electrolyte buffer comprising first leading electrolyte ions with a second effective mobility, wherein said second effective mobility has a magnitude greater than said magnitude of said effective mobility of said high molecular weight nucleic acids; (b) conducting isotachophoresis with said trailing electrolyte ions, said high molecular weight nucleic acids, and said first leading electrolyte ions, thereby separating said high molecular weight nucleic acids from said contaminant and enriching said high molecular weight nucleic acids in an isotachophoresis zone; and (c) eluting said genomic DNA into a solution in an output reservoir, wherein greater than 50% of the mass of nucleic acids within said solution are greater than 30 kilobases.

In some embodiments of aspects provided herein, said lysis buffer does not comprise an alkaline buffer. In some embodiments of aspects provided herein, said lysis buffer comprises octylphenol ethoxylate. In some embodiments of aspects provided herein, greater than 50% of the mass of nucleic acids within said solution are greater than 50 kilobases.

An aspect of the present disclosure provides a method of conducting isotachophoresis, comprising: (a) providing a fluidic device comprising a first channel in fluid communication with a sample input reservoir comprising a tissue sample comprising lysed solid tissue, a first buffer reservoir comprising a first leading electrolyte buffer, and a second buffer reservoir comprising a trailing electrolyte buffer; (b) contacting a first electrode to said first leading electrolyte buffer in said first buffer reservoir; (c) contacting a second electrode to said trailing electrolyte buffer in said second buffer reservoir; and (d) applying an electric field within said fluidic device to conduct isotachophoresis, wherein said isotachophoresis occurs without direct contact between said tissue sample and said first and second electrodes.

In some embodiments of aspects provided herein, said fluidic device further comprises a third buffer reservoir in fluid communication with said first channel and said first buffer reservoir, said third buffer reservoir comprising a lower concentration of said first leading electrolyte buffer than said first buffer reservoir. In some embodiments of aspects provided herein, said third buffer reservoir and said first buffer reservoir are connected by a second channel comprising one or more capillary barriers to limit pressure-driven flow within said second channel and between said third buffer reservoir and said first buffer reservoir. In some embodiments of aspects provided herein, said fluidic device further comprises an elution reservoir. In some embodiments of aspects provided herein, said elution reservoir is in fluid communication with a fourth buffer reservoir.

An aspect of the present disclosure provides a microfluidic system, said microfluidic system comprising: (a) a microfluidic chip comprising a first channel and a first reservoir in fluid communication with said first channel, wherein said first channel and said first reservoir meet at a first junction; and (b) a mechanical member comprising a first tooth, wherein said mechanical member is configured to apply mechanical pressure to said first channel via said first tooth in order to at least partially close said first channel by plastic deformation of at least one wall of said first channel and increase fluid resistance between said first channel and said first reservoir.

In some embodiments of aspects provided herein, said microfluidic chip further comprises a second reservoir in fluid communication with said first reservoir and a second channel connecting said first reservoir and said second reservoir, and wherein said mechanical member further comprises a second tooth configured to apply mechanical pressure to said second channel in order to plastically close said second channel and prevent fluid communication between said first reservoir and said second reservoir. In some embodiments of aspects provided herein, said first tooth is configured to deliver mechanical pressure to said first junction in order to close said first channel by plastic deformation of at least one wall of said first channel. In some embodiments of aspects provided herein, said first tooth is configured to heat said first channel. In some embodiments of aspects provided herein, said mechanical member comprises a material with a Young's modulus of elasticity greater than a Young's modulus of elasticity of said first channel. In some embodiments of aspects provided herein, said microfluidic system is configured to perform isotachophoresis. In some embodiments of aspects provided herein, said first tooth is thermally coupled to a heating element. In some embodiments of aspects provided herein, said first tooth is heated to a temperature greater than the glass transition temperature of said at least one wall of said first channel. Some embodiments of aspects provided herein comprise a method of completing a process in a fluidic system comprising using said microfluidic system to at least partially close said first channel by plastic deformation, thereby increasing resistance to fluid flow between said first channel and said first reservoir. In some embodiments of aspects provided herein, said first tooth of said mechanical member applies a force of at least 0.25 lbs to said first channel. In some embodiments of aspects provided herein, said process in said fluidic system is isotachophoresis.

An aspect of the present disclosure provides a method of performing isotachophoresis on a sample comprising nucleic acids comprising: (a) loading said sample comprising nucleic acids into a first reservoir of a microfluidic chip; (b) loading a trailing electrolyte buffer into a second reservoir of said microfluidic chip, wherein said trailing electrolyte buffer comprises first trailing electrolyte ions with an effective mobility having a magnitude lower than a magnitude of an effective mobility of said nucleic acids; (c) loading a leading electrolyte buffer into a third reservoir of said microfluidic chip, wherein said third reservoir comprises first leading electrolyte ions with a second effective mobility, wherein said second effective mobility has a magnitude greater than said magnitude of said effective mobility of said nucleic acids; (d) applying an electric field within said microfluidic chip to conduct isotachophoresis with said first trailing electrolyte ions, said nucleic acids, and said first leading electrolyte ions, thereby confining said nucleic acids, or a portion thereof, to an isotachophoresis zone; and (e) using a temperature sensor to sense a temperature change in or near said isotachophoresis zone, wherein feedback from said temperature sensor is used to control said electric field.

In some embodiments of aspects provided herein, said control of said electric field results in positioning of said nucleic acids, or portion thereof, in an elution reservoir or region of said microfluidic chip. In some embodiments of aspects provided herein, said temperature sensor is located within at most 8 mm of said elution reservoir. In some embodiments of aspects provided herein, said temperature change is within a range of about 0.2° C. to 5° C. In some embodiments of aspects provided herein, said applied electric field causes said leading electrolyte and said trailing electrolyte to meet at an isotachophoresis interface and said temperature sensor senses said isotachophoresis interface.

An aspect of the present disclosure provides a microfluidic device comprising: (a) a first isotachophoresis region in a microfluidic chip comprising: (i) a first sample reservoir in fluid communication with a first fluidic channel; (ii) a first, a second, and a third buffer reservoir in fluid communication with said first fluidic channel, wherein said first and second buffer reservoirs are separated by a capillary barrier; and (iii) an elution reservoir in fluid communication with said first fluidic channel; (b) a sensor configured to detect a temperature change in said first fluidic channel within said first isotachophoresis region; and (c) an apparatus positioned to supply electrical current within said first channel within said first isotachophoresis region.

Some embodiments of aspects provided herein further comprise a controller configured to trigger a reduction or elimination of said electrical current when said sensor receives a thermal signal. In some embodiments of aspects provided herein, said temperature change is an increase in temperature within a range of about 0.2° C. to 5° C. In some embodiments of aspects provided herein, said microfluidic device is further configured to isolate a sample of nucleic acids in said elution reservoir after said sensor detects a change in temperature. In some embodiments of aspects provided herein, said sensing of said nucleic acids is performed with a sensor located within at most 8 mm of said elution reservoir. In some embodiments of aspects provided herein, said first channel comprises a single sensor.

An aspect of the present disclosure provides a kit comprising: (a) said microfluidic device or said microfluidic chip; (b) a trailing electrolyte buffer comprising trailing electrolytes; and (c) a leading electrolyte buffer comprising leading electrolytes.

In some embodiments of aspects provided herein, said trailing electrolyte buffer comprises a mixture of at least two electrolytes with different effective mobilities. In some embodiments of aspects provided herein, said mixture comprises (i) a first electrolyte that has a lower effective mobility magnitude than a nucleic acid and a higher effective mobility magnitude than a contaminant, and (ii) a second electrolyte which has a lower effective mobility magnitude than said contaminant. In some embodiments of aspects provided herein, said first electrolyte comprises caproic acid. In some embodiments of aspects provided herein, said second electrolyte comprises HEPES (4-(2-hydroxyethyl)-1-piperazineethanesulfonic acid). In some embodiments of aspects provided herein, said kit further comprises sample buffer, wherein said sample buffer comprises leading electrolyte buffer, trailing electrolyte buffer, or urea in any combination. In some embodiments of aspects provided herein, said kit further comprises a sample buffer comprising urea and thiourea.

An aspect of the present disclosure provides a method for sample purification, comprising: (a) loading into a fluidic device (i) a tissue sample comprising nucleic acids and a contaminant, wherein said tissue sample is not an unlysed whole blood sample, (ii) a trailing electrolyte buffer comprising trailing electrolyte ions with an effective mobility having a magnitude greater than a magnitude of an effective mobility of said contaminant and lower than a magnitude of an effective mobility of said nucleic acids, and (iii) a leading electrolyte buffer comprising leading electrolyte ions, with a second effective mobility, wherein said second effective mobility has a magnitude greater than said magnitude of said effective mobility of said nucleic acids; and (b) applying an electrical field within said fluidic device to conduct isotachophoresis with said trailing electrolyte ions, said nucleic acids, and said leading electrolyte ions, thereby purifying said nucleic acids from said contaminant in said tissue sample.

In some embodiments of aspects provided herein, said tissue sample is not a whole blood sample. In some embodiments of aspects provided herein, said trailing electrolyte ions comprise caproic acid. In some embodiments of aspects provided herein, said leading electrolyte ions comprise chloride. In some embodiments of aspects provided herein, said trailing electrolyte buffer comprises second trailing electrolyte ions having a different effective mobility than said first trailing electrolyte ions. In some embodiments of aspects provided herein, said second trailing electrolyte ions comprise HEPES (4-(2-hydroxyethyl)-1-piperazineethanesulfonic acid). In some embodiments of aspects provided herein, said second trailing electrolyte ions comprise MOPS (3-(N morpholino)propanesulfonic acid) In some embodiments of aspects provided herein, said second trailing electrolyte ions comprise HEPES (4-(2-hydroxyethyl)-1-piperazineethanesulfonic acid) and first trailing electrolyte ions are comprised of caproic acid. In some embodiments of aspects provided herein, said second trailing electrolyte ions comprise MOPS (3-(N-morpholino)propanesulfonic acid) and first, trailing electrolyte ions are comprised of caproic acid. In some embodiments of aspects provided herein, said second trailing electrolyte ions comprise HEPES and first trailing electrolyte ions comprise MOPS. In some embodiments of aspects provided herein, said trailing electrolyte buffer comprises second trailing electrolyte ions with a second effective mobility, wherein said second effective mobility has a magnitude about the same as or lower than said magnitude of said effective mobility of said contaminant. In some embodiments of aspects provided herein, said contaminant is selected from the group consisting of crosslinked nucleic acids, embedding material, fixation chemicals, proteins, inhibitors, and combinations thereof. In some embodiments of aspects provided herein, said contaminant comprises crosslinked nucleic acids. In some embodiments of aspects provided herein, said tissue sample is combined with said trailing electrolyte buffer prior to said loading. In some embodiments of aspects provided herein, said tissue sample is combined with said leading electrolyte buffer prior to said loading. In some embodiments of aspects provided herein, said loading of said leading electrolyte buffer is conducted prior to said loading of said tissue sample. In some embodiments of aspects provided herein, the method further comprises eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, a concentration of said crosslinked nucleic acids in said output solution is at least about two-fold lower than a concentration of said crosslinked nucleic acids in said tissue sample. In some embodiments of aspects provided herein, said output solution does not comprise said contaminant. In some embodiments of aspects provided herein, said tissue sample is fresh tissue. In some embodiments of aspects provided herein, said tissue sample is fresh frozen (FF) tissue. In some embodiments of aspects provided herein, said tissue sample is formalin fixed paraffin embedded tissue (FFPE). In some embodiments of aspects provided herein, the method further comprises, prior to said loading, lysing or disrupting said tissue sample. In some embodiments of aspects provided herein, said lysing or disrupting is conducted using urea or thiourea.

An aspect of the present disclosure provides a method for sample purification, comprising: (a) loading into a first channel on a fluidic device (i) a first tissue sample comprising first nucleic acids and a first contaminant, (ii) a first trailing electrolyte buffer comprising first trailing ions, wherein a magnitude of an effective mobility of said first trailing ions is less than a magnitude of an effective mobility of said first nucleic acids, and (iii) a first leading electrolyte buffer comprising first leading ions, wherein a magnitude of an effective mobility of said first leading ions is greater than said magnitude of said effective mobility of said first nucleic acids; (b) loading into a second channel on said fluidic device (iv) a second tissue sample comprising second nucleic acids and a second contaminant, (v) a second trailing electrolyte buffer comprising second trailing ions, wherein a magnitude of said second trailing ions is less than a magnitude of an effective mobility of said second nucleic acids, and (vi) a second leading electrolyte buffer comprising second leading ions, wherein a magnitude of an effective mobility of said second leading ions is greater than said magnitude of said effective mobility of said second nucleic acids; and (c) applying an electrical field within said fluidic device to conduct isotachophoresis in said first channel with said first trailing ions, said first nucleic acids, and said first leading ions, and to conduct isotachophoresis in said second channel with said second trailing ions, said second nucleic acids, and said second leading ions, thereby purifying said first nucleic acids from said first contaminant and purifying said second nucleic acids from said second contaminant.

In some embodiments of aspects provided herein, said first trailing electrolyte buffer or said first leading electrolyte buffer further comprises a lysis agent or a tissue disruption agent. In some embodiments of aspects provided herein, said second trailing electrolyte buffer or said second leading electrolyte buffer further comprises a lysis agent or a tissue disruption agent. In some embodiments of aspects provided herein, said lysis agent or said tissue disruption agent comprises one or more agents selected from the group consisting of a solution with pH greater than about 12, a proteinase, urea, thiourea, and a surfactant.

An aspect of the present disclosure provides a method for sample purification, comprising: (a) loading into a first zone of a fluidic device (i) a tissue sample comprising nucleic acids and a contaminant, (ii) a trailing electrolyte buffer comprising trailing ions, wherein a magnitude of an effective mobility of said trailing ions is lower than a magnitude of an effective mobility of said nucleic acids, and (iii) a leading electrolyte buffer comprising leading ions, wherein a magnitude of an effective mobility of said leading ions is greater than said magnitude of said effective mobility of said nucleic acids; and (b) applying an electrical field on said fluidic device to conduct isotachophoresis in a second zone of said fluidic device with said trailing ions, said nucleic acids, and said leading ions, thereby purifying said nucleic acids from said contaminant, wherein during said applying, said first zone is maintained at a first temperature and said second zone is maintained at a second temperature different from said first temperature.

In some embodiments of aspects provided herein, said trailing electrolyte buffer or said leading electrolyte buffer further comprises a lysis agent or a tissue disruption agent. In some embodiments of aspects provided herein, said lysis agent or said tissue disruption agent comprises one or more agents selected from the group consisting of a solution with pH greater than about 12, a proteinase, urea, thiourea, and a surfactant. In some embodiments of aspects provided herein, said first temperature is between about 4° C. and about 40° C. In some embodiments of aspects provided herein, said first temperature is between about 40° C. and about 80° C.

An aspect of the present disclosure provides a method for sample purification, comprising: (a) loading into a first zone of a fluidic device (i) a tissue sample comprising nucleic acids, (ii) a trailing electrolyte buffer comprising trailing ions, wherein a magnitude of an effective mobility of said trailing ions is lower than a magnitude of an effective mobility of said nucleic acids, and (iii) a leading electrolyte buffer comprising leading ions, wherein a magnitude of an effective mobility of said leading ions is greater than said magnitude of said effective mobility of said nucleic acids; (b) in said first zone, conducting on said tissue sample at least one sample preparation selected from the group consisting of (1) removing embedding material, (2) disrupting tissue, (3) lysing cells, (4) de-crosslinking nucleic acids, (5) digesting proteins and (6) digesting nucleic acids; and (c) applying an electrical field within said fluidic device to conduct isotachophoresis in a second zone of said fluidic device with said trailing ions, said nucleic acids, and said leading ions, thereby purifying said nucleic acids from a contaminant in said tissue sample.

In some embodiments of aspects provided herein, said removing embedding material or said lysing cells comprises, prior to said applying said electric field, incubating said tissue sample in said fluidic device at a temperature of at least about 37° C. for duration of at least about 1 minute. In some embodiments of aspects provided herein, said temperature is from about 40° C. to about 80° C. In some embodiments of aspects provided herein, said duration is from about 1 minute to about 60 minutes. In some embodiments of aspects provided herein, said disrupting tissue or said lysing cells comprises applying mechanical stress to said sample. In some embodiments of aspects provided herein, said disrupting tissue or said lysing cells comprises applying heat to said sample. In some embodiments of aspects provided herein, said applying heat results in a temperature of said tissue sample from about 30° C. to about 65° C. In some embodiments of aspects provided herein, said disrupting tissue or said lysing cells comprises a solution pH of at least 12. In some embodiments of aspects provided herein, said disrupting tissue or said lysing cells comprises proteolytic digestion. In some embodiments of aspects provided herein, said proteolytic digestion is conducted at a temperature greater than about 25° C. In some embodiments of aspects provided herein, said temperature is from about 30° C. to about 65° C. In some embodiments of aspects provided herein, said disrupting tissue or said lysing cells comprises applying at least one surfactant to said tissue or said cells. In some embodiments of aspects provided herein, said disrupting tissue or said lysing cells comprises applying a solution comprising urea to said tissue or said cells. In some embodiments of aspects provided herein, said solution further comprises thiourea. In some embodiments of aspects provided herein, a concentration of said urea in said solution is from about 4 M to about 9 M and a concentration of said thiourea in said solution is from about 0.5 M to about 3.5 M. In some embodiments of aspects provided herein, a concentration of said urea in said solution is from about 6.5 M to about 7.5 M and a concentration of said thiourea in said solution is from about 1.5 M to about 2.5 M. In some embodiments of aspects provided herein, said de-crosslinking nucleic acids comprises digesting crosslinking proteins with proteinase K. In some embodiments of aspects provided herein, said digesting nucleic acids is performed with DNase or RNase.

An aspect of the present disclosure provides a method for sample purification, comprising: (a) loading onto a fluidic device (i) a tissue sample comprising nucleic acids, wherein said tissue sample is embedded or fixed, (ii) a trailing electrolyte buffer comprising trailing electrolytes, wherein said trailing electrolytes have a lower effective mobility than said nucleic acids, and (iii) a leading electrolyte buffer comprising leading electrolytes, wherein said leading electrolytes have a higher effective mobility than said nucleic acids; and (b) applying an electrical field on said fluidic device to conduct isotachophoresis with said trailing electrolytes, said nucleic acids, and said leading electrolytes, thereby purifying said nucleic acids from a contaminant in said tissue sample.

In some embodiments of aspects provided herein, said contaminant is selected from the group consisting of cross-linked nucleic acids, embedding material, fixation chemicals, enzymes, and inhibitors. In some embodiments of aspects provided herein, said embedding material comprises paraffin. In some embodiments of aspects provided herein, said tissue sample is formalin-fixed. In some embodiments of aspects provided herein, said tissue sample is embedded and fixed. In some embodiments of aspects provided herein, said tissue sample is a formalin-fixed paraffin-embedded (FFPE) tissue sample. In some embodiments of aspects provided herein, said tissue sample is a dissected tissue sample. In some embodiments of aspects provided herein, said dissected tissue sample is dissected FFPE sample. In some embodiments of aspects provided herein, the method further comprises the step of comparing a characteristic of said nucleic acids to nucleic acids from other samples. In some embodiments of aspects provided herein, said characteristic is an expression level. In some embodiments of aspects provided herein, said characteristic is a nucleic acid sequence. In some embodiments of aspects provided herein, said characteristic is a molecular weight. In some embodiments of aspects provided herein, said characteristic is a nucleic acid integrity. In some embodiments of aspects provided herein, said characteristic is a nucleic acid purity. In some embodiments of aspects provided herein, the method further comprises a step of administering a drug based on said characteristic of said nucleic acids. In some embodiments of aspects provided herein, said tissue sample is a tumor sample. In some embodiments of aspects provided herein, said trailing electrolyte buffer has a pH of about 7. In some embodiments of aspects provided herein, said trailing electrolyte buffer has a pH of greater than about 7. In some embodiments of aspects provided herein, the method further comprises, prior to said applying said electric field, incubating said tissue sample in said fluidic device at a temperature of at least about 37° C. for duration of at least about 1 minute. In some embodiments of aspects provided herein, said temperature is from about 40° C. to about 80° C. In some embodiments of aspects provided herein, said duration is from about 1 minute to about 60 minutes. In some embodiments of aspects provided herein, said leading electrolyte buffer comprises proteinase K. In some embodiments of aspects provided herein, the method further comprises removing protein crosslinks from said nucleic acids using said proteinase K. In some embodiments of aspects provided herein, the method further comprises, after said applying said electric field, removing protein crosslinks from said nucleic acids using heat. In some embodiments of aspects provided herein, the method further comprises eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, a concentration of said crosslinked nucleic acids in said output solution is at least about two-fold lower than a concentration of said crosslinked nucleic acids in said tissue sample. In some embodiments of aspects provided herein, said output solution does not comprise said contaminant. In some embodiments of aspects provided herein, said output solution has a volume equal to or less than about 50 µL. In some embodiments of aspects provided herein, said tissue sample has a mass of at least about 1 ng. In some embodiments of aspects provided herein, said tissue sample has a volume of less than about 500 µL. In some embodiments of aspects provided herein, said trailing electrolytes have a higher effective mobility than said contaminant. In some embodiments of aspects provided herein, said trailing electrolytes comprise (i) first ions, wherein said first ions have a higher effective mobility magnitude than said contaminant, and (ii) second ions, wherein said second ions have an effective mobility magnitude about the same as or lower than said contaminant. In some embodiments of aspects provided herein, said conducting isotachophoresis quenches a pH of said tissue sample to about 7. In some embodiments of aspects provided herein, the method further comprises, prior to said loading, conducting de-paraffinization on said tissue sample. In some embodiments of aspects provided herein, said tissue sample is a historical formalin-fixed paraffin-embedded (FFPE) sample, further comprising comparing a characteristic of said nucleic acids to a characteristic of different nucleic acids from a different tissue sample. In some embodiments of aspects provided herein, the method further comprises a step of detecting a concentration of said nucleic acids. In some embodiments of aspects provided herein, said concentration is less than or equal to about 1 picogram per microliter (pg/µL). In some embodiments of aspects provided herein, said concentration is less than or equal to about 0.5 pg/µL. In some embodiments of aspects provided herein, said concentration is at least about 1 picogram per microliter (pg/µL).

An aspect of the present disclosure provides a fluidic device, comprising: a sample purification region, comprising: (a) a first zone; (b) a sample inlet located in said first zone; (c) a trailing electrolyte reservoir in fluid communication with said first zone; (d) a second zone in fluid communication with said first zone; (e) a leading electrolyte reservoir in fluid communication with said second zone; (f) a sample outlet in fluid communication with said second zone; (g) a first heater in thermal communication with said first zone; and (h) a second heater configured to transfer heat to said second zone, wherein said first zone is substantially thermally isolated from said second zone.

An aspect of the present disclosure provides a fluidic device, comprising: a sample purification region, comprising: (a) a first zone; (b) a sample inlet located in said first zone; (c) a trailing electrolyte reservoir in fluid communication with said first zone; (d) a second zone in fluid communication with said first zone; (e) a leading electrolyte reservoir in fluid communication with said second zone; (f) a sample outlet in fluid communication with said second zone; and (g) a heater in thermal communication with said first zone and said second zone.

In some embodiments of aspects provided herein, the device further comprises a second sample purification region. In some embodiments of aspects provided herein, said first zone is a de-paraffinization zone. In some embodiments of aspects provided herein, said first zone is a disruption zone. In some embodiments of aspects provided herein, said second zone is an isotachophoresis zone. In some embodiments of aspects provided herein, said first zone or said second zone has a width of less than about 1 mm. In some embodiments of aspects provided herein, said first zone or said second zone has a width of less than about 0.5 mm.

An aspect of the present disclosure provides a kit, comprising a device provided herein, a trailing electrolyte buffer comprising trailing electrolytes, and a leading electrolyte buffer comprising leading electrolytes.

In some embodiments of aspects provided herein, said trailing electrolyte buffer contains a mixture of at least two electrolytes with different effective mobilities. In some embodiments of aspects provided herein, said mixture comprises (i) a first electrolyte that has a lower effective mobility magnitude than a nucleic acid and a higher effective mobility magnitude than a contaminant, and (ii) a second electrolyte which has a lower effective mobility magnitude than said contaminant. In some embodiments of aspects provided herein, said contaminant comprises crosslinked nucleic acids. In some embodiments of aspects provided herein, said first electrolyte comprises caproic acid. In some embodiments of aspects provided herein, said second electrolyte comprises HEPES.

An aspect of the present disclosure provides a method for sample purification, comprising: (a) loading into a fluidic device (i) a tissue sample comprising nucleic acids, (ii) a trailing electrolyte buffer, said trailing electrolyte buffer comprising trailing electrolyte ions with a first effective mobility, wherein said first effective mobility has a magnitude lower than a magnitude of an effective mobility of said nucleic acids, (iii) a first leading electrolyte buffer in a first leading electrolyte reservoir, said first leading electrolyte buffer comprising first leading electrolyte ions with a second effective mobility, wherein said second effective mobility has a magnitude greater than said magnitude of said effective mobility of said nucleic acids, and (iv) a second leading electrolyte buffer in a second leading electrolyte reservoir, said second leading electrolyte buffer comprising second leading electrolyte ions with a third effective mobility, wherein said third effective mobility has a magnitude greater than said magnitude of said effective mobility of said nucleic acids, wherein said first leading electrolyte buffer is different from said second leading electrolyte buffer; (b) first conducting isotachophoresis with said trailing electrolyte ions, said nucleic acids, and said first leading electrolyte ions, thereby purifying said nucleic acids from said contaminant in said tissue sample; and (c) second conducting isotachophoresis with said trailing electrolyte ions, said nucleic acids, and said second leading electrolyte ions.

In some embodiments of aspects provided herein, said second conducting isotachophoresis comprises changing an applied current from a first channel to a second channel. In some embodiments of aspects provided herein, said first leading electrolyte ions are the same as said second leading electrolyte ions, and wherein a concentration of said first leading electrolyte ions in said first leading electrolyte buffer is different from a concentration of said second leading electrolyte ions in said second leading electrolyte buffer. In some embodiments of aspects provided herein, said concentration of said first leading electrolyte ions in said first leading electrolyte buffer is different from said concentration of said second leading electrolyte ions in said second leading electrolyte buffer by a factor of at least 1.5×. In some embodiments of aspects provided herein, said first leading electrolyte ions are different from said second leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said first leading electrolyte buffer comprises third leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said second leading electrolyte buffer comprises third leading electrolyte ions. In some embodiments of aspects provided herein, the method further comprises collecting said nucleic acids in said second leading electrolyte reservoir. In some embodiments of aspects provided herein, the method further comprises removing said nucleic acids from said second leading electrolyte reservoir. In some embodiments of aspects provided herein, said trailing electrolyte buffer is loaded into a trailing electrolyte reservoir that is separate from said first leading electrolyte reservoir and said second leading electrolyte reservoir. In some embodiments of aspects provided herein, said first conducting isotachophoresis and said second conducting isotachophoresis are performed by applying one electric field. In some embodiments of aspects provided herein, said first conducting isotachophoresis and said second conducting isotachophoresis are performed by applying more than one electric field.

An aspect of the present disclosure provides a fluidic device, comprising: a sample purification region, comprising: (a) a channel comprising a first zone and a second zone in fluid communication with said first zone; (b) a sample inlet, a trailing electrolyte reservoir comprising a trailing electrolyte buffer, and a first leading electrolyte reservoir comprising a first leading electrolyte buffer, each in fluid communication with said first zone; and (c) a second leading electrolyte reservoir comprising a second leading electrolyte buffer, wherein said second leading electrolyte buffer is in fluid communication with said second zone and wherein said second leading electrolyte buffer is different from said first leading electrolyte buffer.

In some embodiments of aspects provided herein, said sample inlet is capable of receiving a sample comprising at least some non-liquid biological material. In some embodiments of aspects provided herein, said second leading electrolyte buffer comprises a different leading electrolyte co-ion than said first leading electrolyte buffer. In some embodiments of aspects provided herein, said first leading electrolyte buffer comprises first leading electrolyte ions and said second leading electrolyte buffer comprises second leading electrolyte ions that are the same as said first leading electrolyte ions, and wherein a concentration of said first leading electrolyte ions in said first leading electrolyte buffer is different from a concentration of said second leading electrolyte ions in said second leading electrolyte buffer. In some embodiments of aspects provided herein, said first leading electrolyte buffer comprises first leading electrolyte ions and said second leading electrolyte buffer comprises second leading electrolyte ions, and wherein said concentration of said first leading electrolyte ions in said first leading electrolyte buffer is different from said concentration of said second leading electrolyte ions in said second leading electrolyte buffer by a factor of at least 1.5×. In some embodiments of aspects provided herein, said first leading electrolyte buffer comprises first leading electrolyte ions and said second leading electrolyte buffer comprises second leading electrolyte ions that are different from said first leading electrolyte ions. In some embodiments of aspects provided herein, said first leading electrolyte buffer comprises first leading electrolyte ions and said second leading electrolyte buffer comprises second leading electrolyte ions that are that same as said first leading electrolyte ions, and wherein a concentration of said first leading electrolyte ions in said first leading electrolyte buffer is the same as a concentration of said second leading electrolyte ions in said second leading electrolyte buffer, and wherein said first leading electrolyte buffer comprises third leading electrolyte ions. In some embodiments of aspects provided herein, said first leading electrolyte buffer comprises first leading electrolyte ions and said second leading electrolyte buffer comprises second leading electrolyte ions that are the same as said first leading electrolyte ions, and wherein a concentration of said first leading electrolyte ions in said first leading electrolyte buffer is the same as a concentration of said second leading electrolyte ions in said second leading electrolyte buffer, and wherein said second leading electrolyte buffer comprises third leading electrolyte ions.

An aspect of the present disclosure provides a method, comprising: (a) providing an electrokinetic fluidic device comprising a reservoir in fluidic communication with a channel; (b) loading a sample volume into said reservoir; (c) moving at least 50% of said sample volume from said reservoir to said channel; and (d) applying an ionic current through said channel.

In some embodiments of aspects provided herein, said moving is conducted with the aid of gravity. In some embodiments of aspects provided herein, said ionic current does not substantially pass through said reservoir. In some embodiments of aspects provided herein, said at least 50% of said sample volume comprises at least 80% of said sample volume. In some embodiments of aspects provided herein, said sample volume comprises nucleic acids. In some embodiments of aspects provided herein, said sample volume comprises a tissue sample. In some embodiments of aspects provided herein, said sample volume comprises a formalin-fixed paraffin-embedded (FFPE) sample. In some embodiments of aspects provided herein, said applying an ionic current comprises conducting isotachophoresis (ITP).

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24A shows an exemplary image of DNA extraction and purification from FFPE samples using isotachophoresis.

FIG. 24B shows exemplary DNA yields measured by quantitative PCR for extraction and purification of DNA from FFPE samples using isotachophoresis compared to exemplary results from a typical solid phase column extraction kit.

FIG. 25A shows an image of a single channel ITP chip loaded with nucleic acid (RNA extraction and digest from human cells) stained with dye for visualization.

FIG. 25B shows an image of a single channel ITP chip loaded with nucleic acid (RNA extraction and digest from human cells) stained with dye for visualization.

FIG. 27C shows the chip before ITP (blood lysate and ITP buffers loaded in chip; buffer only in elution well). FIG. 27D shows the chip after ITP (blood lysate and ITP buffers loaded in chip; purified DNA in elution well).

FIG. 31A shows a micrograph of ITP bands with focused DNA in each of 8 samples in the sample channel region of the device.

FIG. 31B shows independent voltage signal data at fixed currents for each of the 8 channels over time.

FIG. 31C shows a micrograph of the same 8 ITP bands with focused DNA from the samples eluted in the elution reservoir.

FIG. 31D is a magnified section of the voltage tracing (monitoring) used for triggering shown in FIG. 31B.

FIG. 45A shows an example of the fluidic layer of the chip.

FIG. 45B shows a cutaway of the pneumatic port.

FIG. 45C shows an implementation of this design.

FIG. 50A1 shows a fluidic surface of a substrate with channel terminating in through-holes that communicate with a reservoir on an opposing, reservoir surface of the substrate.

FIGS. 50A-50B show technical drawings of an exemplary elution reservoir on the chip device.

FIGS. 52A-52D show a fluidic reservoir consisting of an elliptical through-hole, dimensioned such that a pipette tip can be easily positioned for reliable fluid recovery from said device.

FIG. 55 depicts a pneumatic control block diagram for beta prototype and production instrument.

FIGS. 56A-56B and 58A-58C show alternative mechanisms for closing channels without the use of heat or pressure-induced plastic deformation of a fluidic device.

FIG. 67 shows a plot of peak area response to nucleic acid mass for various nucleic acid binding dyes.

FIG. 68 shows a plot of peak width response to nucleic acid mass for various nucleic acid binding dyes.

FIGS. 69A-69C depict Quantifluor® incompatibility with PCR.

FIG. 70 depicts PicoGreen compatibility with Qubit dsDNA Assay.

FIG. 71 depicts Syto13 compatibility with Qubit dsDNA Assay.

FIGS. 72A-72B depict PicoGreen compatibility with PCR.

FIGS. 73A-73C depicts Syto13 compatibility with PCR. gDNA was purified using isotachophoresis in the presence and absence of Syto13.

FIG. 74 depicts PicoGreen compatibility with amplicon-based sequencing library prep.

FIG. 75 shows Syto13 compatibility with amplicon-based sequencing library prep.

FIGS. 76A-76B depict PicoGreen incompatibility with whole genome sequencing library prep.

FIGS. 77A-77B depict Syto13 compatibility with next generation sequencing library prep.

FIG. 78 shows PicoGreen incompatibility with whole genome sequencing library prep.

FIG. 79 depicts Syto13 compatibility with next generation sequencing library prep.

FIGS. 80A-80D depict Syto13 compatibility with whole exome next generation sequencing library prep.

Figure 81:
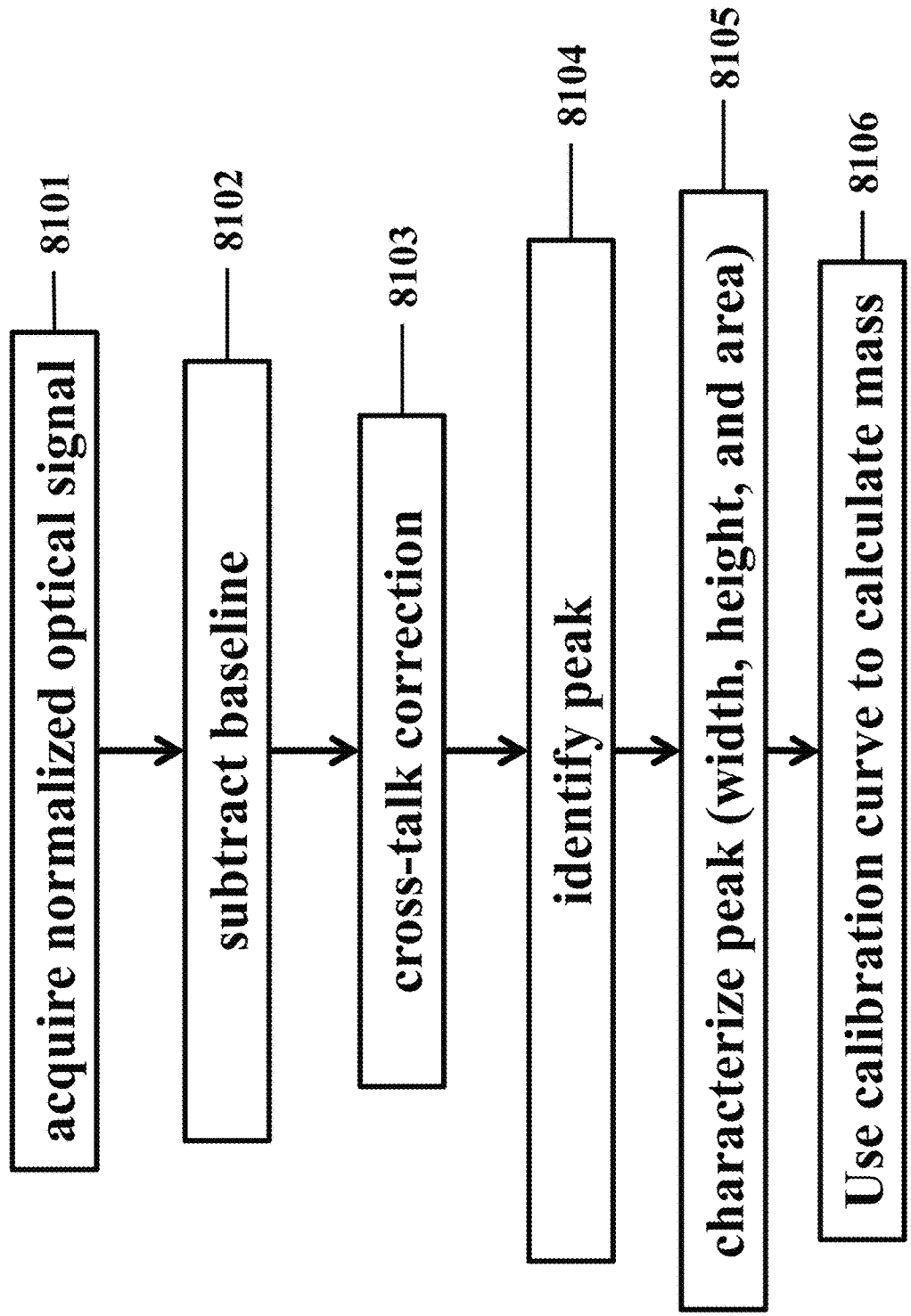

FIG. 81 shows a block diagram that describes an optical signal processing algorithm.

Figure 82:
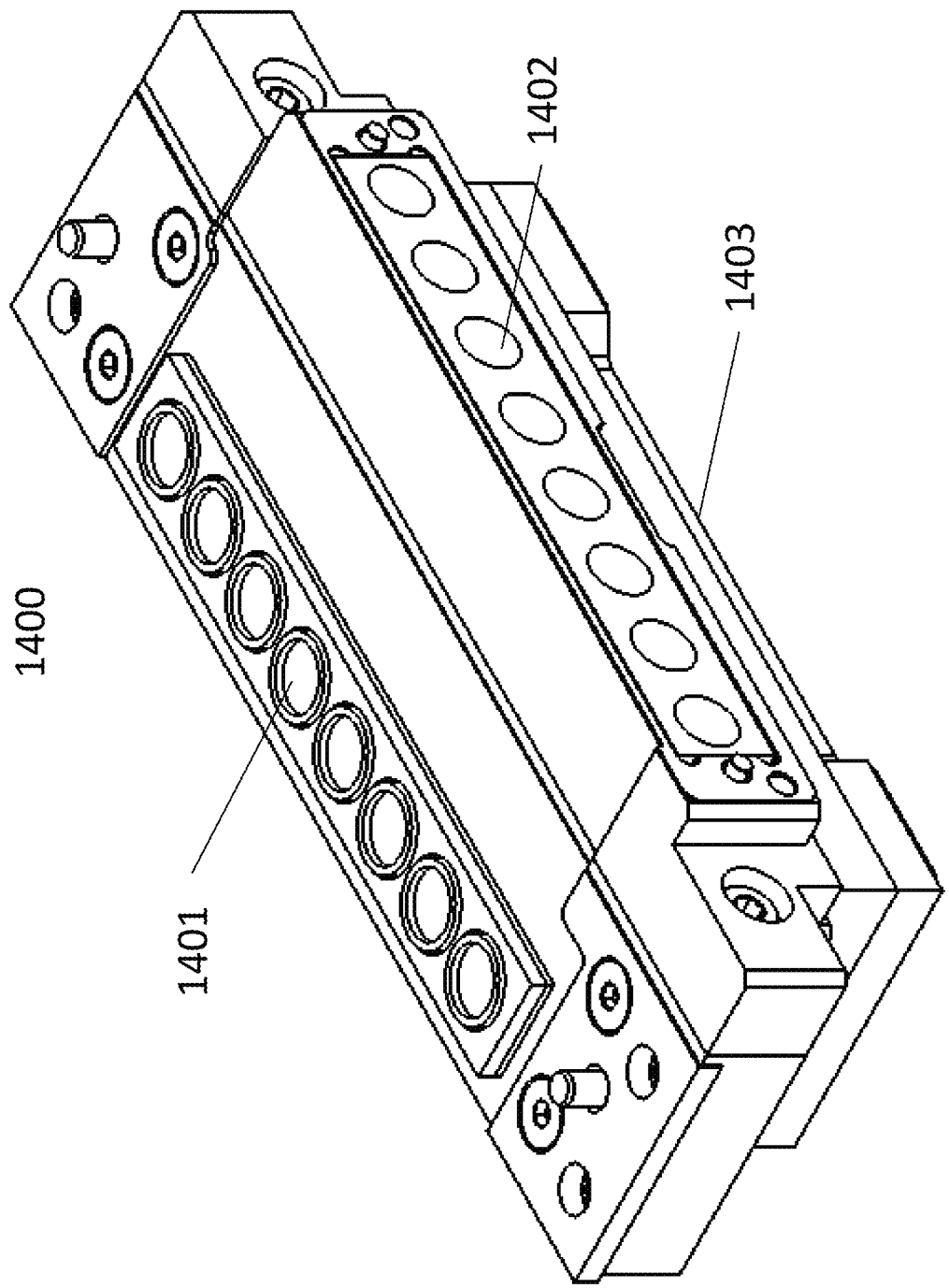

FIG. 82 shows a drawing of a mechanical optical assembly design for illumination and detection of the florescence of a sample bound to a dye.

Figure 83:
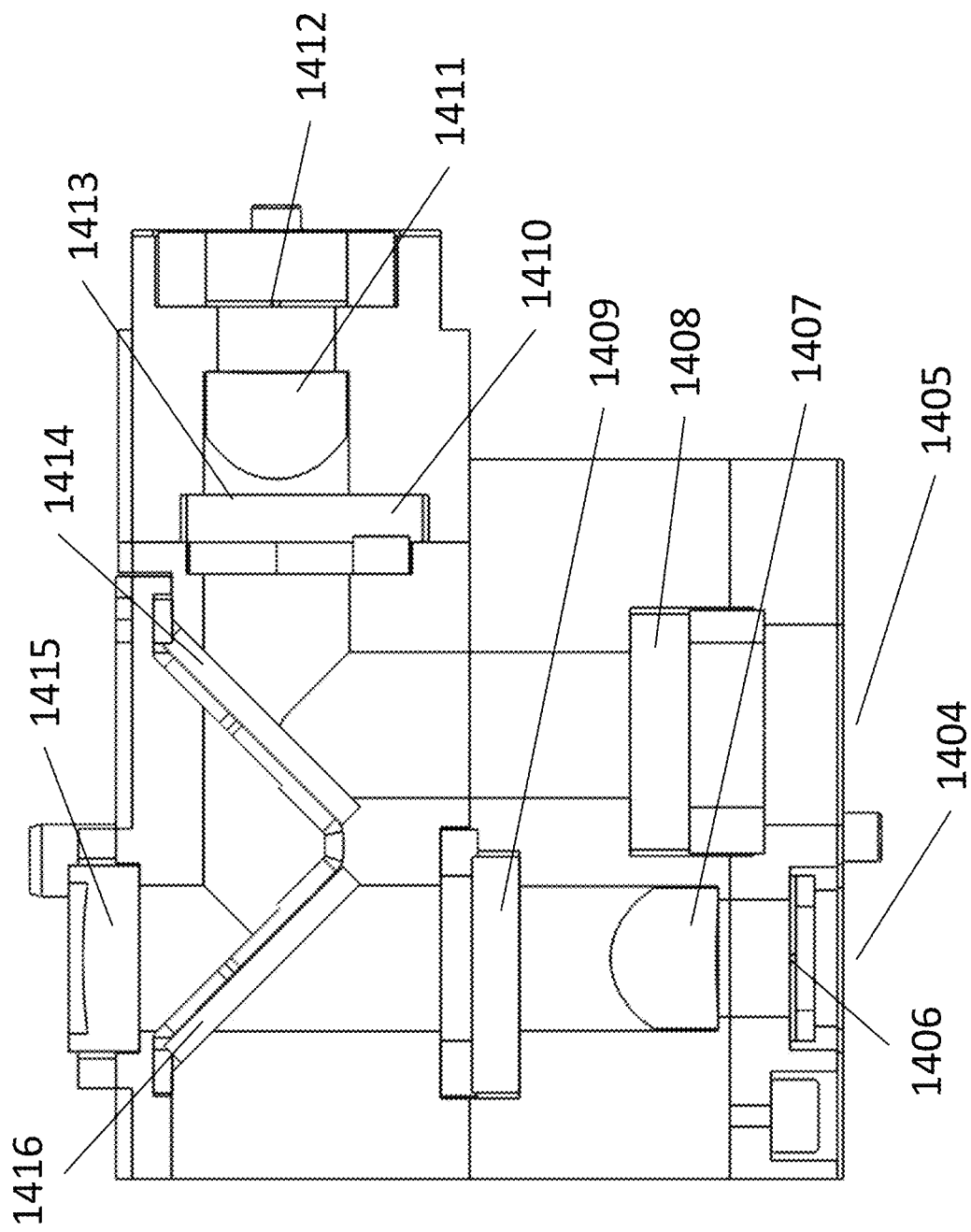

FIG. 83 shows the optical path that achieves excitation of a sample bound dye fluorescence and the capture of the emitted light from the sample bound dye fluorescence.

FIGS. 84A-84F show a control scheme for how an electrical circuit created by electrodes in a channel may be verified.

Figure 85:
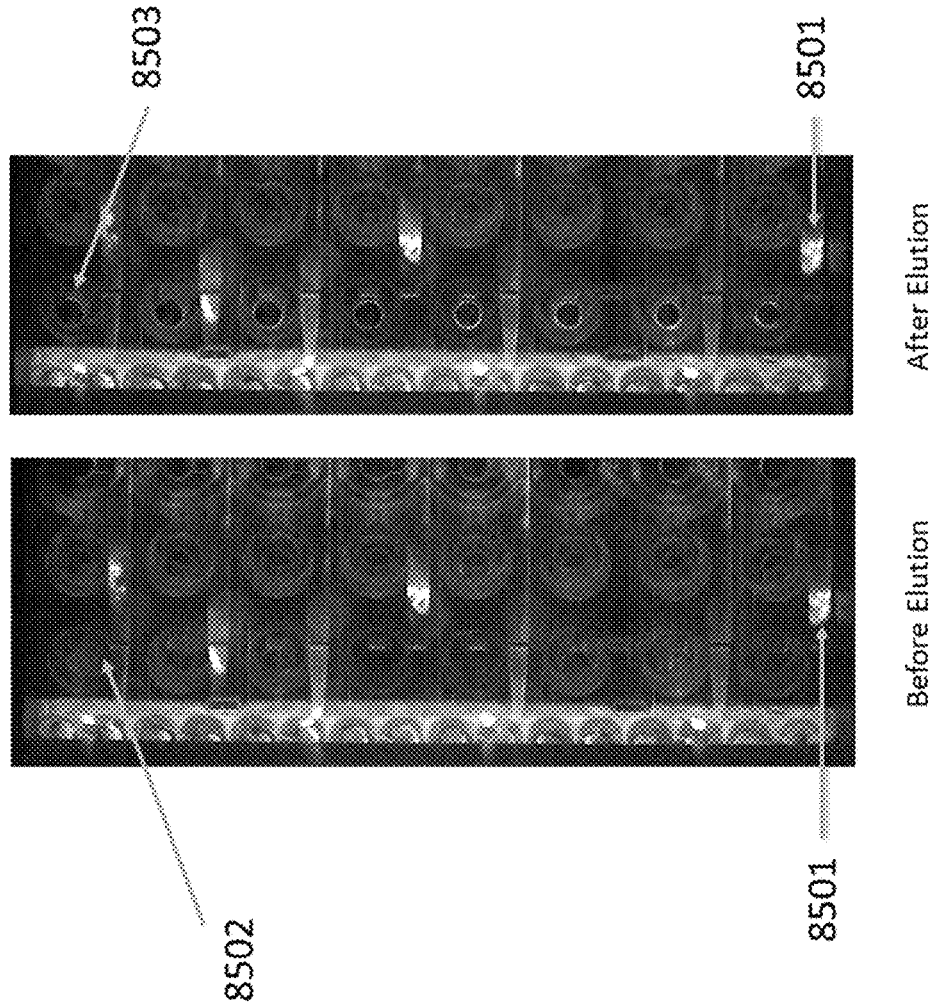

FIG. 85 shows a channel closer—tooth like member with mechanical actuator

Figure 86:
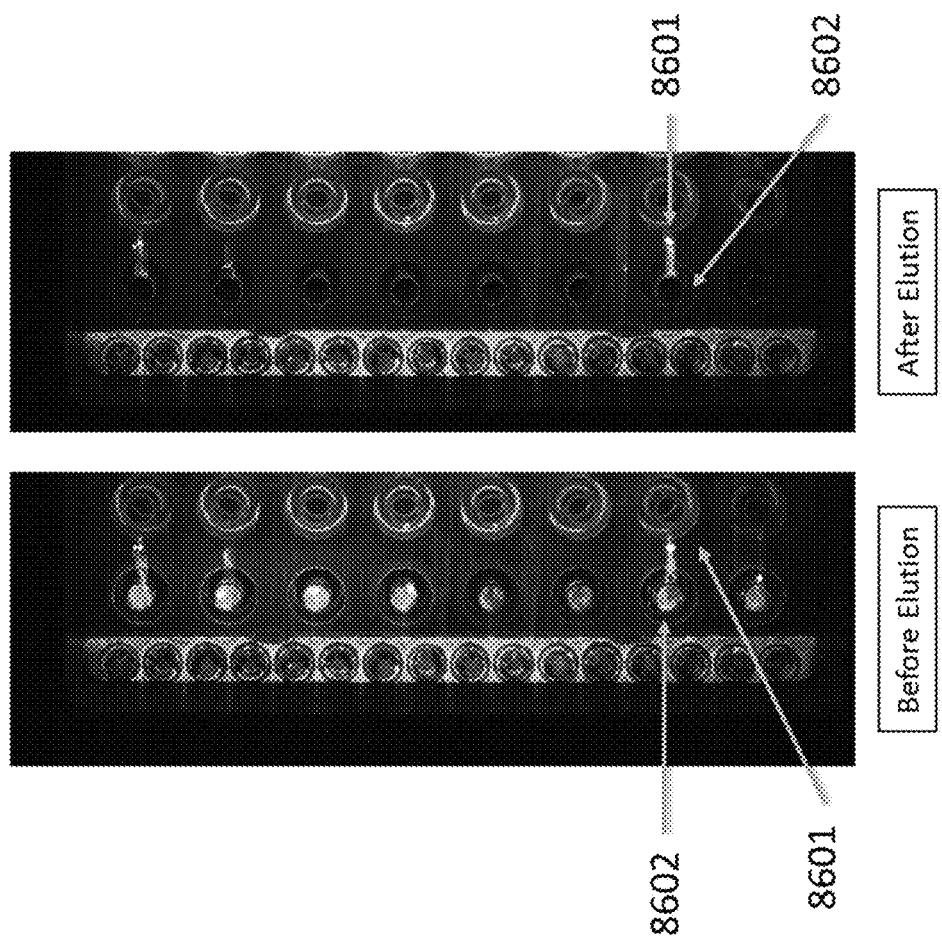

FIG. 86 shows contrast images of dyed analyte material in the channel.

Figure 87A:
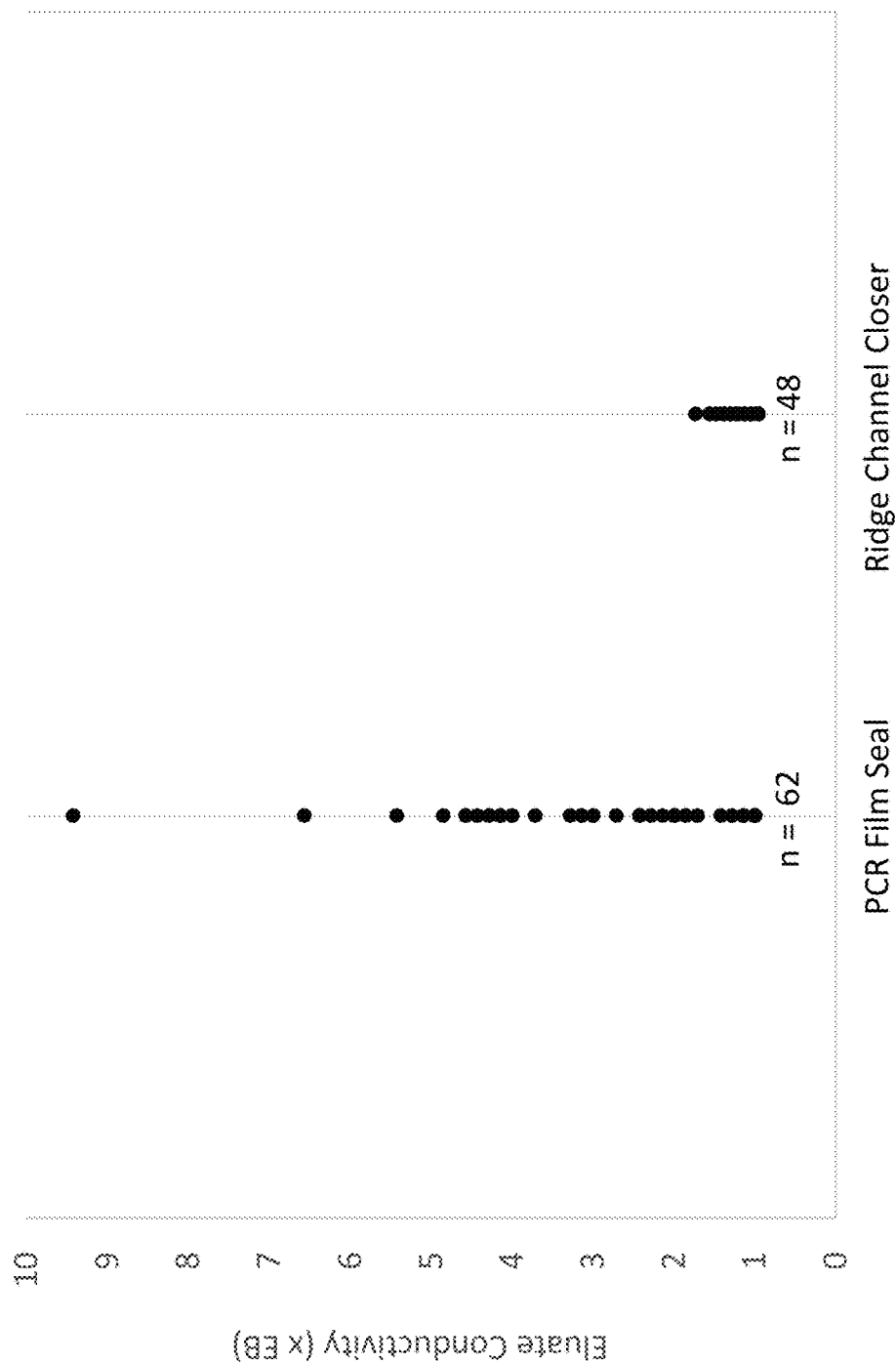

FIG. 87A shows conductivity data that was obtained by using a conductivity meter to measure the conductivity of eluted material.

Figure 87B:
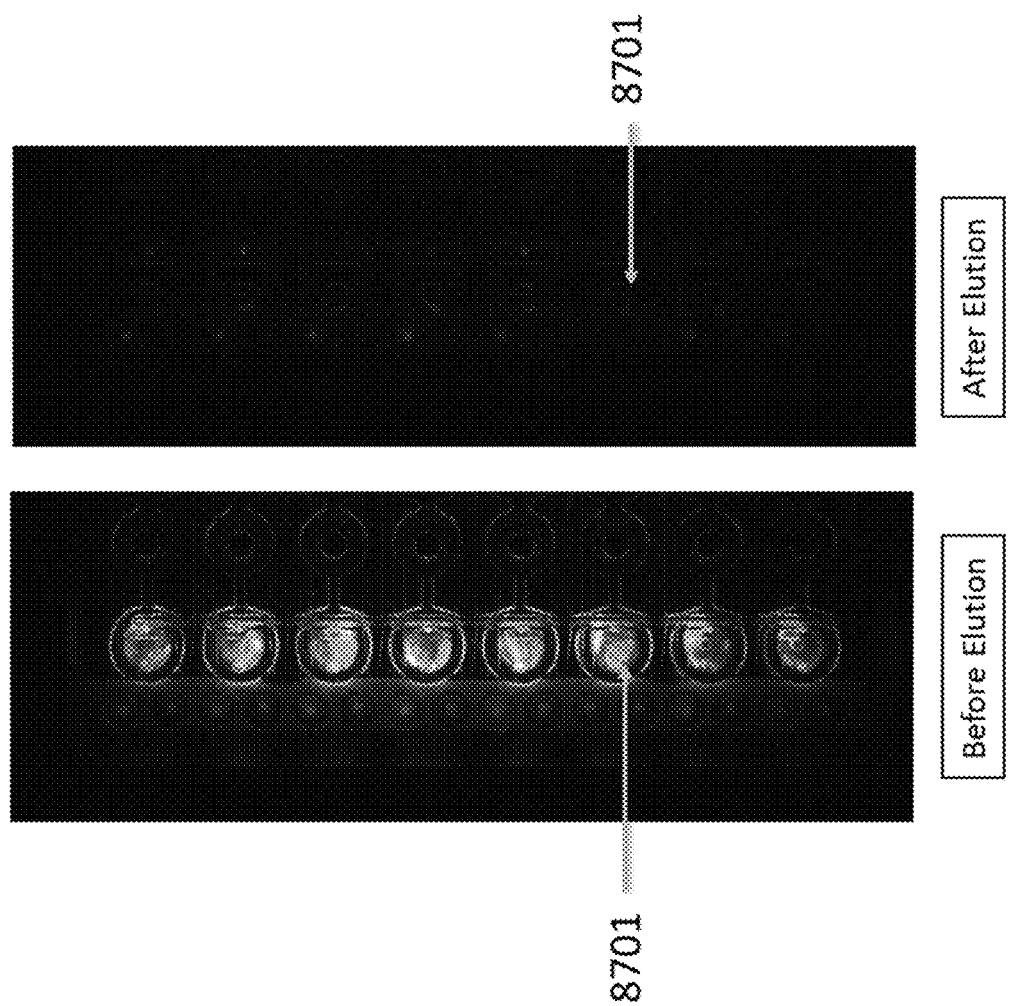

FIG. 87B shows contrast images of dyed analyte material in the channel.

FIG. 88A shows a typical trace of temperature signal captured by IR sensor during the run.

FIG. 88B shows the first-order derivative values of the temperature data in Figure A.

Figure 88C:
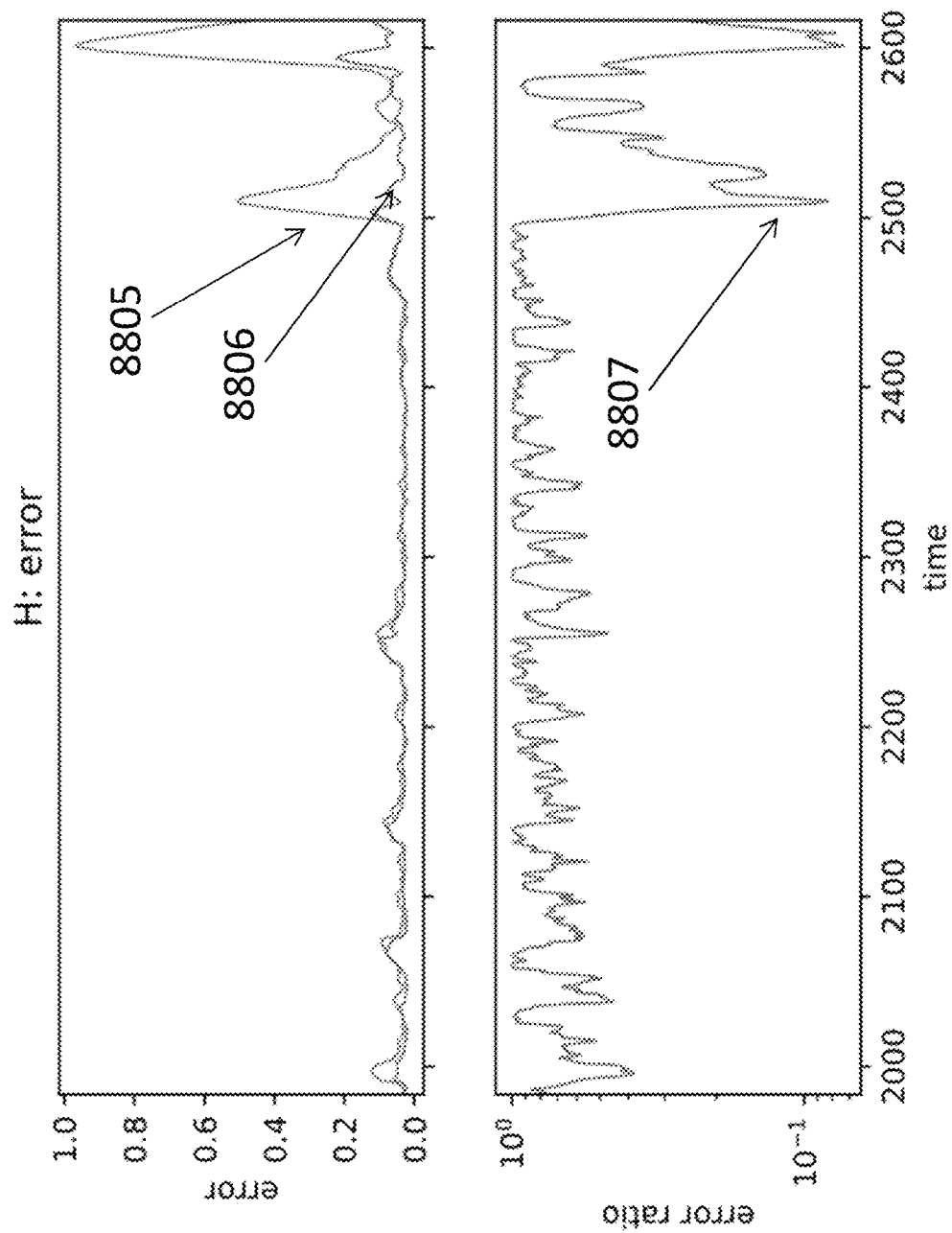

FIG. 88C shows the residual of the data minus the fit (0016) and the data minus the null hypothesis (0015) are compared to produce a likelihood ratio.

Figure 88D:
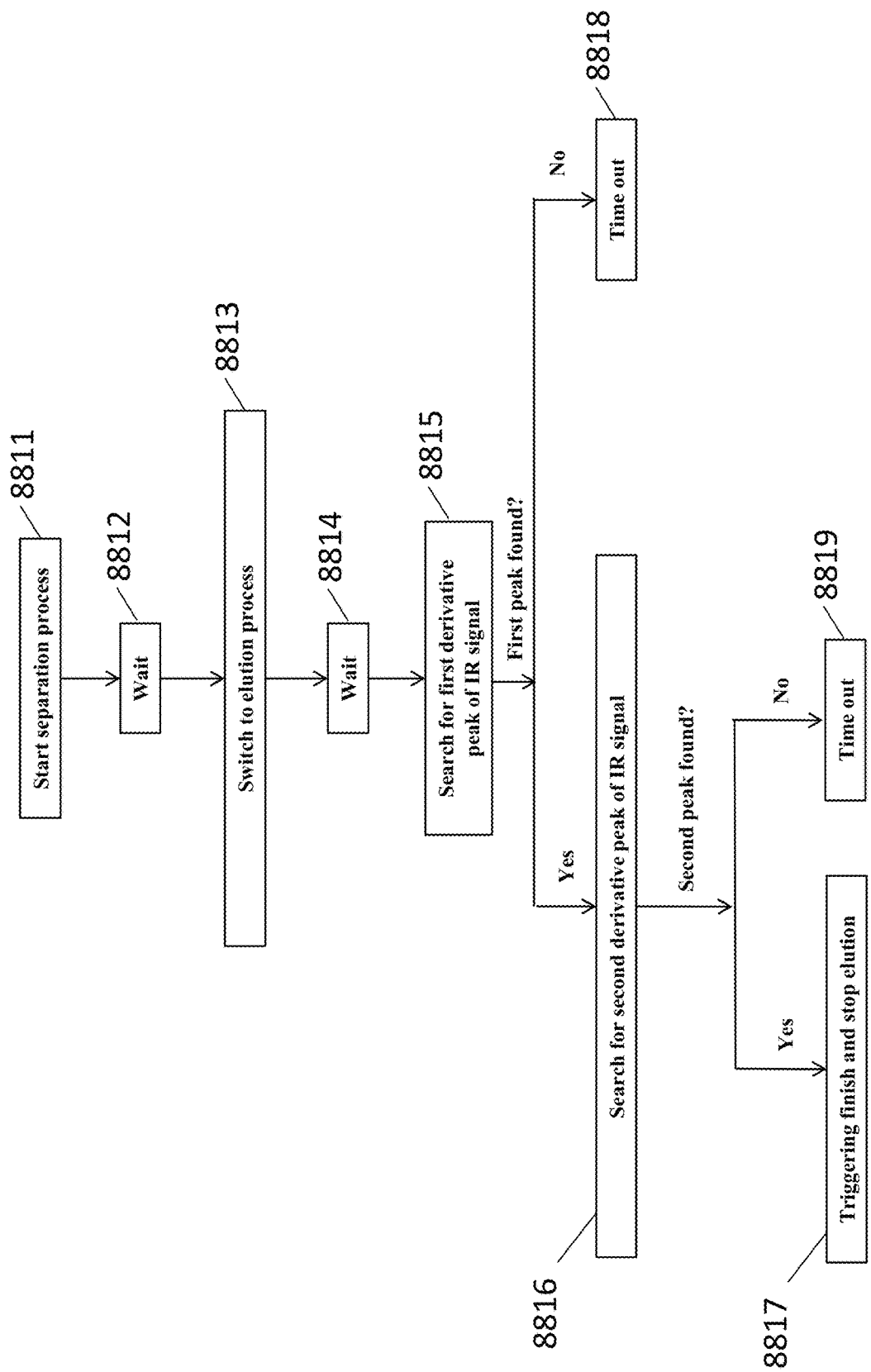

FIG. 88D shows a block diagram of triggering process.

FIG. 88E shows a successful triggering of a nucleic acid extraction process.

FIG. 88F shows a failed triggering run.

FIG. 89A shows the capillary barrier between sample (in this case, sample prepared in leading electrolyte) and leading electrolyte buffer.

FIG. 89B shows the passage of a nucleic acid with adding a slow ion (3-(N-morpholino)propanesulfonic acid) and a control.

FIG. 89C demonstrates the nucleic acid morphology sometime later in the extraction process.

FIG. 89D shows the capillary barrier between leading electrolyte buffer and elution buffer.

FIG. 89E shows examples of adjusting buffer interfaces.

FIG. 89F shows the facilitation of nucleic acid passage by adjusting interfaces position.

Figure 90A:
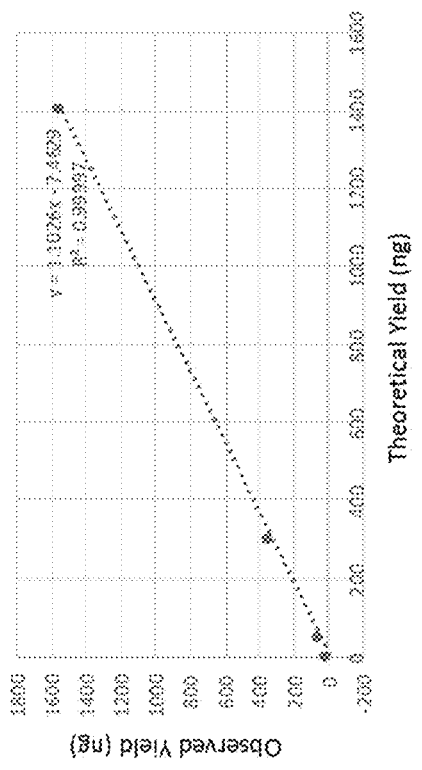
Figure 90B:
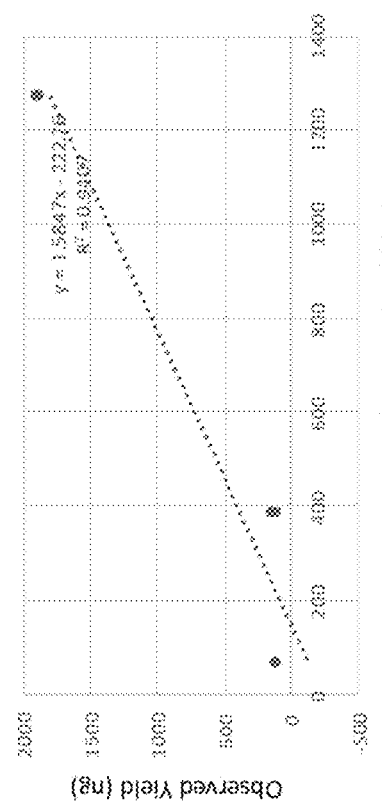
Figure 90C:
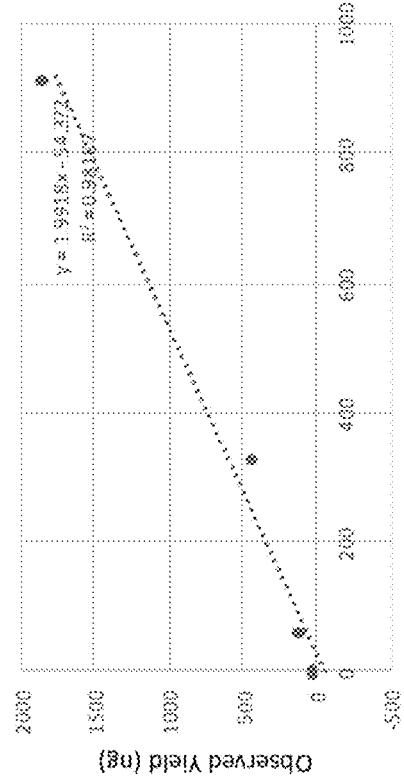

FIGS. 90A-90C show the lysis efficiency of three different cells lines.

FIGS. 91A-91B show exemplary temperature measurement results using an infra-red thermal sensor to trigger a reduction or elimination of an electric current in one of the channels.

Figure 92A:
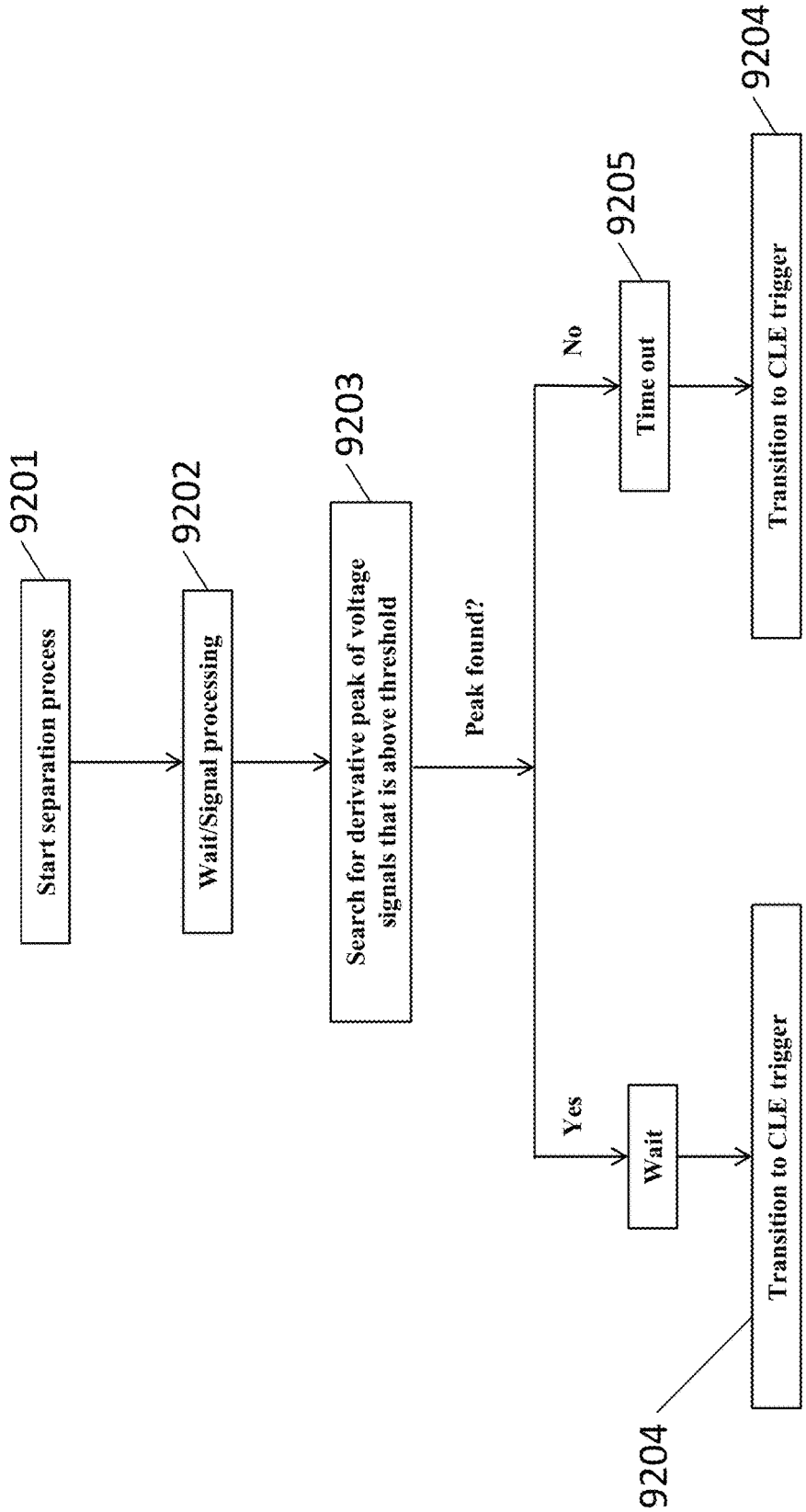

FIG. 92A shows a block diagram of sample channel to LE channel triggering process used.

Figure 92B:
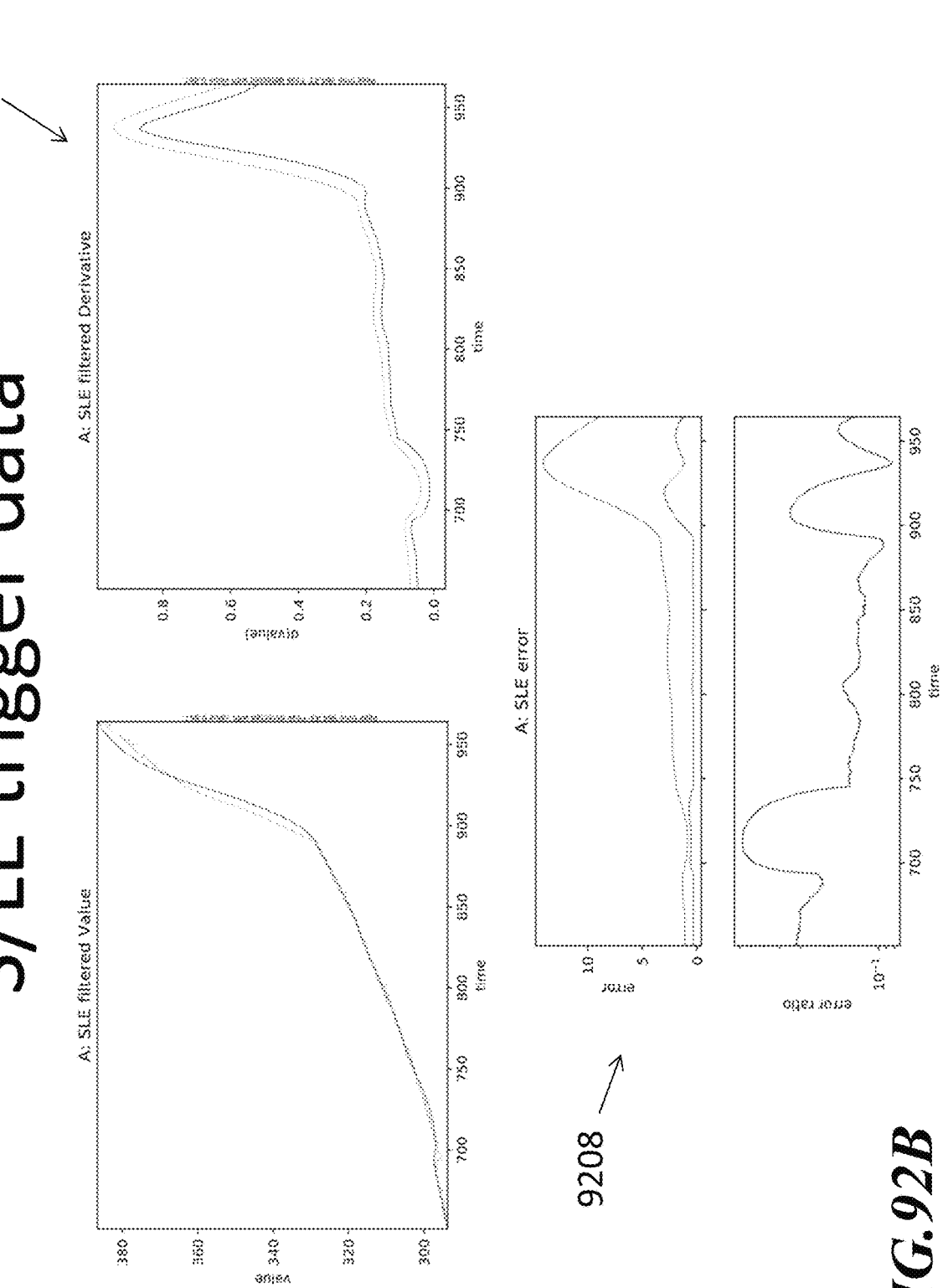

FIG. 92B shows exemplary traces of the voltage, the derivative of the voltage, and the measurement error used for sample channel to LE channel triggering.

Figure 92C:
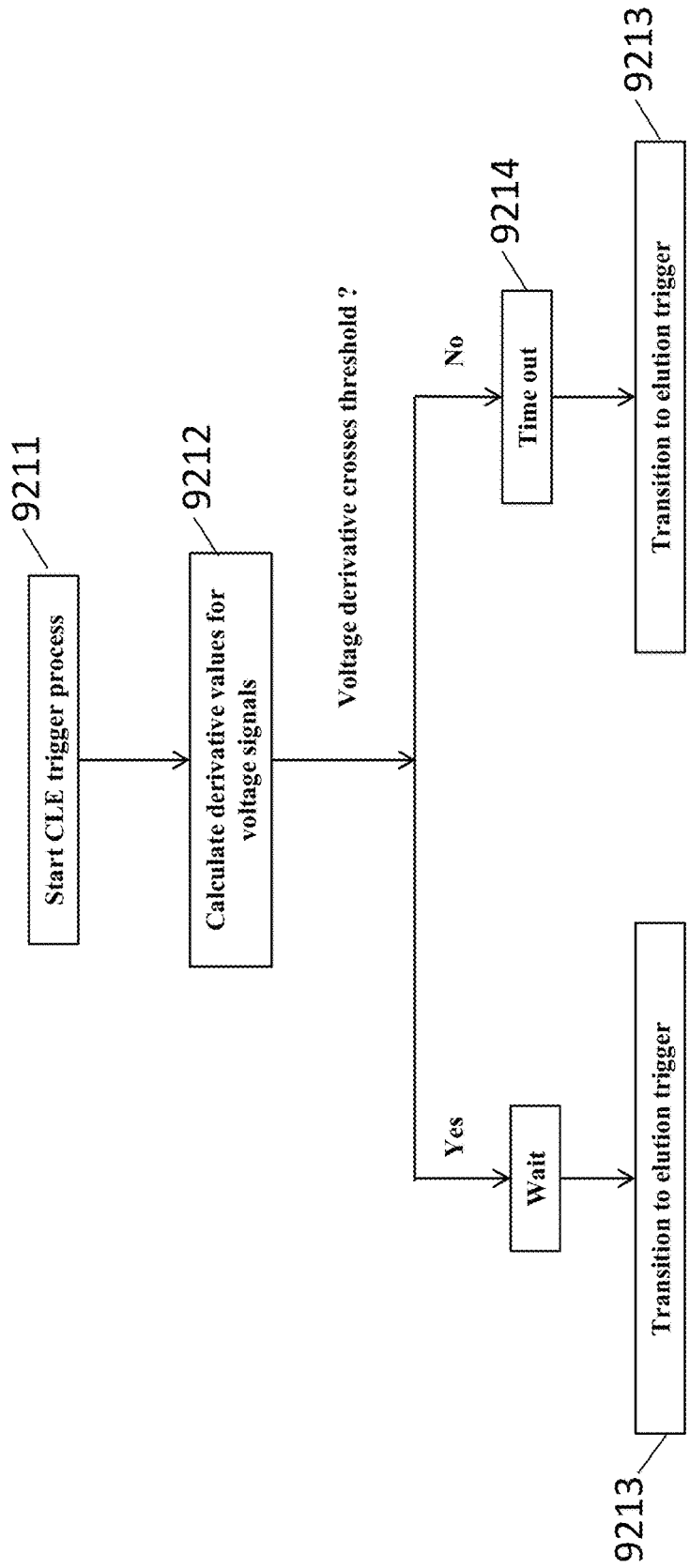

FIG. 92C shows a block diagram of LE channel triggering process used.

Figure 92D:
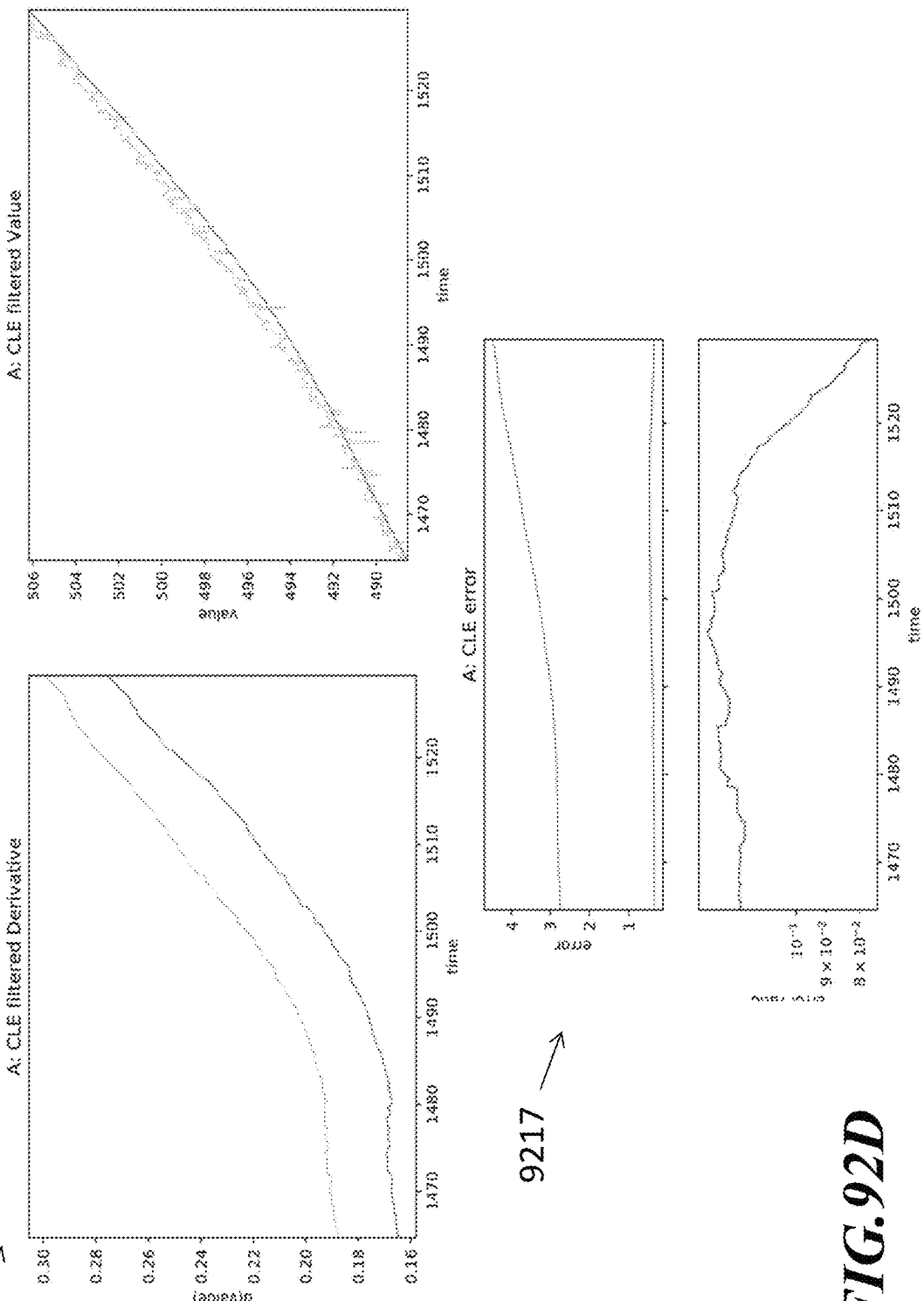

FIG. 92D shows exemplary traces of the voltage, the derivative of the voltage, and the measurement error used for triggering at the narrowing after the capillary barrier within the LE channel.

Figure 92E:
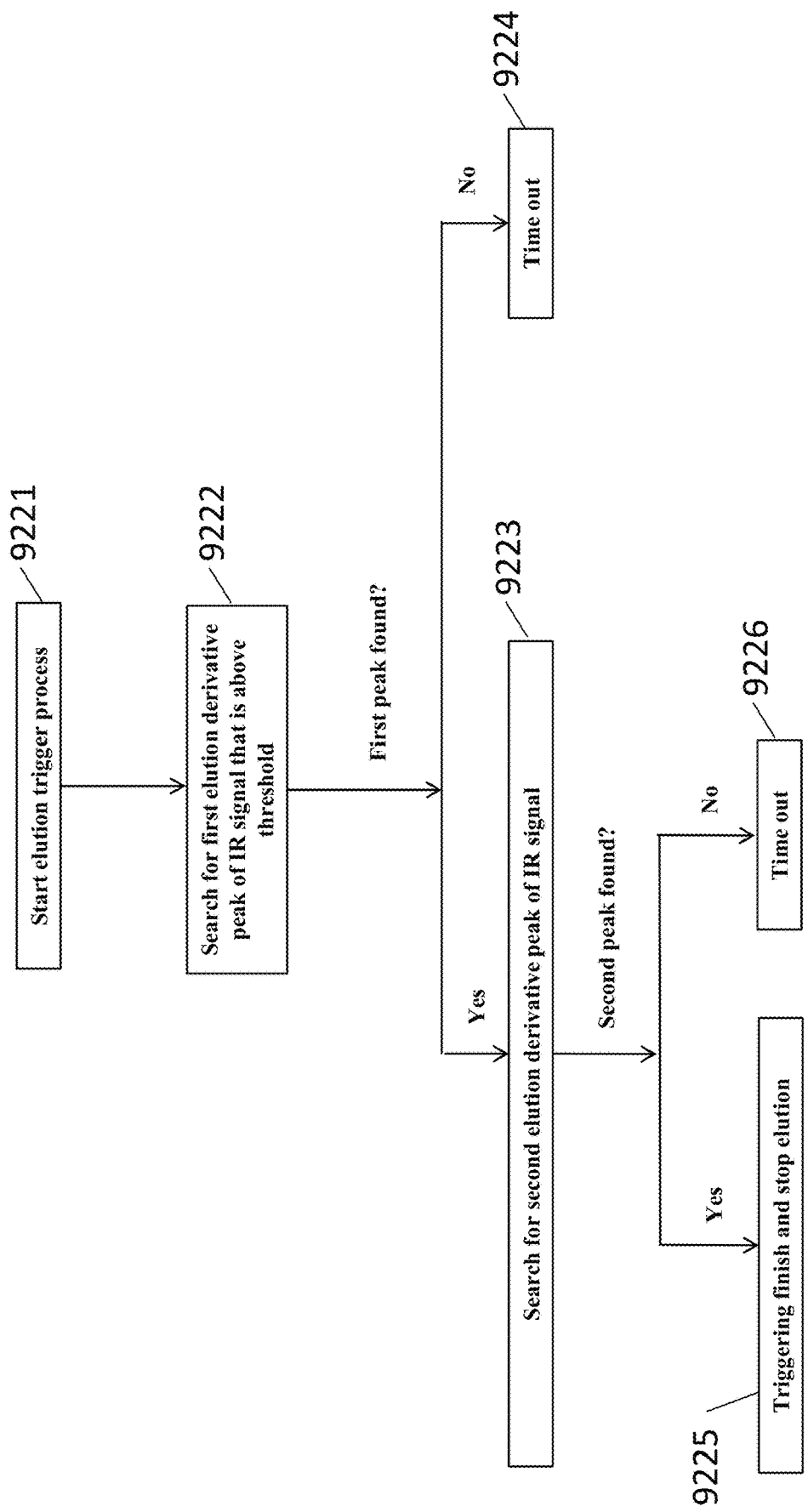

FIG. 92E shows a block diagram of the elution triggering process used.

FIG. 92F shows exemplary traces of the voltage, the derivative of the voltage, and the measurement error used for elution triggering.

DETAILED DESCRIPTION

Overview

Sample preparation is a first step to almost all genomic and transcriptomic analyses, and yet can be a primary source of analysis variability. Sample preparation can also be manually intensive, particularly when the sample is a formalin-fixed paraffin-embedded (FFPE) sample containing cross-linked proteins.

The present disclosure provides processes and devices to improve the efficiency of nucleic acid extraction and purification from tissue and cellular samples, including samples that have been processed in some way, such as paraffin-embedded samples or chemically-fixed samples (e.g., FFPE samples, samples that contain solid tissue). Methods provided herein include methods of on-chip or off-chip preparation of such processed samples prior to conducting isotachophoresis using methods that incorporate leading electrolyte ions and trailing electrolyte ions. In some instances, the methods include treating (e.g., by removal of embedding material, lysis, enzymatic disruption) a fixed solid tissue in a trailing electrolyte buffer or leading electrolyte buffer prior to conducting isotachophoresis on the sample. The methods can also include use of a second leading electrolyte buffer of lower ionic strength in order to produce a sample compatible with downstream processes like amplification or other enzymatic assays. The devices and systems provided herein include devices suitable for conducting isotachophoresis on samples derived from tissues, including microfluidic devices with parallel processing features and automated feedback-control mechanisms that may include thermal sensors that detect changes in temperature within sample processing channels.

The processes and devices of the present disclosure can provide improved nucleic acid recovery from a sample, especially from low abundance samples (e.g., less than 100 ng of nucleic acid), samples with relatively high volumes (e.g., total volume greater than 25 µl, total volume greater than 50 µl, total volume greater than 100 µl, or more) or liquid samples containing solid particles. The processes and devices provided herein also can provide high repeatability, and reduced bias for short nucleic acids. The devices provided herein can integrate sample preparation (e.g., removal of crosslinking or embedding material) and nucleic acid extraction operations within one device. Devices and processes of the present disclosure can also provide for compatibility with process automation, integration with downstream processes, integration with in-line quantitation (e.g., at single picogram resolution), and/or integration with nucleic acid length and sequence distribution analysis.

The methods provided herein are often methods of performing isotachophoresis under conditions suitable to extract nucleic acids from certain samples, especially FFPE samples. In some instances, the disclosed methods include methods of performing isotachophoresis using a trailing electrolyte buffer containing at least two ions with different magnitudes of effective mobilities. The methods may also include methods of conducting isotachophoresis using two different leading electrolyte buffers, one of which may serve as a sample elution buffer. The methods can include process automation and parallel processing of multiple samples.

The present disclosure also includes protocols using buffer and spacer chemistries. These buffer and spacer chemistries can include the use of multiple species of electrolytes for conducting ITP. For example, the trailing electrolytes can comprise a mixture of electrolyte species, capable of separating non-crosslinked nucleic acids from crosslinked nucleic acids, while separating either non-crosslinked nucleic acids or both crosslinked and non-crosslinked nucleic acids from contaminants within a sample.

The devices provided herein include injection-molded fluidic devices with parallel sample processing channels capable of performing ITP in a multiplexed fashion and ITP devices with two or more regions that are connected to a thermal device. Techniques of the present disclosure can employ ITP to simultaneously collect, purify, and focus extracted RNA and DNA, to quantify total extracted nucleic acid on-chip (e.g., via in-line ITP-aided concentration into very small volumes or labeling with an intercalating fluorescent dye), and to deliver nucleic acids downstream to parallel output reservoirs compatible with robotic pipetting.

Techniques of the present disclosure can enable purification of sample material (e.g., nucleic acids) without binding the sample material to a solid support. Techniques of the present disclosure can enable purification of sample material (e.g., nucleic acids) without the use of liquid-phase extraction. This can enable purification without dependence on solubility differences.

The operation of devices of the present disclosure can be automated, largely automated, or partly automated. In some cases, methods of the present disclosure involve only a single off-chip mixing step of dispensing a sample (e.g., FFPE section) into a solution (e.g., alkaline solution, lysis solution, or buffered solution comprising urea and/or thiourea), followed by loading of the sample into a reservoir of a fluidic device for further on-device sample preparation (e.g. deparaffinization, tissue disruption and cell lysing, protease digestion, proteolytic digestion, or other treatment including protein denaturation, or nuclease digestion) and nucleic acid extraction, purification, enrichment, in-line quantitation, and sizing or fractionation (e.g., size selection). In some cases, methods of the present disclosure include dispensing a sample (e.g., FFPE section or other tissue sample) into a reservoir or channel of a fluidic device (e.g., cartridge) pre-filled with a solution (e.g., alkaline solution, lysis solution, or buffered solution comprising urea and/or thiourea) for on-device sample preparation (e.g. deparaffinization, tissue disruption and cell lysing, protease digestion or other treatment including protein denaturation, or nuclease digestion) and nucleic acid extraction, purification, enrichment, in-line quantitation, and sizing or fractionation (e.g., size selection). In some cases, methods of the present disclosure include disruption tissue and/or lysing cells of a sample off-chip, followed by loading of the sample, which may be homogenous or a non-homogenous mixture of lysed solid tissue and nucleic acids, into a reservoir of a fluidic device for further on device sample preparation (e.g. deparaffinization, protease digestion or other treatment including protein denaturation, or nuclease digestion) and nucleic acid extraction, purification, enrichment, in-line quantitation, and sizing or fractionation (e.g., size selection). Nuclease digestion can include removal of DNA for DNA-free RNA extractions or removal of RNA for RNA-free DNA extractions. The fluidic devices provided herein can be used with a benchtop system to automate an electric-field-based method for the extraction of DNA and RNA from samples.

Devices of the present disclosure include systems that can automate and integrate on-chip heating (e.g., to a temperature from 37° C. to 80° C.), sample preparation (e.g., deparaffinization, tissue disruption and cell lysing), buffer exchange, nucleic acid extraction and purification, enrichment of uncrosslinked or amplifiable nucleic acids (e.g., by separating it away and delivering it separately from crosslinked nucleic acids), and delivery of purified nucleic acids to an output reservoir, such as an array compatible with manual or robotic pipetting. For example, the present disclosure includes an eight-channel cartridge in a standard, robotic automation compatible microtiter plate format, as well as integrated benchtop controller prototypes that can afford automated control of loading of buffers and other fluids, application of temperature and electric fields to the device, and automated start and end run processing of samples in parallel. This system can be easily modified in the future, as needed, to afford higher throughput for use in larger, diagnostic or clinical labs (e.g., 96-well sample format).

Figure 1A:
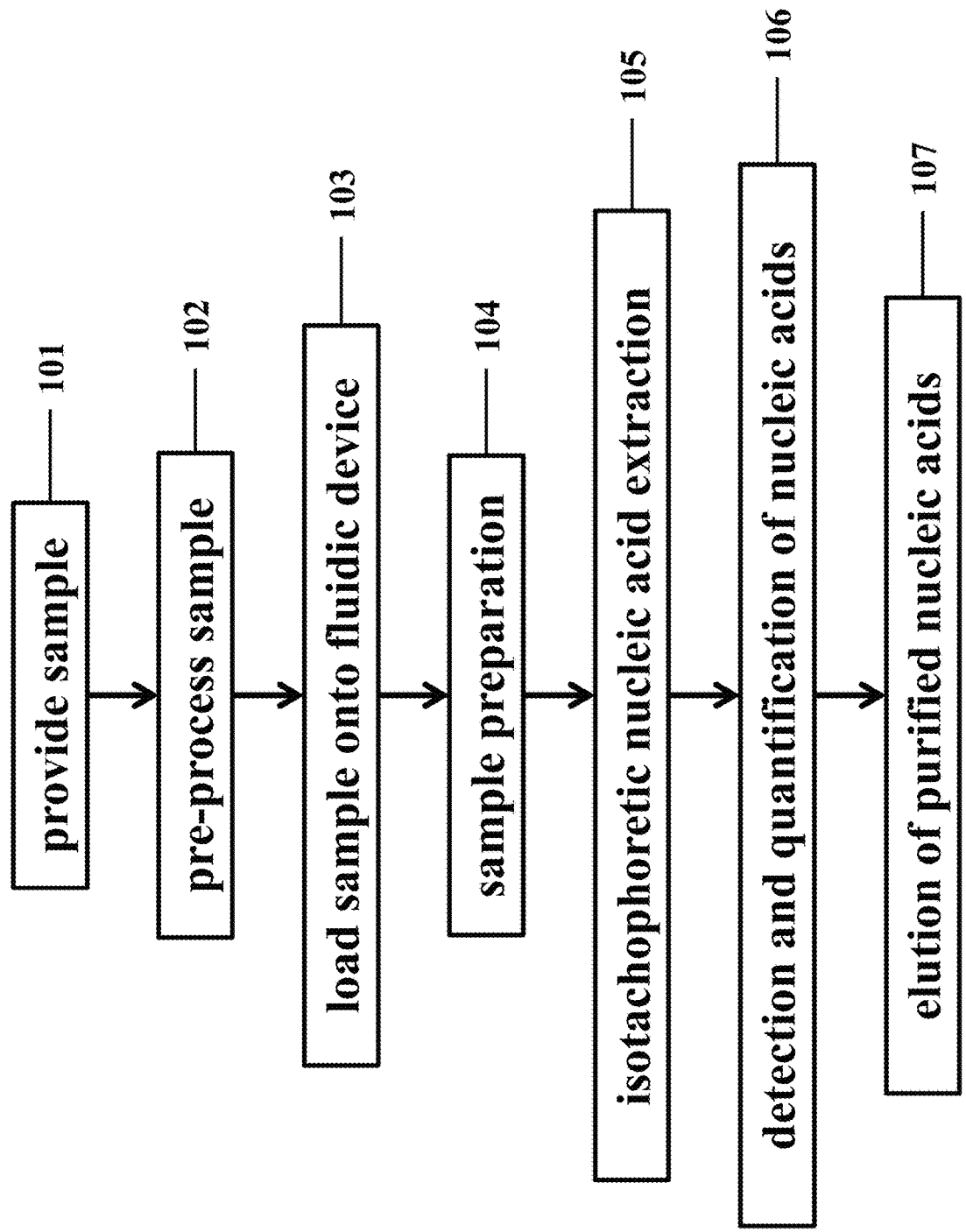
FIG. 1A shows an exemplary protocol for sample processing and nucleic acid extraction or purification.

For example, FIG. 1A shows an exemplary process diagram for sample processing and nucleic acid extraction using techniques of the present disclosure. A sample can be provided 101 and subjected to any pre-processing steps 102, such as mixing with a buffer, lysis, or removal of embedding material (if present). The sample (and, for example, buffer) can then be loaded onto a fluidic device 103. Sample preparation steps 104 can then be performed on the fluidic device, such as removal of embedding material (if present and if not previously removed during pre-processing), tissue disruption, cell lysis, protein or proteolytic digestion and (for example) nuclease digestion. Isotachophoresis 105 can then be performed to separate and purify nucleic acids from contaminants within the sample (e.g. cell debris, plasma membranes, small molecules, embedding material, crosslinked nucleic acids, fixatives such as formalin, inhibitors, enzymes such as digestion or restriction enzymes). Other steps can occur concurrently with isotachophoresis, such as de-crosslinking of crosslinked nucleic acids (e.g. with heat or protease digestion). Nucleic acids can be detected and quantified 106 during or subsequent to isotachophoresis. Once extracted or purified, nucleic acids can then be eluted and recovered from the device 107.

Figure 32A:
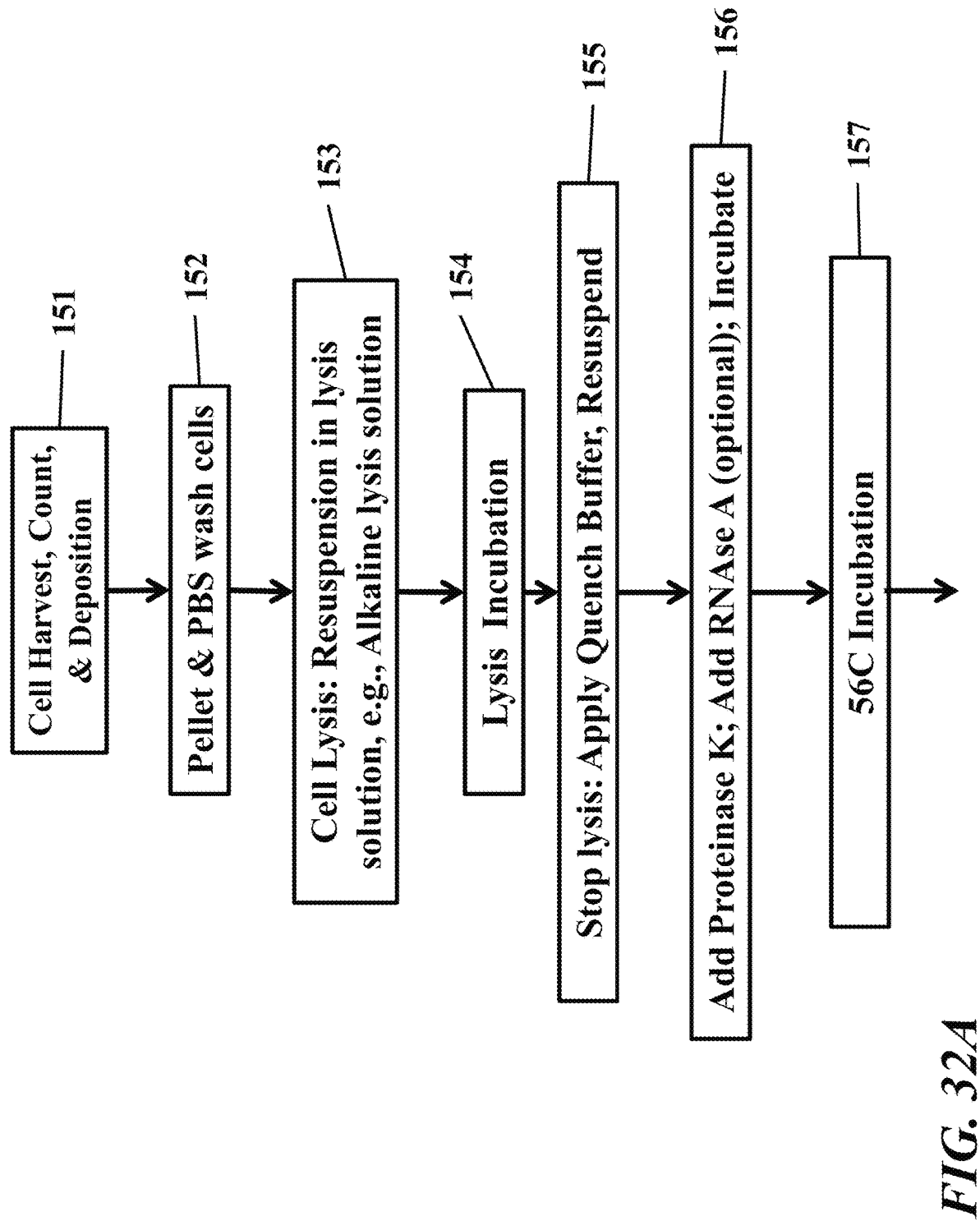
FIG. 32A shows an exemplary method for sample preparation from cultured mammalian cells and ITP for DNA purification.
Figure 32A:
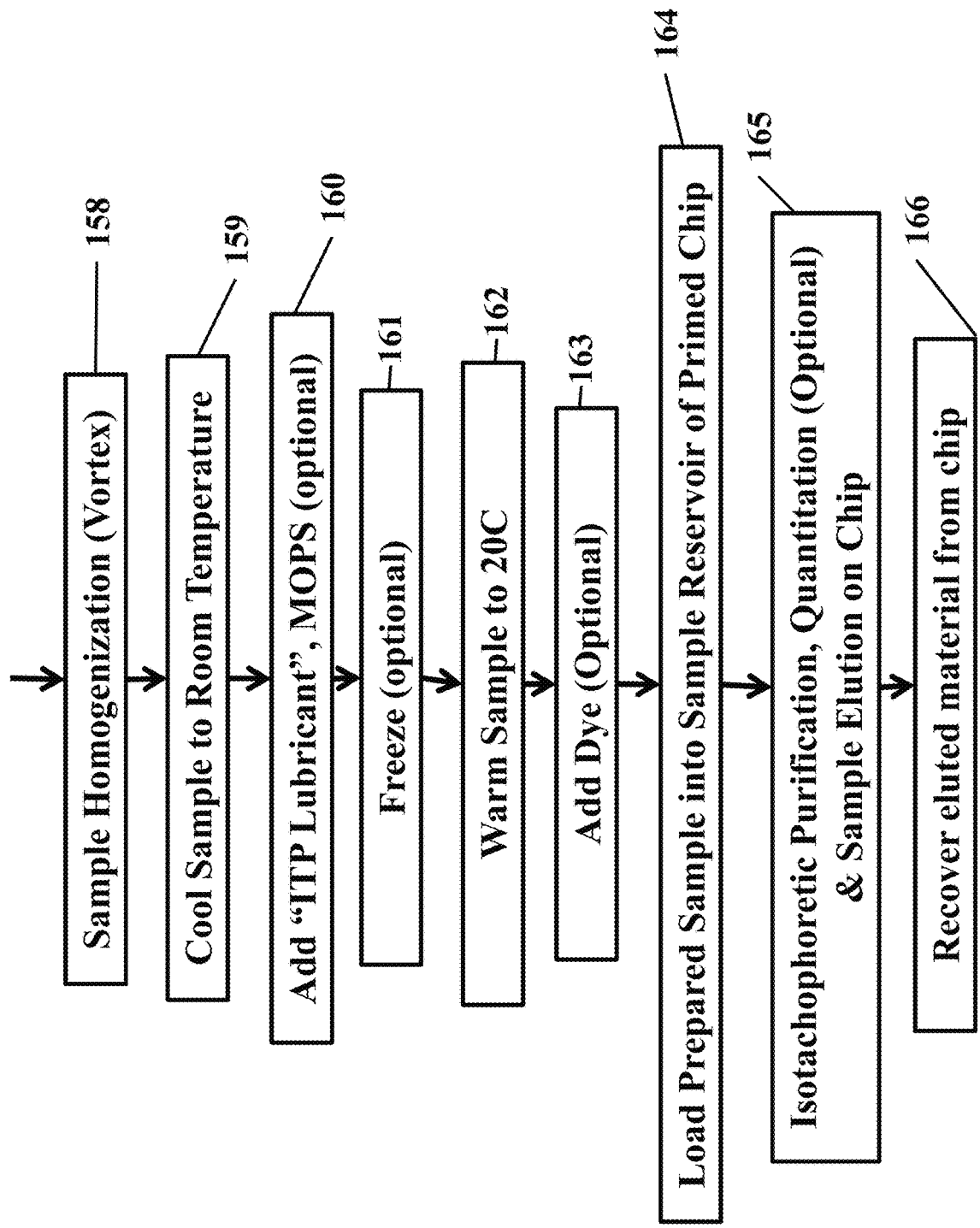

FIG. 32A shows a non-limiting exemplary method for sample preparation from cultured mammalian cells and ITP for DNA purification utilizing the methods and devices provided herein. In general, the steps may include isolation (Step 151) and washing of cells (Step 152), cell lysis (Steps 153-155) and protein degradation (Steps 156-157), and homogenization of liberated DNA in a lysate (Steps 158-159), all while maintaining appropriate ionic content for downstream ITP.

At Step 151, cultured mammalian cells may be pelleted from live, healthy (e.g. >90% viability), log-phase cell culture by centrifugation (e.g. 250 g×5 min). Pelleting may be preceded by trypsinization in at least some instances, for example when using adherent or semi-adherent cells. The spent media may be discarded before washing the cells in fresh media, pelleting the cells, resuspending the cells in fresh media, and counting the cells. A cell suspension of appropriate density (e.g. 100,000 live cells per lane of ITP extraction) may be deposited into a microcentrifuge tube (e.g. a 2 ml Eppendorf Lo-Bind microcentrifuge tube) for downstream processing (e.g. Steps 152-163 below). In some instances, as will be apparent to one of ordinary skill in the art, fluorescence-activated cell sorting (FACS) of the resuspended may be used to isolate and count cells of interest into a recipient tube which may then be prepared as described herein for ITP.

At Step 152, the cells may be washed with a buffer such as phosphate buffered-saline (PBS). The cells may be pelleted by centrifugation (e.g. at 250 g×5 min). The cell culture media may then be discarded and the pellet may be resuspended in PBS (e.g. 190 uL 1×PBS (no Ca2+ or Mg2+)). The resuspended cells may be centrifuged to form a pellet and the PBS supernatant may be removed from the pelleted cells.

At Step 153, the cell pellet may be lysed through pipet resuspension (e.g. by pipetting 5 times using a P1000 pipette) in a lysis buffer, for example in a proprietary alkaline CCD Lysis buffer ("L1"). Lysis may alternatively or in combination be performed using other lysis techniques which will be known to one of ordinary skill in the art, for example via sonication, manual grinding, beadbeating, homogenization, freezing, enzymatic digestion, and/or chemical disruption. The lysed cells may then be vortexed to mix (e.g. for 3 sec). Generally, at step 153, the lysis buffer is highly alkaline. In some cases, an alkaline solution may comprise 30-120 mM NaOH (in some cases, 40-80 mM NaOH) at a pH of about 10-13. An exemplary alkaline solution may comprise 80 mM NaOH, 11 mM DTT, and 0.5% v/v Igepal CA-630.

At Step 154, the cells may be incubated in the lysis buffer at room temperature (e.g. for 2 min) in order to allow the lysis process to lyse the cells.

At Step 155, lysis may be stopped and the sample pH may be neutralized. For example, a proprietary acidic Quench buffer ("Quench") may be applied to the lysed cell sample. In some cases, the Quench buffer may contain LE only, both LE and TE, or TE only. In some cases, including both LE and TE or TE only in the Quench buffer may reduce retention of nucleic acids at a capillary barrier, particularly a capillary barrier between the sample and LE. In some cases, quenching as described in step 155 is not performed in a method disclosed herein (e.g., for high molecular weight DNA applications). For example, it may not be necessary when a lysis solution is within a neutral or non-alkaline pH. In such cases, the LE, LE and TE, or TE may be included in the lysis solution. Quenching is generally useful when an alkaline lysis solution is used during the lysis step (e.g., for cultured cell applications or primary human cells).

The sample may be mixed by pipetting (e.g. by pipetting up and down five times) and then vortexed (e.g. for 3 sec).

At Step 156, the lysed cells suspension may be treated to denature proteins in the cell lysate. Optionally, RNA (or DNA if the sample molecule of interest for ITP is RNA) may be degraded. For example, Proteinase K (e.g. 20 mg/mL) and optionally RNAse A (e.g. 10 mg/mL) may be added. The sample may be vortexed (e.g. for 3 sec) to mix and then pulse-spinned before incubation at room temperature (e.g. for 2 min).

At Step 157, the sample may be incubated at 56° C. incubation for 10 min.

At Step 158, the sample may be homogenized by vortexing (e.g. for 3 sec) and pulse-spinning.

At Step 159, the sample may then be cooled to room temperature (e.g. for 5 min). In some cases, where samples are prepared in LE, a TE can be added after cooling to reduce or minimize retention of nucleic acids at a capillary barrier, particularly a capillary barrier between a sample and LE.

At Step 160, a sample surfactant (e.g. MOPS) may optionally be added to the sample.

At Step 161, the sample may optionally be frozen for use at a later date.

At Step 162, the sample may be warmed to 20° C.

At Step 163, a nucleic acid dye or stain may optionally be added to the sample lysate for visualization and detection (e.g., for quantitation of nucleic acid mass) of nucleic acid. For example, the addition of a nucleic acid stain, such as a nucleic acid binding or intercalating dye, may be used when in-line quantitation of nucleic acid mass is performed during the ITP process.

At Step 164, the sample may be loaded into one or more sample reservoirs. Prior to loading, the sample may be pulse vortexed (e.g. twice) and pulse-spinned to agitate and mix the sample. The ITP channel may be pre-primed with leading electrolyte buffer, trailing electrolyte buffer, and/or other buffers as described herein. Alternatively, the sample may be loaded at the same time as the rest of the liquids in the channel.

At Step 165, ITP may be performed. During the ITP process, the DNA within the sample may be purified (i.e. concentrated) as it moves through the channel until it reaches the elution reservoir as described herein. The sample DNA may be quantified as described herein.

At Step 166, the eluted sample may be recovered by elution (e.g. by pipetting) from the elution reservoir.

Figure 32B:
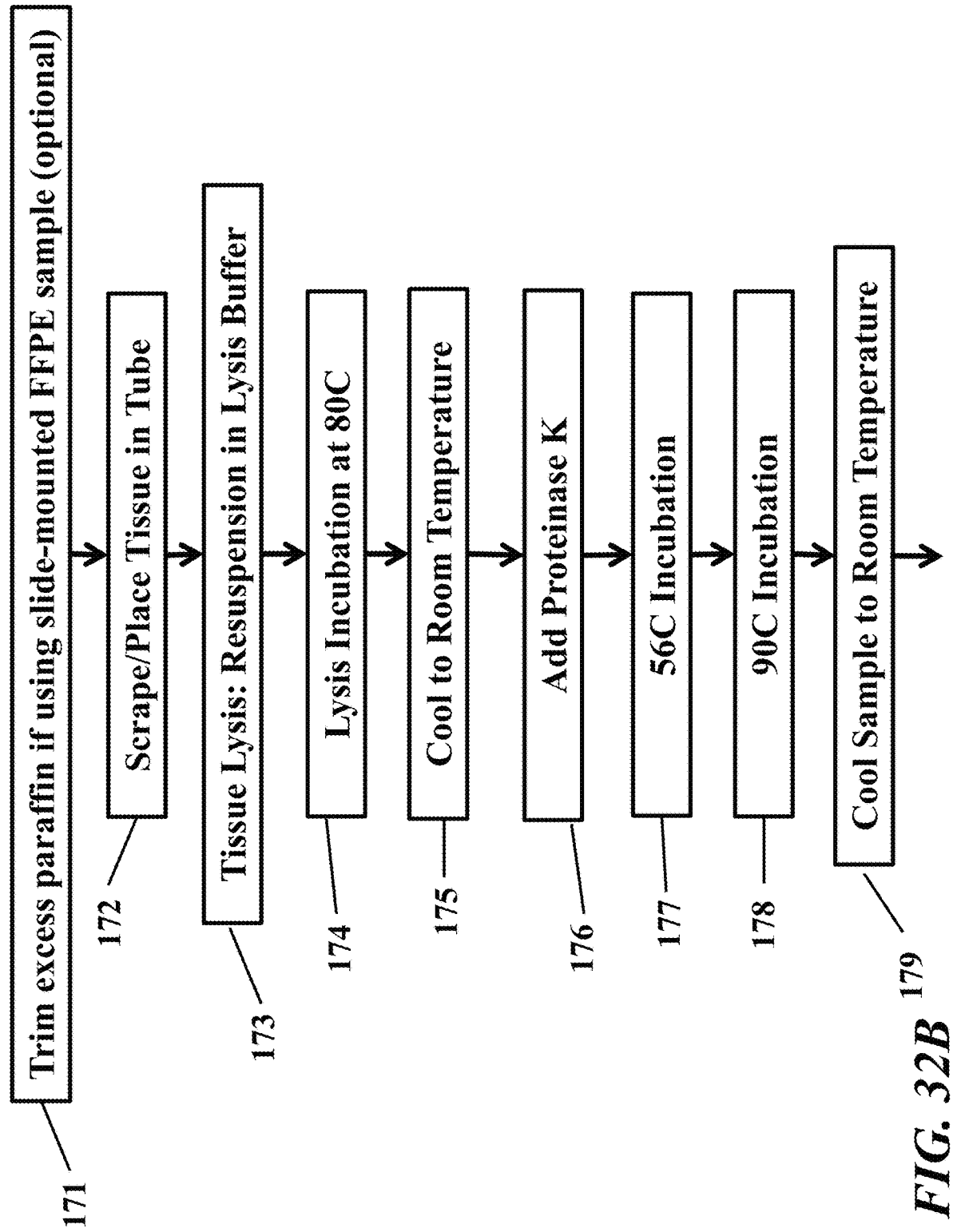
FIG. 32B shows an exemplary method for sample preparation from tissue samples and ITP for DNA purification.
Figure 32B:
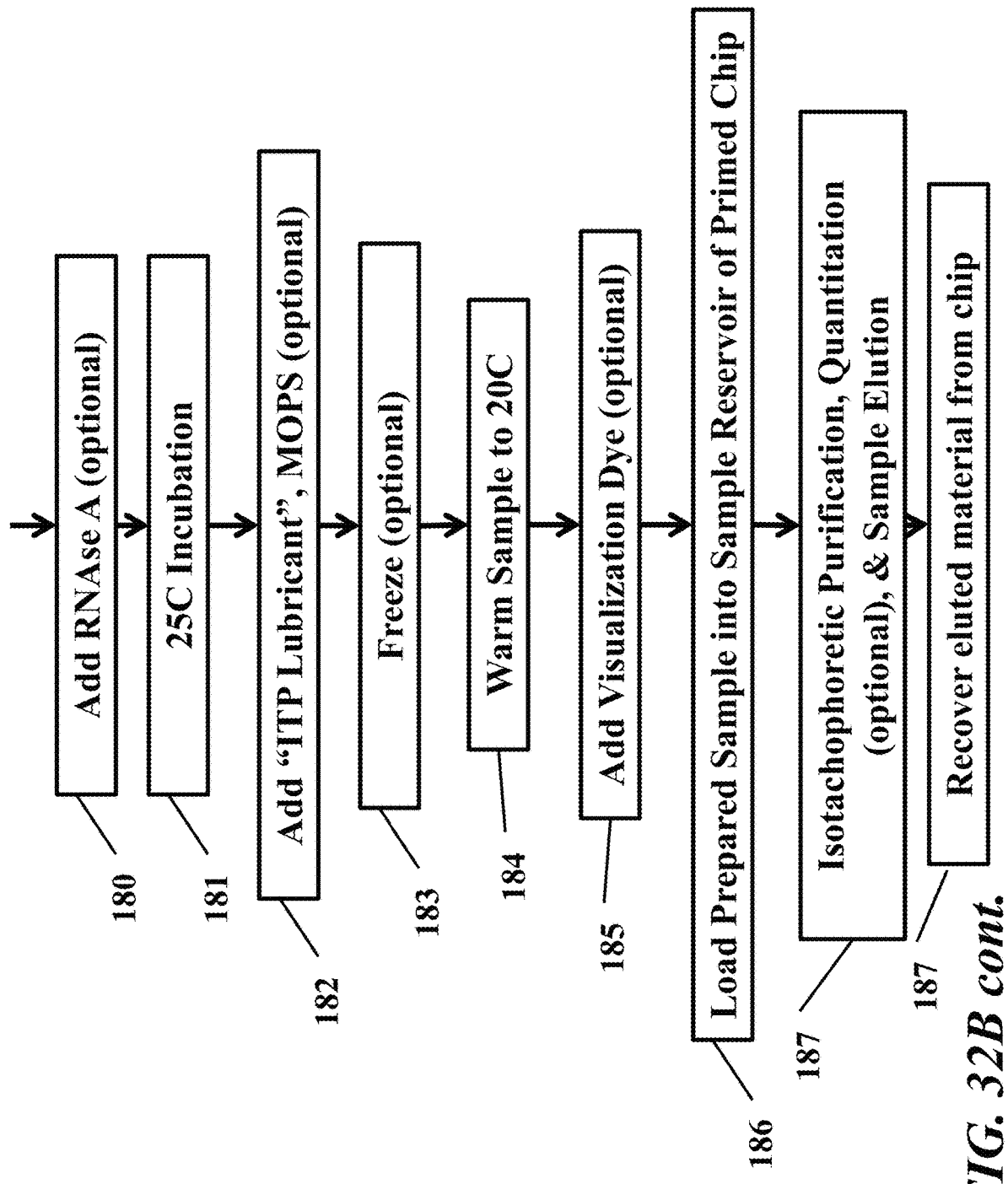

FIG. 32B shows a non-limiting exemplary method for sample preparation from tissue samples (e.g. fresh or FFPE tissue samples) and ITP for DNA purification utilizing the methods and devices provided herein. In general, the steps may include trimming excess paraffin from the tissue (e.g. when using slide-mounted FFPE tissue section)(Step 171), tissue lysis (Steps 172-175) and protein degradation (Steps 176-177), and reversing crosslinking of liberated DNA in the lysate (Steps 178-179), all while maintaining appropriate ionic content for downstream ITP.

At Step 171, excess paraffin may optionally be trimmed or removed from the FFPE tissue sample (e.g., prior to further sample preparation steps). An FFPE tissue sample may be acquired directly from a paraffin block or from a slide-mounted section.

At Step 172, the tissue may be collected in a microcentrifuge tube (e.g. an Eppendorf Lo-Bind microcentrifuge tube). Collection may optionally comprise scraping the FFPE tissue sample off of a slide or otherwise placing a fresh or FFPE tissue sample in the tube.

At Step 173, the tissue may be lysed through pipet resuspension (e.g. by pipetting 5 times using a P1000 pipette) in a lysis buffer, for example in a proprietary alkaline CCD Lysis buffer ("L1"). Lysis may alternatively or in combination be performed using other lysis techniques which will be known to one of ordinary skill in the art, for example via sonication, manual grinding, beadbeating, homogenization, freezing, enzymatic digestion, and/or chemical disruption. The lysed tissue may then be vortexed to mix (e.g. for 5 sec). Generally, at step 173, the lysis buffer is highly alkaline. In some cases, an alkaline solution may comprise 30-120 mM NaOH (in some cases, 40-80 mM NaOH) at a pH of about 10-13. An exemplary alkaline solution may comprise 80 mM NaOH, 11 mM DTT, and 0.5% v/v Igepal CA-630.

At Step 174, the tissue may be incubated in the lysis buffer at 80° C. (e.g. for 3 min) in order to allow the lysis process to lyse the tissue. The sample may then be mixed by pipetting (e.g. by pipetting up and down five times) and then vortexed (e.g. for 3 sec).

At Step 175, the lysed tissue may be incubated at room temperature (e.g. for 3 min) to cool.

At Step 176, the lysed tissue suspension may be treated to denature proteins in the tissue lysate. Optionally, RNA (or DNA if the sample molecule of interest for ITP is DNA) may be degraded. For example, Proteinase K (e.g. 20 mg/mL) may be added.

At Step 177, the sample may be incubated at 56° C. for one hour. The sample may be vortexed and pulse-spinned after incubation.

At Step 178, the sample may be incubated at 90° C. for one hour.

At Step 179, the sample may then be cooled to room temperature (e.g. for 5 min).

At Step 180, RNAse A (e.g. 10 mg/mL) may optionally be added.

At Step 181, the sample may be incubated at 25° C. for 5 min. The sample may be vortexed and pulse-spinned after incubation.

At Step 182, a sample lubricant (e.g. MOPS) may optionally be added to the sample.

At Step 183, the sample may optionally be frozen for use at a later date.

At Step 184, the sample may be warmed to 20° C.

At Step 185, a nucleic acid dye or stain may optionally be added to the sample lysate for visualization and detection (e.g., for quantitation of nucleic acid mass) of nucleic acid. For example, the addition of a nucleic acid stain, such as a nucleic acid binding or intercalating dye, may be used when in-line quantitation of nucleic acid mass is performed during the ITP process.

At Step 186, the sample may be loaded into one or more sample reservoirs. Prior to loading, the sample may be pulse vortexed (e.g. twice) and pulse-spinned to agitate and mix the sample. The ITP channel may be pre-primed with leading electrolyte buffer, trailing electrolyte buffer, and/or other buffers as described herein. Alternatively, the sample may be loaded at the same time as the rest of the liquids in the channel.

At Step 187, ITP may be performed. During the ITP process, the DNA within the sample may be purified (i.e. concentrated) as it moves through the channel until it reaches the elution reservoir as described herein. The sample DNA may be quantified as described herein.

Also at Step 187, the eluted sample can may be recovered by elution (e.g. by pipetting) from the elution reservoir.

Figure 1B:
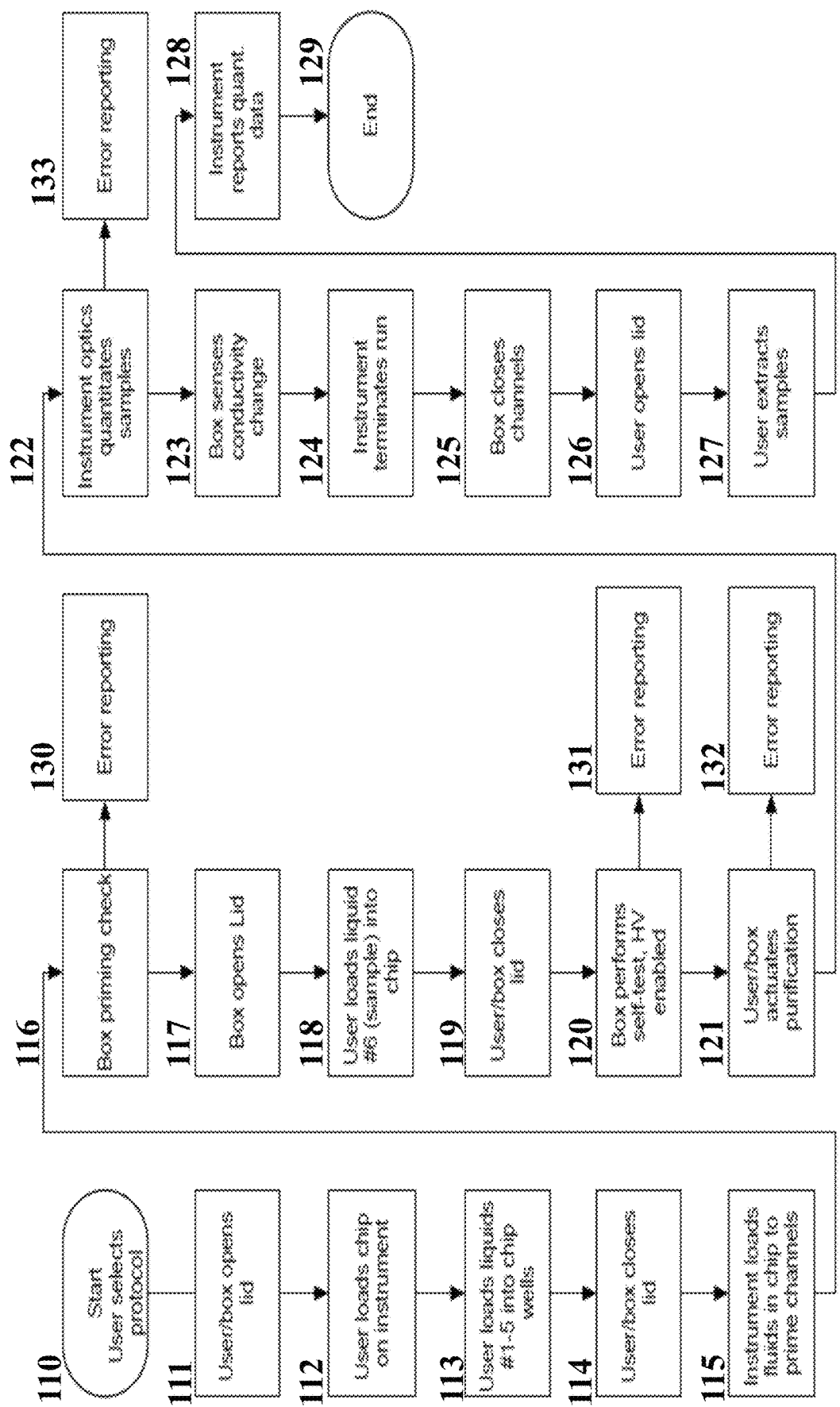
FIG. 1B shows an exemplary protocol for automated sample processing and nucleic acid extraction or purification.

FIG. 1B shows an exemplary process workflow for automated ITP. At step 110, a protocol can be selected, such as by using a graphical user interface on a benchtop device. The user interface software can enable ease of use or hands-free operation. For example, a user can select from a menu (e.g., drop-down menu). Alternatively, the device can scan a barcode (e.g., optical barcode, RFID chip) associated with a sample or a fluidic device chip which can indicate the protocol to be performed. At step 111, the instrument lid can be opened (e.g., manually or automatically via motor). Motorized lid opening can be compatible with robotic laboratory automation. At step 112, the user can load a chip (e.g., fluidic device) onto the benchtop instrument. The chip can comprise a monolithic, multichannel SLAS standard microtiter plate (MTP) footprint for automated ITP. At step 113, ITP liquids can be loaded into the chip wells. Reservoirs for ITP fluids and user samples can be designed for ease of loading, such as via a multichannel pipet (e.g., 9 mm pitch SLAS standard microtiter plate format). Geometrical designs (e.g., capillary barriers) of the channels connecting reservoirs to the ITP channel can resist gravity-driven flow or wetting of liquids into the channel prior to operation. These structures can stop fluids in defined places within the ITP channel, including establishing the leading electrolyte/ trailing electrolyte interface, as well as enable bubble-free loading. In some cases, prior to operation, pneumatic actuation can be applied to prime the channel. Chip material can be selected to prevent or resist wetting or wicking of fluids into channels (e.g., plastic with hydrophobic properties or a high contact angle). The user can load ITP reagents and buffers onto the chip (e.g., 5 different fluids); alternatively, the chip can be provided with reagents preloaded. At step 114, the user or the device can close the device lid. Sample loading can be actuated through gas or air ports on the chip. Wetting and/or gravity-driven flow can be used to fill channels with liquids, for example without active pressure application.

At step 115, the instrument can apply pressure to load fluids in the chip to prime the channels. At step 116, the device can check that the channels have been appropriately primed. For example, optical (e.g., reflectance), electrical, pressure, and/or flow rate sensors can be used to check that fluids have been loaded to the correct locations within the chip. Sensors and device software can enable real time monitoring and control of liquid loading. ITP reagent and buffer loading can be conducted prior to loading sample onto the chip, so that in case of mis-loading, sample material is not wasted. If the channels are not appropriately primed, the device can perform error reporting 130. At step 117, the device lid can be opened. At step 118, the sample can be loaded onto the device. Sample loading can be performed manually by a user, or can be performed in an automated manner, such as via laboratory automation robotics. Other sample preparation steps can also be conducted. For example, a paraffin-embedded sample (e.g., FFPE) can be loaded, and then the device can control the temperature within the sample reservoir to deparaffinize the sample. At step 119, the device lid can be closed. At step 120, the device can perform a self-test. For example, electrical feedback from device electrodes interfacing with on-chip reservoirs can be used to self-test for successful priming of liquids (e.g., bubble detection). Optical sensors can be used to enable feedback on liquid priming status (e.g., whether or not a liquid has reached a designated capillary barrier). Other sensing mechanisms, such as those disclosed herein, can also be used. If the self-test determines that the device is not properly primed, the device can perform error reporting 131.

At step 121, ITP-based purification can be conducted. Feedback control and process timing using sensors (e.g. triggering) as described herein can be used to control and/or automate the ITP purification. The device can determine whether purification was successfully performed, and if not, the device can perform error reporting 132. At step 122, sensors on the device (e.g., optical sensors) can be used to quantitate the samples, for example by fluorescence, UV, or other optical detection. Sample sizing can also be performed. If the device determines that the sample was not properly quantitated or discovers other issues, the device can perform error reporting 133. At step 123, a conductivity change can be detected, which can be used to indicate timing for ending the ITP run (e.g., when the nucleic acids reach a designated elution location or reservoir). Other detection methods described herein, such as temperature or driving voltage, can also be used to determine end of run timing or other triggers. For example, a temperature or voltage sensor may be used to control an electric field applied to a channel within the device in order to automate the ITP process. As an example, an electric field may be applied to a channel to begin ITP purification. A sensed change in voltage may be used to trigger the start of temperature or other sensing at a fixed location within the channel such as at or near the elution reservoir. The voltage may change as the ITP zone comprising confined nucleic acids moves. Changes indicative of the ITP zone passing through channel features such as a section of decreased cross-sectional area may be sensed by a voltage sensor and feedback may be used to alter the electric field, for example by reducing the applied current. A change in temperature may be detected as the ITP zone passes a temperature sensor at or near the elution reservoir and feedback from the sensor may be used to control the electric field, for example by removing it to end the ITP run. At step 124, the device can terminate the run, for example based on a trigger signal. The nucleic acids may be positioned or isolated within the elution reservoir or region when the ITP run is terminated. At step 125, the device can close the channels, which can fix the elution volume to maintain a constant volume for the elution (e.g., by resisting or preventing flow into the elution reservoir or outlet reservoir during pipetting out of the eluted volume). Fixing the elution volume can aid ease of use and can help for reporting the concentration of the eluted sample material. At step 126, the device lid can be opened (e.g., by a user or automatically).

At step 127, purified samples can be extracted from the device. Chips and/or devices can be designed for a given elution volume, as discussed herein. Retrieval of purified material from the device can be performed via pipetting or otherwise removing the material from the chip. Alternatively, sample extraction can be performed by interfacing the ITP chip with another fluidic chip or system (e.g., in the absence of an elution reservoir). Other fluidic systems can then be used to perform other operations on the purified sample material, such as next generation sequencing (NGS) library preparation, sample analysis such as PCR, ddPCR, other sequencing operations, or other downstream processes. At step 128, the device can report quantitative data about the sample, such as sample amount and/or sample concentration. The device can contain an algorithm or other software for converting a measurement (e.g., a fluorescence signal) into a sample quantitation, and can report that data to a user. At step 129, the process ends.

Figure 33:
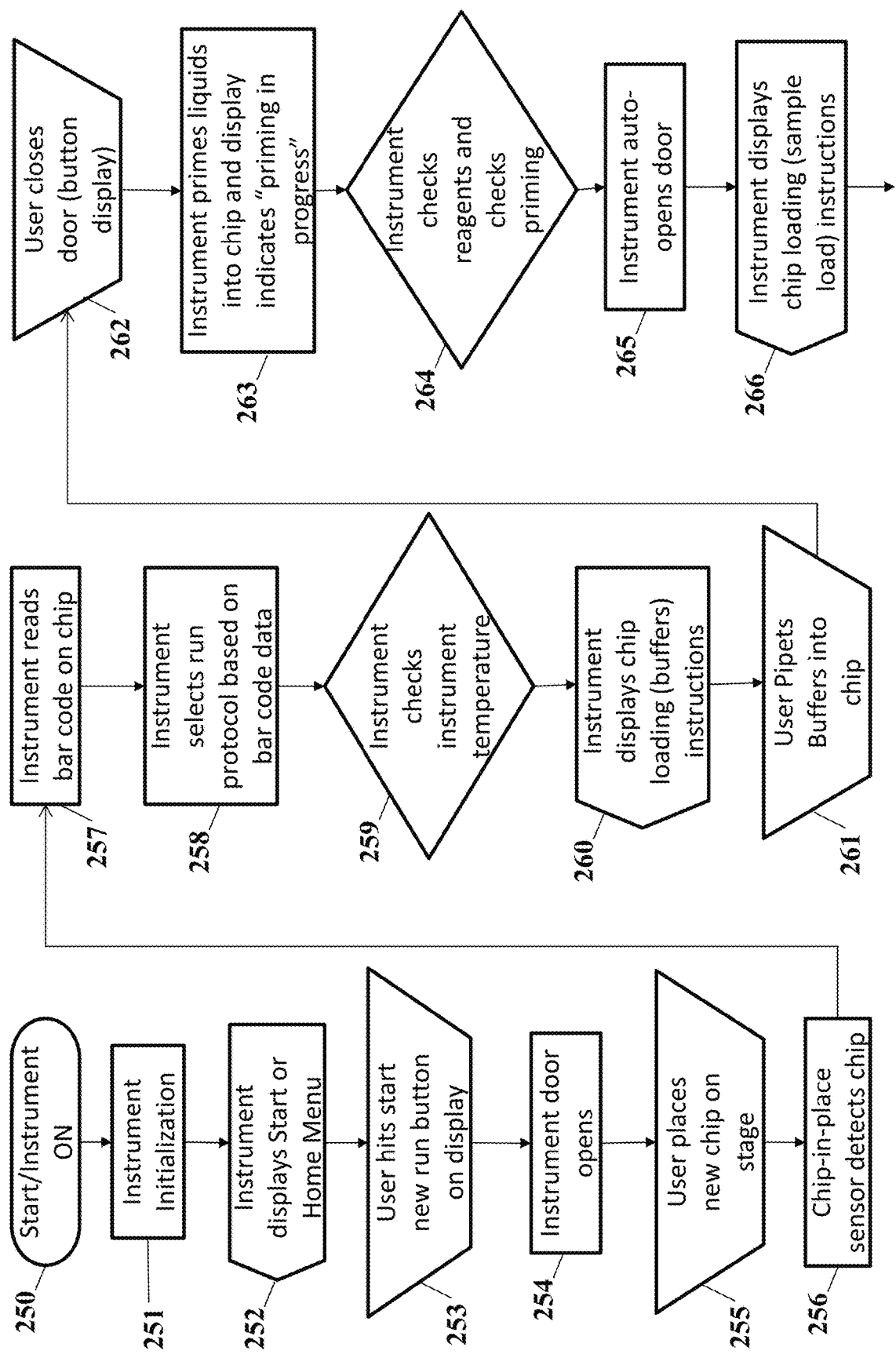
FIG. 33 shows an exemplary process workflow for automated ITP.
Figure 33:
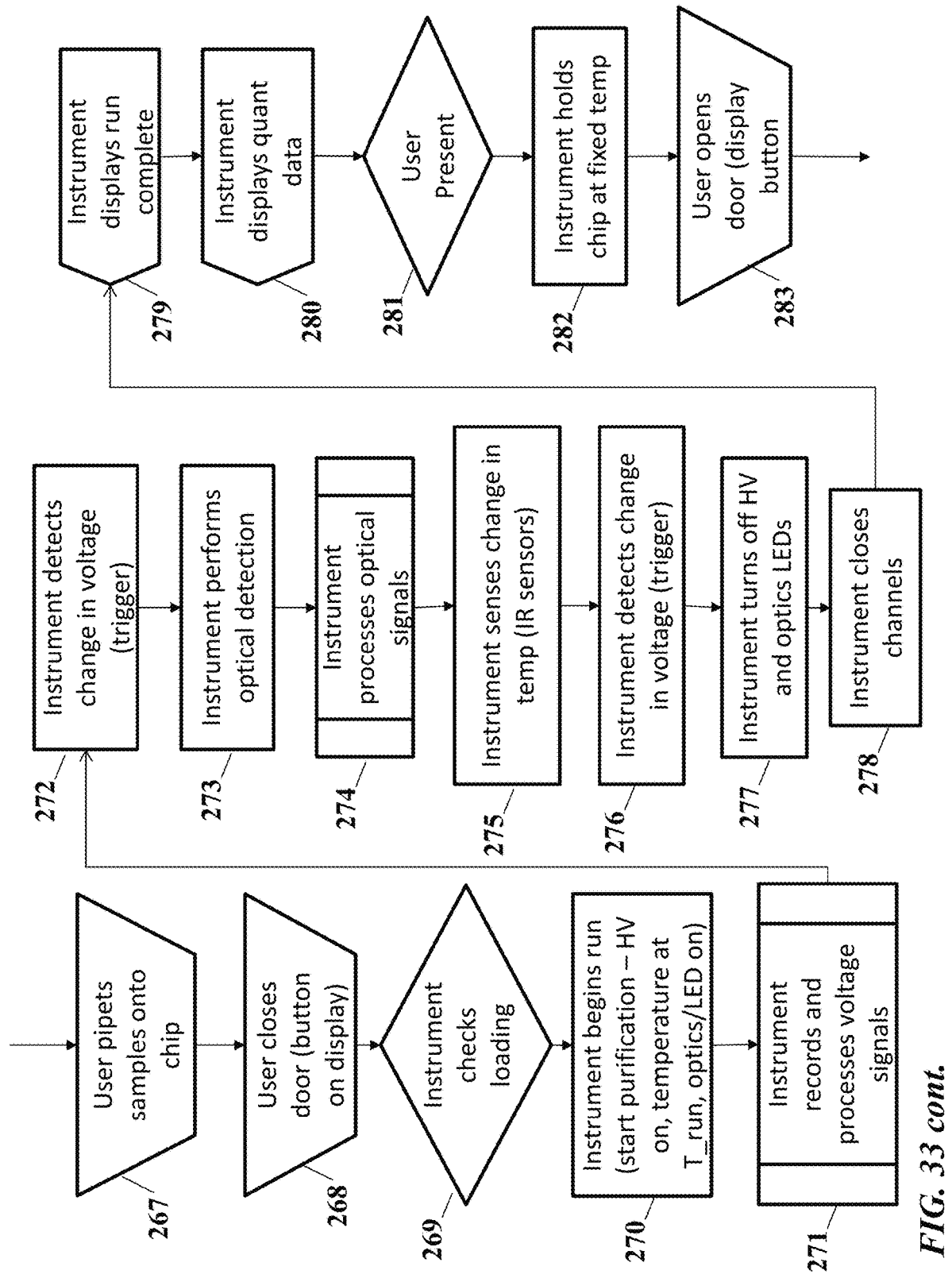
Figure 33:
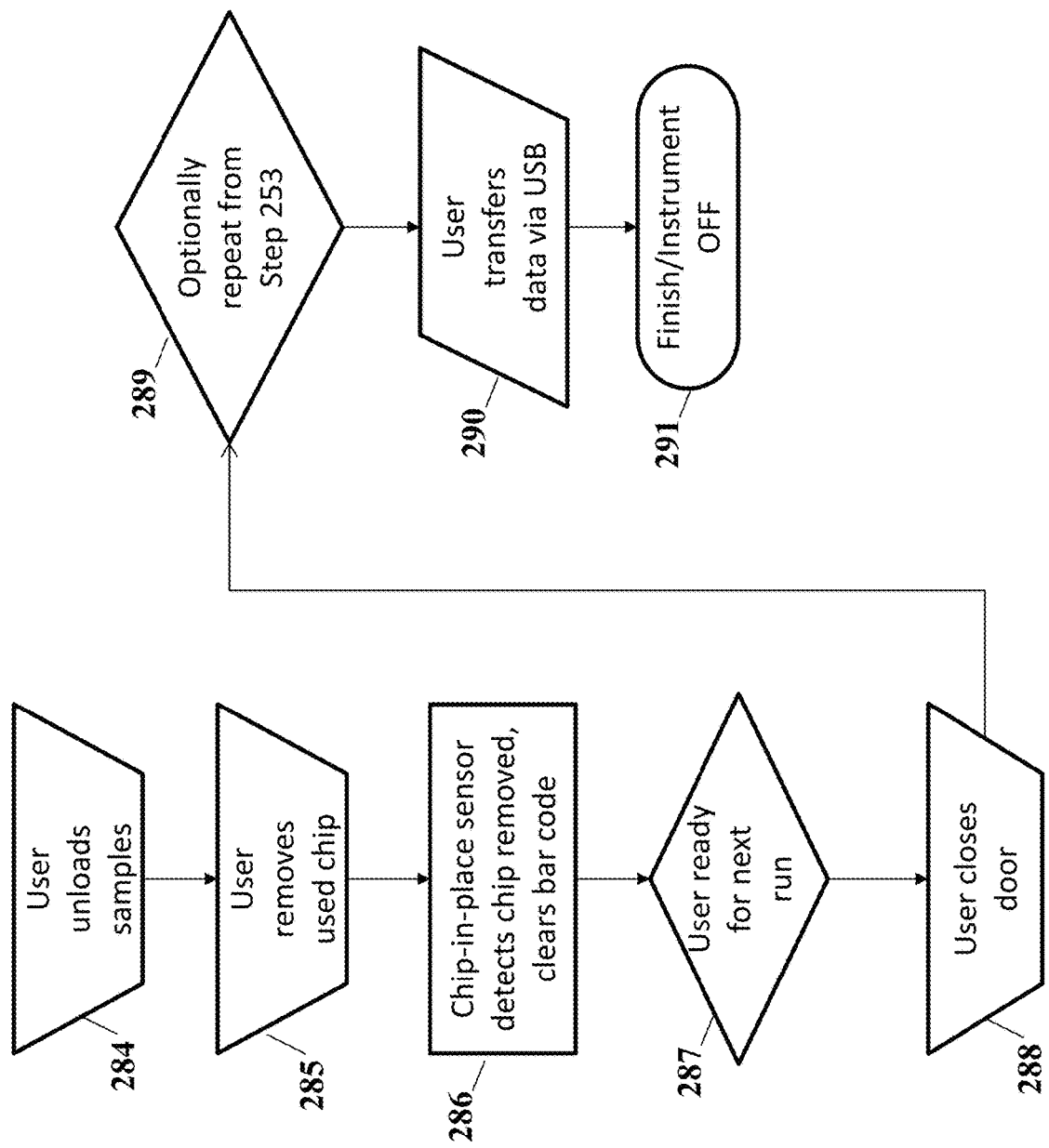

FIG. 33 shows a detailed, non-limiting exemplary process workflow for automated ITP using the methods, devices, and systems described herein.

At Step 250, the user may turn the instrument on.

At Step 251, instrument initialization may optionally be performed. Initialization may for example include one or more of the following checks/steps: (a) the pressure control tolerance may be checked at 0 psi and −0.1 psi; (b) a negligible flow rate within the channels with negative pressure valves closed may be confirmed; (c) the proportional valve value may be observed; (d) the HVS temperature may be checked; (e) the HVS voltage rails may be checked; (f) no voltage with HVS disabled may be confirmed; (g) the optics temperature may be checked; (h) the optics voltage rails may be checked; (i) increases in pickoff value when turning on each LED may be confirmed; (j) increases detector value when turning on each LED may be confirmed; and/or (k) infrared sensors at or near room temperature may be confirmed.

At Step 252, the instrument may optionally display a "Start" or "Home" menu to the user.

At Step 253, the user may optionally hit "Start New Run" on the instrument display.

At Step 254, the instrument door may open.

At Step 255, the user may place a fresh microfluidic chip on the instrument stage.

At Step 256, a "chip-in-place" sensor may optionally be used to detect if the chip has been placed on the instrument stage and/or if the chip has been correctly placed or oriented on the stage.

At Step 257, the instrument may optionally read a bar code identifier on the chip. For example, the user may use a handheld scanner.

At Step 258, the instrument may optionally select a protocol to run based on the bar code identifier scanned.

At Step 259, the instrument may optionally check the temperature of the instrument (e.g. of a heater). For example, the temperature of the heating/cooling element may be read by the instrument. The temperature detected by an optional thermal sensor may be read by the instrument. The temperature range of the instrument may be confirmed, for example by checking that the instrument temperature and the temperature detected by the thermal sensor are different by no more than about 5° C.

Figure 60:
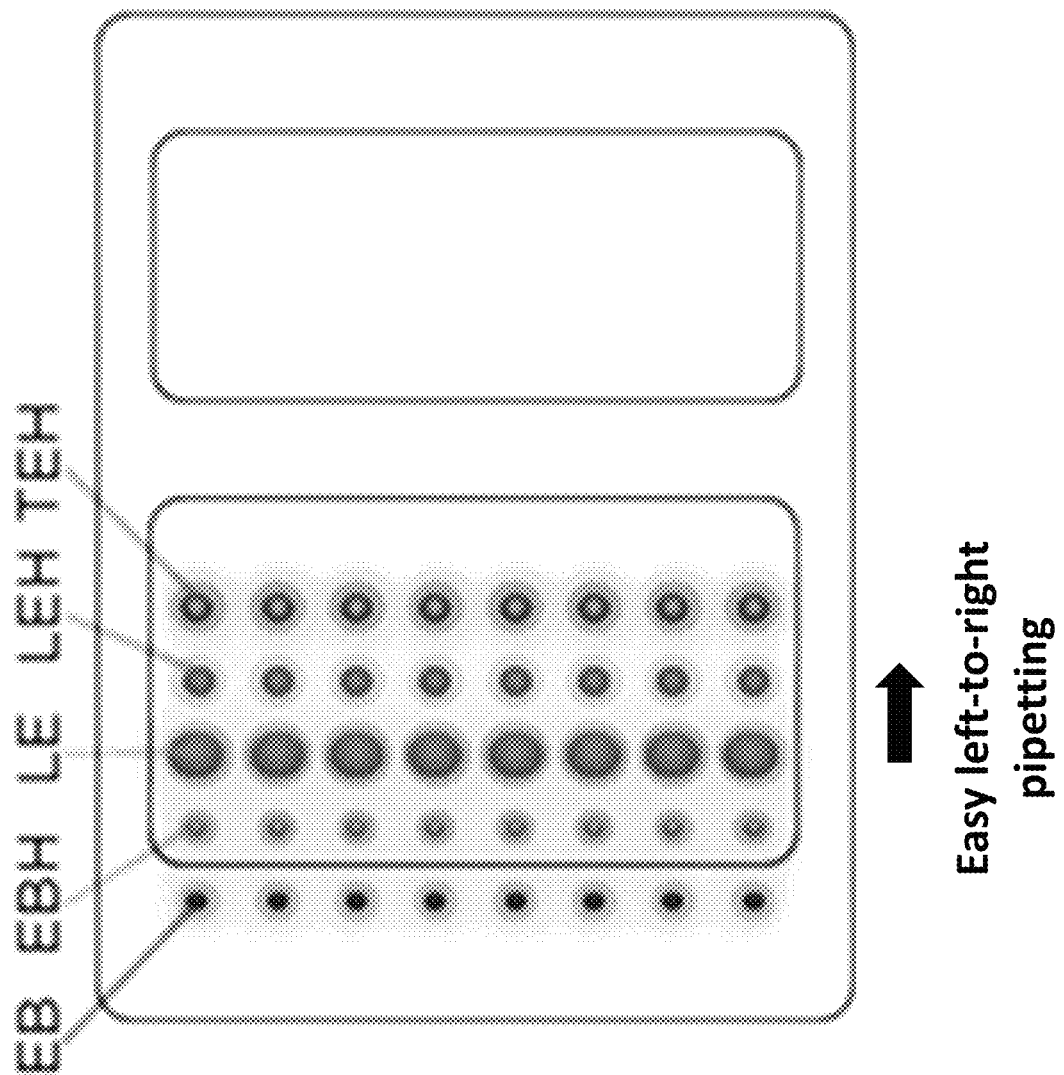
FIG. 60 shows an exemplary image which may be displayed to a user to instruct and guide the user through the reservoir loading process.

At Step 260, the instrument may optionally display instructions for how to load the buffers (e.g. one or more trailing electrolyte buffer, one or more leading electrolyte buffer, one or more elution buffer, etc.) onto the chip. For example, the instrument may display visual and/or color-coded instructions to the user (e.g. as shown in FIG. 60).

At Step 261, the user may pipette the buffers onto the chip.

At Step 262, the user may close the instrument door, for example by pushing a button on the display.

At Step 263, the instrument may load one or more of the buffering liquids into the chip. The display may optionally provide the user with an indication that loading is occurring, for example by displaying a "priming in progress" message.

At Step 264, the instrument may optionally check to make sure that the buffering reagents have been loaded and that the channels have been correctly primed with the buffers. Loading may for example be confirmed by testing the electrical conductivity between two high voltage electrodes as described herein. For example, 10 µA may be sourced from one electrode and 10 µA may be sunk from another electrode. The voltage difference across the two electrodes may be measured as described herein. Priming of the channels may be confirmed prior to, during, or after confirmation of buffer loading. Channel priming may for example be confirmed by ensuring electrical conductivity between a source electrode and a grounding electrode.

At Step 265, the instrument may open the door/lid to allow the user to access the chip following confirmation that the one or more buffers were correctly loaded.

At Step 266, the instrument may optionally display instructions to the user on how to load the sample into the chip.

At Step 267, the user may pipette the sample(s) onto the chip. The user may optionally remove a seal from the sample well(s) of the chip to enable sample loading. The user may optionally add an additional volume of "topper" to the sample reservoir after loading the sample as described herein.

At Step 268, the user may close the instrument door, for example by pushing a button on the display.

At Step 269, the instrument may optionally confirm that the sample has been correctly loaded. Loading of the sample may be confirmed by checking the electrical conductivity of each electrode to ground as described herein. When one or more buffers remains unloaded after sample loading, the instrument may load the remaining buffers onto the chip.

At Step 270, the instrument may begin the ITP run. The instrument may optionally wait a pre-determined amount of time after loading the chip to allow the fluids in the chip to equilibrate. Beginning the ITP run may entail activating a high-voltage ("HV") power supply, adjusting the temperature of the chip to a run temperature ("T_run"), and/or turning on an optical detection system (e.g. a light emitting dioder). The run temperature for a typical ITP procedure may for example be within a range of about 15° C. to about 23° C.

At Step 271, the instrument may optionally record and process voltage signals detected as described herein.

At Step 272, the instrument may optionally detect a change(s) in voltage to act as a trigger to begin ITP as described herein. A change in voltage may optionally act as a trigger to alter the driving electrode(s) polarity and/or driving voltage as described herein.

At Step 273, the instrument may optionally perform optical detection.

At Step 274, the instrument may optionally process the detected optical signals.

At Step 275, the instrument may optionally sense a change in temperature at a pre-determined location within the chip, for example using an infrared sensor as described herein. A change in temperature may optionally act as a trigger to end ITP as described herein.

At Step 276, the instrument may optionally detect a change(s) in voltage to act as a trigger to end ITP as described herein.

At Step 277, the instrument may optionally be triggered to shut off the high-voltage power supply, thereby ending the ITP run. The instrument may also shut down the optical system.

At Step 278, the instrument may optionally close off the channels using a channel closer as described herein.

At Step 279, the instrument may optionally display an indicator or message to the user to alert them that the ITP has been completed.

At Step 280, the instrument may optionally display any quantitative data collected during the ITP run to the user.

At Step 281, the user may return or be present at the machine.

At Step 282, the instrument may optionally hold the chip at a fixed temperature until the user returns to the instrument as in Step 281. The fixed temperature may for example be within a range of about 4° C. to about 20° C.

At Step 283, the user may optionally open the instrument door/lid, for example by pushing a button on the display.

At Step 284, the user may optionally recover the sample from the elution reservoir.

Alternatively or in combination, the instrument may optionally recover the sample from the elution reservoir automatically. The sample may optionally then be used for further downstream assays as desired by the user.

At Step 285, the user may user may remove the used chip from the instrument.

At Step 286, the chip-in-place sensor may optionally detect removal of the chip by the user. The bar code information stored on the instrument may be cleared.

At Step 287, the user may optionally ready their reagents and samples for additional ITP runs with a new chip if desired.

At Step 288, the user may close the door.

At Step 289, the user may optionally repeat Steps 253 to 288 with a new chip, buffers, samples, etc. as many times as desired. The instrument may optionally adjust the temperature of the instrument while idling between runs, for example to a temperature within a range of about 20° C. to about 25° C.

At Step 290, the user may optionally transfer data collected during the ITP run(s), for example via a USB port on the instrument or via a wireless connection.

At Step 291, the user may optionally turn the instrument off. In some instances, the instrument may be programmed to turn off following a pre-determined amount of idle time when the chip-in-place sensor confirms that there are no chips in the instrument.

Table 1 shows typical operating times for various steps, manual (performed by user) or automated (performed by instrument) of the ITP process using the exemplary methods described in FIG. 33.

TABLE 1

| Step: Action | Value |
| --- | --- |
| Step 261: User Loads Buffers Time | =<10 min |
| Step 263: Priming Time | =<20 min |
| Step 267: User Pipettes Sample Time | =<10 min |
| Steps 272-274: Run time, from start to optics window | 10-90 min |
| Steps 275-276: Run time between optical detect and thermal event (IR sensor detect) | 5-20 min |
| Step 277: Remaining run time after thermal event (IR sensor detect) | 1-2 min |
| Step 278: Time to close channels after HV shutoff | =<5 min |
| Step 282: Hold Time | >=5 min |
| Step 283: Idle time before next run | =<5 min |
| Step 284: User unloads samples | =<10 min |

These issues can be especially important to address for precious, difficult to collect, or low-abundance (e.g., less than 100 ng of nucleic acid or samples containing a low abundance of undamaged or uncrosslinked nucleic acids) samples. For such samples, current protocols may lack repeatability, introduce loss of sample material, introduce bias for short or long nucleic acid targets, introduce bias towards sequence of nucleic acid targets, and/or lack repeatability. Such protocols may also lack compatibility with process automation or downstream analyses. Current protocols for nucleic acid preparation can include liquid phase extraction (LPE) such as phenol-chloroform extraction or Trizol extraction, and solid phase extraction (SPE). SPE type approaches can use structures including packed beads, monolithic porous structures, and/or magnetic beads. In some cases, LPE and SPE type approaches can lead to mechanical shearing during processing which can cause fragmentation and/or reduce the yield of long or high molecular weight nucleic acids.

The isotachophoresis methods and devices provided herein are especially well-suited to performing extraction of nucleic acids from lysates of solid or semi-solid tissues. Solid phase extraction (SPE) techniques typically process lysates by pumping the entire lysate sample volume through a column in order to selectively adsorb nucleic acids onto the surfaces of the column. Such pumping of a complex lysate, which may comprise a liquid-particle mixture, through a porous column can result in clogging or fouling of the column which can reduce the efficiency of nucleic acid extraction. In contrast, the isotachophoresis methods and devices described herein often do not involve pumping or "filtering" the entire lysate sample volume through a column. Instead, an electric field may be applied to the lysate in order to cause the charged, solvated nucleic acids dispersed throughout the complex sample lysate to migrate through and out of the continuous liquid phase of the sample. Nucleic acids may comprise a relatively high electrophoretic mobility magnitude relative to other solutes, debris, or contaminants in the sample lysate. Solutes in the sample may have a relatively low electrophoretic mobility and be too low to focus into the isotachophoresis zone located at the interface between the leading electrolytes and trailing electrolytes. Application of an electric field may cause the nucleic acids to migrate while particles and/or other tissue debris (including for example cell debris, unlysed cells, or tissue which may connect cells to other cells) are left behind. The isotachophoresis methods and devices provided herein therefore can be well-suited to extract the charged, solvated nucleic acids out of the complex lysed solid tissue samples without having to process the entire mixture through a column as in SPE.

As used herein, "particles" may refer to components of a sample mixture or a sample lysate mixture which are a different phase than the continuous liquid phase of the sample (e.g., an aqueous solution). Particles may be non-liquid components of the sample mixture. Particles can be, for example, suspended solid particles or colloidal bodies suspended within a sample. Such particles can have a variety of characteristic length scales ranging from about 1 nanometer (nm) to about 1 millimeter (mm). In some instances, particles may not be single-celled organisms or cells.

The isotachophoresis methods and devices provided herein may provide for reduced rates of strain as the sample moves through the channel compared to typical SPE methods. In some cases, the methods and devices provided herein have rates of strain of less than about $250$ $s^{-1}$, $500$ $s^{-1}$, $750$ $s^{-1}$, $1000$ $s^{-1}$, $2000$ $s^{-1}$, $3000$ $s^{-1}$, $4000$ $s^{-1}$, $5000$ $s^{-1}$, $6000$ $s^{-1}$, $7000$ $s^{-1}$, $8000$ $s^{-1}$, $9000$ $s^{-1}$, or $10,000$ $s^{-1}$. In some cases, the methods and devices provided herein have rates of strain of more than about $250$ $s^{-1}$, $500$ $s^{-1}$, $750$ $s^{-1}$, $1000$ $s^{-1}$, $2000$ $s^{-1}$, $3000$ $s^{-1}$, $4000$ $s^{-1}$, $5000$ $s^{-1}$, $6000$ $s^{-1}$, $7000$ $s^{-1}$, $8000$ $s^{-1}$, $9000$ $s^{-1}$, or $10,000$ $s^{-1}$. In some cases, the methods provided herein may be performed without centrifugation.

Isotachophoresis Chemistry and Operation

Figure 2A:
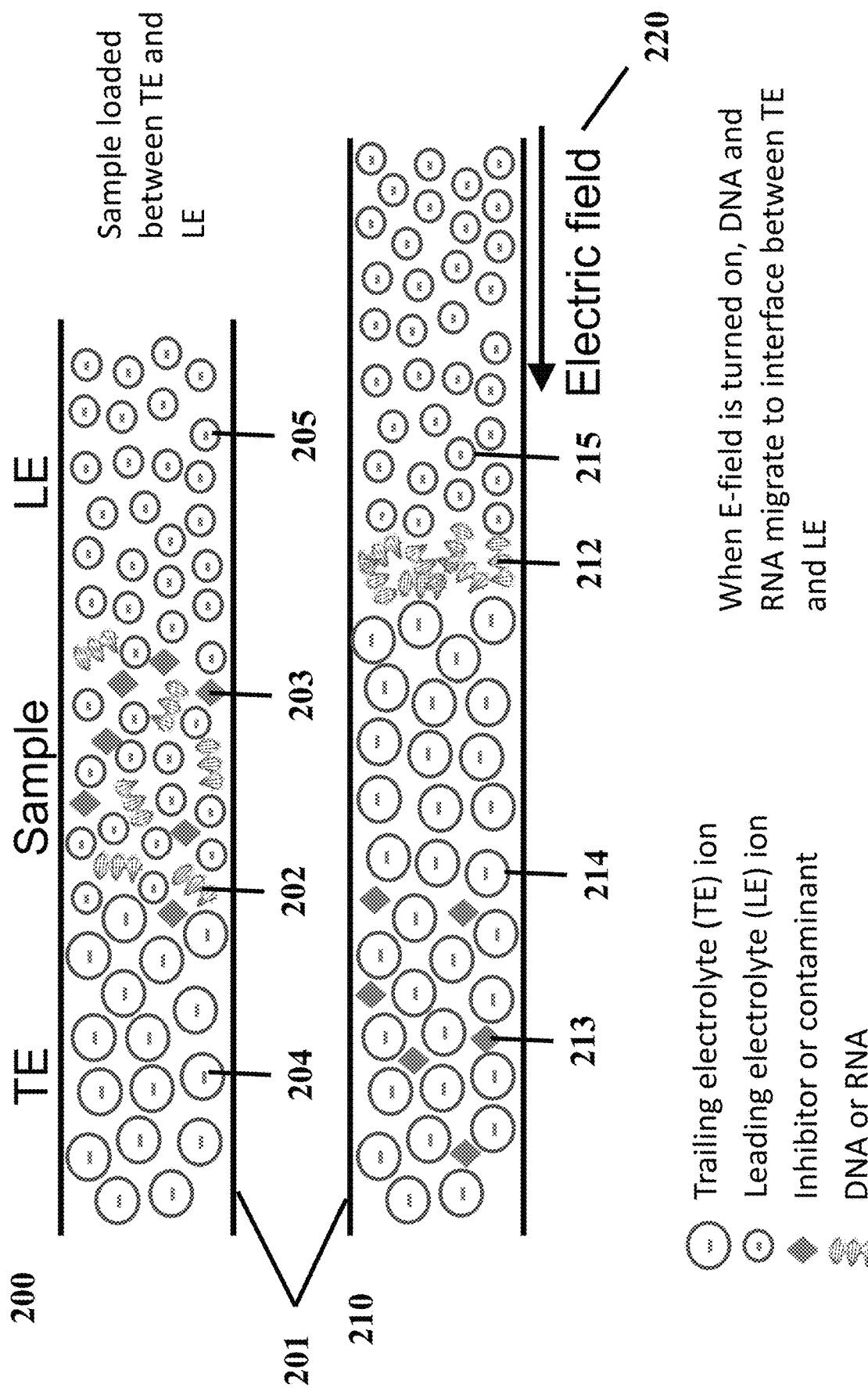
FIG. 2A shows an exemplary schematic of isotachophoretic separation and purification of DNA and RNA from contaminants.

FIG. 2A shows an exemplary schematic of an isotachophoresis (ITP) process purifying nucleic acid. A sample 201, for example a lysed solid tissue sample, comprising nucleic acids (DNA and RNA) 202 and contaminants 203 may be loaded with trailing electrolytes (TE) 204 into an isotachophoresis channel 200 containing leading electrolytes (LE) 205. Under the influence of an electric field 220 applied to the isotachophoresis channel 210, the nucleic acids 212 may migrate away from the contaminants 213. The electric field may also cause the trailing electrolytes 214 to migrate through the channel in a position that is generally behind the nucleic acids, and generally causes the leading electrolytes 215 to migrate through the channel generally ahead of the nucleic acids. The magnitude of the effective mobility of the leading electrolytes is greater than the magnitude of the effective mobility of the nucleic acids, which in turn is greater than the magnitude of the effective mobility of the trailing electrolytes, which is greater than the magnitude of the effective mobility of the contaminants.

Figure 2B:
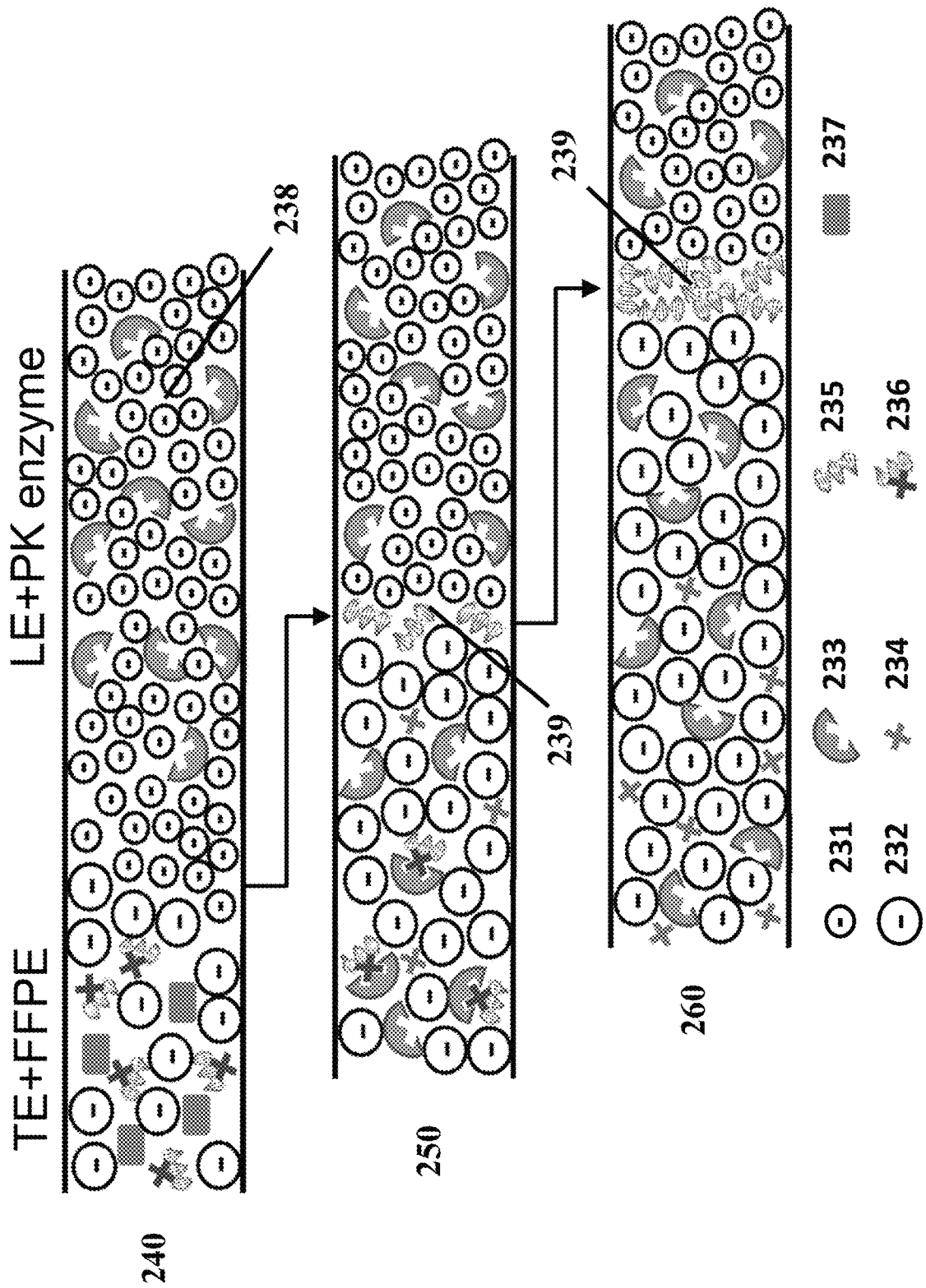
FIG. 2B shows an exemplary schematic of isotachophoretic separation and purification of nucleic acids from paraffin and other possible sample contaminants concurrent with proteinase-mediated tissue disruption and decrosslinking of nucleic acids.

FIG. 2B shows an exemplary schematic of a process to de-crosslink nucleic acids while separating de-crosslinked nucleic acids from crosslinked nucleic acids and contaminants (e.g., paraffin) using isotachophoresis (ITP) on a fluidic device. In some instances, the contaminants may comprise the crosslinked nucleic acids. A paraffin-embedded sample may be loaded onto the fluidic device in an alkaline buffer and incubated for 10-30 minutes at about pH 10 and a temperature from about 50° C. to about 80° C. for tissue lysis and initial deparaffinization. Incubation may occur prior to or while applying an electric field to perform isotachophoresis. Alternatively, the sample can be loaded in a leading electrolyte buffer. After incubation, at a first time point 240, the sample comprising crosslinked nucleic acids 236 and paraffin 237 may be located in an ITP channel with trailing electrolytes 232. Ahead in the ITP channel, in a leading electrolyte (LE) zone 238 are leading electrolytes 231 and Proteinase K enzymes 233. At a second time point 250, at 50° C., ITP-driven pH quenching reduces the pH, and Proteinase K enzymes are contacting and de-crosslinking the crosslinked nucleic acids, producing non-crosslinked nucleic acids 235 which focus at in the ITP zone 239 between the trailing electrolytes and leading electrolytes. Reduction of pH (e.g. to a range from about 10-12 to about 7 (or from about 6.5 to about 8.5)) can provide an environment appropriate for enzymatic activity and improved chemical stability of nucleic acids. At a third time point 260 the Proteinase K has de-crosslinked more nucleic acids, resulting in free protein 234, and the de-crosslinked nucleic acids have further migrated upstream from the paraffin, free protein, and other contaminants. The operation of such a process can be conducted automatically by the fluidic device or by a benchtop system.

In some cases, the sample may be loaded in a sample buffer comprising a concentration of leading electrolytes 205, 231 that differs from the concentration of leading electrolytes 205, 231 used to perform isotachophoresis. In some cases, the sample may be loaded in a sample buffer comprising a second leading electrolyte which differs from the leading electrolyte 215. The second leading electrolyte can have an effective mobility magnitude greater than the magnitude the effective mobility of the nucleic acid. The second leading electrolyte can have an effective mobility magnitude less than the effective mobility magnitude of the leading electrolyte 215.

In some cases, a pH of the sample may be quenched by conducting isotachophoresis. In some instances, the pH of the sample may be quenched within a range of about 6.5 to about 8.5, for example about 7 or 7.5.

Various leading electrolytes and trailing electrolytes can be used to conduct ITP. Leading electrolytes can be selected to have a greater effective mobility magnitude than the extraction target (e.g., nucleic acids), and trailing electrolytes can be selected to have a lesser effective mobility magnitude than the extraction target. Leading and/or trailing electrolytes can be present at a concentration from about 10 mM to about 200 mM. Leading and/or trailing electrolytes can be present at a concentration of about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM. Leading and/or trailing electrolytes can be present at a concentration of at least about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM. Leading and/or trailing electrolytes can be present at a concentration of at most about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM. Leading electrolytes used in a particular instance of ITP can comprise 1, 2, 3, 4, 5, 6, 7, 8, 9, 10, or more different ion species. Trailing electrolytes used in a particular instance of ITP can comprise 1, 2, 3, 4, 5, 6, 7, 8, 9, 10, or more different ion species. Different species of ions in the leading electrolytes and/or trailing electrolytes can be present at different concentrations. Different concentrations of ions, such as within the trailing electrolytes or the leading electrolytes, can be selected to manipulate the size of a spacing zone. The spacing zone can be used to further separate one type of target from another, such as separating decrosslinked from protein crosslinked nucleic acids.

The trailing electrolytes can comprise a mixture of ions with different magnitudes of effective mobilities. Use of a first trailing electrolyte ion with a first effective mobility magnitude and a second trailing electrolyte ion with a second effective mobility magnitude lower than that of the first ion can be used to separate non-crosslinked nucleic acids from protein crosslinked nucleic acids, while separating both (or at least the decrosslinked nucleic acids) from contaminants. In such a case, the non-crosslinked nucleic acids can have a greater effective mobility magnitude than the first trailing electrolyte ions, which can have a greater effective mobility magnitude than the crosslinked nucleic acids, which in turn can have a greater effective mobility magnitude than the second trailing electrolyte ions, which in turn can have a greater effective mobility magnitude than the contaminants. For example, crosslinked and non-crosslinked nucleic acids can be enriched separately by conducting isotachophoresis using a leading electrolyte and two trailing electrolytes, such as caproic acid as the first ion and HEPES as the second ion.

Electrolyte ions can also be selected based on acidity (e.g., pKa). Ions with particular pKa can be selected, for example, to effect a pH change along an ITP channel. Ions can also be selected for non-electrophoretic reasons, such as compatibility with downstream processes (e.g., enzymatic processes such as PCR or next-generation sequencing library preparation). For example, caproic acid, MOPS, and HEPES can be selected for good downstream enzymatic compatibility.

Exemplary leading electrolyte ions include but are not limited to hydrochloric acid, acetic acid, 2-chloroisocrotonic acid, salicylic acid, chlorocrotonic acid, nicotinic acid, gallic acid, trichlorolactic acid, butyric acid, sulfanilic acid, benzoic acid, crotonic acid, trichloroacrylic acid, propionic acid, levulinic acid, sorbic acid, orotic acid, valeric acid, picric acid, 2-naphtalenesulfonic acid, saccharin, dinitrophenol, p-toluenesulfonic acid, aspartic acid, trimethylacrylic acid, isocaproic acid, caproic acid, octylsulfonic acid, nitrophenol, GABA, cacodylic acid, trimetylpyruvic acid, ethylmaleic acid, ethylfumaric acid, toluic acid, enanthylic acid, mandelic acid, cinnamic acid, cresol, glutamic acid, MES, isomers thereof, and combinations thereof.

Exemplary trailing electrolyte ions include but are not limited to caprylic acid, gluconic acid, vanillic acid, decylsulfonic acid, aspirin, glucuronic acid, pelargonic acid, benzylasparatic acid, ascorbic acid, dodecylsulfonic acid, MOPS (3-(N-morpholino)propanesulfonic acid), dichlorophenol, caproic acid, capric acid, tyrosine, HEPES (4-(2-hydroxyethyl)-1-piperazineethanesulfonic acid), isomers thereof, and combinations thereof.

Use of a mixture of different trailing electrolyte ions can be used to achieve mobility bracketed separations (e.g., separation of non-crosslinked nucleic acids from crosslinked nucleic acids from contaminants), compatibility with downstream assays, favorable surface energy or contact angles between fluids and fluidic device materials, buffering capacity, and total ion solubility.

Leading electrolytes may be loaded in a leading electrolyte buffer. The leading electrolyte buffer may comprise one or more leading electrolytes to compact the target nucleic acids behind the leading electrolytes in the channel during ITP. The leading electrolytes may also separate the target nucleic acids from any contaminants or inhibitors which have an effective mobility magnitude greater than that of the target nucleic acids. The leading electrolyte buffer may, for example, comprise chloride. The leading electrolyte buffer may comprise a sufficient concentration of chloride such that the separation capacity of the leading electrolyte buffer is greater than the ionic strength of the sample nucleic acids. The leading electrolyte buffer may comprise a pH compatible with nucleic acid stability. The leading electrolyte buffer may comprise a surfactant (e.g. Tween) in order to reduce or minimize electroosmotic flow. The leading electrolyte buffer may comprise a surfactant (e.g. Brij-35) in order to reduce or minimize surface adsorption. The leading electrolyte buffer may comprise one or more surfactants as described herein. The concentration of the one or more surfactants may be adjusted so as to ensure that the LE does not uncontrollably wet past the capillary barriers (e.g. the plateau capillary barriers) described herein.

In some embodiments, leading electrolytes may be loaded in a high concentration leading electrolyte buffer, which may act to buffer a lower concentration leading electrolyte buffer. The high concentration leading electrolyte buffer may have sufficient buffering capacity so as to not change pH during the electrolysis process that occurs throughout the ITP run. The high concentration leading electrolyte buffer may comprise one or more leading electrolytes, which may be the same as the leading electrolytes of the leading electrolyte buffer but at a higher concentration. The high concentration leading electrolyte buffer may comprise Tris and chloride. The high concentration leading electrolyte buffer may comprise Tris and chloride at a ratio configured to maximize buffering capacity, for example a high Tris:chloride ratio to provide a source of Tris during the ITP run. The high concentration leading electrolyte buffer may comprise one or more surfactant in order to ensure that the high concentration leading electrolyte buffer wets the walls of the high concentration leading electrolyte buffer reservoir and loads to the capillary barriers upon application of negative pressure. The concentration of the one or more surfactants may be adjusted so as to ensure that the LE does not uncontrollably wet past the capillary barriers (e.g. the ramp barriers) described herein.

In some embodiments, leading electrolytes may be loaded in an elution buffer. The elution buffer may comprise one or more leading electrolytes. The one or more leading electrolytes of the elution buffer may have a lower ionic strength than the leading electrolytes of the leading electrolyte buffer. The one or more leading electrolytes may enable a hand-off of the ITP band from the higher ionic strength leading electrolyte buffer to the lower ionic strength elution buffer. The elution buffer may provide compatibility with one or more downstream assays as described herein (e.g. NGS library prep, PCR, etc.). The elution buffer may comprise Tris and chloride, for example 10 mM Tris-HCl. The elution buffer may comprise a pH compatible with nucleic acid stability. The leading electrolyte buffer may comprise a surfactant (e.g. Tween) in order to reduce or minimize electroosmotic flow. The leading electrolyte buffer may comprise a surfactant in order to reduce or minimize bubble growth in the fluidic channel (e.g. during temperature measurements as described herein). The leading electrolyte buffer may comprise a surfactant in order to reduce or minimize surface adsorption. The elution buffer may comprise one or more surfactants as described herein. The concentration of the one or more surfactants may be adjusted so as to ensure that the elution buffer does not uncontrollably wet past the capillary barriers (e.g. the ramp barriers) described herein.

In some embodiments, leading electrolytes may be loaded in a high concentration elution buffer, which may act to buffer a lower concentration elution buffer (e.g. a lower concentration suitable for extraction and use in downstream assays as described herein). The high concentration elution buffer may have sufficient buffering capacity so as to not change pH during the electrolysis process that occurs throughout the ITP run. The high concentration elution buffer may have a minimal (e.g. less than 1 µl) amount of carryover between the high concentration elution buffer and the elution buffer. The high concentration elution buffer may comprise a sufficiently low ion concentration such that this carryover does not impact downstream compatibility. The high concentration elution buffer may comprise Tris and chloride. The high concentration elution buffer may comprise Tris and chloride at a ratio configured to maximize buffering capacity, for example a high Tris:chloride ratio to provide a source of Tris during the ITP run. The high concentration elution buffer may comprise Tris and chloride at a sufficiently high ion concentration to achieve robust buffering while minimizing the impact of carryover. The high concentration elution buffer may comprise one or more surfactant in order to ensure that the high concentration elution buffer wets the walls of the high concentration elution buffer reservoir and loads to the capillary barriers upon application of negative pressure. The concentration of the one or more surfactants may be adjusted so as to ensure that the high concentration elution buffer does not uncontrollably wet past the capillary barriers (e.g. the ramp barriers) described herein.

Trailing electrolyte may be in a trailing electrolyte buffer. The trailing electrolyte buffer may comprise one or more trailing electrolytes compact the target nucleic acids in front of the trailing electrolytes in the channel during ITP. The trailing electrolytes may also separate the target nucleic acids from any contaminants or inhibitors which have an effective mobility magnitude less than that of the target nucleic acids. The trailing electrolyte buffer may have sufficient buffering capacity so as to not change pH during the electrolysis process that occurs throughout the ITP run. The trailing electrolyte buffer may, for example, comprise caproic acid. The trailing electrolyte buffer may comprise MOPS. The trailing electrolyte buffer may comprise caproic acid and MOPS. The trailing electrolyte buffer may comprise a high concentration of caproic acid. A high concentration of caproic acid may lead to an overly wetting fluid. MOPS may be added to the caproic acid of the trailing electrolyte buffer to provide the necessary buffering capacity in the trailing electrolyte reservoir without the increased wetting of too high a concentration of caproic acid. The trailing electrolyte buffer may comprise a pH compatible with nucleic acid stability.

The leading electrolyte buffer may comprise one or more surfactants (e.g. Tween) as described herein. The concentration of the one or more surfactants may be adjusted so as to ensure that the TE does not uncontrollably wet past the capillary barriers (e.g. the plateau capillary barriers) described herein. The concentration of the one or more surfactants may be adjusted to create no or small bubbles during the electrolysis process, as opposed to large bubbles, which may lead to fluid fluctuations that can cause disturbance of the ITP band, the voltage trace, and/or the temperature trace, or very large bubbles, which may move and negatively impact triggering.

Isotachophoresis can quench the pH of a sample to neutral or about neutral. Ions affecting the local pH (e.g., sodium ions (Na+)) can be displaced from the sample zone during isotachophoresis, thereby shifting the pH in the sample zone toward neutral.

Isotachophoresis can be conducted at a range of voltages, currents, and field strengths. For example, isotachophoresis can be conducted at a voltage from about 100 V and about 1500 V. Isotachophoresis can be conducted at a voltage of about 100 V, 200 V, 300 V, 400 V, 500 V, 600 V, 700 V, 800 V, 900 V, 1000 V, 1100 V, 1200 V, 1300 V, 1400 V, or 15000 V. Isotachophoresis can be conducted at a voltage of at least about 100 V, 200 V, 300 V, 400 V, 500 V, 600 V, 700 V, 800 V, 900 V, 1000 V, 1100 V, 1200 V, 1300 V, 1400 V, or 15000 V. Isotachophoresis can be conducted at a voltage of at most about 100 V, 200 V, 300 V, 400 V, 500 V, 600 V, 700 V, 800 V, 900 V, 1000 V, 1100 V, 1200 V, 1300 V, 1400 V, or 15000 V. Isotachophoresis can be conducted at a current from about 10 nA to about 10 mA. Isotachophoresis can be conducted at a current of about 10 nA, 20 nA, 30 nA, 40 nA, 50 nA, 60 nA, 70 nA, 80 nA, 90 nA, 100 nA, 200 nA, 300 nA, 400 nA, 500 nA, 600 nA, 700 nA, 800 nA, 900 nA, 1 mA, 2 mA, 3 mA, 4 mA, 5 mA, 6 mA, 7 mA, 8 mA, 9 mA, or 10 mA. Isotachophoresis can be conducted at a current of at least about 10 nA, 20 nA, 30 nA, 40 nA, 50 nA, 60 nA, 70 nA, 80 nA, 90 nA, 100 nA, 200 nA, 300 nA, 400 nA, 500 nA, 600 nA, 700 nA, 800 nA, 900 nA, 1 mA, 2 mA, 3 mA, 4 mA, 5 mA, 6 mA, 7 mA, 8 mA, 9 mA, or 10 mA. Isotachophoresis can be conducted at a current of at most about 10 nA, 20 nA, 30 nA, 40 nA, 50 nA, 60 nA, 70 nA, 80 nA, 90 nA, 100 nA, 200 nA, 300 nA, 400 nA, 500 nA, 600 nA, 700 nA, 800 nA, 900 nA, 1 mA, 2 mA, 3 mA, 4 mA, 5 mA, 6 mA, 7 mA, 8 mA, 9 mA, or 10 mA. Isotachophoresis can be conducted at a field strength of from about 10 V/cm to about 100 V/cm. Isotachophoresis can be conducted at a field strength of about 10 V/cm, 15 V/cm, 20 V/cm, 25 V/cm, 30 V/cm, 35 V/cm, 40 V/cm, 45 V/cm, 50 V/cm, 55 V/cm, 60 V/cm, 65 V/cm, 70 V/cm, 75 V/cm, 80 V/cm, 85 V/cm, 90 V/cm, 95 V/cm, or 100 V/cm. Isotachophoresis can be conducted at a field strength of at least about 10 V/cm, 15 V/cm, 20 V/cm, 25 V/cm, 30 V/cm, 35 V/cm, 40 V/cm, 45 V/cm, 50 V/cm, 55 V/cm, 60 V/cm, 65 V/cm, 70 V/cm, 75 V/cm, 80 V/cm, 85 V/cm, 90 V/cm, 95 V/cm, or 100 V/cm. Isotachophoresis can be conducted at a field strength of at most about 10 V/cm, 15 V/cm, 20 V/cm, 25 V/cm, 30 V/cm, 35 V/cm, 40 V/cm, 45 V/cm, 50 V/cm, 55 V/cm, 60 V/cm, 65 V/cm, 70 V/cm, 75 V/cm, 80 V/cm, 85 V/cm, 90 V/cm, 95 V/cm, or 100 V/cm.

Isotachophoresis can be used to concentrate nucleic acids in a sample. The concentration of nucleic acids in a sample can be increased after isotachophoresis by at least about 2-fold, 5-fold, 10-fold, 100-fold, 1,000-fold, 10,000-fold, 100,000-fold, 1,000,000-fold, 10,000,000-fold, 100,000,000-fold, or 1,000,000,000-fold. The operation time for concentration of nucleic acids with isotachophoresis can be less than or equal to about 5 hours, 4.5 hours, 4 hours, 3.5 hours, 3 hours, 2.5 hours, 2 hours, 1.5 hours, 1 hours, 50 minutes, 40 minutes, 30 minutes, 20 minutes, 10 minutes, 9 minutes, 8 minutes, 7 minutes, 6 minutes, 5 minutes, 4 minutes, 3 minutes, 2 minutes, 1 minute, 45 seconds, 30 seconds, 20 seconds 10 seconds, or 1 second. In some cases, isotachophoresis can be used to increase the concentration of nucleic acids in a sample by 1,000,000-fold in less than or equal to about 2 minutes. In some cases (e.g., from a sample of 25 µL blood lysate), isotachophoresis can be used to increase the concentration of nucleic acids in a sample by 100,000-fold in less than or equal to about 5 minutes.

Techniques of the present disclosure can be used to reduce the concentration of crosslinked nucleic acids in a sample.

The concentration of crosslinked nucleic acids in a sample can be reduced after isotachophoresis by at least about 2-fold, 5-fold, 10-fold, 100-fold, 1,000-fold, 10,000-fold, 100,000-fold, 1,000,000-fold, 10,000,000-fold, 100,000,000-fold, or 1,000,000,000-fold. Isotachophoresis can be used to reduce the concentration of a contaminant in a sample. The concentration of contaminants in a sample can be reduced after isotachophoresis by at least about 2-fold, 5-fold, 10-fold, 100-fold, 1,000-fold, 10,000-fold, 100,000-fold, 1,000,000-fold, 10,000,000-fold, 100,000,000-fold, or 1,000,000,000-fold.

Nucleic acid samples can contain from about 0.1 picograms (pg) to about 25 micrograms (m). For example, nucleic acid samples can contain from about 5 pg to about 5 µg. Nucleic acid samples can contain about 0.1 pg, 0.2 pg, 0.3 pg, 0.4 pg, 0.5 pg, 0.6 pg, 0.7 pg, 0.8 pg, 0.9 pg, 1 pg, 2 pg, 3 pg, 4 pg, 5 pg, 6 pg, 7 pg, 8 pg, 9 pg, 10 pg, 20 pg, 30 pg, 40 pg, 50 pg, 60 pg, 70 pg, 80 pg, 90 pg, 100 pg, 200 pg, 300 pg, 400 pg, 500 pg, 600 pg, 700 pg, 800 pg, 900 pg, 1 nanogram (ng), 2 ng, 3 ng, 4 ng, 5 ng, 6 ng, 7 ng, 8 ng, 9 ng, 10 ng, 20 ng, 30 ng, 40 ng, 50 ng, 60 ng, 70 ng, 80 ng, 90 ng, 100 ng, 200 ng, 300 ng, 400 ng, 500 ng, 600 ng, 700 ng, 800 ng, 900 ng, 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, or 25 µg.

Nucleic acid samples can comprise deoxyribonucleic acids (DNA), single-stranded DNA, double-stranded DNA, genomic DNA, complementary DNA, ribonucleic acids (RNA), ribosomal RNA, transfer RNA, messenger RNA, micro RNA, or the like, or any combination thereof. Nucleic acid samples can comprise a length of at least about 0.5, 1, 2, 5, 10, 20, 30, 40, 50, 60, 70, 80, 90, 100, 150, 200, 250, 300, 350, 400, 450, or 500 kB or more. Techniques of the present disclosure can be used to extract different sample types in different channels of a fluidic device. For example, different channels may be used to extract nucleic acids of different lengths and/or different types.

In some instances, a characteristic of a nucleic acid sample may be compared to one or more nucleic acids from another sample. The characteristic may for example be an expression level, a nucleic acid sequence, a molecular weight, nucleic acid integrity, nucleic-acid stranded-ness, or nucleic acid purity.

Nucleic acid samples can be of a particular quality before and/or after extraction or other processing. Nucleic acid quality can be assessed by various metrics, including but not limited to RNA integrity number (RIN), DNA integrity number (DIN), size distribution (e.g., using electrophoresis), and ability to be amplified (e.g., by PCR) or otherwise enzymatically processed (e.g. fragmentation, ligation, a-tailing, or hybridization for next generation sequencing library preparation). Techniques of the present disclosure can be used to extract or process nucleic acids and provide extracted or processed nucleic acids with a RIN of at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids with a RIN of at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids with a DIN of at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids with a DIN of at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids such that at least 10%, 20%, 30%, 40%, 50%, 60%, 70%, 80%, 90%, 95%, 96%, 97%, 98%, 99%, 99.9%, or 99.99% of the mass of the nucleic acids of the sample has a molecular weight of at least about 0.5, 1, 2, 5, 10, 20, 30, 40, 50, 60, 70, 80, 90, 100, 150, 200, 250, 300, 350, 400, 450, or 500 kB or more. In some cases, about 90% to about 100% of the mass of the processed nucleic acids are from about 10 to about 1000 bp, from about 200 to about 2000 bp, or from about 200-5000 bp.

Figure 3:
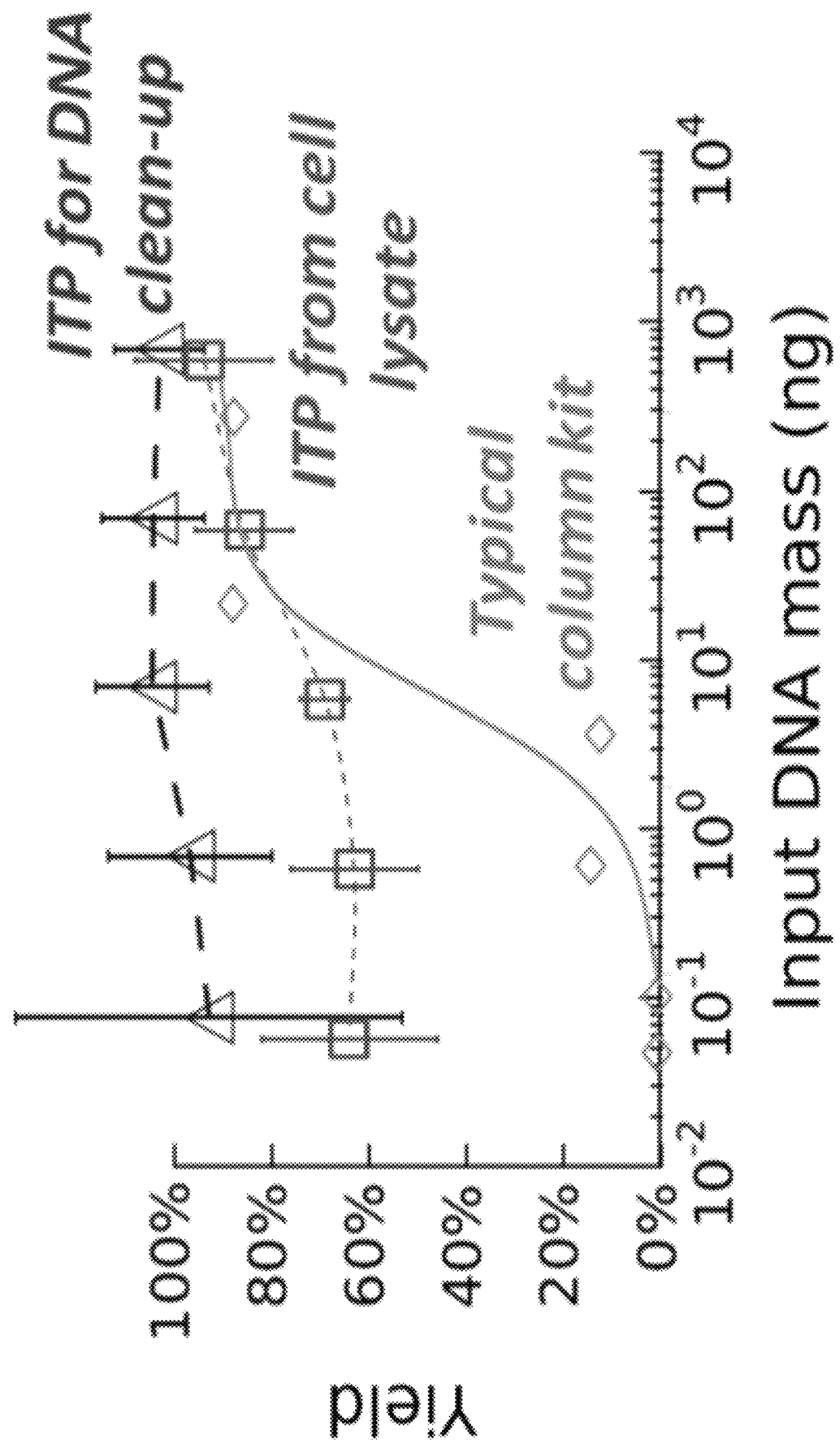
FIG. 3 shows exemplary results of DNA extraction and purification by automated isotachophoresis in a fluidic device compared to exemplary results from a typical solid phase column extraction kit.

Isotachophoresis can be used to extract nucleic acids at an extraction efficiency or yield, characterized as the percent yield of nucleic acid from a given starting amount of nucleic acid. Techniques of the present disclosure can provide extracted nucleic acids at a yield of at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9%. Techniques of the present disclosure can provide high yields even for low input amounts nucleic acid, including less than or equal to about $10^4$ nanograms (ng), $10^3$ ng, $10^2$ ng, $10^1$ ng, $10^0$ ng, $10^{-1}$ ng, or $10^{-2}$ ng. FIG. 3, for example, shows exemplary nucleic acid yields from a range of different input amounts and sources of nucleic acid. High yield and/or low loss of nucleic acids can be important for next generation sequencing library preparations. Recovery of nucleic acids can be at or near 100%.

Techniques of the present disclosure can extract nucleic acids with low or no sequence bias. That is, the sequence composition of the extracted and purified nucleic acids (e.g., ratio of GC-rich nucleic acids to AT-rich nucleic acids) can be similar to or the same as the sequence composition of the input nucleic acids (see, e.g., FIG. 4A). The difference in sequence composition of the extracted nucleic acids from the sequence composition of the input nucleic acids can be less than or equal to about 20%, 15%, 10%, 5%, 4%, 3%, 2%, or 1%.

Techniques of the present disclosure can extract nucleic acids with low or no length bias. That is, the length distribution of the extracted nucleic acids (e.g., the proportions of nucleic acids of different sizes) can be similar to or the same as the length distribution of the input nucleic acids (see, e.g., FIG. 4B). The difference in length distribution of the extracted nucleic acids from the length distribution of the input nucleic acids can be less than or equal to about 20%, 15%, 10%, 5%, 4%, 3%, 2%, or 1%. For example, short nucleic acids (e.g., about 10 to about 300 bp), long nucleic acids (e.g., about 10 kB, 20 kB, 30 kB, 40 kB, 50 kB, 60 kB, 70 kB, 80 kB, 90 kB, 100 kB, or greater), or both short and long nucleic acids can be extracted with reduced drop out or bias. Solid phase columns can, in some cases, lose up to 100% of short and/or long nucleic acid material. Techniques of the current disclosure can recover nucleotides from single base to hundreds of kilobases in size. Techniques of the present disclosure can recover at least about 10%, 20%, 30%, 40%, 50%, 60%, 70%, 80%, 90%, or 95%, 96%, 97%, 98%, 99%, 99.9%, or 100% of short and/or long nucleic acids present in the sample.

Techniques of the present disclosure can result in the removal of contaminants from the sample. Contaminants can include but are not limited to embedding material, cell debris, extracellular matrix components, tissue debris, embedding debris, lipids, carbohydrates, enzymes, ligation by-products, primers, unbound probes or ligators, divalent metals, detergents, preservatives, fixatives, anti-coagulants, collagen fibers, and PCR inhibitors. Contaminants can originate from the tissue or cells of the sample, from preservatives or embedding materials used on the sample, or from previous preparations, reactions, or assays performed on the sample. For example, enzymes such as restriction nucleases can be used to prepare DNA for a fingerprinting assay, and subsequent to digestion (e.g., DNase digestion), DNA can be separated from the enzyme.

Samples

The techniques of the present disclosure can be used to process different sample types, including but not limited to biological samples, solid tissue, biopsies, tissue biopsies, liquid biopsies, organs, tumors, fresh tissue, solid organs, preserved tissue (e.g., FFPE), dissected FFPE, fresh frozen tissue, fixed samples, fixed tissue, embedded samples, lysed samples, un-lysed samples, samples comprising connections between cells (e.g. gap junctions, tight junctions, adherent junctions), samples comprising lysed solid tissue and nucleic acids, multiphasic samples, inhomogeneous liquids or solutions (such as tissue, whole blood, or unlysed cell suspensions), biological samples comprising genomic DNA, lysed and un-lysed whole blood, plasma and serum, buccal swabs, dried blood spots and other forensic samples, fresh or fresh frozen (FF) tissues, cultured or harvested cells (lysed and un-lysed) from blood or tissues, fixed cells, stool, and bodily fluids (e.g., saliva, urine), or any combination thereof. Non-limiting examples of solid organs include liver, pancreas, brain, heart, gall bladder, colon, lung and reproductive organs. Samples can include cellular and cell-free nucleic acids, for both eukaryotic and prokaryotic organisms. Fixed samples can be chemically fixed or physically fixed (e.g., heating or freezing). For example, samples can be chemically fixed with a chemical fixative such as formalin, neutral buffered formalin (NBF), formaldehyde, paraformaldehyde, glutaraldehyde, glyoxal, mercuric chloride, zinc salts, Bouin's fluid, alcohol-formalin-acetic acid (AFA or FAA), citrate-acetone-formalin (CAF), acetone, methanol, ethanol, Clarke's fluid, Carnoy's fluid, or Puchtler's methacarn. Embedded samples can be embedded in materials including but not limited to wax (e.g., paraffin), agar, gelatin, or plastic resins. Formalin-fixed paraffin-embedded (FFPE) samples can be processed using techniques of the present disclosure. Samples can comprise buccal swabs, blood spots, and other forensic samples. Samples can comprise clinical samples, fine needle aspirates, biopsies, whole blood, lysed blood, serum, plasma, urine, cell culture lysate or freshly harvested cell (e.g., blood cell, dissociated fresh tissue, stem cell) lysate, blood cells, circulating cells (e.g., circulating tumor cells (CTCs)), nucleic acids from blood or other bodily fluid, and other sample categories. Cell-free nucleic acids (e.g., cfDNA or cfRNA) can be recovered, such as from whole un-lysed blood, using techniques of the present disclosure; often the cell-free nucleic acids are circulating cell-free nucleic acids. Samples can be from a variety of sources, including but not limited to normal tissue, benign neoplasms, malignant neoplasms, stem cells, human tissue, animal tissue, plant tissue, bacteria, viruses, and environmental sources (e.g., water). Human or animal tissues can include but are not limited to epithelial tissue, connective tissue (e.g., blood, bone), muscle tissue (e.g., smooth muscle, skeletal muscle, cardiac muscle), and nervous tissue (e.g., brain, spinal cord).

Samples can comprise one or more particles in suspension. The one or more particles may range from colloidal size to visible. The one or more particles can have a size of at least about 1 nanometer (nm), 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 600 nm, 700 nm, 800 nm, 900 nm, 950 nm, 1 micrometer (µm), 10 µm, 20 µm, 30 µm, 40 µm, 50 µm, 60 µm, 70 µm, 80 µm, 90 µm, 100 µm, 150 µm, 175 µm, 200 µm, 225 µm, 250 µm, 275 µm, 300 µm, 350 µm, 400 µm, 450 µm, 500 µm, 550 µm, 600 µm, 650 µm, 700 µm, 750 µm, 800 µm, 850 µm, 900 µm, 950 µm, or 1 millimeter (mm). The one or more particles can have a size of at most about 1 nanometer (nm), 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 600 nm, 700 nm, 800 nm, 900 nm, 950 nm, 1 micrometer (µm), 10 µm, 20 µm, 30 µm, 40 µm, 50 µm, 60 µm, 70 µm, 80 µm, 90 µm, 100 µm, 150 µm, 175 µm, 200 µm, 225 µm, 250 µm, 275 µm, 300 µm, 350 µm, 400 µm, 450 µm, 500 µm, 550 µm, 600 µm, 650 µm, 700 µm, 750 µm, 800 µm, 850 µm, 900 µm, 950 µm, or 1 millimeter (mm). The one or more particles can be the same size or different sizes. A sample may for example comprise a plurality of particles ranging in size from 1 nm to 500 µm.

Samples of various volumes can be processed on a fluidic device (e.g., to extract and purify nucleic acids). For example, a sample volume (with or without buffer) can be at least about 1 nanoliter (nL), 10 nL, 20 nL, 50 nL, 100 nL, 200 nL, 500 nL, 1 microliter (µL), 10 µL, 20 µL, 30 µL, 40 µL, 50 µL, 60 µL, 70 µL, 80 µL, 90 µL, 100 µL, 150 µL, 175 µL, 200 µL, 225 µL, 250 µL, 275 µL, 300 µL, 350 µL, 400 µL, 450 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, or 10 mL. A sample volume (with or without buffer) can be at most about 1 nanoliter (nL), 10 nL, 20 nL, 50 nL, 100 nL, 200 nL, 500 nL, 1 microliter (µL), 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, or 10 mL. In some cases, a sample volume can be from about 1 nL to about 10 nL. A sample volume (with or without buffer) can be at least about 1 nanoliter (nL), 10 nL, 20 nL, 50 nL, 100 nL, 200 nL, 500 nL, 1 microliter (µL), 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, or 10 mL. In some cases, a sample volume can be from about 1 nL to about 10 nL.

Samples with different numbers of cells can be processed on a fluidic device (e.g., to extract and purify nucleic acids). For example, a sample can contain less than or equal to about 20,000 cells, 15,000 cells, 10,000 cells, 9,000 cells, 8,000 cells, 7,000 cells, 6,000 cells, 5,000 cells, 4,500 cells, 4,000 cells, 3,500 cells, 3,000 cells, 2,500 cells, 2,000 cells, 1,500 cells, 1,000 cells, 900 cells, 800 cells, 700 cells, 600 cells, 500 cells, 400 cells, 300 cells, 200 cells, 100 cells, 90 cells, 80 cells, 70 cells, 60 cells, 50 cells, 40 cells, 30 cells, 20 cells, 10 cells, 5 cells, 2 cells, or 1 cell. In some cases, a sample contains at least about 10,000,000 cells, 5,000,000 cells, 1,000,000 cells, 500,000 cells, 100,000 cells, 50,000 cells, 20,000 cells, 15,000 cells, 10,000 cells, 9,000 cells, 8,000 cells, 7,000 cells, 6,000 cells, 5,000 cells, 4,500 cells, 4,000 cells, 3,500 cells, 3,000 cells, 2,500 cells, 2,000 cells, 1,500 cells, 1,000 cells, 900 cells, 800 cells, 700 cells, 600 cells, 500 cells, 400 cells, 300 cells, 200 cells, or 100 cells.

Samples of different masses can be processed on a fluidic device (e.g., to extract and purify nucleic acids). For example, a sample can contain from about 0.001 milligrams (mg) and about 10 mg of tissue. A sample can contain at most about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of tissue. A sample can contain at least about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of tissue. A sample can contain about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of tissue.

Samples with different amounts of nucleic acid can be processed on a fluidic device (e.g., to extract and purify nucleic acids). For example, samples can contain less than or equal to about 1 microgram (1 µg), 100 nanograms (ng), 10 ng, 1 ng, 100 picograms (pg), 10 pg, or 1 pg of nucleic acid. In some cases, samples can contain greater than or equal to about 1 microgram (1 µg), 100 nanograms (ng), 10 ng, 1 ng, 100 picograms (pg), 10 pg, or 1 pg of nucleic acid.

Samples can be loaded in a sample buffer. The sample buffer may comprise a lysis agent or surfactant to lyse the input sample during off-chip processing to provide access to the target nucleic acids. The sample buffer may comprise one or more leading electrolytes. The sample buffer may have sufficient wettability so as to self-load into the sample channel due to gravity and/or surface tension. The sample buffer may comprise one or more surfactants in order to reduce or minimize adsorption of the target nucleic acids to the walls of the fluidic channel. The sample buffer may comprise an ion content optimized to have sufficient salt for lysis and/or nucleic acid preservation while still accommodating the separation of nucleic acids. One of ordinary skill in the art will understand that the higher the ion content of the sample buffer (or any of the buffers described herein), the more current which will be required to transfer the charge of the sample buffer.

Samples can be loaded in a buffer comprising trailing electrolyte or leading electrolyte. Samples can be loaded in a buffer comprising a second leading electrolyte which differs from the leading electrolyte used to perform ITP. Samples can be loaded in a buffer, such as an aqueous alkaline or a neutral aqueous buffer. Exemplary alkaline solutions or buffers (e.g., for DNA extraction) can comprise 30-120 mM NaOH (in some cases, 40-80 mM NaOH) at a pH of about 10-13 (in some cases, with at least one additional component). In some instances, when the sample is lysed via treatment with an alkaline solution or buffer prior to loading onto the chip, the lysed sample may subsequently be quenched by adding an acidic solution or buffer to bring the pH of the lysed sample within a range of about 7.5 to about 8.5 prior to performing isotachophoresis. Exemplary aqueous buffers (e.g., for DNA or RNA extraction) can comprise 2-150 mM Tris-HCl (at a pH of about 7 to about 8) or BisTris-HCl at a pH of about 5.8 to about 7.3, with at least one additional component. Additional components used in buffers can include non-ionic surfactants or detergents, ionic or zwitter-ionic surfactants or detergents, chaotropic agents, disulfide bond reducing agents, proteases, nucleases, and other additives or components that digest, denature, disrupt, or degrade for the purpose of extracting, purifying, enriching, or otherwise isolating nucleic acids.

Samples can be loaded in a buffer comprising trailing electrolyte or leading electrolyte added to reduce or minimize retention of nucleic acids at a capillary barrier, particularly a capillary barrier between a sample and LE. For example, a small amount of trailing electrolyte (e.g. MOPS and/or caproic) may be added to a lysate sample to intentionally slow compaction of the DNA ITP band. Not wanting to be limited by a particular theory, it is believed that this may help to maintain the DNA in a more dispersed state as it passes through a constricted space of the capillary barrier (e.g. a cliff capillary barrier at the junction between the sample and LE) which may otherwise impair passage of a more compact ITP band. Because the spiked-in TE has a slower magnitude of mobility than both the DNA and the LE, once the ITP band enters the LE buffer the TE may fall behind and allow the ITP band to fully compact before it reaches the elution reservoir.

Non-ionic surfactants or detergents can include but are not limited to surfactants from the following classes: octylphenol ethoxylate, polysorbate, poloxamer, or polyoxyethylene. Octylphenol ethoxylate surfactants can include but are not limited to branched octylphenoxy polyethoxy ethanol (IGEPAL CA-630), t-octylphenoxypolyethoxyethanol (Triton™ X-100), or other polyethylene oxide chains with an aromatic hydrocarbon lipophilic or hydrophobic group. Polysorbate surfactants can include but are not limited to polyethylene glycol sorbitan monolaurate (Tween 20), polyethylene glycol sorbitan monooleate (Tween® 80), or sorbitan monooleate (Span® 80). Poloxamer surfactants (i.e. block copolymers based on ethylene oxide and propylene oxide) can include but are not limited to polyoxyethylene-polyoxypropylene block copolymer (Pluronic® F-68) or polyethylene-polypropylene glycol block copolymer (Pluronic® F-127). Polyoxyethylene surfacts can include but are not limited to nonyl phenoxypolyethoxylethanol (NP-40).

Non-ionic surfactants or detergents can include but are not limited to IGEPAL® (e.g., IGEPAL® CA-630), Triton™ X-100, Tween® 20, Tween® 80, NP-40, other block copolymers including Pluronic® (e.g., F-68 or F-127), Span® 80, and pegylated polymers or copolymers. Non-ionic surfactants or detergents can be used to reduce or prevent biological molecule adsorption to channel walls, or to control wetting and/or surface tension properties of fluids to control loading of sample into fluidic devices. Non-ionic surfactants or detergents can be present at concentrations from about 0.0005-5% v/v or w/v. For example, IGEPAL CA-630 can be used at about 0.05-0.5% v/v. Ionic surfactants or detergents can include but are not limited to sodium dodecyl sulfate (e.g., at 0.01-2% w/v), sodium dodecylbenzenesulfonate (e.g., at 0.01-2% w/v), sodium cholesteryl sulfate (e.g., at 0.01%-2% w/v), and sodium deoxycholate (e.g., at about 10-1000 mM). Chaotropic agents can include but are not limited to urea (e.g., at about 0.5-9.5 M, or in some cases, 5-9.5 M) thiourea, butanol, ethanol, guanidinium chloride, lithium perchlorate, lithium acetate, lithium chloride, magnesium chloride, phenol, and propanol. For example, 7.0 M urea and 2.0 M thiourea can be used in a 5-50 mM Tris-HCl (in some cases, 10-20 mM Tris-HCl) buffered solution for either RNA or DNA extractions, or for total nucleic acid extractions. The ratio of urea to thiourea can be at least about 1:1, 1.5:1, 2:1, 2.5:1, 3:1, 3.5:1, 4:1, 4.5:1, 5:1, 6:1, 6.5:1, 7:1, 7.5:1, or 8:1. Disulfide bond reducing agents can include but are not limited to DTT (e.g. at about 0.1-40 mM, or in some cases about 10 mM) and betamercaptoethanol (e.g., at about 0.5-2%, or in some cases about 1%). Proteases can include but are not limited to Proteinase K, proteases, endoproteinases (e.g., trypsin, LysC, GluC, AspN), peptidases, pepsin, and papain. Nucleases can include but are not limited to non-specific nucleic acid digestion enzymes such as DNases including DNase I (e.g., to prepare DNA-free RNA extractions) and RNase, such as RNase A, RNase T, or combinations thereof (e.g., to prepare RNA-free DNA extractions). Nucleases can also include specific nucleic acid digestion enzymes (e.g., restriction enzymes) which can cut at specific nucleic acid sequences and can produce predictable fragment sizes and fragment size distributions. In some cases, one or more methods or processes provided herein are performed without use of a nuclease, without use of a DNAse, or without use of an RNAase. For example, the methods provided herein include extraction of RNA without use of DNAase.

Restriction enzymes can include but are not limited to Type 1 through Type V restriction enzymes, BamHI, EcoP15I, EcoRI, EcoRII, EcoRV, HaeIII, HgaI, HindIII, HinFI, KpnI, NotI, PstI, PvuII, SacI, SalI, SmaI, SpeI, SphI, XbaI, and StuI. Nucleases can be used at concentrations including 50-400 µg/mL. Nuclease digestions can be performed at temperatures including from about 20° C. to about 37° C. Other nucleic acid modifying enzymes can be used, such as transposases, ligases, polymerases, and phosphatases. Other protein or polynucleotide digestion or degradation agents can be used, such as lysozymes.

Prior to loading onto a fluidic device, samples can be subjected to various degrees of pre-processing. In some cases, a sample can be simply loaded into buffer prior to loading onto a fluidic device, and any other necessary or desired sample preparation steps can be conducted on the device. In other cases, sample can be added to a sample reservoir that is prefilled with a processing fluid such as a solution or buffer. In other cases, a sample can be subjected to removal of embedding material, tissue disruption, cell lysis, or digestion prior to loading on a fluidic device. In one example, a sample is deparaffinized prior to loading onto a fluidic device, and de-crosslinking of nucleic acids is conducted on the fluidic device. In another example, a sample is deparaffinized, disrupted, and lysed prior to loading onto a fluid device, and, optionally, de-crosslinking of nucleic acids is conducted on the fluidic device. In another example, a sample is deparaffinized prior to loading onto a fluidic device, and tissue disruption and cell lysis are conducted on the fluidic device. In another example, a sample is loaded onto a fluidic device, and deparaffinization, tissue disruption, cell lysis, and de-crosslinking of nucleic acids are all conducted on the fluidic device. Sample preparation steps are discussed further in this disclosure.

Sample Preparation

Samples can be prepared prior to isotachophoresis. Sample preparation can involve steps including but not limited to removal of embedding material, tissue disruption, cell lysis, digestion of proteins, removal of nucleic acid crosslinking, isothermal enzymatic process, enzymatic amplification, enzymatic digestion, disruption of cell-cell junctions, disruption of extracellular matrix, disruption of connective tissue, and combinations thereof. Sample preparation can involve techniques such as polymerase chain reaction (PCR) or other nucleic acid amplification, isolation or purification of material (e.g., cells, nucleic acids) of interest, probe hybridization, and antibody hybridization (e.g., hybridization of antibodies to nucleosomes). In some cases, samples can be prepared by isolating a portion of material from cells from the sample for further analysis. For example, circulating tumor cells can be isolated from a heterogenous population of cells using a cell sorting devices such as a flow cytometer or magnetized column. In another example, peripheral blood lymphocytes (PBLs) or peripheral blood mononuclear cells (PBMCs) can be isolated from a blood sample. Sample preparation can be conducted on-device or off-device. In some cases, some sample preparation steps are conducted off-device, and then the sample is loaded onto a fluidic device where additional sample preparation steps are conducted.

Biological material (e.g., cells, tissue, nucleic acids) in an embedded sample can be removed from the embedding material. For example, a paraffin-embedded sample can be deparaffinized. Removal of embedding material can be conducted using techniques including but not limited to heat treatment, chemical treatment (e.g., acid or base), enzymatic treatment, and combinations thereof. Deparaffinization can be performed by chemical treatment of a sample, by heat-treating a sample, by enzymatic treatment of a sample, or by other methods. For example, deparaffinization can be conducted at an elevated temperature (e.g. from about 50° C. to about 80° C.) in the presence of a neutral buffer or somewhat acidic buffer (e.g., down to pH about 5.5) buffer or somewhat basic (up to pH about 9) or alkaline solution (e.g., pH from about 12 to about 13). Removal of embedding material can be conducted off-device or on-device. In one example, an embedded sample can be incubated at an elevated temperature in a vessel and subsequently loaded onto a fluidic device. In another example, an embedded sample can be loaded onto a fluidic device and incubated at an elevated temperature on the device, for example in the channel or a reservoir.

Removal of embedding material can be conducted by heat treatment. Incubation for removal of embedding material can be conducted at a temperature of at least about 35° C., 37° C., 40° C., 45° C., 50° C., 55° C., 60° C., 65° C., 70° C., 75° C., 80° C., 85° C., 90° C., 95° C., 96° C., 97° C., 98° C., 99° C., 99.5° C., or 100° C. Incubation for removal of embedding material can be conducted at a temperature from about 40° C. to about 80° C., from about 50° C. to about 80° C., from about 50° C. to about 99.9° C., or about 95 to about 99.5° C. Incubation for removal of embedding material can be conducted for a duration of at least about 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes. Incubation for removal of embedding material can be conducted for a duration from about 1 minute to about 20 minutes, from about 1 minute to about 30 minutes, from about 1 minute to about 60 minutes, from about 1 minute to about 120 minutes, or from about 5 minutes to about 20 minutes. Incubation for removal of embedding material can for example be conducted at a temperature of at least about 37° C. for a duration of at least about 1 minute. Incubation for removal of embedding material can be conducted in the presence of an alkaline buffer or a neutral buffer (e.g. lysis buffer). An alkaline buffer (e.g. lysis buffer) can have a pH of at least about 8.5, 9.0, 9.5, 10.0, 10.5, 11.0, 11.5, 12.0, 12.5, 13.0, or 13.5. A neutral buffer can have a pH of about 7.0 (e.g., from about 7 to about 8).

Tissues or cells can be disrupted or lysed, releasing nucleic acids for separation, purification, or extraction. Tissue disruption or cell lysis can be conducted using techniques including but not limited to mechanical stress, sonication, electroporation, osmotic pressure, chemical treatment (e.g., acid or base), enzymatic treatment, heat treatment, and combinations thereof. For example, pressure can be used to drive tissue through a structure (e.g., a channel, a resin such as a frit or porous resin, or a glass material) to mechanically disrupt tissue or lyse cells. In some cases, the trailing electrolyte buffer can comprise one or more tissue disruption agents and/or cell lysis agents. In some cases, the leading electrolyte buffer can comprise one or more tissue disruption agents and/or cell lysis agents. In some cases, removal of embedding material can be achieved by the same process as tissue disruption or cell lysis. For example, incubation at an elevated temperature (e.g. from about 30° C. to about 80° C., from about 50° C. to about 80° C., or from about 30° C. to about 65° C.) can achieve removal of embedding material, tissue disruption, and cell lysis. Tissue disruption or cell lysis can be conducted off-device or on-device. In one example, a tissue sample is disrupted in a vessel and subsequently loaded onto a fluidic device. In another example, a tissue sample previously loaded onto a fluidic device is disrupted on the device.

Samples comprising tissue or cells can be lysed before or after loading onto a fluidic device using a lysis solution or buffer compatible with isotachophoresis. Lysis buffers compatible with isotachophoresis can include non-ionic surfactants or detergents, ionic or zwitter-ionic surfactants or detergents, chaotropic agents, disulfide bond reducing agents, proteases, nucleases, and other additives or components that digest, denature, disrupt, or degrade for the purpose of extracting, purifying, enriching (concentrating), or otherwise isolating nucleic acids. In some cases, a lysis buffer may comprise an alkaline buffer. In some cases, a lysis buffer may not comprise an alkaline buffer. An exemplary lysis buffer may include 0.5 M to 9.5 M, 4 M to 9 M, or 6.5 M to 7 M urea as described herein. An exemplary lysis buffer may include 0.5 M to 3.5 M or 1.5 M to 2.5 M thiourea as described herein. An exemplary lysis buffer may include 0.5-9.5 M urea and thiourea, for example 7M urea and 2 M thiourea with a non-ionic surfactant as described herein. The use of urea alone or in combination with thiourea may be used to lyse cells for nucleic acid purification. In combination, urea and thiourea may act synergistically to lyse cells and may provide an uncharged isotachophoresis-compatible buffer for nucleic acid purification.

An exemplary lysis buffer may include a non-ionic surfactant such as 0.05-0.5% v/v IGEPAL CA-630 as described herein. In some cases, the lysis buffer may comprise one or more trailing electrolytes. In some cases, the lysis buffer may comprise a trailing electrolyte buffer with additives for tissue disruption or cell lysis as described herein. In some cases, the lysis buffer may comprise one or more leading electrolytes. In some cases, the lysis buffer may comprise a leading electrolyte buffer with additives for tissue disruption or cell lysis as described herein. In some cases, the lysis buffer may comprise one or more leading electrolytes and one or more trailing electrolytes. In some cases, the lysis buffer may comprise one or more leading electrolytes and one or more trailing electrolytes with additives for tissue disruption or cell lysis as described herein.

In some cases, a method or process herein may involve lysing a cell or tissue sample using a lysis buffer that minimizes mechanical disruption of DNA and/or RNA during the lysis reaction. For example, cells or tissue may be lysed in a buffer solution containing Tris (e.g., 5 mM, 10 mM, 20 mM, 30 mM Tris) with HCl (e.g., 1 mM, 5 mM, 10 mM HCl) and a non-ionic surfactant. The non-ionic detergent (e.g., IGEPAL CA-630) may be present at about 1%, about 2%, about 3%, about 4%, or greater in the lysis buffer, or less than about 1%. Cells or tissue may be lysed in the lysis buffer by gentle mixing such as by inversion and low-speed (automated pipette). An enzyme such as proteinase K may, in some cases, be included in the lysate or lysis buffer. In some cases, the lysis is conducted without centrifugation. In some cases, centrifugation is used in the lysis method. The lysate may be introduced into an isotachophoresis device in order to purify a desired analyte such as high molecular weight DNA fragments.

Proteins in a sample can be digested, for example via enzymatic digestion with proteases. Proteases can include but are not limited to Proteinase K, proteases, endoproteinases (e.g., trypsin, LysC, GluC, AspN), peptidases, pepsin, and papain. Other protein or polynucleotide digestion or degradation agents can be used, such as lysozymes. Digestion of proteins can remove crosslinking proteins from crosslinked nucleic acids, converting them into non-crosslinked nucleic acids. Digestion of proteins can occur at room temperature or at elevated temperatures described herein (e.g. greater than about 25° C.).

Sample can be processed on a device (e.g., an electrokinetic device or system with at least one reservoir connected to at least one channel), such that the sample volume passes through the reservoir into the channel with less than 20% of the sample volume left behind in the reservoir, and subsequently an ionic current can be applied through the sample volume in the channel. The ionic current may not substantially pass through the channel. In some cases, less than 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, or 1% of the sample volume is left behind in the reservoir.

Sample can be processed on a device (e.g., an electrokinetic device or system with at least one reservoir connected to at least one channel), such that the sample volume which passes through the reservoir into the channel is at least 50% of the sample volume loaded into the reservoir, and subsequently an ionic current can be applied through the sample volume in the channel. In some cases, at least 50%, 55%, 60%, 65%, 70%, 75%, 80%, 85%, 90%, 95%, 99%, or more of the sample volume is moved from the reservoir to the channel. In some instances, the total volume loaded into the reservoir is less than or equal to an internal volume of the reservoir. The ionic current may not substantially pass through the channel. In some cases, applying an ionic current comprises conducting isotachophoresis.

In some embodiments, after the sample volume has been loaded into the reservoir, and subsequently loaded into the channel, a topper buffer may be added to the reservoir to facilitate movement of the sample volume into the channel. A volume of topper buffer may be added to the reservoir to "push" additional sample volume into the channel. For example, a volume of topper buffer greater than or equal to the volume of sample left behind in the reservoir may be added to the reservoir so as to move at least a portion of the remaining sample volume into the channel. The topper buffer may, for example, comprise the same buffer as the sample buffer but have no analyte therein.

Isotachophoresis Devices

Figure 5A:
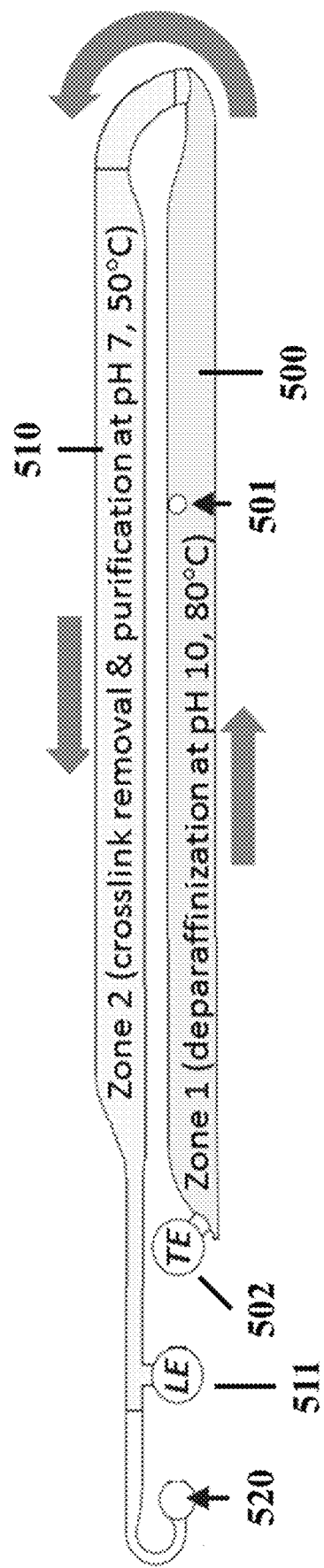
FIG. 5A shows an exemplary schematic of a channel with a sample preparation zone and an isotachophoretic purification zone.
Figure 5B:
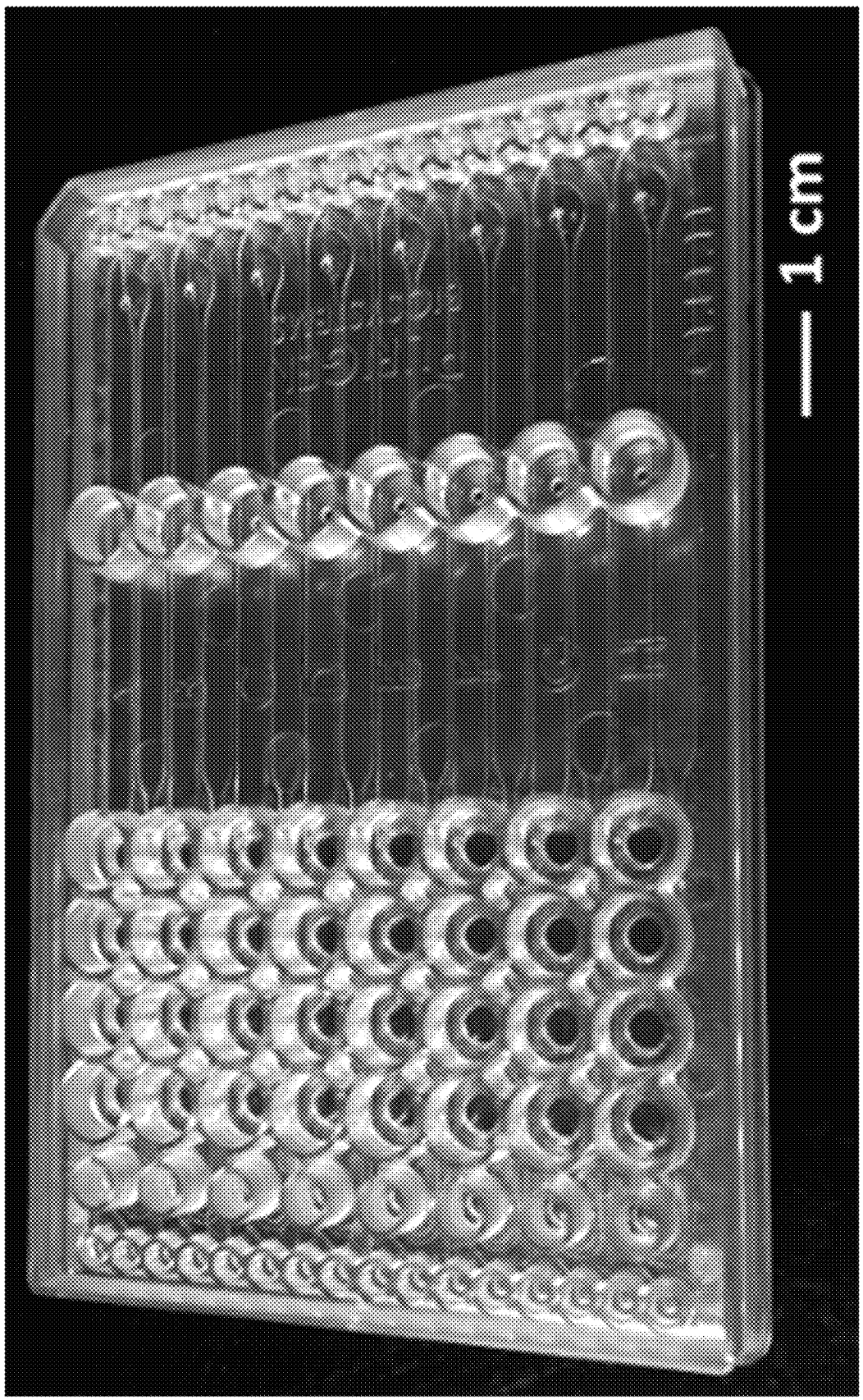
FIG. 5B shows an exemplary fluidic device cartridge comprising eight parallel fluidic channels and reservoirs for simultaneous processing of up to eight samples as shown in FIG. 5A.
Figure 5C:
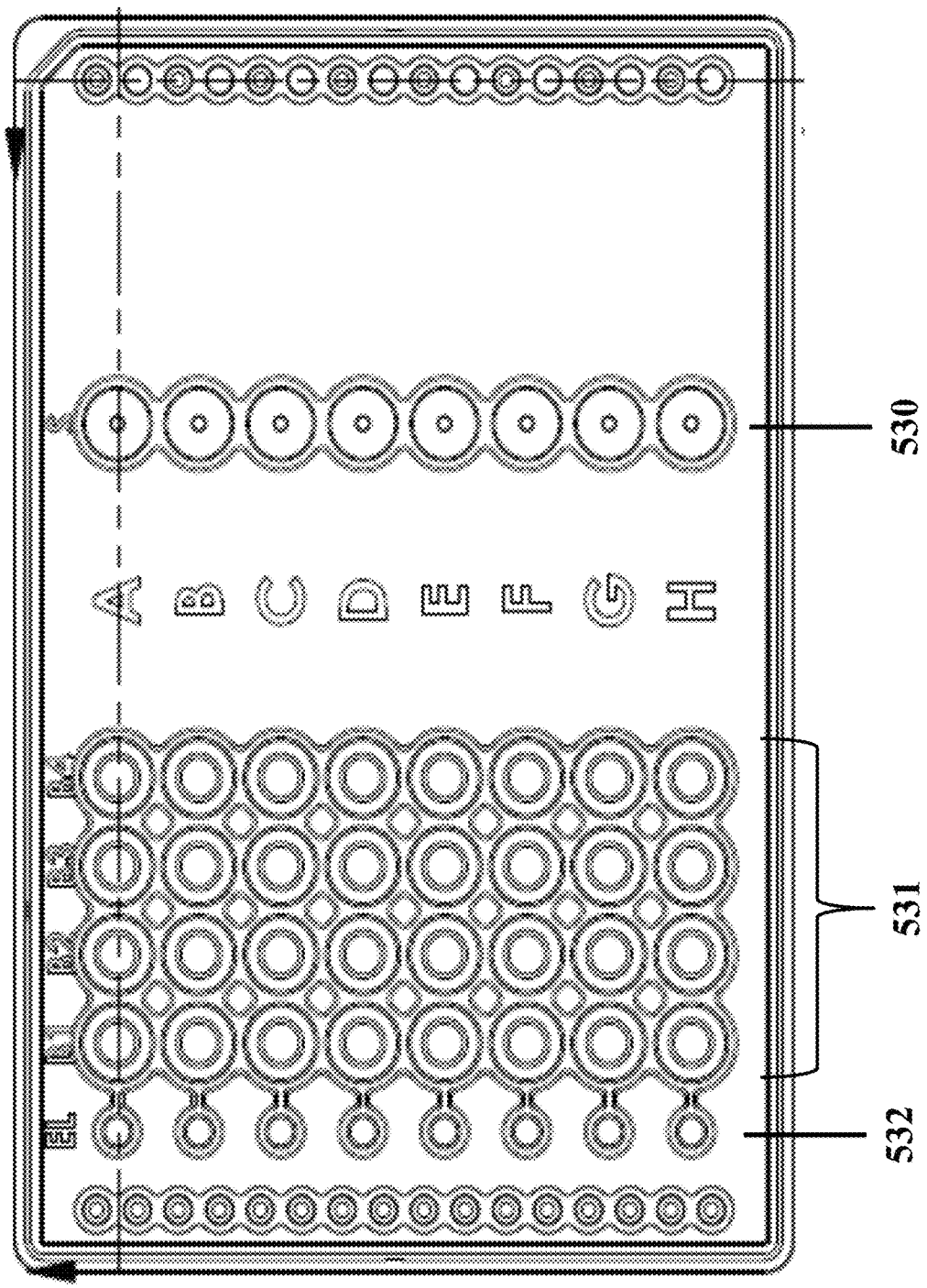
FIG. 5C shows an exemplary top view schematic of one channel and its connected reservoirs for a fluidic device cartridge as shown in FIG. 5B, further exemplifying use of gas ports for external pressure or vacuum application to the channels within the fluidic device cartridge.
Figure 5D:
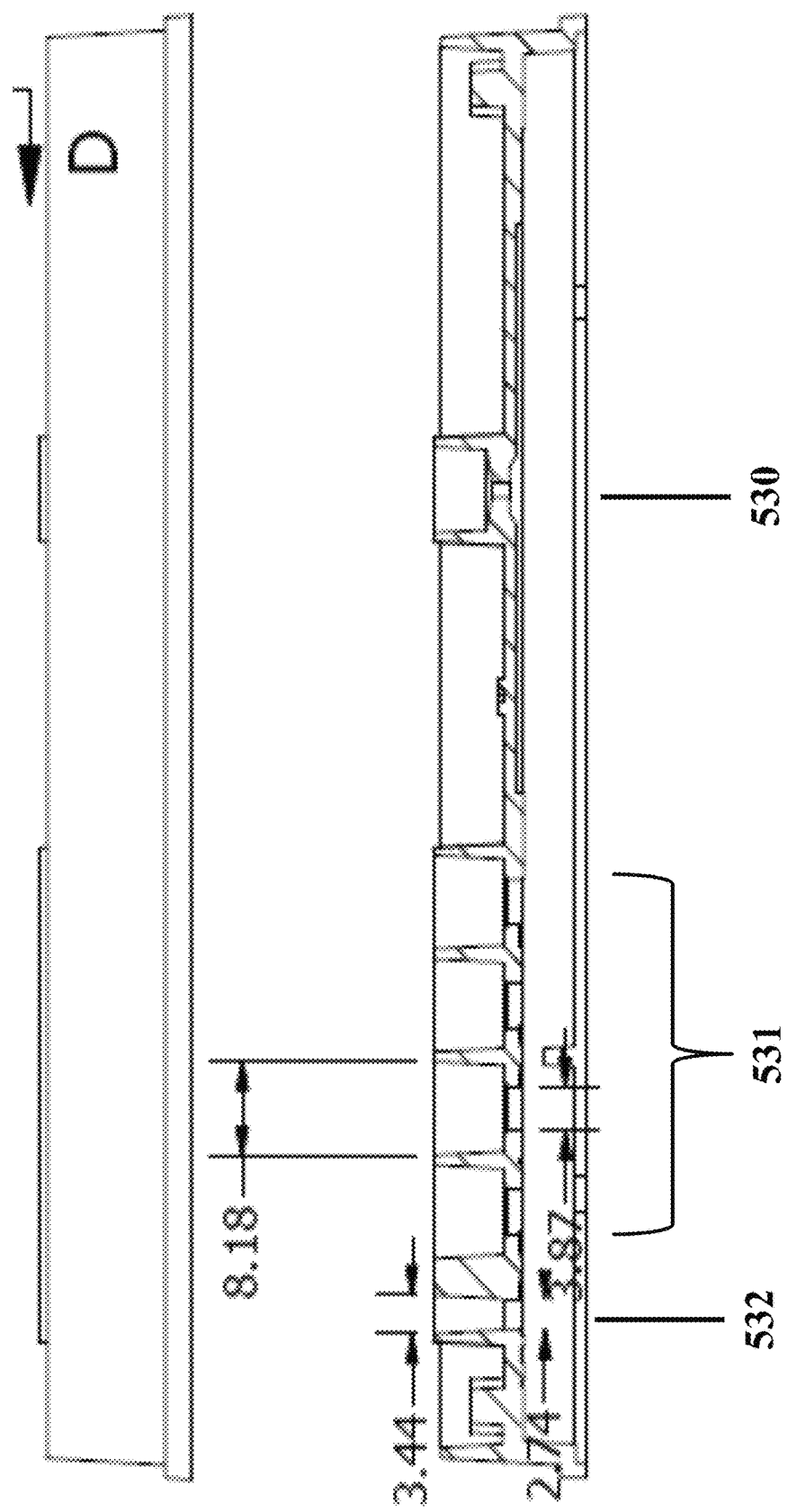
FIG. 5D shows an exemplary side view schematic of a fluidic device cartridge as shown in FIG. 5B.
Figure 5E:
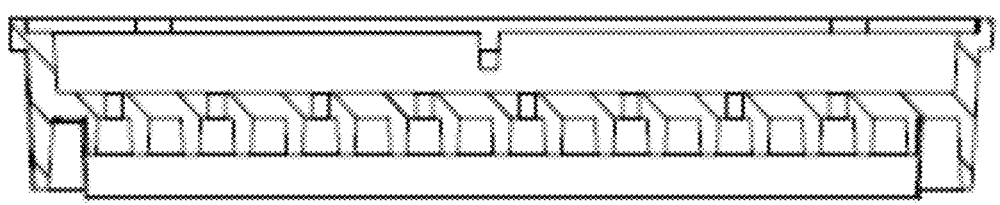
FIG. 5E shows an exemplary end view schematic of a fluidic device cartridge as shown in FIG. 5B.

Isotachophoresis and/or sample preparation (e.g., deparaffinization, digestion, lysis) can be conducted in a fluidic device, for example a microfluidic chip. For example, FIG. 5A shows a schematic of a channel with a sample preparation (e.g., deparaffinization) zone 500 with a sample inlet 501 and a trailing electrolyte reservoir 502, a purification (e.g., isotachophoresis) zone 510 with a leading electrolyte reservoir 511, and an elution outlet 520. A capillary barrier may provide an interface between the sample fluid and the leading electrolyte buffer prior to applying voltage. A capillary barrier may be provided between the sample preparation zone 500 and the trailing electrolyte reservoir 502 in order to limit, reduce, or prevent mixing or pressure-driven flow of the sample fluid and the trailing electrolyte buffer. A capillary barrier may be provided between the purification zone 510 and the leading electrolyte reservoir 511 so as to limit, reduce, or prevent mixing or pressure-driven flow of the contents of zone 510 and the leading electrolyte reservoir 511. In another example, deparaffinization can be performed first off-chip, or can be unnecessary due to the starting material, in which case the channel can comprise a lysis and digestion zone (e.g., pH 7, 56° C.) and a crosslink removal and purification (e.g., isotachophoresis) zone (e.g., pH 7, 80° C.). In another example, deparaffinization can be performed first off-chip, or can be unnecessary due to the starting material, in which case the channel can comprise a lysis and digestion zone (e.g., pH 7, temperature T1) and a crosslink removal and/or purification (e.g., isotachophoresis) zone (e.g., pH 7, temperature T2). In another example, deparaffinization can be performed first off-chip, or can be unnecessary due to the starting material, in which case the channel can comprise a disruption and/or lysis zone (e.g., pH 7, temperature T1) and a digestion and/or purification (e.g., isotachophoresis) zone (e.g., pH 7, temperature T2). In another example, deparaffinization can be performed first off-chip, or can be unnecessary due to the starting material, in which case the channel can comprise a disruption and/or lysis zone (e.g., pH 7, temperature T1) and an isothermal enzymatic amplification zone (e.g., pH 7, temperature T2). In another example, deparaffinization can be performed first off-chip, or can be unnecessary due to the starting material, in which case the channel can comprise a disruption and/or lysis zone (e.g., pH 7, temperature T1) and an isothermal enzymatic digestion zone (e.g., pH 7, temperature T2). In some cases, the channel may comprise three zones, for example a disruption and/or lysis zone (e.g. pH 7, temperature T1), an isothermal enzymatic amplification zone (e.g., pH 7, temperature T2), and a purification (e.g. isotachophoresis) zone (e.g. pH 7, temperature T3). FIG. 5B shows an exemplary fluidic device cartridge with eight parallel channels each as shown in FIG. 5A. FIG. 5C shows a top-view schematic of the fluidic device shown in FIG. 5B, while FIG. 5D and FIG. 5E show side and end views, respectively. The devices can comprise sample inlets or reservoirs 530, ITP electrolyte buffer reservoirs 531, and sample elution outlets or reservoirs 532. The channels and/or reservoirs may be coupled to one or more pneumatic ports. Each of the eight parallel channels of the fluidic device may be independently operated from each of the other channels. In some cases, each channel has a dedicated set of electrodes and electric circuitry to drive ITP. Electrodes may for example be located in the trailing electrolyte reservoir 502 and the leading electrolyte reservoir 511 such that the electrodes do not directly contact sample material.

In some instances, there may be little or no fluid or ion flow between parallel channels. In some cases, the parallel channels may not be in fluid communication with one another. The fluid leakage rate between parallel channels may be less than about 0.1, 0.2, 0.3, 0.4, 0.5, 0.6, 0.7, 0.8, 0.9, or 1 µL per hour.

In some instances, there may be little or no electrical communication between parallel channels such that the parallel channels are electrically isolated from one another. Each of the parallel channels may be independently electrically controlled so as to apply an independent electric field to each of the channels. In some instances, current leakage between the channels is less than about 0.1 microamperes (µA), 0.2 µA, 0.3 µA, 0.4 µA, 0.5 µA, 0.6 µA, 0.7 µA, 0.8 µA, 0.9 µA, or 1 µA. In some instances, the impedance between channels may be greater than 0.1 mega Ohm (MOhm), 0.2 MOhm, 0.3 MOhm, 0.4 MOhm, 0.5 MOhm, 0.6 MOhm, 0.7 MOhm, 0.8 MOhm, 0.9 MOhm, 1 MOhm, 5 MOhm, 10 MOhm, 20 MOhm, 30 MOhm, 40 MOhm, or 50 MOhm.

In some instances, each of the parallel channels may be coupled to the same current or voltage source and independently electrically controlled. In some instances, each of the parallel channels may be coupled to a different current or voltage source and independently electrically controlled.

Figure 34:
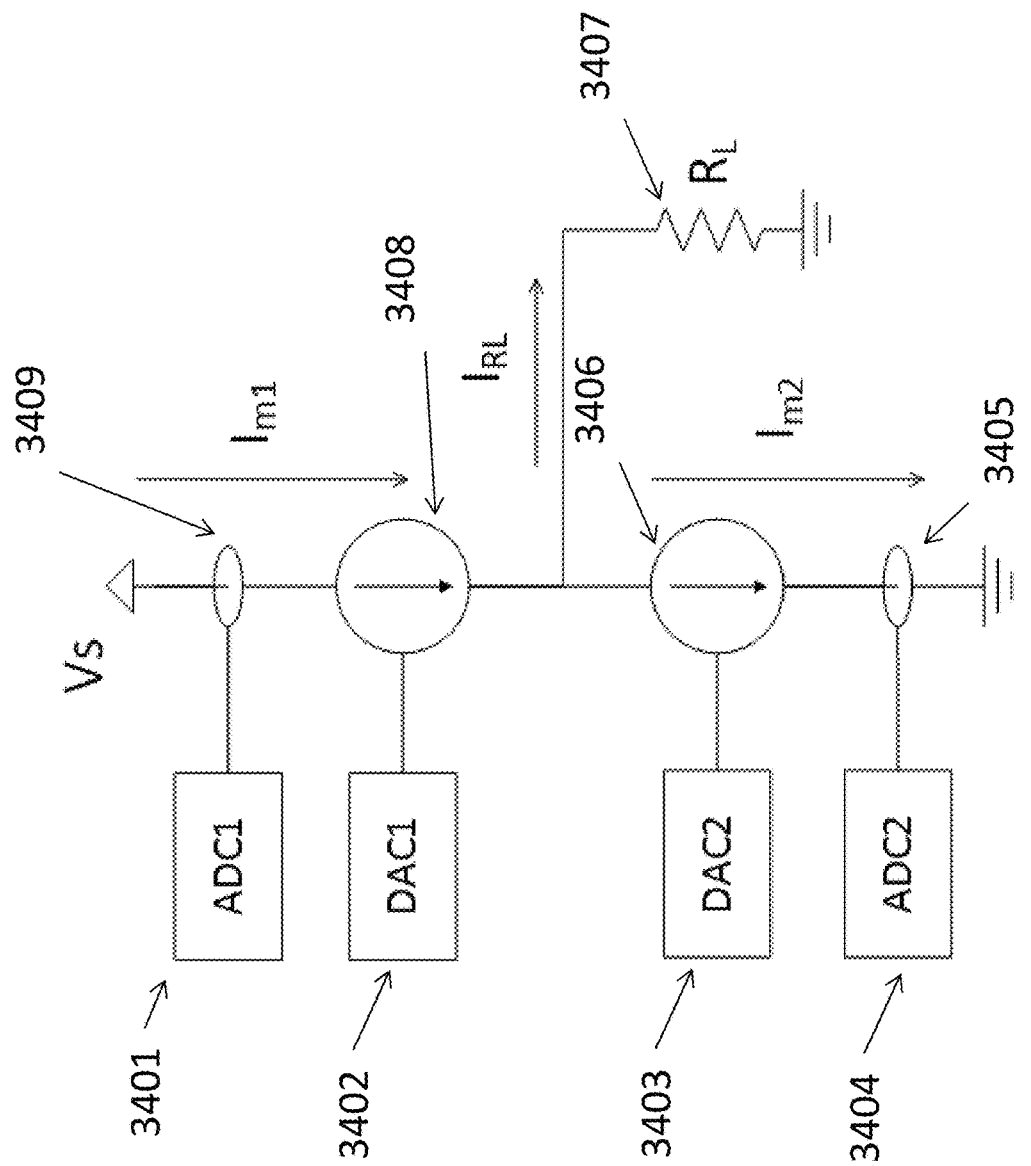
FIG. 34 shows a circuit configured to detect and prevent current leakage during ITP.

FIG. 34 shows a circuit configured to detect and prevent current leakage during ITP in parallel channels. The circuit may be configured to monitor the current into the ITP system from a single HV electrode and the current that leaks through the high-voltage board. By measuring the two currents at regular intervals or continuously, the current into the chip can be precisely controlled even if the leakage current changes. This may allow the electrode to be run in either net source or net sink configuration. The circuit may comprise a voltage source Vs, a sink current controller 3406, a source current controller 3408, and two current measurement circuits 3405 and 3409 that measure the current flowing through the controlled current sources 3406 and 3408. The controlled current sources can be controlled by a microprocessor through the use of digital-to-analog (DAC) convertors 3402 and 3403. DAC converter 3402 may control current into the electrode and the leak path. DAC converter 3403 may control current into the leak path. The measured currents can be read by a microprocessor through the use of analog-to-digital converters (ADC) 3401 and 3404. ADC 3401 may measure current at the source Vs. ADC 3404 may measure current at the leak path, which is directed to ground. The current controlled sources 3406 and 3408 may be joined with a load 3407 so that the current source 3408 can source a current into the load 3407 and so that the current source 3406 can sink a current from the load 3407. The current that flows into the load 3407 can be denoted $I_{RL}$. The current that flows through the controlled current source 3408 can be denoted $I_{m1}$. The current that flows through the controlled current source 3406 can be denoted $I_{m2}$. The current that will flow in to or out of the load 3407 can thus be described by the equation $I_{RL}=I_{m1}-I_2$. The current $I_{m1}$ is comprised of both the current commanded by the controlled source 3408 which will be denoted by $I_{c1}$ and a leakage current denoted by $I_{L1}$ due to parasitic conductive paths present in any physically realizable circuit. The current $I_{m1}$ can be described by the equation $I_{m1}=I_{c1}+I_{L1}$ and similarly the current $I_{m2}$ can be described by $I_{m2}=I_{c2}+I_{L2}$. By extension, the current flowing in to or out of load 3407 can thus be described by the equation $I_{RL}=I_{c1}+I_{L1}-I_{c2}-I_{L2}$. In some applications it may be desired to command the circuit to an off-state so that $I_{RL}=0$. To accomplish this, the controlled current sources will typically be commanded so that $I_{c1}=0$ and $I_{c2}=0$, however, due to the leakage currents $I_{L1}$ and $I_{L2}$, the current flowing in to or out of the load 3407 during the off-state may be some non-zero current described by $I_{RL}=I_{L1}-I_{L2}$. In order to reduce the off-state current $I_{RL}$ to a value significantly less than the leakage currents $I_{L1}$ or $I_{L2}$, the circuit can steer additional current through either the controlled current source 3406 or 3408 until the balance of current flowing in to $I_{RL}$ is nulled. For example, the circuit can set either $I_{c1}=I_{c2}+I_{L2}-I_{L1}$ or $I_{c2}=I_{c1}+I_{L1}-I_{L2}$. In either case, the resulting current $I_{RL}$ will reduce to $I_{RL}=0$. In other words, the circuit may adjust current(s) from the current source(s) 3406, 3408 to balance and counteract the leakage current to drive the net flow between parallel channels to 0.

In many applications where a controlled current source is to be applied to a load for a period of time and then removed from the load for a period of time, such as in isotachophoresis, it may be desirable for the current source circuit to leak as little current into the load when the controlled current source is to be removed. Many or all circuit components used to construct current sources may allow for some parasitic leakage current to flow through the circuit when the control circuit is intended to be off. Minimizing this leakage typically requires the use of more sophisticated and higher quality components that exhibit lower parasitic leakage properties, however, doing so comes at higher cost and often requires more physical volume to implement the circuit. The disclosure disclosed allows for the leakage current applied to a load to be reduced by steering the leakage current away from the load. The disclosure thus may allow for simpler circuit components to be used in the construction of the current source enabling a current source that may realize a lower leakage current with circuit components that are optimized for other purposes such as lower cost or physical size. Current leakage may result from liquid leaking between fluidic channels where a layer of material closes fluidic channels in a surface of a substrate. Ensuring secure bonding of the layer across the substrate surface may reduce such leakage. Current leakage also can result from liquid moving between ports of different fluidic circuits, in particular ports that are a source of negative pressure to a fluidic channel. Provision of hydrophobic barriers at such ports may reduce such leakage.

In some instances, each zone on the isotachophoresis device can be heated. In some instances, the zones are heated to the same temperature. In some instances, individual zones are heated to different temperatures. In some instances, a first zone may be heated to a temperature above 37° C., for example within a range of about 60° C. to about 100° C. In some instances a second zone may be heated to a temperature above 37° C., for example within a range of about 40° C. to about 60° C.

An isotachophoresis fluidic device can comprise one or more reservoirs, including but not limited to buffer loading reservoirs, sample loading reservoirs (including reservoirs that accept solid, multiphasic, or other inhomogeneous liquids or solutions such as tissue, whole blood, or unlysed cell suspensions), leading electrolyte reservoirs, trailing electrolyte reservoirs, reagent reservoirs, elution reservoirs (e.g., for unloading processed samples), and gas or air reservoirs. In some cases, one physical reservoir can be used for multiple purposes, such as buffer loading and sample loading. Liquid or air reservoirs can be used to apply external pressure for liquid loading (e.g., positive pressure on liquid wells or vacuum on gas only reservoirs). It will be understood by one of ordinary skill in the art that any of the reservoirs described herein may be used to load or retrieve any of the buffers and/or samples described herein.

Reservoirs can be in thermal communication with a heating or cooling source, allowing control of the temperature of the reservoir and any material within (e.g., reagent, sample, product). For example, an elution reservoir can be thermally controlled to control the temperature of the eluted product (e.g., for preservation of structure, integrity) while within the fluidic device.

Reagent reservoirs can be used to load one or more reagents for processing the sample before, during, or after isotachophoresis. Reagents can include digestion reagents, amplification reagents, reverse transcription reagents, linear polymer solutions for size-based separations, probes for hybridization reactions, ligation reagents, dyes (e.g. intercalating dyes described herein), tracers, labels, and other reagents. Reagent reservoirs can be connected to a reaction channel, or a reaction section of another channel, where reactions can occur. Heating or cooling can be applied (e.g., with thermal controllers as discussed herein) to catalyze reactions (such as enzymatic reactions with nucleic acids or proteins), to hybridize or melt nucleic acids, or remove intercalated dyes from nucleic acids (for example, prior to elution). Heating and cooling can also be used to control a fixed operating temperature for conducting ITP (e.g., cooling can be applied to reduce effects of Joule heating), or to keep a reservoir (e.g., an elution reservoir) at a fixed temperature (e.g., cooler than room temperature), such as for stable storage of purified nucleic acids. Light can be applied (e.g., with light sources as discussed herein) for purposes including optical interrogation, fluorescent excitation, and reaction energy or catalysis.

Gas or air reservoirs, or gas or air outlets, can be connected via gas channels to liquid channels within a fluidic device to allow purging of air or other gases from the fluidic device (e.g., during liquid filling of the fluidic device). Gas or air reservoirs, or pneumatic pressure ports, can be connected via gas channels to liquid channels to allow for pumping of fluids onto or within the fluidic device (e.g., for pumping of fluids from reservoirs into channels).

A device can comprise multiple purification (e.g., isotachophoresis) zones in connection with each other. For example, a second isotachophoresis zone can split from and run in parallel to a first isotachophoresis zone, allowing splitting of a sample band at a specified ratio (e.g., based on a ratio of currents between the two zones) for parallel processing.

A fluidic device can comprise multiple purification zones in parallel (see, e.g., FIG. 5C). For example, a fluidic device can comprise more than one set of purification zones, each with associated reservoirs, inlets, outlets, channels, and any other components described herein (e.g., sample preparation zones, electrodes, heaters, detectors) in parallel, separate from each other and each capable of independently processing a sample. A fluidic device can comprise at least 2, 3, 4, 5, 6, 7, 8, 9, 10, 11, 12, 13, 14, 15, 16, 17, 18, 19, 20, 24, 48, 96, or more purification zones in parallel. A fluidic device can comprise multiple channels in parallel. A fluidic device can comprise at least 2, 3, 4, 5, 6, 7, 8, 9, 10, 11, 12, 13, 14, 15, 16, 17, 18, 19, 20, 24, 48, 96, or more channels in parallel. Components, such as purification zones or channels, located in parallel can be side-by-side, located in different device layers (e.g., horizontal or vertical layers), or placed in different arrangements. Parallel components can be identical, or can be designed differently but function equivalently or nearly equivalently. For example, parallel channels can have different geometries to allow a smaller overall fluidic device footprint, but still function similarly. Alternatively, parallel components can be designed to function differently, for example to process different types of samples in parallel, or to subject samples to different operations. In some cases, parallel components can be designed to subject different sample types to different operations in parallel. In some cases, parallel components can be designed to subject the same sample types to different operations in parallel. In some cases, parallel components can be designed to subject different sample types to the same operations in parallel. In some cases, parallel components can be designed to subject the same sample types to the same operations in parallel. In some cases, parallel components can be designed to simultaneously and/or independently subject two or more samples to one or more operations in parallel. In some cases, a leakage rate between two or more channels (or between two or more purification zones) may be less than 0.5 µper hour, less than 1 µl per hour, less than 5 µl per hour, less than 10 µl per hour. In some embodiments, a current leakage rate between two or more channels (or between two or more purification zones) may be less than 0.5 µA, less than 1 µA, less than 5 µA, or less than 10 µA. In some embodiments, an impedance between channels or zones may be greater than 0.5 megaOhm, greater than 1 megaOhm, greater than 5 megaOhm, or greater than 10 megaOhm.

As discussed herein, a fluidic device can be designed to process different sample volumes. For example, FIG. 6A, FIG. 6B, FIG. 6C, and FIG. 6D show top, side, bottom, and top three-quarters views, respectively, of a rapid purification ITP fluidic device 600 for sample volumes greater than or equal to about 200 µL. The device comprises a channel 600 connected to sample input wells 601, ITP buffer wells 602, and sample output (elution) wells 603 by through-holes or apertures as described herein. The ITP buffer wells 602 can include an elution buffering reservoir 605, a leading electrolyte reservoir 606, a leading electrolyte buffering reservoir 607, and a trailing electrolyte reservoir 608. Elution reservoir 603 may be connected to elution buffering reservoir 605 by an elution buffering channel 609. A capillary barrier (e.g. a plateau capillary barrier, a ramp capillary barrier, or a cliff capillary barrier as described herein) may be provided in the elution buffering channel 609 to reduce or prevent mixing or pressure driven flow between the contents of the elution buffering reservoir 605 and the elution reservoir 603. Leading electrolyte reservoir 606 may be connected to leading electrolyte buffering reservoir 607 by a leading electrolyte buffering channel 610. A capillary barrier (e.g. a plateau capillary barrier, a ramp capillary barrier, or a cliff capillary barrier) may be provided in the leading electrolyte buffering channel 610 to reduce or prevent mixing or pressure-driven flow between the contents of the leading electrolyte buffering reservoir 607 and the leading electrolyte reservoir 606. Buffering reservoir 605 may contain elution buffer electrolytes at a higher ionic strength than those in elution reservoir 603, while buffering reservoir 607 may contain leading electrolytes at a higher ionic strength than those in leading electrolyte reservoir 606. The device may further comprise pneumatic ports 604 along its edges which are configured to couple to a pneumatic device, for example a vacuum source on a benchtop instrument. The pneumatic ports 604 may be coupled to the channel 600 and reservoirs by gas channels as described herein. Application of suction at the pneumatic ports 604 may load the sample, leading electrolyte, and elution buffer into the channel 600. In some cases, the trailing electrolyte buffer fluid remains in the trailing electrolyte reservoir 608. Suction may be applied simultaneously or sequentially to the pneumatic ports 604 so as to load the channel 600 simultaneously or in stages, respectively. The sample may be loaded into a first zone or sub-channel of channel 600 which extends from the trailing electrolyte reservoir 608 to a capillary barrier 611 at a 180° low dispersion turn in the channel 600. The capillary barrier 611 may provide an interface between the sample and the leading electrolyte buffer during loading so as to limit, reduce, or prevent mixing or pressure-driven flow. The capillary barrier 611 may comprise a cliff capillary barrier as described herein. A capillary barrier (e.g. a cliff capillary barrier, a ramp capillary barrier, or a plateau capillary barrier) may be provided between the trailing electrolyte reservoir 608 and the first zone or sub-channel so as to limit, reduce, or prevent mixing or pressure-driven flow between the contents of the trailing electrolyte reservoir 608 and the sample. The leading electrolyte may be loaded into the second zone or sub-channel of the channel 600 which extends from capillary barrier 611 to capillary barrier 612. The capillary barrier 612 (e.g. a plateau capillary barrier, a ramp capillary barrier, or a cliff capillary barrier) may provide an interface between the leading electrolyte buffer and the elution buffer. The elution buffer may be loaded into a third zone or sub-channel of channel 600 which extends from capillary barrier 612 to elution reservoir 603. In some embodiments, the ITP buffer wells 602 may further comprise a trailing electrolyte buffering reservoir (not shown) containing trailing electrolytes at a higher ionic strength than those in the trailing electrolyte reservoir 608. The trailing electrolyte buffering reservoir may be connected to the trailing electrolyte reservoir 608 by a trailing electrolyte buffering channel (not shown). The trailing electrolyte buffering channel may comprise a capillary barrier (e.g. a ramp capillary barrier, a plateau capillary barrier, or a cliff capillary barrier) to limit, reduce, or prevent mixing or pressure-driven flow between the contents of the trailing electrolyte buffering reservoir and the trailing electrolyte reservoir 608.

Electrodes may for example be located in the trailing electrolyte reservoir 608, a trailing electrolyte buffering reservoir (not shown), the leading electrolyte reservoir 606, and/or the leading electrolyte buffering reservoir 607 such that the electrodes do not directly contact sample material. The electrodes may be triggered to alter or control the applied electric field in response to feedback from a sensor, for example a voltage, current, conductivity, or temperature sensor as described herein. For example, passage of the nucleic acids within the ITP zone from the second zone of channel 600 to the third zone of channel 600 may be detected and feedback from the detector may trigger the applied current to change. The current may for example be increased, decreased, or ended according to the protocol of the instrument. The current may for example be paused (e.g. dropped temporarily to zero) in order to enable on-chip quantification of the nucleic acids. Alternatively or in combination, the current may be decreased in order to slow isotachophoresis within the third zone to allow the nucleic acids which may have dispersed upon transition from the leading electrolyte buffer to the elution buffer (or second leading electrolyte buffer) time to concentrate further before reaching the elution well 603.

The methods and processes provided herein include methods and processes that use any of the devices provided herein. Devices provided herein with multiple channels for processing multiple samples in parallel may be used in a variety of contexts. In some cases, a method may include use of a device to process multiple samples (e.g., by conducting isotachophoresis on such samples) that share a certain feature (e.g., solid tissue lysate, cell lysate, solid tissue, fixed tissue). In some cases, the multiple samples may be different samples. For example, the method may involve performing isotachophoresis on a tissue sample in one zone of the device while simultaneously, but independently, conducting isotachophoresis on a different sample such as a cellular sample or sample comprising cross-linked nucleic acids.

In some cases, a method or multiplexing process provided herein may involve conducting isotachophoresis on a sample in a channel in parallel with conducting isotachophoresis on a second sample in a second channel using leading electrolyte and/or trailing electrolyte buffers that are the same or similar. In some cases, a sample in one of the channels is processed using a first leading electrolyte buffer and a sample in a different channel is processed using a second leading electrolyte buffer that is different from the first. For example, the first leading electrolyte buffer can contain one or more leading electrolyte ions that are different from those contained in the second leading electrolyte buffer. In another example, the first leading electrolyte buffer can contain one or more leading electrolyte ions that are the same as those contained in the second leading electrolyte buffer but the concentration of such leading electrolyte ions in the first leading electrolyte buffer is different from the concentration of such ions in the second leading electrolyte buffer. In some cases, a method or process provided herein may involve conducting isotachophoresis on a sample in a channel in parallel with conducting isotachophoresis on a second sample in a second channel using trailing electrolyte or trailing electrolyte buffers that are the same or similar. In some cases, a sample in one of the channels is processed using a first trailing electrolyte buffer and a sample in a different channel is processed using a second trailing electrolyte buffer that is different from the first. For example, the first trailing electrolyte buffer can contain one or more trailing electrolyte ions that are different from those contained in the second trailing electrolyte buffer. In another example, the first trailing electrolyte buffer can contain one or more trailing electrolyte ions that are the same as those contained in the second trailing electrolyte buffer the concentration of such trailing electrolyte ions is different in the first trailing electrolyte buffer is different from the concentration in the second trailing electrolyte buffer.

In some embodiments, one or more reservoirs may be connected to two channels or sub-channels. For example, elution reservoir 603 may be connected to both channel 600 and elution buffering channel 609. Alternatively or in combination, leading electrolyte reservoir 606 may be connected to both channel 600 and leading electrolyte buffering channel 610. Alternatively or in combination, trailing electrolyte reservoir 608 may be connected to both 600 and a trailing electrolyte buffering channel. Alternatively or in combination, sample input well 601 may be connected to a mid-point in channel 600 such that channel 600 extends to the left (as a first sub-channel) and right (as a second sub-channel) of the input well 601. The two channels or sub-channels may be connected to the one or more reservoirs with an angle between the two channels (swept in the major plane of the fluidic device) of at least about 5°, 10°, 20°, 30°, 40°, 45°, 50°, 60°, 70°, 80°, 90°, 100°, 110°, 120°, 130°, 135°, 140°, 150°, 160°, 170°, or 180°. The two channels or sub-channels may be connected to the one or more reservoirs with an angle between the two channels (swept in the major plane of the fluidic device) of at most about 5°, 10°, 20°, 30°, 40°, 45°, 50°, 60°, 70°, 80°, 90°, 100°, 110°, 120°, 130°, 135°, 140°, 150°, 160°, 170°, or 180.

The device may comprise, for example, 8 channels as shown. Each channel may hold a sample volume of about 50 µL to about 275 µL and a total volume of about 500 µL. The 180° low dispersion turn in each channel may facilitate such large sample volumes in an 8-channel multi-channel plate with a standard SLAS footprint.

FIG. 7A, FIG. 7B, FIG. 7C, and FIG. 7D show top, side, bottom, and bottom three-quarters views, respectively, of a rapid purification ITP fluidic device 700 for sample volumes less than or equal to about 100 µL. The device comprises sample input wells 701, ITP buffer wells 702, and sample output (elution) wells 703. The device 700 may be substantially similar to device 600 but with different channel geometry (and corresponding reservoir geometry) that does not include a 180° turn in the channel.

The device may comprise, for example, 8 channels as shown. Each channel may hold a sample volume of about 10 µL to about 100 µL. A device with smaller sample volumes may be useful for PCR cleanup or other reaction cleanup applications or for smaller sample sizes (for example a sample with a low number of cells or a small amount of tissue).

FIG. 8A, FIG. 8B, FIG. 8C, and FIG. 8D show top, side, bottom, and three-quarters bottom views, respectively, of another rapid purification ITP fluidic device 800 for sample volumes less than or equal to about 100 µL. The device comprises sample input wells 801, ITP buffer wells 802, and sample output (elution) wells 803. The device 800 may be substantially similar to devices 600 and 700 but comprises multiple different channel geometries on a single chip.

Any of the fluidic devices described herein can comprise one or more electrodes that apply an electric field to a fluidic device or a part of the fluidic device. Applied electric fields can be used for conducting isotachophoresis. The fluidic device may comprise one or more electrodes that apply a single electric field to all channels of the fluidic device. The fluidic device may comprise one or more electrodes that apply more than one electric field to the fluidic device, for example one electric field per channel on the device. In some instance, a first and second electric field are generated from a single electrode pair. In some instances, a first and second electric field are generated from different electrode pairs. The electric fields may be applied simultaneously, sequentially, and/or independently or one another. Electrodes can be external, such as a wire that drops into a reservoir. Electrodes can be internal, such as a microfabricated, printed, or other embedded element included within the fabrication of the fluidic device. Electrode materials can include but are not limited to metals (e.g., platinum, titanium), and carbon.

The one or more electrodes of the fluidic device may be part of one or more electric circuits that apply an electric field to a fluidic device or part of a fluidic device. The fluidic device may comprise one or more electric circuits that apply a single electric field to all channels or isotachophoresis regions of zones of the fluidic device. The fluidic device may comprise one or more electric circuits that apply more than one electric field to the fluidic device, for example one electric field per channel on the device. In some instance, first and second electric fields may be generated from a single electric circuit. In some instances, first and second electric fields may be generated from different electric circuits. The electric fields may be applied simultaneously, sequentially, and/or independently or one another by the one or more electric circuits. In some instances the device (or benchtop instrument) may be configured to control a first electric circuit simultaneously with and independently of a second electric circuit.

Electrodes can be located in reservoirs, such as trailing and leading electrolyte reservoirs, which can be separated from sample reservoirs by buffering channels. In some cases, electrodes are located in buffering channels or buffering reservoirs. Location of electrodes in electrolyte reservoirs or electrolyte buffering reservoirs can isolate the electrodes from analytes such as nucleic acids to reduce or eliminate contamination of electrodes by sample material. This approach can allow reuse of electrodes without cross-contamination between samples. In one example, a trailing electrolyte reservoir or trailing electrolyte channel is connected by a buffering channel to a buffering reservoir which contains trailing electrolyte ions and an electrode, and the trailing electrolyte reservoir is also connected to a sample reservoir or sample channel, which in turn is connected to a leading electrolyte reservoir by a leading electrolyte channel; the leading electrolyte reservoir is also connected by a buffering channel to a buffering reservoir which also contains leading electrolytes and an electrode. In another example, or as a continuation of the previous example, an elution reservoir containing elution buffer is connected to a leading electrolyte reservoir by an elution channel and is also connected to a buffering reservoir containing elution buffer electrolytes and an electrode. The buffering channels between the buffering reservoirs and their corresponding reservoirs can include capillary barriers and/or a low cross-sectional area to limit, reduce, or prevent mixing and pressure-driven flow as described herein. The buffering reservoirs may contain electrolytes at the same or higher ionic strength as their corresponding reservoirs. For example, the elution reservoir can be connected to a buffering reservoir containing elution buffer electrolytes at the same or higher ionic strength or concentration as the elution reservoir. The trailing electrolyte reservoir can be connected to a buffering reservoir containing trailing electrolytes at the same or higher ionic strength or concentration as the trailing electrolyte reservoir. The leading electrolyte reservoir can be connected to a buffering reservoir containing leading electrolytes at the same or higher ionic strength or concentration as the leading electrolyte reservoir. Providing dedicated buffering reservoirs connected to the elution reservoir, trailing electrolyte reservoir, and/or leading electrolyte reservoir with higher ionic strengths can provide a pool of additional ions to maintain pH and conductivity in the channel as the sample moves through the channel.

Figure 9B:
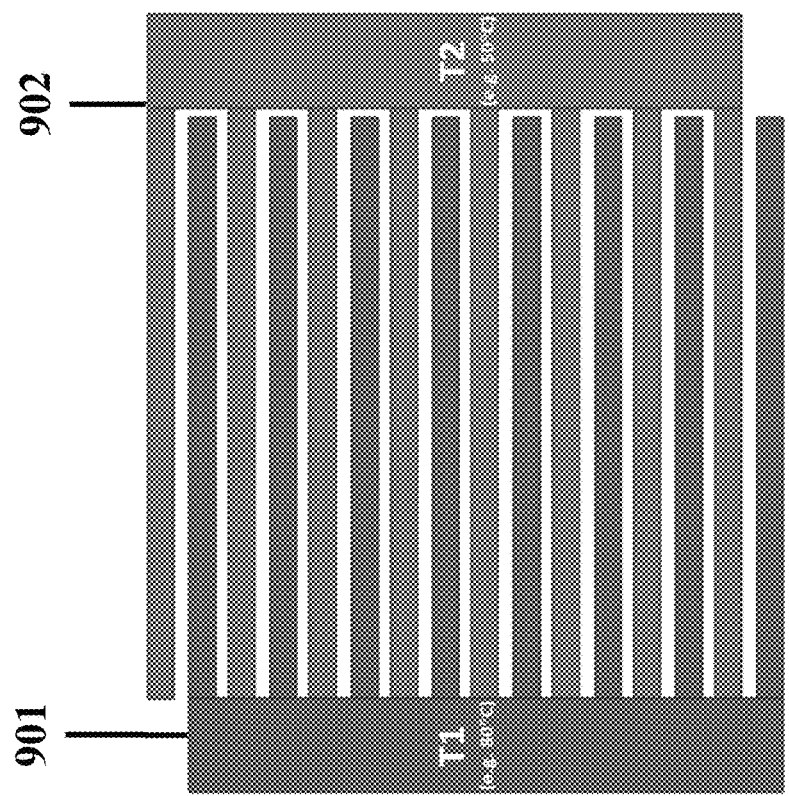
FIG. 9B shows an exemplary schematic of two thermal controllers, each aligned with a zone of the eight parallel channels shown in FIG. 9A.
Figure 9A:
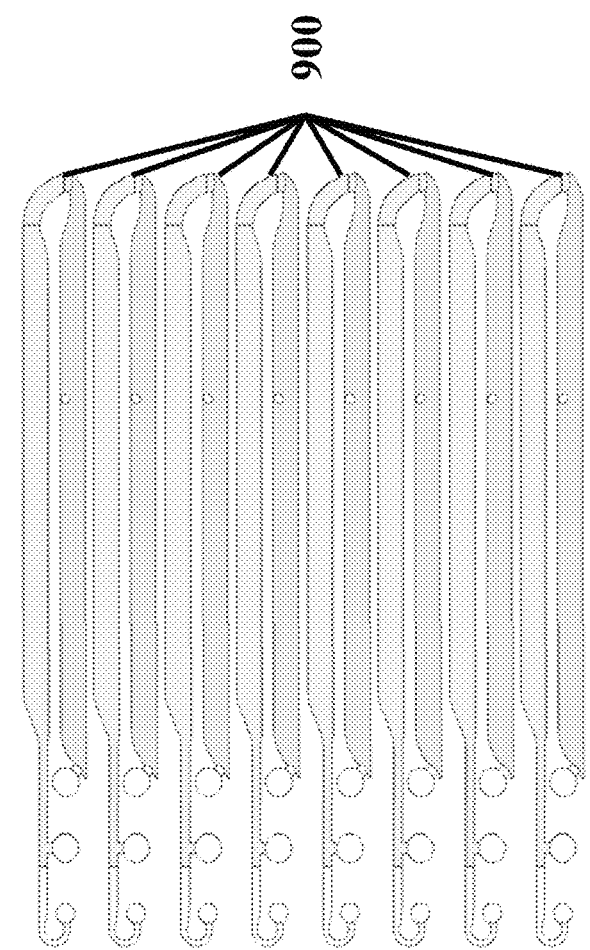
FIG. 9A shows an exemplary schematic of a fluidic device cartridge comprising eight parallel channels as shown in FIG. 5B.

Fluidic devices can be used with one or more thermal controllers. For example, FIG. 9A shows a schematic of an eight-plex sample preparation and isotachophoresis device, comprising eight parallel channels 900 of the design shown in FIG. 5A. FIG. 9B shows a schematic of a first and a second thermal controller 901, 902. A first thermal controller 901 at temperature T1 (e.g., 80° C.) is aligned with the sample preparation zones of the channels and a second thermal controller 902 at temperature T2 (e.g., 50° C.) is aligned with the isotachophoresis zones of the channels. In some cases, additional thermal controllers may be aligned with additional zones of the channels (not shown), for example a third thermal controller at temperature T3 may be aligned with a third zone at temperature T3. In some cases, each zone of each channel can have its own separate thermal controller, rather than sharing a common thermal controller with the respective zones of the other channels. In other cases, all the zones or channels can share one thermal controller. In other cases, more than one but less than all the zones or channels can share one thermal controller. Thermal controllers can comprise components including but not limited to resistive heaters, fluid-based heating or cooling systems, and Peltier devices. Thermal controllers can be fabricated from materials including but not limited to metals (e.g., platinum, titanium, copper, gold), carbon, and indium tin oxide (ITO). Thermal controllers can comprise temperature sensors, which can be used to monitor the temperature being controlled and provide temperature feedback for thermal control. Thermal controllers can be used with computer control systems, as discussed further in this disclosure. In some cases, thermal controllers are operated without temperature feedback. Thermal controllers can be integrated into fluidic devices or located externally, such as within a benchtop system.

Fluidic devices can be used with one or more light sources. Light sources can be integrated into fluidic devices or located externally to a fluidic device, such as within a benchtop system or in a separate device. Light sources can provide light for optical interrogation, fluorescent excitation, temperature sensing, reaction energy or catalysis, and other purposes.

Fluidic devices can be designed such that their outermost frame or dimensions meet microtiter plate standards (e.g., SLAS microtiter plate standards). Fluidic devices can be designed to use the defined ports of a microtiter plate (e.g., SLAS standard microtiter plate) as liquid reservoirs, with pneumatic actuation ports located on the unused surface external to the liquid reservoirs. Pneumatic ports can be arranged at the edges of a fluidic device with a microtiter plate-compatible layout such that cross-contamination through pneumatic actuation across liquid reservoirs is avoided, and such that the ports are easy to access with pneumatic hardware. A subset of defined ports can also be used for pneumatic actuation in addition to their other functions. In some cases, a fluidic device can be designed and fabricated in two interlocking parts: first, an insert that includes a channel unit (e.g. a layer with a flat surface enabling ease of film bonding), wells, and pneumatic ports; and second, an outer ring or cover piece to provide conformity to a microtiter plate standard (e.g., SLAS microtiter plate dimensional standards), including alignment features for aligning the fluidic device to a benchtop system and mating features to interlock with the first part. Wells can be connected to form bosses, which can be more compatible with injection molding. In some cases, a fluidic device can be designed and fabricated in three connecting parts; first, a chip or substrate that includes wells and pneumatic ports on its top face and etched or molded channels on its bottom face, second, a layer of material (e.g. a film) which seals to the bottom face of the chip to form closed channels (which, together, suffice to form a fluidic chip) and, third, a cover piece an outer ring or cover piece to provide conformity to a microtiter plate standard (e.g., SLAS microtiter plate dimensional standards), including alignment features for aligning the fluidic device to a benchtop system and mating features to interlock with the first part. Such a device can also be referred to as a cartridge.

Figure 35A:
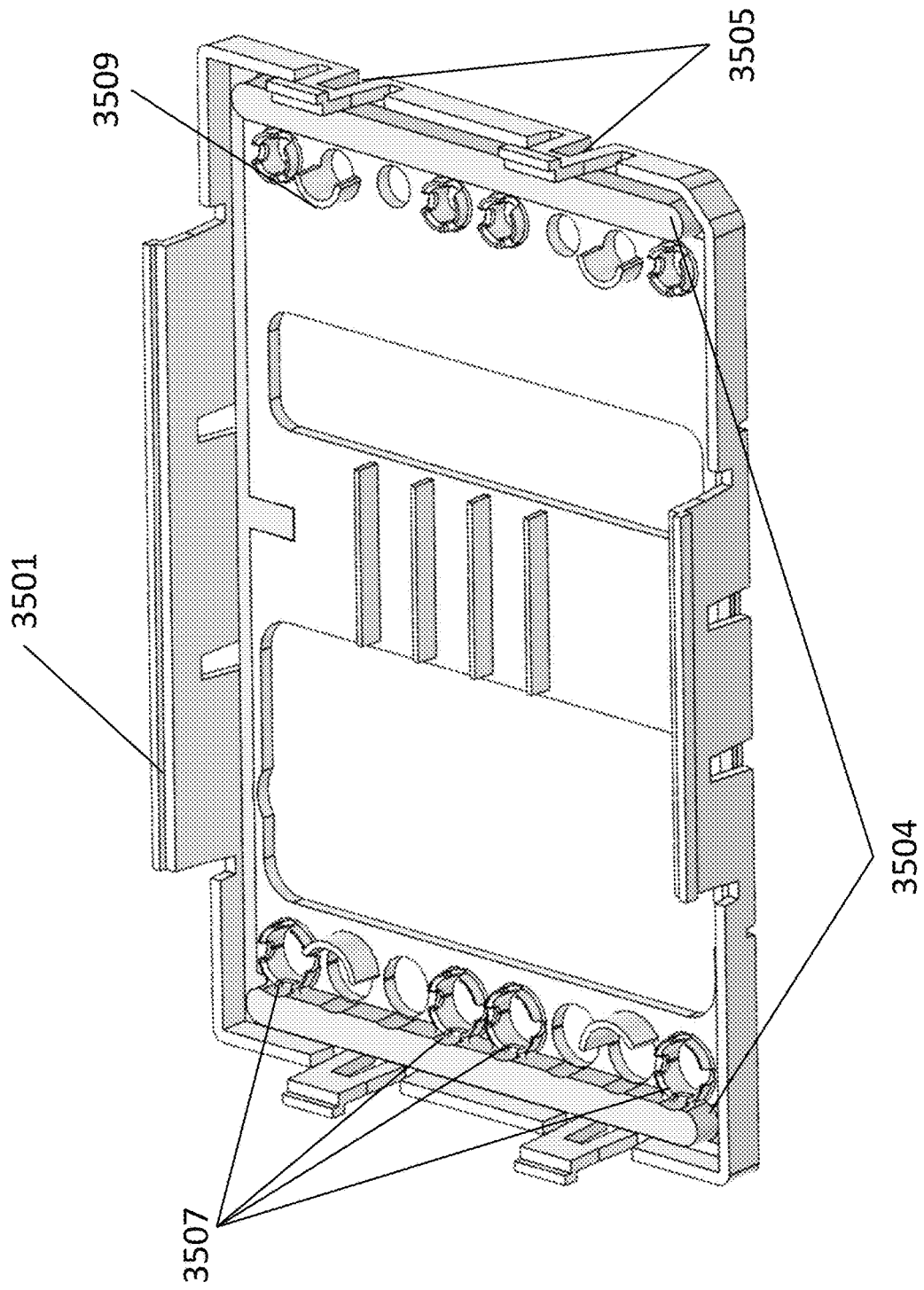
FIGS. 35A-35B show an exemplary fluidic device which comprises two interlocking parts.
Figure 35B:
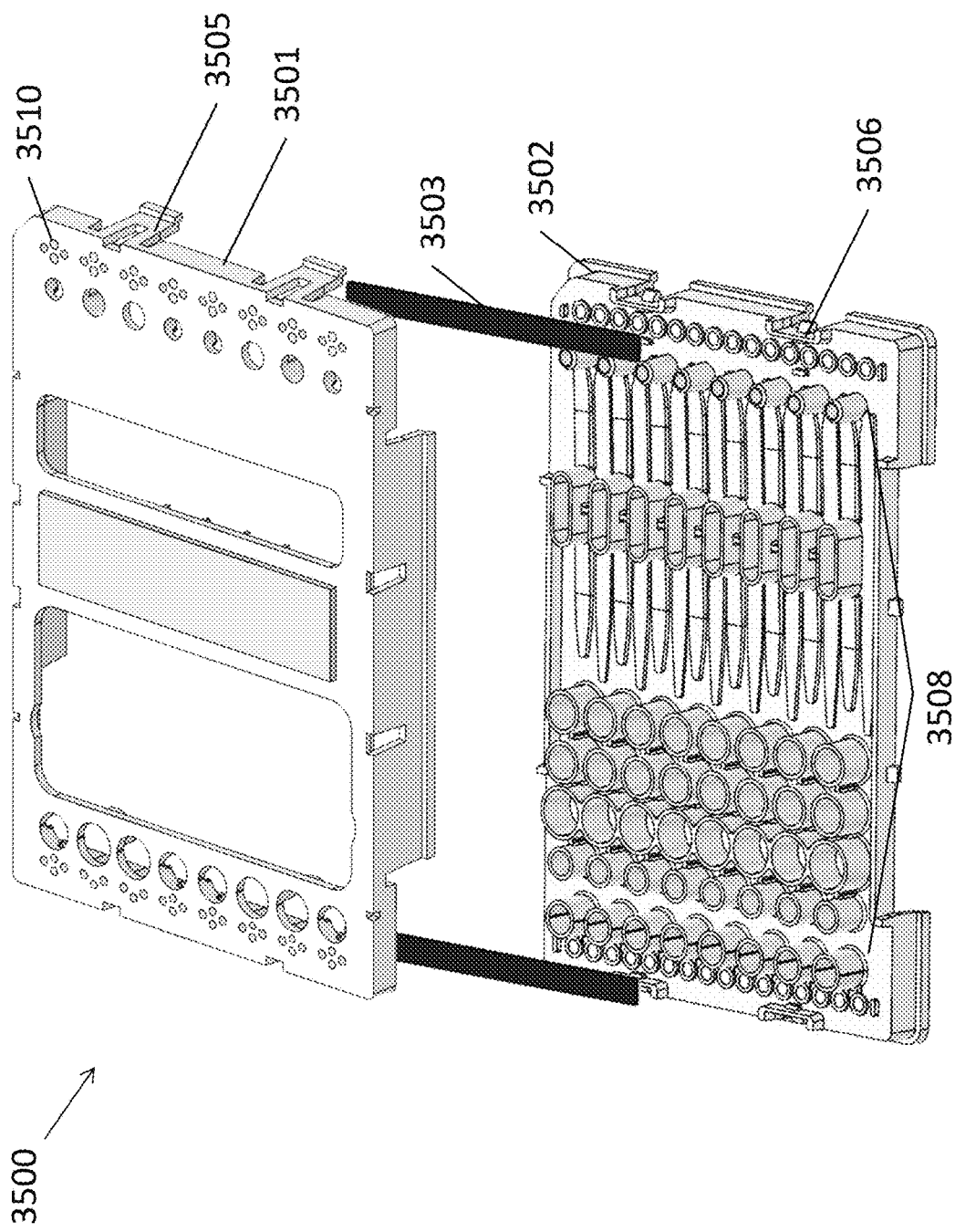

FIGS. 35A-35B show an example of a fluidic device 3500 which comprises two interlocking parts. FIG. 35A shows a cover piece 3501 which fits onto a microfluidic chip insert part 3502 as shown in FIG. 35B. FIG. 35B shows an exploded view between the chip 3502 and the cover 3501. The chip or substrate 3502 may have a first face and a second face. The first face may comprise a plurality of reservoirs 3508 configured to hold a liquid. The second face may comprise a plurality of channels. The reservoirs 3508 may communicate with channels via through holes in the substrate 3502. A hydrophobic membrane 3503 may be sandwiched between the chip 3502 and the cover 3501. The cover 3501 may be configured to capture and compress two hydrophobic membrane filters 3503 that can act as valves that can allow air, but not fluid, to pass. When the cover 3501 is assembled onto the microfluidic chip 3502, the compressible gaskets 3504 on the underside of the cover 3501 (as shown in FIG. 35A) may provide a constant compressive force downward onto the chip 3502, thereby creating a seal to prevent or reduce leaking between channels and/or the instrument. This downward force may initially be created during assembly with two sets of features between the chip 3502 and the cover 3501 engaging. First, the set of snaps 3505 around the cover may engage with mating features 3506 on the chip 3502, thereby ensuring alignment between the cover 3501 and chip 3502 and providing initial compression from the gasket feature onto the membrane 3503. As additional force is applied during assembly, the interference fit features 3507 on the cover may engage with the external walls of a limited set of fluid reservoirs 3508 on the chip 3502. The interference fit 3507 may be designed to maintain a fixed displacement, and therefore a fixed compressive force on the gasket 3504, when the assembly force is removed. The fixed height standoffs 3509 adjacent to the interference features 3507 may limit the distance the cover 3502 can be pressed down onto the reservoirs 3508. The cover piece 3501 may comprise a mating surface 3510 for interfacing with a pneumatic device, for example a pneumatic manifold as described herein.

The chip 3502 may, for example, comprise any number of interference fit features 3507 as desired by one of ordinary skill in the art. For example, the chip 3502 may comprise 1, 2, 3, 4, 5, 6, 7, 8, 9. 10, 11, 12, 13, 14, 15, 16, 17, 18, 19, or 20 interference fit features 3507. As will be understood by one of ordinary skill in the art, the holding capacity of the interference fit features 3507 may depend on the number of interference fit features 3507 on the chip 3502. For example, four interference fit features 3507 may have a holding capacity of 4 lb-f per feature 3507 while eight interference fit features 35o7 may have a holding capacity of 2 lb-f per feature 3507 for the same decoupling force. The interference fit features 3507 may have a radial interference within a range of about 10 um to about 120 um, for example within a range of about 30 um to about 60 um, for example about 45 um.

Figure 36A:
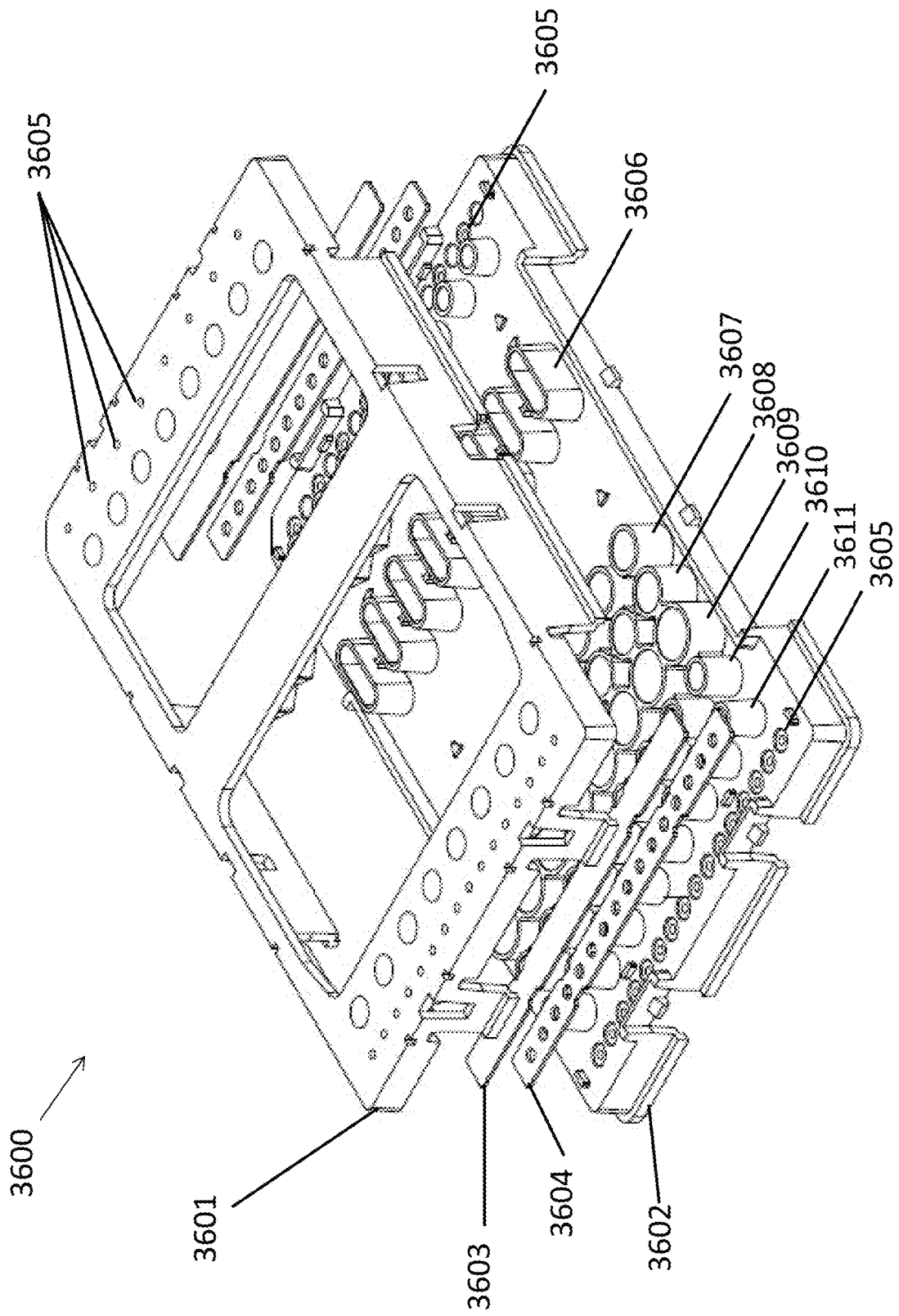
FIGS. 36A-36B show an example of a fluidic device which comprises multiple parts.
Figure 36B:
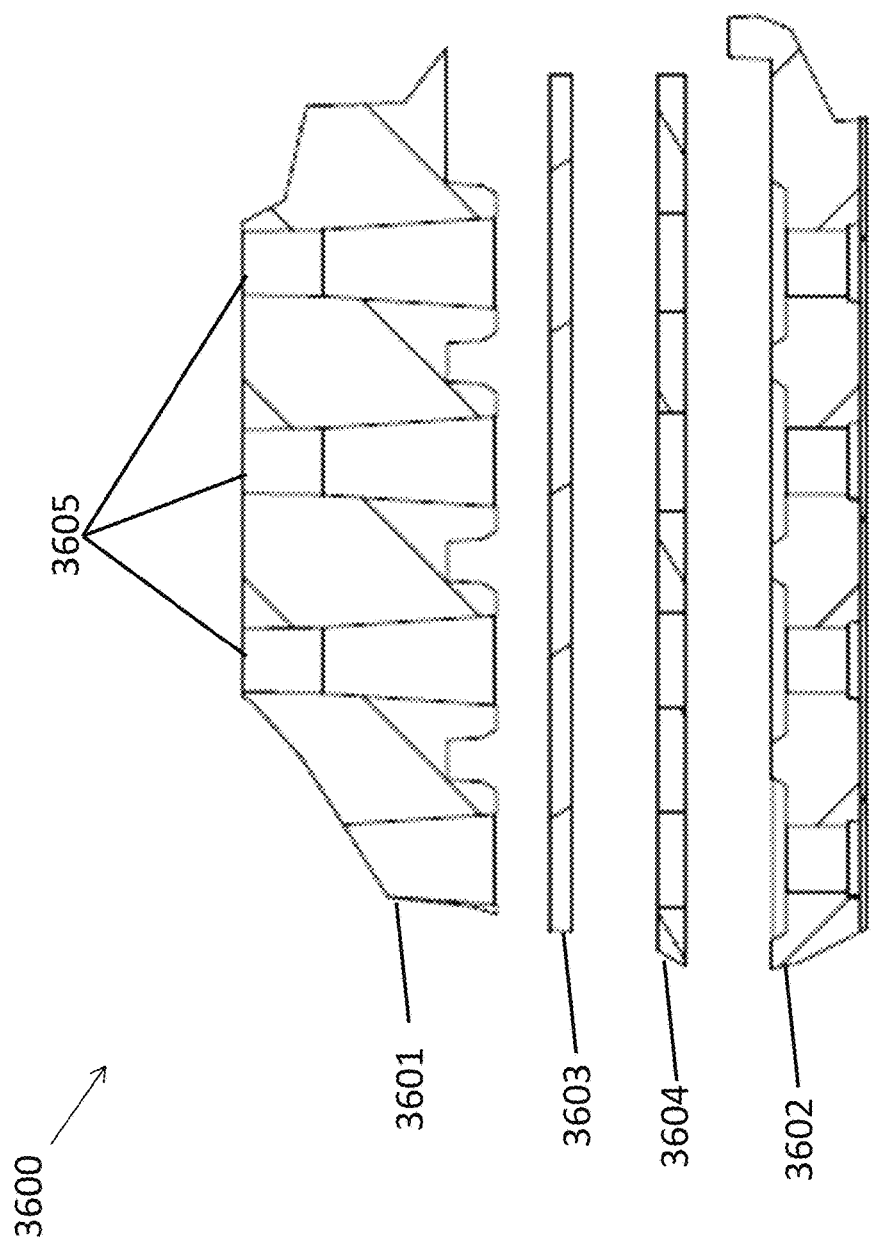

FIGS. 36A-36B show an example of a fluidic device 3600 which comprises multiple parts. FIG. 36A shows an exploded perspective view of the three-part fluidic device 3600. FIG. 36B shows an exploded cross-sectional view of the three-part fluidic device 3600. The fluidic device 3600 may comprise a cover piece or cover layer 3601, a chip plate or substrate 3602, a hydrophobic membrane 3603, and a compressible gasket 3604. The hydrophobic membrane 3603 may comprise a strip of hydrophobic membrane 3603 disposed within and/or across the pneumatic ports 3605 and sandwiched between the cover 3601 and the substrate 3602. The compressible gasket 3604 may comprise a strip of gasket material comprising apertures which are shaped and spaced to correspond to the pneumatic ports 3605. The compressible gasket strip 3604 may be sandwiched between the cover 3601, the hydrophobic membrane 3603, and the chip 3602 to provide a constant compressive force on the chip 3602 and create a seal to reduce or prevent leakage between channels. The cover 3601 and the chip 3602 may comprise one or more mating features (e.g. snaps, interference fits, clamps, adhesives, screws, bolts, height standoffs, etc.) configured to couple the two pieces together as described herein. The mating features may be configured to apply force to the compressible gasket 3604 to seal the pneumatic ports 3605 as described herein. The cover 3601 may be configured to interface with a pneumatic device and/or other elements of an instrument, for example any of the instruments described herein.

The pneumatic ports 3605 may comprise vertical cylindrical through-holes or apertures that extend from the pneumatic channels of the chip 3605 and through the cover layer 3601. The portion of the pneumatic ports 3605 on the chip layer 3602 may have a height at or near the height of the channels of the chip 3602. The pneumatic ports 3605 on the substrate 3602 may be configured to have a height to minimize sample loss. The pneumatic ports 3605 on the substrate 3602 may have a height within a range of about −1 mm to about 2 mm relative to a top surface of the substrate 3602, for example within a range of about −500 µm to about 1000 µm relative to a top surface of the substrate 3602. One or more of the pneumatic ports 3605 may be inset from the top surface of the substrate 3602 (e.g. with a height within a range of about −1 um to about −1 mm, or within a range of about −1 um to about −500 um relative to the top surface). One or more of the pneumatic ports 3605 may protrude relatively perpendicularly from the top surface of the substrate 3602 (e.g. with a height within a range of about 0 um to about 2 mm, or within a range of about 0 um to about 1000 um relative to the top surface). The position of the hydrophobic membrane 3603 and gasket 3604 within the pneumatic ports 3605 above the chip layer 3602 may reduce or prevent liquid loss through the pneumatic ports 3605 when negative pressure is applied thereto.

In some embodiments, the hydrophobic membrane 3603 and/or the compressible gasket 3604 may be attached to the cover 3601 prior to interlocking of the layers. Alternatively, the hydrophobic membrane 3603 and/or the compressible gasket 3604 may be attached to the chip 3602 prior to interlocking of the layers.

The chip 3602 may comprise any of the fluidic elements described herein. The chip 3602 may, for example, comprise a sample inlet reservoir 3606, a trailing electrolyte reservoir 3607, a leading electrolyte buffering reservoir 3608, a leading electrolyte reservoir 3609, an elution buffering reservoir 3610, and an elution reservoir 3611 as described herein. A first (e.g. top) face or side of the chip 3602 may comprise the reservoirs 3606-3611 as shown. A second (e.g. bottom) face or side of the chip 3602 may comprise one or more ITP channels (also referred to herein as fluidic circuits). The second side of the chip 3602 may comprise any of the ITP channels, or any combination of ITP channels, described herein. For example, the second side of the chip 3602 may comprise the 8 parallel channels shown in FIG. 38.

Figure 37A:
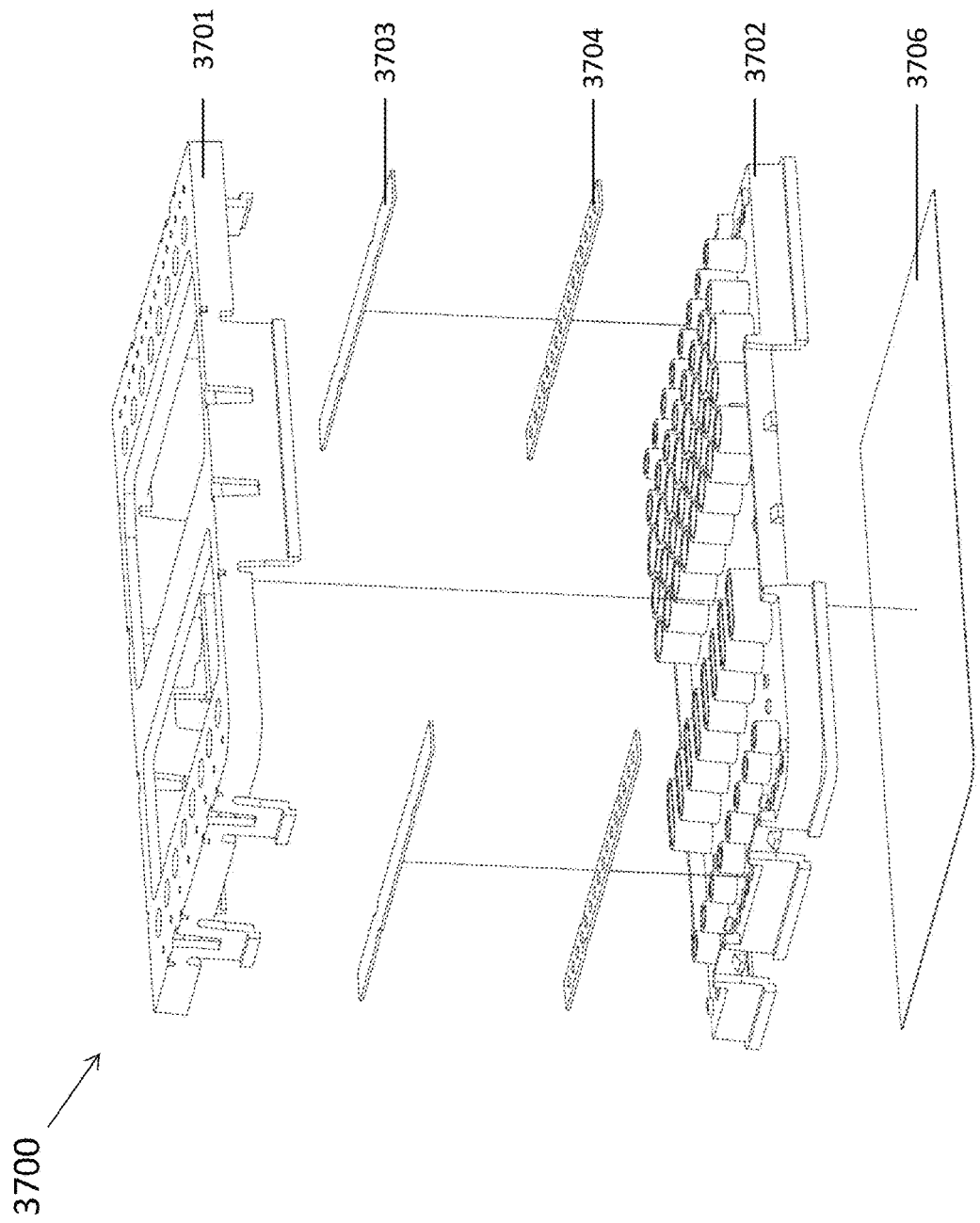
FIGS. 37A-37B show an example of a fluidic device which comprises three parts.
Figure 37B:
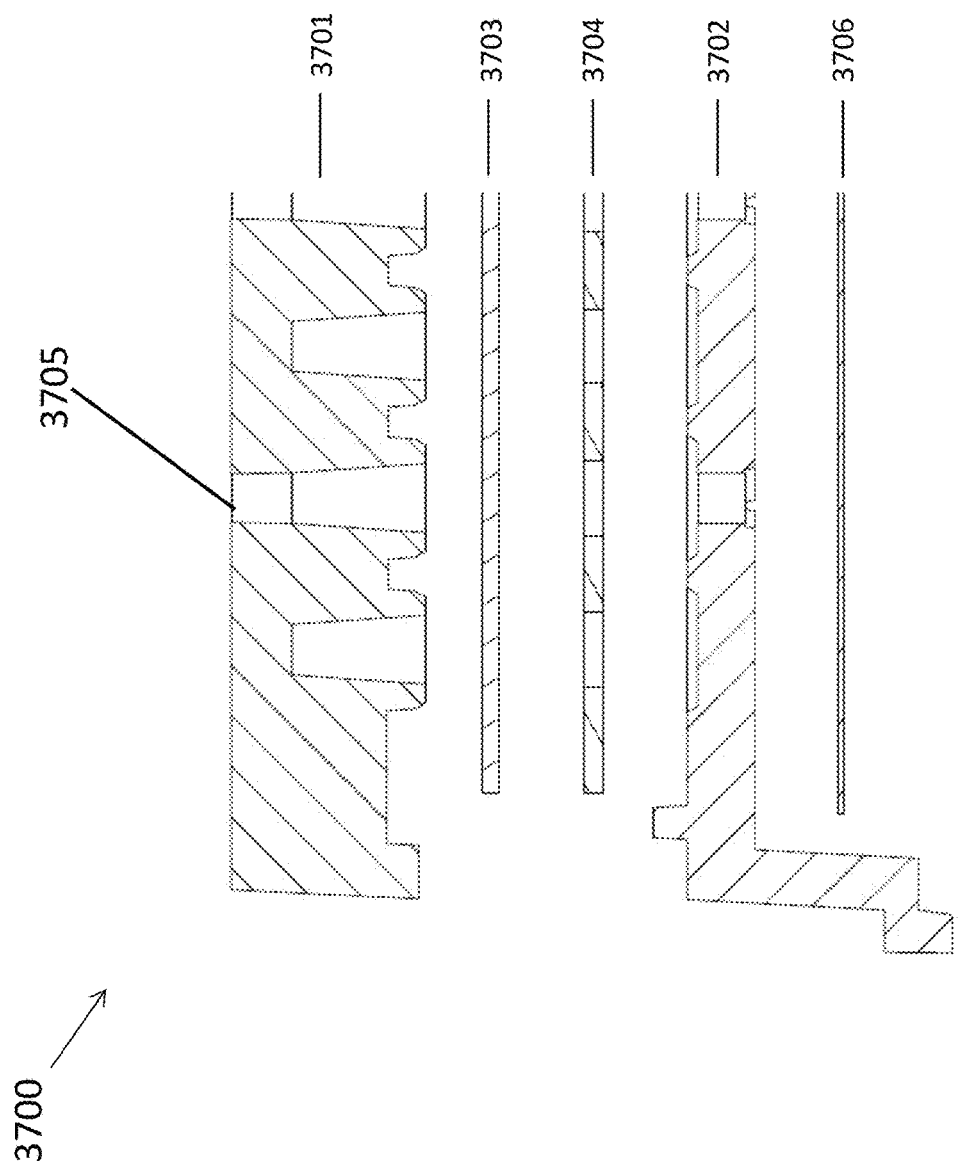

FIGS. 37A-37B show an example of a fluidic device 3700 which comprises three parts. FIG. 37A shows an exploded perspective view of the three-part fluidic device 3700. FIG. 37B shows an exploded cross-sectional view of the three-part fluidic device 3700. The fluidic device 3700 may comprise a cover piece or cover layer 3701, a chip plate or substrate 3702, a hydrophobic membrane 3703, and a compressible gasket 3704, which may be substantially similar to those of device 3600. The hydrophobic membrane 3703 may comprise a strip of hydrophobic membrane 3703 disposed within and/or across the pneumatic ports 3705 and sandwiched between the cover 3701 and the substrate 3702. The compressible gasket 3704 may comprise a strip of gasket material comprising apertures which are shaped and spaced to correspond to the pneumatic ports 3705. Pneumatic ports 3705 may be substantially similar to those of device 3600. The cover 3701 and the chip 3702 may comprise one or more mating features (e.g. snaps, interference fits, height standoffs, etc.) configured to couple the two pieces together as described herein. The mating features may be configured to apply force to the compressible gasket 3704 to seal the pneumatic ports 3705 as described herein. The cover 3701 may be configured to interface with a pneumatic device and/or other elements of an instrument, for example any of the instruments described herein. The device 3700 may further comprise a bottom layer of material 3706. The chip 3702 may be manufactured such that three walls of the channels are formed on a bottom layer or underside of the chip 3702. The bottom layer of material 3706 may be coupled to the underside of the chip 3702 in order to form the fourth wall of the channels, thereby creating closed channels. The bottom layer of material 3706 may be coupled to the underside of the chip 3702 through the use of a solvent, heat, a solvent heat bond, pressure, adhesive bond, laser weld, or a combination thereof. For example, the material can be a heat seal which bonds to the chip surface through application of heat which partially melts the materials, thereby bonding them. In certain embodiments, bonding may be achieved through the use of a solvent which dissolves the materials, thereby causing them to flow together and bond.

In some embodiments, the bottom layer of material 3706 may comprise a cyclic olefin copolymer as described herein. For example, the bottom layer of material 3706 may comprise TOPAS® 8007.

In some embodiments, bonding of the bottom layer of material 3706 to the underside of the chip 3702 may be achieved through the use of an organic solvent, for example toluene.

Figure 38:
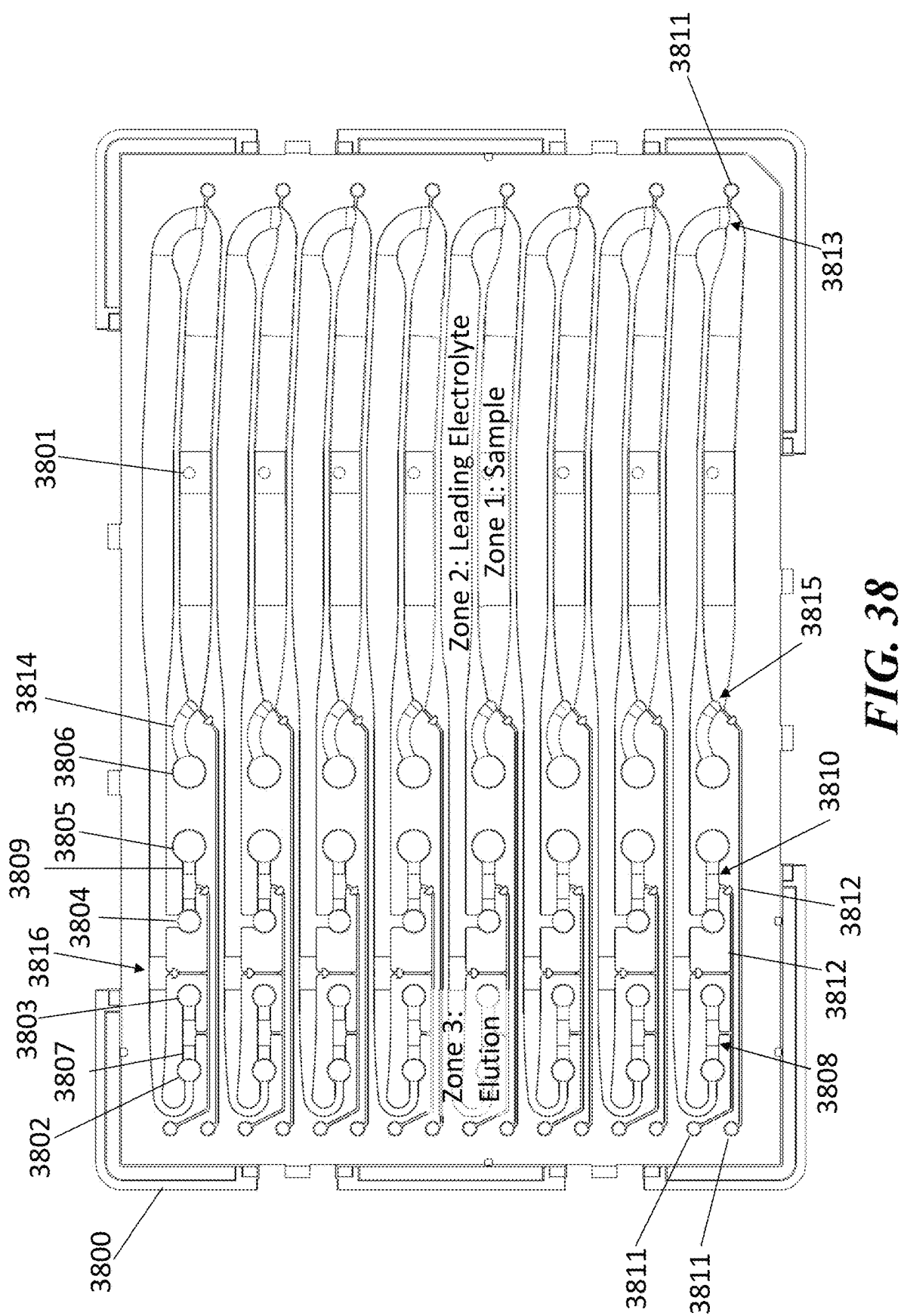
FIG. 38 shows an exemplary channel schematic for 8 parallel channels on the underside of the chip of a three part fluidic device.

FIG. 38 shows an exemplary channel schematic for 8 parallel channels on the underside of the chip of a three part fluidic device 3800. The device 3800 may comprise a multi-part device which may be substantially similar to devices 3500, 3600, or 3700 described herein. The device 3800 may comprise 8 parallel channels as described herein. Each channel may be connected to a sample input well or reservoir 3801, an elution reservoir 3802, an elution buffering reservoir 3803, a leading electrolyte reservoir 3804, a leading electrolyte buffering reservoir 3805, and a trailing electrolyte reservoir 3806. Reservoirs 3801-3806 may be coupled to the channel by through-holes or apertures as described herein. Elution reservoir 3802 may be connected to elution buffering reservoir 3803 by an elution buffering channel 3807. A capillary barrier 3808 (e.g. a plateau capillary barrier as described herein) may be provided in the elution buffering channel 3807 to reduce or prevent mixing or pressure driven flow between the contents of the elution buffering reservoir 3803 and the elution reservoir 3802. Leading electrolyte reservoir 3804 may be connected to leading electrolyte buffering reservoir 3805 by a leading electrolyte buffering channel 3809. A capillary barrier 3810 (e.g. a plateau capillary barrier) may be provided in the leading electrolyte buffering channel 3809 to reduce or prevent mixing or pressure-driven flow between the contents of the leading electrolyte buffering reservoir 3805 and the leading electrolyte reservoir 3804. Buffering reservoir 3803 may contain elution buffer electrolytes at a higher ionic strength than those in elution reservoir 3802, while buffering reservoir 3805 may contain leading electrolytes at a higher ionic strength than those in leading electrolyte reservoir 3804. The device may further comprise pneumatic ports 3811 along its edges which are configured to couple to a pneumatic device, for example a vacuum source on a benchtop instrument. The pneumatic ports 3811 may be coupled to the channels and reservoirs by gas channels 3812 as described herein. Application of suction (i.e. negative pneumatic pressure) at the pneumatic ports 3811 may load the sample, leading electrolyte, and elution buffer into the channels. The gas channels 3812 may be coupled to the channels at one or more capillary barriers such that the negative pressure is applied to said capillary barriers. Suction may be applied simultaneously or sequentially to the pneumatic ports 3811 so as to load the channels simultaneously or in stages, respectively. The sample may be loaded into a first zone or sub-channel which extends from the trailing electrolyte reservoir 3806 to a capillary barrier 3813 at a 180° low dispersion turn in the channel. The capillary barrier 3813 may provide an interface between the sample and the leading electrolyte buffer during loading so as to limit, reduce, or prevent mixing or pressure-driven flow. The capillary barrier 3813 may comprise a cliff capillary barrier as described herein. The trailing electrolyte reservoir 3806 may be connected to channel first zone or sub-channel by a trailing electrolyte channel 3814. A capillary barrier 3815 (e.g. a cliff capillary barrier) may be provided in the trailing electrolyte channel 3814 between the trailing electrolyte reservoir 3806 and the first zone or sub-channel so as to limit, reduce, or prevent mixing or pressure-driven flow between the contents of the trailing electrolyte reservoir 3806 and the sample. The leading electrolyte may be loaded into the second zone or sub-channel of the channel which extends from capillary barrier 3813 to capillary barrier 3816. The capillary barrier 3816 (e.g. a plateau capillary barrier) may provide an interface between the leading electrolyte buffer and the elution buffer. The first zone or sub-channel and the second zone or sub-channel may make up an ITP branch of the fluidic channel or circuit. The elution buffer may be loaded into a third zone or sub-channel of channel which extends from capillary barrier 3816 to elution reservoir 3802. The third zone or sub-channel may make up an elution branch of the fluidic channel or circuit.

Electrodes may for example be located in the trailing electrolyte reservoir 3806, the leading electrolyte reservoir 3804, and/or the leading electrolyte buffering reservoir 3805 such that the electrodes do not directly contact sample material. The electrodes may be triggered to alter or control the applied electric field in response to feedback from a sensor, for example a voltage, current, conductivity, or temperature sensor as described herein. For example, passage of the nucleic acids within the ITP zone from the second zone of channel to the third zone of channel may be detected and feedback from the detector may trigger the applied current to change. The current may for example be increased, decreased, or ended according to the protocol of the instrument. The current may for example be paused (e.g. dropped temporarily to zero) in order to enable on-chip quantification of the nucleic acids. Alternatively or in combination, the current may be decreased in order to slow isotachophoresis within the third zone to allow the nucleic acids which may have dispersed upon transition from the leading electrolyte buffer to the elution buffer (or second leading electrolyte buffer) time to concentrate further before reaching the elution well 3802.

Capillary barrier 3808 may comprise any capillary barrier desired by one of ordinary skill in the art. For example, capillary barrier 3808 may comprise a ramp capillary barrier, a plateau capillary barrier, or a cliff capillary barrier.

Capillary barrier 3810 may comprise any capillary barrier desired by one of ordinary skill in the art. For example, capillary barrier 3810 may comprise a ramp capillary barrier, a plateau capillary barrier, or a cliff capillary barrier.

Capillary barrier 3813 may comprise any capillary barrier desired by one of ordinary skill in the art. For example, capillary barrier 3813 may comprise a ramp capillary barrier, a plateau capillary barrier, or a cliff capillary barrier.

Capillary barrier 3815 may comprise any capillary barrier desired by one of ordinary skill in the art. For example, capillary barrier 3815 may comprise a ramp capillary barrier, a plateau capillary barrier, or a cliff capillary barrier.

Capillary barrier 3816 may comprise any capillary barrier desired by one of ordinary skill in the art. For example, capillary barrier 3816 may comprise a ramp capillary barrier, a plateau capillary barrier, or a cliff capillary barrier.

Figure 39:
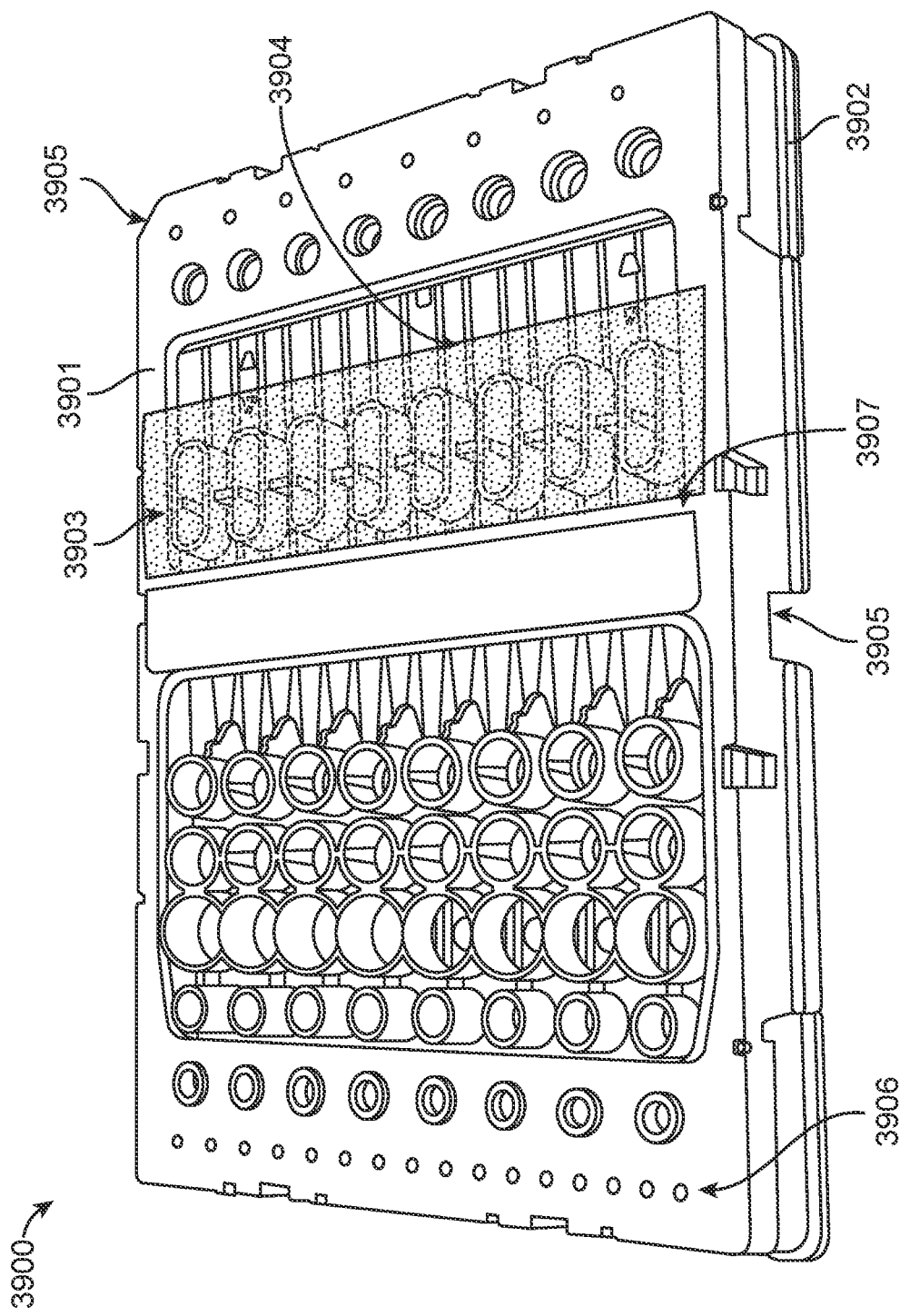
FIG. 39 shows an exemplary multi-part fluidic device.

FIG. 39 shows an exemplary multi-part device 3900 which may be substantially similar to the multi-part devices described herein. The device 3900 may comprise a cover layer 3901 and a chip or substrate 3902 as described herein. The device 3900 may comprise a sample well 3903 which may be connected to a sample channel via a through-hole or aperture as described herein. The sample well 3903 may comprise any of the sample wells described herein. Prior to use, the device 3900 may comprise a sample seal layer 3904 configured to seal the sample well 3903 prior to loading the sample, for example to enable pneumatic loading of one or more liquids from the other reservoirs into the channel before the sample as described herein. The sample seal layer 3904 may comprise a removable material. The sample seal layer 3904 may comprise a heat-seal material or an adhesive material. The sample seal layer 3904 may comprise a thermoplastic film. The sample seal layer 3904 may comprise a polymer or a plastic. The sample seal layer 3904 may, for example, comprise a peelable polymer seal such as the 4titude® Clear Heat Seal Plus. The device 3900 may further comprise one or more orienting features 3905 configured to prevent mis-insertion of the device 3900 into an instrument (e.g. any of the instruments described herein). The orienting features 3905 may further prevent movement of device 3900 after insertion into the instrument. The cover 3901 may comprise a mating interface 3906 configured to interface with a pneumatic device of the instrument, for example any of the instruments described herein. The device 3900 may further comprise one or more elements to facilitate use of the chip with the instrument, for example a barcode tracking label 3907 configured to aid a user in tracking the device 3900 when in use as described herein.

Fluidic devices can be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS).

Any of the fluidic devices described herein may comprise a multi-part fluidic device. Multi-part fluidic devices may be made from one or more materials described herein. In some embodiments, all of the parts of the multi-part fluidic devices described herein may be made from the same material(s). In some embodiments, one or more of the parts of the multi-part fluidic devices described herein may be made from the same material(s). In some embodiments, all of the parts of the multi-part fluidic devices described herein may be made from different material(s).

The cover piece may be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS).

The chip or substrate may be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS). The chip or substrate may for example comprise a COC such as TOPAS 8007.

The bottom layer may be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS). The chip or substrate may for example comprise a COC such as TOPAS 8007. In some embodiments, the bottom layer can comprise the same or a similar material as the chip. For example, both materials can have the same melting temperature.

The hydrophobic membrane may comprise an air-permeable hydrophobic membrane. The hydrophobic membrane may not be liquid-permeable. The hydrophobic membrane may be porous. The hydrophobic membrane may comprise a flexible material such that it may be compressed by the cover and/or compressible gasket to seal the pneumatic ports and reduce or prevent fluid leakage as described herein.

The compressible gasket may be made from a variety of materials, including but not limited to, neoprene.

Figure 40:
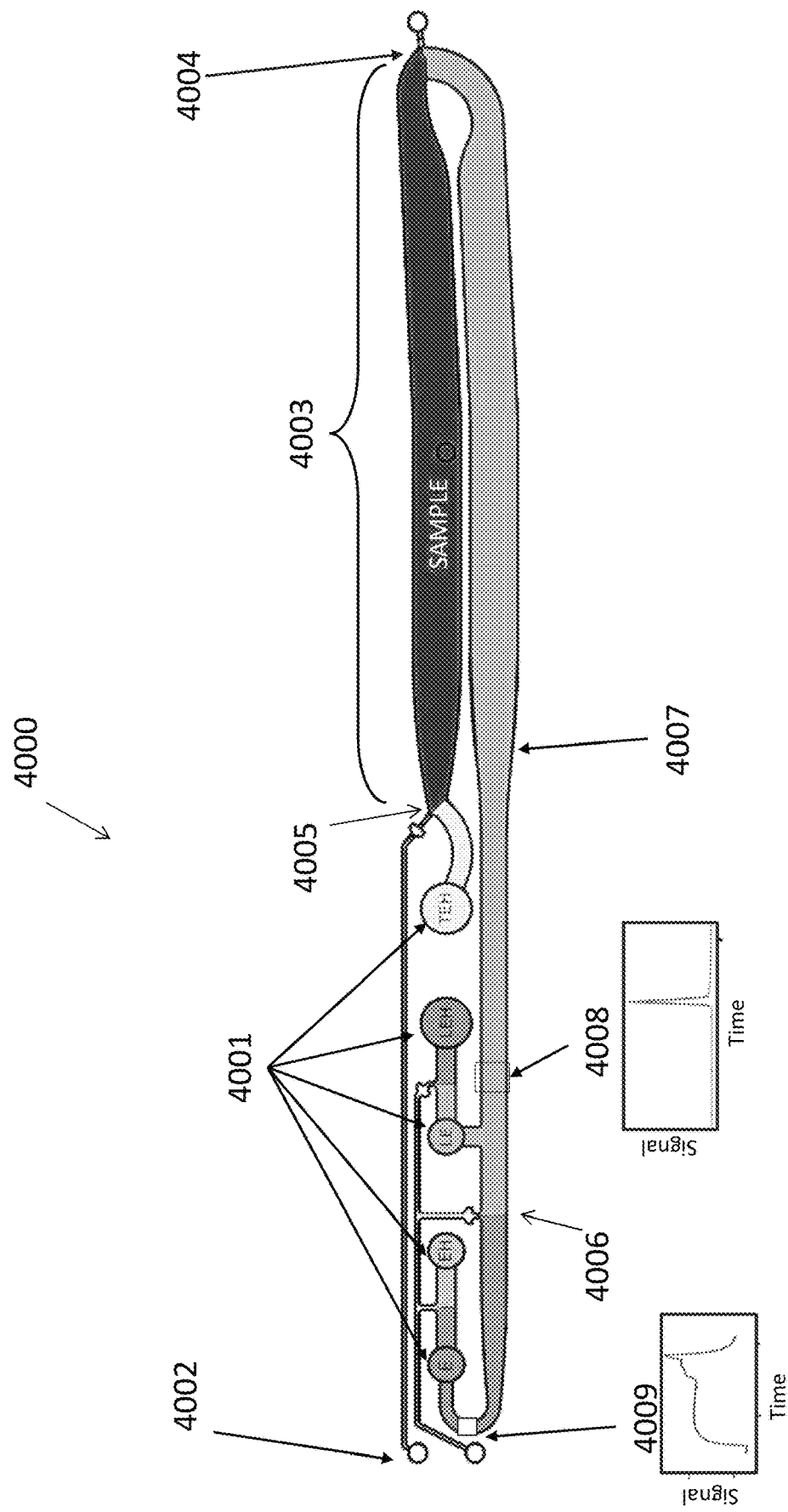
FIG. 40 shows an exemplary fluidic circuit comprising voltage and temperature sensing.

FIG. 40 shows an exemplary fluidic circuit 4000 comprising voltage and temperature sensing. The fluidic circuit 4000 may be substantially similar to the circuits described in FIG. 38. The fluidic circuit 4000 may be comprise a channel connected to a sample input well or reservoir, an elution reservoir (EB), an elution buffering reservoir (EBH), a leading electrolyte reservoir (LE), a leading electrolyte buffering reservoir (LEH), and a trailing electrolyte reservoir (TEH) as described herein. The reservoirs 4001 may be positioned in the device (e.g. device 3800) such that the wells 4001 are at standard locations for a microtiter plate as described herein. Reservoirs 4001 may be coupled to the channel by through-holes or apertures as described herein. A capillary barrier (e.g. a plateau capillary barrier) may be provided in the leading electrolyte buffering channel (between LE and LEH) to reduce or prevent mixing or pressure-driven flow between the contents of the leading electrolyte buffering reservoir (LEH) and the leading electrolyte reservoir (LE) as described herein. The device 4000 may further comprise pneumatic ports 4002 along its edges which are configured to couple to a pneumatic device, for example a vacuum source on a benchtop instrument. The pneumatic ports 4002 may be positioned in the device at standard locations for interfacing with commonly-available pneumatic manifolds. The pneumatic ports 4002 may be coupled to the channels and reservoirs by gas channels as described herein. Application of suction (i.e. negative pneumatic pressure) at the pneumatic ports 4002 may load the sample, leading electrolyte, and elution buffer into the channels as described herein. The gas channels 4002 may be coupled to the channels at one or more capillary barriers such that the negative pressure is applied to said capillary barriers as described herein. Suction may be applied simultaneously or sequentially to the pneumatic ports 4002 so as to load the channels simultaneously or in stages, respectively. The sample may be loaded into a first zone or sub-channel 4003 which extends from the trailing electrolyte reservoir (TEH) to a capillary barrier 4004 at a 180° low dispersion turn in the channel. The capillary barrier 4004 may provide an interface between the sample and the leading electrolyte buffer during loading so as to limit, reduce, or prevent mixing or pressure-driven flow. The capillary barrier 4004 may comprise a cliff capillary barrier as described herein. The capillary barrier 4004 may enable bubble-free priming or loading of the sample and elution buffer within the channel 4000 as described herein. The capillary barrier 4004 may be used for feedback triggering as described herein. For example, when the ITP band passes the capillary barrier 4004, the derivative of the voltage may exhibit a peak as shown in FIG. 92B. This peak may trigger the instrument to perform additional voltage signal processing as described herein. The trailing electrolyte reservoir (TEH) may be connected to channel first zone or sub-channel by a trailing electrolyte channel. A capillary barrier 4005 (e.g. a cliff capillary barrier) may be provided in the trailing electrolyte channel between the trailing electrolyte reservoir (TEH) and the first zone or sub-channel 4003 so as to limit, reduce, or prevent mixing or pressure-driven flow between the contents of the trailing electrolyte reservoir (TEH) and the sample as described herein. The leading electrolyte may be loaded into the second zone or sub-channel of the channel which extends from capillary barrier 4004 to a capillary barrier 4006 (e.g. a plateau capillary barrier) which may provide an interface between the leading electrolyte buffer and the elution buffer. A narrowing or construction 4007 may be provided within the second zone of the channel. The construction 4007 may be used for feedback triggering as described herein. For example, when the ITP band passes the construction 4007, the derivative of the voltage may exhibit a peak as shown in FIG. 92D. This peak may trigger the instrument to perform additional signal processing (e.g. temperature signal processing) as described herein. An integrated quantitation region 4008 may also be provided within the second zone of the channel. The integrated quantitation region 4008 may be used to perform in-line (i.e. on-chip) quantitation of nucleic acids in the passing ITP band as described herein. The first zone or sub-channel 4003 and the second zone or sub-channel may make up an ITP branch of the fluidic channel or circuit 4000. The elution buffer may be loaded into a third zone or sub-channel of channel which extends from capillary barrier 4006 to the elution reservoir (EB). The third zone or sub-channel may make up an elution branch of the fluidic channel or circuit 4000. The third zone may comprise an infrared temperature sensor 4009 as described herein.

Capillary barrier 4004 may comprise any capillary barrier desired by one of ordinary skill in the art. For example, capillary barrier 4004 may comprise a ramp capillary barrier, a plateau capillary barrier, or a cliff capillary barrier.

Capillary barrier 4005 may comprise any capillary barrier desired by one of ordinary skill in the art. For example, capillary barrier 4005 may comprise a ramp capillary barrier, a plateau capillary barrier, or a cliff capillary barrier.

Capillary barrier 4006 may comprise any capillary barrier desired by one of ordinary skill in the art. For example, capillary barrier 4006 may comprise a ramp capillary barrier, a plateau capillary barrier, or a cliff capillary barrier.

Materials used for the fabrication of fluidic devices can be selected for their optical properties. For example, materials can be used that exhibit low auto-fluorescence, low scatter, and high transmission at wavelengths of interest (e.g., excitation and emission wavelengths for nucleic acid labels or dyes). Different materials can be used in one fluidic device; for example, a detection region can be fabricated with materials exhibiting useful optical properties, while other regions of the device can comprise other materials.

Materials used for the fabrication of fluidic devices can be selected for their thermal properties. For example, materials can be selected for high thermal conductivity. Alternatively, materials can be selected for low thermal conductivity (e.g., to thermally insulate a fluidic device or a region of a fluidic device. Different materials can be used in one fluidic device; for example, a heating region can have materials with high thermal conductivity for improved thermal communication with a thermal controller, while the heating region is surrounded by materials with low thermal conductivity for thermal isolation from other regions of the device.

Materials used for the fabrication of fluidic devices or microchannels therein can be selected for their elastomeric or deformation properties. For example, materials can be selected for low elasticity so as to allow for plastic channel closure as described herein. Alternatively, materials can be selected for high elasticity. Different materials can be used in one fluidic device; for example poly(methyl methacrylate) (PMMA), cyclic olefin copolymer (COC), cyclo-olefin polymer (COP), or the like can be used in a single fluidic device. Materials may have a modulus of elasticity of at least 1 GPa, 1.5 GPa, 2 GPa, 2.5 GPa, 3 GPa, 3.5 GPa, 4 GPa, 4.5 GPa, or 5 GPa. Materials may have a modulus of elasticity of at most 1 GPa, 1.5 GPa, 2 GPa, 2.5 GPa, 3 GPa, 3.5 GPa, 4 GPa, 4.5 GPa, or 5 GPa. Materials may have a tensile strength of at least 10 MPa, 20 MPa, 30 MPa, 40 MPa, 50 MPa, 60 MPa, 70 MPa, 80 MPa, 90 MPa, 100 MPa, 110 MPa, 120 MPa, 130 MPa, 140 MPa, 150 MPa, 160 MPa, 170 MPa, 180 MPa, 190 MPa, 200 MPa. Materials may have a tensile strength of at most 10 MPa, 20 MPa, 30 MPa, 40 MPa, 50 MPa, 60 MPa, 70 MPa, 80 MPa, 90 MPa, 100 MPa, 110 MPa, 120 MPa, 130 MPa, 140 MPa, 150 MPa, 160 MPa, 170 MPa, 180 MPa, 190 MPa, 200 MPa.

In some cases, surfaces of a fluidic device can be used without surface treatments or coatings. In other cases, surfaces of a fluidic device can be used with surface coatings, such as hydrophobic treatments, hydrophilic treatments, or selective binding agents (e.g., antibodies). Different regions of a fluidic device can comprise different surface treatments (or the lack thereof). For example, some channels, reservoirs, or parts thereof can be hydrophobic, while others are hydrophilic.

Fluidic devices can include a range of flow control units and techniques, including but not limited to capillary barriers, air outlet reservoirs, gas/air lines, fill level monitors (e.g., by electrode measurement), particular reservoir geometries, particular fluidic resistances of channels, and fluid loading orders.

A capillary barrier is a constriction in the internal cross-sectional area of a fluidic channel that prevents flow of a liquid across the barrier through capillary forces. The longitudinal shape of the constriction can be abrupt or tapered.

Capillary barrier shapes can take many forms. However, three forms are particularly contemplated herein, "plateau" capillary barrier, "cliff" capillary barrier and "ramp" capillary barrier.

As used herein, a "plateau" capillary barrier comprises first and second tapered areas, referred to as "ramps", oriented in opposite directions and typically separated by a plateau at which the internal cross-sectional area of the channel remains substantially the same. Accordingly, in a plateau barrier, the internal cross-sectional area of the channel experiences a decrease followed by an increase. The shapes of the ramps and the plateau can be flat (linear), such as a plane or wedge, or curved (non-linear), such as a hump, and can have a longitudinal shape of a circle, ellipse or parabola, to name a few. A linear shape allows for equal pressure to move liquid across the barrier in a linear fashion. The angle between the base of the ramp to the point of greatest constriction can be, for example, between about 25 degrees and about 70 degrees, e.g., between about 30 degrees to 45 degrees. The internal cross-sectional diameter of the channel at the base of the ramp can be between about 50 microns to 2000 microns (e.g., 400 microns to 1200 microns). The internal cross-sectional diameter of the channel at the top of the ramp or plateau can be between about 10 microns to about 300 microns. The ratio between the two can be 2×. The plateau can serve to separate the meniscus of a liquid on the first side of the barrier from touching the meniscus of a liquid on the second side of the barrier until sufficient pressure is applied, such as negative pressure applied between the two menisci.

The "cliff" capillary barrier comprises a first tapered area and a cliff, typically separated by a plateau. The first tapered area and plateau can have shapes and dimensions as described for the plateau capillary barrier. The cliff creates an abrupt change in the internal cross-sectional area of the channel. Typically, the cliff takes the shape of a steep wall, which can be flat or curved, and which rises at an angle from the floor of the channel at an angle of about 80 degrees to about 100 degrees, e.g., about 90 degrees. The plateau can be present for ease of manufacturing, by avoiding sharp angles.

The "ramp" capillary barrier, as used herein, comprises a first tapered area and a cliff. Optionally, a "ramp" capillary barrier may include a plateau. The first tapered area and the plateau, if present, can have shapes and dimensions as described for the plateau capillary barrier. The cliff creates an abrupt change in the internal cross-sectional area of the channel. Typically, the cliff takes the shape of a steep wall, which can be flat or curved, and which rises at an angle from the floor of the channel at an angle of about 80 degrees to about 100 degrees, e.g., about 90 degrees. The plateau can be present for ease of manufacturing, by avoiding sharp angles.

The term capillary barrier refers to a constriction in a fluidic channel that prevents or restricts fluid flow across the constriction by capillary forces. Typically, the constriction is formed from an object disposed in the channel. A capillary barrier may be breached by application of a minimum positive or negative pressure to the fluid whose flow is restricted by the barrier. Certain embodiments of capillary barriers are described in Patent Application Publication US 2016/0160208 (Santiago). Capillary barriers can be paired with air outlet reservoirs to purge air (e.g., to prevent bubbles), thereby positioning and successfully establishing a liquid-liquid interface (i) between leading and trailing electrolyte solutions that is required for isotachophoresis, and (ii) between buffering reservoirs and leading electrolyte or trailing electrolyte and/or sample solutions. Capillary barriers can be designed in combination with channel geometry to automate filling of channels in a preferred order. Channel resistances can be selected, such as by design of channel dimensions, to provide differential fluidic resistances. Ordering of liquid loading can allow the correct formation of liquid-liquid interfaces without air bubbles for performing electrokinetic processes. In one example, a trailing ion reservoir is directly connected to the analyte or sample channel.

Capillary barriers may be used to position a meniscus of a fluid at a fluid-interface region using capillary forces. The capillary barrier may act as a passive stopping mechanism and utilize surface forces to hold or pin the liquid meniscus of a fluid in a desired and stationary location. Once the meniscus of the fluid is pinned at a junction, different liquids may be loaded and backfilled to the meniscus of the first fluid to create a liquid-to-liquid interface. A capillary barrier may for example comprise a constriction or expansion (e.g., a change in cross-sectional area) within the channel. Fluid flow within the channel may rely in part on capillary forces, which may result from the surface tension forces between the fluid and the channel walls. The magnitude of the capillary forces may be determined by the contact angle between the fluid and the channel walls. A capillary barrier may be configured to introduce an abrupt change in the capillary force the liquid experiences while flowing through the channel, for example by changing an effective diameter of the channel (either enlarging or narrowing the channel). The change in the capillary forces may be proportional to the difference in the surface tensions of the fluid on each side of the capillary barrier. Fluid flow may be arrested by the capillary barrier due to surface forces caused by the change in cross-sectional area within the channel. Fluid at the cross-sectional area change may face an energetic barrier associated with the different surface tensions on each side of the capillary barrier.

As used herein, the term "burst pressure" refers to the minimum pressure required to move a meniscus of a stopped liquid over a capillary barrier.

A "ramp capillary barrier", for example as described in Patent Application Publication US 2016/0160208 (Santiago), may comprise a ramp and a cliff without a plateau region therebetween.

Figures 41A, 41B:
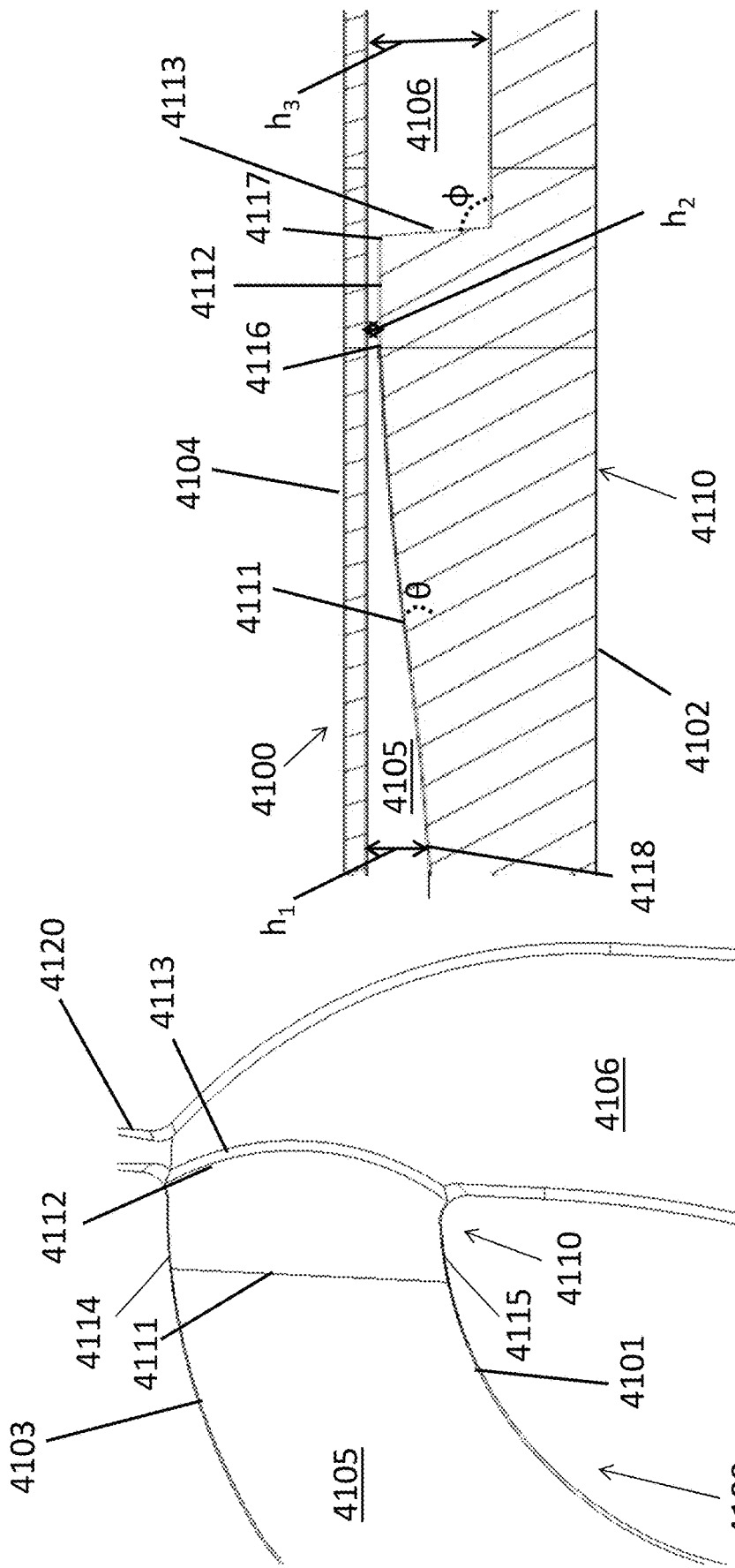
FIGS. 41A-41B show an exemplary "cliff capillary barrier".

FIGS. 41A-41B show an exemplary "cliff capillary barrier" 4110. FIG. 41A shows a top view of a channel 4100 having a cliff capillary barrier 4110 disposed therein. FIG. 41B shows a longitudinal cross-sectional side view of the cliff capillary barrier 4110 in the channel 4100. The cliff capillary barrier 4110 may comprise a trapezoidal cross-section having a constriction within the channel 4100 formed by an angled surface 4111 and a plateau surface 4112 of the cliff capillary barrier 4110 followed by a sudden expansion within the channel formed by a cliff surface 4113. The channel 4100 may comprise a first wall 4101, a second wall 4102, a third wall 4103, and a fourth wall 4104 to form a closed channel. The channel 4100 may for example have a square or rectangular cross-section (taken along a lateral axis of the channel 4100) comprising four walls. The first and the third walls 4101, 4103 may be substantially parallel to one another. The second and the fourth walls 4102, 4104 may be substantially parallel to one another. The cliff capillary barrier 4110 may protrude from the second channel wall 4102 into the channel 4100. The cliff capillary barrier 4110 may be disposed on the second wall 4102. Alternatively, the cliff capillary barrier 4110 may form a part of the second wall 4102. The cliff capillary barrier 4110 may comprise sides that are disposed on, coextensive with, or integrated in an interior surface of the second wall 4102. The cliff capillary barrier 4110 may extend substantially the width of the channel 4100. For example, the cliff capillary barrier 4110 may extend substantially between the first and third walls 4101, 4103 as shown in FIG. 41A. The cliff capillary barrier 4110 may comprise a first and a second lateral wall or side 4114, 4115. The first and second lateral walls or sides 4114, 4115 may be connected to the first and third channel walls 4101, 4103, respectively. Alternatively, the first and second lateral walls or sides 4114, 4115 may be coextensive with the first and third channel walls 4101, 4103, respectively. Alternatively, the first and second lateral walls or sides 4114, 4115 may be adjacent to the first and third channel walls 4101, 4103, respectively. The first and second lateral walls or sides 4114, 4115 may each comprise a cross-sectional area with a trapezoidal shape (for example the cross-sectional area shown in FIG. 41B). The trapezoidal cross-section may comprise a plateau surface or side 4112 that is substantially parallel to the second channel wall 4102. The plateau surface or side 4112 may be situated in the channel 4100 between the second and fourth channel walls 4102, 4104. An angled surface or side (also referred to herein as a ramp) 4111 may connect the second wall 4102 to the plateau surface or side 4112 at a first edge 4116. A cliff surface or side 4113 may connect the second wall 4102 to the plateau surface or side 4112 at a second, opposite edge 4117.

The angled surface or side 4111 may be configured to gradually reduce the height of the channel 4100 from a first height $h_1$ to a second, smaller height $h_2$, over a distance along the length of the channel. The first height $h_1$ may be at least twice as large as the second height $h_2$. The angled surface or side 4111 may for example be an incline plane rising from a bottom wall of the channel 4100 or a decline plane lowering from a top wall of the channel 4100. The angled surface or side 4111 may for example be an angled plane extending into the channel 4100 from a side wall of the channel 4100. The angled surface or side 4111 may have a first edge 4116 which intersects with the plateau region or side 4112 to form an interior obtuse angle of the cliff capillary barrier and a second, opposing edge 4118 which intersects with the second channel wall 4102 to form an interior acute angle θ of the cliff capillary barrier 4110.

The cliff surface or side 4113 may be configured to suddenly increase the height of the channel 4100 from a first height $h_2$ to a second, larger height $h_3$, over a very short distance or no distance along the length of the channel 4100. The cliff surface or side 4113 may for example be a vertical surface (relative to the second wall 4102) connecting the plateau surface or side 4112 to the second wall 4102. The cliff surface or side 4113 may for example be substantially perpendicular to the second wall 4102.

Liquid wicking up the angled surface or side to the plateau surface or side 4111 may face an energetic barrier associated with expanding past the plateau surface or side 4112 (as additional liquid surface area or pressure is required to advance the liquid) which may result in the liquid being stopped by the cliff capillary barrier 4110 and a meniscus of the liquid being positioned at the edge 4116 of the plateau surface or side 4112 nearest the angled surface or side 4111 or the edge 4116 above the cliff surface or side 4113. The cliff capillary barrier 4110 may be configured such that the liquid stopped by the capillary barrier 4110 can be wetted by liquid approaching the cliff capillary barrier 4110 from its other side (e.g. from the cliff side 4113) to create a bubble-free liquid-to-liquid interface. The cliff capillary barrier 4110 may be disposed adjacent a gas channel 4120 configured to facilitate air bubble removal from the channel 4100 as the liquid enters the channel 4100 and the meniscus of the liquid is stopped at the cliff capillary barrier 4110 as described herein.

Figure 47A:
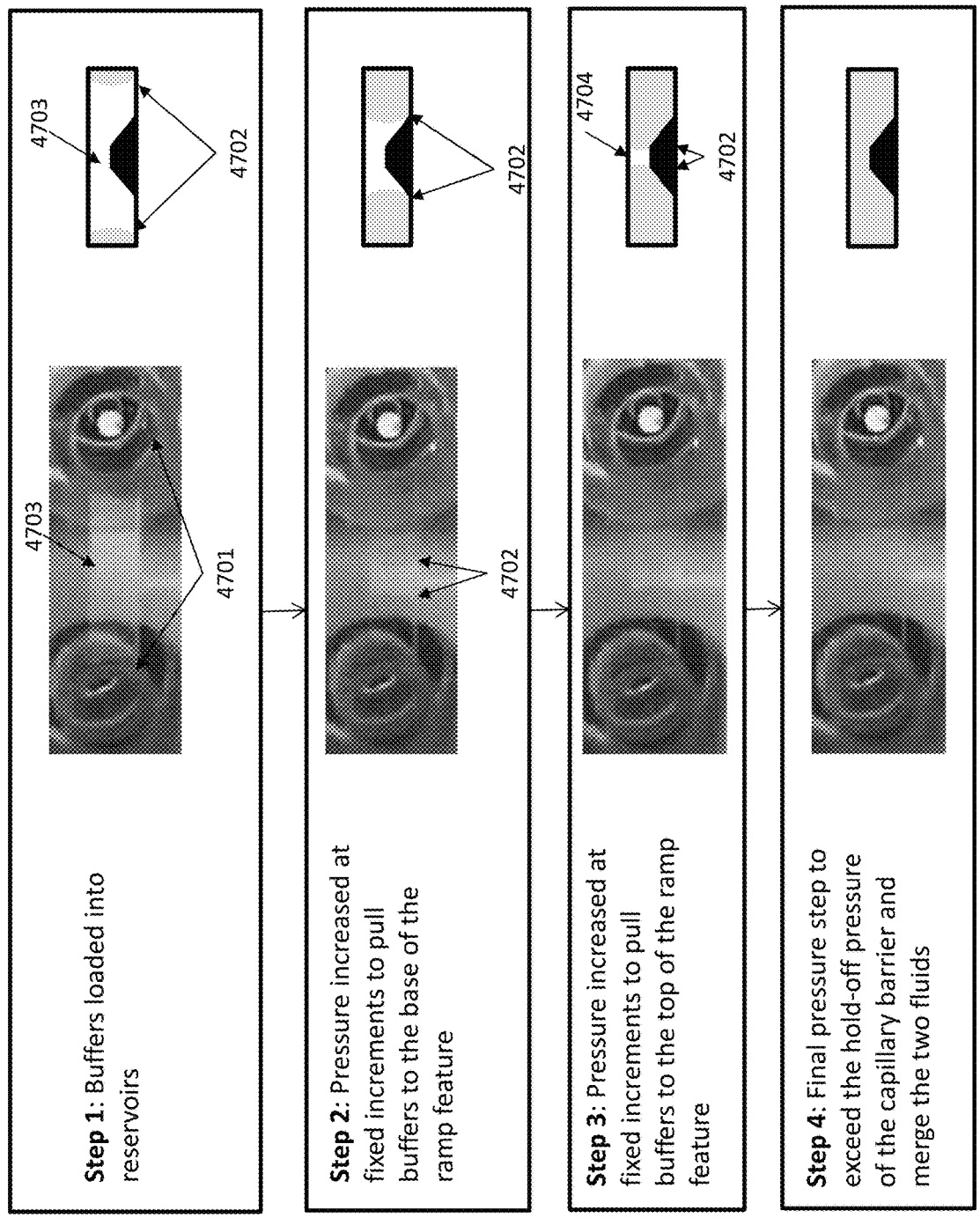
FIGS. 47A-47B show an exemplary pneumatic control scheme for staged liquid loading.

The cliff capillary barrier 4110 may be configured to hold the menisci of the liquids on either side of the cliff capillary barrier 4110 separate, with an air gap between them spanning the plateau surface or side 4112 until a pressure applied across the capillary barrier via the air channel 4120 exceeds the burst pressure of the cliff capillary barrier 4110 and one or both of the liquids cross the plateau surface or side 4112 to meet each other and form a liquid-to-liquid interface as described herein (e.g., as shown in FIG. 47A).

The cliff capillary barrier 4110 may be configured to hold or stop a liquid when a pneumatic pressure is applied thereto. The cliff capillary barrier 4110 may be configured to hold the liquid under a pressure within a range of about 0 mpsi to about 200 mpsi, for example within a range of about 10 mpsi to about 80 mpsi. The cliff capillary barrier 4110 may be configured to hold the liquid until a burst pressure (e.g. the minimum pressure required to move the stopped liquid over plateau 4112 and/or the cliff 4113 and past the cliff capillary barrier 4110) is reached. It will be understood by one of ordinary skill in the art that the burst pressure of the cliff capillary barrier 4110 may depend on the liquid(s) being held by the cliff capillary barrier 4110, with more wetting liquids having a lower burst pressure than less wetting liquids.

The angled surface or side 4111 may be configured to gradually reduce the height of the channel 4100 from a first height $h_1$ within a range of about 50 um to about 2 mm to a second height $h_2$ within a range of about 10 um to about 30 um. The first height $h_1$ may for example be within a range of about 400 um to about 1.2 um.

The angled surface or side 4111 may have a first edge 4116 which intersects with the plateau region or side 4112 to form an interior obtuse angle of the cliff capillary barrier 4110.

The angled surface or side 4111 may have a second, opposing edge 4118 which intersects with the second channel wall 4102 to form an interior acute angle θ of the cliff capillary barrier 4110. The interior acute angle θ may be within a range of about 0 degrees to about 70 degrees, for example within a range of about 30 degrees to about 45 degrees or within a range of about 30 degrees to about 60 degrees.

The plateau surface or side 4112 may have a length along a longitudinal axis of the channel 4110 within a range of about 500 um to about 1 mm, for example about 750 um.

The cliff surface or side 4113 may be substantially perpendicular to the second channel wall 4102 and/or the plateau surface or side 4112. The cliff surface or side 4113 may intersect the second channel wall 4102 to form an interior angle φ within a range of about 60 degrees to about 90 degrees.

The ramp 4111, plateau area 4112, or cliff area 4113, in any combination, may have a substantially flat surface.

The ramp 4111, plateau area 4112, or cliff area 4113, in any combination, may have a curved surface.

The ramp 4111, plateau area 4112, or cliff area 4113, in any combination, may have a surface that comprises one or more grooves, ridges, indentations, steps, etchings, or protrusions.

The ramp 4111, plateau area 4112, or cliff area 4113, in any combination, may have a surface that comprises regions with faces at different angles.

The cliff capillary barrier 4110 may be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS). The chip or substrate may for example comprise a COC such as TOPAS 8007. The cliff capillary barrier 4110 may be made from the same material(s) as the channel or a different material(s) as the channel 4100.

The depth of the channels 4100 on either side of the cliff capillary barrier 4110 may be the same. Alternatively, each side 4111, 4113 of the cliff capillary barrier 4110 may be coupled to channels 4110 of different depths. For example, the ramp portion 4111 of the cliff capillary barrier 4110 may be coupled to a sample channel 4105 comprising a depth within a range of about 10 um to about 2 mm, for example within a range of about 400 um to about 1.2 mm as described herein. The cliff portion 4113 of the cliff capillary barrier 4110 may be coupled to a leading electrolyte channel 4106 comprising a depth within a range of about 10 um to about 1 mm, for example within a range of about 10 um to about 600 um as described herein.

So, for example, referring to FIG. 41B, when the elements are positioned adjacently as ramp-plateau-cliff 4111-4112-4113, the cliff capillary barrier 4110 can comprise a ramp 4111 rising from a surface 4102 of the channel 4100 at a shallow angle θ, a plateau area 4112 having a surface about parallel to other portions of the channel surface 4102, 4104, and a cliff 4113 falling to the surface 4102 and having an angle φ substantially steeper than the angle θ of the ramp 4111. The shallow angle θ can be less than 60 degrees, e.g., no more than 45 degrees or no more than 30 degrees. The cliff angle φ can be greater than 60 degrees, e.g., about 90 degrees. The plateau 4112 can be no more than 10 degrees off parallel to the channel surface 4102.

Figure 42A:
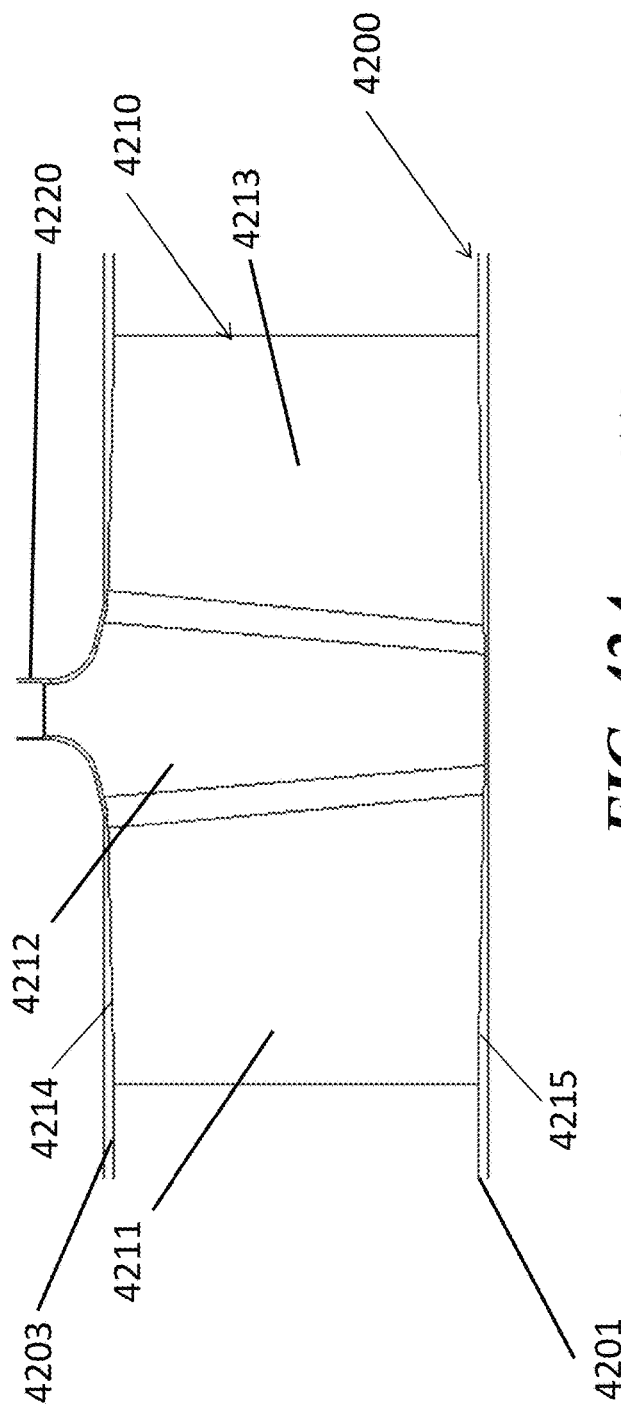
FIGS. 42A-42B show an exemplary "plateau capillary barrier".
Figure 42B:
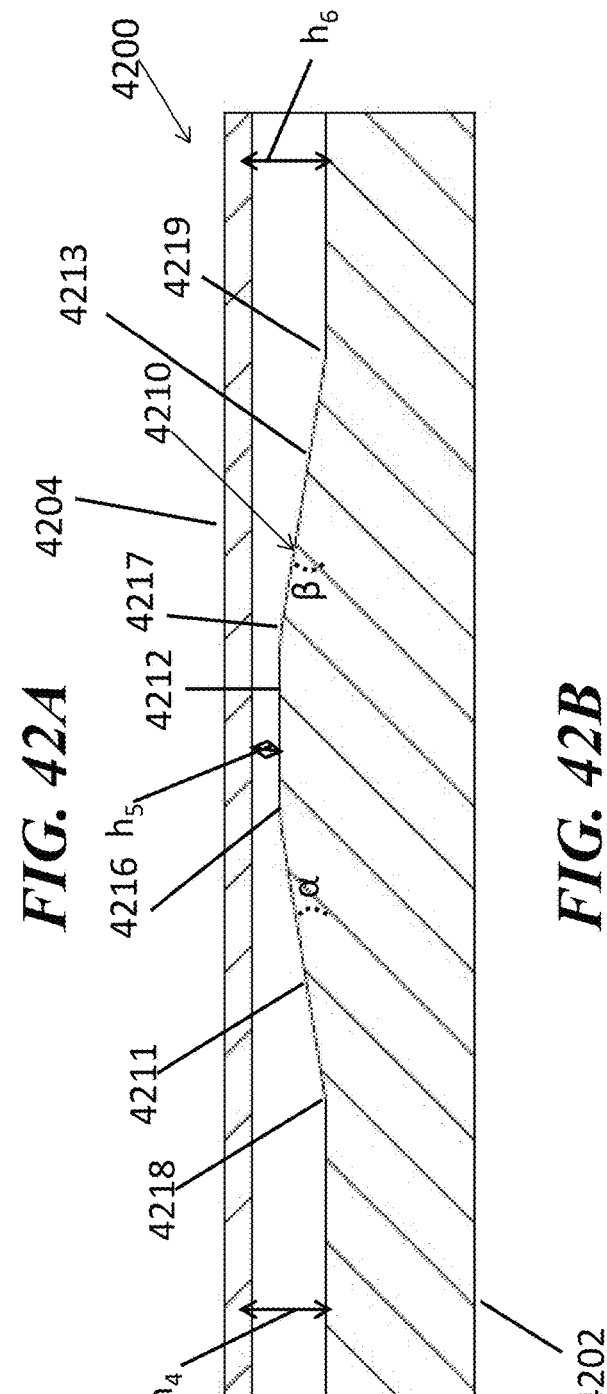

FIGS. 42A-42B show an exemplary "plateau capillary barrier" 4210. FIG. 42A shows a top view of a channel 4200 having a plateau capillary barrier 4210 disposed therein. FIG. 42B shows a longitudinal cross-sectional side view of the plateau capillary barrier 4210 in the channel 4200. The plateau capillary barrier 4210 may comprise a trapezoidal cross-section having a constriction within the channel 4200 formed by a first angled surface 4211 and a plateau surface 4212 of the plateau capillary barrier 4210 followed by a gradual expansion within the channel 4200 formed by a second angled surface 4213. The channel 4200 may comprise a first wall 4201, a second wall 4202, a third wall 4203, and a fourth wall 4204 to form a closed channel. The channel 4200 may for example have a square or rectangular cross-section (taken along a lateral axis of the channel 4200) comprising four walls. The first and the third walls 4201, 4203 may be substantially parallel to one another. The second and the fourth walls 4202, 4204 may be substantially parallel to one another. The plateau capillary barrier 4210 may protrude from the second channel wall 4202 into the channel 4200. The plateau capillary barrier 4210 may be disposed on the second wall 4202. Alternatively, the plateau capillary barrier 4210 may form a part of the second wall 4202. The plateau capillary barrier 4210 may comprise sides that are disposed on, coextensive with, or integrated in an interior surface of the second wall 4202. The plateau capillary barrier 4210 may extend substantially the width of the channel 4200. For example, the plateau capillary barrier 4210 may extend substantially between the first and third walls 4101, 4013 as shown in FIG. 42A. The plateau capillary barrier 4210 may comprise a first and a second lateral wall or side 4214, 4215. The first and second lateral walls or sides 4214, 4215 may be connected to the first and third channel walls 4201, 4203, respectively. Alternatively, the first and second lateral walls or sides 4214, 4215 may be coextensive with the first and third channel walls 4201, 4203, respectively. Alternatively, the first and second lateral walls or sides 4214, 4215 may be adjacent to the first and third channel walls 4201, 4203, respectively. The first and second lateral walls or sides 4214, 4215 may each comprise a cross-sectional area with a trapezoidal shape (for example the cross-sectional area shown in FIG. 42B). The trapezoidal cross-section may comprise a plateau surface or side 4212 that is substantially parallel to the second channel wall 4202. The plateau surface or side 4212 may be situated in the channel 4200 between the second and fourth channel walls 4202, 4204. A first angled surface or side 4211 (also referred to herein as a ramp) may connect the second wall 4202 to the plateau surface or side 4212 at a first edge. A second angled surface or side 4213 may connect the second wall 4204 to the plateau surface or side 4212 at a second, opposite edge 4217.

The first angled surface or side 4211 may be configured to gradually reduce the height of the channel 4200 from a first height $h_4$ to a second, smaller height $h_5$, over a distance along the length of the channel 4200. The first height $h_4$ may be at least twice as large as the second height $h_5$. The first angled surface or side 4211 may for example be an incline plane rising from a bottom wall of the channel 4200 or a decline plane lowering from a top wall of the channel 4200. The first angled surface or side 4211 may for example be an angled plane extending into the channel 4200 from a side wall of the channel 4200. The first angled surface or side 4211 may have a first edge 4216 which intersects with the plateau region or side 4212 to form an interior obtuse angle of the plateau capillary barrier 4210 and a second, opposing edge 4218 which intersects with the second channel wall 4202 to form an interior acute angle α of the plateau capillary barrier 4210.

The second angled surface or side 4213 may be configured to gradually increase the height of the channel 4200 from a first height $h_5$ to a second, larger height $h_6$, over a distance along the length of the channel 4200. The first height $h_5$ may be at least twice as small as the second height $h_6$. The second angled surface or side 4213 may for example be a decline plane lowering from a bottom wall of the channel 4200 or an incline plane rising from a top wall of the channel 4200. The second angled surface or side 4213 may for example be an angled plane extending towards a side wall of the channel 4200 from the plateau surface or side 4212. The second angled surface or side 4213 may have a first edge 4217 which intersects with the plateau region or side 4212 to form an interior obtuse angle of the plateau capillary barrier 4210 and a second, opposing edge 4219 which intersects with the second channel wall 4202 to form an interior acute angle β of the plateau capillary barrier 4210.

Liquid wicking up the first angled surface or side 4211 to the plateau surface or side 4212 may face an energetic barrier associated with expanding past the plateau surface or side 4212 (as additional liquid surface area or pressure is required to advance the liquid) which may result in the liquid being stopped by the plateau capillary barrier 4210 and a meniscus of the liquid being positioned at the edge 4216 of the plateau surface or side 4212 nearest the first angled surface or side 4211 or the edge 4217 above the second angled surface or side 4213. The plateau capillary barrier 4210 may be configured such that the liquid stopped by the plateau capillary barrier 4210 can be wetted by liquid approaching the plateau capillary barrier 4210 from its other side (e.g. from the second angled side) to create a bubble-free liquid-to-liquid interface. The plateau capillary barrier 4210 may be disposed adjacent a gas channel 4220 configured to facilitate air bubble removal from the channel 4200 as the liquid enters the channel 4200 and the meniscus of the liquid is stopped at the plateau capillary barrier 4210 as described herein.

The plateau capillary barrier 4210 may be configured to hold the menisci of the liquids on either side of the plateau capillary barrier 4210 separate, with an air gap between them spanning the plateau surface or side 4212 until a pressure applied across the capillary barrier 4210 via the air channel 4220 exceeds the burst pressure of the plateau capillary barrier 4210 and one or both of the liquids cross the plateau surface or side 4212 to meet each other and form a liquid-to-liquid interface as described herein (e.g., as shown in FIG. 47A).

The plateau capillary barrier 4210 may be configured to hold or stop a liquid when a pneumatic pressure is applied thereto. The plateau capillary barrier 4210 may be configured to hold the liquid under a pressure within a range of about 0 mpsi to about 200 mpsi, for example within a range of about 10 mpsi to about 80 mpsi. The plateau capillary barrier 4210 may be configured to hold the liquid until a burst pressure (e.g. the minimum pressure required to move the stopped liquid over plateau 4112 and/or onto the second angled region 4213 and past the plateau capillary barrier 4210) is reached. It will be understood by one of ordinary skill in the art that the burst pressure of the plateau capillary barrier 4210 may depend on the liquid(s) being held by the plateau capillary barrier 4210, with more wetting liquids having a lower burst pressure than less wetting liquids.

In some embodiments, the burst pressure of the cliff capillary barrier 4110 may be the same as the burst pressure of the plateau capillary barrier 4210.

In some embodiments, the burst pressure of the cliff capillary barrier 4110 may be higher than the burst pressure of the plateau capillary barrier 4210. The higher burst pressure of the cliff capillary barrier 4110 may facilitate loading (and stopping) of liquids which have lower surface tensions, for example liquids comprising one or more surfactants or detergents. For example, the sample may have a low enough surface tension so as to wet across a plateau capillary barrier 4220 under the negative pneumatic pressure applied by the instrument to the channel. In such case, the sample may be bounded within the channel by cliff capillary barriers 4110 (e.g. a first cliff capillary barrier 4110 between the sample and the LE and a second cliff capillary barrier 4110 between the sample and the TE as described herein) so as to hold the sample in the channel during loading of the chip.

The first angled surface or side 4211 may be configured to gradually reduce the height of the channel 4200 from a first height $h_4$ within a range of about 50 um to about 2 mm to a second height $h_5$ within a range of about 10 um to about 30 um. The first height $h_4$ may for example be within a range of about 400 um to about 1.2 um.

The first angled surface or side 4211 may have a first edge 4216 which intersects with the plateau region or side 4212 to form an interior obtuse angle of the cliff capillary barrier 4210.

The first angled surface or side 4211 may have a second, opposing edge 4218 which intersects with the second channel wall 4202 to form an interior acute angle $\alpha$ of the plateau capillary barrier 4210. The interior acute angle $\alpha$ may be within a range of about 0 degrees to about 70 degrees, for example within a range of about 30 degrees to about 45 degrees or within a range of about 30 degrees to about 60 degrees.

The plateau surface or side 4212 may have a length along a longitudinal axis of the channel within a range of about 500 um to about 1 mm, for example about 750 um.

The second angled surface or side 4213 may be configured to gradually increase the height of the channel from a first height $h_5$ within a range of about 10 um to about 30 um to a second height $h_6$ within a range of about 50 um to about 2 mm. The first height $h_5$ may for example be within a range of about 400 um to about 1.2 um.

The second angled surface or side 4213 may have a first edge 4217 which intersects with the plateau region or side 4212 to form an interior obtuse angle of the plateau capillary barrier 4210.

The second angled surface or side 4213 may have a second, opposing edge 4219 which intersects with the second channel wall 4202 to form an interior acute angle $\beta$ of the plateau capillary barrier 4210. The interior acute angle $\beta$ may be within a range of about 0 degrees to about 70 degrees, for example within a range of about 30 degrees to about 45 degrees or within a range of about 30 degrees to about 60 degrees.

The first angled surface 4211 (i.e. ramp), plateau area 4212, or second angled surface area 4213, in any combination, may have a substantially flat surface.

The first angled surface 4211 (i.e. ramp), plateau area 4212, or second angled surface area 4213, in any combination, may have a curved surface.

The first angled surface 4211 (i.e. ramp), plateau area 4212, or second angled surface area 4213, in any combination, may have a surface that comprises one or more grooves, ridges, indentations, steps, etchings, or protrusions.

The first angled surface 4211 (i.e. ramp), plateau area 4212, or second angled surface area 4213, in any combination, may have a surface that comprises regions with faces at different angles.

So, for example, referring to FIG. 42B, the ramp barrier can comprise two ramps separated by a plateau. A first ramp 4211 can rise from a surface of the channel 4202 at a shallow angle $\alpha$, a plateau area 4212 can be about parallel to the channel 4200 and a second ramp 4213 can fall to the channel surface 4202 at a shallow angle $\beta$. The shallow angles $\alpha$, $\beta$ can be no more than 60 degrees, no more than 45 degrees or no more than 30 degrees. The shallow angles $\alpha$, $\beta$ can be the same angle or different angles.

The plateau capillary barrier 4210 may be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS). The chip or substrate may for example comprise a COC such as TOPAS 8007. The plateau capillary barrier 4210 may be made from the same material(s) as the channel 4200 or a different material(s) as the channel 4200.

The depth of the channels 4200 on either side of the plateau capillary barrier 4210 may be the same. Alternatively, each side of the plateau capillary barrier 4210 may be coupled to channels 4200 of different depths as described herein.

Figure 43:
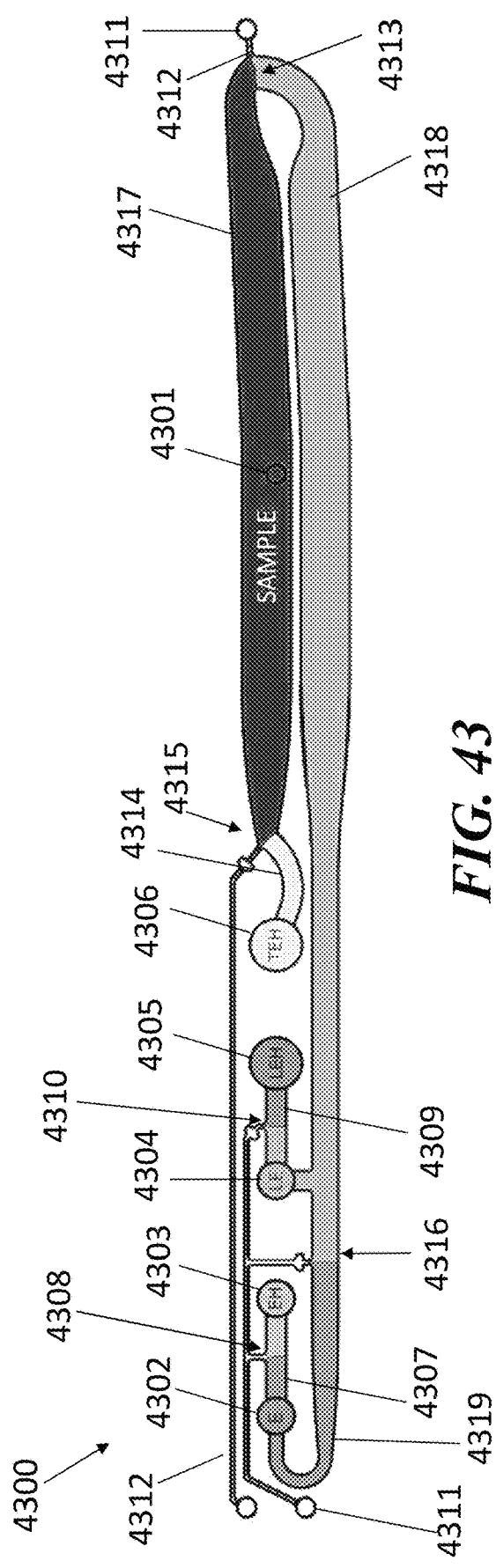
FIG. 43 shows an exemplary channel or fluidic circuit highlighting the initial fluid interface positions after loading.

FIG. 43 shows an exemplary channel or fluidic circuit 4300 highlighting the initial fluid interface positions after loading. The fluidic circuit 4300 may be substantially similar to the circuits described in FIG. 38. The fluidic circuit 4300 may be connected to a sample input well or reservoir 4301, an elution reservoir 4302, an elution buffering reservoir 4303, a leading electrolyte reservoir 4304, a leading electrolyte buffering reservoir 4305, and a trailing electrolyte reservoir 4306. Reservoirs 4301-4306 may be coupled to the channel by through-holes or apertures as described herein. Elution reservoir 4302 may be connected to elution buffering reservoir 4303 by an elution buffering channel 4307. A capillary barrier 4308 (e.g. a plateau capillary barrier as described herein) may be provided in the elution buffering channel 4307 to reduce or prevent mixing or pressure driven flow between the contents of the elution buffering reservoir 4303 and the elution reservoir 4302. Leading electrolyte reservoir 4304 may be connected to leading electrolyte buffering reservoir 4305 by a leading electrolyte buffering channel 4309. A capillary barrier 4310 (e.g. a plateau capillary barrier) may be provided in the leading electrolyte buffering channel 4309 to reduce or prevent mixing or pressure-driven flow between the contents of the leading electrolyte buffering reservoir 4305 and the leading electrolyte reservoir 4304. Buffering reservoir 4303 may contain elution buffer electrolytes at a higher ionic strength than those in elution reservoir 4302, while buffering reservoir 4305 may contain leading electrolytes at a higher ionic strength than those in leading electrolyte reservoir 4304. The device may further comprise pneumatic ports 4311 along its edges which are configured to couple to a pneumatic device, for example a vacuum source on a benchtop instrument. The pneumatic ports 4311 may be coupled to the channels and reservoirs by gas channels 4312 as described herein. Application of suction (i.e. negative pneumatic pressure) at the pneumatic ports 4311 may load the sample, leading electrolyte, and elution buffer into the channels. The gas channels 4312 may be coupled to the channels at one or more capillary barriers such that the negative pressure is applied to said capillary barriers. Suction may be applied simultaneously or sequentially to the pneumatic ports 4311 so as to load the channels simultaneously or in stages, respectively. The sample may be loaded into a first zone or sub-channel which extends from the trailing electrolyte reservoir 4306 to a capillary barrier 4313 at a 180° low dispersion turn in the channel. The capillary barrier 4313 may provide an interface between the sample and the leading electrolyte buffer during loading so as to limit, reduce, or prevent mixing or pressure-driven flow. The capillary barrier 4313 may comprise a cliff capillary barrier as described herein. The trailing electrolyte reservoir 4306 may be connected to channel first zone or sub-channel 4317 by a trailing electrolyte channel 4314. A capillary barrier 4315 (e.g. a cliff capillary barrier) may be provided in the trailing electrolyte channel 4314 between the trailing electrolyte reservoir 4306 and the first zone or sub-channel 4317 so as to limit, reduce, or prevent mixing or pressure-driven flow between the contents of the trailing electrolyte reservoir 4306 and the sample. The leading electrolyte may be loaded into the second zone or sub-channel 4318 of the channel 4300 which extends from capillary barrier 4313 to capillary barrier 4316. The capillary barrier 4316 (e.g. a plateau capillary barrier) may provide an interface between the leading electrolyte buffer and the elution buffer. The first zone or sub-channel 4317 and the second zone or sub-channel 4318 may make up an ITP branch of the fluidic channel or circuit. The elution buffer may be loaded into a third zone or sub-channel 4319 of channel 4300 which extends from capillary barrier 4316 to elution reservoir 4302. The third zone or sub-channel 4319 may make up an elution branch of the fluidic channel or circuit. Upon loading the fluids into the channel, the interfaces between liquids may be located above or situated at their respective capillary barriers. The interface between the trailing electrolyte buffer and the sample may be situated at cliff capillary barrier 4315. The interface between the leading electrolyte buffer and the sample may be situated at cliff capillary barrier 4313. The interface between the leading electrolyte buffer and the elution buffer may be situated at ramp capillary barrier 4316. The interface between the leading electrolyte buffer and the high concentration leading electrolyte buffer may be situated at ramp capillary barrier 4310. The interface between the high concentration elution buffer and the elution buffer may be situated at ramp capillary barrier 4308.

Figure 44:
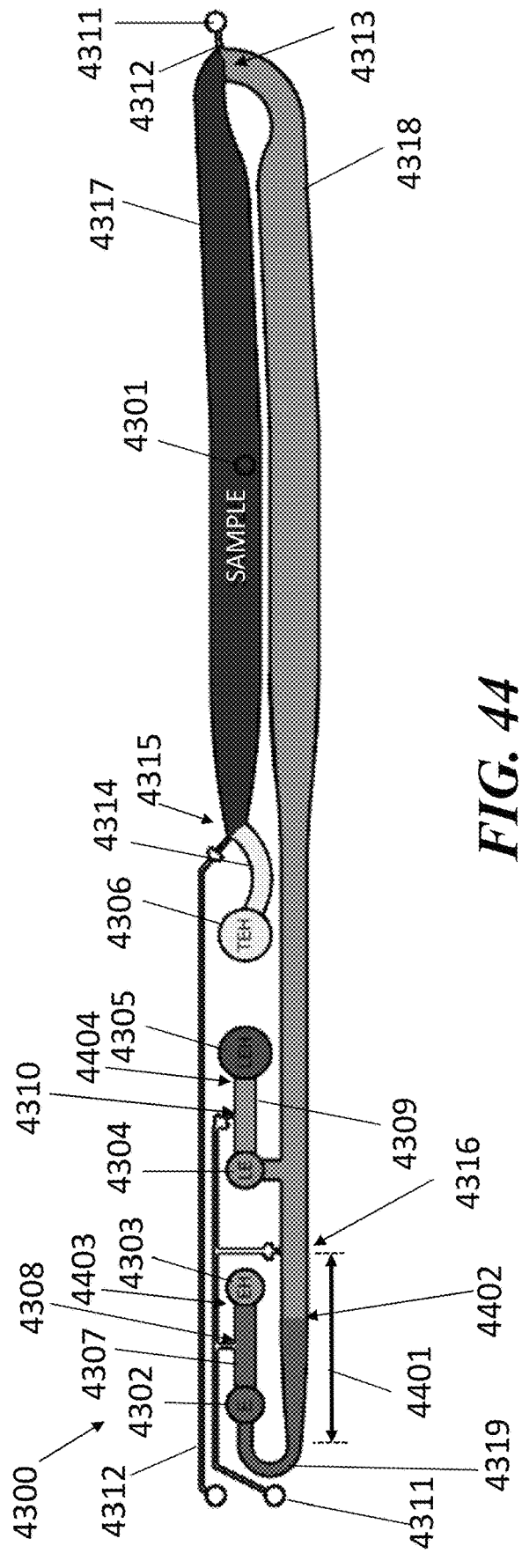
FIG. 44 shows an exemplary channel or fluidic circuit highlighting the final fluid interface positions after loading.

FIG. 44 shows an exemplary channel or fluidic circuit 4300 highlighting the final fluid interface positions after loading. After loading the various buffers into the channel 4300, one or more fluid interface formed between the buffers may be flowed within the channel to move the interface away from the capillary barrier(s) which formed the fluid interface(s).

Moving an interface may reduce or minimize retention of nucleic acids at a capillary barrier, particularly between the leading electrolyte buffer and the elution buffer. Not wanting to be limited by a particular theory, it is believed that this may help to maintain the DNA in a more compact state as it passes through a constricted space of the capillary barrier (e.g. a cliff capillary barrier 4316 at the junction between the LE and elution buffer) which may otherwise impair passage of a more dispersed ITP band. For example, the interface 4402 between the leading electrolyte buffer and the elution buffer may be moved downstream towards the elution reservoir 4302 such that the cliff capillary barrier 4316 is fully engulfed by the leading electrolyte buffer when the interface 4402 is arrested within a zone 4401. When flow of the interface 4402 is arrested, the DNA may pass through the constricted space of the capillary barrier 4316 more easily in the leading electrolyte buffer than it would have had it passed through the interface 4402 and the capillary barrier 4316 at the same time, as the transition from the leading electrolyte buffer to the elution buffer may have cause the ITP band to expand, making it harder to pass over the barrier.

Alternatively or in combination, moving an interface may reduce or minimize mixing of buffers and undesired contamination of buffers, particularly between the elution buffer and the high concentration elution buffer or between the leading electrolyte buffer and the high concentration leading electrolyte buffer. For example, the interface 4403 between the elution buffer and the high concentration elution buffer may be moved downstream towards the elution buffering reservoir 4303 in order to increase the distance between the interface 4403 and the elution reservoir 4302 and reduce or minimize contamination of the elution buffer with the high concentration elution buffer, which could negatively affect the compatibility of the elution buffer with downstream assays. Similarly, interface 4404 between the leading electrolyte buffer and the high concentration leading electrolyte buffer may be moved downstream towards the leading electrolyte buffering reservoir 4305 in order to increase the distance between the interface 4404 and the leading electrolyte reservoir 4304 and reduce or minimize contamination of the leading electrolyte buffer with the high concentration leading electrolyte buffer.

In some embodiments, one or more interfaces may be flowed away from its corresponding capillary barrier by applying a negative pressure to one or more pneumatic ports of the channel.

Alternatively or in combination, the one or more interfaces may be flowed away from its corresponding capillary barrier due to gravity. For example, the liquid head heights in the reservoirs may be adjusted to generate gravity-driven flow within the channel. After loading, the fluid pressures within the channel may be allowed to equilibrate such that one or more interfaces between the fluids in the channel flows within the channel towards its final fluid interface position. The final position of the fluid interface may be adjusted by adjusting the relative head heights of the fluids within the reservoirs as will be understood by one of ordinary skill in the art.

Figure 10B:
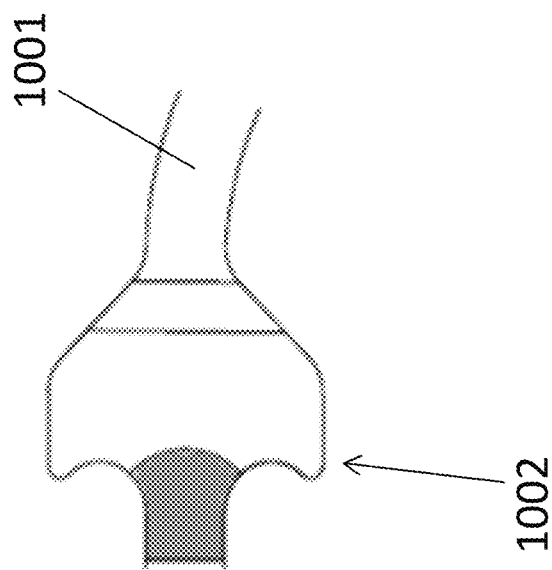
FIG. 10B is a magnified schematic of the gas channel of FIG. 10A.
Figure 10A:
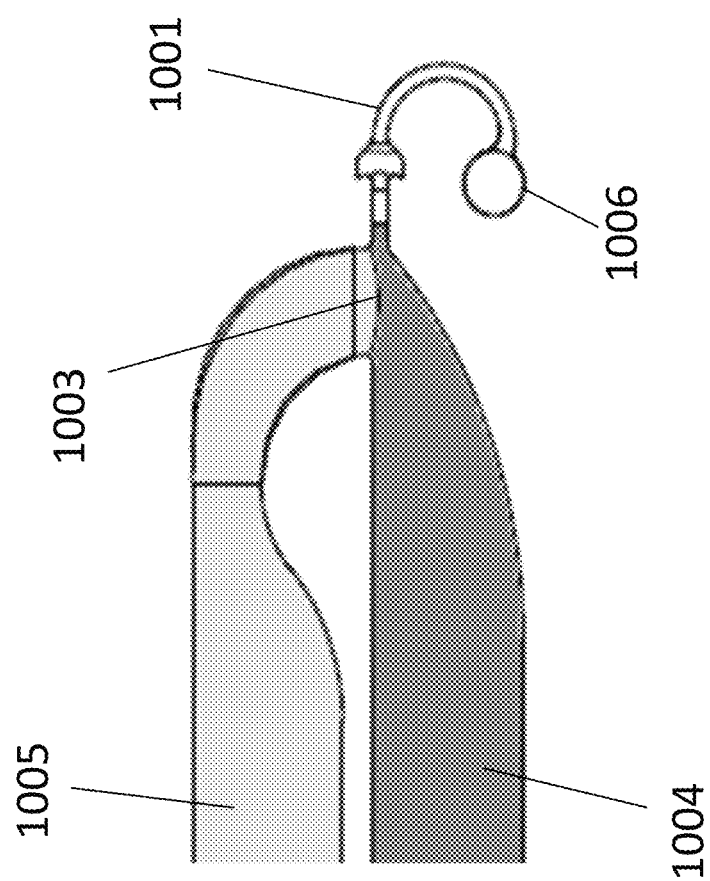
FIG. 10A shows an exemplary gas channel which may comprise a capillary barrier.

Gas (e.g., air) channels or lines can be used to provide actuated pneumatic pressure to capillary barriers or other regions of a fluidic device. Gas channels can connect to external gas pressure sources via pneumatic ports. Gas channels can have higher fluidic resistance than the liquid channels they provide pressure to, for example to reduce or prevent liquid flow into the gas channel. For example, gas channels can have less than half the cross sectional area of a main isotachophoresis channel. Multiple gas channels can be connected to a single gas reservoir or port (e.g., with branching channels). Capillary valves can be employed with branched air lines to prevent upstream liquid movement. FIG. 10A shows an exemplary gas channel 1001 which may comprise a capillary barrier 1002 connected to the liquid channel interface 1003 between the sample 1004 and leading electrolyte buffer 1005 sub-channels. FIG. 10B is a magnified schematic of the gas channel 1001 highlighting the capillary barrier 1002 which prevents upstream liquid movement towards the pneumatic port 1006.

FIG. 45A shows an example of the fluidic layer of the chip. Pneumatic actuation channels (also referred to herein as air channels or air lines) 4501 in this example are narrow, shallow, and straight to minimize total volume. The minimum dimensions may be set by manufacturing requirements or by the maximum allowable pressure drop across these pneumatic channels. These dimensions are between 50 um and 500 um for both the width and height of the channel. These pneumatic channels lead to the pneumatic ports 4502. The ports are vertical cylindrical holes terminating at membrane rest plane. In comparison to the pneumatic channels, the liquid channels on the chip layer are wider and deeper. This may allow a low fraction of the liquid to be drawn into the pneumatic lines. The pneumatic channels 4501 may comprise a constriction at the junctions between the pneumatic channels 4501 and the liquid channel, which may act as a capillary barrier to reduce or prevent liquid from entering the pneumatic channels 4501. FIG. 45B shows a cutaway of the pneumatic port 4502. 4504 is the connection of the port to the pneumatic channel on the fluidic layer. 4503 is the membrane rest plane. A hydrophobic membrane is applied to this surface and held in place by a compressed gasket, by an adhesive, or by a thermal bond. Air can pass this membrane, but liquid cannot. The diameter of this port is controlled by manufacturing requirements, and can have a diameter below 1 mm. The height of the vertical cylinder should be below 2 mm. FIG. 45C shows an implementation of this design. The hydrophobic membrane is marked as 4505. The fluorescent liquid 4506 is confined to the vertical column of the pneumatic port, but doesn't spread beyond. Pneumatic actuation can be used to move liquids in fluidic channels. When doing so, it can be valuable to minimize liquid loss into the pneumatic actuation channel, as this may be liquid volume that is not processed. This design is for a fluidic air port and channel design that minimizes loss by manipulating channel and port geometry, and including a hydrophobic membrane that prevents liquid transfer but allows air transfer.

Figure 46A:
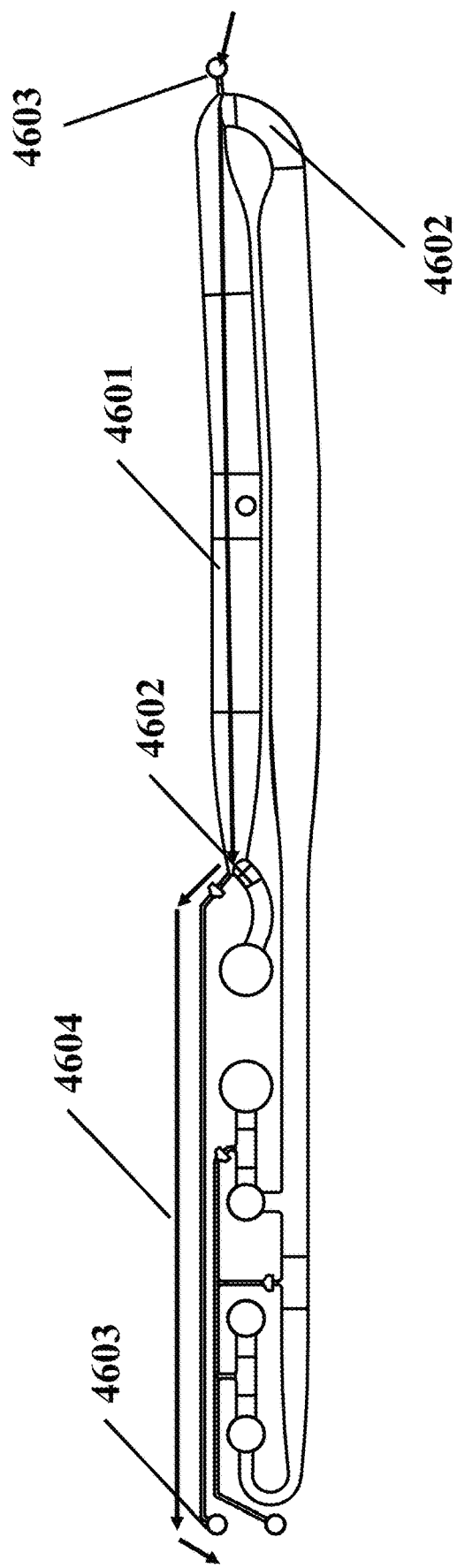
FIG. 46A shows an exemplary microfluidic channel in which an empty sample channel can be detected.
Figure 46B:
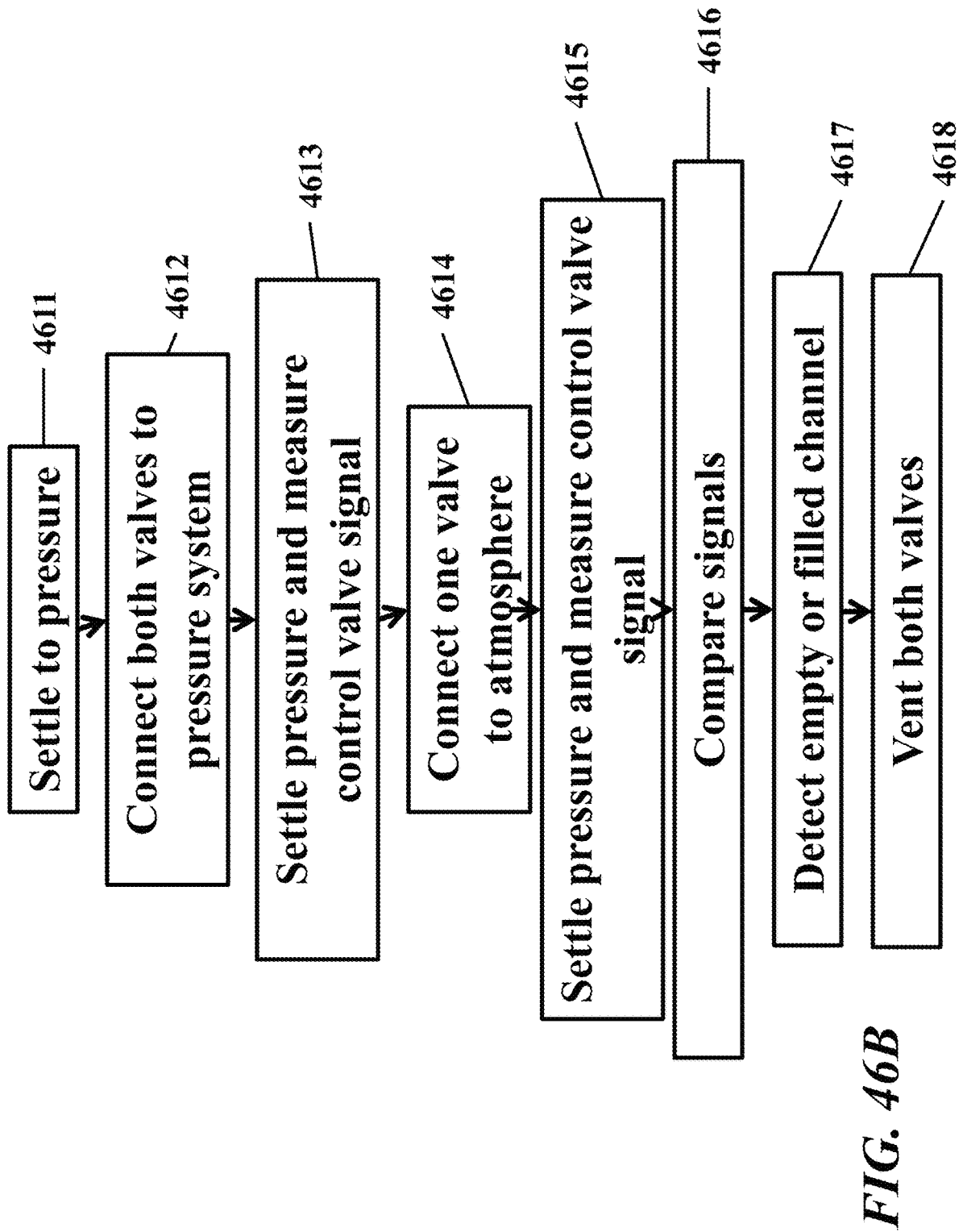
FIG. 46B shows the sequence of events for detection of whether this channel is empty or filled.
Figure 46C:
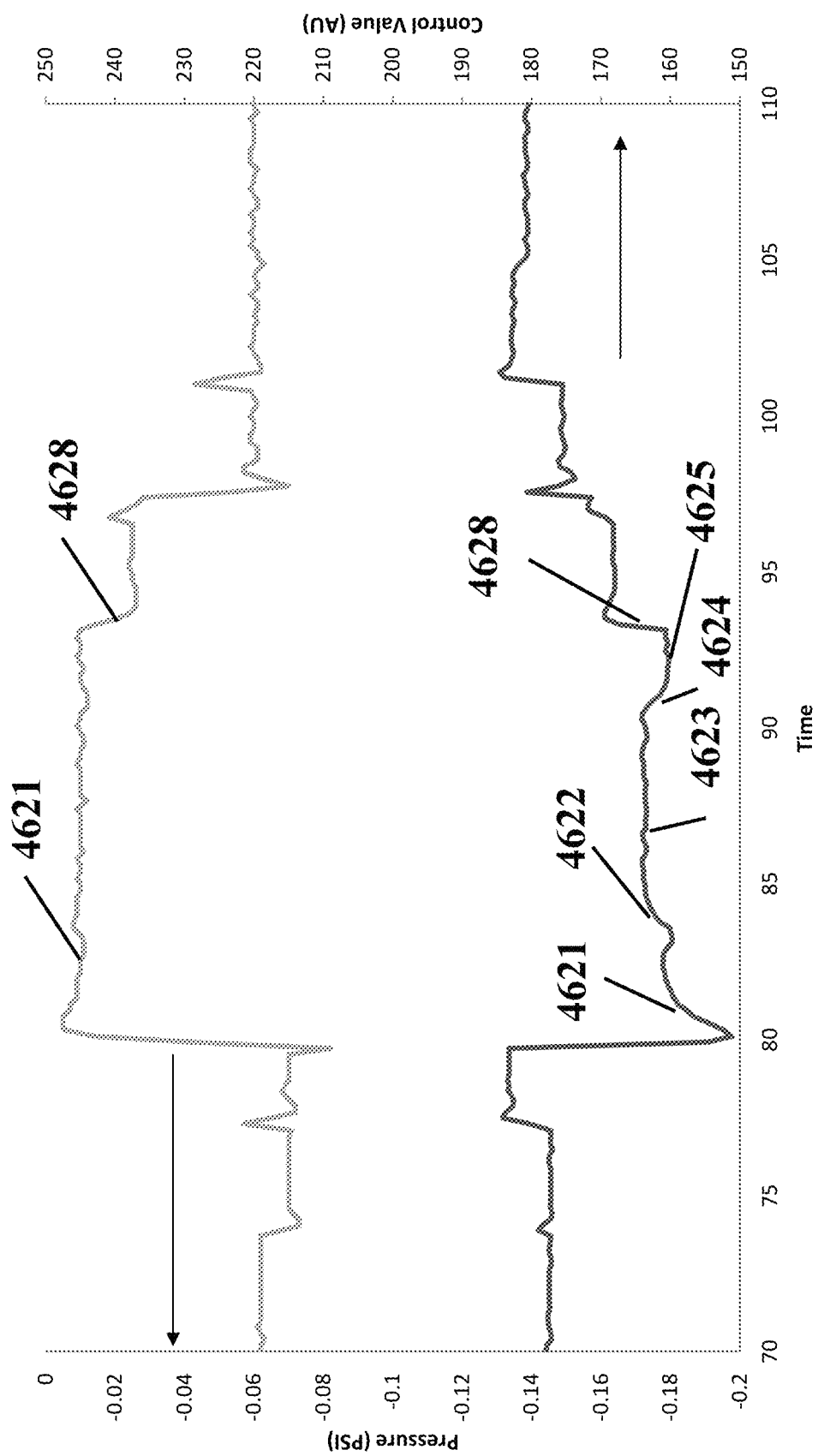
FIG. 46C shows pressure traces and control signal traces from the implementation of this technique.

FIG. 46A shows an exemplary microfluidic channel in which an empty sample channel can be detected. The sample channel 4601 is terminated on both sides 4602 by channels that may have liquid loaded prior to sample loading (e.g. trailing electrolyte and leading electrolyte, respectively). This loading is subject to failure by the liquid moving into the sample channel 4601, which is intended to be empty prior to loading. The sample channel 4601 is also connected on both ends to pneumatic actuation ports 4603 that can be connected to a pressure control circuit or allowed to vent to the atmosphere or a pneumatic manifold as described herein. The arrows 4604 on the drawing show the detection path, which passes from one pneumatic port 4603, through the sample channel 4601, and through the other pneumatic port 4603. FIG. 46B shows the sequence of events for detection of whether this channel 4601 is empty or filled. First the pneumatic control circuit is set (Step 4611) to achieve a target pressure, between 1 psig and −1 psig. Second, both of the valves connected to the channel are connected to the pneumatic control circuit (Step 4612). The pressure is allowed to return to the control point if there is a disturbance caused by the valves opening, then the signal of the pneumatic control circuit is read (Step 4613). This signal may commonly be associated with the voltage applied to a pneumatic proportional valve. After this, either one of the valves connected to the channel can be changed to a state where it vents the channel to atmosphere. This allows air to flow through the detection path previously shown (Step 4614, e.g., FIG. 46A). This increased air flow will cause a change in the signal to the control circuit, commonly a change in voltage to further open the proportional valve allowing air flow. The pressure is once again allowed to settle, and the signal on the control circuit is measured (Step 4615). The two measured control signals are subtracted and compared to a threshold (Step 4616) and the channel is determined to be either empty or full (Step 4617). After this, both sides of the channel may be returned to some default state, commonly by venting them to atmosphere (Step 4618). FIG. 46C shows pressure traces and control signal traces from the implementation of this technique. On the top trace, the pressure reading, the settling to pressure 4621 and the venting of the valves 4628 is visible. The control signal, below, does correspond to the voltage applied to a pneumatic proportional valve to regulate pressure. This shows settling to pressure 4621, both valves opening 4622, the settled value after opening 4623, a single valve closing 4624, the measurement of the signal 4625, and the venting of the channel 4628. This pneumatic control and detection scheme allows detection of a completely empty channel prior to a user loading sample. This is useful in cases in which sample loading requires a completely empty channel prior to loading for successful completion of the load. If a previous step has wetted the channel, this allows the user to avoid sample loading in this channel, conserving sample. This detection technique uses the same pneumatic detection and actuation hardware as pneumatic priming.

Negative pressure or vacuum can be applied to the gas channels via the gas ports in order to load a fluidic channel. Each fluidic channel on a microfluidic device may be loaded simultaneously or independently (e.g. sequentially) of one another. Within a channel, the fluids may be loaded simultaneously or independently of one another. For example, leading electrolyte buffer, high concentration leading electrolyte buffer, trailing electrolyte buffer, high concentration trailing electrolyte buffer, the elution buffer, high concentration elution buffer, or any combination thereof may be loaded prior to, simultaneously with, or after loading the sample. For example, negative pressure may be applied to the gas ports on one side of the chip to load one or more fluids (e.g. trailing electrolyte buffer, elution buffer, etc.). Subsequently, negative pressure may be applied to the gas ports on the other side of the chip to load additional fluids (e.g. leading electrolyte buffer). Alternatively, negative pressure may be applied to the gas ports on one side of the chip to load one or more fluids (e.g. leading electrolyte buffer and trailing electrolyte buffer). Subsequently, negative pressure may be applied to the gas ports on the other side of the chip to load additional fluids (e.g. trailing electrolyte buffer, elution buffer, etc.). Alternatively, negative pressure may be applied to all of the gas ports connected to a channel at the same time. The sample may be loaded by applying negative pressure or vacuum before, during, or after loading of the isotachophoresis buffers. The sample may be loaded without applying negative pressure or vacuum, for example by wetting or gravity.

Figure 47B:
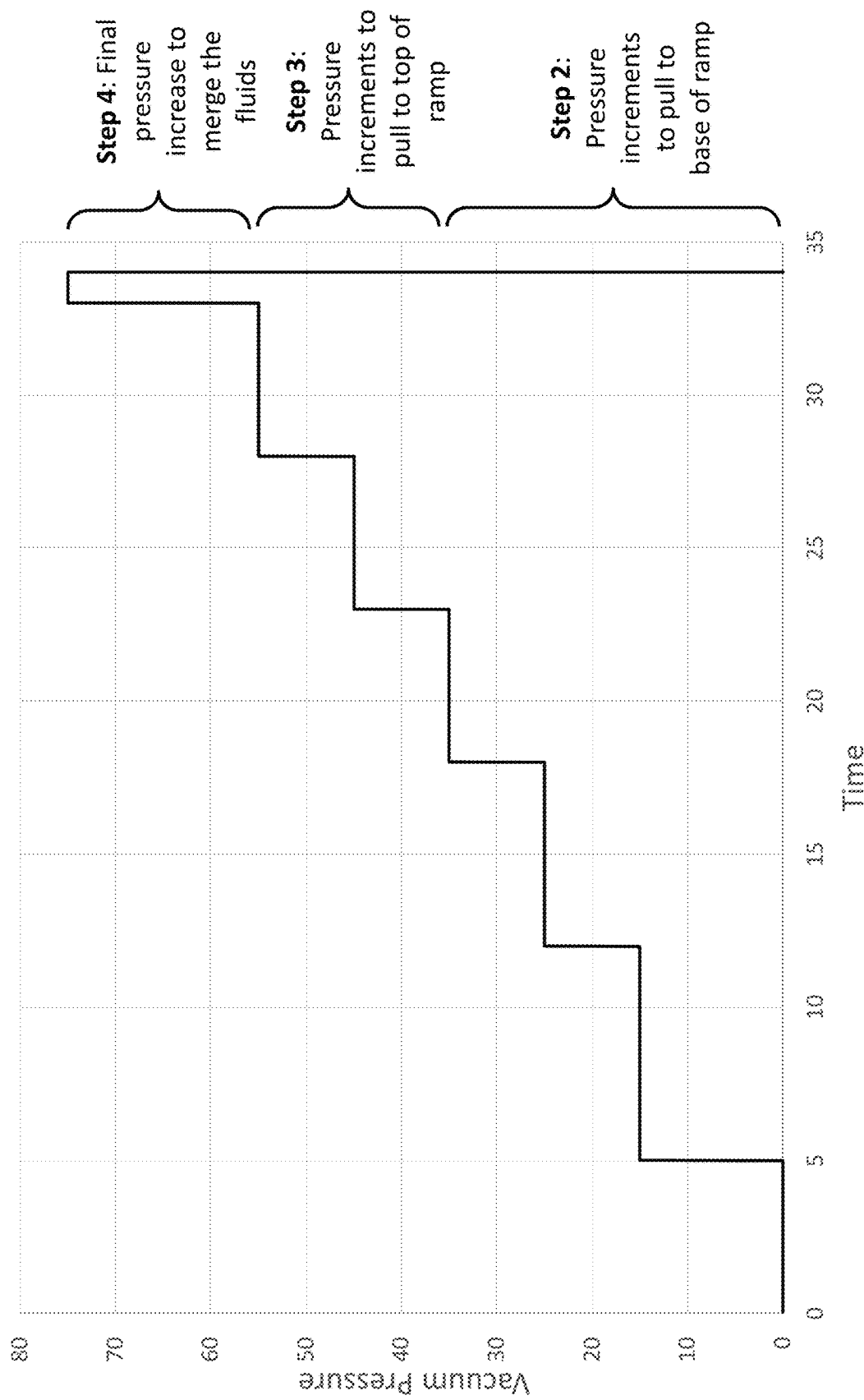

FIGS. 47A-47B show an exemplary pneumatic control scheme for staged liquid loading. For each step described in FIG. 47A, a top view of a channel with a plateau capillary barrier 4703 is shown in the center and a side view schematic of the plateau capillary barrier 4703 is shown on the right. Fluids may be loaded into the reservoirs 4701 on the microfluidic cartridge and controllably primed to a fixed location and then merged without creating a bubble as described herein. At Step 1, the two fluids may initially be loaded into reservoirs 4701 connected by a microfluidic channel with a capillary barrier 4703 between them. At Step 2, the pressure may then be increased and held at fixed pressures in order to move the menisci 4702 of the two fluids from the reservoir/channel boundary into the channel and up to the base of the capillary barrier 4703. At Step 3, the pressure may again be increased incrementally to pull the menisci 4702 to the top of the capillary barrier 4703. An air gap 4704 may be disposed across the plateau region of the capillary barrier 4703 in order to maintain a distance between the menisci 4702. At Step 4, the pressure may be increased beyond a holdoff pressure (also referred to herein as a burst pressure) of the barrier 4703 in order to merge the two fluids and form a liquid-to-liquid interface as described herein. FIG. 47B shows a schematic illustrating Steps 2-4 of the pressure control scheme used to merge fluids at the capillary barriers 4703 within the microfluidic channel system. The vacuum pressure may be increased in discrete steps to move the menisci 4702 of the two fluids to the capillary barrier 4703 and then to a connect the fluids as described in FIG. 47A. By increasing the negative pneumatic pressure in a stepwise manner, the menisci 4702 may be merged to form a liquid-to-liquid barrier with little to no active mixing occurring between the two liquids. This may be of use when one liquid arrives at the capillary barrier 4703 before the other liquid. By holding the menisci at opposite ends of the plateau region, the chance of the earlier fluid bursting past the capillary barrier 4703 and into the other side of the channel, which may lead to mixing or formation of the liquid-to-liquid interface at an undesirable location, may be greatly reduced compared to a capillary barrier having no plateau region. As will be understood by one of ordinary skill in the art, the pressure values, increments, and times, can be adjusted to accommodate a range of barrier geometries and fluid wetting properties.

Sensors (e.g., electrodes) can be used to detect liquid filling levels or bubbles (e.g., via current or voltage sensing) and provide feedback. Geometric features (e.g. constrictions, expansions, or turns) can be used in combination with electrodes to monitor impedance of channels and thereby the time progression of isotachophoresis. For example, during ITP the nucleic acids are focused, and voltage can be used to track the focused band location in the channel from start to finish. In one example, monitoring of fluid expansion into a reservoir (such as an elution reservoir) from a connected channel with smaller cross sectional area can be used to determine the time the analyte is eluting, thereby allowing for automated elution and end-process control. In another example, a channel constriction can be designed to allow detection of the timing (or triggering) of a step in an electrokinetic process, such as when the focused analyte is entering a channel zone where a reaction is to take place or where an optical detection event is to take place, allowing control of reaction timing or detector triggering.

Figure 21:
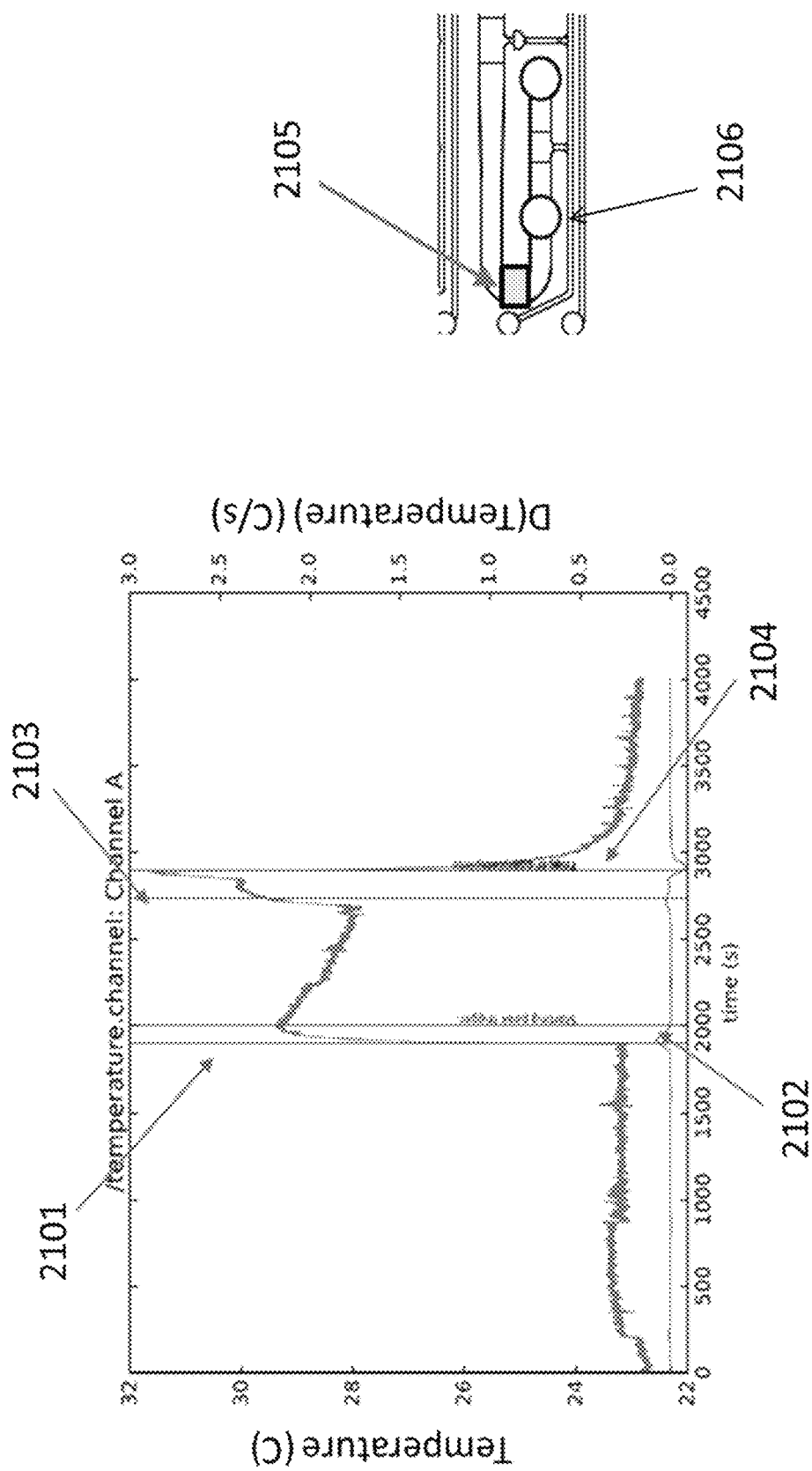
FIG. 21 shows a graph of temperature measurement and temperature derivative over time during an ITP run.

For example, FIG. 21 shows one such geometric feature which may be used for triggering purposes. An infrared sensor may be positioned at the center of a turn of the microfluidic channel in detector location 2105. During isotachophoresis run, this geometric turn feature can facilitate the generation of a higher local resistance relative to other sections of the channel. The high local resistance may be detected in temperature and/or voltage traces as shown on the left of FIG. 21. For example, an increase between 2101 and 2012 in the trace of temperature signal captured by the infrared sensor during the run may indicate switching from separation to elution process. The two-step temperature rise between 2103 and 2104 can indicate the geometric turn-enabled feature for triggering. The arriving time of triggering feature may vary between lanes, chips, and instruments. The generic pattern of temperature trace may persist for the same extraction chemistry. In at least some instances, such geometric features may provide reduced disturbance from external features.

Figure 11:
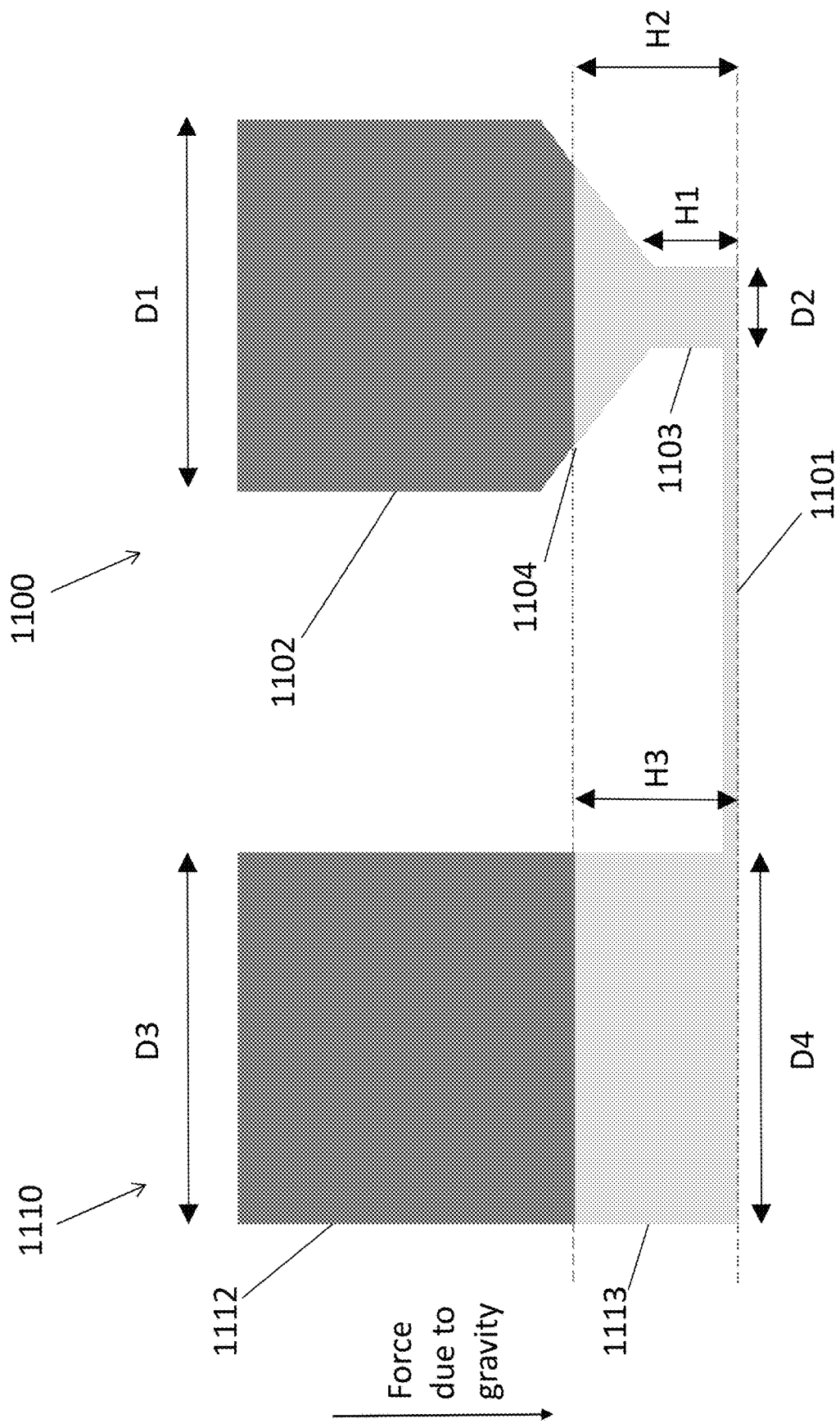
FIG. 11 shows an exemplary low-loss sample reservoir.

Reservoir and channel features can be designed to control or prevent pressure driven flow. For example, a reservoir (e.g., sample and elution reservoirs) can have an internal shape designed so that large changes in liquid height produce only small variations in internal volume at the intended head height as shown in FIG. 11. This can provide more precise control of the liquid volume contained in the reservoir. For other reservoirs, liquid volume can vary without detriment to a separation process; such reservoirs can be designed to have large volume changes in response to small liquid height changes, and can help stabilize liquid height throughout the fluidic device. Low fluidic resistances between reservoirs can be used to enable fast equilibration times of head pressures and to enable minimal flow of liquids in channels before, during, or after an electrokinetic process.

Reservoirs can be designed to minimize evaporation, for example by controlling the surface area within the reservoir to maintain a constant or fixed volume. Reservoirs can be designed to maximize liquid recovery from the reservoirs, for example by using drafted angle wall designs to minimize dead zones. Reservoirs can be designed to prevent the flow of liquids in connecting channels into the reservoir during unloading, which can help maintain purity or separation of material (e.g., nucleic acids) being unloaded. Reservoirs can be designed for easy loading or unloading via pipetting, for example by having dimensions amenable to admitting a pipet tip or having volumes within typical pipet operation. For example, the elution reservoir may be configured to admit a pipet tip for extraction of nucleic acids. Reservoirs can be designed or spaced to accept multi-channel pipettors (e.g., having a pitch of about 9 mm).

Reservoirs (e.g., sample reservoirs) can be located directly above the channels to be filled, which can minimize liquid lost in connecting channels between reservoirs and the channels they fill. Reservoirs (e.g., sample reservoirs) can have a conical shaped bottom and a cylindrical through-hole or aperture; the large inner diameter at the top of such a reservoir can allow it to contain a large volume while the liquid meniscus at the bottom of the reservoir has a smaller inner diameter, reducing the amount of liquid left behind after dispensing. Such a design can also reduce or prevent wicking of wetting fluids into concave corners. In some cases, a through-hole from a reservoir (e.g., sample reservoir) into a channel is less than or equal to about 2 millimeters (mm).

FIG. 11 shows a sample reservoir 1100 configured to reduce the amount of sample left behind (or lost) in the reservoir 1100 after moving the sample to the connected channel 1101. The low-loss sample reservoir 1100 may reduce the amount of sample left in the reservoir 1100 after moving the sample to the connected channel 1101 without adding or pumping in additional volume (of sample or other fluid) in to the sample reservoir 1100 following or during delivery of the sample into the connected channel 1101. The low-loss sample reservoir 1100 may comprise an upper or top portion 1102 with an inner hydraulic diameter $D_1$ configured to contain a sample volume prior to loading the sample into the channel 1101, a lower or bottom portion 1103 with an inner hydraulic diameter or through-hole $D_2$ and height $H_1$ configured to contain a sample volume after loading the sample into the channel 1101, and a tapered or conical portion 1104 therebetween. In some cases, the upper portion 1102 and/or the lower portion 1103 are non-symmetrical, in which case the dimensions $D_1$ to $D_2$ may represent the maximum dimension across of the upper and/or lower portions 1102, 1103, respectively.

The sample reservoir 1100 may be configured to produce a head height $H_2$ of sample left behind which equals or nearly equals the head height $H_3$ of the buffers in the other reservoirs 1110 connected to the channel 1101 in order to limit, prevent, or reduce pressure-driven flow and mixing in the channel 1101. A standard buffer reservoir 1110 may comprise an upper portion 1112 with an inner hydraulic diameter $D_3$ and a lower portion 1113 with an inner hydraulic diameter $D_4$. Unlike in the sample well, $D_3$ may be substantially similar to $D_4$ such that a larger volume of fluid is held within the buffer well 1110 compared to the sample well 1100 when the head heights $H_2$ and $H_3$ are equal or nearly equal.

The sample reservoir 1100 may be configured to hold a sample volume (with or without buffer) of at least about 1 nanoliter (nL), 10 nL, 20 nL, 50 nL, 100 nL, 200 nL, 500 nL, 1 microliter (μL), 10 μL, 20 μL, 30 μL, 40 μL, 50 μL, 60 μL, 70 μL, 80 μL, 90 μL, 100 μL, 200 μL, 300 μL, 400 μL, 500 μL, 600 μL, 700 μL, 800 μL, 900 μL, μL, 1 milliliter (mL), 2 mL, 3 mL, 4 mL, 5 mL, 6 mL, 7 mL, 8 mL, 9 mL, or 10 mL. In some cases, the sample reservoir 1100 may be configured to hold a sample volume within a range of from about 1 nL to about 10 nL.

The inner hydraulic diameter $D_1$ may be larger than the through-hole hydraulic diameter $D_2$. The inner hydraulic diameter $D_1$ of the upper portion may be at least about 1 mm, 2 mm, 3 mm, 4 mm, 5 mm, 6 mm, 7 mm, 8 mm, 9 mm, 10 mm, 11 mm, 12, mm 13 mm, 14 mm, or 15 mm. The inner hydraulic diameter $D_1$ of the upper portion may be at most about 1 mm, 2 mm, 3 mm, 4 mm, 5 mm, 6 mm, 7 mm, 8 mm, 9 mm, 10 mm, 11 mm, 12, mm 13 mm, 14 mm, or 15 mm. The inner hydraulic diameter $D_2$ of the lower portion may be at least about 0.5 mm, 1 mm, 1.5 mm, 2 mm, 2.5 mm, 3 mm, 3.5 mm, 4 mm, 4.5 mm, or 5 mm. The inner hydraulic diameter $D_2$ of the lower portion may be at most about 0.5 mm, 1 mm, 1.5 mm, 2 mm, 2.5 mm, 3 mm, 3.5 mm, 4 mm, 4.5 mm, or 5 mm.

The ratio of $D_1$ to $D_2$ may determine the amount of sample left in the sample reservoir after the sample is moved into the channel. In some cases the ratio of $D_1$ to $D_2$ is at least about 2:1, 5:1, 10:1, 15:1, 20:1, 25:1, 30:1, 35:1, 40:1, 45:1, or 50:1. In some cases the ratio or $D_1$ to $D_2$ is at most about 2:1, 5:1, 10:1, 15:1, 20:1, 25:1, 30:1, 35:1, 40:1, 45:1, or 50:1. A ratio of $D_1$ to $D_2$ may be greater than 2:1 in order to facilitate moving at least 50% of the sample volume from the low-loss sample reservoir 1100 into the channel 1101.

The cross-sectional area of the upper portion may be at least about 3 $mm^2$, 5 $mm^2$, 10 $mm^2$, 15 $mm^2$, 20 $mm^2$, 25 $mm^2$, 30 $mm^2$, 35 $mm^2$, 40 $mm^2$, 45 $mm^2$, 50 $mm^2$, 55 $mm^2$, 60 $mm^2$, 65 $mm^2$, 70 $mm^2$, 75 $mm^2$. The cross-sectional area of the upper portion may be at most about 3 $mm^2$, 5 $mm^2$, 10 $mm^2$, 15 $mm^2$, 20 $mm^2$, 25 $mm^2$, 30 $mm^2$, 35 $mm^2$, 40 $mm^2$, 45 $mm^2$, 50 $mm^2$, 55 $mm^2$, 60 $mm^2$, 65 $mm^2$, 70 $mm^2$, 75 $mm^2$. The cross-sectional area of the lower portion may be at least about 0.2 $mm^2$, 0.3 $mm^2$, 0.4 $mm^2$, 0.5 $mm^2$, 1 $mm^2$, 1.5 $mm^2$, 2 $mm^2$, 2.5 $mm^2$, 3 $mm^2$, 3.5 $mm^2$, 4 $mm^2$, 4.5 $mm^2$, 5 $mm^2$, 6 $mm^2$, 7 $mm^2$, 8 $mm^2$, 9 $mm^2$, 10 $mm^2$, 11 $mm^2$, 12 $mm^2$. The cross-sectional area of the lower portion may be at most about 0.2 $mm^2$, 0.3 $mm^2$, 0.4 $mm^2$, 0.5 $mm^2$, 1 $mm^2$, 1.5 $mm^2$, 2 $mm^2$, 2.5 $mm^2$, 3 $mm^2$, 3.5 $mm^2$, 4 $mm^2$, 4.5 $mm^2$, 5 $mm^2$, 6 $mm^2$, 7 $mm^2$, 8 $mm^2$, 9 $mm^2$, 10 mm, 11 $mm^2$, 12 $mm^2$.

The ratio of the cross-sectional area of the upper portion to the cross-sectional area of the lower portion may determine the amount of sample left in the sample reservoir after the sample is moved into the channel. In some cases, the ratio for the upper portion cross-sectional area to the lower portion cross-sectional area is at least about 4:1, 5:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 600:1, 700:1, 800:1, 900:1, 1000:1, 1500:1, 2000:1, or 2500:1. In some cases, the ratio for the upper portion cross-sectional area to the lower portion cross-sectional area is at most about 4:1, 5:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 600:1, 700:1, 800:1, 900:1, 1000:1, 1500:1, 2000:1, or 2500:1.

The tapered portion between the upper portion and the lower portion may comprise an angle so as to facilitate wetting of sample into the lower portion and movement of the sample from the low-loss sample well to the channel. In some cases, the tapered portion of the low-loss sample reservoir may comprise a half-angle between the upper portion and the lower portion of less than about 10°, 20°, 30°, 40°, 45°, 50°, 60°, 70°, 80°, or 90°. In some cases, the tapered portion of the low-loss sample reservoir may comprise a half-angle between the upper portion and the lower portion of more than about 10°, 20°, 30°, 40°, 45°, 50°, 60°, 70°, 80°, or 90°.

In some cases, the height $H_1$ of the lower portion can be configured so as to produce a head height of sample left behind which equals or nearly equals the head height of the buffers in the other reservoirs connected to the channel in order to limit, prevent, or reduce pressure-driven flow and mixing in the channel. The height $H_1$ of the lower portion may be at least about 1 mm, 2 mm, 3 mm, 4 mm, 5 mm, 6 mm, 7 mm, 8 mm, 9 mm, or 10 mm. The height $H_2$ of the lower portion may be at most about 1 mm, 2 mm, 3 mm, 4 mm, 5 mm, 6 mm, 7 mm, 8 mm, 9 mm, or 10 mm.

Reservoirs (e.g., elution reservoirs) can have diameters that are large compared to the diffusion length scale of analytes (e.g., nucleic acids) to reduce the diffusion of analytes out of a reservoir. In some cases, the reservoir diameter length scale can be on the order of millimeters, and the resulting diffusion time of analyte from the reservoir can be on the order of hours. Connections (e.g. through-holes or apertures) between channels and reservoirs (e.g., elution reservoirs) can be designed without sharp corners, thereby reducing the prevalence of high electric field regions at these connections and increasing the residence time of analytes within the reservoir. In some cases, the cross section of a reservoir (e.g., elution reservoir) normal to the electric field can be significantly greater than the cross section of the channel normal to the electric field, thereby reducing the electric field strength in the reservoir and increasing the residence time of analyte within the reservoir.

In some cases, an elution channel and/or an elution reservoir can comprise a second leading electrolyte buffer, different in type or concentration from the first leading electrolyte buffer used in the main channel. This can allow purified material to be eluted in the second leading electrolyte buffer (e.g., an elution buffer or output solution). The effective mobility magnitude of the second leading electrolyte ions within the second leading electrolyte buffer can be greater than the effective mobility magnitude of the nucleic acids. The second leading electrolyte buffer can have low ionic strength, for example an ionic strength compatible with downstream assays (e.g., qPCR, next generation sequencing). In some cases, the second leading electrolyte buffer is the same as the first leading electrolyte buffer but present at a different concentration or ionic strength (e.g., an ionic strength lower than that of the first leading electrolyte buffer). For example, the first leading electrolyte buffer may have an electrolyte ion concentration of 70-100 mM (e.g. 70-100 mM Tris HCl) while the second leading electrolyte buffer may have an electrolyte ion concentration of less than 70 mM, less than 60 mM, or less than 50 mM (e.g., less than 50 mM Tris HCl).

Reservoirs (e.g. sample reservoir) can be configured for injection via the application of pressure or via direct injection. Using a direct injection reservoir, the sample may be injected into the microfluidic channel via a pipette. The reservoir may be configured such that the outlet of a pipette tip may be directly coupled to the inlet of the channel. Proper tip placement in the reservoir may allow the sample to be injected into the channel while minimizing sample loss to the sides and/or interior of the reservoir.

FIGS. 48A-48H show exemplary sample inlet reservoir designed for direct injection.

Figure 48C:
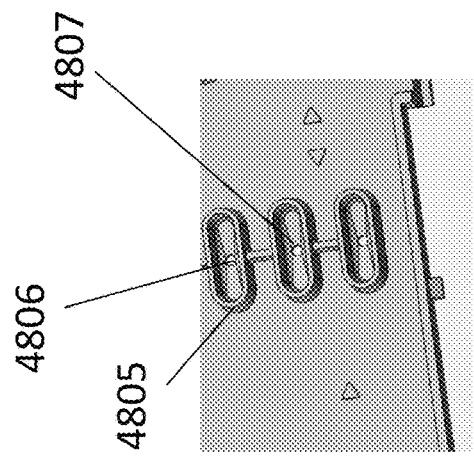
FIGS. 48A-48H show exemplary sample inlet reservoir designed for direct injection.
Figure 48B:
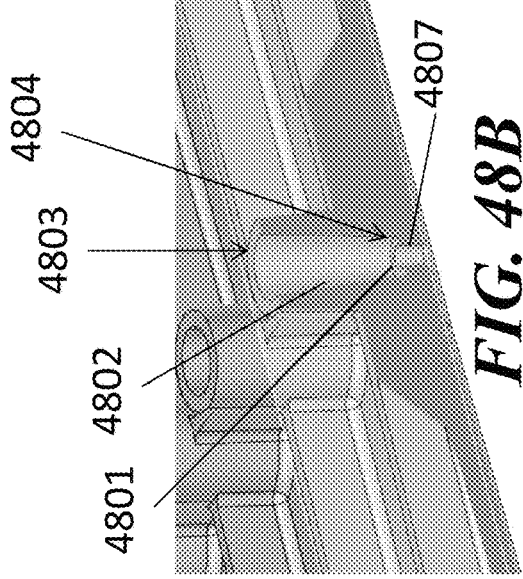
Figure 48A:
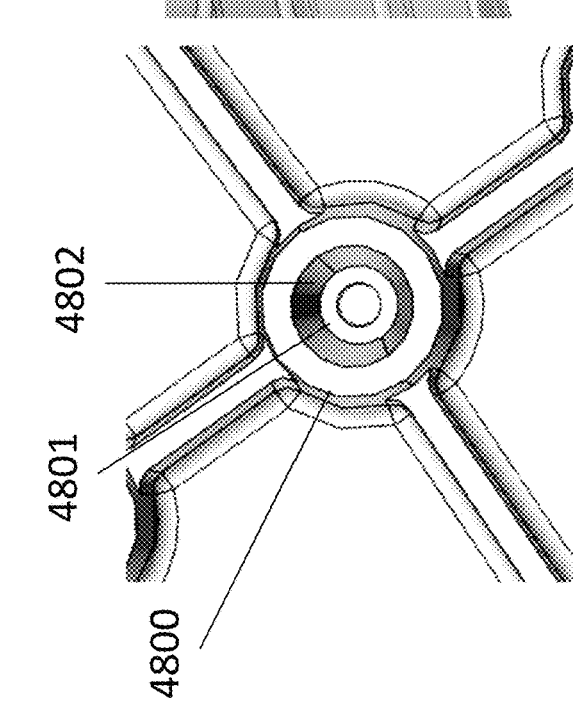

FIGS. 48A-48B show an exemplary design of a sample loading reservoir 4800 (or buffer reservoir) designed to promote direct injection of a sample (or buffer) into the channel of a microfluidic device. The loading reservoir 4800 may be configured to guide placement of a pipette towards a resting place 4801 for the end of the pipette tip by a guide wall 4802. The resting place 4801 is generally an aperture or through-hole that penetrates the chip surface. The guide wall 4802 may be configured to constrain the pipette tip orientation and position to properly align the pipette tip into the resting place 4801. The guide wall 4802 may, for example, have a frustoconical shape, with the narrower region of the cone 4804 located at the resting place 4801 and the wider region of 4803 of the cone located at the entry way for ambient air 4807 of the loading reservoir 4800. The wider portion 4803 and the narrower portion 4804 may have a circular cross-section. The guide wall 4802 may taper between the wider portion 4803 and the narrower portion 4804 at an angle configured to guide the pipette to the resting place 4801. By placing the pipette tip in this location 4801, the user can inject sample directly into the channel by dispensing to the first stop with a standard laboratory micropipette.

The sample (or buffer) loading reservoir 4800 may be configured to minimize the amount of sample (or buffer) volume that is held in the well 4800 at a fixed head height by minimizing the diameter of the well 4800. The total fluid head height may be within a range of about 1 mm to about 6 mm from the bottom surface of the channel, for example about 2.8 mm from the bottom surface of the channel. The volume of fluid which remains in the well after loading into the channel, which may be contained between the top of the channel and the sample reservoir 4800 (e.g. within the through-hole 4807), may be less than about 15 ul, for example about 7 ul.

The sample (or buffer) loading reservoir 4800 may be configured to load the sample (or buffer) into the channel therebelow under gravitational force. The through-hole 4807 may have a diameter within a range of about 0.5 mm to about 5 mm, for example about 1.5 mm, for example about 1 mm.

The sample (or buffer) loading reservoir 4800 may comprise a frustoconical shape with a diameter at the fluid head height (e.g. a diameter at the resting place 4801 in the narrower portion 4804) within a range of about 0.1 mm to about 4 mm, for example within a range of about 1 mm to about 4 mm, for example about 1.8 mm.

The sample (or buffer) loading reservoir 4800 may have a height of no more than about 20 mm, no more than about 15 mm, no more than about 10 mm, or greater than 10 mm. For example, the sample (or buffer) loading reservoir 4800 may have a height of about 6 mm. Alternatively, the sample (or buffer) loading reservoir 4800 may have a height within a range of about 8 mm to about 10 mm.

The wider portion 4803 of the sample (or buffer) loading reservoir 4800 may have a maximum dimension across of about 4.2 mm.

The narrower portion 4804 of the sample (or buffer) loading reservoir 4800 may have a maximum dimension across of about 1.5 mm.

The guide wall 4802 of the sample (or buffer) loading reservoir 4800 may taper between the wider portion 4803 and the narrower portion 4804 at an angle within a range of about 60 degrees to about 90 degrees.

Figure 48D:
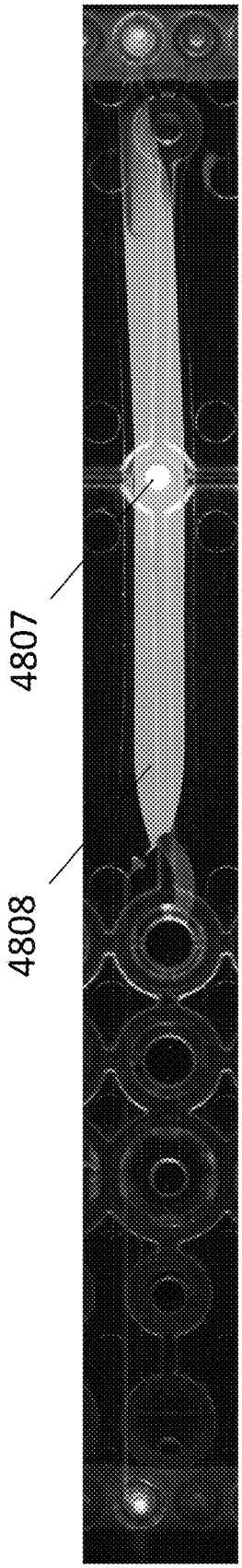

FIG. 48C shows another exemplary reservoir 4805 geometry which may be compatible with direct injection. Unlike the geometry shown in FIGS. 48A-48B, the reservoir 4805 lacks a guide wall to ensure proper placement. The user may manually position their pipette tip to rest on the resting plane 4806 and then dispense the sample into the channel below via the aperture 4807 in the resting plan 4806. The reservoir 4805 may for example have an elongate cross-sectional shape configured to capture overflow liquid from the pipette during injection and ensure bubble-free loading of the entire liquid volume. FIG. 48D shows the result of using the reservoir 4805 in FIG. 48A to inject a fluorescent aqueous solution 4808 into a microfluidic channel. Liquid 4808 was injected via the aperture 4807 in the guide plane 4806 of the reservoir 4805 and was able to fill the adjoining channel without bubble formation.

The sample (or buffer) loading reservoir 4805 may be configured to minimize the amount of sample (or buffer) volume that is held in the well 4805 at a fixed head height by minimizing the diameter of the well 4805. The total fluid head height may be within a range of about 1 mm to about 6 mm from the bottom surface of the channel, for example about 2.8 mm from the bottom surface of the channel. The volume of fluid which remains in the well after loading into the channel, which may be contained between the top of the channel and the sample reservoir 4805 (e.g., within the through-hole 4807), may be less than about 15 ul, for example about 7 ul.

The sample (or buffer) loading reservoir 4805 may be configured to load the sample (or buffer) into the channel therebelow under gravitational force. The through-hole 4807 may have a diameter within a range of about 0.5 mm to about 5 mm, for example about 1.5 mm, for example about 1 mm.

The sample (or buffer) loading reservoir 4805 may comprise an elongate shape, for example an elliptical shape, having a maximum diameter across of about 10 mm and a minimum diameter across of about 3 mm.

The sample (or buffer) loading reservoir 4805 may have a height of no more than about 20 mm, no more than about 15 mm, no more than about 10 mm, or greater than 10 mm. For example, the sample (or buffer) loading reservoir 4805 may have a height of about 6 mm. Alternatively, the sample (or buffer) loading reservoir 4805 may have a height within a range of about 8 mm to about 10 mm.

Figures 48E, 48F:
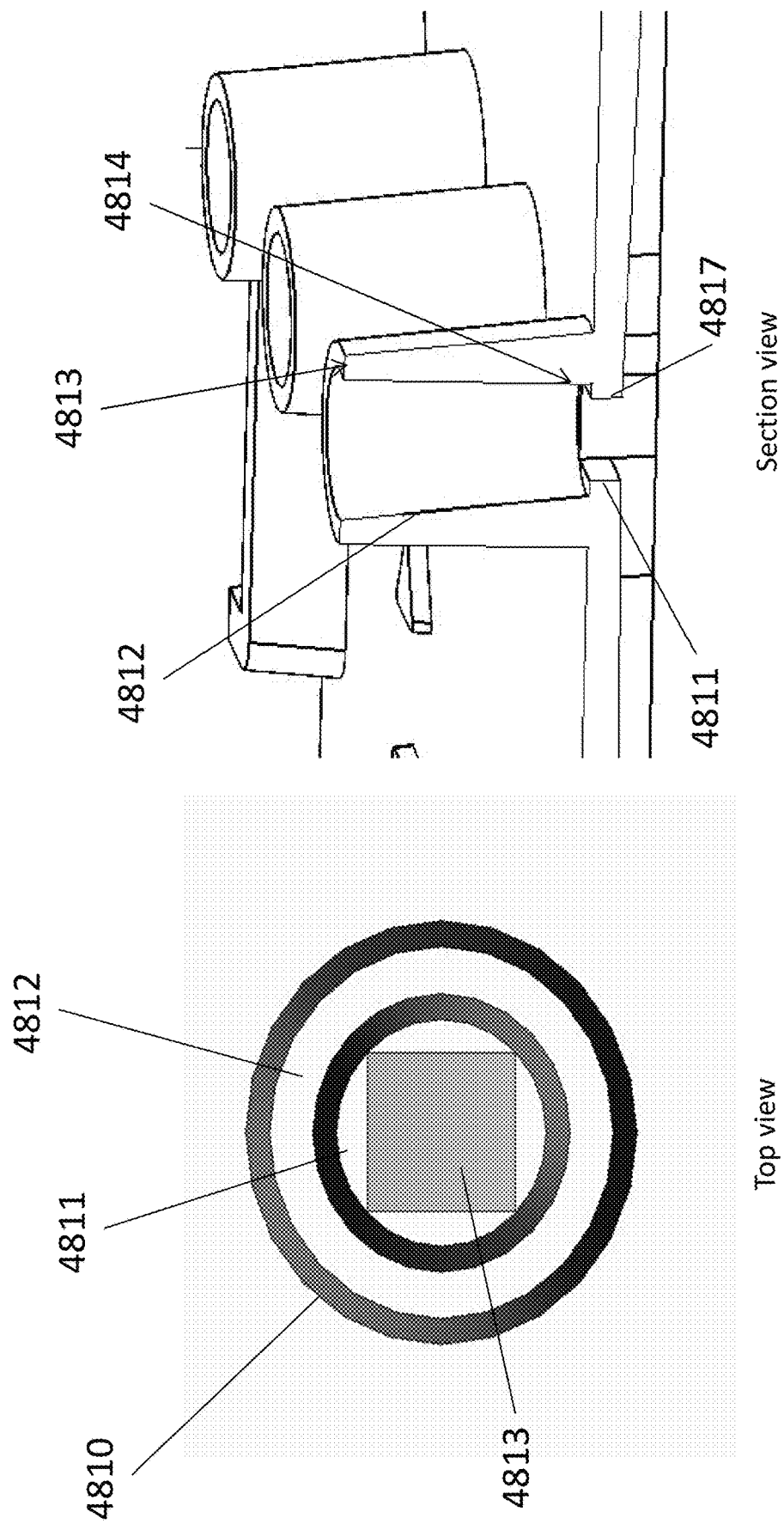

FIGS. 48E-48F shows an exemplary design of a sample loading reservoir 4810 (or buffer reservoir) which may facilitate direct injection of a sample (or buffer) into the channel of a microfluidic device. The loading reservoir 4810 may be substantially similar to the reservoir 4800 of FIGS. 48A-48B except that the resting place 4811 form may be a square aperture 4813 instead of a circular aperture. The loading reservoir 4810 may be configured to guide placement of a pipette towards a resting place 4811 for the end of the pipette tip by a guide wall 4812. The guide wall 4812 may be configured to constrain the pipette tip orientation and position to properly align the pipette tip into the resting place 4811. The guide wall 4812 may for example have a frusto-conical shape, with a narrower region 4814 of the cone located at the resting place 4811 and the wider region 8413 of the cone located at the entryway for ambient air 4817 of the loading reservoir 4810. The wider portion 4813 and the narrower portion 4814 may have a circular cross-section. The resting place 4811 may have a square cross-section at the base of the guide wall 4812. The guide wall 4812 may taper between the wider portion 4813 and the narrower portion 4814 at an angle configured to guide the pipette to the resting place 4811. By placing the pipette tip in this location 4811, the user can inject sample directly into the channel by dispensing to the first stop with a standard laboratory micropipette.

The sample (or buffer) loading reservoir 4810 may be configured to minimize the amount of sample (or buffer) volume that is held in the well 4810 at a fixed head height by minimizing the diameter of the well 4810. The total fluid head height may be within a range of about 1 mm to about 6 mm from the bottom surface of the channel, for example about 2.8 mm from the bottom surface of the channel. The volume of fluid which remains in the well after loading into the channel, which may be contained between the top of the channel and the sample reservoir 4810 (e.g., within the through-hole 4817), may be less than about 15 ul, for example about 7 ul.

The sample (or buffer) loading reservoir 4810 may be configured to load the sample (or buffer) into the channel therebelow under gravitational force. The through-hole 4817 may have a diameter within a range of about 0.5 mm to about 5 mm, for example about 1.5 mm, for example about 1 mm.

The sample (or buffer) loading reservoir 4810 may have a height of no more than about 20 mm, no more than about 15 mm, no more than about 10 mm, or greater than 10 mm. For example, the sample (or buffer) loading reservoir 4810 may have a height of about 6 mm. Alternatively, the sample (or buffer) loading reservoir 4810 may have a height within a range of about 8 mm to about 10 mm.

The wider portion 4813 of the sample (or buffer) loading reservoir 4810 may have a maximum dimension across of about 2.1 mm.

The narrower portion 4814 of the sample (or buffer) loading reservoir 4810 may have a maximum dimension across of about 1.5 mm.

The guide wall 4812 of the sample (or buffer) loading reservoir 4810 may taper between the wider portion 4813 and the narrower portion 4814 at an angle within a range of about 60 degrees to about 90 degrees.

The sample (or buffer) reservoir 4810 can have one or more through-holes 4817 having a shape configured to allow some portion of a current passing through the sample channel bellow the reservoir 4810 to enter the sample reservoir 4810, and to carry analyte out of the reservoir 4810 and into the channel below. The through holes 4817 can have a dimension substantially or entirely co-extensive with the width of the channel over which the reservoir 4817 is positioned. This dimension of co-extension can be, e.g., at least 50% to 150% the width of the channel, e.g, between about 1 mm and about 5 mm. For example, through-hole 4817 can take a rectangular shape, including a square. The through-hole 4817 also can assume a rounded shape, including a circle or an oval.

The rectangular aperture 4813 may be large enough to allow some portion of the electric field applied to the fluidic circuit to interact with the target nucleic acids of the sample. For example, if a portion of the sample remains in the reservoir 4810 after loading, when the electric field is applied, the electric field may induce migration of the remaining sample nucleic acids from the reservoir 4810 into the channel for ITP concentration. Thus, even if some of the sample buffer volume remains in the well 4810 after loading, the target nucleic acids may still enter the channel and less of the analyte may be lost to the well 4810.

When an electric field is applied to the ITP branch, greater than 10% of an electric current applied may travel above a top surface of said sample channel across a length of said sample reservoir.

The rectangular aperture 4813 may have a width within a range of about 80% to about 120% of a width of said sample channel, for example about 100% of the sample channel (e.g. a width of 2.2 mm for a 2.2 mm channel).

Figure 48H:
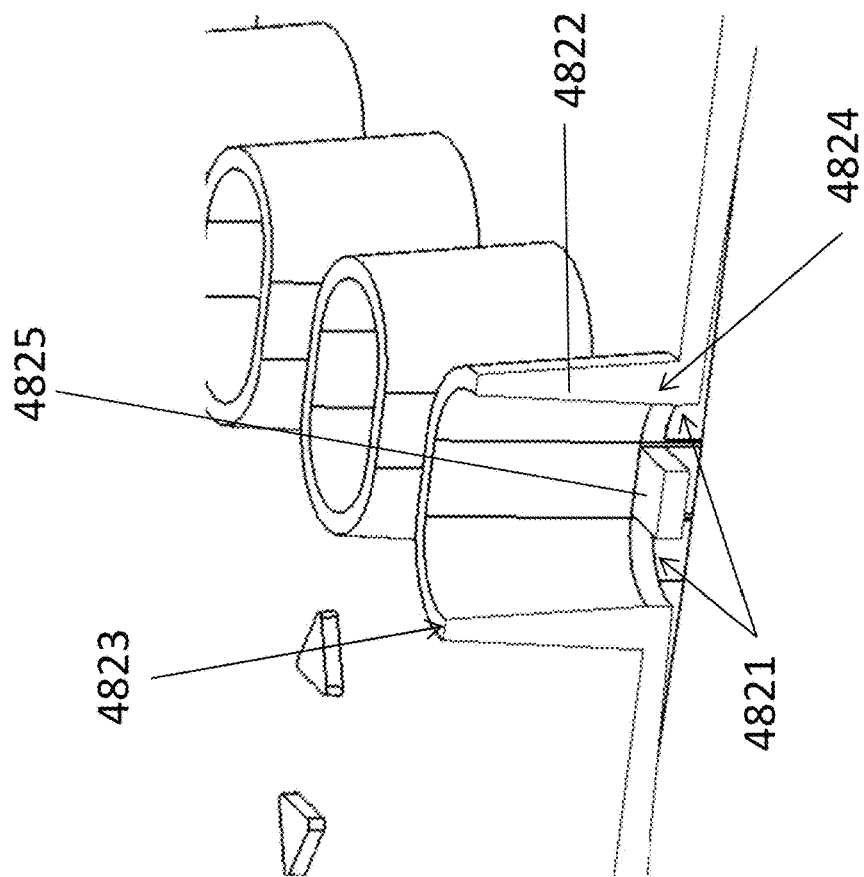
Figure 48G:
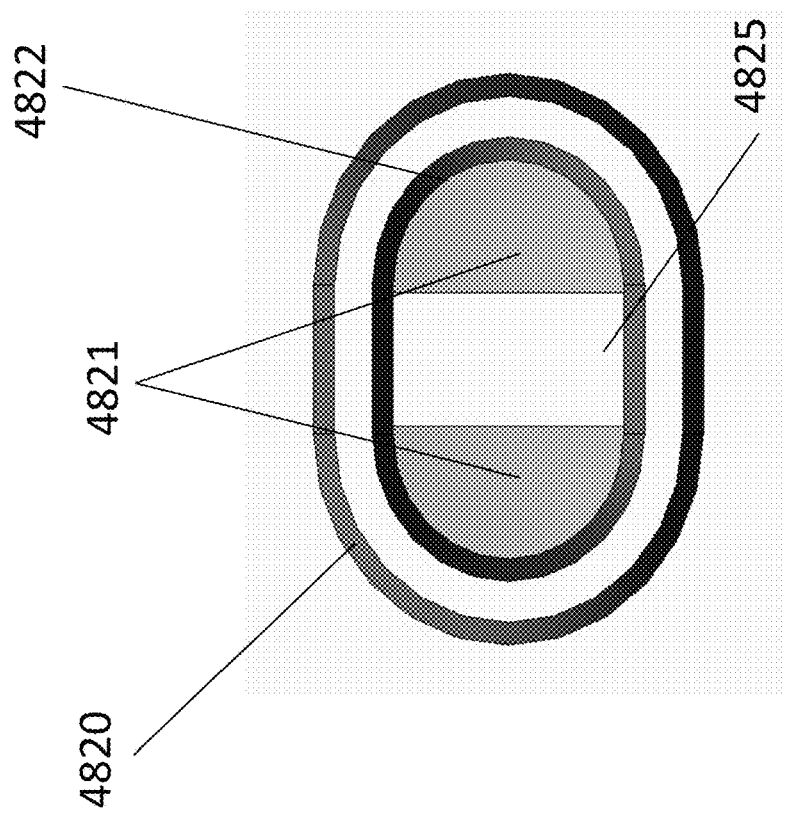

FIGS. 48G-48H shows an exemplary design of a sample loading reservoir 4820 (or buffer reservoir) which may facilitate direct injection of a sample (or buffer) into the channel of a microfluidic device. The sample loading reservoir 4820 may comprise an oval-shaped reservoir having two sample injection ports 4821 through which the user can inject sample into the channel. The reservoir 4810 may comprise a guide wall 4822 configured to guide placement of a pipette towards one or both of the sample injection ports 4821. The guide wall 4822 may for example have a narrower region 4814 of the cone located at the resting place 4811 and the wider region 8413 of the cone located at the entryway for ambient air 4817 of the loading reservoir 4810. The wider portion 4823 and the narrower portion 4824 may have an oval or elongate cross-section. The guide wall 4822 may taper between the wider portion 4823 and the narrower portion 4824 at an angle configured to guide the pipette to one or both of the sample injection ports 4821. By placing the pipette tip in either port 4821, the user can inject sample directly into the channel by dispensing to the first stop with a standard laboratory micropipette.

The sample (or buffer) loading reservoir 4820 may be configured to minimize the amount of sample (or buffer) volume that is held in the well 4820 at a fixed head height by minimizing the diameter of the well 4820. The total fluid head height may be within a range of about 1 mm to about 6 mm from the bottom surface of the channel, for example about 2.8 mm from the bottom surface of the channel. The volume of fluid which remains in the well after loading into the channel, which may be contained between the top of the channel and the sample reservoir 4820 (e.g., within the through-holes 4821), may be less than about 15 ul, for example about 7 ul.

The sample (or buffer) loading reservoir 4820 may be configured to load the sample (or buffer) into the channel therebelow under gravitational force. The through-holes 4821 may have a diameter within a range of about 0.5 mm to about 5 mm, for example about 1.5 mm, for example about 1 mm.

The through-holes 4821 may be large enough to allow some portion of the electric field applied to the fluidic circuit to interact with the target nucleic acids of the sample. For example, if a portion of the sample remains in the reservoir 4820 after loading, when the electric field is applied, the electric field may induce migration of the remaining sample nucleic acids from the reservoir 4820 into the channel for ITP concentration. Thus, even if some of the sample buffer volume remains in the well 4820 after loading, the target nucleic acids may still enter the channel and less of the analyte may be lost to the well 4820.

The reservoir 4820 may be oval-shaped to provide a path for the electric field.

The through-holes 4821 may be separated by a bar or filler block 4825. The bar 4825 across the bottom of the well may 4820 help direct the electric field into the fluid held in the reservoir 4820 (above the channel). The bar 4825 may also help stabilize the fluid in the well 4820 against secondary flows due to buoyant effects as described herein.

When an electric field is applied to the ITP branch, greater than 10% of an electric current applied may travel above a top surface of said sample channel across a length of said sample reservoir 4820.

The through-holes 4821 may have a width within a range of about 80% to about 120% of a width of said sample channel, for example about 100% of the sample channel (e.g. a width of 2.2 mm for a 2.2 mm channel).

The through-holes 4821 may have areas within a range of about 0.2 mm² to about 7 mm², for example within a range of about 0.8 mm² to about 1.5 mm² or within a range of about 1 mm² to about 2.75 mm².

The through-holes 4821 may have substantially the same shape. The through-holes 4821 may have different shapes.

The filler block or bar 4825 may have a width of about 3.7 mm spanning the well 4820 along a lateral axis of the well 4820. The filler block or bar 4825 may have a width of about 2 mm spanning the well 4820 along a longitudinal axis of the well 4820.

The sample reservoir 4820 may comprise a filler block 4825 between 0.2 mm and 2 mm in height in the channel, for example about 1.2 mm. The filler block 4825 may bifurcate the electric current into upper and lower branches.

The sample (or buffer) loading reservoir 4820 may comprise an elongate shape, for example an elliptical shape, having a maximum diameter (i.e. length) across of about 7.5 mm and a minimum diameter across (i.e. width) of about 5 mm.

The sample (or buffer) loading reservoir 4820 may have a height of no more than about 20 mm, no more than about 15 mm, no more than about 10 mm, or greater than 10 mm. For example, the sample (or buffer) loading reservoir 4820 may have a height of about 6 mm. Alternatively, the sample (or buffer) loading reservoir 4820 may have a height within a range of about 8 mm to about 10 mm.

The wider portion 4823 of the sample (or buffer) loading reservoir 4820 may have a maximum dimension across of about 2.1 mm.

The narrower portion 4824 of the sample (or buffer) loading reservoir 4820 may have a maximum dimension across of about 1.5 mm.

The guide wall 4822 of the sample (or buffer) loading reservoir 4820 may taper between the wider portion 4823 and the narrower portion 4824 at an angle within a range of about 60 degrees to about 90 degrees.

Figures 49A, 49B:
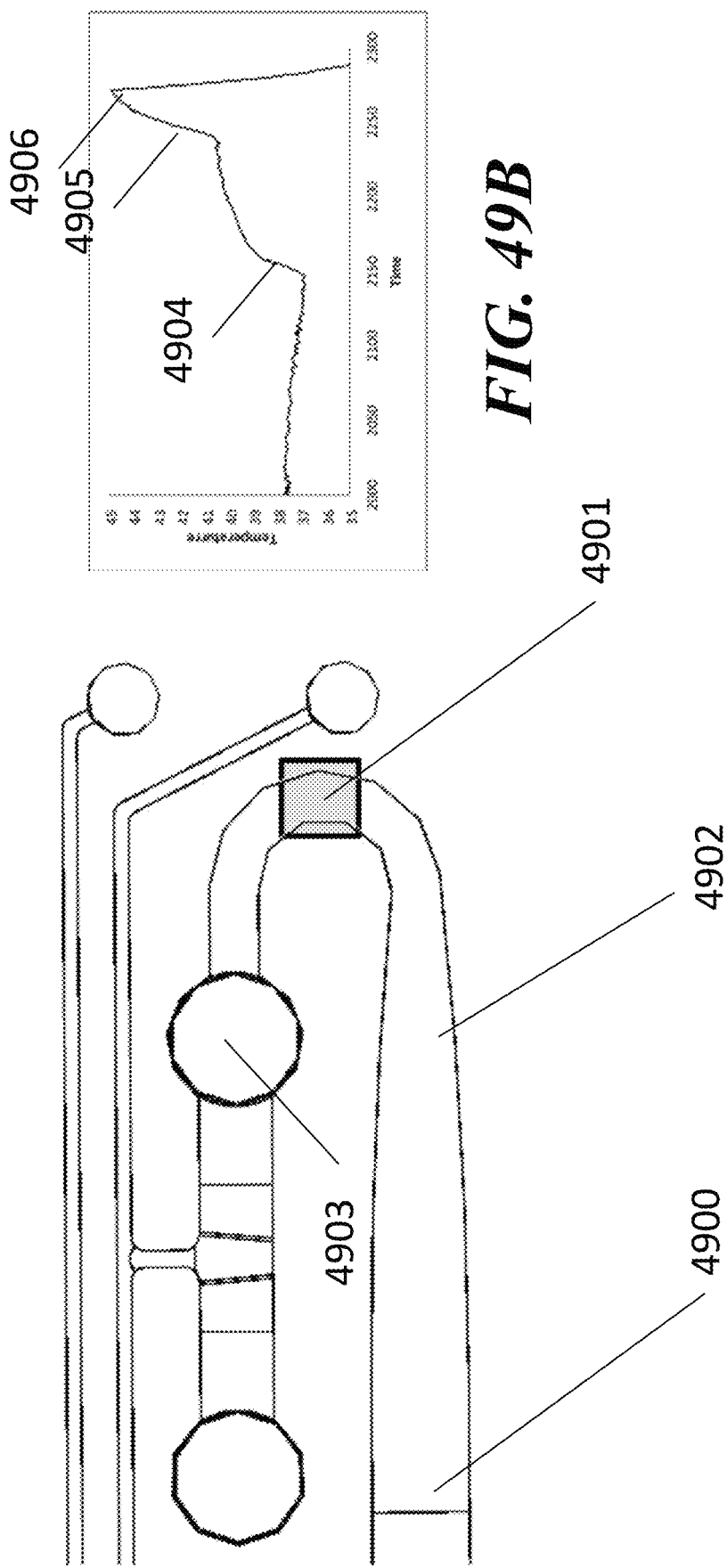
FIGS. 49A and 49B show an exemplary low-dispersion elution channel.

FIGS. 49A and 49B show an exemplary elution channel configured for reducing dispersion while retaining high fluidic and electrical resistance for automated sensing. FIG. 49A shows the channel design. The channel may begin as a wide channel 4900 before narrowing 4902. The axial distance along which the channel narrows may be between 2 and 50 times the maximum channel width. The channel may narrow to a minimum width before completing a 90 degree turn 4901. This slow transition into a narrow passage may generate a low-dispersion turn which can retain the nucleic acid sample in a tight band while turning. As described herein, the detection point for temperature, conductivity, and/or voltage measurements for automated signal processing may be located at the center of the turn 4901, which may also be the narrowest point of the channel. This detection point may be located a short distance from the elution reservoir 4903, thereby allowing signal processing decisions (e.g. triggering) to be made in advance of DNA elution. FIG. 49B shows an example of data collected from the channel in FIG. 49A. The x-axis is the time since the beginning of the separation. The y-axis is the temperature of the detection point 4901. At time 4904, the ion in front of the detector is replaced by a new, lower-mobility ion (e.g. leading electrolyte) via isotachophoresis. At time 4905, a third ion (e.g. ITP band) displaces the second, resulting in a second temperature rise. At time 4906, the automated signal processing system detects this change and turns off the voltage (and current), causing a rapid decrease in temperature within the turn 4901.

The elution reservoir can be configured to collect analyte during isotachophoresis. For example, the elution chamber can be positioned over a channel which comprises a break. Through-holes from the break points into the reservoir will require current to flow through the channel, into the reservoir through a first through-hole, and out a second through-hole into the continuation of the channel. That is, the fluidic circuit is designed so that current cannot flow directly under the elution reservoir, but must pass into and out of the reservoir. Such a configuration is shown in FIG. 50A1, which shows a fluidic surface 5050 of a substrate with first channel 5051 terminating in through-holes 5052, 5053 that communicate with a reservoir on an opposing, reservoir surface of the substrate. (See. e.g., FIGS. 51C and 51D.) In some embodiments, the through-hole 5052 entering the reservoir in the direction of analyte flow from channel 5051 is positioned lower in the reservoir than the through hole 5053 leaving the reservoir towards second channel 5054. This creates a volume in the reservoir between the through holes 5052, 5053 which must be filled to create an electrical path into and out of the reservoir. The first channel 5051 may communicate with a first electrode and the second channel 5054 may communicate with a second electrode. The channels 5051, 5054 and reservoir may comprise an electrically conductive fluid (e.g. elution buffer and/or high concentration elution buffer). Application of a voltage across the first and second electrodes may produce a current that travels through the reservoir. Analyte moving into the reservoir tends to remain in the reservoir rather than moving in an upward and outward direction via channel 5054 toward additional reservoir(s) 5055 (e.g. elution buffering reservoir). The reservoir can include a step or platform positioned, e.g., about 0.5 mm to about 3 mm above the floor of the reservoir (e.g., as shown in FIG. 52B). The second through-hole 5053 can penetrate this step. Such a step or ramp also creates a well-shaped area adapted for pipetting.

In some instances, there may be two steps within the reservoir between the first and second through-holes 5052, 5053. The second through-hole 5053 may penetrate the higher step which may be further away from the first through-hole 5052 than the lower step. Alternatively, the second through-hole 5053 may penetrate the lower step which may be closer the first through-hole 5052 than the higher step.

FIG. 50A is a technical drawing top view of an exemplary elution reservoir 5000 which may be located on any of the chip devices described herein. The reservoir 5000 may be configured to hold a volume of elution buffer as described herein. Upon completion of an ITP run, the target nucleic acids may reside within this volume as described herein. The reservoir 5000 may comprise a first through-hole or aperture 5001 and a second through-hole or aperture 5002. The first and second through-holes 5001, 5002 may penetrate the chip surface and be in communication with a fluidic channel 5003 located below the reservoir 5000 as described herein. The fluidic channel 5003 may for example be an elution channel as described herein. The first and second through-holes 5001, 5002 may be generally aligned with each other and with a longitudinal axis of the fluidic channel 5003 such that application of a fluid into the channel 5003 via the second through-hole 5002 pushes the fluid along the channel 5003 towards the first through-hole 5001. A user may for example remove a first volume out of the first through-hole 5001, for example using a pipet. Subsequently, fresh elution buffer may be added to the channel 5003 via the second through-hole 5002, for example using a pipet. The user may then perform a final evacuation of all remaining buffer from the first through-hole 5001, for example using a pipet. In this way, the user may improve the overall yield of the ITP purification process and ensure that the majority of the purified target nucleic acids may be retrieved from the device in two elution steps.

The first through-hole 5001 may for example have an elliptical shape. Alternatively, the first through-hole 5001 may be circular. The first through-hole 5001 may have any shape desired by one or ordinary skill in the art.

The second through-hole 5002 may for example be circular. Alternatively, the second through-hole 5002 may have an elliptical shape. The second through-hole 5002 may have any shape desired by one or ordinary skill in the art.

The first through-hole 5001 may have a diameter within a range of about 100 um to about 3 mm.

The first through-hole 5001 may have a maximum dimension across of less than about 1.5 mm, for example less than about 1 mm.

The second through-hole 5002 may have a diameter within a range of about 100 um to about 3 mm.

The second through-hole 5002 may have a maximum dimension across of less than about 1.5 mm, for example less than about 1 mm.

In some embodiments, the channel 5003 below the reservoir 5000 may comprise a break as shown in FIG. 50A1 and the first and second through-holes 5001, 5002 may be in fluidic and/or electrical communication with first and second terminating ends of the channel 5003 as described herein. The first and second through-holes 5001, 5002 may be positioned at different heights within the reservoir. The first through-hole 5001 may enter the reservoir 5000 at a position lower in the reservoir than the second through-hole 5002. The first and second through-holes 5001, 5002 may be separated by a step or platform as described herein.

The reservoir 5000 may be circular. The reservoir 5000 may have a diameter of about 5.3 mm.

The reservoir 5000 may be defined by a wall having a height of no more than 25 mm, no more than 15 mm, no more than 10 mm, or greater than 10 mm. The reservoir 5000 may have height of about 6 mm. The reservoir 5000 may have height within a range of about 8 mm to about 10 mm.

The first and second through holes 5001, 5002 may have areas within a range of about 0.2 mm$^2$ to 7 mm2. The first through-hole 5001 may have an area within a range of about 1 mm$^2$ to about 2.75 mm$^2$. For example the second through-hole 5002 may have an area within a range of about 0.8 mm$^2$ to about 1.5 mm$^2$.

The through-holes 5001, 5002 may have substantially the same shape. The through-holes 5001, 5002 may have different shapes.

The first through-hole 5001 may have a shape of a square, a rectangle, an oval, or have an elongated direction in a direction of the width of the channel 5003 or the width of the reservoir 5000.

The second through-hole 5002 may have a shape of a square, a rectangle, an oval, or have an elongated direction in a direction of the width of the channel 5003 or the width of the reservoir 5000.

The through-holes 5001, 5002 may be arranged along a longitudinal axis of the channel 5003.

The first through-hole 5001 may have a maximum distance across (i.e. length) of about 1.75 mm and a minimum distance across (i.e. width) of about 1.3 mm.

The second through-hole 5002 may be relatively circular with a diameter of about 1.2 mm. The second through-hole 5002 may be shaped so as to spread the electrical field evenly across the reservoir 5000.

The volume of the reservoir 5000 between the first and second through-holes 5001, 5002 may be no more than about 2.5 ml, 1 ml, or 0.5 ml. The volume of the reservoir 5000 between the first and second through-holes 5001, 5002 may be about 0.1 mL.

At least part of each through-hole 5001, 5002 may be substantially co-extensive with the fluidic channel 5003 across said width of said fluidic channel 5003.

The first through-hole 5001 may comprise at least one side, for example one or two sides, that span the width of the fluidic channel 5003 and/or a width of the reservoir 5000. The at least one side(s) may (each) be at least 75% linear.

The second through-hole 5002 may comprise at least one side, for example one or two sides, that span the width of the fluidic channel 5003 and/or a width of the reservoir 5000. The at least one side(s) may (each) be at least 75% linear.

The first and second through-holes 5001, 5002 may have a shape that, when said fluidic channel 5003 and said reservoir 5000 comprise an electrically conductive fluid and an electric current is passed through said fluidic channel 5003, at least 5%, at least 6%, at least 7%, at least 10%, or at least 20% of said electric current passes through said reservoir 5000 between the first and the second through-holes 5001, 5002.

Figure 50B:
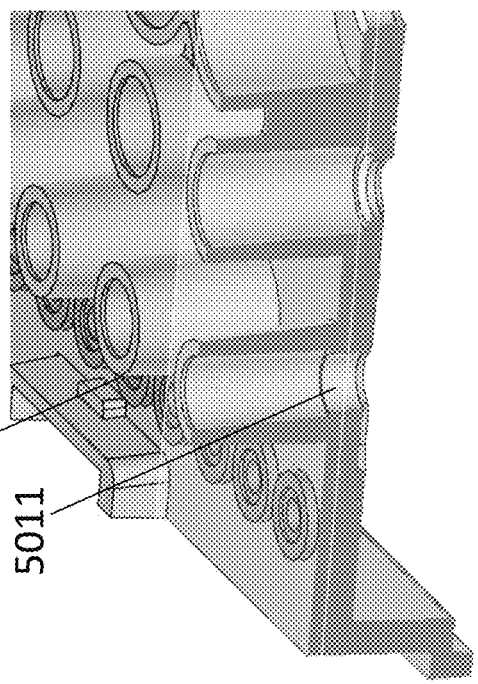
Figure 50A:
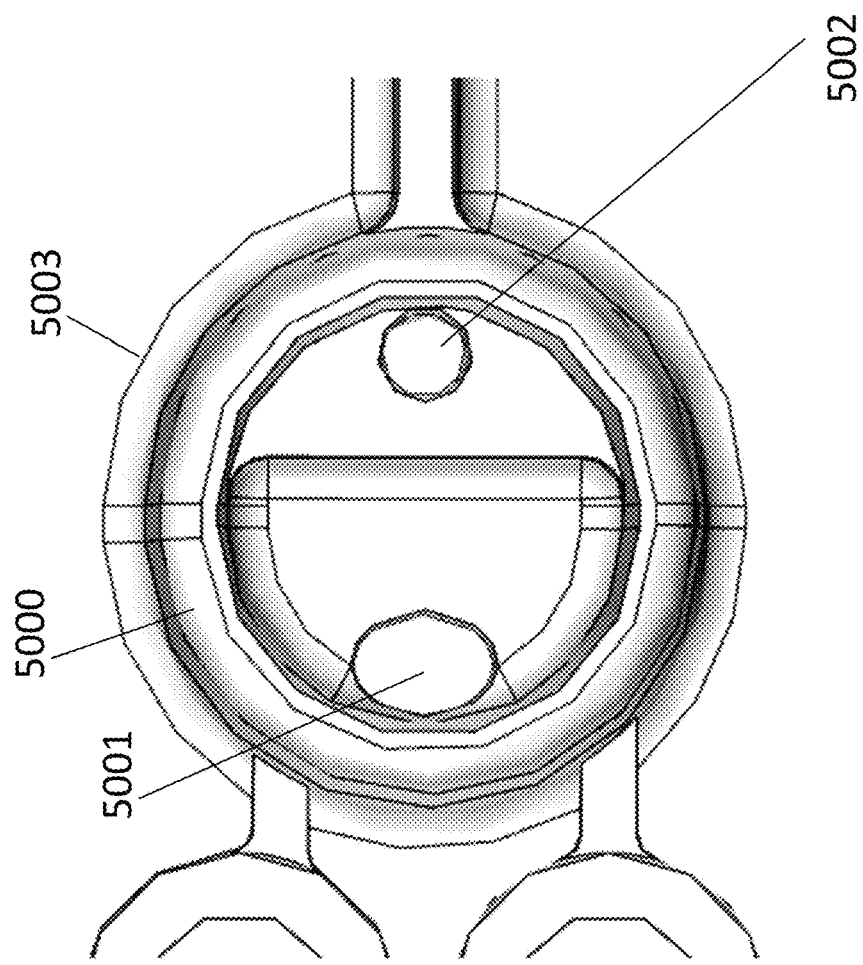

FIG. 50B shows a cross-sectional view of another exemplary elution reservoir 5010 which may be located on any of the chip devices described herein. FIG. 50B shows another view of the elution reservoir design 603 shown in FIG. 6A. The reservoir 5010 may be configured to hold a volume of elution buffer as described herein. Upon completion of an ITP run, the target nucleic acids may reside within this volume as described herein. The reservoir 5010 may comprise a single through-hole or aperture 5011. The through-hole 5011 may penetrate the chip surface and be in communication with a fluidic channel located below the reservoir 5010 as described herein. The fluidic channel may for example be an elution channel as described herein. A user may, for example, remove a first volume of fluid out of the reservoir 5010 via the through-hole 5011, for example using a pipet. Subsequently, fresh elution buffer may be added to the channel via the through-hole 5011 of reservoir 5010, for example using a pipet. The user may then perform a final evacuation of all remaining buffer from the through-hole 5011, for example using a pipet. In this way, the user may improve the overall yield of the ITP purification process and ensure that the majority of the purified target nucleic acids may be retrieved from the device in two elution steps.

Figure 50E:
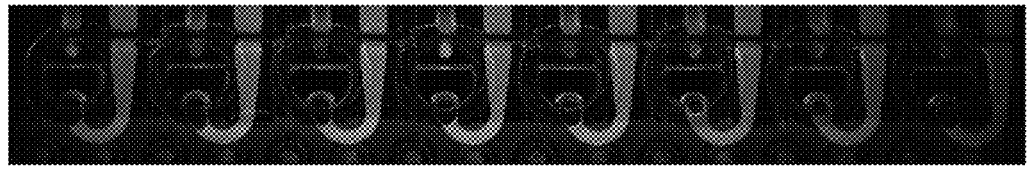
FIGS. 50C-50E are background subtracted fluorescence images of the fluidic device at different steps of elution for design in FIG. 50A.
Figure 50D:
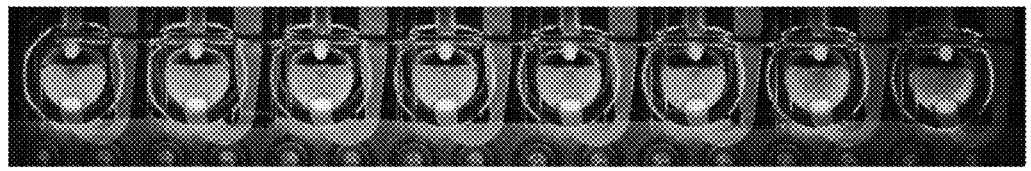
Figure 50C:
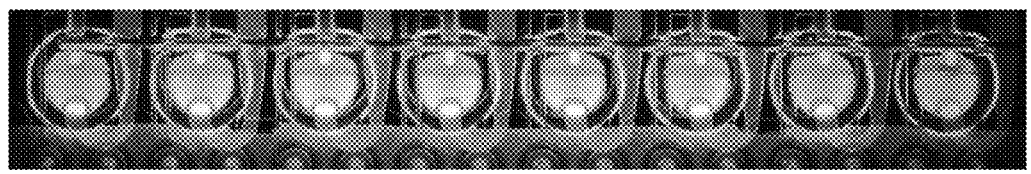
Figure 50F:
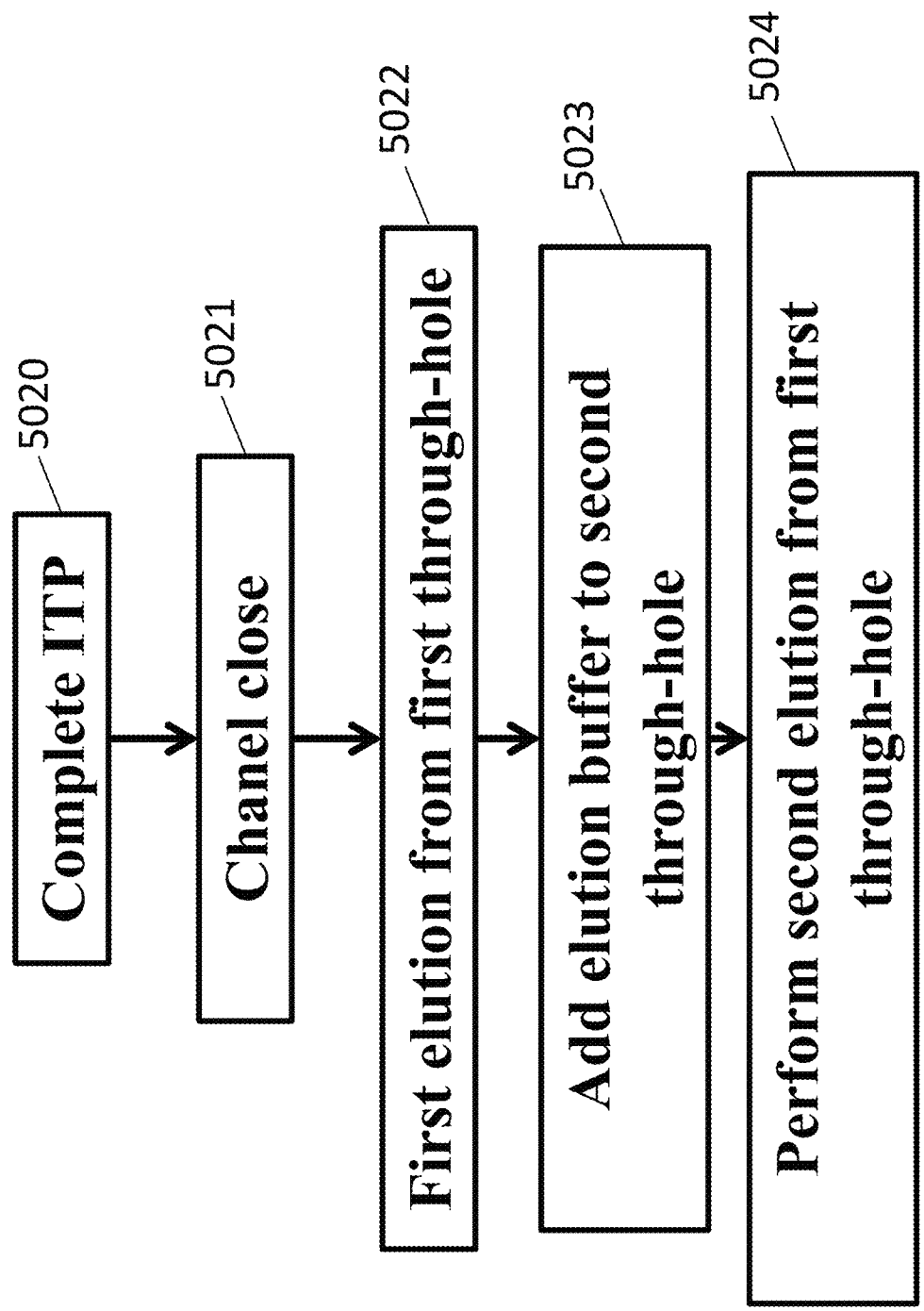
FIG. 50F is a block diagram that represents the steps in the elution workflow.

FIG. 50C-50E are background subtracted fluorescence images of a fluidic device at different steps of elution for reservoir design 5000 in FIG. 50A. FIG. 50C represents the state of the chip immediately after the completion of an ITP run, with successful channel closure to prevent fluid movement within the elution reservoir 5000 and channels (e.g. channel 5003) as described herein. FIG. 50D shows the same chip, after the initial elution from the first through-hole 5001 as described herein. FIG. 50E is the final state of the chip, after the user has added additional elution buffer to the second through-hole 5002, and fully evacuated the elution reservoir 5000 via pipetting from the first through-hole 5001. As is evident by these background-subtracted images, the majority of the DNA material may be obtained from the first elution, but the second elution step may enable the user to wash and retrieve the remaining DNA from the reservoir. FIG. 50F is a block diagram showing the steps in the elution workflow for reservoir 5000. At Step 5020, ITP may be completed as described herein. At Step 5021, the elution channel may be closed as described herein. At Step 5022, a first elution may be performed by removing the eluate from the first through-hole 5001 of the elution reservoir 5000. At Step 5023, additional elution buffer may be added to the second through-hole 5002 of the elution reservoir 5000. At Step 5024, a second elution may be performed by removing the eluate from the first through-hole 5001 of the elution reservoir 5000.

Provided herein are elution methods or processes that can be used with more than one elution reservoir design after completing an ITP run (Step 5020). The instrument channel closer can isolate the DNA in a stabilizing buffer (elution buffer) (Step 5021). The elution strategy described herein is generally designed to take advantage of this isolation, and maximize the total DNA yield. The first step of the elution technique may be to remove the majority of the liquid volume (i.e. elution buffer plus nucleic acid that has made it to the reservoir) in the reservoir 5000 (or any elution reservoir described herein). This may be done by placing a pipette at the first reservoir through-hole 5001 and aspirating between 30 and 90 uL of fluid therefrom (Step 5022). Secondly, the user may wash the reservoir 5000 using clean buffer (Step 5023). The user may wash from the second through-hole 5002 toward the first through-hole 5001 in an attempt to drive the maximum amount of analyte to the aspiration point of the first through-hole 5001. The user may, for example, accomplish this by pipetting 10 to 50 uL of fresh buffer into the second through-hole 5002 of the elution reservoir 5000. Finally, the user may recover the remaining analyte by aspirating as much volume as possible from the first through-hole 5001 (Step 5024). This multi-step elution workflow can allow the user to obtain higher or the maximum possible DNA yield.

The final stage of nucleic acid (NA) processing in the chip device may generally be to transfer the nucleic acids from a microfluidic channel into a reservoir (elution reservoir). This reservoir may be accessible via a pipette, unlike the channel. This may allow a user to recover the material (nucleic acid) following completion of the ITP run and any subsequent on-chip processing as described herein.

Decreasing the volume in this reservoir may be beneficial because it may increase the concentration of the recovered nucleic acid. Provided herein is a reservoir designed with low liquid volume (~50 uL), but which takes a long time for nucleic acid to traverse.

Figures 51A, 51B:
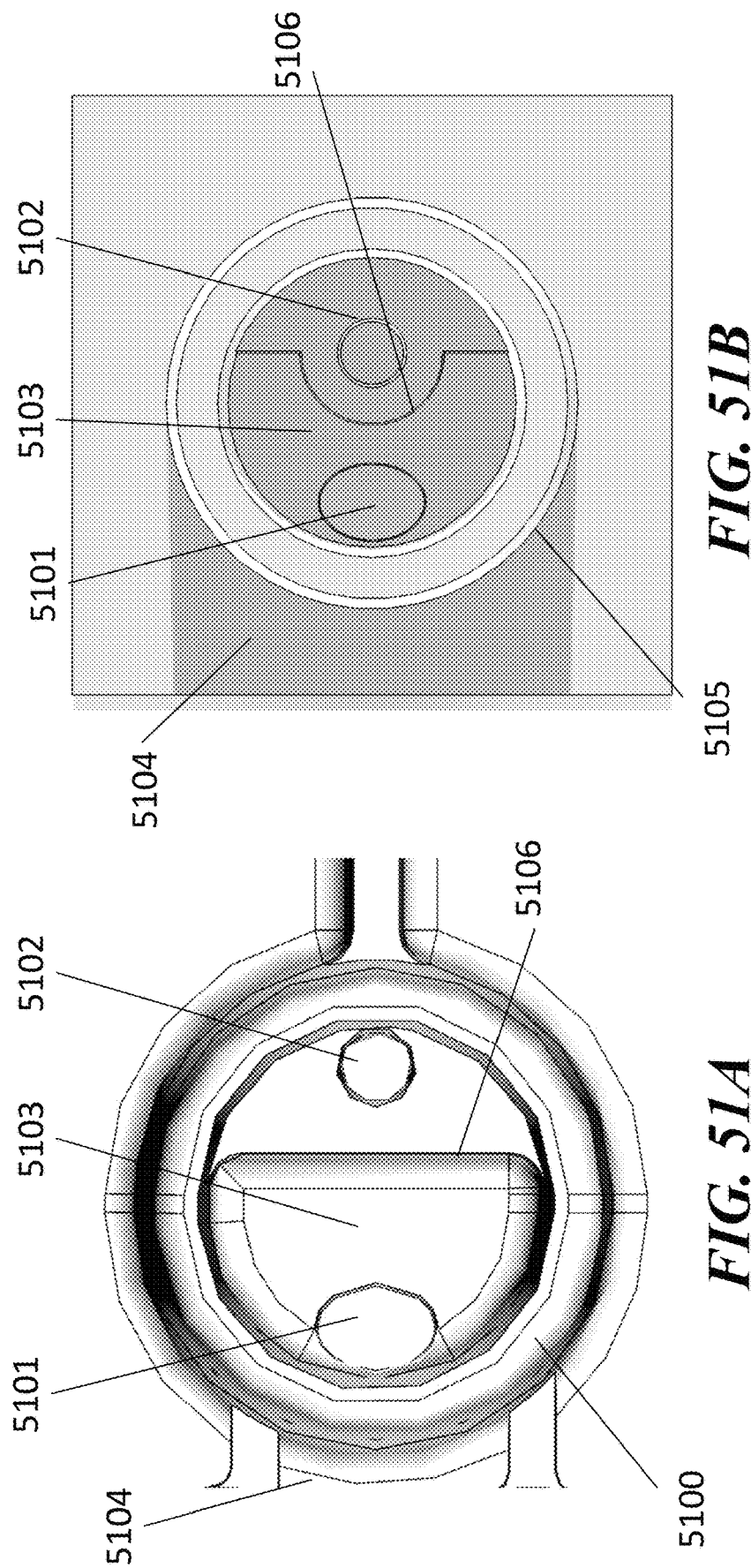
FIG. 51A shows an exemplary fluidic reservoir which can be used for nucleic acid elution.
FIG. 51B shows a second embodiment of the reservoir, with further changes for injection molding compatibility.

FIG. 51A shows an exemplary fluidic reservoir 5100 which can be used for nucleic acid elution. The reservoir 5100 may be located on any of the chip devices described herein. The reservoir 5100 may have a circular cross-section. The reservoir 5100 may be configured to hold a volume of elution buffer as described herein. Upon completion of an ITP run, the target nucleic acids may reside within this volume as described herein. The reservoir 5100 may comprise a first through-hole or aperture 5101 and a second through-hole or aperture 5102. Each of the two through-holes 5101, 5102 may be connected to a fluidic channel 5104 on a bottom layer of the fluidic device. The first and second through-holes 5101, 5102 may penetrate the chip surface and be in communication with a fluidic channel 5104 located below the reservoir 5100 as described herein. The fluidic channel 5104 may for example be an elution channel as described herein. The first through-hole 5101 may include a steep rise in fluid height (e.g. from 100-400 um at the channel to 2-3 mm within the well) from the channel 5104 to a plateau 5103 on which the target nucleic acid may be captured prior to elution. Another vertical rise 5106 within the reservoir 5100 may couple the plateau 5103 to the second through-hole 5102. The first through-hole 5101 and the second through-hole 5102 may be one different vertical planes within the reservoir 5100. The first and second through-holes 5101, 5102 may be generally aligned with each other and with a longitudinal axis of the fluidic channel 5104 such that application of a fluid into the channel 5104 via the second through-hole 5102 pushes the fluid along the channel 5104 towards the first through-hole 5101 as described herein. The second through-hole 5102 may be used to create a fluidic connection and electrical connection to a high-voltage electrode. FIG. 51B shows another embodiment of the reservoir 5105, which may be substantially similar to reservoir 5100 with further changes for injection molding compatibility. For example, the second through-hole step 5106 may be minimized in size except where needed for the second through-hole wall.

The first through-hole 5101 may for example have an elliptical shape. Alternatively, the first through-hole 5101 may be circular. The first through-hole 5101 may have any shape desired by one or ordinary skill in the art.

The second through-hole 5102 may for example be circular. Alternatively, the second through-hole 5102 may have an elliptical shape. The second through-hole 5002 may have any shape desired by one or ordinary skill in the art.

The first through-hole 5101 may have a diameter within a range of about 100 um to about 3 mm.

The first through-hole 5101 may have a maximum dimension across of less than about 1.5 mm, for example less than about 1 mm.

The second through-hole 5102 may have a diameter within a range of about 100 um to about 3 mm.

The second through-hole 5102 may have a maximum dimension across of less than about 1.5 mm, for example less than about 1 mm.

The first through-hole 5101 may be an elongate through-hole that penetrates the surface of the chip to couple the reservoir 5100 to the channel 5104. The first through-hole 5101 may, for example, be cylindrical as described herein. The first through-hole 5101 may, for example, have a height from the channel 5104 to the reservoir 5100 within a range of about 1 mm to about 3 mm.

The second through-hole 5102 may be an elongate through-hole that penetrates the surface of the chip to couple the reservoir 5100 to the channel 5104. The second through-hole 5102 may, for example, be cylindrical as described herein.

The second through-hole 5102 may have a height above the channel 5104 greater than the height above the channel of the first through-hole 5101.

The reservoir 5100 may comprise a circular cross-section. Alternatively, the reservoir 5100 may comprise an elongate or oval cross-section.

In some embodiments, the channel 5104 below the reservoir 5100 may comprise a break as shown in FIG. 50A1 and the first and second through-holes 5101, 5102 may be in fluidic and/or electrical communication with first and second terminating ends of the channel 5104 as described herein. The first and second through-holes 5101, 5102 may be positioned at different heights within the reservoir. The first through-hole 5101 may enter the reservoir 5100 at a position lower in the reservoir than the second through-hole 5102. The first and second through-holes 5101, 5102 may be separated by a step or platform 5106 as described herein.

The reservoir 5100 may be circular. The reservoir 5100 may have a diameter of about 5.3 mm.

The reservoir 5100 may be defined by a wall having a height of no more than 25 mm, no more than 15 mm, no more than 10 mm, or greater than 10 mm. The reservoir 5100 may have height of about 6 mm. The reservoir 5100 may have height within a range of about 8 mm to about 10 mm.

The first and second through holes 5101, 5102 may have areas within a range of about 0.2 mm$^2$ to 7 mm2. The first through-hole 5101 may have an area within a range of about 1 mm$^2$ to about 2.75 mm$^2$. For example the second through-hole 5102 may have an area within a range of about 0.8 mm$^2$ to about 1.5 mm$^2$.

The through-holes 5101, 5102 may have substantially the same shape. The through-holes 5101, 5102 may have different shapes.

The first through-hole 5101 may have a shape of a square, a rectangle, an oval, or have an elongated direction in a direction of the width of the channel 5104 or the width of the reservoir 5100.

The second through-hole 5102 may have a shape of a square, a rectangle, an oval, or have an elongated direction in a direction of the width of the channel 5104 or the width of the reservoir 5100.

The through-holes 5101, 5102 may be arranged along a longitudinal axis of the channel 5003.

The first through-hole 5101 may have a maximum distance across (i.e. length) of about 1.75 mm and a minimum distance across (i.e. width) of about 1.3 mm.

The second through-hole 5102 may be relatively circular with a diameter of about 1.2 mm. The second through-hole 5102 may be shaped so as to spread the electrical field evenly across the reservoir 5100.

The second through-hole 5102 may enter the reservoir though a platform 5106 in the reservoir 5100 positioned about 1 mm to about 6 mm above a point of entry into the reservoir 5100 of the first through-hole 5101.

The volume of the reservoir 5100 between the first and second through-holes 5101, 5102 may be no more than about 2.5 ml, 1 ml, or 0.5 ml. The volume of the reservoir 5100 between the first and second through-holes 5101, 5102 may be about 0.1 mL.

At least part of each through-hole 5101, 5102 may be substantially co-extensive with the fluidic channel 5104 across said width of said fluidic channel 5104.

The first through-hole 5101 may comprise at least one side, for example one or two sides, that span the width of the fluidic channel 5104 and/or a width of the reservoir 5100. The at least one side(s) may (each) be at least 75% linear.

The second through-hole 5102 may comprise at least one side, for example one or two sides, that span the width of the fluidic channel 5104 and/or a width of the reservoir 5100. The at least one side(s) may (each) be at least 75% linear.

The first and second through-holes 5101, 5102 may have a shape that, when said fluidic channel 5104 and said reservoir 5100 comprise an electrically conductive fluid and an electric current is passed through said fluidic channel 5104, at least 5%, at least 6%, at least 7%, at least 10%, or at least 20% of said electric current passes through said reservoir 5100 between the first and the second through-holes 5101, 5102.

Figure 51D:
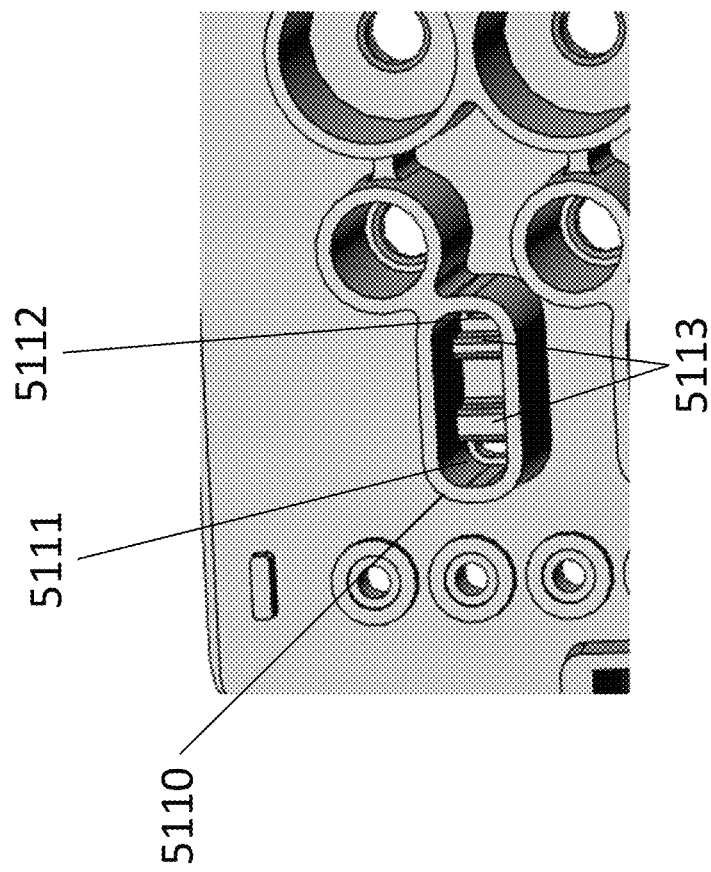
FIGS. 51C and 51D show two views of a third embodiment of this reservoir design.
Figure 51C:
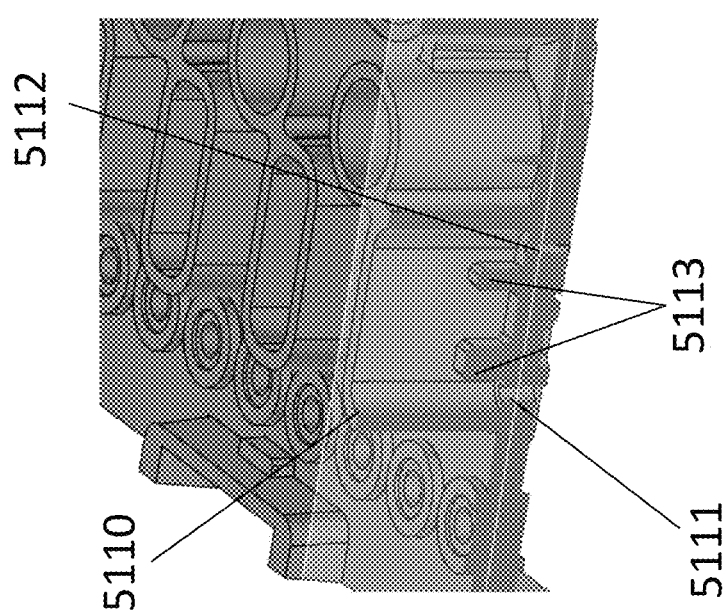

FIGS. 51C and 51D show two views of another embodiment of a reservoir 5110. The reservoir 5110 may be located on any of the chip devices described herein. The reservoir 5110 may have an elongate or oval cross-section. The reservoir 5110 may be configured to hold a volume of elution buffer as described herein. Upon completion of an ITP run, the target nucleic acids may reside within this volume as described herein. The reservoir 5110 may comprise a first through-hole or aperture 5111 and a second through-hole or aperture 5112. Each of the two through-holes 5111, 5112 may be connected to a fluidic channel on a bottom layer of the fluidic device. The first and second through-holes 5111, 5112 may penetrate the chip surface and be in communication with a fluidic channel located below the reservoir 5110 as described herein. The fluidic channel may for example be an elution channel as described herein.

The first through-hole 5111 and the second through-hole 5111 may be on the same plane within the reservoir 5110. The first through-hole 5111 and the second through-hole 5111 may be separated by vertical gates 5113 that rise above the plane of the through-holes 5111, 5112. The vertical gates 5113 may act to drive the target nucleic acids up into the reservoir 5110. This may facilitate the buoyant effect described herein and aid in lifting the target nucleic acids from the channel into the reservoir 5110. In some instances, ITP may be performed at a lower driving current than necessary to lift the target nucleic acids into the reservoir by the buoyant effect alone (without the aid of the vertical gates 5113). The first and second through-holes 5111, 5112 may be generally aligned with each other and with a longitudinal axis of the fluidic channel such that application of a fluid into the channel via the second through-hole 5112 pushes the fluid along the channel towards the first through-hole 5111 as described herein. The second through-hole 5112 may be used to create a fluidic connection and electrical connection to a high-voltage electrode.

The first through-hole 5111 may for example have a D-shaped cross-section with a straight wall defied by one of the vertical gates 5113. Alternatively, the first through-hole 5111 may have an elliptical shape. Alternatively, the first through-hole 5111 may be circular. The first through-hole 5111 may have any shape desired by one or ordinary skill in the art.

The second through-hole 5112 may for example have a D-shaped cross-section with a straight wall defied by one of the vertical gates 5113. Alternatively, the second through-hole 5112 may have an elliptical shape Alternatively, the second through-hole 5112 may be circular. The second through-hole 5112 may have any shape desired by one or ordinary skill in the art.

The first through-hole 5111 may have a diameter within a range of about 100 um to about 3 mm. The first through-hole 5111 may have a diameter of about 1.2 mm.

The first through-hole 5111 may have a maximum dimension across of less than about 1.5 mm, for example less than about 1 mm.

The second through-hole 5112 may have a diameter within a range of about 100 um to about 3 mm. The first through-hole 5111 may have a diameter of about 1.2 mm.

The second through-hole 5112 may have a maximum dimension across of less than about 1.5 mm, for example less than about 1 mm.

The first through-hole 5111 may be an elongate through-hole that penetrates the surface of the chip to couple the reservoir 5110 to the channel. The first through-hole 5111 may, for example, be cylindrical as described herein. The first through-hole 5111 may, for example, have a height from the channel to the reservoir 5110 within a range of about 1 mm to about 3 mm.

The second through-hole 5112 may be an elongate through-hole that penetrates the surface of the chip to couple the reservoir 5110 to the channel. The second through-hole 5112 may, for example, be cylindrical as described herein.

The vertical gate 5113 may have a height above the channel greater than the height above the channel of the first through-hole 5111.

The vertical gate 5113 may have a height above the channel greater than the height above the channel of the second through-hole 5112.

The reservoir 5110 may comprise a circular cross-section. Alternatively, the reservoir 5110 may comprise an elongate or oval cross-section.

The reservoir 5110 may comprise an elongate shape, for example an elliptical shape, having a maximum diameter (i.e. length) across of about 7 mm and a minimum diameter across (i.e. width) of about 3.4 mm.

The reservoir 5110 may have a height of no more than about 20 mm, no more than about 15 mm, no more than about 10 mm, or greater than 10 mm. For example, reservoir 5110 may have a height of about 6 mm. Alternatively, the reservoir 5110 may have a height within a range of about 8 mm to about 10 mm.

In some embodiments, the channel below the reservoir 5110 may comprise a break as shown in FIG. 50A1 and the first and second through-holes 5111, 5112 may be in fluidic and/or electrical communication with first and second terminating ends of the channel as described herein. The first and second through-holes 5111, 5112 may be positioned at different heights within the reservoir 5110. The first through-hole 5111 may enter the reservoir 5110 at a position lower in the reservoir than the second through-hole 5112. The first and second through-holes 5111, 512 may be separated steps or gates 5113 as described herein.

The reservoir 5110 may be defined by a wall having a height of no more than 25 mm, no more than 15 mm, no more than 10 mm, or greater than 10 mm. The reservoir 5110 may have height of about 6 mm. The reservoir 5110 may have height within a range of about 8 mm to about 10 mm.

The first and second through holes 5111, 5112 may have areas within a range of about 0.2 mm² to 7 mm2. The first through-hole 5111 may have an area within a range of about 1 mm² to about 2.75 mm². For example the second through-hole 5102 may have an area within a range of about 0.8 mm² to about 1.5 mm².

The through-holes 5111, 5112 may have substantially the same shape. The through-holes 5101, 5102 may have different shapes.

The first through-hole 5111 may have a shape of a square, a rectangle, an oval, or have an elongated direction in a direction of the width of the channel or the width of the reservoir 5110.

The second through-hole 5112 may have a shape of a square, a rectangle, an oval, or have an elongated direction in a direction of the width of the channel or the width of the reservoir 5110.

The through-holes 5111, 5112 may be arranged along a longitudinal axis of the channel.

The first through-hole 5111 may have a maximum distance across (i.e. length) of about 1.2 mm.

The second through-hole 5112 may have a maximum distance across (i.e. length) of about 1.2 mm.

The volume of the reservoir 5110 between the first and second through-holes 5111, 5112 may be no more than about 2.5 ml, 1 ml, or 0.5 ml. The volume of the reservoir 5110 between the first and second through-holes 5111, 5112 may be about 0.1 mL.

At least part of each through-hole 5111, 5112 may be substantially co-extensive with the fluidic channel across said width of said fluidic channel.

The first through-hole 5111 may comprise at least one side, for example one or two sides, that span the width of the fluidic channel and/or a width of the reservoir 5110. The at least one side(s) may (each) be at least 75% linear.

The second through-hole 5112 may comprise at least one side, for example one or two sides, that span the width of the fluidic channel and/or a width of the reservoir 5110. The at least one side(s) may (each) be at least 75% linear.

The first and second through-holes 5111, 5112 may have a shape that, when said fluidic channel and said reservoir

5110 comprise an electrically conductive fluid and an electric current is passed through said fluidic channel, at least 5%, at least 6%, at least 7%, at least 10%, or at least 20% of said electric current passes through said reservoir 5110 between the first and the second through-holes 5111, 5112.

Figure 51E:
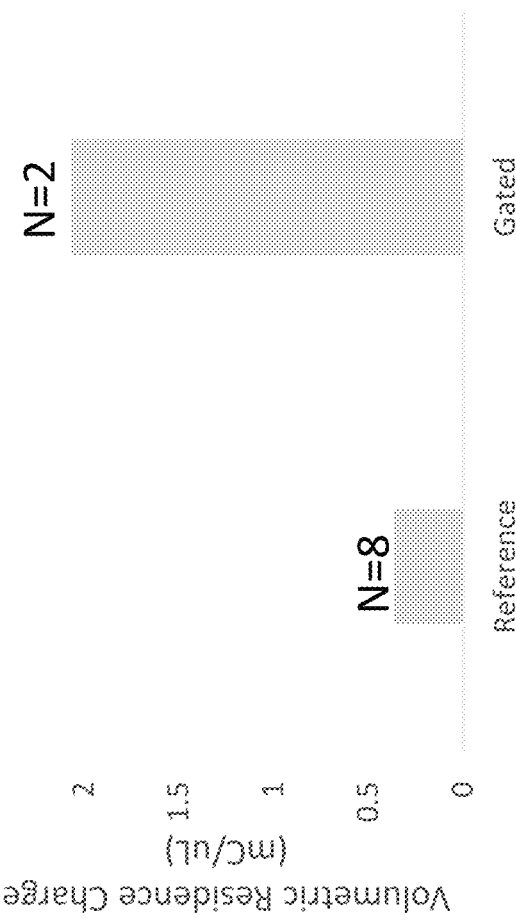
FIG. 51E shows a comparison of the residence time of nucleic acid between the disclosed design and a reference design.
Figure 51F:
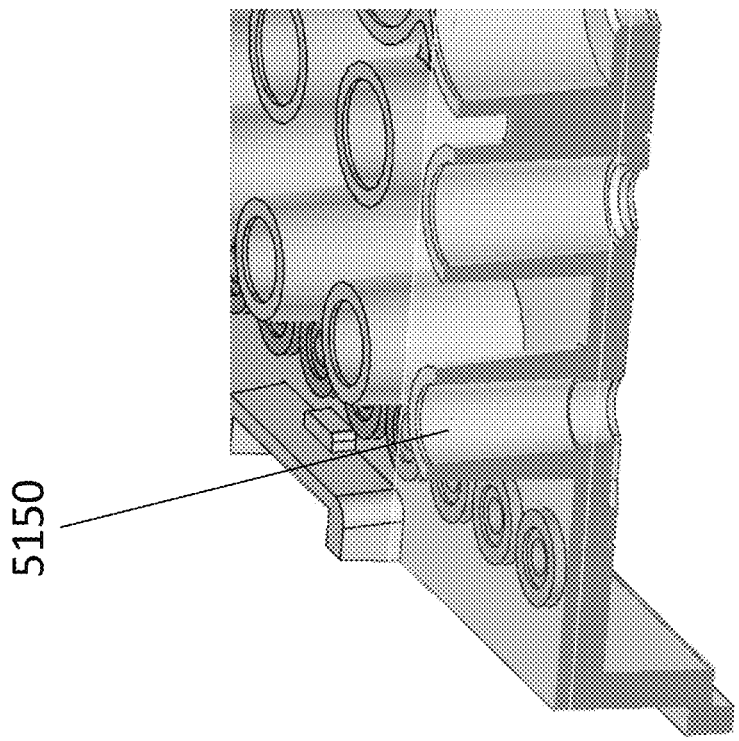
FIG. 51F shows a cross-section of the reference design. It is a drafted vertical cylinder without any internal structure.

FIG. 51E shows a comparison of the residence time of nucleic acid between the reservoir design 5110 and a reference design 5150. The residence time is scaled by applied current and the liquid volume inside the reservoir to produce a volumetric residence charge, with units C/uL. There was a greater than four-fold increase in volumetric residence charge from the gated design 5110 (n=2) compared to the reference design 5150 without a gate (n=8). FIG. 51F shows a cross-section of the reference design 5150 having a drafted vertical cylinder without any internal structure. The reference design 5150 was substantially similar to the reservoir described in FIG. 50B.

FIG. 52A shows another embodiment of a fluidic reservoir 5200. The reservoir 5200 may be located on any of the chip devices described herein. The reservoir 5200 may have a circular cross-section. The reservoir 5200 may be configured to hold a volume of elution buffer as described herein. Upon completion of an ITP run, the target nucleic acids may reside within this volume as described herein. The reservoir 5200 may comprise a first through-hole or aperture 5201 and a second through-hole or aperture 5202. Each of the two through-holes 5201, 5202 may be connected to a fluidic channel on a bottom layer of the fluidic device. The first and second through-holes 5201, 5202 may penetrate the chip surface and be in communication with a fluidic channel located below the reservoir 5200 as described herein. The fluidic channel may for example be an elution channel as described herein. The first through-hole 5201 and the second through-hole 5202 may open onto different plane within the reservoir 5200. The first through-hole 5201 may be an elliptical through-hole 5201 dimensioned such that a pipette tip can be easily positioned for reliable fluid recovery from the channel of the device. The first and second through-holes 5201, 5202 may be generally aligned with each other and with a longitudinal axis of the fluidic channel such that application of a fluid into the channel via the second through-hole 5202 pushes the fluid along the channel towards the first through-hole 5201 as described herein. The second through-hole 5202 may be used to create a fluidic connection and electrical connection to a high-voltage electrode. As shown in FIG. 52B, a pipette tip 5203 can be inserted into the first through-hole 5201 until interference between pipette tip and one or more walls of the first through-hole 5201 prevents further insertion at a defined coupling position. The coupling position can be defined to ensure an unrestricted path between the fluid volume of the fluidic device and the inlet hole of the pipette tip. Retraction force may be reduced by minimizing points of contact to two points 5204. Shown in FIG. 52C, the major and minor axes of the first through-hole 5201 can be dimensioned such that, when the coupling position is achieved, a fluidic pathway 5205 is maintained around the pipette tip 5203.

The first through-hole 5201 may for example have an elliptical shape. Alternatively, the first through-hole 5201 may be circular. The first through-hole 5201 may have any shape desired by one or ordinary skill in the art.

The second through-hole 5202 may for example have an elliptical shape Alternatively, the second through-hole 5202 may be circular. The second through-hole 5202 may have any shape desired by one or ordinary skill in the art.

The first through-hole 5201 may have a diameter within a range of about 100 um to about 3 mm.

The first through-hole 5201 may have a maximum dimension across of less than about 1.5 mm, for example less than about 1 mm.

The second through-hole 5202 may have a diameter within a range of about 100 um to about 3 mm.

The second through-hole 5202 may have a maximum dimension across of less than about 1.5 mm, for example less than about 1 mm.

The first through-hole 5201 may be an elongate through-hole that penetrates the surface of the chip to couple the reservoir 5200 to the channel. The first through-hole 5201 may, for example, be cylindrical as described herein. The first through-hole 5201 may, for example, have a height from the channel to the reservoir 5200 within a range of about 1 mm to about 3 mm.

The second through-hole 5202 may be an elongate through-hole that penetrates the surface of the chip to couple the reservoir 5200 to the channel. The second through-hole 5202 may, for example, be cylindrical as described herein.

The second through-hole 5202 may have a height above the channel greater than the height above the channel of the first through-hole 5201.

The reservoir 5200 may comprise a circular cross-section. Alternatively, the reservoir 5200 may comprise an elongate or oval cross-section.

In some embodiments, the channel below the reservoir 5200 may comprise a break as shown in FIG. 50A1 and the first and second through-holes 5201, 5202 may be in fluidic and/or electrical communication with first and second terminating ends of the channel as described herein. The first and second through-holes 5201, 5202 may be positioned at different heights within the reservoir. The first through-hole 5201 may enter the reservoir 5200 at a position lower in the reservoir than the second through-hole 5102. The first and second through-holes 5201, 5202 may be separated by a step or platform 5206 as described herein.

The reservoir 5200 may be circular. The reservoir 5200 may have a diameter of about 5.3 mm.

The reservoir 5200 may be defined by a wall having a height of no more than 25 mm, no more than 15 mm, no more than 10 mm, or greater than 10 mm. The reservoir 5200 may have height of about 6 mm. The reservoir 5200 may have height within a range of about 8 mm to about 10 mm.

The first and second through holes 5201, 5202 may have areas within a range of about 0.2 mm$^2$ to 7 mm2. The first through-hole 5201 may have an area within a range of about 1 mm$^2$ to about 2.75 mm$^2$. For example the second through-hole 5202 may have an area within a range of about 0.8 mm$^2$ to about 1.5 mm$^2$.

The through-holes 5201, 5202 may have substantially the same shape. The through-holes 5201, 5202 may have different shapes.

The first through-hole 5201 may have a shape of a square, a rectangle, an oval, or have an elongated direction in a direction of the width of the channel or the width of the reservoir 5200.

The second through-hole 5202 may have a shape of a square, a rectangle, an oval, or have an elongated direction in a direction of the width of the channel or the width of the reservoir 5200.

The through-holes 5201, 5202 may be arranged along a longitudinal axis of the channel 5003.

The first through-hole 5201 may have a maximum distance across (i.e. length) of about 1.75 mm and a minimum distance across (i.e. width) of about 1.3 mm.

The second through-hole 5202 may be relatively circular with a diameter of about 1.2 mm. The second through-hole 5202 may be shaped so as to spread the electrical field evenly across the reservoir 5200.

The second through-hole 5202 may enter the reservoir though a platform 5126 in the reservoir 5200 positioned about 1 mm to about 6 mm above a point of entry into the reservoir 5200 of the first through-hole 5201.

The volume of the reservoir 5200 between the first and second through-holes 5201, 5202 may be no more than about 2.5 ml, 1 ml, or 0.5 ml. The volume of the reservoir 5200 between the first and second through-holes 5201, 5202 may be about 0.1 mL.

At least part of each through-hole 5201, 5202 may be substantially co-extensive with the fluidic channel across said width of said fluidic channel.

The first through-hole 5201 may comprise at least one side, for example one or two sides, that span the width of the fluidic channel and/or a width of the reservoir 5200. The at least one side(s) may (each) be at least 75% linear.

The second through-hole 5202 may comprise at least one side, for example one or two sides, that span the width of the fluidic channel and/or a width of the reservoir 5200. The at least one side(s) may (each) be at least 75% linear.

The first and second through-holes 5201, 5202 may have a shape that, when said fluidic channel and said reservoir 5200 comprise an electrically conductive fluid and an electric current is passed through said fluidic channel, at least 5%, at least 6%, at least 7%, at least 10%, or at least 20% of said electric current passes through said reservoir 5200 between the first and the second through-holes 5201, 5202.

Figure 52D:
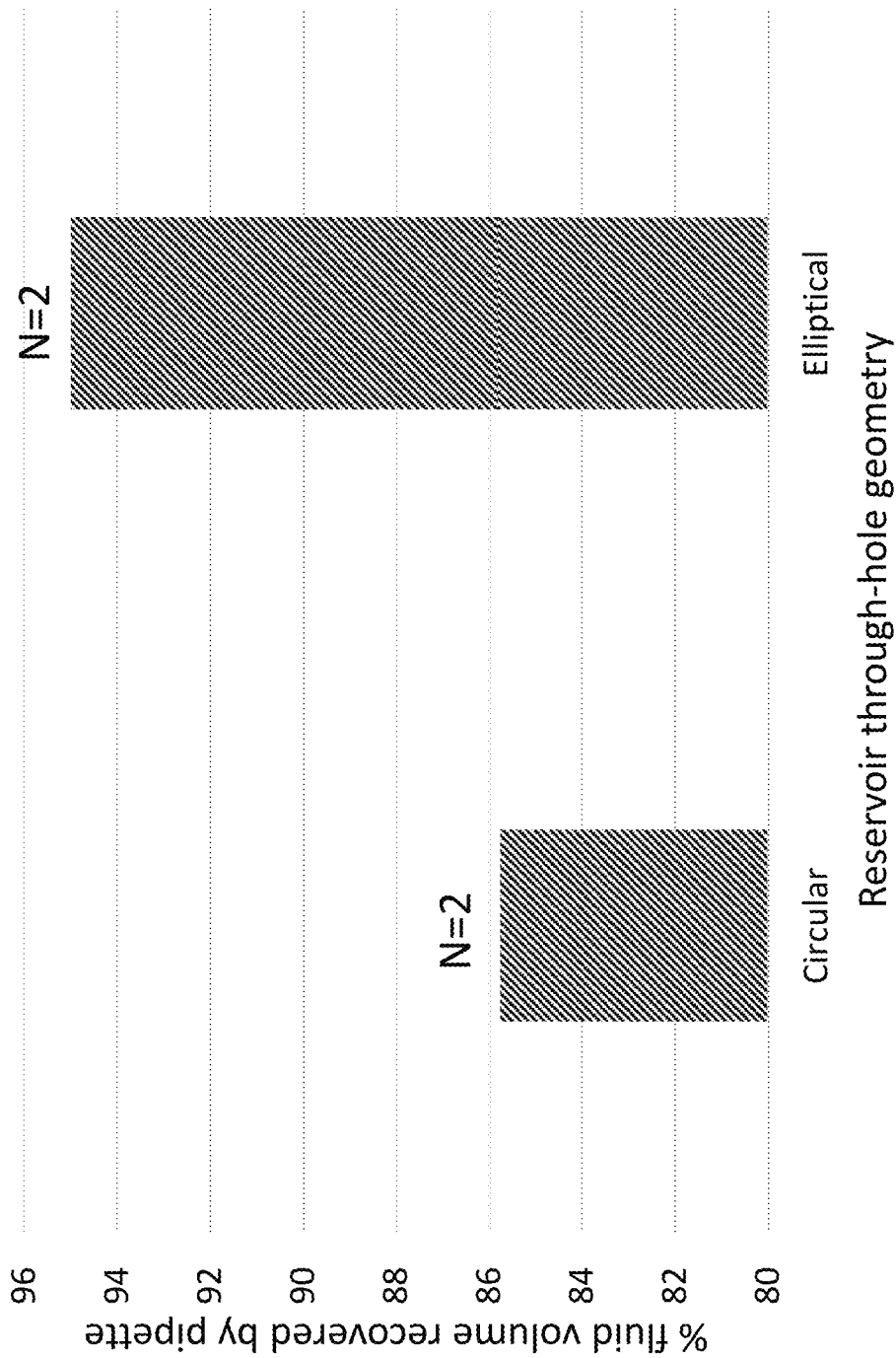

FIG. 52D shows a comparison between a reservoir 5200 with a circular first through-hole 5201 pipette interface (n=2) and one with an elliptical first through-hole 5201 interface (n=2) for fluidic volume recovery. The circular through-hole design served as a control whereby the pipette tip was not constrained to a precise coupling position. The present disclosure provides, in some embodiments, a fluidic reservoir 5200 with an elliptical through-hole interface 5201 that may allow for the precise positioning of a pipette for maximized fluid evacuation. The fluidic reservoir 5200 may be incorporated in a larger fluidic device. Positioning may be achieved by the constraining of the pipette tip upon insertion to a final coupling position. The elliptical geometry of the through-hole 5201 may allow unrestricted fluid flow around the pipette tip and may reduce the force required to retract the pipette tip from its coupling position. Retraction force may be minimized by the design limiting contact between pipette tip and reservoir through-hole 5201 to two points 5204. Minimized retraction force mitigates the risk of disturbing the position of the fluidic device upon retraction.

Figures 53A, 53B:
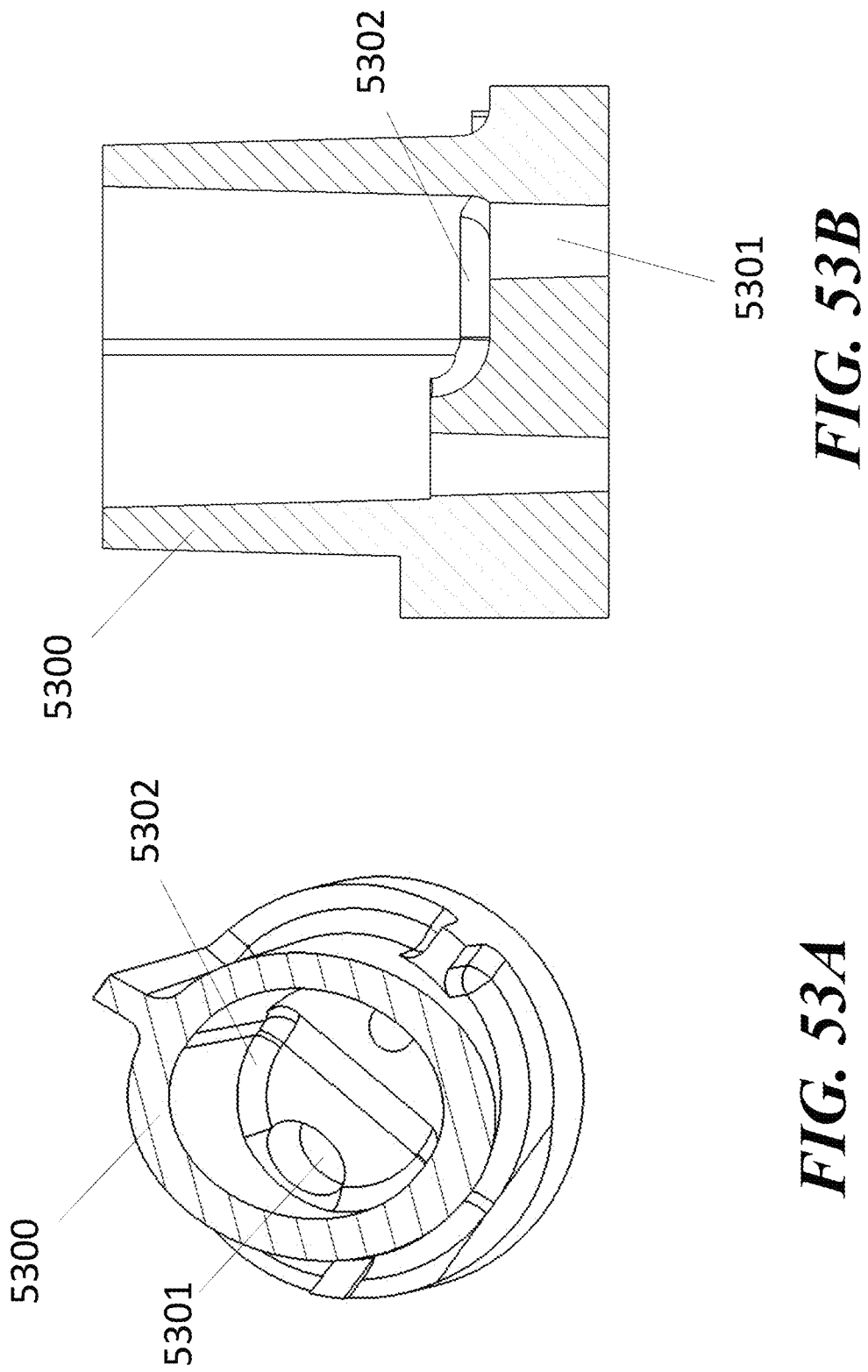
FIGS. 53A-53C show another exemplary fluidic reservoir.
Figure 53C:
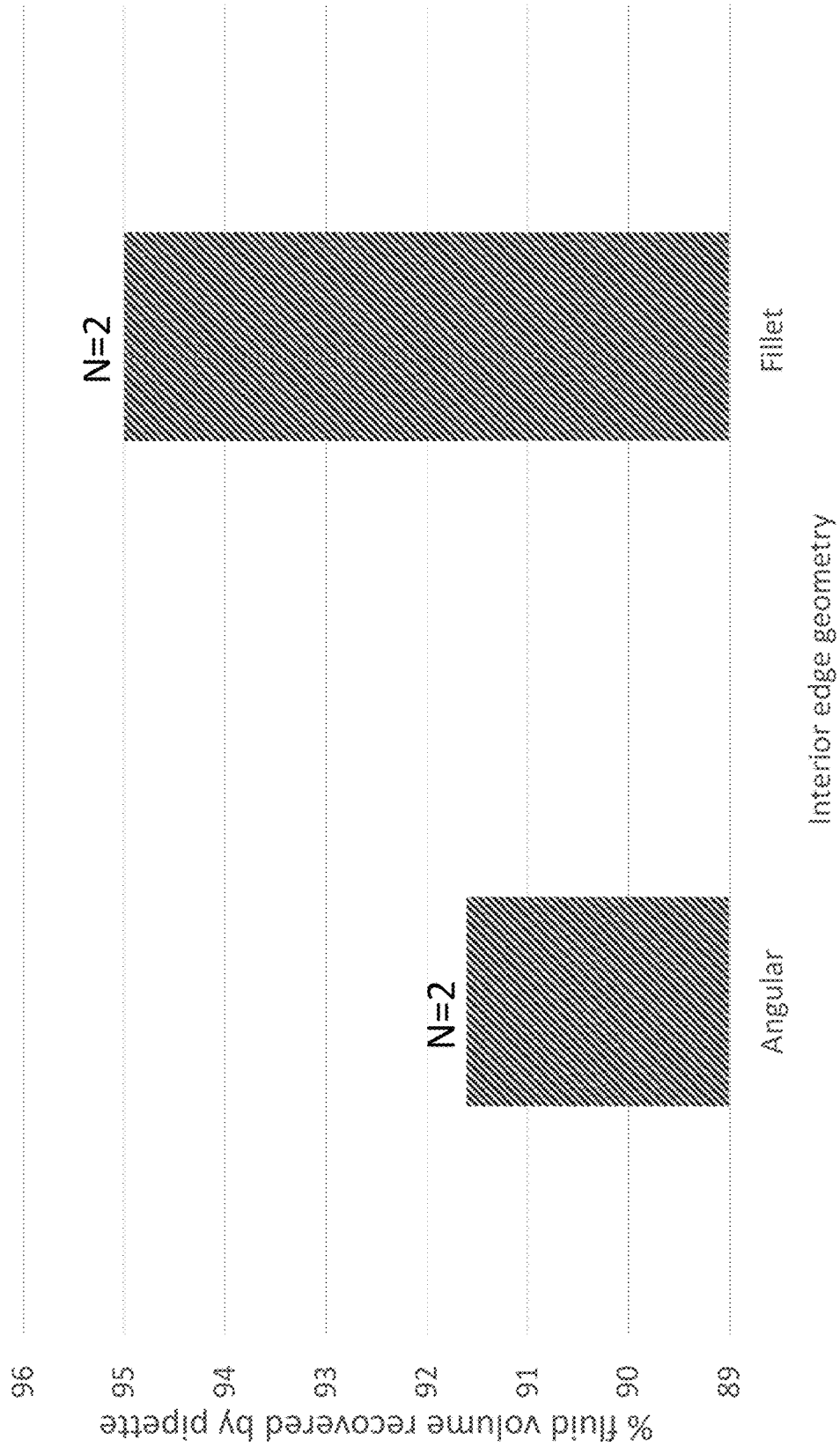

FIG. 53A shows an exemplary fluidic reservoir 5300. The reservoir 5300 may be substantially similar to reservoir 5200 but with rounded edge 5302 that may favor drainage toward the first through-hole extraction site 5301. FIG. 53B depicts an alternate view of reservoir 5300. FIG. 53C shows a comparison between a reservoir with angular interior edges (e.g. reservoir 5200) and one with filleted interior edges 5304 (e.g. reservoir 5300) for fluidic volume recovery.

Figure 53E:
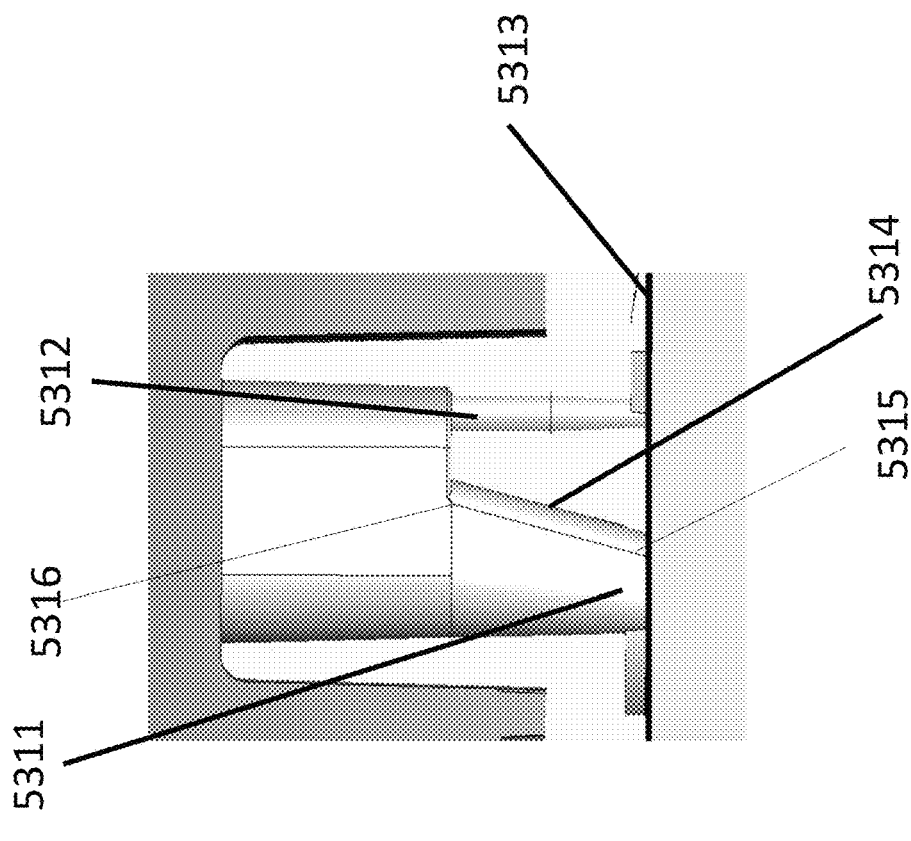
FIG. 53E shows a section view of the elution reservoir of FIG. 53D.
Figure 53D:
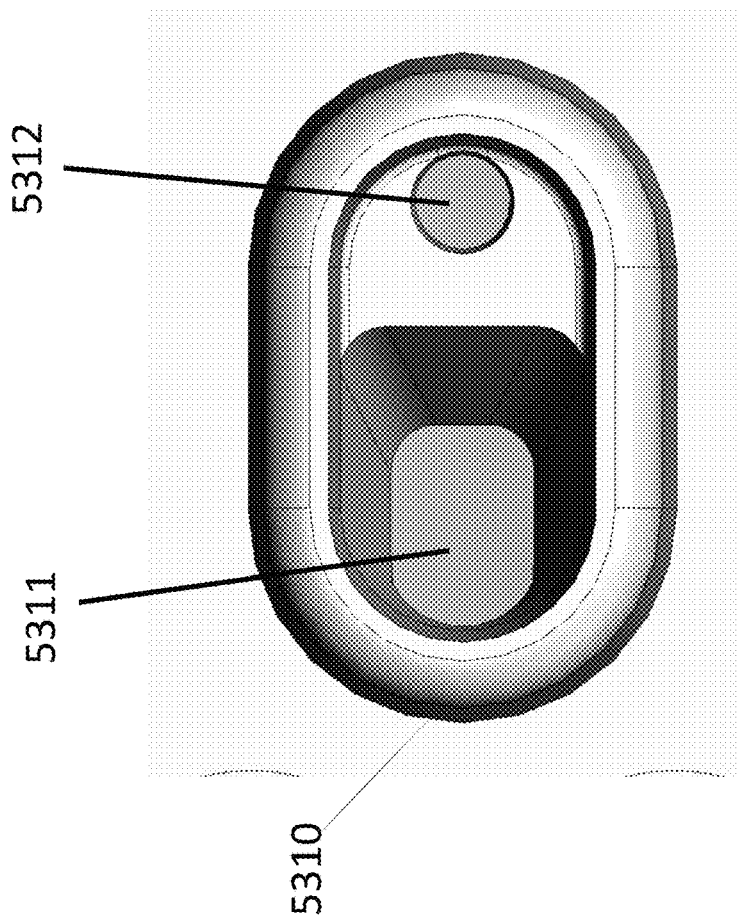
FIG. 53D shows a top view of an exemplary elution reservoir.

FIG. 53D shows a top view of an exemplary elution reservoir 5310. FIG. 53E shows a section view of the elution reservoir 5310. The reservoir 5310 may be located on any of the chip devices described herein. The reservoir 5310 may have an elongate or oval cross-section. The reservoir 5310 may be configured to hold a volume of elution buffer as described herein. Upon completion of an ITP run, the target nucleic acids may reside within this volume as described herein. The reservoir 5310 may comprise a first through-hole or aperture 5311 and a second through-hole or aperture 5312. Each of the two through-holes 5311, 5312 may be connected to a fluidic channel 5313 on a bottom layer of the fluidic device. The first and second through-holes 5311, 5312 may penetrate the chip surface and be in communication with a fluidic channel 5313 located below the reservoir 5310 as described herein. The fluidic channel 5313 may for example be an elution channel as described herein. The first through-hole 5311 and the second through-hole 5311 may be on the same plane within the reservoir 5310. The first through-hole 5311 may be dimensioned such that a pipette tip can be easily positioned for reliable fluid recovery from said device. For example, the first through-hole 5311 may comprise a guide wall 5314 configured to guide placement of the pipette tip toward the channel 5313. The guide wall 5314 may be configured to constrain the pipette tip orientation and position to properly align the pipette tip with the channel 5313. The guide wall 5314 may, for example, have a narrower region 5315 located at the channel 5313 and the wider region of 5316 located at the entry way for ambient air of the loading reservoir 5300. The wider portion 5316 and the narrower portion 5315 may have a D-shaped cross-section. The guide wall 5314 may taper between the wider portion 5316 and the narrower portion 5315 at an angle configured to guide the pipette to channel 5313.

The first and second through-holes 5311, 5312 may be generally aligned with each other and with a longitudinal axis of the fluidic channel 5313 such that application of a fluid into the channel 5313 via the second through-hole 5312 pushes the fluid along the channel 5313 towards the first through-hole 5311 as described herein. The second through-hole 5312 may be used to create a fluidic connection and electrical connection to a high-voltage electrode.

The first through-hole 5311 may for example have a D-shaped cross-section. Alternatively, the first through-hole 5311 may have an elliptical shape. Alternatively, the first through-hole 5311 may be circular. The first through-hole 5311 may have any shape desired by one or ordinary skill in the art.

The second through-hole 5312 may for example have a D-shaped cross-section. Alternatively, the second through-hole 5312 may have an elliptical shape Alternatively, the second through-hole 5312 may be circular. The second through-hole 5312 may have any shape desired by one or ordinary skill in the art.

The first through-hole 5211 may have a diameter within a range of about 100 um to about 3 mm.

The wider portion 5316 of the first through-hole 5211 may have a diameter within a range of about 100 um to about 3 mm.

The narrower portion 5315 of the first through-hole 5211 may have a diameter within a range of about 100 um to about 3 mm.

The first through-hole 5311 may have a maximum dimension across of less than about 1.5 mm, for example less than about 1 mm.

The guide wall 5314 may taper between the wider portion 5316 and the narrower portion 5315 at an angle configured to guide the pipette to channel 5313. The guide wall 5314 may taper at an angle within a range of about 60 degrees to about 90 degrees.

The second through-hole 5312 may have a diameter within a range of about 100 um to about 3 mm.

The second through-hole 5312 may have a maximum dimension across of less than about 1.5 mm, for example less than about 1 mm.

The first through-hole 5311 may be an elongate through-hole that penetrates the surface of the chip to couple the reservoir 5310 to the channel. The first through-hole 5311 may, for example, be tapered as described herein. The first through-hole 5311 may, for example, have a height from the channel to the reservoir 5310 within a range of about 1 mm to about 3 mm.

The second through-hole 5312 may be an elongate through-hole that penetrates the surface of the chip to couple the reservoir 5310 to the channel. The second through-hole 5312 may, for example, be cylindrical as described herein.

The reservoir 5310 may comprise a circular cross-section. Alternatively, the reservoir 5310 may comprise an elongate or oval cross-section.

In some embodiments, the channel 5313 below the reservoir 5310 may comprise a break as shown in FIG. 50A1 and the first and second through-holes 5311, 5312 may be in fluidic and/or electrical communication with first and second terminating ends of the channel 5313 as described herein. The first and second through-holes 5311, 5312 may be positioned at different heights within the reservoir 5310. The first through-hole 5311 may enter the reservoir 5310 at a position lower in the reservoir than the second through-hole 5312. The first and second through-holes 5311, 5312 may be separated by a step or platform as described herein.

The reservoir 5310 may comprise an elongate shape, for example an elliptical shape, having a maximum diameter (i.e. length) across of about 7 mm and a minimum diameter across (i.e. width) of about 3.4 mm.

The reservoir 5310 may be defined by a wall having a height of no more than 25 mm, no more than 15 mm, no more than 10 mm, or greater than 10 mm. The reservoir 5310 may have height of about 6 mm. The reservoir 5310 may have height within a range of about 8 mm to about 10 mm.

The first and second through holes 5311, 5312 may have areas within a range of about 0.2 mm$^2$ to 7 mm2. The first through-hole 5311 may have an area within a range of about 1 mm$^2$ to about 2.75 mm$^2$. For example the second through-hole 5312 may have an area within a range of about 0.8 mm$^2$ to about 1.5 mm$^2$.

The through-holes 5311, 5312 may have substantially the same shape. The through-holes 5311, 5312 may have different shapes.

The first through-hole 5311 may have a shape of a square, a rectangle, an oval, or have an elongated direction in a direction of the width of the channel 5313 or the width of the reservoir 5310. The first through-hole 5311 may be D-shaped.

The second through-hole 5312 may have a shape of a square, a rectangle, an oval, or have an elongated direction in a direction of the width of the channel 5313 or the width of the reservoir 5310.

The through-holes 5311, 5312 may be arranged along a longitudinal axis of the channel 5313.

The first through-hole 5311 may have a maximum distance across (i.e. length) of about 1.75 mm and a minimum distance across (i.e. width) of about 1.3 mm.

The second through-hole 5312 may be relatively circular with a diameter of about 1.2 mm. The second through-hole 5312 may be shaped so as to spread the electrical field evenly across the reservoir 5310.

The volume of the reservoir 5310 between the first and second through-holes 5311, 5312 may be no more than about 2.5 ml, 1 ml, or 0.5 ml. The volume of the reservoir 5200 between the first and second through-holes 5311, 5312 may be about 0.1 mL.

At least part of each through-hole 5311, 5312 may be substantially co-extensive with the fluidic channel 5313 across said width of said fluidic channel 5313.

The first through-hole 5311 may comprise at least one side, for example one or two sides, that span the width of the fluidic channel 5313 and/or a width of the reservoir 5310. The at least one side(s) may (each) be at least 75% linear.

The second through-hole 5312 may comprise at least one side, for example one or two sides, that span the width of the fluidic channel 5313 and/or a width of the reservoir 5310. The at least one side(s) may (each) be at least 75% linear.

The first and second through-holes 5311, 5312 may have a shape that, when said fluidic channel and said reservoir 5310 comprise an electrically conductive fluid and an electric current is passed through said fluidic channel, at least 5%, at least 6%, at least 7%, at least 10%, or at least 20% of said electric current passes through said reservoir 5310 between the first and the second through-holes 5311, 5312.

In some embodiments, this disclosure provides a fluidic reservoir with rounded interior edges that maximize drainage toward a through-hole upon extraction of fluid from the through-hole. The rounded edges maximize recovery of fluid from the reservoir by reducing the fluid volume required to wet between the horizontal floor and vertical walls of the reservoir. Additionally, the rounded edges minimize wetted surface area inside of the reservoir, improving recovery of fluid.

Channels on a fluidic device can be closed. For example, a mechanical actuator coupled to a mechanical member can be used to apply pressure to completely or partially close a channel (e.g., by deformation of the channel). Elution reservoirs can be closed off from the ITP channel to define a fixed elution volume. Channel closing can result in reduced flow or completely blocked flow. Channel closing can result in increased resistance to fluid flow. In some instances, channel closing can increase fluidic resistance by a factor of at least 2, 3, 4, 5, 10, 20, 30, 40, 50, 60, 70, 80, 90, or 100.

Figure 6A:
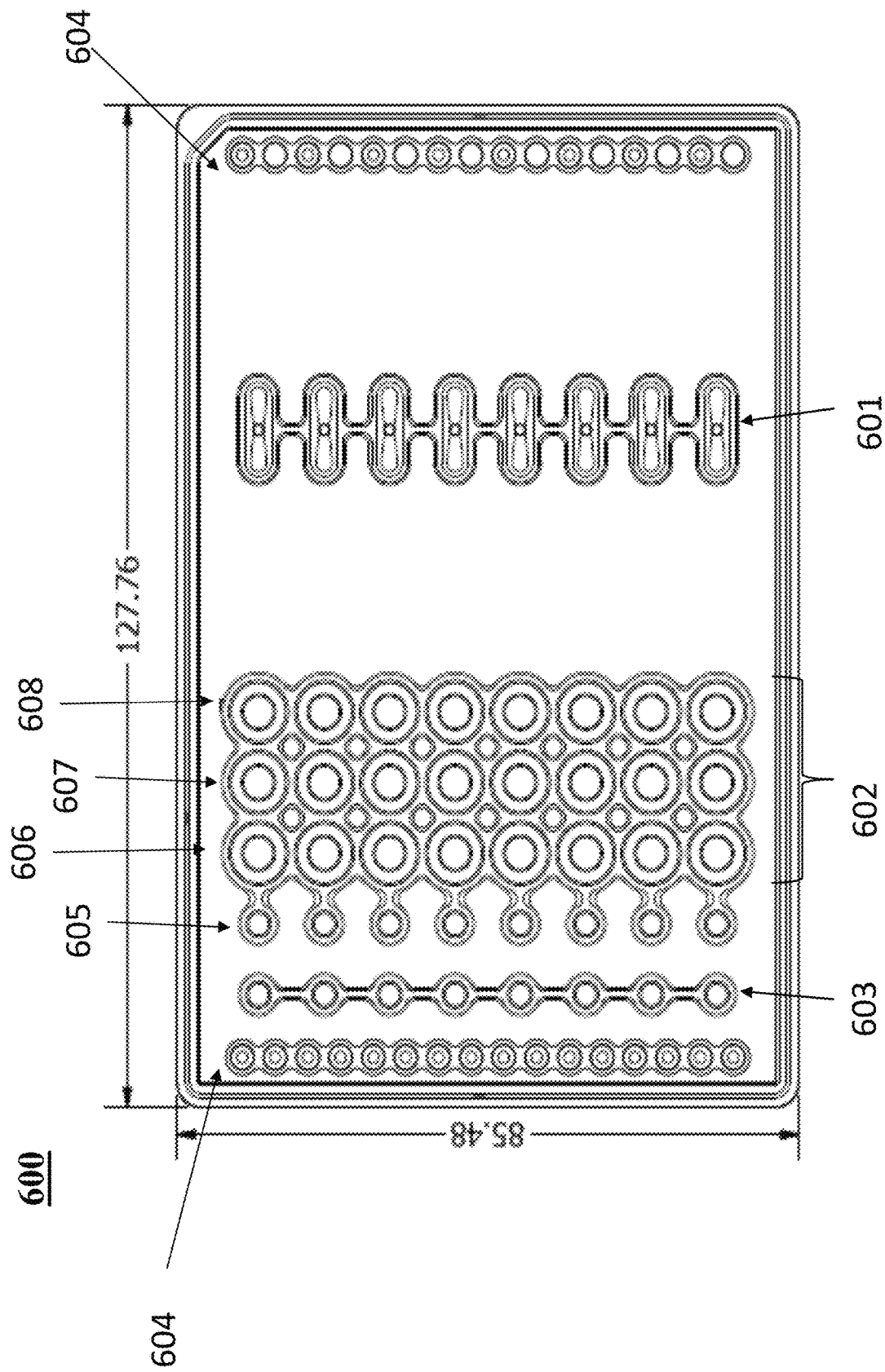
FIG. 6A shows an exemplary top view schematic of a fluidic device cartridge.
Figure 6B:
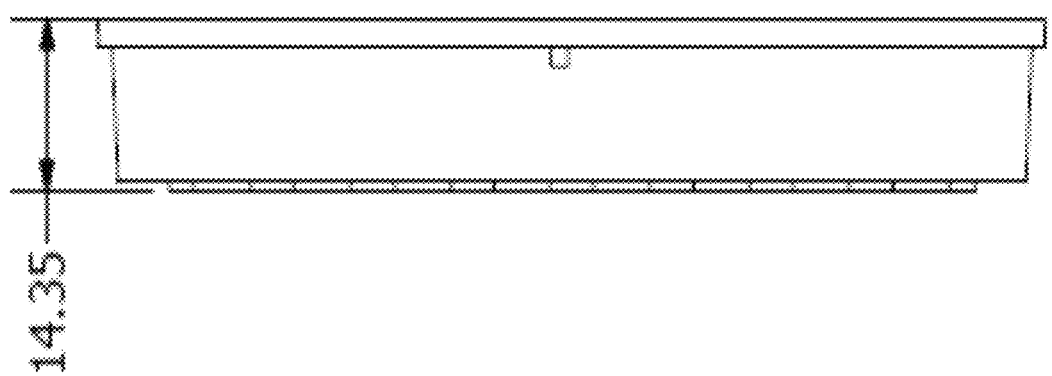
FIG. 6B shows an exemplary side view schematic of a fluidic device cartridge.
Figure 6C:
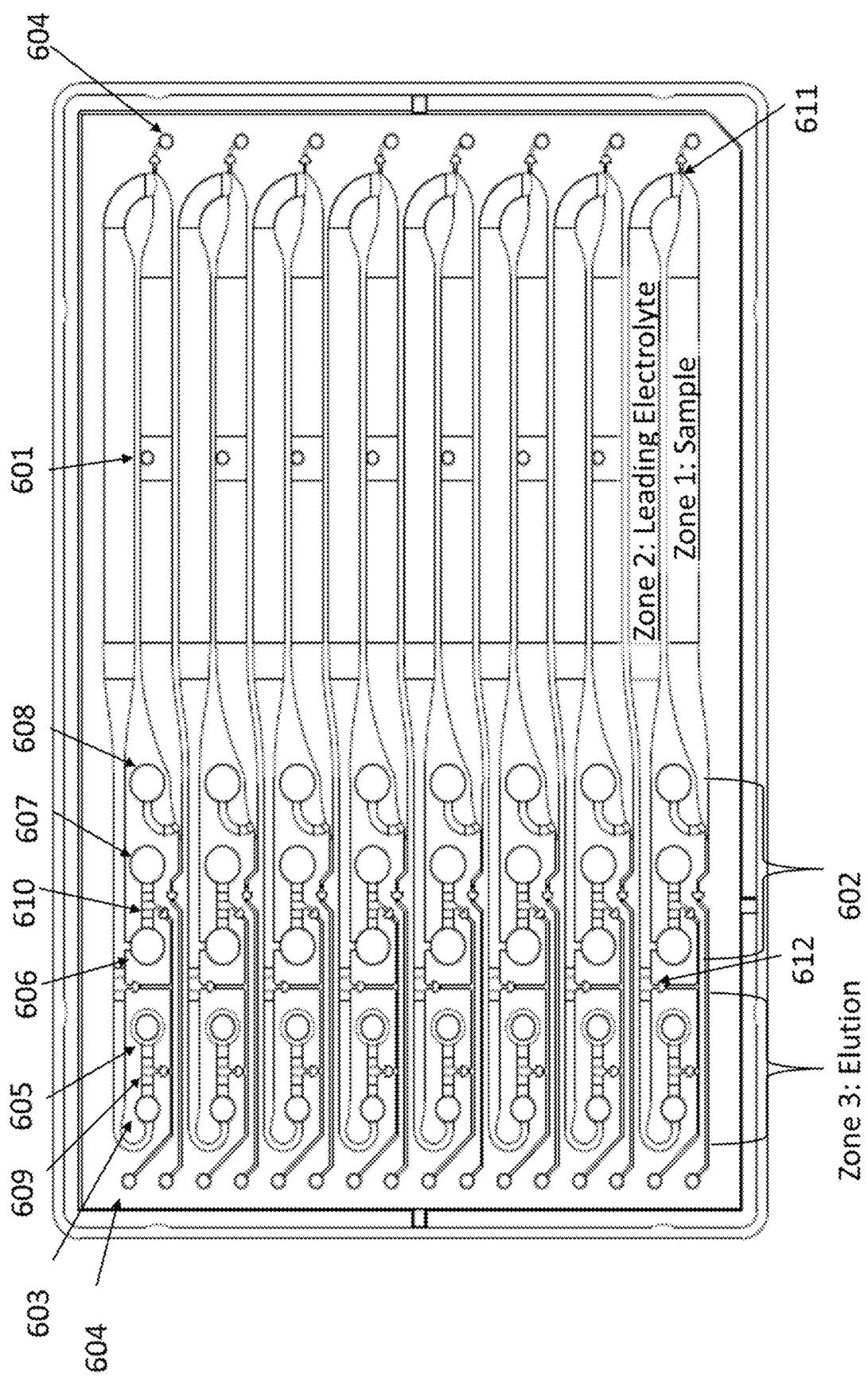
FIG. 6C shows an exemplary bottom view schematic of a fluidic device cartridge.
Figure 6D:
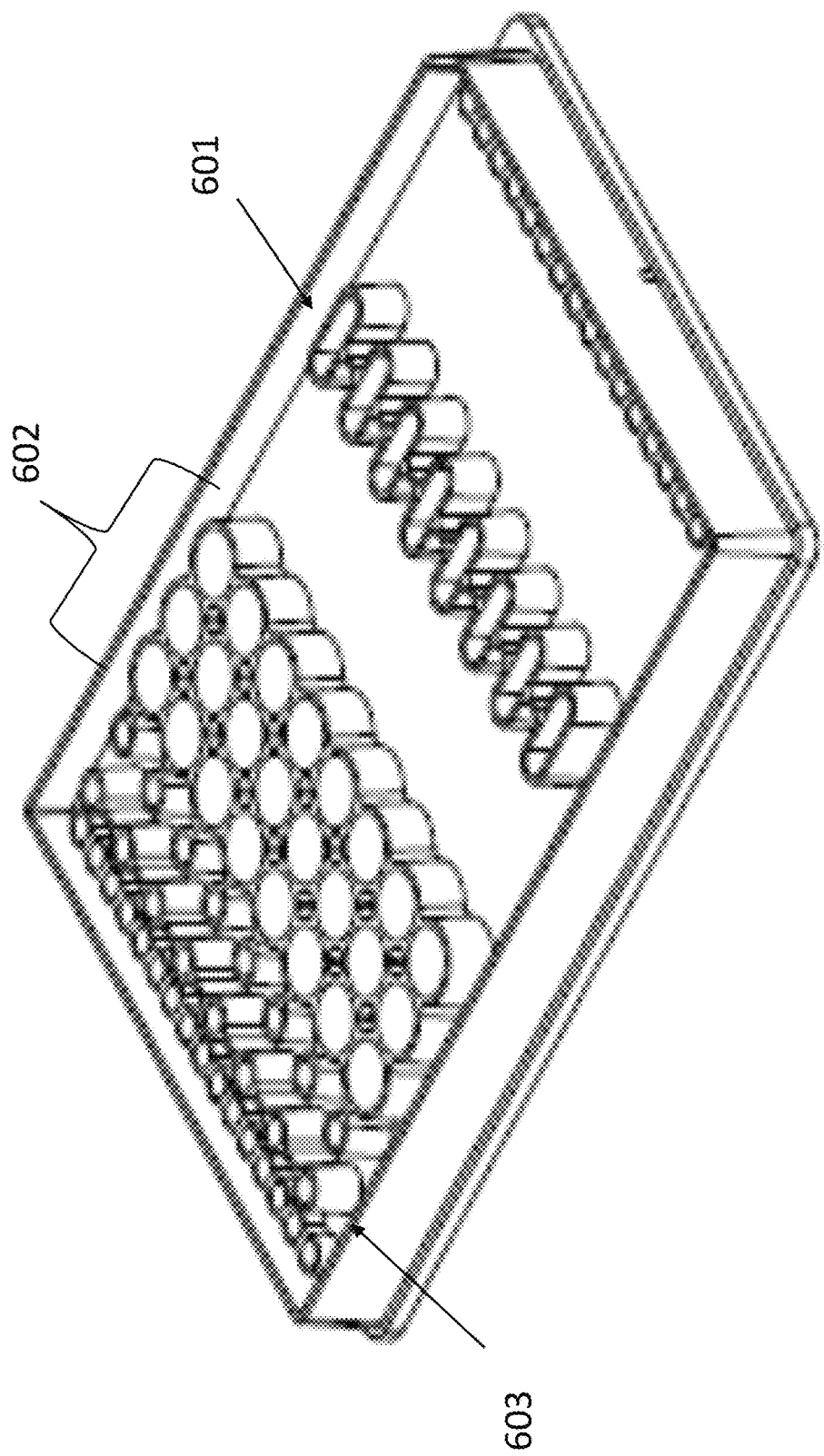
FIG. 6D shows an exemplary top full view schematic in three dimensions of a fluidic device cartridge.
Figure 7A:
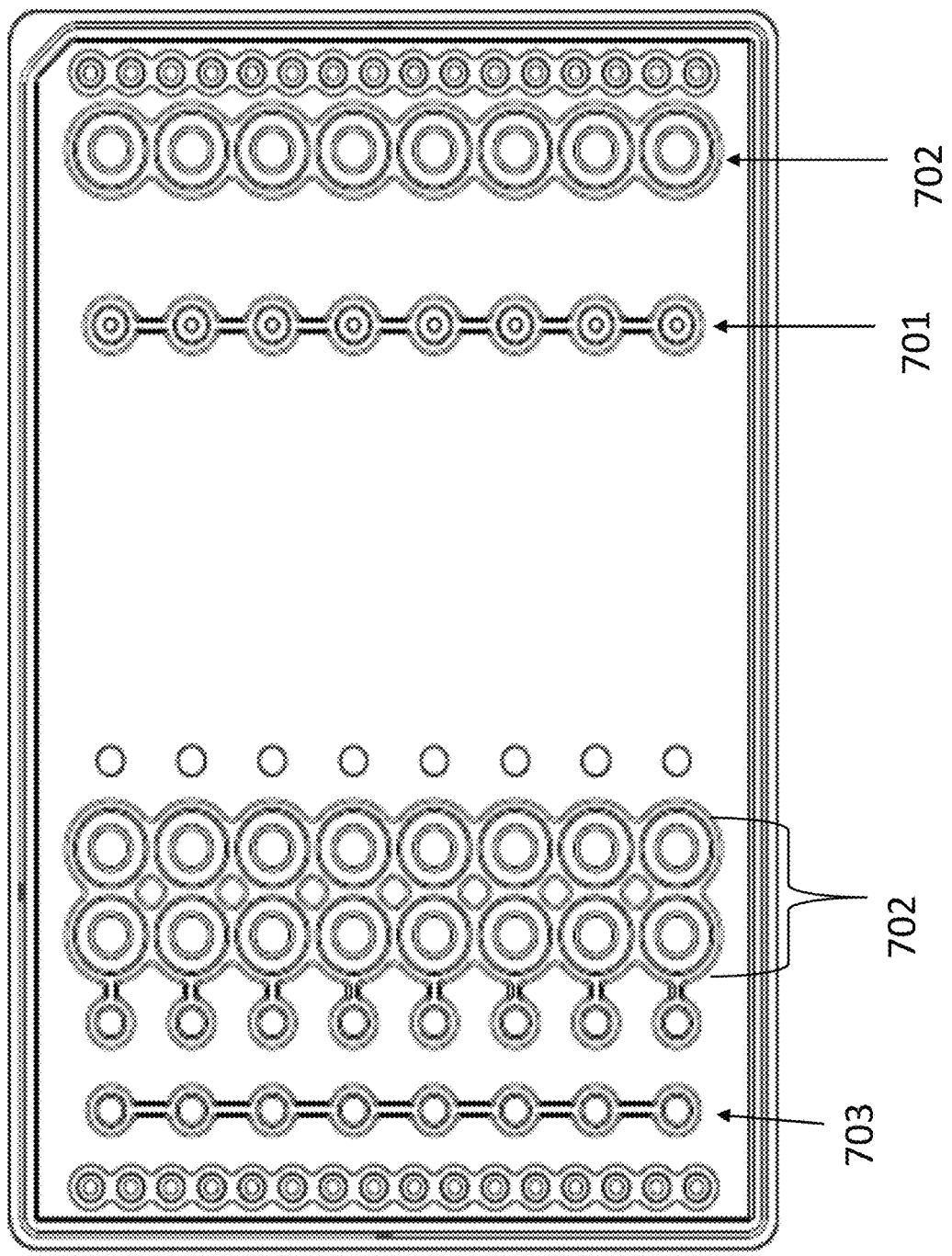
FIG. 7A shows an exemplary top view schematic of a fluidic device cartridge.
Figure 7B:
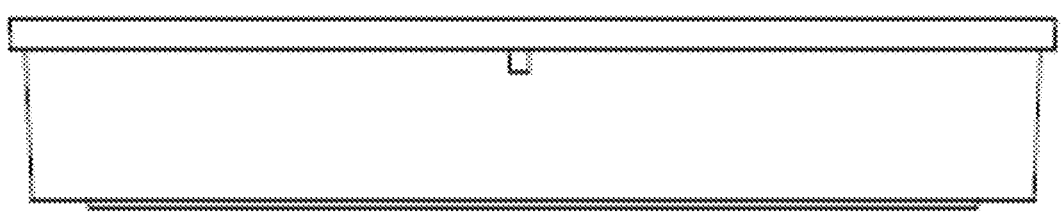
FIG. 7B shows an exemplary side view schematic of a fluidic device cartridge.
Figure 7C:
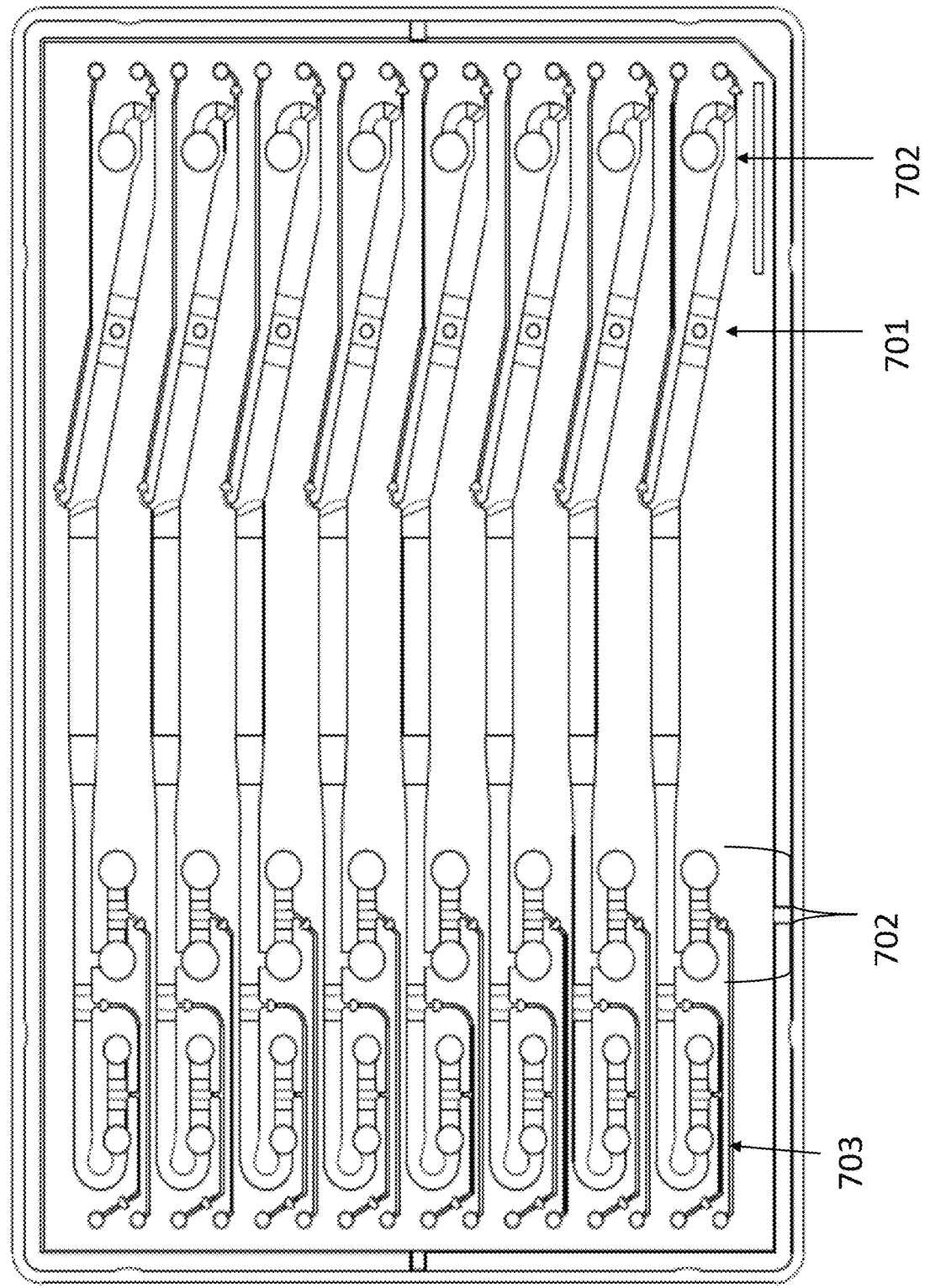
FIG. 7C shows an exemplary bottom view schematic of a fluidic device cartridge.
Figure 7D:
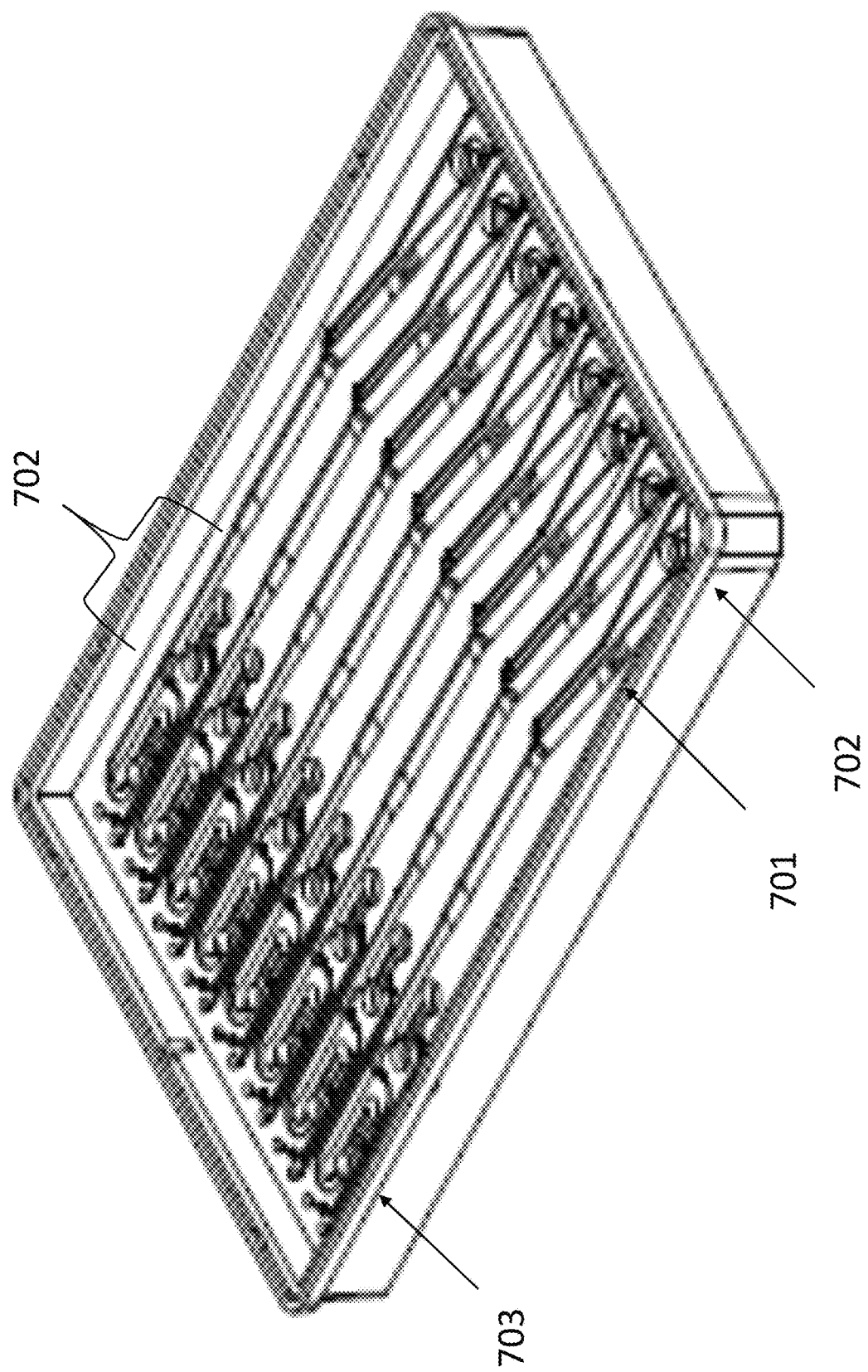
FIG. 7D shows an exemplary bottom full view schematic in three dimensions of a fluidic device cartridge.
Figure 8A:
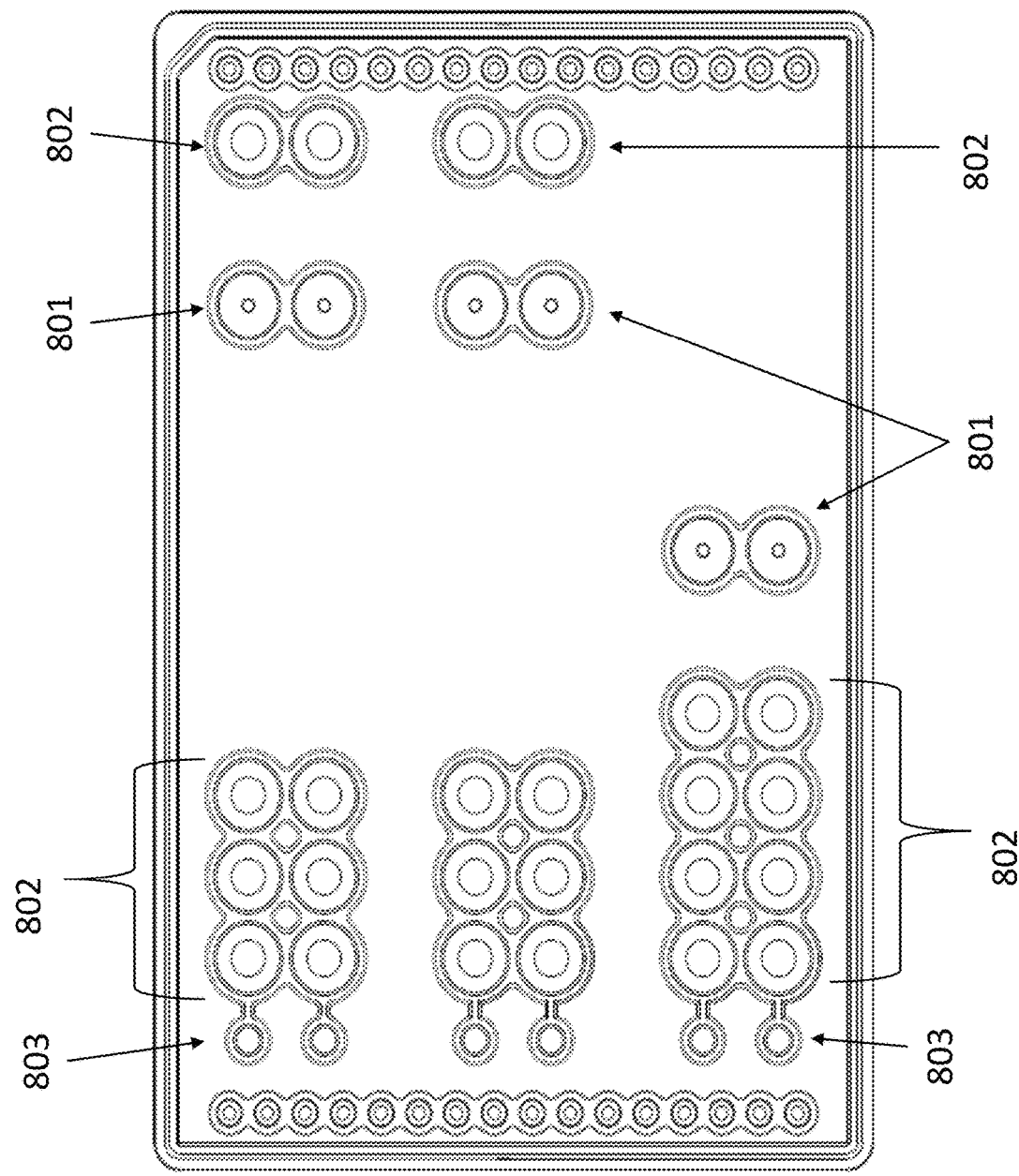
FIG. 8A shows an exemplary top view schematic of a fluidic device cartridge.
Figure 8B:
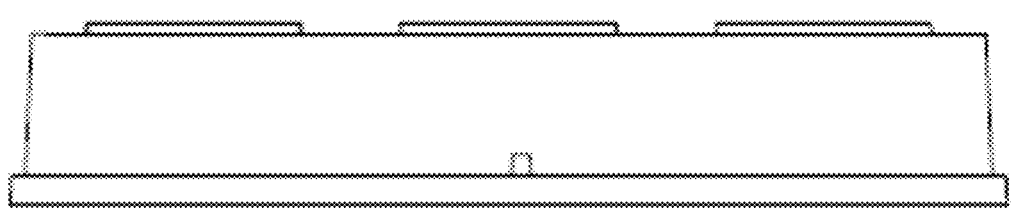
FIG. 8B shows an exemplary side view schematic of a fluidic device cartridge.
Figure 8C:
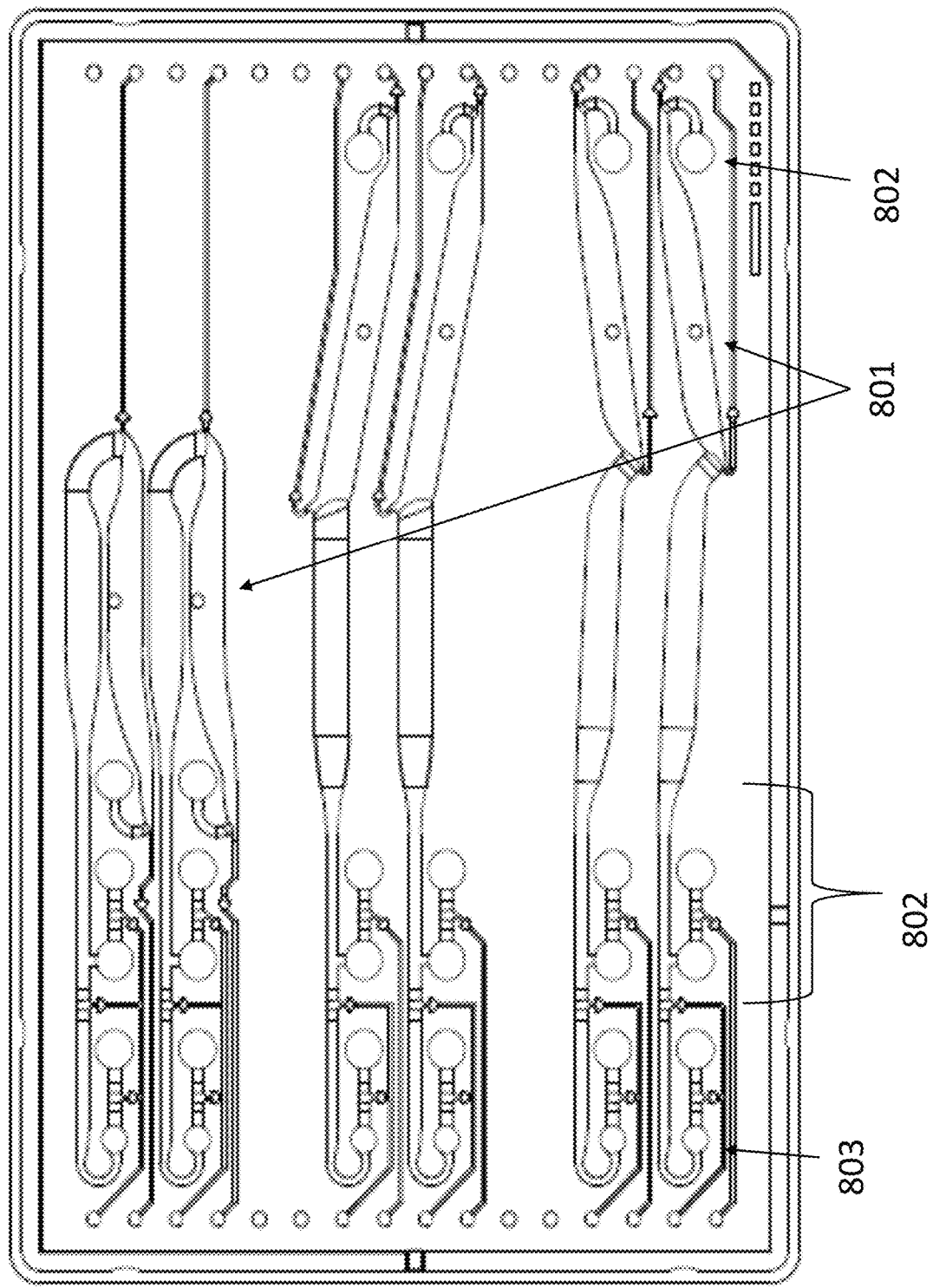
FIG. 8C shows an exemplary bottom view schematic of a fluidic device cartridge.
Figure 8D:
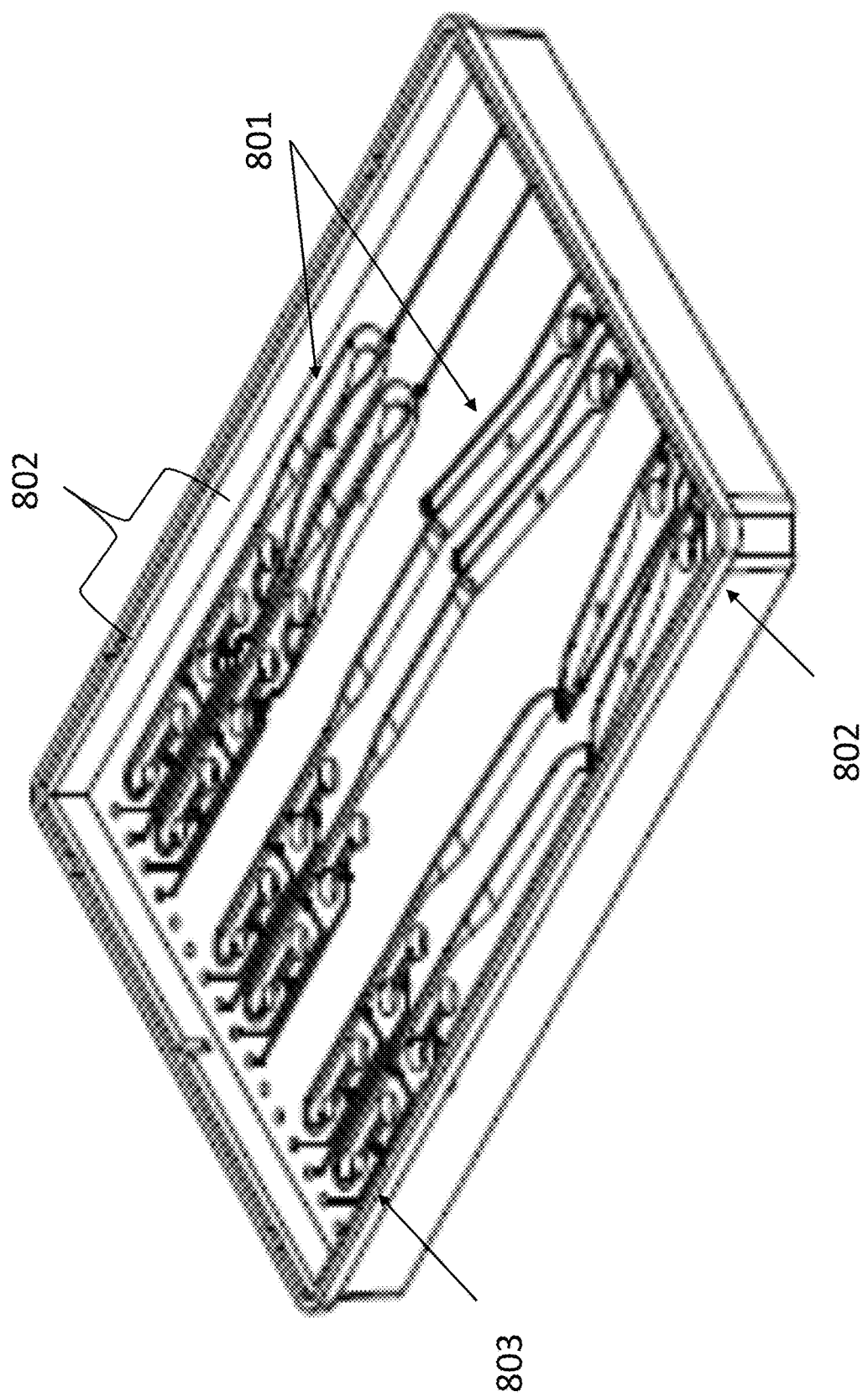
FIG. 8D shows an exemplary bottom full view schematic in three dimensions of a fluidic device cartridge.
Figure 12B:
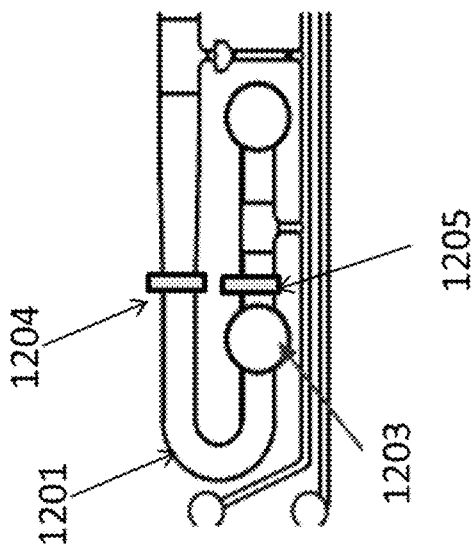
FIG. 12B shows an exemplary comb-like mechanical member.
Figure 12A:
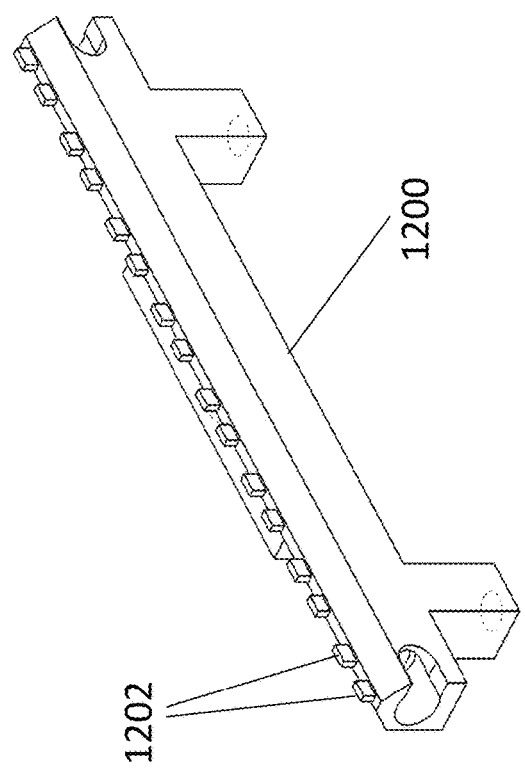
FIG. 12A shows an exemplary mechanical member which can be used to apply pressure to close the channels of a fluidic device.
Figure 12C:
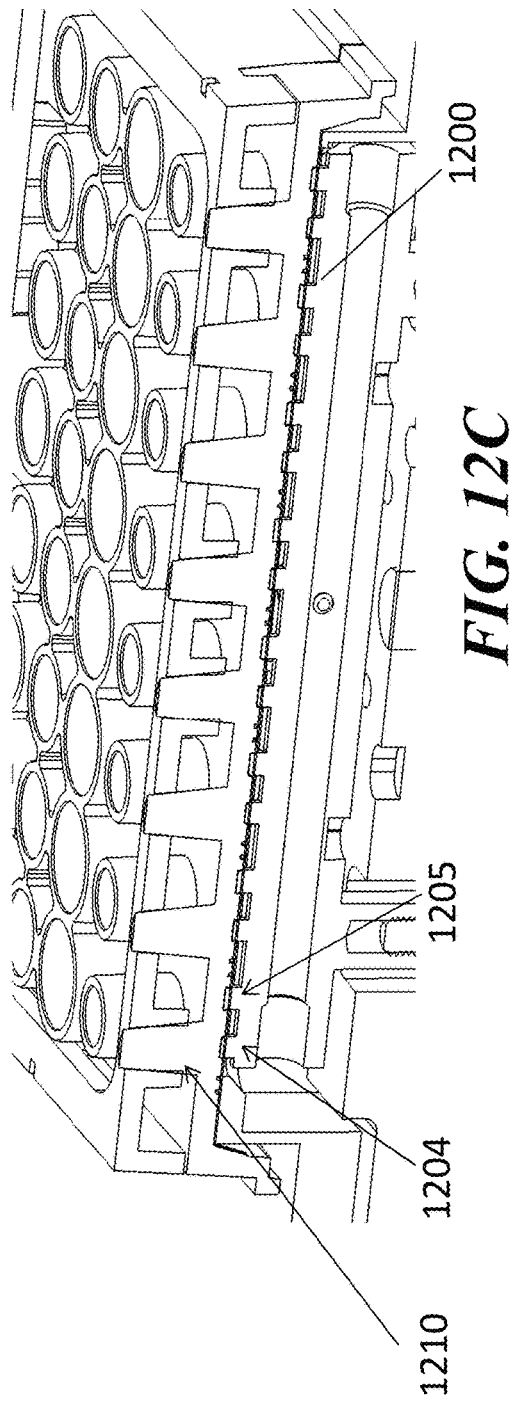
FIG. 12C shows the alignment of a comb-like mechanical member and the channels of a fluidic device.

FIG. 12A shows an exemplary mechanical member 1200 which can be used to apply pressure to close or at least partially close the channels 1201 of a fluidic device 1210, the fluidic device 1210 comprising multiple channels in parallel (for example the device of FIG. 6C comprising eight independent parallel channels). The mechanical member 1200 can comprise a comb-like structure with teeth 1202 that line up with two locations 1204, 1205 in each of the eight channels of the chip as shown in FIG. 12B. Mechanical pressure can be applied by the teeth 1202 to permanently or plastically close or at least partially close the channels 1201 to limit, reduce, or prevent liquid flow to or from the elution reservoirs 1203 and control the elution volume. At least partially closing the channels 1201 may increase resistance to fluid flow between the channels 1201 and the elution reservoirs 1203. The mechanical member 1200 may be coupled to a mechanical actuator which generates the force applied to the channel 1201 by the teeth 1202 of the mechanical member 1200. The mechanical member 1200 may comprise a material with a Young's modulus of elasticity greater than a Young's modulus of elasticity of the channel 1201. One or more teeth 1202 of the mechanical member 1200 may be configured to heat a channel 1201. One or more teeth 1202 of the mechanical member 1200 may be thermally coupled to a heater or heating element. The mechanical member 1200 may optionally comprise a heater or heating element. Heat can optionally be applied by the teeth 1202 to permanently or plastically close the channels 1201. One or more teeth 1202 may be heated to a temperature greater than the glass transition temperature of at least one wall of one or more channels 1201. FIG. 12C shows how the sixteen teeth 1202 of the mechanical member 1200 line up with the sixteen locations 1204, 1205 on the chip 1210 (two per channel). Each tooth 1202 may be configured to deliver mechanical pressure to the channel 1201 in order to plastically deform at least one wall of the channel 1201. Each channel 1201 is contacted by the mechanical member 1200 and plastically deformed at a first close location 1204 and a second close location 1205 to isolate the elution reservoir volume and increase fluid resistance between the channel 1201 and the reservoir 1203. In some instances, a tooth 1202 may apply mechanical pressure to the channel location 1204 upstream of the reservoir 1203. In some instances, a tooth 1202 may apply mechanical pressure to a junction where the reservoir 1203 and the channel 1201 meet. In some instances, a tooth 1202 may apply mechanical pressure to a junction 1205 where the reservoir and a buffering channel meet to prevent fluid communication between the reservoir 1203 and a buffering reservoir.

In some cases, the mechanical member 1200 may comprise one tooth 1202 per channel which aligns with the first close location 1204. For example, the channel shown in FIG. 5A does not comprise a buffer channel or reservoir connected to the elution reservoir and thus may not need a second close location 1205 beyond the elution reservoir. In some cases, the mechanical member 1200 is configured to close each of the channels 1201 on a chip 1210 at one or more locations. In some cases, the mechanical member 1200 is configured to leave one or more channel 1201 on the chip 1210 open such that only a fraction of channels 1201 on the chip 1210 are closed.

The mechanical member 1200 may apply a force of at least 0.25 lbs per channel via teeth 1202. Each tooth 1202 of the mechanical member 1200 may apply a force of at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, or 5 pounds to a channel 1201.

Figure 54B:
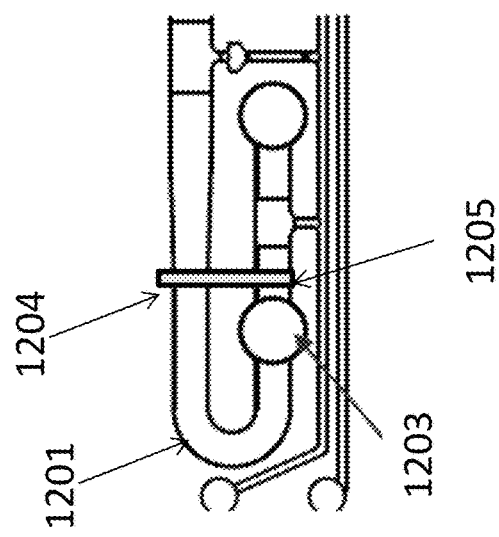
FIG. 54B shows an exemplary ridge-like mechanical member.
Figure 54A:
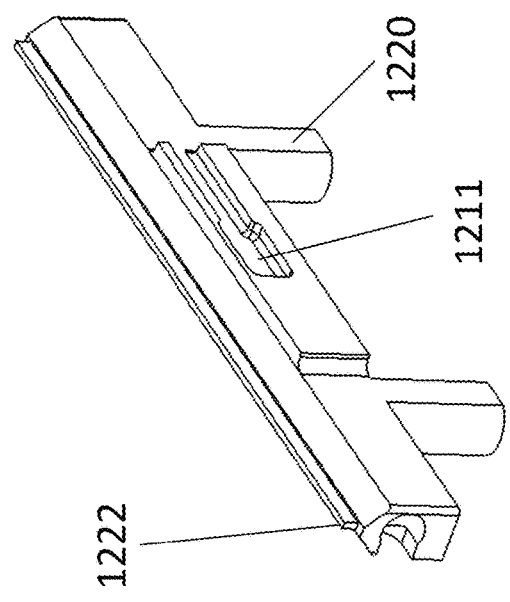
FIG. 54A shows an exemplary mechanical member which can be used to apply pressure to close the channels of a fluidic device.
Figure 54C:
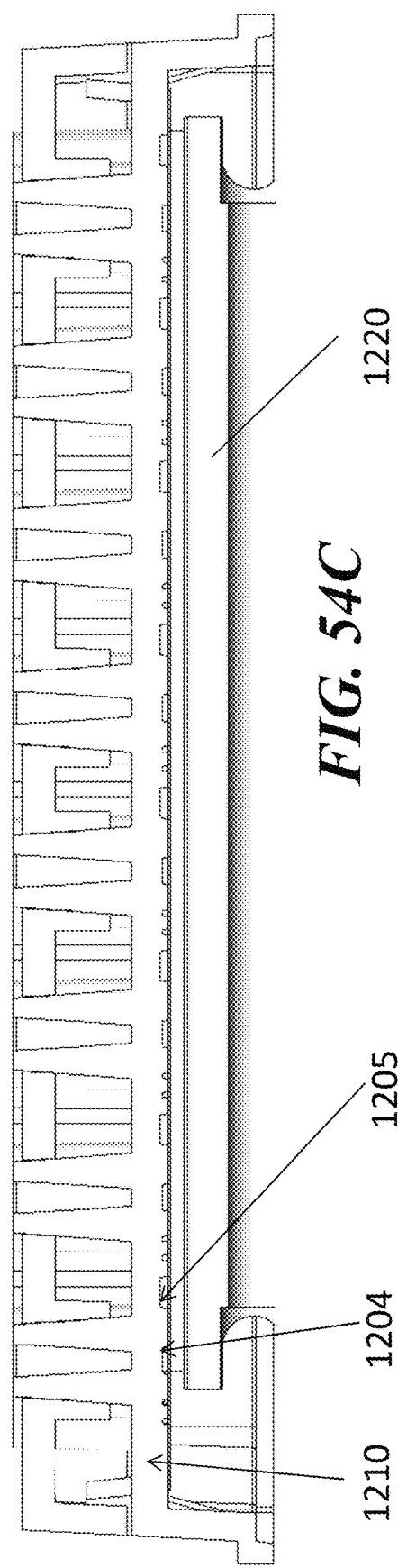
FIG. 54C shows the alignment of a ridge-like mechanical member and the channels of a fluidic device.

FIG. 54A shows an exemplary mechanical member 1220 which can be used to apply pressure to close or at least partially close the channels 1201 of a fluidic device 1210, the fluidic device 1210 comprising multiple channels in parallel (for example the device of FIG. 6C comprising eight independent parallel channels). The mechanical member 1220 can comprise a ridge-like structure similar to that of mechanical member 1200 but without teeth. The ridge-like structure may extend across and compress each of the eight channels of the chip at two locations 1204, 1205 as shown in FIG. 54B. Mechanical pressure can be applied by the ridge 1222 to permanently or plastically close or at least partially close the channels 1201 in order to limit, reduce, or prevent liquid flow to or from the elution reservoirs 1203 and control the elution volume. At least partially closing the channels 1201 may increase resistance to fluid flow between the channels 1201 and the elution reservoirs 1203. The mechanical member 1220 may be coupled to a mechanical actuator 1213 which generates the force applied to the channel 1201 by the ridge 1222 of the mechanical member 1220. The mechanical member 1220 may comprise a material with a Young's modulus of elasticity greater than a Young's modulus of elasticity of the channel 1201. The ridge-like structure 1222 of the mechanical member 1220 may be configured to heat a channel 1201. The ridge-like structure 1222 of the mechanical member 1220 may be thermally coupled to a heater or heating element. The mechanical member 1220 may optionally comprise a heater or heating element. Heat can optionally be applied by the ridge-like structure 1222 to permanently or plastically close the channels 1201. The ridge-like structure 1222 may be heated to a temperature greater than the glass transition temperature of at least one wall of one or more channels 1201. FIG. 54C shows how the ridge 1222 of the mechanical member 1220 line up with the sixteen locations 1204, 1205 on the chip 1210 (two per fluidic channel). The ridge 1222 may be configured to deliver mechanical pressure to the channel 1201 in order to plastically deform at least one wall of the channel 1201. Each channel 1201 is contacted by the mechanical member 1220 and plastically deformed at a first close location 1204 and a second close location 1205 to isolate the elution reservoir volume and increase fluid resistance between the channel 1201 and the reservoir 1203. In some instances, the ridge structure 1222 may apply mechanical pressure to the channel location 1204 upstream of the reservoir 1203. In some instances, the ridge structure 1222 may apply mechanical pressure to a junction where the reservoir 1203 and the channel 1201 meet. In some instances, the ridge structure 1222 may apply mechanical pressure to a junction 1205 where the reservoir and a buffering channel meet to prevent fluid communication between the reservoir 1203 and a buffering reservoir.

Figure 54D:
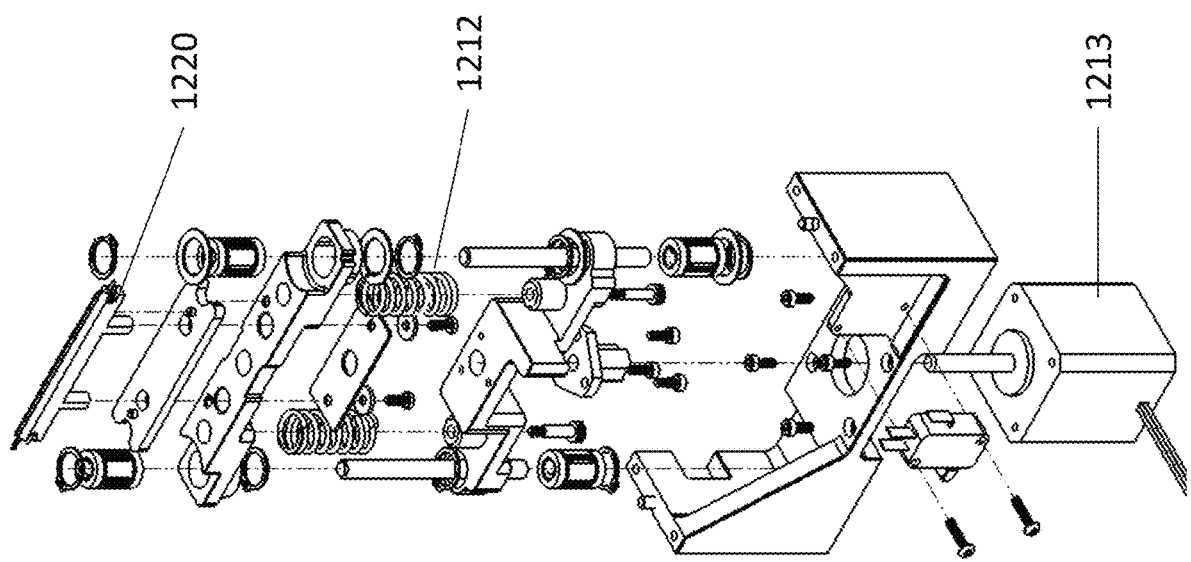
FIG. 54D shows a break out component assembly diagram for the mechanical actuator coupled to a ridge-like structure for closing channels.

FIG. 54D shows a break out component assembly diagram for the mechanical actuator coupled to a ridge-like structure 1220 for closing channels. This assembly may be a stand-alone assembly or incorporated as a sub-assembly of any of the instruments described herein. This design may be configured to be modular and can accommodate different member structure designs including the tooth or ridge, or alternate structures as will be apparent to one of ordinary skill in the art.

In some embodiments, any of the mechanical members described herein may be triggered to close one or more channels by the cessation of the electrical field applied to one or more channels of the device.

FIG. 55 depicts a pneumatic control block diagram for beta prototype and production instrument.

FIGS. 56A-56B and 58A-58C show alternative mechanisms for closing channels without the use of heat or pressure-induced plastic deformation of a fluidic device. A physical member may be used to close or partially close the channels of the fluidic device by applying a membrane that provides a seal to chip reservoirs on a fluidic device. The mechanisms may use adhesion or self-healing of membrane, with or without applied mechanical pressure, to close or partially close the channels without causing deformation of the chip device or material. The mechanism may apply constant force and/or pressure passively (e.g. by applying a fixed mechanical load) to the fluid reservoirs of a fluidic device.

Figures 56A, 56B:
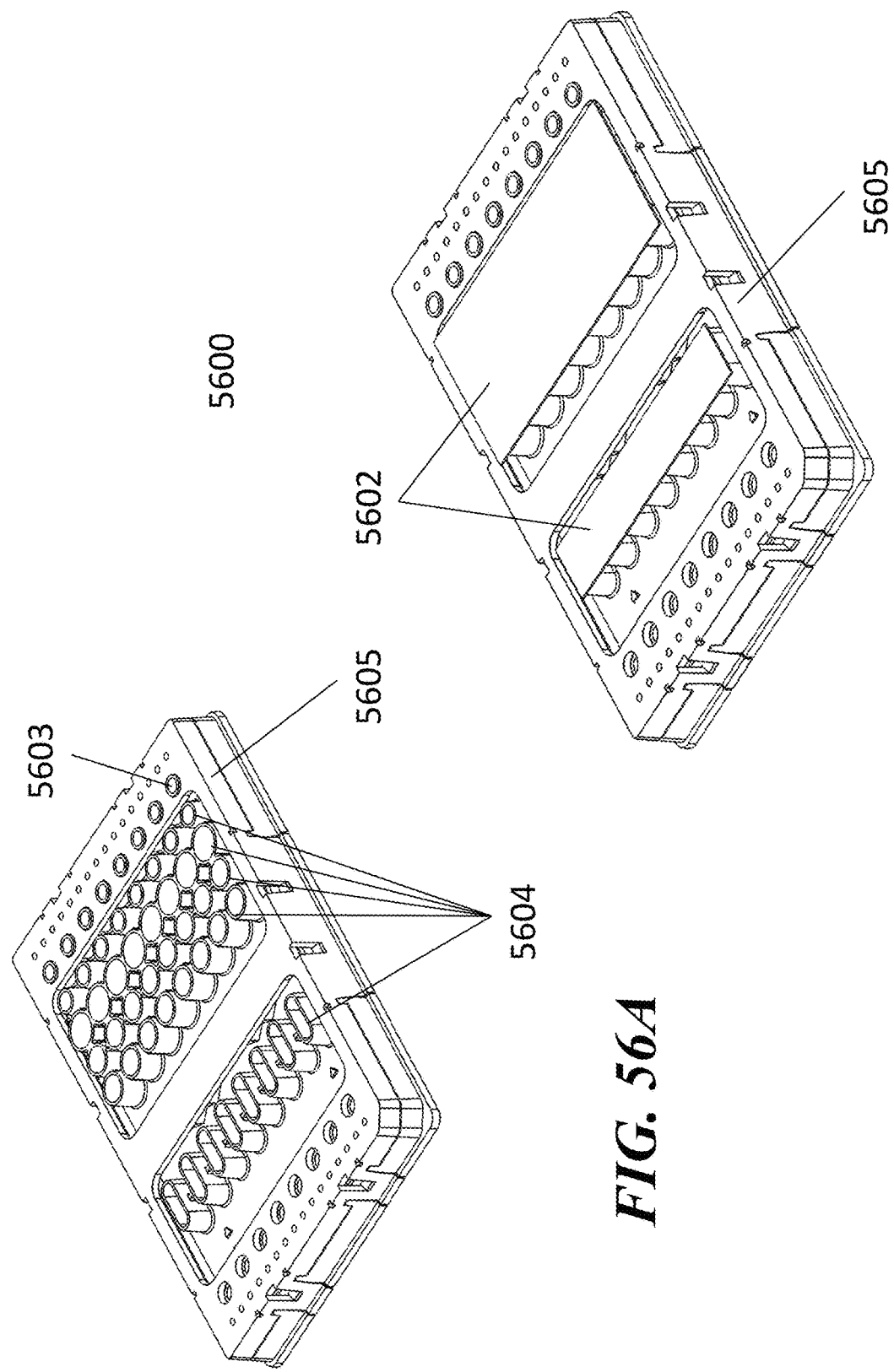

FIGS. 56A-56B show an exemplary mechanical member 5600 which can be used to close or at least partially close the reservoirs 5604 of a fluidic device 5605, the fluidic device 5605 comprising multiple channels in parallel (e.g. 8 parallel channels in a fluidic device). The mechanical member 5600 can comprise a compliant structure 5602 that lines up with a series of reservoirs connected to an individual channel in a fluidic device (e.g. 5 reservoirs). The elution reservoir 5603 is intentionally left open to the atmosphere to allow extraction (e.g. by pipetting) of material processed in the fluidic device 5605 while the mechanical member 5600 is closing or partially closing the other five reservoirs 5604. Mechanical pressure can be applied to the compliant structure 1502 to temporarily close or at least partially close the reservoirs 5604 to limit, reduce, or prevent liquid flow to or from the elution reservoirs 5603 and control the elution volume. At least partially closing the reservoirs 5604 may increase resistance to fluid flow between the sample/buffer reservoirs 5604 and the elution reservoirs 5603.

The compliant structure 5602 may comprise or be similar to a PCR film seal or membrane. A PCR film seal is a type of disposable membrane that can be adhesively applied over the fluidic reservoirs to seal them and prevent flow in the connected channels. The process of adhesion may be improved with applied mechanical pressure. Mechanical pressure may be applied so as to not apply pressure to the fluids in the reservoir in order to prevent or minimize liquid flowing within the chip during channel closing. A PCR film/membrane may represent a low-cost, disposable option for channel closing that may reduce cross-contamination which can sometimes occur with repeated application of the same membrane (i.e. a reusable membrane) from chip to chip.

The compliant structure 5602 may comprise or be similar to a compliant or self-healing membrane seal. A compliant or self-healing membrane seal is a type of disposable or reusable membrane that can be applied with or without mechanical pressure over the fluidic reservoirs to seal them and prevent or reduce flow in the connected channels. One type of such seal is a compliant rubber gasket material. This rubber sealing member can be disposable or re-usable. A reusable rubber sealing member may require cleaning of the membrane material between uses with a compatible cleaning solvent in order to prevent or reduce the risk of cross-contamination between uses. The compliant rubber seal may be applied with a fixed mechanical load or pressure. The mechanical pressure may be applied so as to not apply pressure to the fluids in the reservoir in order to prevent or minimize liquid flowing within the chip during channel closing.

Figure 57:
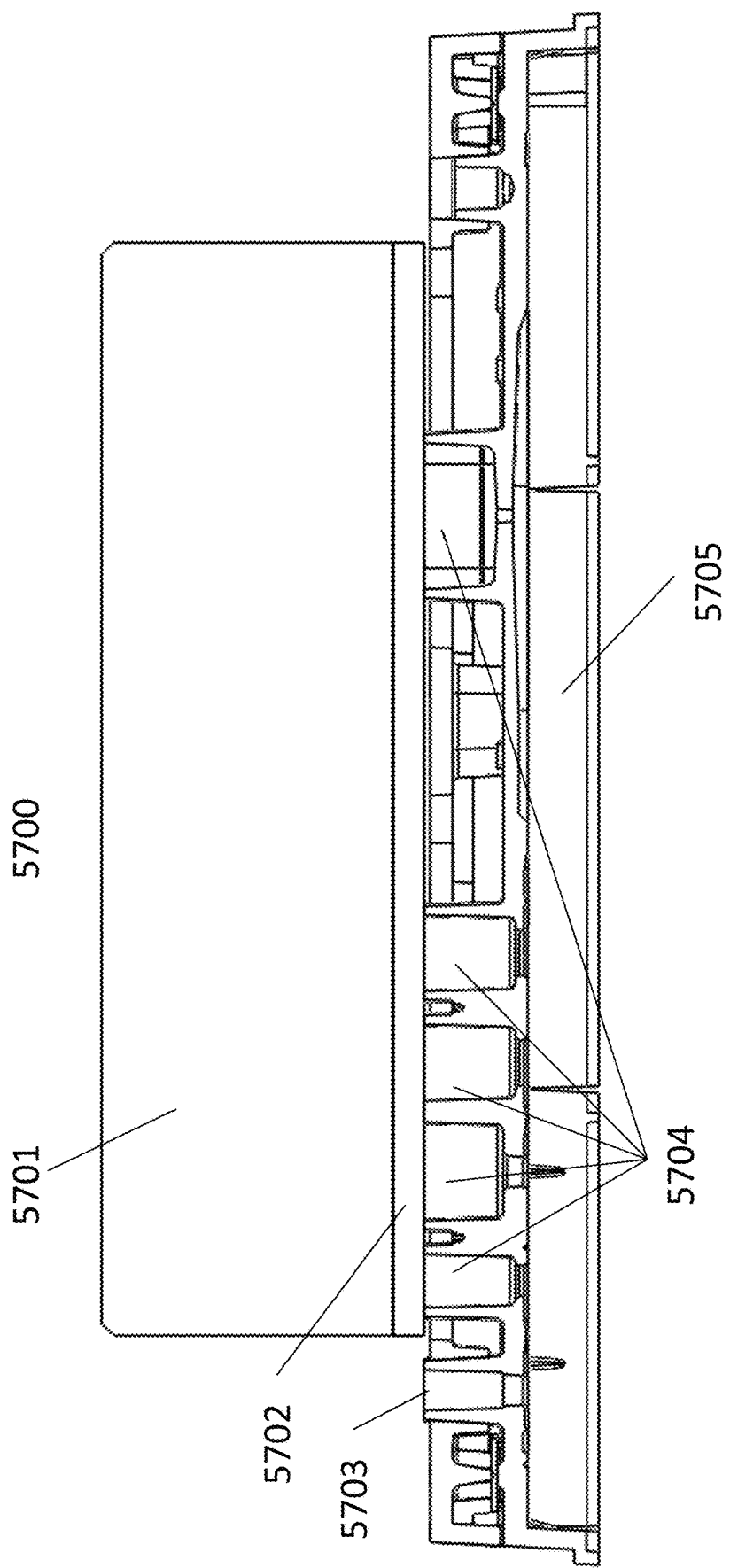

FIG. 57 shows an exemplary mechanical member 5700 which can be used to apply pressure to close or at least partially close the reservoirs 5704 of a fluidic device 5705, the fluidic device 5705 comprising multiple channels in parallel. The mechanical member 5700 can comprise a load bearing structure 5701 and compliant structure 5702 that lines up with open buffer or sample reservoirs on the fluidic device. The elution reservoir 5703 on the fluidic device is intentionally left open to atmosphere to allow extraction of material processed in the fluidic device 5705 while the mechanical member is closing or partially closing the other five reservoirs 5704. Mechanical pressure can be applied by the rigid structure 5701 to the compliant structure 5702 to temporarily close or at least partially close the reservoirs 5704 to limit, reduce, or prevent liquid flow to or from the elution reservoirs 5703 and control the elution volume. At least partially closing the reservoirs 5704 may increase resistance to fluid flow between the sample/buffer reservoirs 5704 and the elution reservoirs 5703.

FIGS. 58A-58C show an exemplary channel closer with rubber sealing member and mechanical actuator to provide a mechanical load for sealing. FIG. 58A shows an image of the side view of a channel closing device 5800 comprising a compliant rubber sealing member 5801 and a structure for applying mechanical load 5802 to close or at least-partially close the reservoirs 5803 of a fluidic device. Varying materials (e.g. polyurethane, silicone, vinyl), durometers (Extra soft to soft, or 30OO-50 durometer), and thicknesses (e.g. 0.05" to 0.25") may be employed as will be understood by one of ordinary skill in the art. In one example, the rubber may be polyurethane with a durometer of 40OO and a thickness of 0.060". The rubber member 5801 can be configured to cover all reservoirs 5803 but the elution reservoir(s) 5805 on the fluidic device. The rubber member 5801 can be mounted to a flat, solid support 5804 (e.g. plastic, glass, or a metal such as aluminum) in order to provide a flat sealing surface to the chip reservoirs 5801. A mechanical load 5802 (such as about 0 to about 2 kg) can be applied to the flat support 5804 by a mechanical actuator in order to further compress the compliant rubber member 5801 and provide sealing to the chip reservoirs 5803. Alternatively or in combination, the solid support element 5804, for example a weighted solid support, may be used to passively apply the mechanical load to the rubber member 5801.

FIGS. 58B and 58C show two exemplary configurations for the rubber member 5801. FIG. 58B shows an example wherein a rubber membrane 5801 is configured to specifically interface only with the tops of the reservoirs 5803 on the top of the fluidic device (as opposed to interfacing with every structure at the top of the device). FIG. 58C shows an example wherein the rubber membrane 5801 is configured as a simple sheet or layer and generally interfaces with all structures on the top of the device but elution reservoir(s) 5805.

Channels on a fluidic device (e.g., sample preparation zones, isotachophoresis zones) can have a large enough width, height, or diameter such that contaminants, such as embedding material (e.g., paraffin), can deposit on the channel walls while still leaving adequate room for fluid flow within the channel. In some cases, a channel on a fluidic device has a width, height, or diameter of less than or equal to 20 millimeters (mm), 19 mm, 18 mm, 17 mm, 16 mm, 15 mm, 14 mm, 13 mm, 12 mm, 11 mm, 10 mm, 9 mm, 8 mm 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, or 0.1 mm. In some cases, a channel on a fluidic device has a width, height, or diameter of at least 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. In some cases, a channel on a fluidic device has a width within a range of about 1 mm to about 3.8 mm. In some cases, a channel on a fluidic device has a height within a range of about 0.1 mm to about 1.2 mm.

Sample channels on the fluidic device can have a height within a range of about 10 um to about 2 mm, for example within a range of about 400 um to about 1.2 mm. In some cases, one or more sample channels on the fluidic device can have a height within a range bounded by any two of the following values: 10 um, 20 um, 30 um, 40 um, 50 um, 60 um, 70 um, 80 um, 90 um, 100 um, 110 um, 120 um, 130 um, 140 um, 150 um, 160 um, 170 um, 180 um, 190 um, 200 um, 200 um, 210 um, 220 um, 230 um, 240 um, 250 um, 260 um, 270 um, 280 um, 290 um, 300 um, 310 um, 320 um, 330 um, 340 um, 350 um, 360 um, 370 um, 380 um, 390 um, 400 um, 410 um, 420 um, 430 um, 440 um, 450 um, 460 um, 470 um, 480 um, 490 um, 500 um, 510 um, 520 um, 530 um, 540 um, 550 um, 560 um, 570 um, 580 um, 590 um, 600 um, 610 um, 620 um, 630 um, 640 um, 650 um, 660 um, 670 um, 680 um, 690 um, 700 um, 710 um, 720 um, 730 um, 740 um, 750 um, 760 um, 770 um, 780 um, 790 um, 800 um, 810 um, 820 um, 830 um, 840 um, 850 um, 860 um, 870 um, 880 um, 890 um, 900 um, 910 um, 920 um, 930 um, 940 um, 950 um, 960 um, 970 um, 980 um, 990 um, 1000 um, 1010 um, 1020 um, 1030 um, 1040 um, 1050 um, 1060 um, 1070 um, 1080 um, 1090 um, 1100 um, 1110 um, 1120 um, 1130 um, 1140 um, 1150 um, 1160 um, 1170 um, 1180 um, 1190 um, 1200 um, 1210 um, 1220 um, 1230 um, 1240 um, 1250 um, 1260 um, 1270 um, 1280 um, 1290 um, 1300 um, 1310 um, 1320 um, 1330 um, 1340 um, 1350 um, 1360 um, 1370 um, 1380 um, 1390 um, 1400 um, 1410 um, 1420 um, 1430 um, 1440 um, 1450 um, 1460 um, 1470 um, 1480 um, 1490 um, 1500 um, 1510 um, 1520 um, 1530 um, 1540 um, 1550 um, 1560 um, 1570 um, 1580 um, 1590 um, 1600 um, 1610 um, 1620 um, 1630 um, 1640 um, 1650 um, 1660 um, 1670 um, 1680 um, 1690 um, 1700 um, 1710 um, 1720 um, 1730 um, 1740 um, 1750 um, 1760 um, 1770 um, 1780 um, 1790 um, 1800 um, 1810 um, 1280 um, 1830 um, 1840 um, 1850 um, 1860 um, 1870 um, 1880 um, 1890 um, 1900 um, 9110 um, 1920 um, 1930 um, 1940 um, 1950 um, 1960 um, 1970 um, 1980 um, 1990 um, and 2000 um Leading electrolyte buffer channels on the fluidic device can have a height within a range of about 10 um to about 1 mm, for example less than about 600 um. In some cases, one or more leading electrolyte buffer channels on the fluidic device can have a height within a range bounded by any two of the following values: 10 um, 20 um, 30 um, 40 um, 50 um, 60 um, 70 um, 80 um, 90 um, 100 um, 110 um, 120 um, 130 um, 140 um, 150 um, 160 um, 170 um, 180 um, 190 um, 200 um, 200 um, 210 um, 220 um, 230 um, 240 um, 250 um, 260 um, 270 um, 280 um, 290 um, 300 um, 310 um, 320 um, 330 um, 340 um, 350 um, 360 um, 370 um, 380 um, 390 um, 400 um, 410 um, 420 um, 430 um, 440 um, 450 um, 460 um, 470 um, 480 um, 490 um, 500 um, 510 um, 520 um, 530 um, 540 um, 550 um, 560 um, 570 um, 580 um, 590 um, 600 um, 610 um, 620 um, 630 um, 640 um, 650 um, 660 um, 670 um, 680 um, 690 um, 700 um, 710 um, 720 um, 730 um, 740 um, 750 um, 760 um, 770 um, 780 um, 790 um, 800 um, 810 um, 820 um, 830 um, 840 um, 850 um, 860 um, 870 um, 880 um, 890 um, 900 um, 910 um, 920 um, 930 um, 940 um, 950 um, 960 um, 970 um, 980 um, 990 um, and 1000 um.

Elution channels on the fluidic device can have a height within a range of about 10 um to about 1 mm, for example less than about 600 um. In some cases, one or more elution buffer channels on the fluidic device can have a height within a range bounded by any two of the following values: 10 um, 20 um, 30 um, 40 um, 50 um, 60 um, 70 um, 80 um, 90 um, 100 um, 110 um, 120 um, 130 um, 140 um, 150 um, 160 um, 170 um, 180 um, 190 um, 200 um, 200 um, 210 um, 220 um, 230 um, 240 um, 250 um, 260 um, 270 um, 280 um, 290 um, 300 um, 310 um, 320 um, 330 um, 340 um, 350 um, 360 um, 370 um, 380 um, 390 um, 400 um, 410 um, 420 um, 430 um, 440 um, 450 um, 460 um, 470 um, 480 um, 490 um, 500 um, 510 um, 520 um, 530 um, 540 um, 550 um, 560 um, 570 um, 580 um, 590 um, 600 um, 610 um, 620 um, 630 um, 640 um, 650 um, 660 um, 670 um, 680 um, 690 um, 700 um, 710 um, 720 um, 730 um, 740 um, 750 um, 760 um, 770 um, 780 um, 790 um, 800 um, 810 um, 820 um, 830 um, 840 um, 850 um, 860 um, 870 um, 880 um, 890 um, 900 um, 910 um, 920 um, 930 um, 940 um, 950 um, 960 um, 970 um, 980 um, 990 um, and 1000 um.

In some cases, a channel on a fluidic device has a length of at least about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 35 mm, 40 mm, 45 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, 300 mm, 310 mm, 320 mm, 330 mm, 340 mm, 350 mm, 360 mm, 370 mm, 380 mm, 390 mm, 400 mm, 410 mm, 420 mm, 430 mm, 440 mm, 450 mm, 460 mm, 470 mm, 480 mm, 490 mm, or 500 mm. In some cases, a channel on a fluidic device has a length of less than or equal to about 500 mm, 490 mm, 480 mm, 470 mm, 460 mm, 450 mm, 440 mm, 430 mm, 420 mm, 410 mm, 400 mm, 390 mm, 380 mm, 370 mm, 360 mm, 350 mm, 340 mm, 330 mm, 320 mm, 310 mm, 300 mm, 290 mm, 280 mm, 270 mm, 260 mm, 250 mm, 240 mm, 230 mm, 220 mm, 210 mm, 200 mm, 190 mm, 180 mm, 170 mm, 160 mm, 150 mm, 140 mm, 130 mm, 120 mm, 110 mm, 100 mm, 90 mm, 80 mm, 70 mm, 60 mm, 50 mm, 45 mm, 40 mm, 35 mm, 30 mm, 25 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm.

Channels on a fluidic device can have a large enough width, height, or diameter so as to accommodate a large sample volume. In some cases, a channel on a fluidic device has a width greater than its height so as to reduce a temperature rise due to Joule heating in the channel. In some cases, a channel on a fluidic device has a ratio of width to height of at least 2:1, 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In some cases, a channel on a fluidic device has a ratio of width to height of at most 2:1, 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In some cases, a channel on a fluidic device has a cross-sectional area less than about 0.1 $mm^2$, 0.2 $mm^2$, 0.3 $mm^2$, 0.4 $mm^2$, 0.5 $mm^2$, 0.6 $mm^2$, 0.7 $mm^2$, 0.8 $mm^2$, 0.9 $mm^2$, 1 $mm^2$, 1.1 $mm^2$, 1.2 $mm^2$, 1.3 $mm^2$, 1.4 $mm^2$, 1.5 $mm^2$, 1.6 $mm^2$, 1.7 $mm^2$, 1.8 $mm^2$, 1.9 $mm^2$, 2 $mm^2$, 2.1 $mm^2$, 2.2 $mm^2$, 2.3 $mm^2$, 2.4 $mm^2$, 2.5 $mm^2$, 2.6 $mm^2$, 2.7 $mm^2$, 2.8 $mm^2$, 2.9 $mm^2$, 3 $mm^2$, 3.1 $mm^2$, 3.2 $mm^2$, 3.3 $mm^2$, 3.4 $mm^2$, 3.5 $mm^2$, 3.6 $mm^2$, 3.7 $mm^2$, 3.8 $mm^2$, 3.9 $mm^2$, 4 $mm^2$, 4.1 $mm^2$, 4.2 $mm^2$, 4.3 $mm^2$, 4.4 $mm^2$, 4.5 $mm^2$, 4.6 $mm^2$, 4.7 $mm^2$, 4.8 $mm^2$, 4.9 $mm^2$, 5 $mm^2$, 6 $mm^2$, 7 $mm^2$, 8 $mm^2$, 9 $mm^2$, 10 $mm^2$, 11 $mm^2$, 12 $mm^2$, 13 $mm^2$, 14 $mm^2$, or 15 $mm^2$. In some cases, a channel on a fluidic device has a cross-sectional area more than about 0.1 $mm^2$, 0.2 $mm^2$, 0.3 $mm^2$, 0.4 $mm^2$, 0.5 $mm^2$, 0.6 $mm^2$, 0.7 $mm^2$, 0.8 $mm^2$, 0.9 $mm^2$, 1 $mm^2$, 1.1 $mm^2$, 1.2 $mm^2$, 1.3 $mm^2$, 1.4 $mm^2$, 1.5 $mm^2$, 1.6 $mm^2$, 1.7 $mm^2$, 1.8 $mm^2$, 1.9 $mm^2$, 2 $mm^2$, 2.1 $mm^2$, 2.2 $mm^2$, 2.3 $mm^2$, 2.4 $mm^2$, 2.5 $mm^2$, 2.6 $mm^2$, 2.7 $mm^2$, 2.8 $mm^2$, 2.9 $mm^2$, 3 $mm^2$, 3.1 $mm^2$, 3.2 $mm^2$, 3.3 $mm^2$, 3.4 $mm^2$, 3.5 $mm^2$, 3.6 $mm^2$, 3.7 $mm^2$, 3.8 $mm^2$, 3.9 $mm^2$, 4 $mm^2$, 4.1 $mm^2$, 4.2 $mm^2$, 4.3 $mm^2$, 4.4 $mm^2$, 4.5 $mm^2$, 4.6 $mm^2$, 4.7 $mm^2$, 4.8 $mm^2$, 4.9 $mm^2$, 5 $mm^2$, 6 $mm^2$, 7 $mm^2$, 8 $mm^2$, 9 $mm^2$, 10 $mm^2$, 11 $mm^2$, 12 $mm^2$, 13 $mm^2$, 14 $mm^2$, or 15 $mm^2$. In some cases, a channel on a fluidic device has a minimum length scale for heat dissipation less than about 1 micrometer (μm), 5 μm, 10 μm, 20 μm, 30 μm, 40 μm, 50 μm, 100 μm, 150 μm, 200 μm, 250 μm, 300 μm, 350 μm, 400 μm, 450 μm, 500 μm, 550 μm, or 600 μm. In some cases, a channel on a fluidic device has a minimum length scale for heat dissipation more than about 1 micrometer (μm), 5 μm, 10 μm, 20 μm, 30 μm, 40 μm, 50 μm, 100 μm, 150 μm, 200 μm, 250 μm, 300 μm, 350 μm, 400 μm, 450 μm, 500 μm, 550 μm, or 600 μm.

In some cases, a channel on a fluid device has a total volume of at least about 1 microliter (μL), 10 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 350 μL, 400 μL, 450 μL, 500 μL, 600 μL, 700 μL, 800 μL, 900 μL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL. In some cases, a channel on a fluid device has a total volume of at most about 1 microliter (μL), 10 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 350 μL, 400 μL, 450 μL, 500 μL, 600 μL, 700 μL, 800 μL, 900 μL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL.

Sample channels on the fluidic device can have a volume within a range of about 10 uL to about 1 mL, for example within a range of about 50 uL to about 500 uL. In some cases, one or more sample channel on the fluidic device can have a volume within a range bounded by any two of the following values: 10 uL, 20 uL, 30 uL, 40 uL, 50 uL, 60 uL, 70 uL, 80 uL, 90 uL, 100 uL, 110 uL, 120 uL, 130 uL, 140 uL, 150 uL, 160 uL, 170 uL, 180 uL, 190 uL, 200 uL, 200 uL, 210 uL, 220 uL, 230 uL, 240 uL, 250 uL, 260 uL, 270 uL, 280 uL, 290 uL, 300 uL, 310 uL, 320 uL, 330 uL, 340 uL, 350 uL, 360 uL, 370 uL, 380 uL, 390 uL, 400 uL, 410 uL, 420 uL, 430 uL, 440 uL, 450 uL, 460 uL, 470 uL, 480 uL, 490 uL, 500 uL, 510 uL, 520 uL, 530 uL, 540 uL, 550 uL, 560 uL, 570 uL, 580 uL, 590 uL, 600 uL, 610 uL, 620 uL, 630 uL, 640 uL, 650 uL, 660 uL, 670 uL, 680 uL, 690 uL, 700 uL, 710 uL, 720 uL, 730 uL, 740 uL, 750 uL, 760 uL, 770 uL, 780 uL, 790 uL, 800 uL, 810 uL, 820 uL, 830 uL, 840 uL, 850 uL, 860 uL, 870 uL, 880 uL, 890 uL, 900 uL, 910 uL, 920 uL, 930 uL, 940 uL, 950 uL, 960 uL, 970 uL, 980 uL, 990 uL, and 1000 uL.

Sample channels on the fluidic device can have a volume of less than about 1 mL, for example less than about 500 ul, for example less than about 200 uL. In some cases, one or more sample channel on the fluidic device can have a volume of less than about 10 uL, 20 uL, 30 uL, 40 uL, 50 uL, 60 uL, 70 uL, 80 uL, 90 uL, 100 uL, 110 uL, 120 uL, 130 uL, 140 uL, 150 uL, 160 uL, 170 uL, 180 uL, 190 uL, 200 uL, 200 uL, 210 uL, 220 uL, 230 uL, 240 uL, 250 uL, 260 uL, 270 uL, 280 uL, 290 uL, 300 uL, 310 uL, 320 uL, 330 uL, 340 uL, 350 uL, 360 uL, 370 uL, 380 uL, 390 uL, 400 uL, 410 uL, 420 uL, 430 uL, 440 uL, 450 uL, 460 uL, 470 uL, 480 uL, 490 uL, 500 uL, 510 uL, 520 uL, 530 uL, 540 uL, 550 uL, 560 uL, 570 uL, 580 uL, 590 uL, 600 uL, 610 uL, 620 uL, 630 uL, 640 uL, 650 uL, 660 uL, 670 uL, 680 uL, 690 uL, 700 uL, 710 uL, 720 uL, 730 uL, 740 uL, 750 uL, 760 uL, 770 uL, 780 uL, 790 uL, 800 uL, 810 uL, 820 uL, 830 uL, 840 uL, 850 uL, 860 uL, 870 uL, 880 uL, 890 uL, 900 uL, 910 uL, 920 uL, 930 uL, 940 uL, 950 uL, 960 uL, 970 uL, 980 uL, 990 uL, or 1000 uL.

Leading electrolyte buffer channels on the fluidic device can have a volume within a range of about 10 uL to about 1 mL. In some cases, one or more leading electrolyte buffer channel on the fluidic device can have a volume within a range bounded by any two of the following values: 10 uL, 20 uL, 30 uL, 40 uL, 50 uL, 60 uL, 70 uL, 80 uL, 90 uL, 100 uL, 110 uL, 120 uL, 130 uL, 140 uL, 150 uL, 160 uL, 170 uL, 180 uL, 190 uL, 200 uL, 200 uL, 210 uL, 220 uL, 230 uL, 240 uL, 250 uL, 260 uL, 270 uL, 280 uL, 290 uL, 300 uL, 310 uL, 320 uL, 330 uL, 340 uL, 350 uL, 360 uL, 370 uL, 380 uL, 390 uL, 400 uL, 410 uL, 420 uL, 430 uL, 440 uL, 450 uL, 460 uL, 470 uL, 480 uL, 490 uL, 500 uL, 510 uL, 520 uL, 530 uL, 540 uL, 550 uL, 560 uL, 570 uL, 580 uL, 590 uL, 600 uL, 610 uL, 620 uL, 630 uL, 640 uL, 650 uL, 660 uL, 670 uL, 680 uL, 690 uL, 700 uL, 710 uL, 720 uL, 730 uL, 740 uL, 750 uL, 760 uL, 770 uL, 780 uL, 790 uL, 800 uL, 810 uL, 820 uL, 830 uL, 840 uL, 850 uL, 860 uL, 870 uL, 880 uL, 890 uL, 900 uL, 910 uL, 920 uL, 930 uL, 940 uL, 950 uL, 960 uL, 970 uL, 980 uL, 990 uL, and 1000 uL.

Leading electrolyte buffer channels on the fluidic device can have a volume of less than about 1 mL, for example less than about 500 ul. In some cases, one or more leading electrolyte buffer channel on the fluidic device can have a volume of less than about 10 uL, 20 uL, 30 uL, 40 uL, 50 uL, 60 uL, 70 uL, 80 uL, 90 uL, 100 uL, 110 uL, 120 uL, 130 uL, 140 uL, 150 uL, 160 uL, 170 uL, 180 uL, 190 uL, 200 uL, 200 uL, 210 uL, 220 uL, 230 uL, 240 uL, 250 uL, 260 uL, 270 uL, 280 uL, 290 uL, 300 uL, 310 uL, 320 uL, 330 uL, 340 uL, 350 uL, 360 uL, 370 uL, 380 uL, 390 uL, 400 uL, 410 uL, 420 uL, 430 uL, 440 uL, 450 uL, 460 uL, 470 uL, 480 uL, 490 uL, 500 uL, 510 uL, 520 uL, 530 uL, 540 uL, 550 uL, 560 uL, 570 uL, 580 uL, 590 uL, 600 uL, 610 uL, 620 uL, 630 uL, 640 uL, 650 uL, 660 uL, 670 uL, 680 uL, 690 uL, 700 uL, 710 uL, 720 uL, 730 uL, 740 uL, 750 uL, 760 uL, 770 uL, 780 uL, 790 uL, 800 uL, 810 uL, 820 uL, 830 uL, 840 uL, 850 uL, 860 uL, 870 uL, 880 uL, 890 uL, 900 uL, 910 uL, 920 uL, 930 uL, 940 uL, 950 uL, 960 uL, 970 uL, 980 uL, 990 uL, or 1000 uL.

Elution channels on the fluidic device can have a volume within a range of about 10 uL to about 1 mL. In some cases, one or more elution channel on the fluidic device can have a volume within a range bounded by any two of the following values: 10 uL, 20 uL, 30 uL, 40 uL, 50 uL, 60 uL, 70 uL, 80 uL, 90 uL, 100 uL, 110 uL, 120 uL, 130 uL, 140 uL, 150 uL, 160 uL, 170 uL, 180 uL, 190 uL, 200 uL, 200 uL, 210 uL, 220 uL, 230 uL, 240 uL, 250 uL, 260 uL, 270 uL, 280 uL, 290 uL, 300 uL, 310 uL, 320 uL, 330 uL, 340 uL, 350 uL, 360 uL, 370 uL, 380 uL, 390 uL, 400 uL, 410 uL, 420 uL, 430 uL, 440 uL, 450 uL, 460 uL, 470 uL, 480 uL, 490 uL, 500 uL, 510 uL, 520 uL, 530 uL, 540 uL, 550 uL, 560 uL, 570 uL, 580 uL, 590 uL, 600 uL, 610 uL, 620 uL, 630 uL, 640 uL, 650 uL, 660 uL, 670 uL, 680 uL, 690 uL, 700 uL, 710 uL, 720 uL, 730 uL, 740 uL, 750 uL, 760 uL, 770 uL, 780 uL, 790 uL, 800 uL, 810 uL, 820 uL, 830 uL, 840 uL, 850 uL, 860 uL, 870 uL, 880 uL, 890 uL, 900 uL, 910 uL, 920 uL, 930 uL, 940 uL, 950 uL, 960 uL, 970 uL, 980 uL, 990 uL, and 1000 uL.

Elution channels on the fluidic device can have a volume of less than about 1 mL, for example less than about 500 ul. In some cases, one or more elution channel on the fluidic device can have a volume of less than about 10 uL, 20 uL, 30 uL, 40 uL, 50 uL, 60 uL, 70 uL, 80 uL, 90 uL, 100 uL, 110 uL, 120 uL, 130 uL, 140 uL, 150 uL, 160 uL, 170 uL, 180 uL, 190 uL, 200 uL, 200 uL, 210 uL, 220 uL, 230 uL, 240 uL, 250 uL, 260 uL, 270 uL, 280 uL, 290 uL, 300 uL, 310 uL, 320 uL, 330 uL, 340 uL, 350 uL, 360 uL, 370 uL, 380 uL, 390 uL, 400 uL, 410 uL, 420 uL, 430 uL, 440 uL, 450 uL, 460 uL, 470 uL, 480 uL, 490 uL, 500 uL, 510 uL, 520 uL, 530 uL, 540 uL, 550 uL, 560 uL, 570 uL, 580 uL, 590 uL, 600 uL, 610 uL, 620 uL, 630 uL, 640 uL, 650 uL, 660 uL, 670 uL, 680 uL, 690 uL, 700 uL, 710 uL, 720 uL, 730 uL, 740 uL, 750 uL, 760 uL, 770 uL, 780 uL, 790 uL, 800 uL, 810 uL, 820 uL, 830 uL, 840 uL, 850 uL, 860 uL, 870 uL, 880 uL, 890 uL, 900 uL, 910 uL, 920 uL, 930 uL, 940 uL, 950 uL, 960 uL, 970 uL, 980 uL, 990 uL, or 1000 uL.

In some cases, a fluidic device comprises more than one channel. The channels may be spaced within the fluidic device at a given density. In some cases, the edge to edge distance between channels is at least about 0.2 mm, 0.3 mm, 0.4 mm, 0.5 mm, 0.6 mm, 0.7 mm, 0.8 mm, 0.9 mm, 1 mm, 1.25 mm, 1.5 mm, 1.75 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm. In some cases, the edge to edge distance between channels is at most about 0.2 mm, 0.3 mm, 0.4 mm, 0.5 mm, 0.6 mm, 0.7 mm, 0.8 mm, 0.9 mm, 1 mm, 1.25 mm, 1.5 mm, 1.75 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm. The density of channels may be defined as a ratio of the width of the channels to the space (or distance) between channels. In some cases, the ratio of channel width to distance between channels is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, 11:1, 12:1, 13:1, 14:1, 15:1, 16:1, 17:1, 18:1, 19:1, or 20:1.

In some cases, the total volume of all channels within a microfluidic device (e.g., chip) is 1 microliter (µL), 10 µL, 20 µL, 30 µL, 40 µL, 50 µL, 60 µL, 70 µL, 80 µL, 90 µL, 100 µL, 150 µL, 175 µL, 200 µL, 225 µL, 250 µL, 275 µL, 300 µL, 350 µL, 400 µL, 450 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL. In some cases, the total volume of all channels within a microfluidic device (e.g., chip) is at most about 1 microliter (µL), 10 µL, 20 µL, 30 µL, 40 µL, 50 µL, 60 µL, 70 µL, 80 µL, 90 µL, 100 µL, 150 µL, 175 µL, 200 µL, 225 µL, 250 µL, 275 µL, 300 µL, 350 µL, 400 µL, 450 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL.

Inlets and/or outlets of a fluidic device can be arranged and spaced such that they are compatible with standard fluid handling formats. For example, inlets and/or outlets can be spaced to line up with wells on a 5"×3.33" titer plate. A device can comprise eight inlets and/or outlets, spaced to correspond with a standard eight-tip pipettor and/or the eight wells in a dimension of a standard 24-, 48-, or 96-well plate. A device can comprise twelve inlets and/or outlets, spaced to correspond with a standard twelve-tip pipettor and/or with the twelve wells in a dimension of a standard 96-well plate. A device can comprise sixteen inlets and/or outlets, spaced to correspond with a standard sixteen-tip pipettor and/or with the sixteen wells in a dimension of a standard 384-well plate. A device can comprise twenty-four inlets and/or outlets, spaced to correspond with a standard twenty-four-tip pipettor and/or with the twenty-four wells in a dimension of a standard 384-well plate. This can enable easier fluid handling from such plates onto the device, for example via robotic pipet systems or other multi-pipets.

Devices comprising fluidic elements disclosed herein, such as fluidic and pneumatic channels, ports, reservoirs, capillary barriers and/or fluidic circuits can be used for purposes other than isotachophoresis. For example, application of pressure at external ports or reservoirs can be used to move liquids through a fluidic circuit. Such devices can be combined with other elements, such as mechanical valves, to control flow of liquids. Compartments separated by barriers (e.g. capillary barriers) can be used to perform biochemical reactions, such as amplification reactions such as PCR, and reaction product can be moved to another compartment separated by barriers for subsequent processing.

Figure 13A:
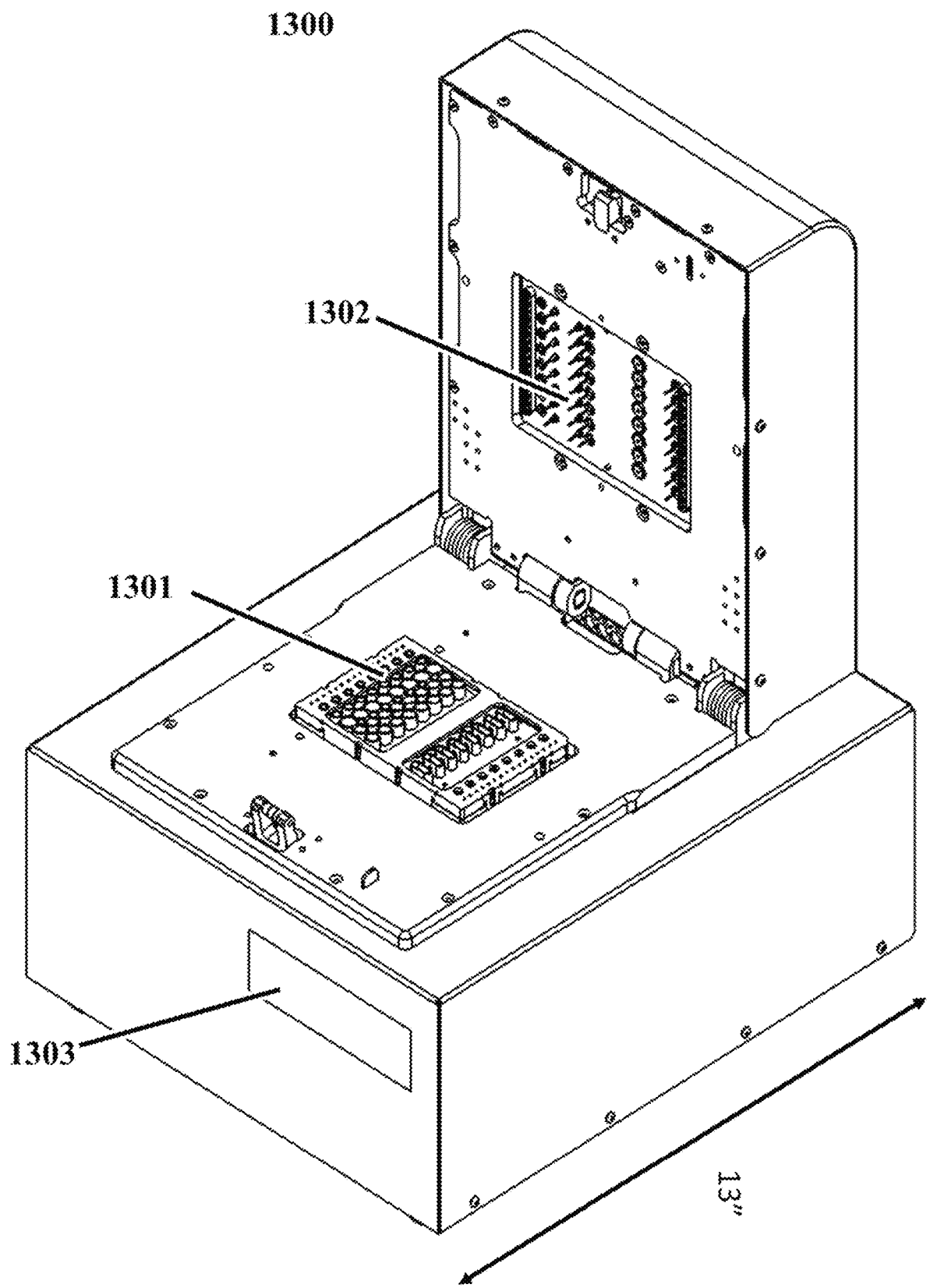
FIG. 13A shows an exemplary benchtop device for conducting automated sample preparation and isotachophoresis on a fluidic device cartridge.

Isotachophoresis can be conducted using a benchtop system or base station. For example, FIG. 13A shows a benchtop system 1300 for conducting sample preparation and isotachophoresis on a fluidic device cartridge 1301. The fluidic device cartridge can be loaded onto the benchtop system as shown, and a lid with matching covers and controls 1302 can be lowered onto the fluidic device cartridge. The benchtop system can also include a control panel 1303 with a user interface (e.g., touch screen) for operation of the system.

The system 1300 can comprise an interface assembly configured to receive and engage the fluidic device pneumatically, electrically and/or fluidically. The interface assembly can comprise a key or orientation device to properly orient the fluidic device 1301 within the instrument 1300. The interface assembly also can comprise one or more electrodes which, when the fluidic device 1301 is engaged, may be positioned in various device reservoirs. The interface assembly can further comprise pneumatic lines which, when the device is engaged, may communicate with pneumatic ports in the device 1301 as described herein. The system 1300 can include a power supply as described herein to apply current and/or voltage to the electrodes. The system 1300 can comprise electronics as described herein to measure voltage across various electrodes. The system 1300 can include one or more pumps to supply positive or negative pneumatic pressure to the pneumatic lines as described herein. The system 1300 can comprise a temperature sensor as described herein to measure temperature at determined positions in fluidic circuits in the device 1301. The system 1300 can comprise an optical assembly comprising one or more light sources to transmit light to one or more determined positions in the fluidic device and to detect light, e.g., fluorescent light, emitted from the fluidic device, for example, upon excitation of fluorescent species in the device 1301 as described herein. The system 1300 can include a display as described herein to display operating parameters of the system, such as voltage, temperature, detected light, engagement of a fluidic device, time, stage of processing. The system 1300 can be connected through a communications network, such as the internet, to a remote server through which operation of the system can be controlled remotely as described herein.

Negative pneumatic pressure may be applied to pneumatic ports in the device in order to load one or more of the buffers or samples into the channel(s) of the device 1301 as described herein. The system 1300 may be configured to apply a negative pneumatic pressure within a range of about 0 mpsi to about 200 mpsi, for example within a range of about 10 mpsi to about 80 mpsi.

Figure 59A:
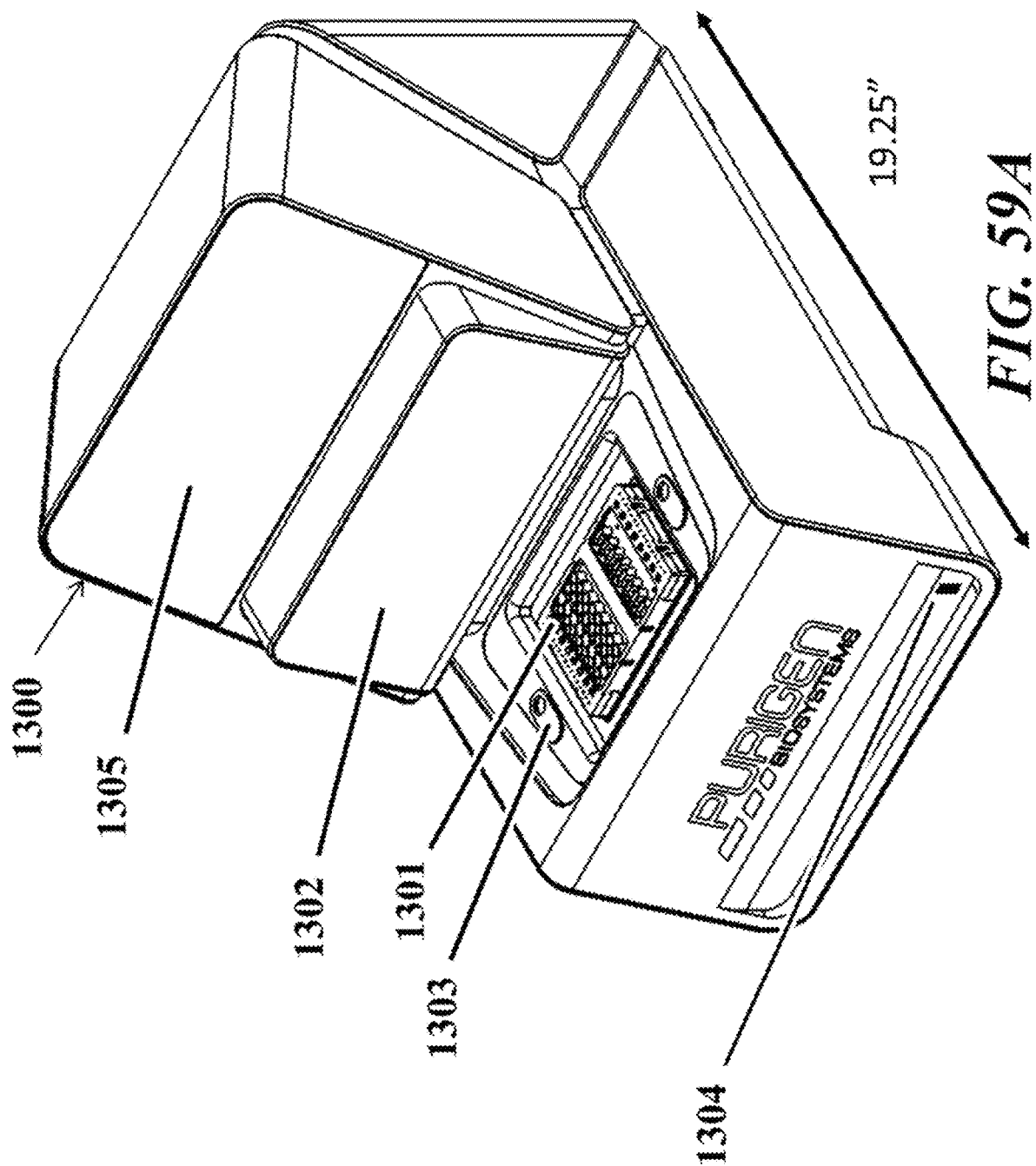
FIGS. 59A-59C show an exemplary benchtop device for conducting automated isotachophoresis and/or sample preparation on a fluidic device cartridge.
Figure 59B:
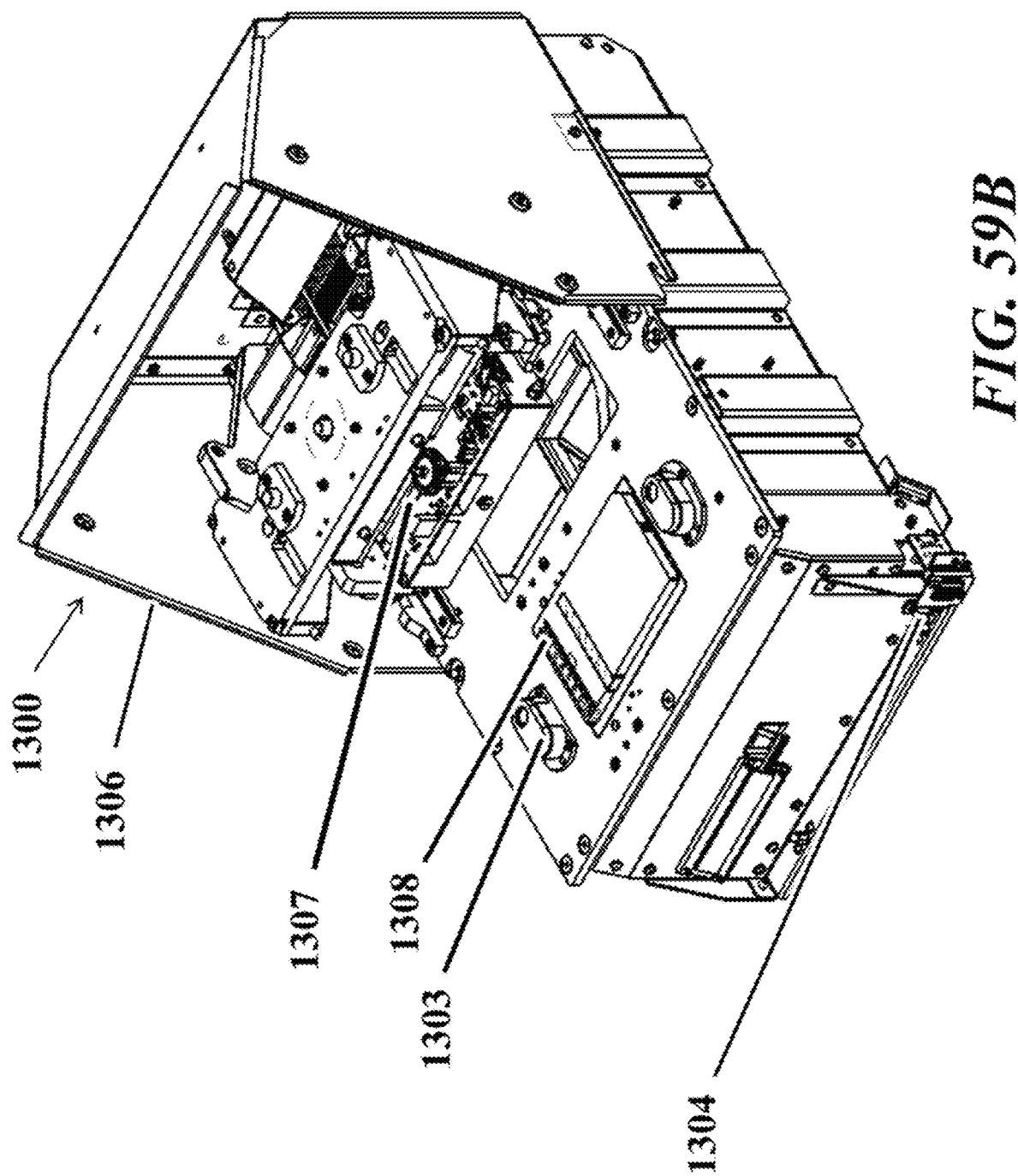
Figure 59C:
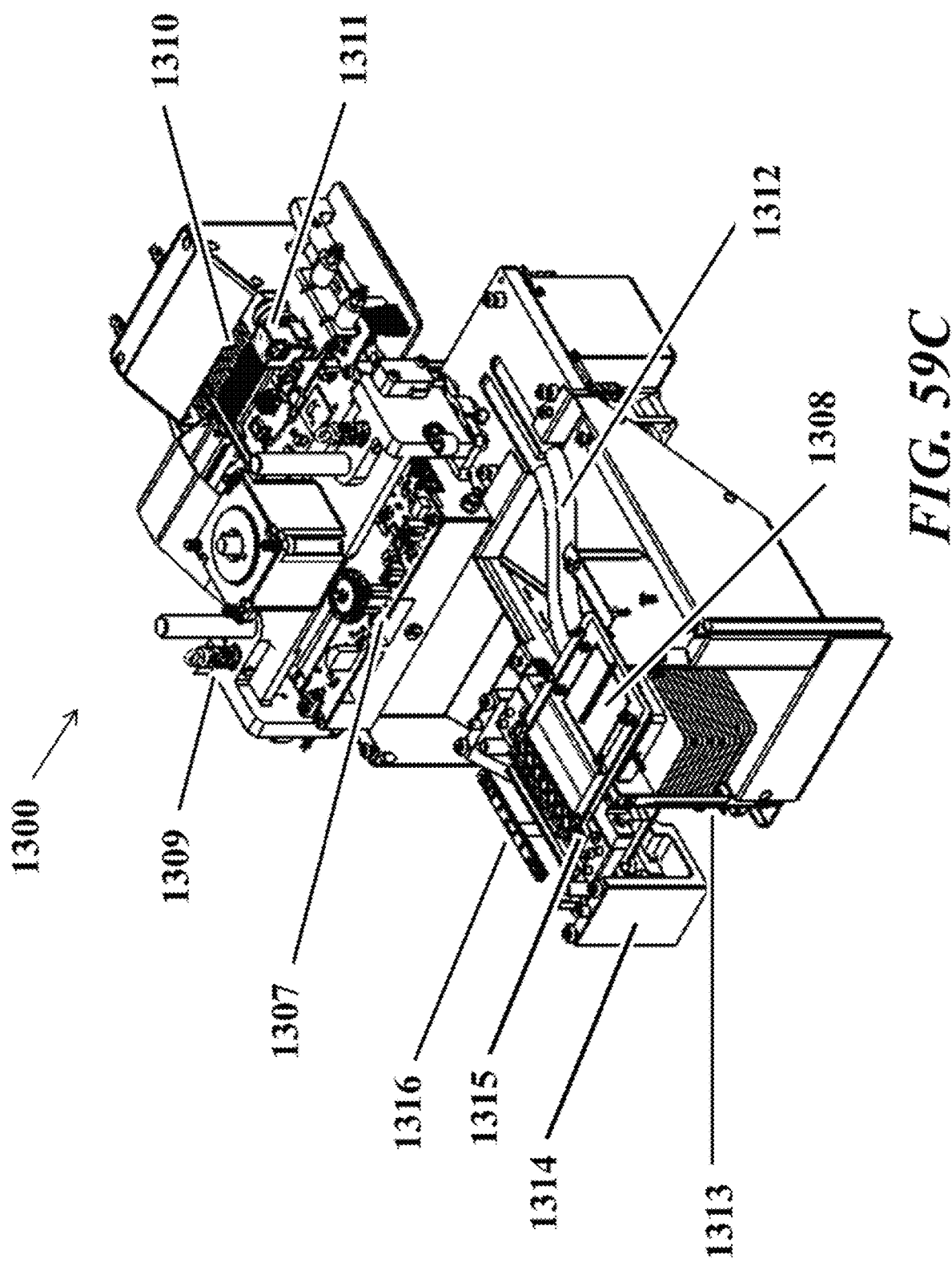

FIGS. 59A-59C show drawings of an exemplary benchtop system or instrument 1300 for conducting isotachophoresis on a fluidic device cartridge 1301. The fluidic device cartridge 1301 can be loaded onto the instrument 1300 on a holder 1308 and engaged by manifold 1307. The system may include a cover 1302, for example an articulating manifold, which allows for loading and unloading of the fluidic device cartridge 1301 from the instrument 1300. The cover 1302 may optionally facilitate coupling of the device 1301 to the instrument 1300. The instrument 1300 may comprise manifold and/or electrode alignment features 1303 to aid in coupling of a pneumatic manifold 1307 and/or electrodes to the correct locations on the chip 1301. A USB port 1304 may be provided to allow a user to access data generated by the instrument before, during, or after one or more ITP runs. The instrument may comprise a display 1305, for example an LCD screen, as described herein. The instrument may optionally comprise a chassis with integrated cooling 1306. The instrument may optionally comprise a passive manifold return mechanism 1309 which may be used to manually access the chip, for example in the event of power loss. The instrument may comprise a high-voltage power supply 1310, a pneumatic pump 1311, a thermal controller (e.g. cooler or heater) 1312, a processor (e.g. a printed circuit board) 1313, a channel closer 1314, an optical detection system 1315, and/or a triggering sensor(s) (e.g. an infrared sensor) 1316 for run automation, or any combination thereof.

FIG. 60 shows an exemplary image which may be displayed to a user to instruct and guide the user through the reservoir loading process. For example, the instrument may display visual and/or color-coded instructions to the user which indicate which buffers go in which reservoirs, as well as in which order the buffers should be loaded into the chip. The chip may be configured to enable an easy right-left or left-right pipetting scheme to facilitate ease of use by the user. For example, the chip may be configured to guide the user, which color-coded instructions, to load the reservoirs in a left-right manner, starting with the elution buffer (EB), continuing with the high concentration elution buffer (EBH), the leading electrolyte buffer (LE), the high concentration leading electrolyte buffer (LEH), and ending with the trailing electrolyte buffer (TEH) as shown.

Figure 61:
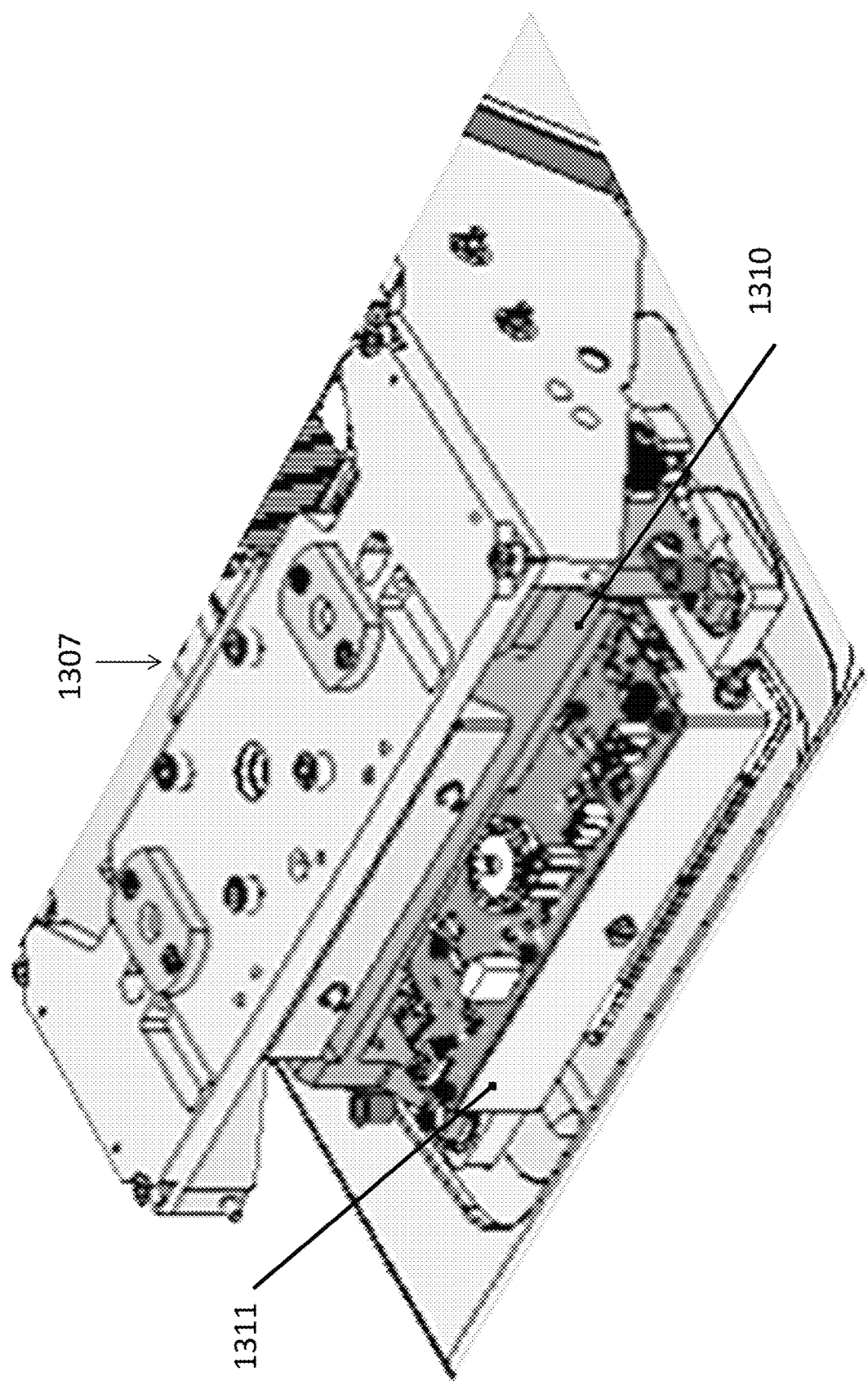
FIG. 61 shows a pneumatic manifold which may facilitate engagement of the microfluidic chip with the instrument.

FIG. 61 shows a pneumatic manifold 1307 which may facilitate engagement of the microfluidic chip with the instrument. The pneumatic chip manifold 1307 may comprise a pneumatic pump or system 1311. The pneumatic chip manifold 1307 may optionally comprise high voltage electronics (e.g. power supply 1310). The instrument can comprise a motor that moves the manifold into engagement with the fluidic device. Pressure can maintain fluidic, electrical and pneumatic connections.

Figure 62:
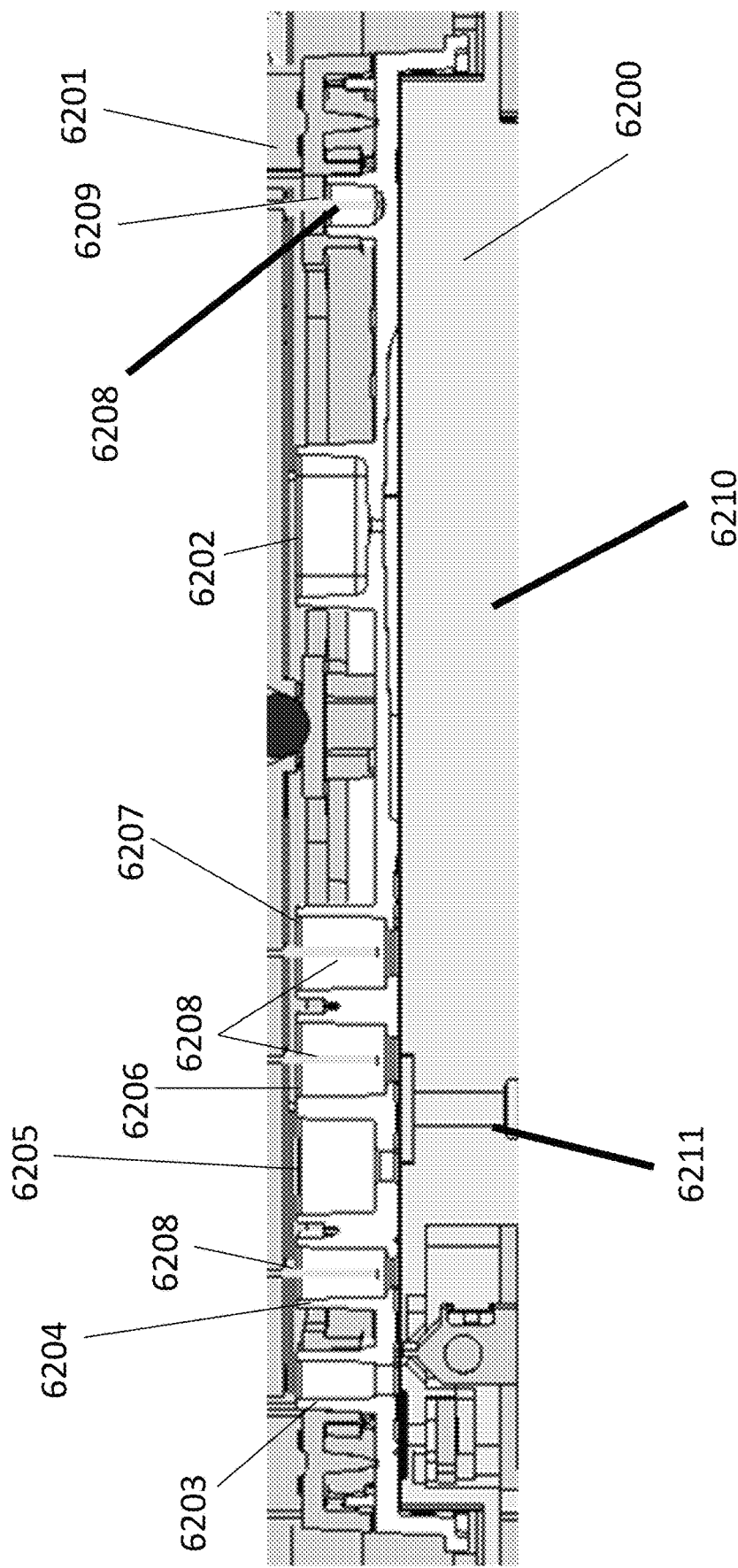
FIG. 62 shows a cross-section of a chip in an instrument.

FIG. 62 shows a cross-section of a chip 6201 in an instrument 6200. The instrument 6200 may be substantially similar to any of the instruments described herein (e.g. instrument 1300). The instrument 6200 may comprise a manifold comprising a gasket and mating holes configured to couple to the top of the chip 6201 in order to align the chip 6201 with the instrument 6200. The instrument may further comprise a low temperature cooling block 6210 (also referred to herein as a thermal controller) and/or an optical detection system 6211 for on-chip nucleic acid quantitation as described herein. The chip 6201 may be substantially similar to any of the chips described herein (e.g. chip 3800). The chip 6201 may for example comprise a sample reservoir 6202, an elution reservoir 6203, an elution buffering reservoir 6204, a leading electrolyte reservoir 6205, a leading electrolyte buffering reservoir 6206, and a trailing electrolyte reservoir 6207. The instrument 6200 may comprise one or more electrodes 6208 as described herein. The electrodes 6208 may be disposed within the instrument 6200 at a fixed height such that they are correctly inserted into the desired reservoirs when the cover of the instrument 6200 is closed. In some instances, the electrodes 6208 may enter the corresponding reservoirs every time the instrument is closed. Electrodes 6208 may for example be located in the trailing electrolyte reservoir 6207, the leading electrolyte buffering reservoir 6205, and/or the leading electrolyte buffering reservoir 6206 such that the electrodes do not directly contact sample material. The electrodes may be triggered to alter or control the applied electric field in response to feedback from a sensor, for example a voltage, current, conductivity, or temperature sensor as described herein. The chip may optionally comprise one or more additional reservoirs 6209 in which additional electrodes 6208 may be disposed. It will be apparent to one of ordinary skill in the art that the location of the electrodes, and the number of electrodes, may be altered as desired to perform a desired ITP run.

Figure 63:
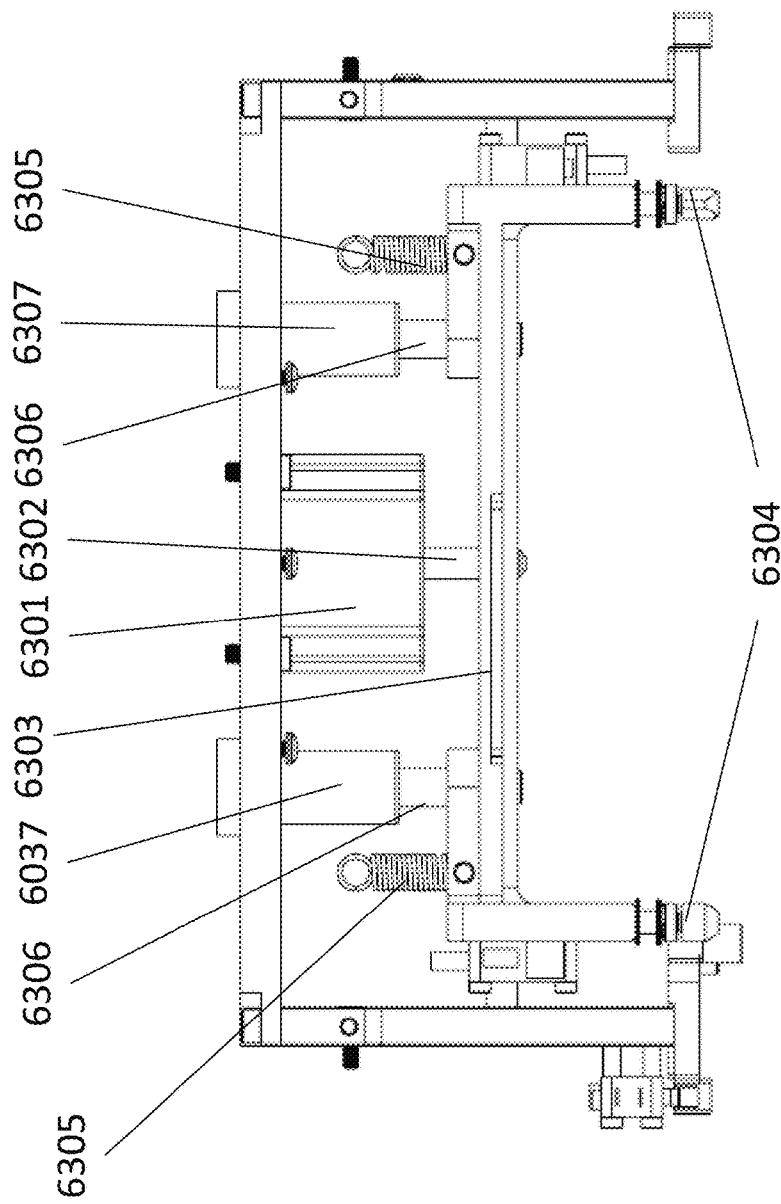
FIG. 63 depicts a vertical manifold motion mechanism comprising a mechanical assembly design for motion with alignment and auto-retraction.

FIG. 63 depicts a vertical manifold motion mechanism comprising a mechanical assembly design for motion with alignment and auto-retraction. The drawing depicts a motor with a lead screw that may drive a mechanism into a position guided by alignment pins. Tension springs may automatically retract the mechanism by back-driving the motor in case of power or software failure. FIG. 63 shows a motor 6301 with lead screw 6302 which may drive a bracket 6303 into a position guided by alignment pins 6304. Tension springs 6305 may automatically retract the mechanism by back-driving the motor in case of power or software failure. The path of travel may be constrained by the shafts 6306 traveling through linear bearings 6307. The vertical manifold motion mechanism may be located in the mechanism that controls the motion of the articulating manifold. The vertical manifold motion mechanism may allow the instrument to open itself in the event of an unrecoverable loss of power with a chip in place. This may allow the chip to be removed prior to shipping for service.

Figure 64:
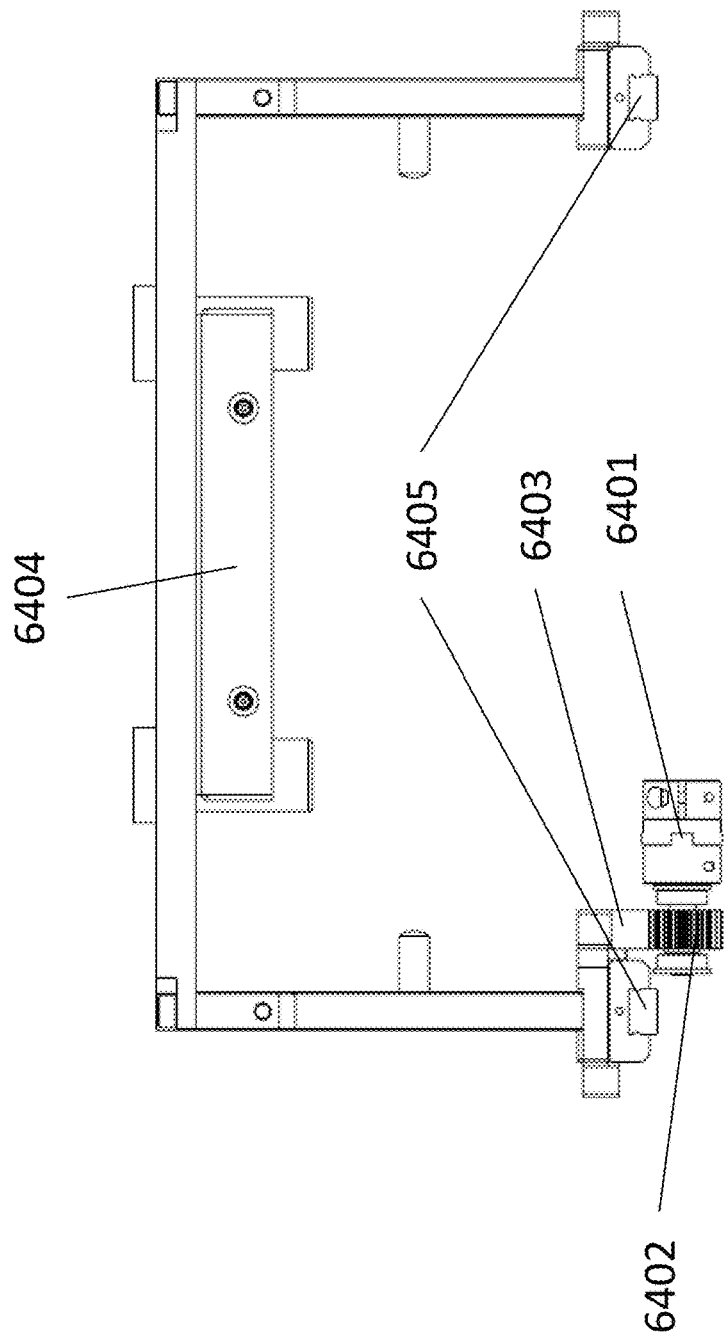
FIG. 64 shows a design for a horizontal manifold motion mechanism including a mechanical assembly design for horizontal motion using a rack and pinion.

FIG. 64 shows a design for a horizontal manifold motion mechanism including a mechanical assembly design for horizontal motion using a rack and pinion. A motor drives a mechanism using a rack and pinion along a path constrained by guide rails. The drawing shows a motor 6401 attached to a pinion 6402 which may drive the corresponding rack 6403 on a bracket 6404 along a path constrained by guide rails 6405. The horizontal manifold motion mechanism may be located on the mechanism that controls the motion of the articulating manifold. This may facilitate movement of the manifold forward and backward.

The benchtop system can comprise pressure controls that provide pressure to handle fluids (e.g., sample, buffer, reagents, enzyme solutions, electrolyte solutions) on a fluidic device. The benchtop system can receive pressure feedback signals to regulate or control the fluid handling. Fluid handling can be used to load fluids onto a fluidic device (e.g., reagents, buffers, samples). Fluid handling can be used to prime fluids (e.g., reagent solutions) into dry channels on a fluidic device. Pressure can be regulated using, for example, solenoid valves.

The benchtop system can comprise electrodes or electrical contacts. Electrodes can be part of an electric circuit and can insert into reservoirs or other openings on a fluidic device to allow application of an electric field within the fluidic device by the completed circuit. Electrical contacts can couple to corresponding contacts on a fluidic device, for example a fluidic device with integrated electrodes.

The benchtop system can comprise one or more detectors or sensors, such as optical detectors, reflectance sensors, infrared (IR) detectors, electrical detectors, thermal sensors, flow sensors, and pressure sensors, including detectors described further in this disclosure. Optical detectors can include but are not limited to three-axis point detectors, complementary metal-oxide semiconductor (CMOS) detectors, charge-coupled device (CCD) detectors, photodiode light sensors, photoresistors, photomultiplier tubes, and phototransistors. Electrical detectors can include electrodes or other detectors capable of detecting a voltage, voltage differential, current, charge, or other electrical property. Electrical detectors can be used to detect the passage of a band of extracted or purified nucleic acids, for example by detecting a change in conductivity at the interface between trailing electrolytes and leading electrolytes. Thermal sensors can include infrared (IR) sensors, probe temperature sensors, thermistors, negative temperature coefficient (NTC) thermistors, resistance temperature detectors (RTDs), thermocouples, semiconductor-based sensors, or the like.

The one or more detectors or sensors can be simultaneously or independently operated and controlled. In some instances, a single channel may have a dedicated sensor, for example a thermal or voltage sensor, which operates independently of other sensors dedicated to other channels on the microfluidic device. Feedback from the independent sensor may be used to independently control one or more electric fields on the device. For example, a sensor may detect a change in voltage over time within a well as described herein and feedback from that sensor may be used to control the current within the channel. A second sensor may act on a second channel in a similar, but independent, manner. In some instances, a sensor may detect a change in current over time within a well and feedback from that sensor may be used to control the voltage within the cannel.

The benchtop system can comprise one or more thermal controllers that control a temperature on a fluidic device or a part of a fluidic device. Thermal controllers can comprise components including but not limited to resistive heaters, fluid-based heating or cooling systems, and Peltier devices. Thermal controllers can be fabricated from materials including but not limited to metals (e.g., platinum, titanium, copper, gold), carbon, and indium tin oxide (ITO). Thermal controllers can comprise temperature sensors, which can be used to monitor the temperature being controlled and provide temperature feedback for thermal control. Thermal controllers can be used with computer control systems, as discussed further in this disclosure. For example, temperature sensors (e.g., infrared sensors) can be used to monitor a change in temperature in channels on a chip. Such temperature changes can be indicative of a location of an ITP band (e.g, a band of nucleic acid) during an ITP process, which temperature difference can be due to a change in conductivity between the leading electrolytes and trailing electrolytes. In some cases, thermal controllers are operated without temperature feedback.

Figure 65:
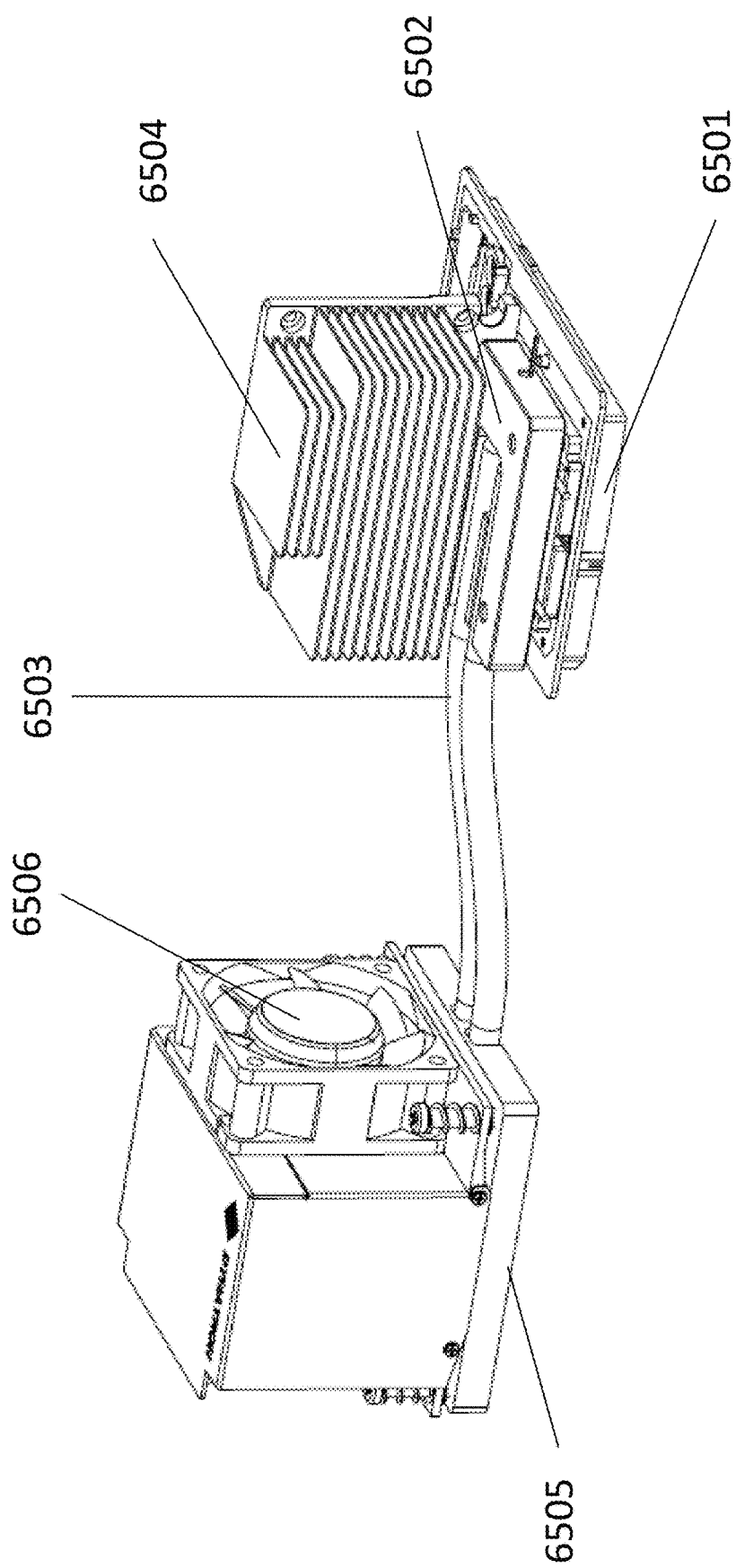
FIG. 65 depicts a heat pipe with thermoelectric cooler design for keeping an area at a prescribed temperature remote from the location of the thermoelectric cooler.

FIG. 65 depicts a heat pipe with thermoelectric cooler design for keeping an area at a prescribed temperature remote from the location of the thermoelectric cooler. FIG. 65 shows a surface 6501 to be cooled to a specific temperature through a large thermal contact 6502 which may lead to copper heat pipes 6503 and a heat sink 6504. Cooling may be provided through the thermoelectric cooler 6505 and fan 6506. The copper heat pipe 6503 and auxiliary heat sink 6504 may be configured cool surface 6501 to a prescribed temperature without the need for the thermoelectric cooler to be directly adjacent to the surface 6501.

Figure 66:
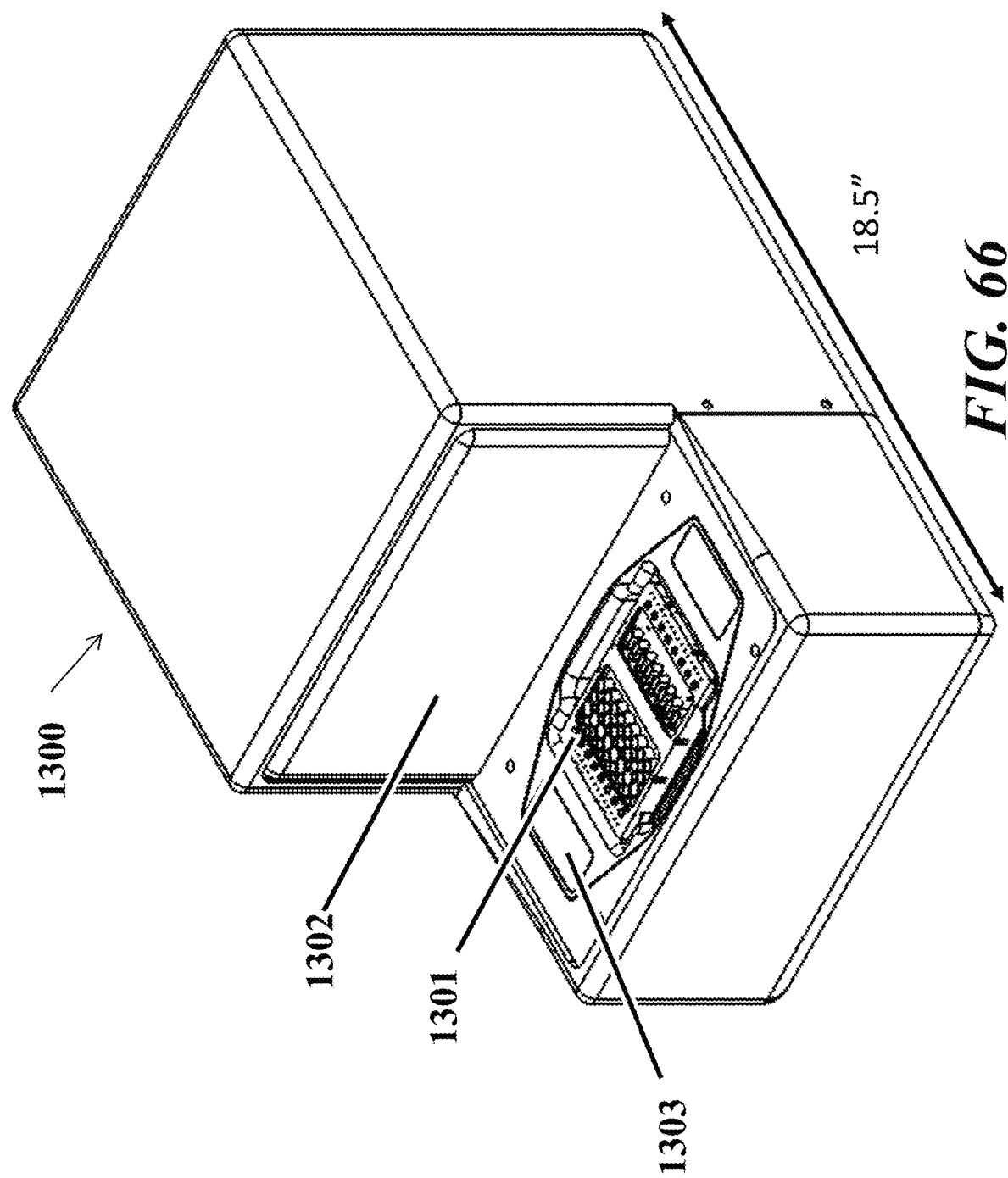
FIG. 66 shows another exemplary benchtop device for conducting automated isotachophoresis and/or sample preparation on a fluidic device cartridge.

FIG. 66 shows another exemplary benchtop instrument 1300 for conducting automated isotachophoresis and/or sample preparation on a fluidic device cartridge. FIG. 66 shows a drawing of a beta prototype instrument 1300 showing the, location of placement of the fluidic device or chip 1301 to be controlled. The instrument 1300 may comprise an articulating manifold 1302 configured to allow for loading and unloading of fluidic device 1301 and coupling of instrument 1300 to device 1301. The instrument 1300 may further comprise a strike plate 1303 for electromagnetic eanifold sealing to the fluidic device 1301.

Techniques of the present disclosure (including, e.g., the use of fluidic devices and/or benchtop systems discussed herein) can provide quick processing times. For example, a sample comprising nucleic acids can be prepared (e.g., removal of embedding material, tissue disruption, cell lysis, nucleic acid de-crosslinking) and have nucleic acids extracted or purified for subsequent analysis, use, or storage.

Detection and Quantitation

Techniques of the present disclosure can employ one or more detectors. Detectors can be integrated into fluidic devices or located externally to a fluidic device. Detectors can be used for quantitation of nucleic acid in a sample, for example by fluorescent measurement or ultraviolet (UV) radiation (e.g., for measurement of quantity or purity, such as by measurement of A260/A280), or for providing a qualitative measure of the nucleic acids in the sample. Nucleic acids can be detected while located on a fluidic device, for example while within a purification zone (e.g., ITP channel) or reservoir (e.g., elution reservoir). The concentration of the nucleic acids may be detected (or calculated based on a quantity measurement in a known volume such as in the elution well as described herein). Nucleic acids can be labeled, such as with dyes, and the fluorescence intensity of the nucleic acids can be measured by a detector and used to quantify the nucleic acids present (see, e.g., FIG. 14). Nucleic acids can be labeled prior to loading on a fluidic device, while in a fluidic device, or after recovery from a fluidic device.

Use of a detector can enable quantitation of nucleic acids from samples with a high sensitivity or a low limit of detection. For example, nucleic acids can be detected (e.g., in-line in an isotachophoresis channel) at limit of detection of less than or equal to about 1000 picograms per microliter (pg/µL), 100 pg/µL, 10 pg/µL, 1 pg/µL, 0.9 pg/µL, 0.8 pg/µL, 0.7 pg/µL, 0.6 pg/µL, 0.5 pg/µL, 0.4 pg/µL, 0.3 pg/µL, 0.2 pg/µL, or 0.1 pg/µL. Nucleic acids can be detected (e.g., in-line in an isotachophoresis channel) at a limit of detection of less than or equal to about 1000 picograms (pg), 100 pg, 10 pg, 1 pg, or 0.1 pg.

Use of a detector can enable identification or qualification of nucleic acids in a sample. For example, techniques such as nucleic acid amplification (including, e.g., PCR, real-time PCR, and reverse-transcription PCR), hybridization (including, e.g., fluorescent in situ hybridization (FISH) and Q-FISH), and sequencing can be used to identify the presence or absence of, and optionally quantify, a particular sequence within nucleic acids in a sample.

Detectors can be used in the control of nucleic acid extraction or purification operations. For example, a detector can detect a band of nucleic acids concentrated by isotachophoresis. When the concentrated nucleic acids reach a certain location within the device, the process can be ended (e.g., electric fields can be turned off) and extracted or purified sample can be recovered from the device.

Detectors can include but are not limited optical detectors and electrical detectors, thermal sensors, and pressure sensors (e.g., pressure transducers). Optical detectors can include but are not limited to three-axis point detectors, complementary metal-oxide semiconductor (CMOS) detectors, charge-coupled device (CCD) detectors, photodiode light sensors, photoresistors, photomultiplier tubes, and phototransistors. Optical detection can be achieved by LED illumination paired with photodiode detection. Electrical detectors can include electrodes or other detectors capable of detecting a voltage, voltage differential, current, charge, or other electrical property. For example, electrical detectors can be used to detect the passage of a band of extracted or purified nucleic acids.

Nucleic acids can be labeled with one or more nucleic acid dyes, for example a fluorescent intercalating dye. The nucleic acids may be labeled with one or more of the following intercalating dyes: ethidium bromide, propidium iodide, DAPI, 7-AAD, YOYO-1, DiYO-1, TOTO-1, DiTO-1, BOBO-1, POPO-1, YO-PRO-1, TO-PRO-1, TO-PRO-3, TO-PRO-5, SYBR® Green I, SYBR® Green II, SYTO™ 9, SYTO™ 13, Quantifluor®, EvaGreen®, PicoGreen®, Acridine Orange, or the like. It will be apparent to one of ordinary skill in the art that the fluorescent dye may be chosen based on the desired detection location, detection method, and/or the downstream process(es) which the DNA may be used for following ITP.

Figure 67:
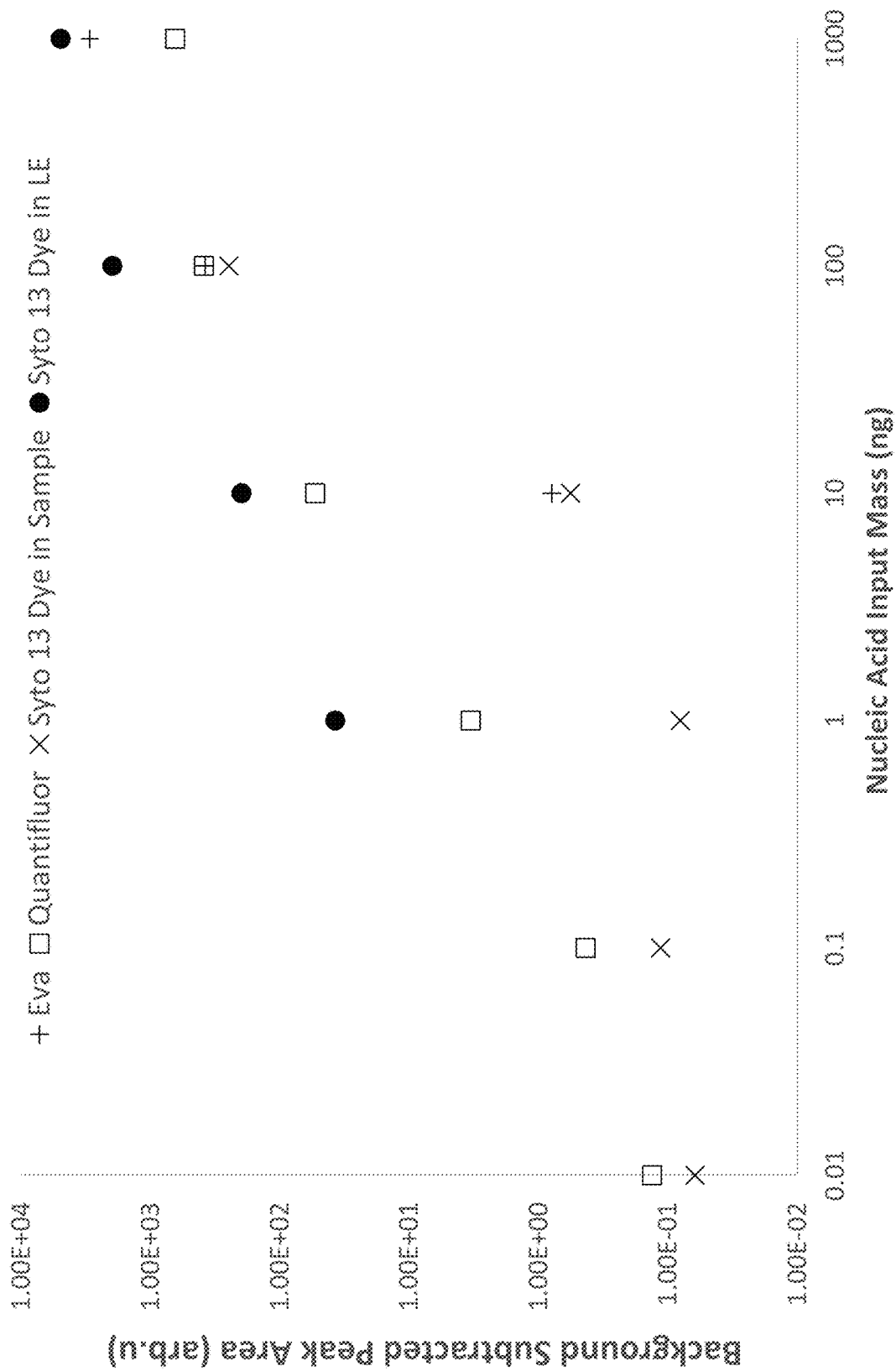

FIG. 67 shows a plot of peak area response to nucleic acid mass for various nucleic acid binding dyes to assess the possible feasibility of each dye for in-line (i.e., on-chip) nucleic acid quantitation during and/or after ITP. The background-subtracted peak area responses were plotted as a function of input nucleic acid mass (in ng) and shown on a log-log plot. EvaGreen®, Quantifluor®, Syto™ 13 in sample, and Syto™ 13 in sample with added LE was assessed for nucleic acid input masses of 0.01 ng, 0.1 ng, 1 ng, 10 ng, 100 ng, and 1000 ng. Only one of the candidate dyes, Qunatifluor®, demonstrated a linear response below 1 µg (1000 ng) input mass of nucleic acid. Some of the nonlinearilty of the Syto™ 13 response can be explained by dye being stripped off the DNA during ITP. Adding dye to the LE in addition to the sample recovered the linear relationship between nucleic acid input mass and peak area. EvaGreen® had both high background and a nonlinear response for all nucleic acid input masses assessed. All of the dyes tested lost linearity at high input mass (not shown). The preferred embodiments for dye addition to the ITP system for in line quantitation are (1) intercalating dye added to the LE and not the sample (e.g. PicoGreen, Syto 9, Syto 13 or EvaGreen dyes) or (2) dye added to the sample and the LE (e.g. PicoGreen, Syto 9, Syto 13 or EvaGreen dyes), or optionally (3) dye added to sample only (e.g. PicoGreen and EvaGreen dyes).

Figure 68:
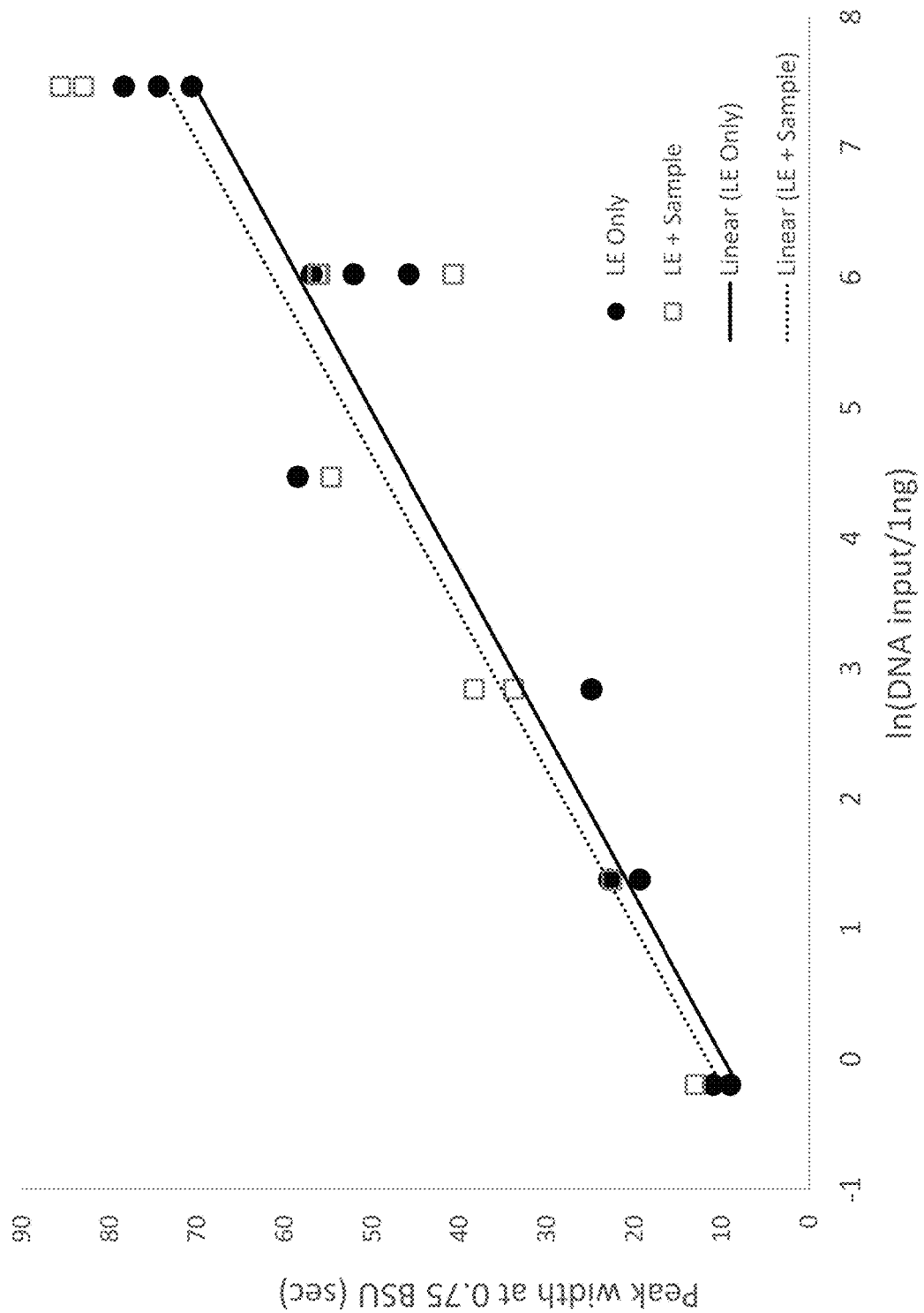

FIG. 68 shows a plot of peak width response to nucleic acid mass for various nucleic acid binding dyes which may, for example, be used to quantify the amount of nucleic acid in the ITP system. Several characteristics of the peak can be measured in order to calculate the amount of nucleic acid passing the detector. Traditional chromatographic methods consider the peak height and/or area (e.g. as shown in FIG. 67). Assuming the generation of fluorescence is linearly proportional to the mass of nucleic acid present, either of these approaches will produce a response that is linear with nucleic acid mass. If the underlying relationship is not linear, then there will be no fundamental relationship between peak area or peak height and nucleic acid mass. In such instances, the width of the peak at a fixed signal value can be shown to be linearly proportional to the natural logarithm of nucleic acid mass even when the response is fundamentally non-linear. Data shown in FIG. 68 demonstrate this log-linear relationship between peak width and nucleic acid input for the dye Syto™ 13 when present in both sample and LE, or solely in LE. Unlike the peak areas shown in FIG. 67, both conditions of Syto™ showed a linear relationship between the measured peak width and the input mass of the nucleic acids, which may be of use for on-chip quantification of the mass of the ITP band.

Figure 69C:
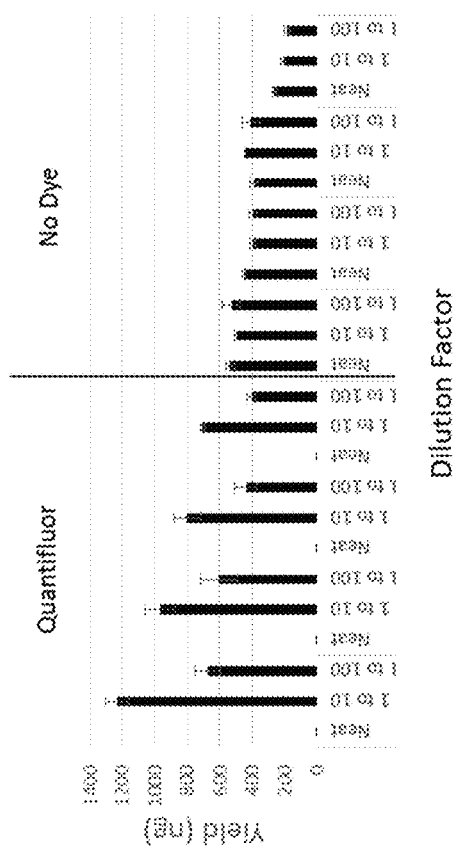
Figure 69A:
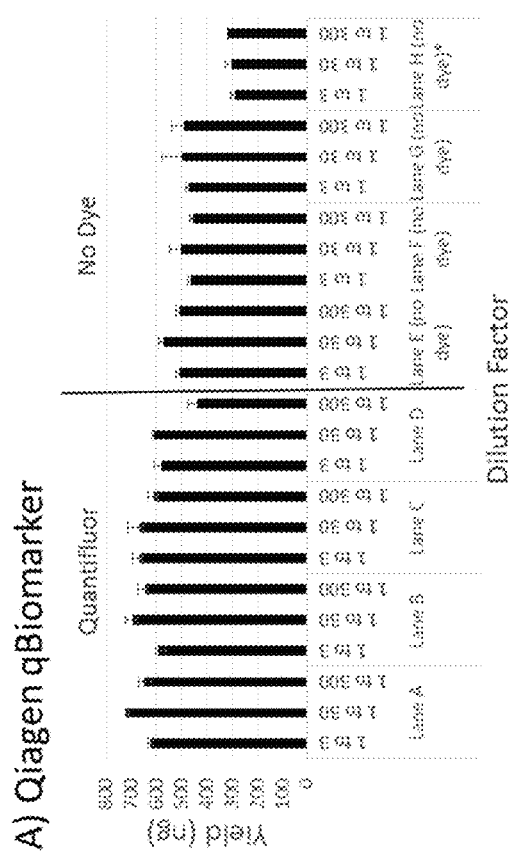
Figure 69B:
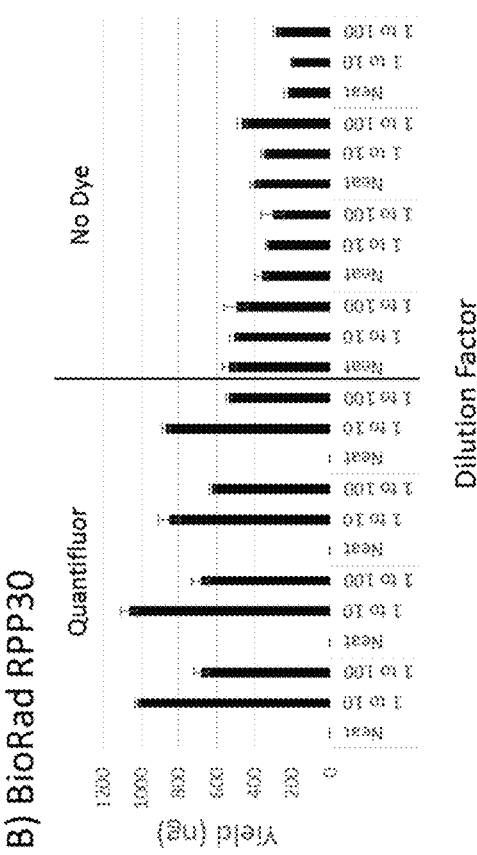

FIGS. 69A-69C depict Quantifluor® incompatibility with PCR. gDNA was purified using isotachophoresis in the presence and absence of Promega Quantifluor® at a concentration that was empirically determined to ensure linearity of fluorescence intensity up to 5 ug DNA (1× in 225 ul total sample volume). Recovered eluates were then serially diluted ("df"=dilution factor) and run through qPCR using Qiagen qBiomarker MRef assay (FIG. 69A) to test compatibility with intercalator-based (SYBR Green I) qPCR and BioRad RPP30 HEX (FIG. 69B) and BioRad RPP30 FAM assays (FIG. 69C) to test compatibility with Taqman-probed based qPCR. Dilutions were made using 10 mM Tris-Cl pH 8.0. Dilution corrected yields from qBiomarker Mref assay were similar for all samples, consistent with a lack of dye-induced inhibition in intercalator-based qPCR. However, a drop in dilution correct yield was observed with Quantifluor samples in both of the Taqman probe-based qPCR assays, indicating Quantifluor inhibits Taqman probe-based qPCR.

Figure 70:
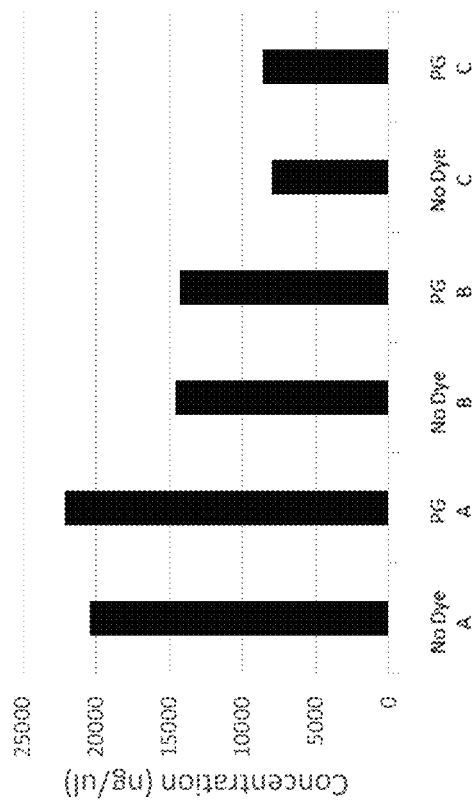

FIG. 70 depicts PicoGreen compatibility with Qubit dsDNA Assay. ThermoFisher Qubit dsDNA Assay is a fluorescence-based DNA quantitation assay that is ubiquitously used upfront of many downstream applications. Purified gDNA at three different concentrations was mixed with PicoGreen to a final concentration of 5.7× in a 35 ul eluate volume, the estimated maximum concentration needed to ensure linearity in fluorescence across 5 ng-5 ug dynamic range of DNA inputs in one implementation of DNA purification through a microfluidic isotachophoretic chip. Samples along with no dye controls were quantified using Qubit dsDNA Broad Range Assay. Comparable quants from samples with and without dye support a lack of interference of PicoGreen with the Qubit dsDNA Assay.

Figure 71:
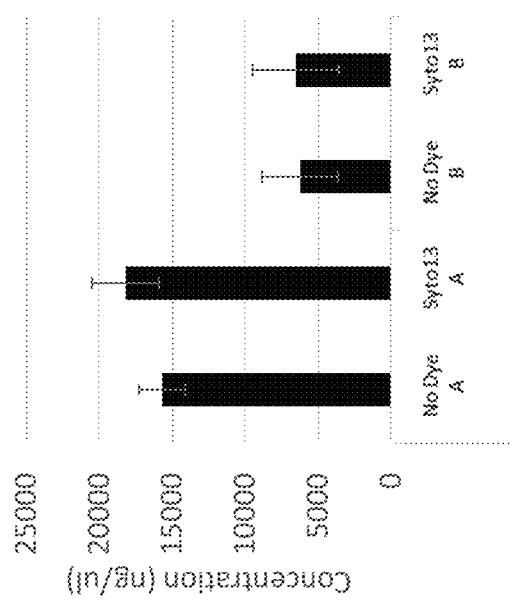

FIG. 71 depicts Syto13 compatibility with Qubit dsDNA Assay. Purified gDNA at two different concentrations was mixed with Syto13 to a final concentration of 5.7× in a total volume of 35 ul, the estimated maximum concentration needed to ensure linearity in fluorescence across 5 ng-5 ug dynamic range of DNA inputs in one implementation of DNA purification through a microfluidic isotachophoretic chip. Samples along with no dye controls were quantified using Qubit dsDNA High Sensitivity Assay from samples with and without dye support a lack of interference of Syto13 with the Qubit dsDNA Assay.

FIGS. 72A-72B depict PicoGreen compatibility with PCR. Purified genomic DNA at varying concentrations of DNA was mixed with PicoGreen at 0.0057×, 0.057×, 0.57×, 5.7× and 28.4× or 57× concentrations, each in a final volume of 100 ul. Samples were run through qPCR using either KAPA hgDNA Quant & QC Assay (FIG. 72A) to test compatibility with intercalator-based (SYBR Green I) qPCR and BioRad RPP30 FAM qPCR (FIG. 72B) to test compatibility with Taqman probe-based qPCR. Elevated baselines were observed with the 28.4× and 57× reactions resulting in delayed Ct values. However, Ct values for reactions containing 5.7× or less were similar, supporting the compatibility of PicoGreen with both classes of qPCR assays up to 5.7× concentration.

FIGS. 73A-73C depicts Syto13 compatibility with PCR. gDNA was purified using isotachophoresis in the presence and absence of Syto13 at a concentration that was empirically determined to ensure linearity of fluorescence intensity up to 5 ug DNA (1× in 225 ul total sample volume). Recovered eluates were then serially diluted ("df"=dilution factor) and run through qPCR using Qiagen qBiomarker MRef assay (FIG. 73A) to test compatibility with intercalator-based (SYBR Green I) qPCR and BioRad RPP30 HEX (FIG. 73B) and BioRad RPP30 FAM assays (FIG. 73C) to test compatibility with Taqman-probed based qPCR. Dilutions were made using 10 mM Tris-Cl pH 8.0. Dilution corrected yields within each assay were similar, supporting the compatibility of Syto13 with both classes of qPCR assays.

FIG. 74 depicts PicoGreen compatibility with amplicon-based sequencing library prep. Illumina TruSight Tumor 15 is a multiplexed PCR-based sequencing library prep assay designed for the targeted enrichment of 15 genes commonly mutated in solid tumors. TruSight 15 sequencing libraries were prepared from gDNA that was mixed with PicoGreen at 1× and 4.4× concentrations in a total volume of 298.5 ul. (4.4× is the estimated maximum concentration needed to ensure linearity in fluorescence across 5 ng-5 ug dynamic range of DNA inputs in a second implementation of DNA purification through a microfluidic isotachophoretic chip.) A control library (no dye) was also prepped. The three libraries were barcoded and then sequenced using Illumina sequencing technology, and sequencing data was downsampled to normalize coverage across the three conditions. Shown are Bland-Altman correlation plots for the two PicoGreen libraries. Also shown are statistical metrics for each library. Slight coverage bias or differences in top level sequencing metrics were observed between libraries.

Figure 75:
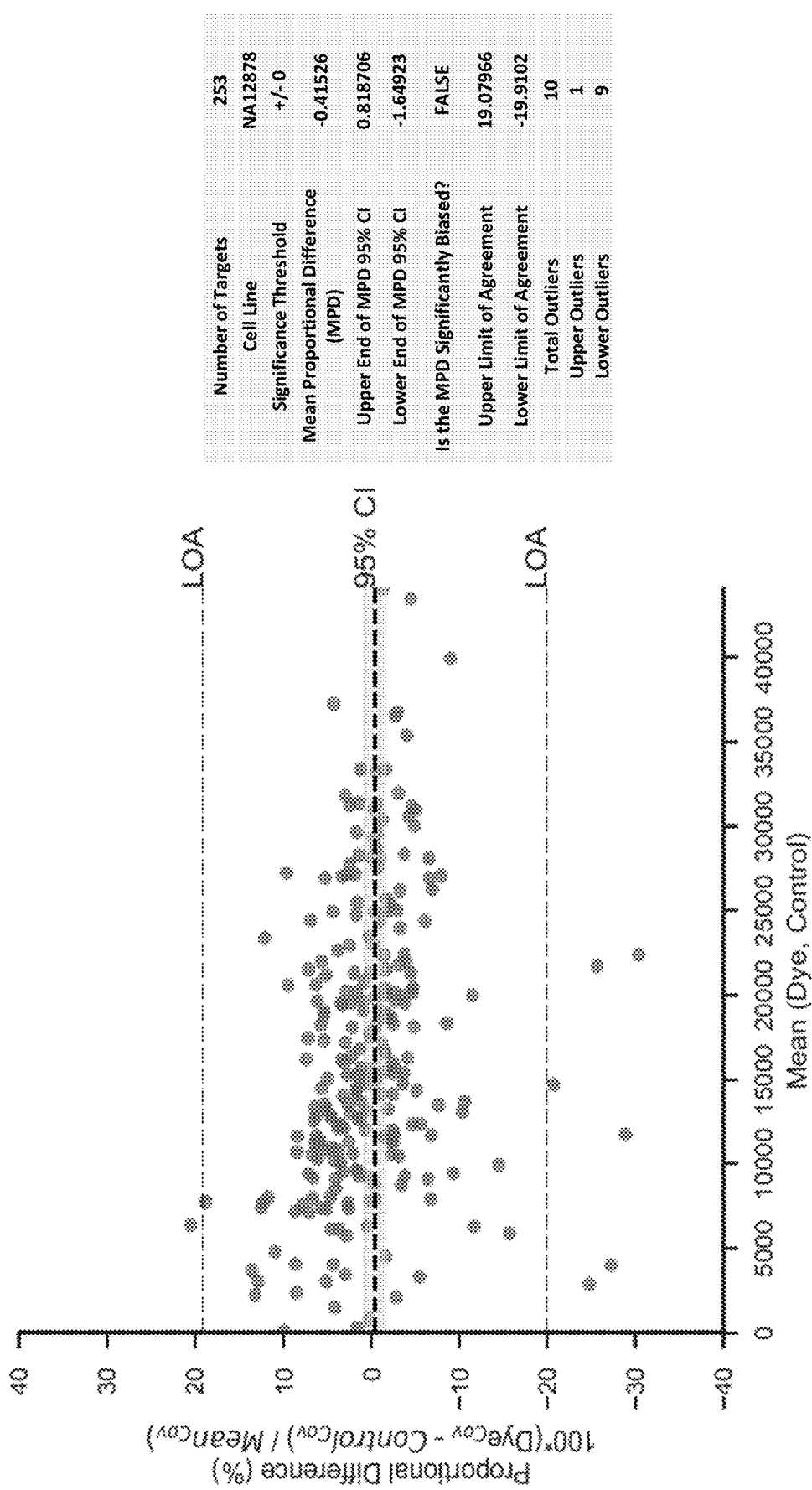

FIG. 75 shows Syto13 compatibility with amplicon-based sequencing library prep. gDNA was purified using isotachophoresis in the presence and absence of Syto13 at a sample concentration empirically determined to ensure saturation of DNA up to 5 ug. Recovered eluates were then used to generate TruSight 15 sequencing libraries. Control libraries (no dye) were also prepped. The libraries were barcoded and sequenced using Illumina sequencing technology. Raw reads were then used to calculate normalized coverage for each of the 253 targets. Shown is Bland-Altman correlation plot. Also shown are statistical metrics for the library. No bias was observed between libraries.

Figure 76B:
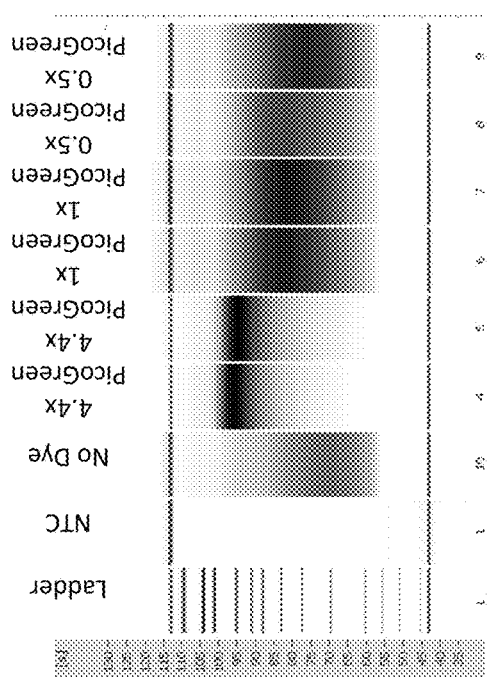
Figure 76A:
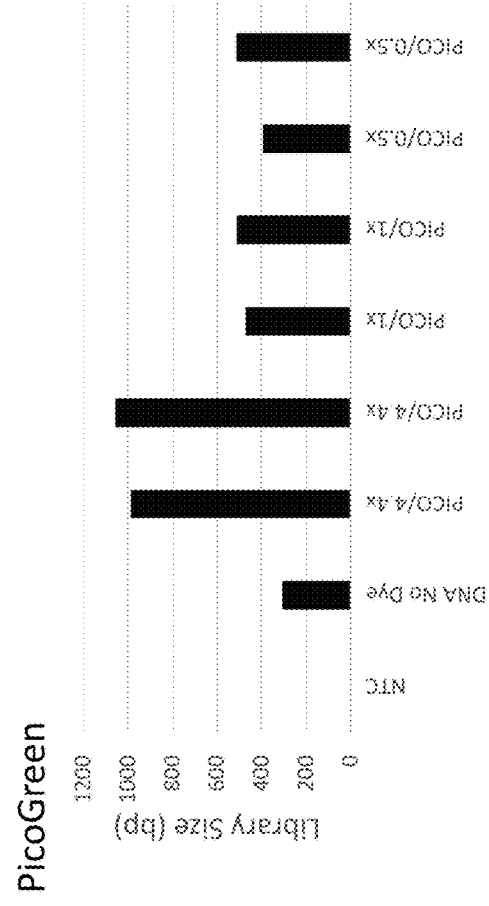

FIGS. 76A-76B and 78 depict PicoGreen incompatibility with whole genome sequencing library prep. KAPA HyperPlus generates a whole genome sequencing library using fragmentase to enzymatically shear gDNA before end-repair and A-tailing the gDNA fragments. The A-tailed genomic fragments are then ligated to sequencing adapters before being PCR amplified and purified using AMPure magnetic bead technology. Shown in FIGS. 76A-76B is fragment length metrics as determined using Agilent's BioAnalyzer DNA High Sensitivity Assay for whole genome KAPA HyperPlus libraries prepared from gDNA purified using isotachophoresis without PicoGreen and with PicoGreen at 4×, 1×, and 0.5× concentrations. Mode fragment lengths (left) and gel images (right) show that samples purified with PicoGreen were longer than control, with the 4× PicoGreen samples being nearly 2× as long as control. Shown in FIG. 78 is library quantitation by Qubit dsDNA High Sensitivity Assay. Samples purified in the presence of PicoGreen exhibited comparable yields as control samples.

Figure 77B:
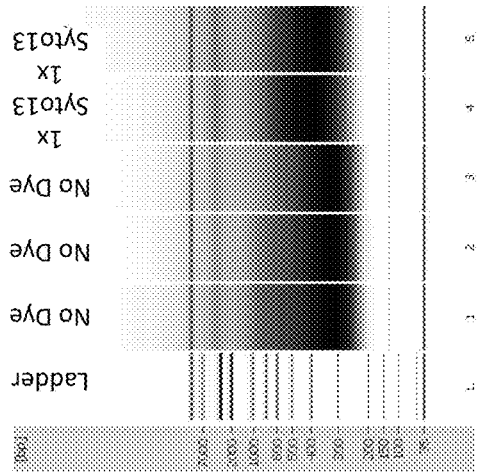
Figure 77A:
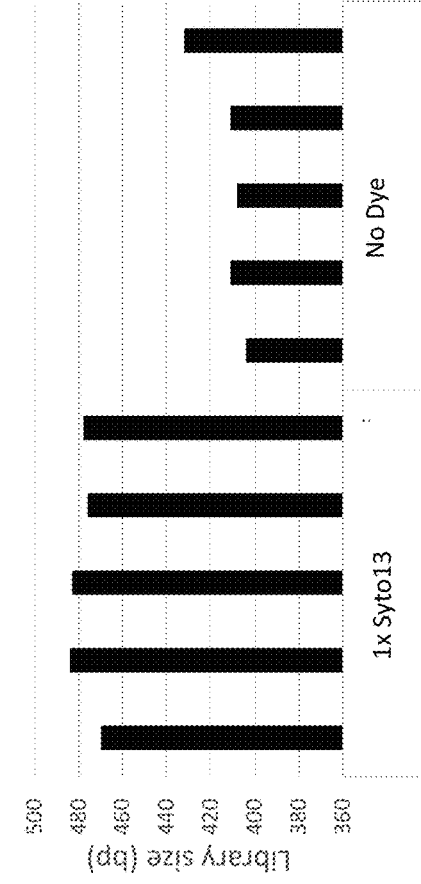

FIGS. 77A-77B and 79 depict Syto13 compatibility with next generation sequencing library prep. KAPA HyperPlus generates a whole genome sequencing library using fragmentase to enzymatically shear gDNA before end-repair and A-tailing the gDNA fragments. The A-tailed genomic fragments are then ligated to sequencing adapters before being PCR amplified and purified using AMPure magnetic bead technology. Shown in FIGS. 77A-77B is fragment length metrics as determined using Agilent's BioAnalyzer DNA High Sensitivity Assay for whole genome KAPA HyperPlus libraries prepared from gDNA purified using isotachophoresis in the presence and absence of Syto13. Mode fragment lengths (left) and gel images (right) show that samples purified with Syto13 were only slightly longer than both control (no Syto13) and samples purified in the presence of 1× Syto13. Shown in FIG. 79 is library quantitation by Qubit dsDNA High Sensitivity Assay. Samples purified in the presence of Syto13 exhibited comparable yields as control samples.

Figure 80D:
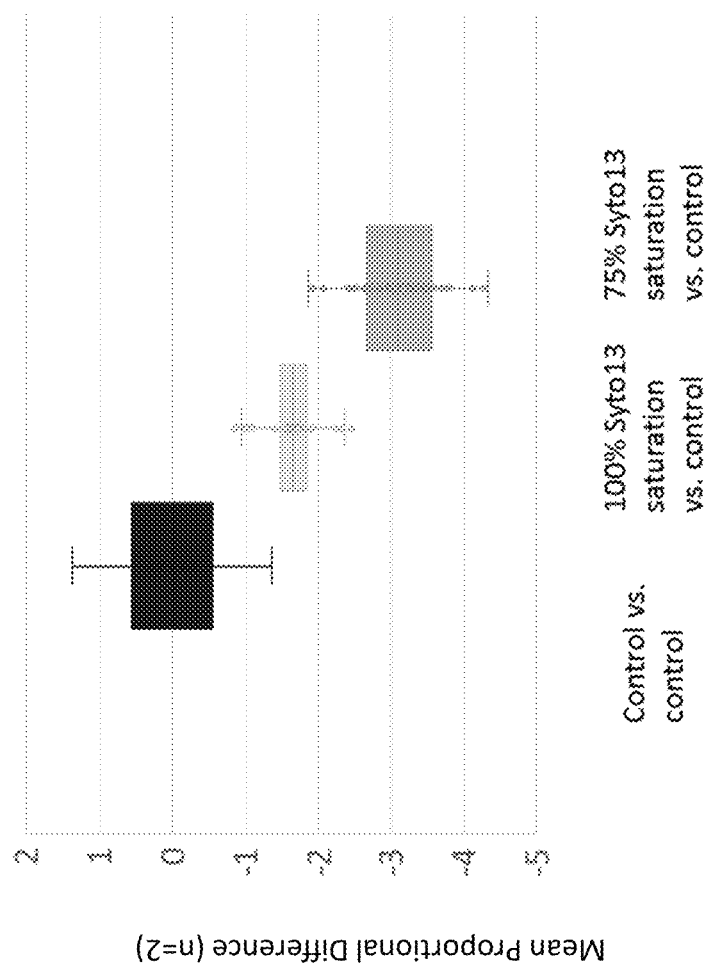

FIGS. 80A-80D depict Syto13 compatibility with whole exome next generation sequencing library prep. Agilent SureSelect XT Technology is hybrid-capture based technology that is designed to target enrich genomic regions of interest through solution-phase hybridization to ultralong cRNA baits. Because whole genome libraries generated with and without Syto13 showed a modest difference in fragment length, libraries were subjected to double sided size selection using AMPure XP beads followed by whole exome target enrichment using SureSelect XT Exome V6. The whole exome libraries were then sequenced using Illumina sequencing technology. Raw reads were then used to calculate normalized coverage for each of the targets. Shown are percent aligned reads, percent Q20 high quality aligned reads, and percent aligned with MAPQ>=20 for each library (FIGS. 80A-80C) and box plots of the mean proportional differences as determined by combinatorial (n=2) Bland-Altman analysis (FIG. 80D). Coverage bias was observed with both the 75% and 100% saturation Syto13 libraries relative to control.

FIG. 81 shows a block diagram that describes an optical signal processing algorithm for an optical detector. The raw optical signal acquired by the optical detector may for example be measured as photodiode current at each lane. Individual current readings may optionally be summed by the processor (for example in firmware) in order to increase the signal to noise ratio (SNR) of the readings before being recorded into a run data file. The summed values may be corrected for lane to lane variation in firmware using instrument specific parameters stored in firmware.

In Step 8101, the normalized signal may be recoded into a data file.

In Step 8102, the baseline may be subtracted from the normalized signal in order to approximate and correct for temporal shifts the optical baseline. The baseline can represent several imperfections of the system such as DC offset in the analog electronics, auto-fluorescence background from the chip and optical components, stray light, error in the normalization model, and/or temperature effects. Any, a combination, or all of these effects can change as a function of time. However, it is expected that they should change more slowly than the fluorescent band passes the optical detector. Therefore, two techniques may be used alone or in combination to estimate the baseline of the peak. In the first technique, a median filter with a time window much greater than the peak width may be used. Such a technique may provide an easy to implement strategy which may produce a non-linear baseline. In some instances, however, this first technique may generate a peak which can influence the baseline value, thereby potentially skewing the data. A second technique for estimating the baseline of the peak includes using a linear regression of data prior to the peak in order to create a linear model of the baseline during the peak window. While this technique may be slightly more difficult to implement than other techniques in at least some instances, the technique may have the benefit of being more robust.

In Step 8103, the extent of cross-talk within the chip and/or system may be corrected for. Due to optical scatter inside the optics sub-assembly and the within the chip, fluorescence can be recorded at neighboring detectors from material in other lanes. In order to correct for this, each instrument and/or chip model may have the extent of cross-talk characterized. This may allow for the deconvolution of the simultaneously recorded intensities from all eight channels into the "true" intensities arising from each lane.

At Step 8104, the location of the peak may then be determined by selecting the maximum value within a time window of each channels optical signal.

At Step 8105, several characteristics of the peak can be measured in order to calculate the amount of nucleic acid passing the detector. Traditional chromatographic methods often consider the peak height and/or area of the recorded fluorescence signal. Assuming the generation of fluorescence is linearly proportional to the mass of nucleic acid present, either of these approaches may produce a response that is linear with nucleic acid mass. If the underlying relationship is not linear, then there is no fundamental relationship between peak area or peak height and nucleic acid mass. The width of the peak at a fixed signal value can be shown to be linearly proportional to the natural logarithm of nucleic acid mass even when the response is fundamentally non-linear. Any combination of, or all of the three peak characteristics (i.e. width, height, and/or area) may be calculated. If a fundamental model can be constructed either from a linear response to peak area, or a log-linear response to peak width, a calibration model can be determined for each instrument and stored in system memory. The model may use one or both characteristics to determine the mass of nucleic acid with the lowest uncertainty possible. In the event that no fundamental relationship can be established, calibration data can be collected at high density and stored in system memory as a lookup table.

At Step 8106, linear interpolation between points on the lookup table can allow for calculation and estimation of nucleic acid mass across the characterized measurement range.

FIG. 82 shows a drawing of a mechanical optical assembly design for illumination and detection of the florescence of a sample bound to a dye. This design is an intended sub-assembly in a benchtop controller instrument. A mechanical housing 1400 contains optical components that, when a source is applied at the plane 1402, directs the excitation light through the sample plane 1401 and captures the sample fluorescence at the detection plane 1403.

FIG. 83 shows the optical path that achieves excitation of a sample bound dye fluorescence and the capture of the emitted light from the sample bound dye fluorescence. The source light is shown through a spatial filter 1412 and into a lens 1413 that collimates the light. This light then passes through a spectral filter 1410 after which a small percentage of that light is reflected by the coated glass 1414 and the rest of the light, dominant percentage, passes through the coated glass 1414. The reflected light path travels down through a light diffuser 1408 and on to the feedback sensor detection plane 1405. This light is used as a feedback loop to help calibrate and normalize the detection algorithm in software. The light that passes through continues to a second glass pain 1416 where it is reflected up to the sample/dye plane after passing through a lens 1415. Once the light reaches the sample bound dye and excites the dye, light is emitted back through the lens 1415 and through a spectral filter 1409. The light then continues on to a lens 1407 where it is focused and passes through a spatial filter 1406 onto an electro-optical sensor at the detection plane 1404.

End of Run Triggering

When purifying a sample using ITP, it can be important to accurately stop applying current when the sample ITP zone is in the elution location (e.g., a channel or a reservoir). The present disclosure provides techniques for assessing the ITP zone position, which can be used to trigger the end of a purification run. These techniques can include measurement of driving voltage, measurement of conductivity, and measurement of temperature.

Figure 15:
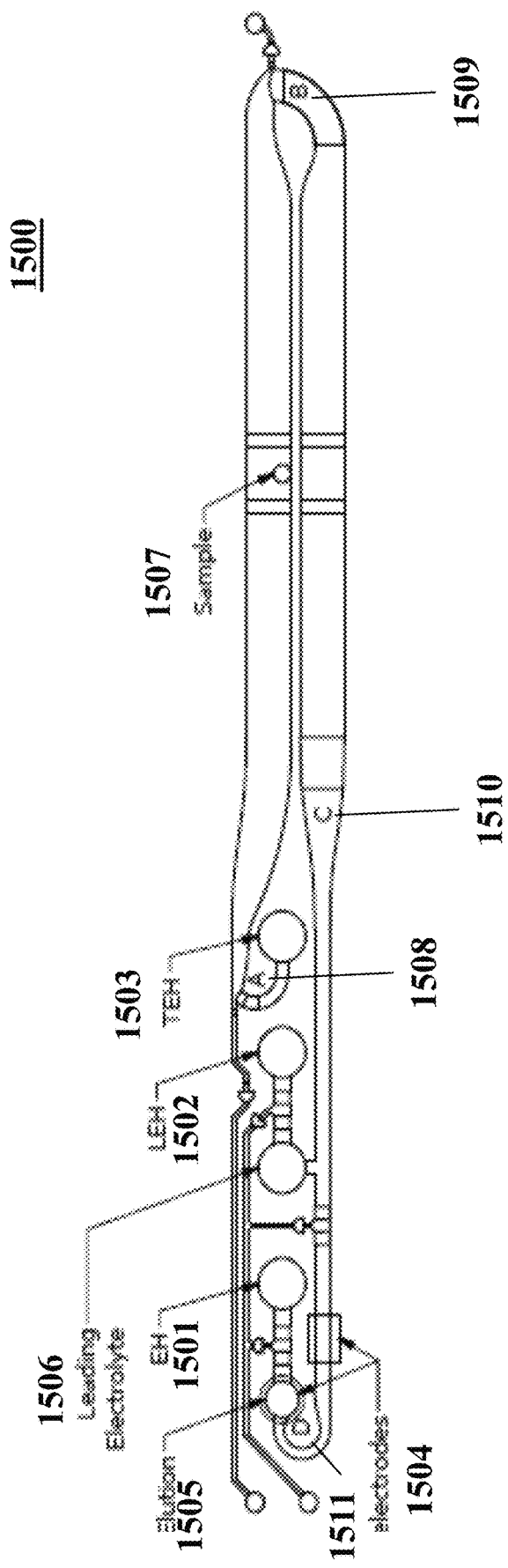
FIG. 15 shows a schematic of an exemplary design of a fluidic channel with connected reservoirs, contactless electrode(s) (may be used as conductivity sensor) and gas port(s) for conducting automated fluid loading into channel/device and automated isotachophoresis.

FIG. 15 shows a schematic of an ITP channel 1500, with driving electrodes placed in the buffered elution electrode (EH) reservoir 1501 and the buffered leading electrolyte (LEH) reservoir 1502, and a ground electrode placed in the buffered trailing electrolyte (TEH) reservoir 1503. Conductivity detector (e.g., capacitively-coupled contactless conductivity detector (C4D)) electrodes 1504 can be placed outside of the chip, such as near the elution reservoir 1505, as shown on the left side of the figure. The channel can also comprise a leading electrolyte reservoir 1506 and a sample reservoir or injection point 1507. Gas ports are indicated by small circles on the far left and right edges of the channel. Gas ports can be used to automatically load or prime fluids into the channels from the attached reservoirs, for example using vacuum or applied pressure.

Figure 84A:
Figure 84B:
Figure 84C:

FIGS. 84A-84F show a control scheme for how the electrical circuit created by the electrodes in channel 1500 of FIG. 15 may be verified (i.e. checked for continuity). Electrical continuity may be detected during channel priming with the buffers prior to user input of the sample, as shown in FIG. 84A, or after inputting the sample into the channel 8402 (e.g. via direct injection), as shown in FIGS. 84B-84C. FIG. 84A shows an electrical circuit path 8401 between high-voltage electrodes located in the buffered elution electrode (EH) reservoir (i.e. 1501 of FIG. 15) and the buffered leading electrolyte (LEH) reservoir (i.e. 1502 of FIG. 15). The circuit being tested does not cross the sample channel 8402, therefore loading in the channel which defines path 8401 can be verified prior to sample loading. Testing path 8401 before loading the sample may in some instances prevent the user from inputting sample into the sample channel 8402 if priming has failed. FIG. 84B shows an electrical circuit path 8403 between high-voltage electrodes located in the buffered elution electrode (EH) reservoir (i.e. 1501 of FIG. 15) and buffered trailing electrolyte (TEH) reservoir (i.e. 1503 of FIG. 15). FIG. 84C shows an electrical circuit path 8404 between high-voltage electrodes located in the buffered leading electrolyte (LEH) reservoir (i.e. 1502 of FIG. 15) and buffered trailing electrolyte (TEH) reservoir (i.e. 1503 of FIG. 15).

Figure 84D:
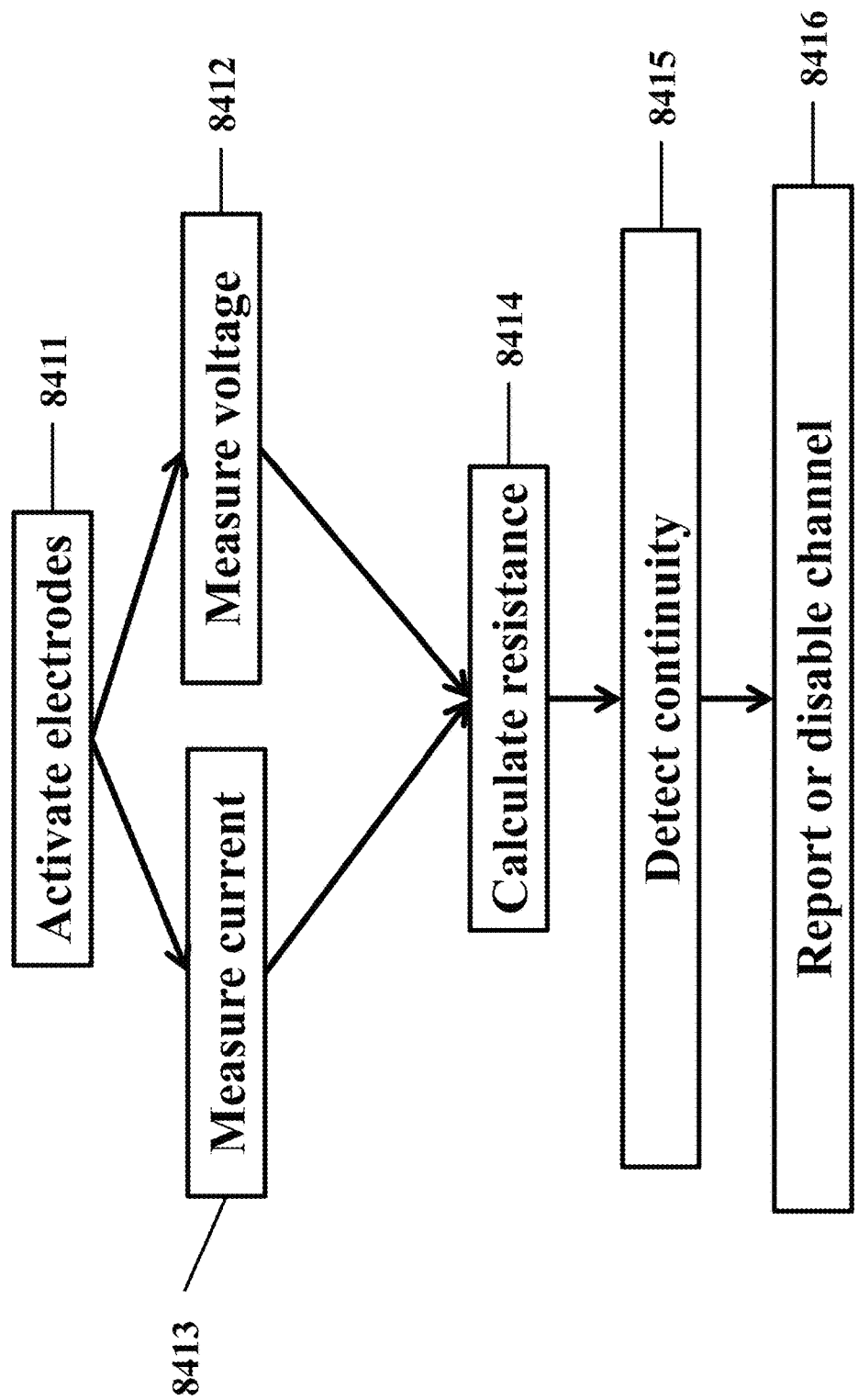
Figure 84E:
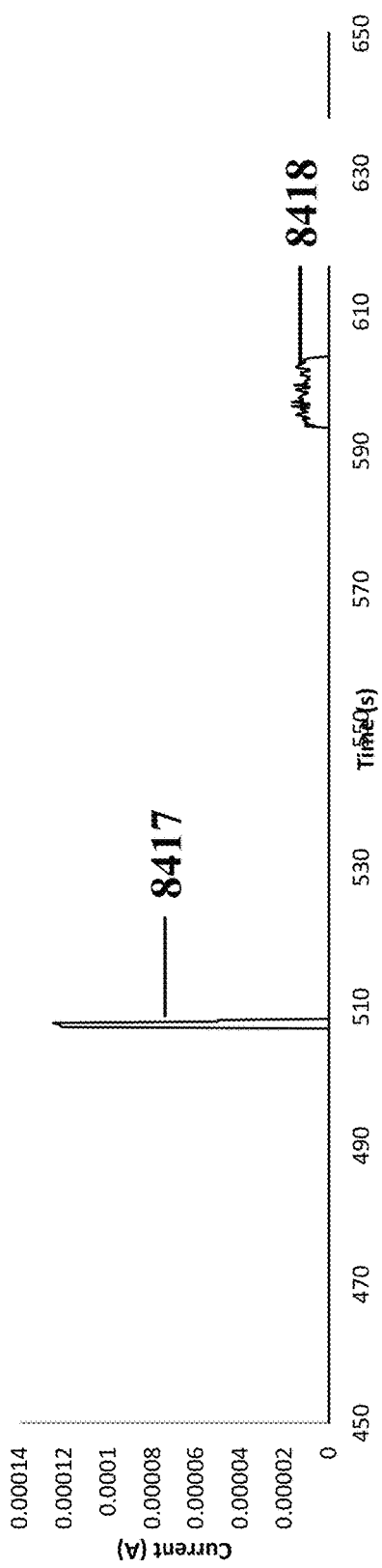
Figure 84F:
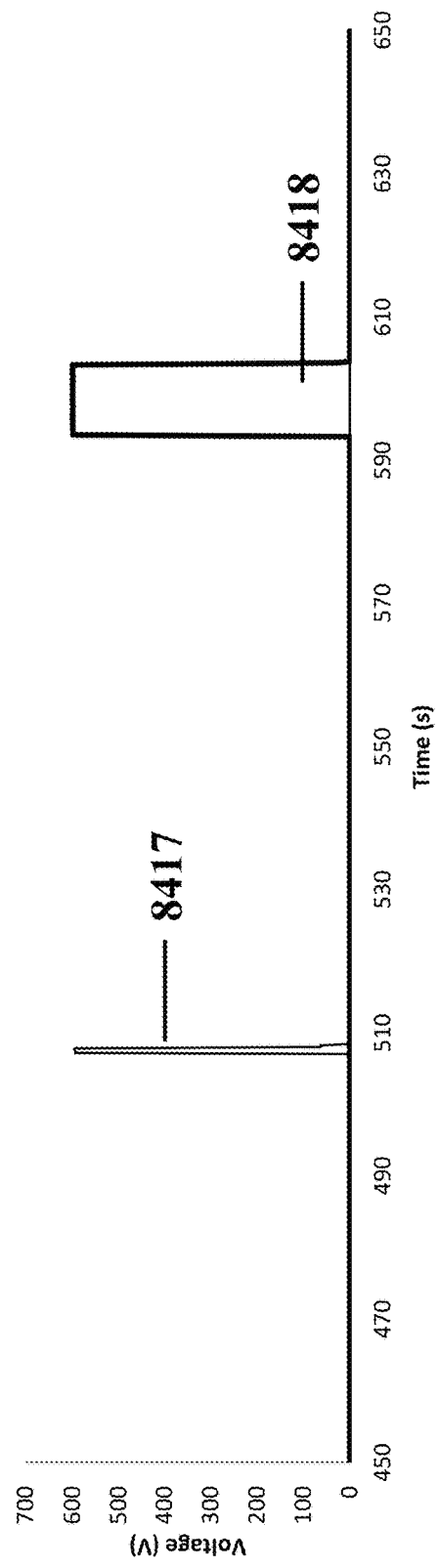

FIG. 84D shows a schematic of a method for detecting if a channel (e.g. channel 1500 of FIG. 15) has electrical continuity. At Step 8411, the electrode pair of interest may be activated. A source current and sink current may be set at a pair of electrodes. The sink current may be taken from a grounded electrode that will sink all available current. Alternatively, both electrodes may be actuated by current control circuits. This circuit can for example be set to supply at least 10 µA. Alternatively or in combination, voltage control may be used. The voltage on the source electrode may for example be set to at least 10 V. Measurements may be taken of the electrode voltage difference (Step 8412) and of the total current flowing (Step 8413) along the path. In the case of a broken fluidic connection in the microfluidic channel, an electronic circuit attempting to supply constant current may not be able to fulfill its target, so a measure of the real current may be done. At Step 8414, the ratio of the voltage to the current may be taken in order to determine the channel resistance. At Step 8415, the resistance may be subjected to a threshold to determine channel continuity. In some instances, the resistance may be checked continuously or nearly continuously prior to a timeout in order to enable the current to be deactivated as soon as the resistance drops below a pre-determined threshold value. Alternatively, the resistance may be measured throughout a separation, and a failure of continuity may be determined by detecting a pre-determined number of timepoints are above threshold. At Step 8416, a failure event may be reported to the user and/or the channel or electrodes may be disabled by the instrument. Shutting down poorly-loaded channels may prevent damage to adjacent channels and/or the instrument itself during ITP. FIG. 84E shows an exemplary current trace from a successful connection 8417 followed by a failed connection 8418 in a single channel. FIG. 84F shows an exemplary voltage trace from a successful connection 8417 followed by a failed connection 8418 in a single channel.

One method for measuring the position of an ITP band is to measure the voltage or the resistance of the channel, such as between the driving electrode and the ground electrode. In systems with more than two electrodes, this measurement may be taken between any pair of electrodes. This measurement can be made readily, as the voltage driving electrophoresis is also the measurement voltage. Throughout the purification process, the voltage can increase as the trailing ion fills the channel. However, the elution reservoir can have a large cross-section, so the contribution to overall resistance can be small. Hence, changes in the buffer conductivity in this region may not strongly impact the overall channel resistance, and the voltage can stop rising when the ITP zone enters the elution reservoir. This can be used as a signal to stop applying current and end the run.

Figure 16:
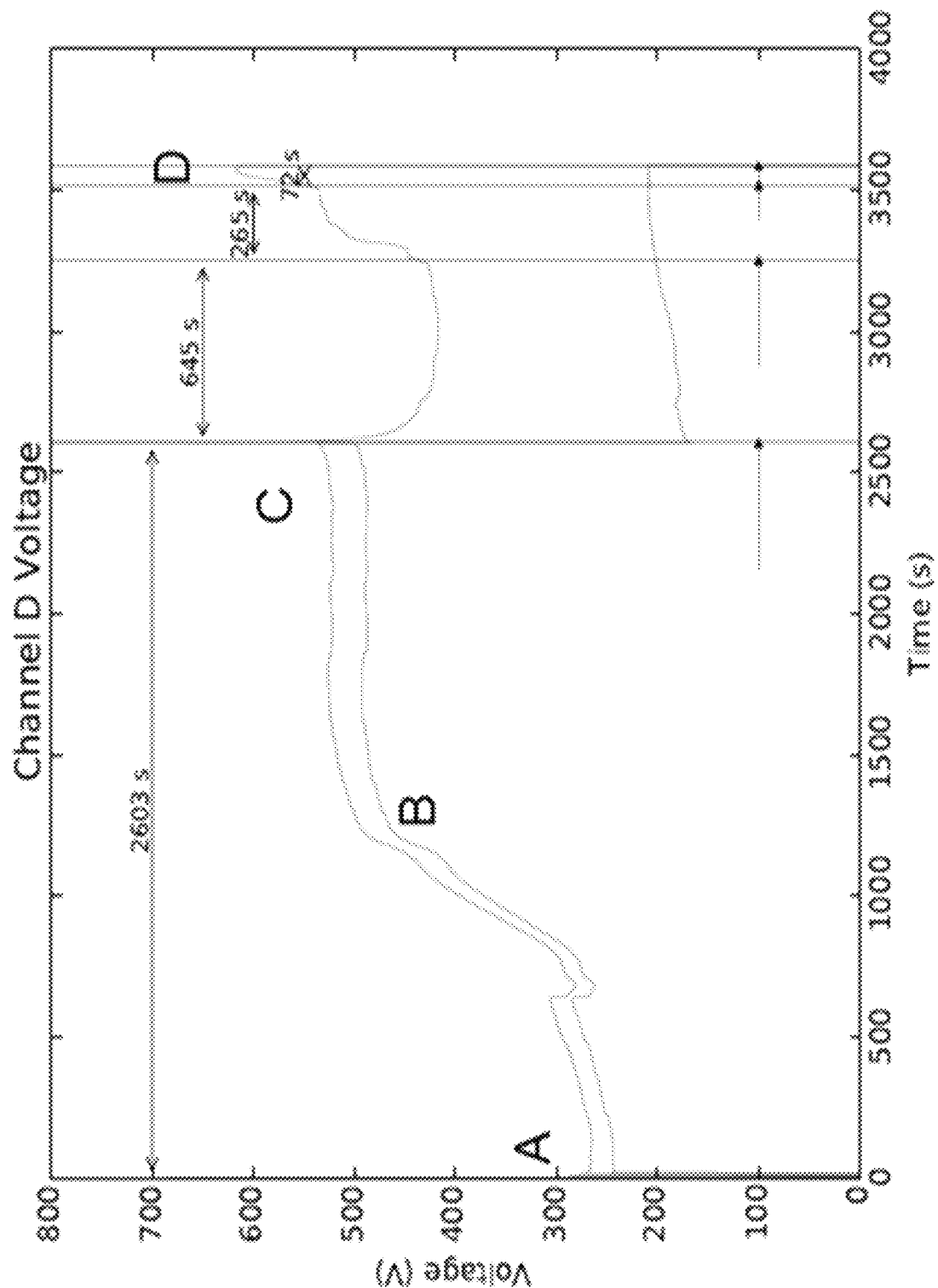
FIG. 16 shows a graph of voltage measurement over time in an ITP channel during a run.
Figure 17:
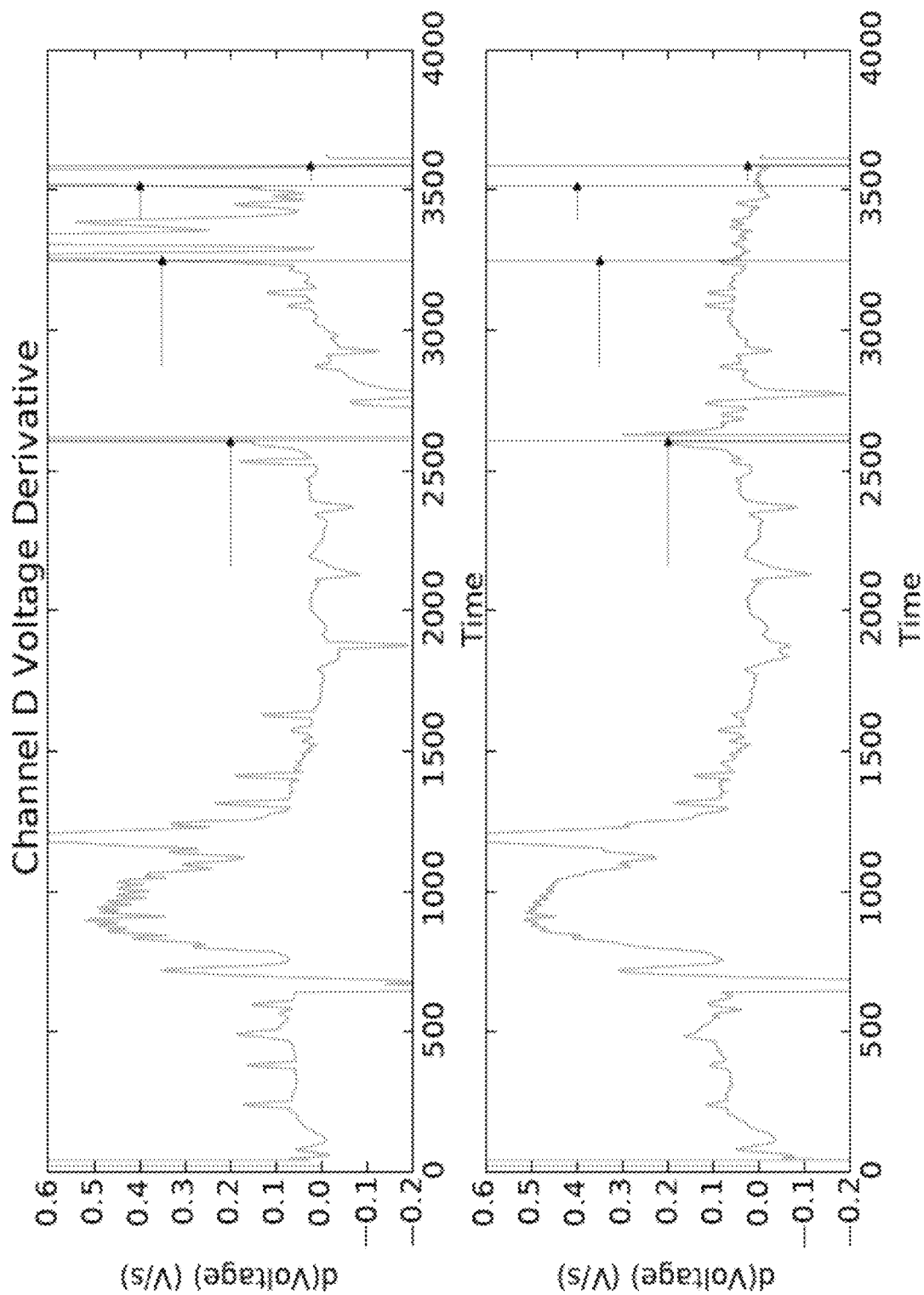
FIG. 17 shows two graphs of derivative analysis of the voltage measurements from FIG. 16.

To assess this voltage change, the derivative of voltage can be calculated, for example as shown in FIG. 16. The Lanzcos differentiation method can be used to suppress high frequency noise. Thresholds can be set for the derivative, and when the derivative passes the threshold, a trigger is performed. In some cases, introducing additional triggers can improve the robustness of the control. For example, FIG. 16 shows four trigger points. In some cases only two of these triggers are used to change the driving current (e.g., triggers 1 and 4), while the others (e.g., triggers 2 and 3) are used to mark time points in the run, which can improve the timing of trigger 4. FIG. 17 shows derivative analysis of the voltages in FIG. 16, with arrows representing the derivative thresholds used to choose the trigger points.

FIG. 16 shows example data from measuring the driving voltage. Each vertical line represents a trigger point. The two lines represent two electrodes, the electrodes in the EH and LEH reservoirs, with respect to the ground electrode. Points A, B, C, and D correspond to the time at which the ITP zone is in the corresponding location marked in FIG. 15 (A, B, C, and D; labeled 1508, 1509, 1510, and 1511, respectively). In some cases, the conductivity everywhere in the channel can affect the overall driving voltage, which may make it more difficult to assess what is happening near the elution reservoir.

Figure 18:
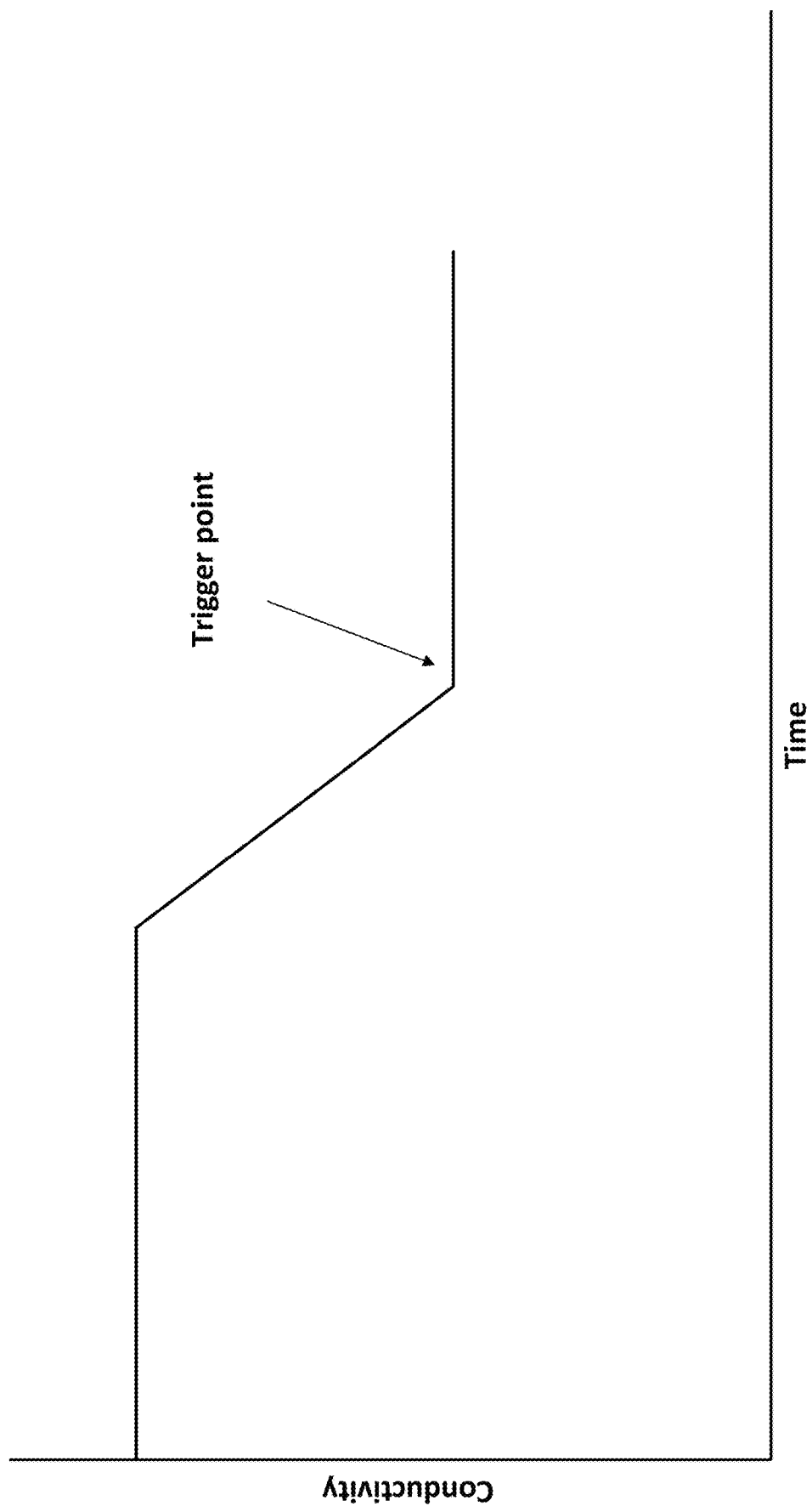
FIG. 18 shows an example of conductivity measurement over time in an ITP channel near an elution reservoir.

A second method for detecting the position of an ITP band is to make a localized measurement of the conductivity. This can be done using a capacitively coupled contactless conductivity detector (C4D). This method can use high frequency alternating current to pass through the channel wall and couple to the electrolyte. This localized measurement can be taken at the elution reservoir itself. This technique can reduce or remove the ambiguity associated with measurements taken over the entire channel. In this technique, the end of run trigger can be chosen as soon as a change is seen in the conductivity at the elution reservoir conductivity detector, for example as shown in FIG. 18.

Figure 19:
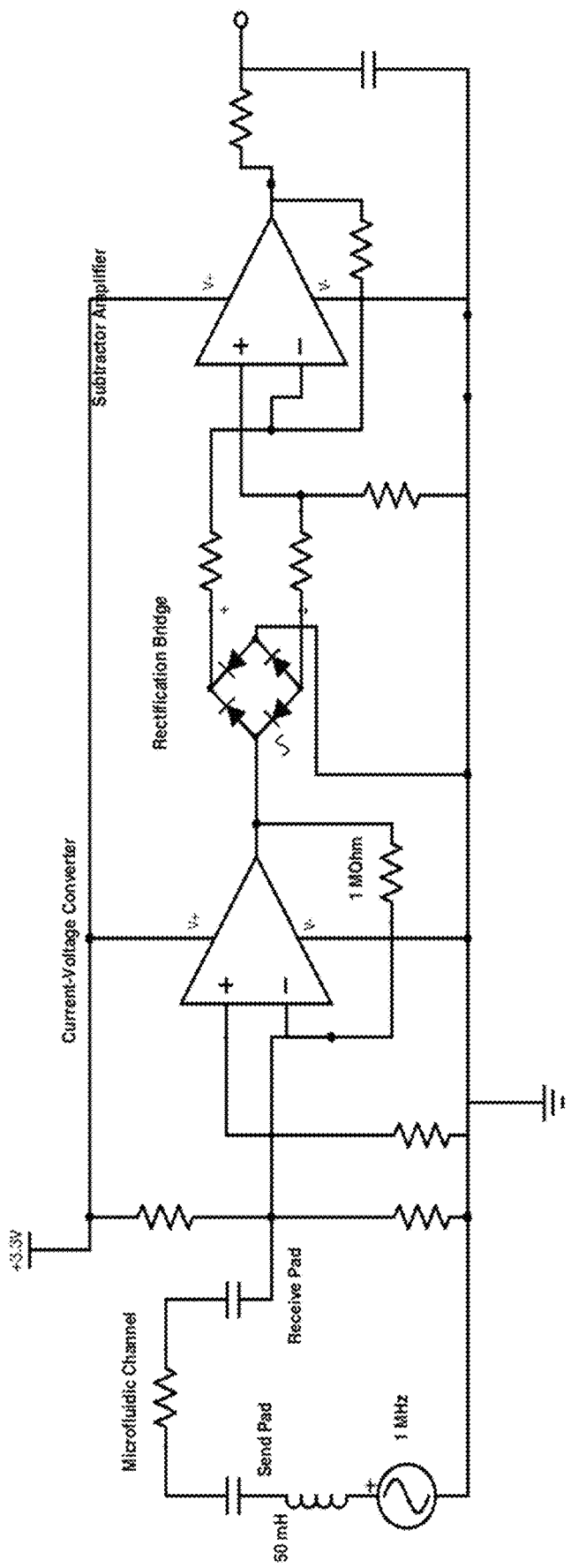
FIG. 19 shows an exemplary schematic of a C4D sensor implementation.

C4D detection can be performed with electrodes placed below the elution channel. Maximizing the electrode area can reduce the necessary driving frequency. For example, driving frequencies can be used from about 100 kHz to about 10 MHz, with electrode contact pads between about 0.2 mm$^2$ and about 50 mm$^2$. C4D sensors can be implemented with electrical components including resistors, capacitors, a diode bridge, and high-frequency operational amplifiers, with a high frequency signal source such as from a direct digital synthesizer. FIG. 19 shows an exemplary schematic of a C4D sensor implementation.

A third method for detecting the position of an ITP band is to make a localized measurement of temperature near the elution reservoir. This measurement can be made with temperature sensors including a thermocouple or an infrared temperature sensor. The sensor can be placed under the channel near the elution reservoir and can monitor the temperature over time. When the lower-mobility trailing ions displace the higher-mobility leading ions (e.g. the LE-TE interface of the ITP zone), the electric field in the channel can increase, and the temperature can rise. During isotachophoresis, lower mobility trailing electrolyte ions and higher mobility leading electrolyte ions may meet at an isotachophoresis interface. The ITP interface may comprise the sample nucleic acids concentrated between the leading electrolyte ions and trailing electrolyte ions. A temperature rise can detect the presence of the ITP interface between the higher-mobility leading ions and the lower-mobility trailing ions, and thus also indicates the presence of the nucleic acids therebetween. This temperature rise can be 1-10° C.

Figure 20A:
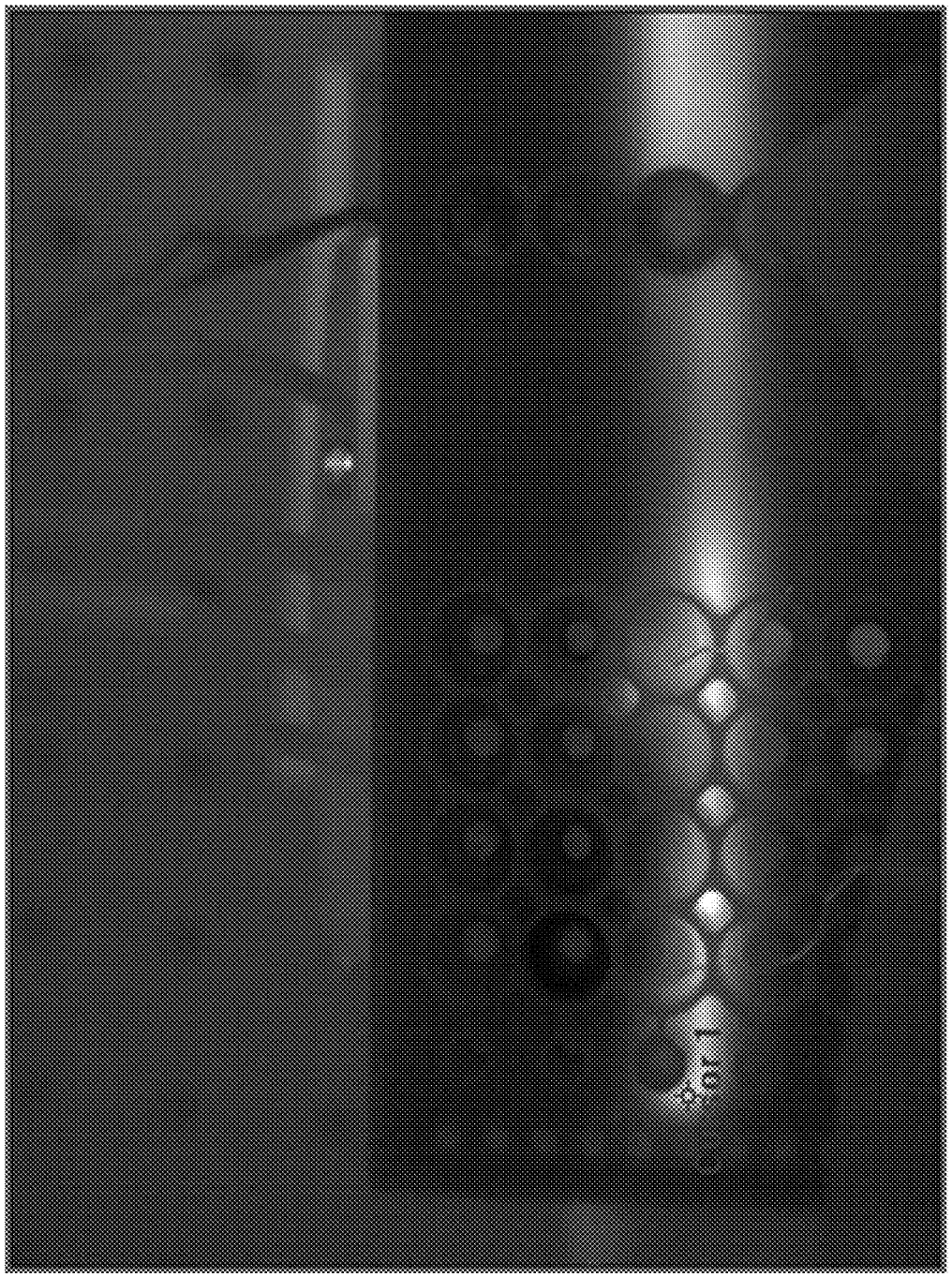
FIG. 20A shows an exemplary temperature map of an ITP channel taken using a thermal imaging camera.
Figure 20B:
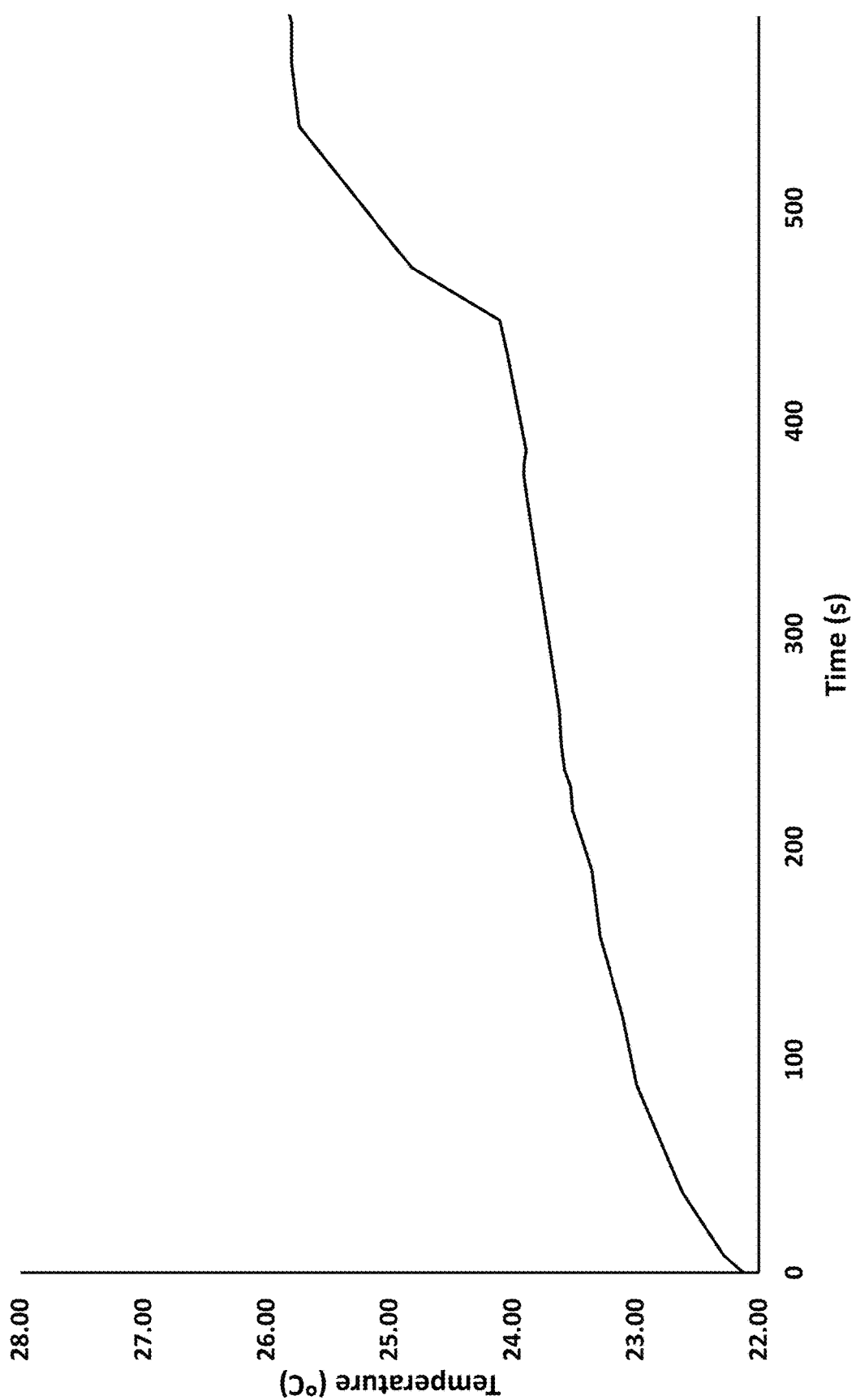
FIG. 20B shows a plot of temperature over time at the position of Cursor 1 in FIG. 20A.

FIG. 20A and FIG. 20B show exemplary temperature measurement results using a thermal imaging camera. These images show a clear rise in temperature as the trailing ion enters the channel. FIG. 20A shows a temperature map of an ITP channel taken using a thermal imaging camera; the orientation of the channel is the same as in FIG. 15. FIG. 20B shows a plot of temperature over time at the position of Cursor 1 in FIG. 20A. At about 450 seconds, the ITP interface and trailing ion enters the region, causing an increase in temperature. This temperature rise can be detected and used as a triggering signal to alter the electric current applied to the channel.

The temperature may be measured at a detection location at or near the elution reservoir (e.g. as shown in FIG. 21). In some instances, the detection location may be located at least about 5 mm from the elution reservoir. In some instances, the detection location may be located at least about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir. In some instances, the detection location may be located at most about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir. In some instances, the temperature sensor may be located at least about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir. In some instances, the temperature sensor may be located at most about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir.

The temperature sensor may trigger a change in electric current when a change in temperature is sensed. In some instances, the detected change in temperature is within a range of about 0.2° C. to about 5° C. In some instances, the detected change in temperature is at least about 0.2° C., 0.3° C., 0.4° C., 0.5° C., 1° C., 2° C., 3° C., 4° C., 5° C., 6° C., 7° C., 8° C., 9° C., or 10° C. In some instances, the detected change in temperature is at most about 0.2° C., 0.3° C., 0.4° C., 0.5° C., 1° C., 2° C., 3° C., 4° C., 5° C., 6° C., 7° C., 8° C., 9° C., or 10° C.

In some cases, detection of the ITP zone, for example by voltage monitoring, conductivity measurements, and/or temperature sensing, at one or more trigger points may cause the benchtop controller to alter the electric current applied to the microfluidic chip. The change may be applied immediately upon detection or after a pre-determined delay. Detection of the ITP zone may trigger a decrease, increase, or removal of current. For example, detection of the ITP zone at point C 1510 may trigger a decrease in current in order to increase the residence time of the ITP zone in the channel leading to the elution reservoir. Alternatively or in combination, detection of the ITP zone at point D 1511 located at or near the elution reservoir may trigger the removal of electric current in order to position the ITP zone (and nucleic acids) or a portion thereof within the elution reservoir, well, or region of the channel or chip. In some instances, detection of the ITP zone may trigger a change in electric current after a pre-determined amount of time. For example, a detection location (for example 1504 or the position of cursor 1) may be positioned at or near the elution reservoir at a known distance such that the time needed for the ITP zone to travel between the detection location and the elution reservoir can be calculated for a given current. The controller may pre-determine a travel time and detection of the ITP zone at the detection location may trigger a delayed removal of the current after the pre-determined amount of time. In some instances—detecting the ITP zone at a specific detection location may offer a space-time relationship of the ITP zone which may result in more precise triggering than other sensing methods.

In some cases, detection of the ITP zone at a trigger point may cause the electric current applied to the microfluidic chip to change directions or paths. For example, the electric current may be triggered to reverse such that the ITP zone reverses direction of travel within the channel. In another example, the system may be triggered to stop applying current between a first pair of electrodes and begin applying current to a second pair of electrodes to drive the flow of ions along a different path. For example, a channel may be "y-shaped" with a first channel leading into two side channels which split from the first channel at different directions. Current may initially be driven between first and second electrodes connected to the first channel and a first side channel, respectively. Without interruption of current, the ITP zone may travel from the first channel to the first side channel. Detection of the ITP zone at a connection between a first channel and two side channels may trigger the first and second electrodes to stop driving current and third and fourth electrodes connected to the first channel and a second side channel, respectively, to begin driving current. The ITP zone will then travel from the first channel to the second side channel. In some cases, the first and third electrodes are the same electrode. In this way, the trigger may cause the current to change such that the path of the ITP zone changes along the channel.

In some cases, the position of an ITP band may be detected using any combination of the detection methods described herein.

In some embodiments, the position of an ITP band may be detected by measuring the voltage or resistance of the channel in combination with making a localized measurement of temperature near the elution reservoir. The voltage may be measured as described herein. For example, the voltage may be measured during the entire ITP run. In some cases, the voltage may be monitored and changes in voltage, or in the derivative of the voltage, may be used as triggers to change the driving current as described herein. Alternatively or in combination, changes in the voltage, or in the derivative of the voltage, may be used to mark time points in the run in order to improve the timing of later triggers as described herein. For example, a first voltage change may indicate that the ITP band has reached the capillary barrier between the sample channel and the leading electrolyte channel, which may be used to mark a time point in the run and improve triggering overall. A second voltage change may indicate that the ITP band has reached the narrowing (i.e. constriction) portion of the LE channel shown in FIG. 40. The second voltage change may trigger a change in the driving current after a pre-determined amount of time. For example, the second voltage change may trigger the driving current to switch from the electrodes in the leading electrolyte buffering well and the trailing electrolyte well (as shown in FIG. 84C) to the electrodes in the elution buffering well and the trailing electrolyte well (as shown in FIG. 84B). The electrode in the leading electrolyte buffering reservoir may be turned off after the pre-determined amount of time. Alternatively, the polarity of the electrode in the leading electrolyte buffering reservoir may be reversed after the pre-determined amount of time. In some embodiments, the pre-determined amount of time may be configured to coincide with the ITP band reaching the integrated quantitation region shown in FIG. 40. After switching the driving current between electrode pairs, the temperature may be measured as described herein. For example, an infrared temperature sensor can be placed under the channel near the elution reservoir as described herein and as shown in FIG. 40. The temperature sensor may be configured to monitor the temperature at the sensor over time as described herein. Temperature differences may be generated between the ions at the ITP interface due to the electric field applied to the channel and the ionic strength of the ions. The ITP interface may comprise the sample nucleic acids concentrated between the leading electrolyte ions and trailing electrolyte ions. A temperature rise can detect the presence of the ITP interface between the higher-mobility leading ions and the lower-mobility trailing ions, and thus also indicates the presence of the nucleic acids therebetween. Upon detection of a temperature rise with the temperature sensor (e.g. as shown in FIGS. 91A-91B), the electrical current may be removed after a pre-determined amount of time (which may correspond to the distance between the IR sensor and the elution reservoir) as described herein. The purified nucleic acids may then be eluted from the elution reservoir and optionally used for further processing as described herein.

In some embodiments, the current applied across the fluidic device may generate a first temperature difference at an interface between the nucleic acid analyte in the ITP band and the trailing electrolyte. The trailing electrolyte may be warmer than the nucleic acids in the ITP band due to their lower ionic strength. The current applied across the fluidic device may generate a second temperature difference at an interface between the nucleic acid analyte in the ITP band and the leading electrolyte. The leading electrolyte may be cooler than the nucleic acids in the ITP band. The temperature sensor may be configured to detect the temperature difference between the cooler leading electrolyte and the ITP band, and subsequently detect the temperature difference between the ITP band and the warmer trailing electrolyte.

In at least some instances, the current applied across the fluidic device may generate a first temperature at the interface between the analyte and the trailing electrolyte. The current applied across the fluidic device may generate a second temperature an interface between the analyte and the leading electrolyte. The current may be applied across the fluidic device such that the temperature difference between the first and second temperatures is sufficient to generate a thermal effect therebetween (e.g. at a sufficiently high current to generate a thermal effect). When the current is stopped within the channel under the elution reservoir (e.g. at the aperture between the two), this thermal effect may be sufficient to create a buoyant effect on the ITP band and facilitate entry of the nucleic acids of the ITP into the elution reservoir via the aperture.

Further Processing and Use of Purified Samples

Extracted or purified nucleic acids can be used for sequencing, genotyping, analysis of mutations or polymorphisms, analysis of gene expression levels, disease diagnosis, disease prediction, cytological classification, paternity or genealogical analysis, or indication of suggested treatment modalities.

In preferred embodiments, the extracted or purified nucleic acids (e.g. DNA, RNA) can be used in amplification reactions such as PCT reactions. In some cases, extracted or purified nucleic acids can be used in amplification reactions, including but not limited to loop-mediated isothermal amplification (LAMP), strand displacement amplification (SDA), helicase-dependent amplification (HDA), rolling circle amplification (RCA), nicking enzyme amplification reaction (NEAR), PCR, reverse transcription PCR, real-time PCR, quantitative PCR (qPCR), digital PCR, and methylation-specific PCR.

Extracted or purified nucleic acids can be used in sequencing reactions, including Maxam-Gilbert sequencing, chain termination sequencing (e.g., Sanger sequencing), shotgun sequencing, pyrosequencing, bridge PCR, colony sequencing, polony sequencing, sequencing by synthesis, ion semiconductor sequencing, nanopore sequencing, nanoball sequencing, sequencing by ligation, sequencing by hybridization, and single molecule real-time sequencing.

Extracted or purified nucleic acids can be used in protein binding assays, such as DNA footprinting assays. For example, DNase (e.g., DNase I) can be used to randomly cut DNA molecules of interest. The techniques of the present disclosure can be used to separate digested DNA from the DNase enzymes, preventing further digestion. In some cases, DNase digestion can be performed off of a fluidic device, and then the sample can be loaded onto a fluidic device for purification. In other cases, DNase digestion can be performed on a fluidic device, and once digestion is performed, the nucleic acids can be purified on the fluidic device.

Samples, such as fixed or embedded samples (e.g., FFPE samples), can be used for longitudinal studies, genome-wide association studies, and other large-scale analysis across populations.

Vertical or Column ITP

Planar ITP device designs, such as discussed herein, can utilize horizontal space for ITP bands to travel. To process samples at high throughput, such as in the 96-well plate format, it can be advantageous to fit an entire ITP separation system for a sample in a given footprint, such as 9 mm×9 mm footprint. One way of doing this is to increase the height of the system to accommodate more sample volume. This can provide the option to increase total sample volumes into the milliliter range and still process samples with reasonable run times.

In some cases, it can be important to reduce or prevent gravity-driven flow and/or buoyant flow through such a system. It can also be important to assemble the electrolyte zones needed for ITP without mixing the electrolytes.

A vertical or column ITP system can comprise several ITP stages, where each stage comprises a column (e.g., plastic) with gel (e.g., agarose) or similar material at the bottom. The gel can have high electrolytic conductivity. Each stage can be prepared by introducing an electrolyte on top of the gel. The gel can slow or prevent liquid flow. To create the column, the stages can be stacked with the trailing electrolyte at the top and the leading electrolyte at the bottom. Current can then be driven through the system. Purified analyte can be recovered by de-stacking the columns and pipetting out.

Figure 22B:
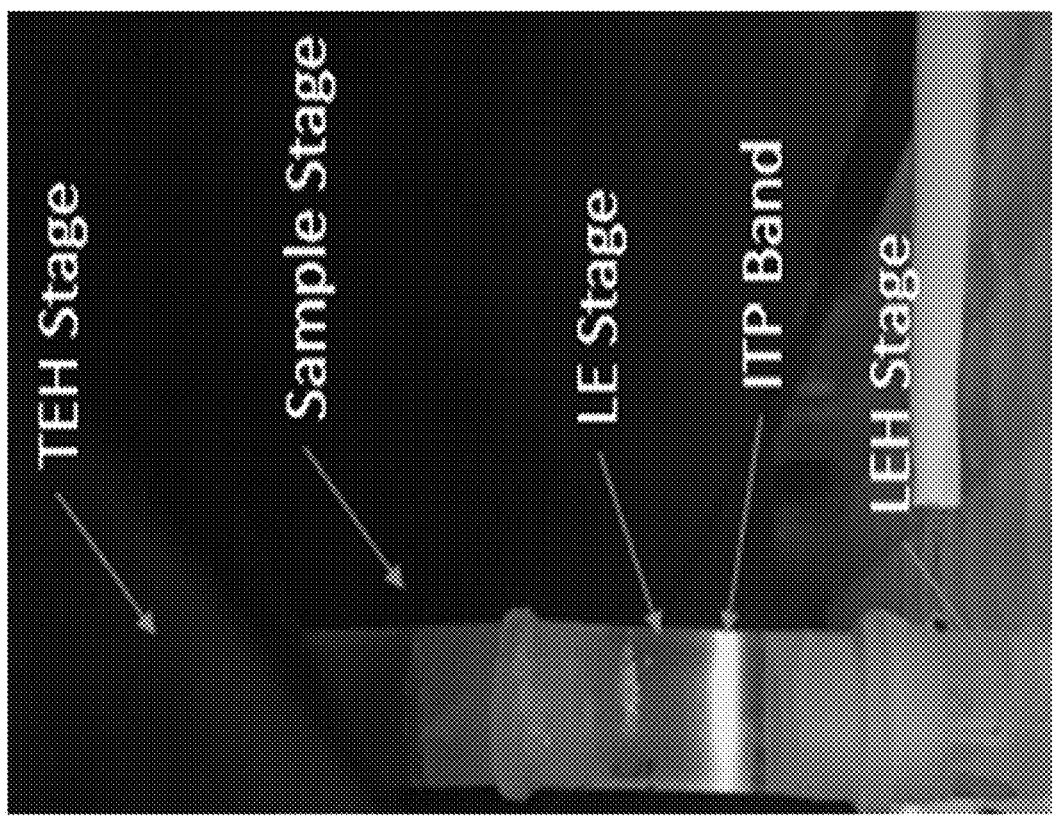
FIG. 22B shows an exemplary image of a vertical ITP set up with an DNA ITP band.
Figure 22A:
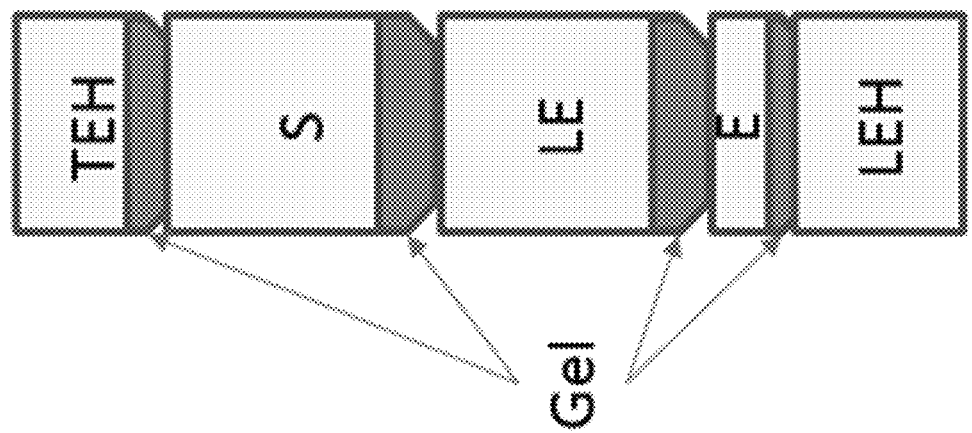
FIG. 22A shows an exemplary schematic of a vertical (or column) ITP setup.

FIG. 22A shows an exemplary schematic of a vertical (or column) ITP setup. The vertical ITP device may comprise a column having a plurality of gel plugs disposed within an interior channel thereof. The gel plugs may be separated by spaces configured to receive one or more of the buffers or sample fluids described herein. Each gel plug and space may make up a stage of the vertical ITP column. The gel plugs in each stage may comprise a gel material that can support the weight of the water (e.g., aqueous electrolyte solution or sample volume) added to the space above the gel plug. Each gel plug may support a free solution disposed above it. The vertical ITP device may for example comprise five stages. The first stage may comprise a trailing electrolyte buffer and a first gel plug configured to support the trailing electrolyte buffer. The second stage, located below the first stage, may comprise a sample or analyte as described herein and a second gel plug. The third stage, located below the second stage, may comprise a leading electrolyte buffer and a third gel plug. The fourth stage, located below the third stage, may comprise an elution buffer and a fourth gel plug. The fifth stage, located below the fourth stage, may comprise a high concentration leading electrolyte buffer and fifth gel plug. When an electrical field is applied to the vertical ITP device, the analyte may migrate in the direction of gravity from the second stage, through the second gel plug, into the third stage (leading electrolyte buffer), through the third gel plug, and down into the fourth stage (elution buffer). The analyte may compact into an ITP band as described herein with respect to ITP performed within a channel. The cross-sectional area of the ITP column can be approximately 9 mm×9 mm. Such a system may be configured to process a sample with an approximate cross sectional column area of 9 mm×9 mm. The design can be scaled-up as desired by one of ordinary skill in the art, for example to 96 samples (columns), with overall device dimensions conforming to a standard microtiter plate. FIG. 22B shows an exemplary image of a vertical ITP set up with a DNA ITP band. The stages are: Trailing Electrolyte High (TEH), Sample, Leading Electrolyte (LE) and Leading Electrolyte High (LEH). The ITP zone is moving downward through the system. This image does not show the elution stage (E, shown in FIG. 22A) which is the final destination of the analyte.

Computer Control Systems

Figure 13B:
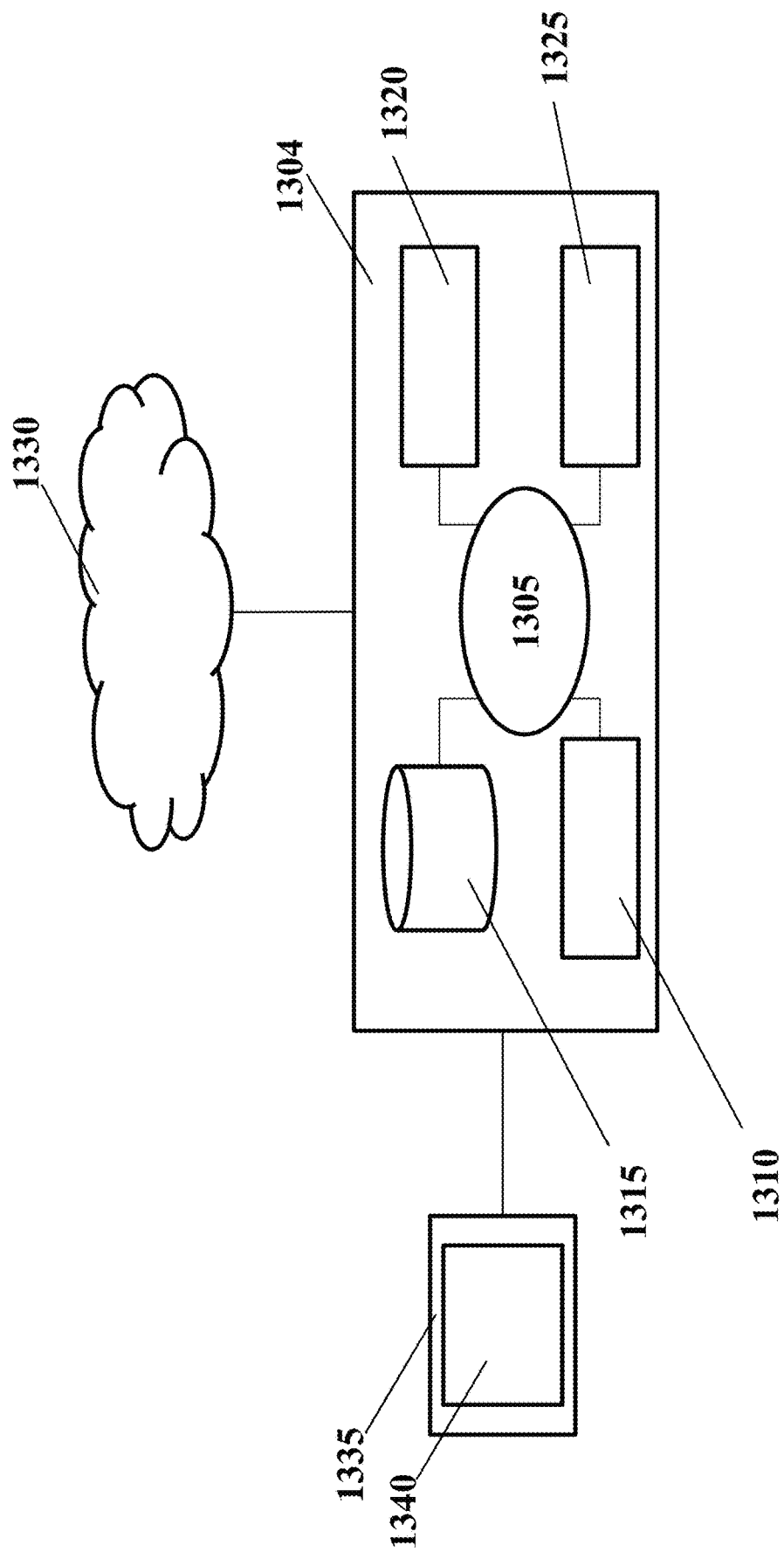
FIG. 13B shows an exemplary computer control system that is programmed or otherwise configured to implement methods provided herein.

The present disclosure provides computer control systems that are programmed to implement methods of the disclosure. FIG. 13B shows a computer system 1304 that is programmed or otherwise configured to control sample preparation, sample extraction or purification, or detection. The computer system 1304 can regulate various aspects of extraction, purification, and detection processes of the present disclosure, such as, for example, application of pressure or electric fields, thermal control, detection, quantitation, feedback, and beginning or ending a process. The computer system 1304 can be an electronic device of a user or a computer system that is remotely located with respect to the electronic device. The electronic device can be a mobile electronic device.

The computer system 1304 includes a central processing unit (CPU, also "processor" and "computer processor" herein) 1305, which can be a single core or multi core processor, or a plurality of processors for parallel processing. The computer system 1304 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1304 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1304, can implement a peer-to-peer network, which may enable devices coupled to the computer system 1304 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1304 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1304 in some cases can include one or more additional data storage units that are external to the computer system 1304, such as located on a remote server that is in communication with the computer system 1304 through an intranet or the Internet.

The computer system 1304 can communicate with one or more remote computer systems through the network 1330. For instance, the computer system 1304 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1304 via the network 1330.

Methods as described herein can be implemented by way of machine (e.g., computer processor) executable code stored on an electronic storage location of the computer system 1304, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1304, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1304 can include or be in communication with an electronic display 535 that comprises a user interface (UI) 1340 for providing, for example, operational parameters (e.g., processing time, temperature, field strength), nucleic acid quantitation information, or other information. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1305. The algorithm can, for example, regulate thermal controllers, calculate nucleic acid quantitation, control process functions, and begin or end a process.

Kits

This disclosure provides kits useful for conducting isotachophoresis processes. Generally, such kits comprise a microfluidic device provided herein and one or more buffers. The buffers may include one or more sample buffers, one or more leading electrolyte buffers, one or more trailing electrolyte buffers, one or more lysis buffers and/or one or more elution buffers, in any combination. In some cases, the kit may in include one or more enzymes (e.g., RNase, DNAs, nucleases, proteases, proteinases, polymerase). The buffers may be supplied in separate tubes. In some cases, the microfluidic device is pre-loaded with one or more buffers. The kits may include a set of instructions for operating the device and/or processing a sample.

EXAMPLES

Example 1—DNA Extraction from FFPE Samples

An FFPE sample from a human patient is obtained. A 1.1× aqueous alkaline buffer solution (Solution A1) is prepared with 80 mM NaOH, 11 mM DTT, and 0.5% v/v Igepal CA-630 in nuclease-free distilled or deionized water. A 10× quenching solution (Solution A2) is prepared with 776 mM HCl and 100 mM Tris base or Trizma base in nuclease-free distilled or deionized water. Commercially available Proteinase K solutions and RNases are also provided. Alternatively, a neutrally-buffered (e.g., pH from about 7.0 to about 8.0) 5-50 mM Tris-HCl solution with 0-80 mM NaCl, 5-10 mM DTT, and 0.1-0.5% v/v IGEPAL CA-630 can be prepared in nuclease-free distilled or deionized water.

An FFPE section or scroll is added to a 1.5-2.0 mL microcentrifuge tube. 175 µL of Solution A1 is added to the tube. The tube contents are incubated for 1-20 minutes at 50-99.9° C. (in some cases, the tube contents are incubated for 5-20 minutes at 95-99.9° C.) to deparaffinize the sample. 20 of Solution A2 are added to the tube to quench Solution A1 and achieve a buffered solution with pH of about 7-8.25. Alternatively, an FFPE section or scroll can be incubated in 195 µL of quenched or neutral buffer (e.g., pH from about 7.0 to about 8.0) for 1-30 minutes at 50-80° C. to deparaffinize the sample. Other deparaffinization protocols that can be used include (1) treating the sample with xylene, followed by one or more washes with 96%-100% ethanol at room temperature, followed by drying of the tissue; (2) incubating the sample at an elevated temperature (e.g., 50-100° C.) for 1-30 minutes in a buffered aqueous solution at about pH 7 to about pH 8.25; (3) incubating the sample at an elevated temperature (e.g., 50-100° C.) for 1-30 minutes in an alkaline aqueous solution followed by quenching to a buffered solution with pH of about 7 to about 8.25; or (4) incubating the sample at an elevated temperature (e.g., 50-100° C.) for 1-30 minutes in mineral oil.

5 µL of Proteinase K solution is added to the deparaffinized sample solution to a final concentration of 400-1000 µg/mL (typically 600-700 µg/mL) and a final volume of 200 µL. The solution is then incubated for 15-60 minutes at about 56° C. Optionally, the solution is further incubated for 2-60 minutes at 80-90° C. Optionally, 3 µL of RNase A (or about 50-200 µg/mL RNase A) is added to the solution. The solution is then cooled to room temperature, and the FFPE lysate is loaded onto a fluidic device for further processing, such as by isotachophoresis (ITP).

Example 2—Comparison of DNA Extraction Yields

DNA was extracted using a bench top controller device to automate isotachophoresis in a fluidic device from (i) qPCR buffer as a post-PCR clean-up (FIG. 3, triangle data points), and (ii) cell culture lysate (FIG. 3, square data points), with yield calculated using qPCR. Published DNA yield data using a traditional solid-phase extraction column (SPE; FIG. 3, diamond data points) are provided for comparison. FIG. 3 shows DNA yield versus input DNA mass. The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. The cellular lysate sample was prepared in a second leading electrolyte buffer (sample buffer) comprising 10 mM Tris with 5.6 mM HCl. Extraction of DNA from human Jurkat cell culture lysate was performed at yields from about 60% to about 90% for input DNA masses from about $10^{-2}$ nanograms (ng) to about $10^3$ ng. Cells were lysed in an aqueous solution comprising 40 mM NaOH for 1 minute and subsequently quenched at a 1:1 volume ratio with a buffered acidic solution to bring the final cell lysate sample to 10 mM Tris with 5.6 mM HCl and 20 mM NaCl at pH 8. Proteinase K was added to a final concentration of 400 µg/ml within the cell lysate sample volume and incubated for 10 minutes and 56° C. The lysed sample was then brought to room temperature and loaded onto the fluidic device for isotachophoresis. Extraction of genomic DNA (pre-purified from human Jurkat cells using a commercial SPE kit) spiked into a buffer comprising 10 mM Tris-HCl pH 8 was performed at yields from about 90% to about 100% for input DNA masses from about $10^{-1}$ ng to about $10^3$ ng.

Compared to traditional SPE column kits, the isotachophoresis method and device used here allowed for higher yields. This may have been due to a higher off-chip lysis efficiency with the indicated lysis chemistry followed by a more efficient recovery of nucleic acids using isotachophoresis. The isotachophoresis methods and devices described herein may provide lower adsorption of nucleic acids samples to the surfaces of the chip compared to a standard column and/or lower dead volumes within the fluidic device than a column. The isotachophoresis methods and devices described herein may enable less biased or unbiased recovery of nucleic acids based on length and/or sequence, which may also provide for higher efficiency recovery. The spiked-in genomic DNA sample performed had a very high recovery (yield) which may indicate that isotachophoresis has very little systematic loss of sample due to the isotachophoresis process itself (whereas the cell lysate sample may have other factors which contribute to loss of efficiency such as the lysis chemistries used which may be improved for higher yields).

Example 3—Separation of Crosslinked and Non-Crosslinked Nucleic Acids

Figure 23:
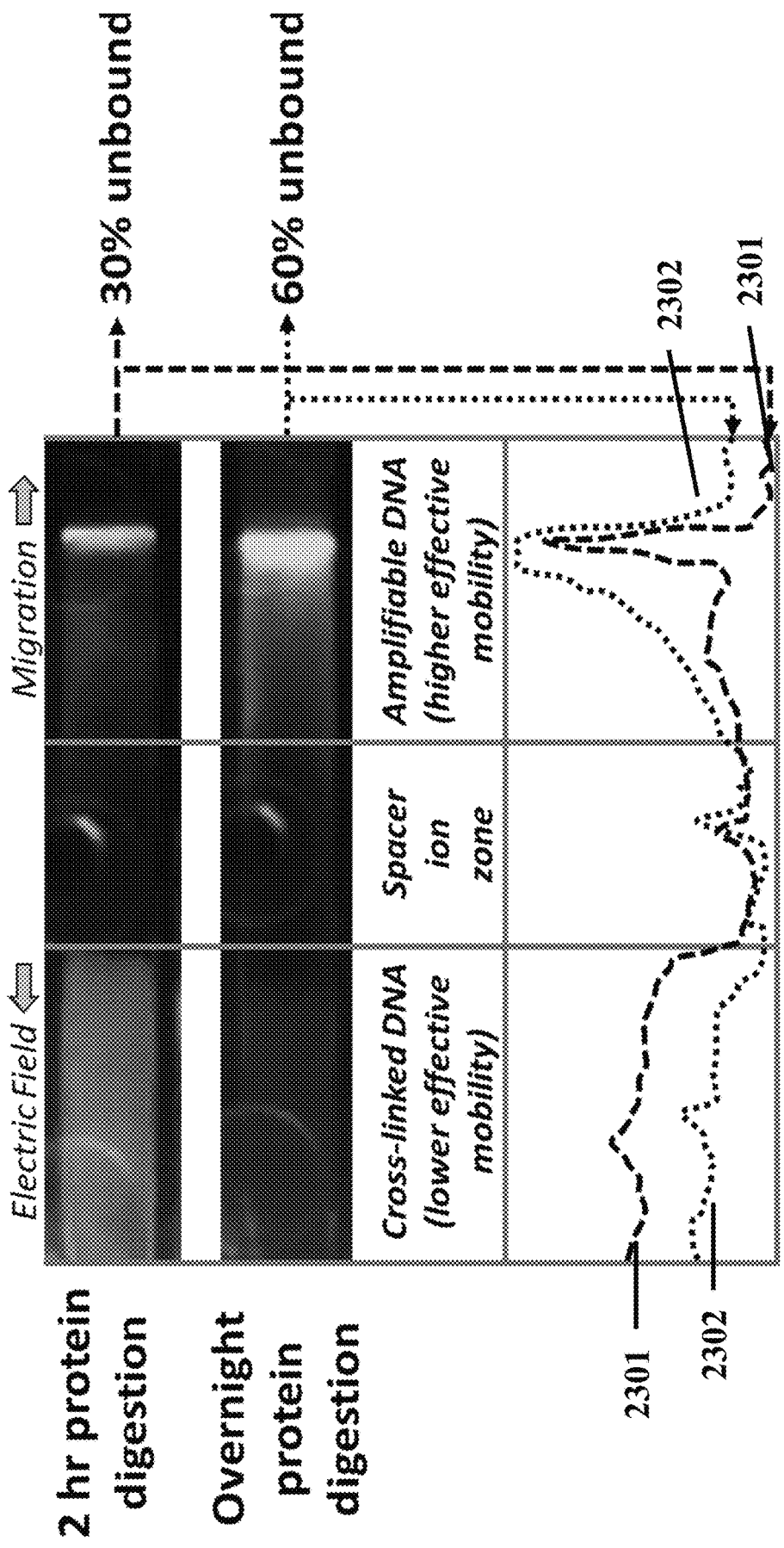
FIG. 23 shows exemplary images and corresponding fluorescence intensity traces of extraction and separation of amplifiable (e.g., decrosslinked) DNA from crosslinked DNA from an FFPE sample using isotachophoresis.

A deparaffinized and lysed mouse FFPE tissue sample (processed as described in Example 1) comprising crosslinked and non-crosslinked nucleic acids was loaded onto a fluidic device for isotachophoresis with leading electrolyte and trailing electrolyte. The sample was lysed as described in Example 1 and prepared in a leading electrolyte solution to a final concentration of 10 mM Tris with 5.6 mM HCl. The leading electrolyte comprised 140 mM Tris with 70 mM HCl. The trailing electrolyte comprised a mixture of 2.1 M Tris with 0.5 M caproic acid as a spacer ion with a higher effective mobility magnitude than HEPES and 0.7 M HEPES as an ion with a lower effective mobility magnitude. During isotachophoresis, non-crosslinked nucleic acids, having a higher effective mobility magnitude, focus ahead of the caproic acid zone and behind the leading electrolyte zone. Crosslinked nucleic acids and sample contaminants focus behind the caproic acid zone, and either ahead of or within the HEPES zone depending on the degree of crosslinking and their effective mobility magnitude. FIG. 23 shows two images of DNA separation in an isotachophoresis channel subsequent to a two hour (upper) or an overnight (lower) digestion to remove crosslinking proteins from the DNA. Proteinase K was added to the deparaffinized lysed tissue (quenched to pH 8.2) at final concentration of 700 μg/ml for digestion. Crosslinked DNA appears at the left end of the channel, separated by spacer ions from the amplifiable non-crosslinked DNA at the right end of the channel. The graph in FIG. 23 shows intensity of DNA signal versus position in the channel for the two hour 2301 and overnight 2302 digestions.

Example 4—Extraction and Purification of DNA from Lung and Liver FFPE Samples Formalin-fixed paraffin-embedded (FFPE) mouse lung and liver samples were obtained (e.g., Zyagen). Seven pairs of FFPE sections (1 cm by 1 cm by 5-10 μm) were processed, with one section from each pair processed by on-device isotachophoresis and one section processed by a different method (Promega ReliaPrep FFPE DNA kit) for comparison. The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. Samples were deparaffinized by incubation in a 10 mM Tris-HCl buffer with 10 mM DTT, 72 mM NaCl and 0.5% IGEPAL CA-630 at pH 8.0 for approximately 1 minute at 80° C., and subsequently treated with proteinase K in the same solution for 60 minutes at 56° C. The digested sample was then incubated for 15 minutes at 90° C. ITP was conducted on one sample from each pair of sections by dispensing 200 μL of pre-processed sample mixture, including embedding and FFPE tissue debris, into the sample inlet of a fluidic device. The other section from each pair was extracted using Promega's ReliaPrep FFPE gDNA kit according to manufacturer's protocol. FIG. 24A shows an image of two neighboring ITP channels on a fluidic device with DNA from FFPE samples, labeled with intercalating dye for visualization. Extracted DNA from the samples was quantified with qPCR. FIG. 24B shows the quantified extracted DNA in nanograms (ng) for each of the seven sample pairs. For each pair, the darker left-hand bar shows results for ITP and the lighter right-hand bar shows results for the ReliaPrep kit. The leftmost two sample pairs are human liver samples, and the remaining five sample pairs are human lung samples. For all seven sample pairs, the amount of amplifiable nucleic acids extracted via ITP is significantly higher (typically about 1.5 to 8 times higher amplifiable yields) than the amount of nucleic acids extracted by the ReliaPrep kit.

Example 5—ITP-Based Quantitation of Nucleic Acids

Quantitation of nucleic acids using ITP was tested and compared to qPCR. The comparison was performed over the full range of sample amounts using an RNaseP human reference gene assay (ABI). Standard or calibration curves were generated from 50 qPCR runs (10 replicates each at 5 orders of magnitude concentrations) and were used to quantify qPCR measurement uncertainty for this range of DNA amounts.

DNA was extracted from 4 million Jurkat cells using a standard kit (e.g., Invitrogen PureLink Genomic DNA kit). For on-device ITP, Jurkat cells were lysed off-chip using a pH 12.7 NaOH solution for 2 minutes, quenched to buffered solution at pH 7.5-8 using a solution of hydrochloric acid and Tris base, and then treated with Proteinase K for at pH 8 and 56° C. for 10 minutes.

Figure 14:
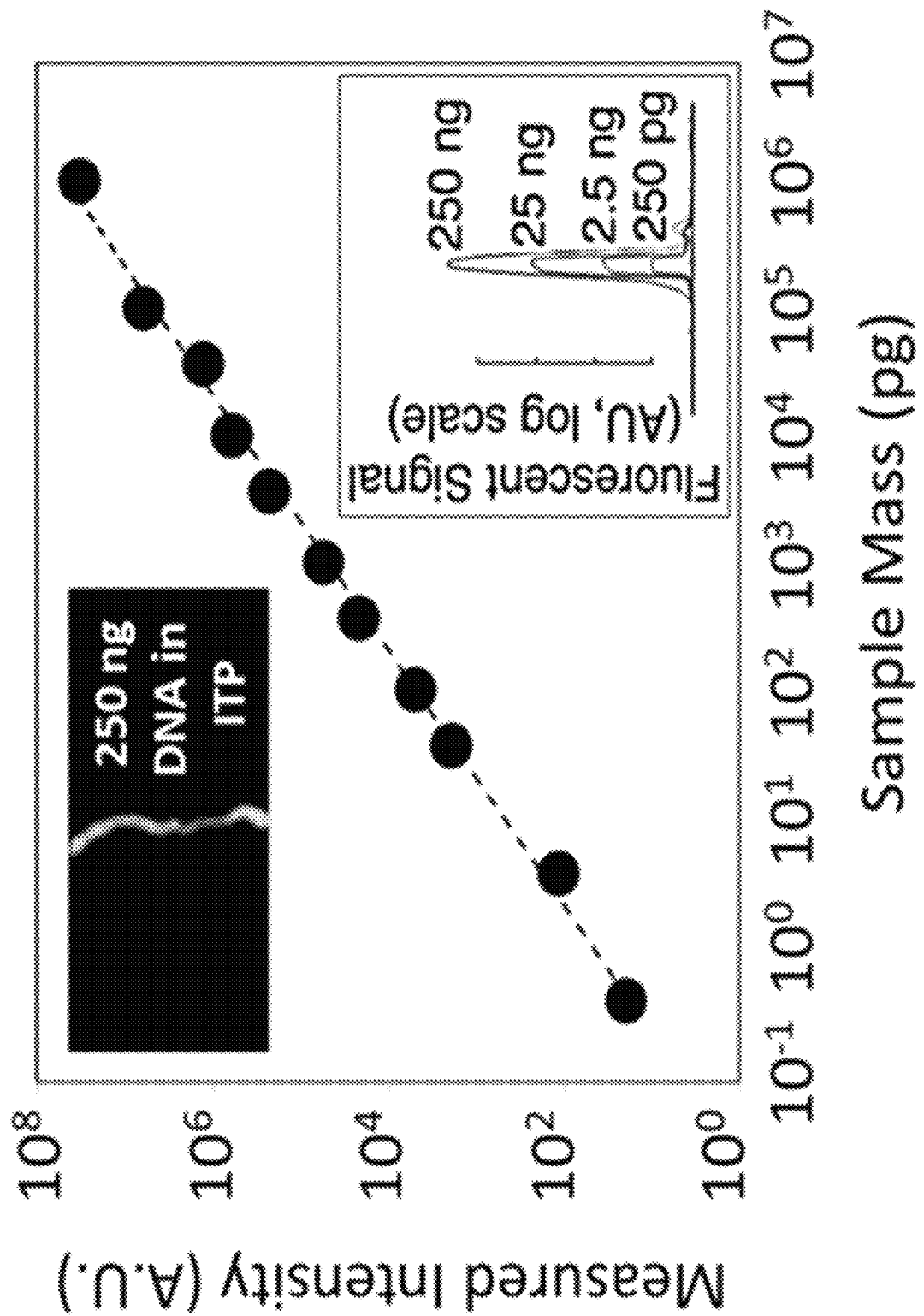
FIG. 14 shows exemplary results of fluorescence-based measurements and quantitation for a titration series of nucleic acids using isotachophoresis.

Pre-purified DNA was processed via ITP and quantified in the ITP channel via fluorescent intensity. The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. The sample was prepared in a leading electrolyte buffer (sample buffer) comprising 10 mM Tris with 5.6 mM HCl. FIG. 14 shows a titration curve of measured fluorescent intensity from DNA compared to known DNA sample mass, and is linear over seven orders of magnitude, from 0.4 picograms (pg) to about $10^6$ pg. The upper left inset of FIG. 14 shows an image of 250 ng of DNA in an ITP channel. The lower right inset of FIG. 14 shows point detector fluorescent signal intensity on a logarithmic scale for ITP-extracted DNA in an ITP channel, at 250 pg, 2.5 ng, 25 ng, and 250 ng of DNA.

Example 6—Lack of Bias in ITP Extraction and Purification

Figure 4B:
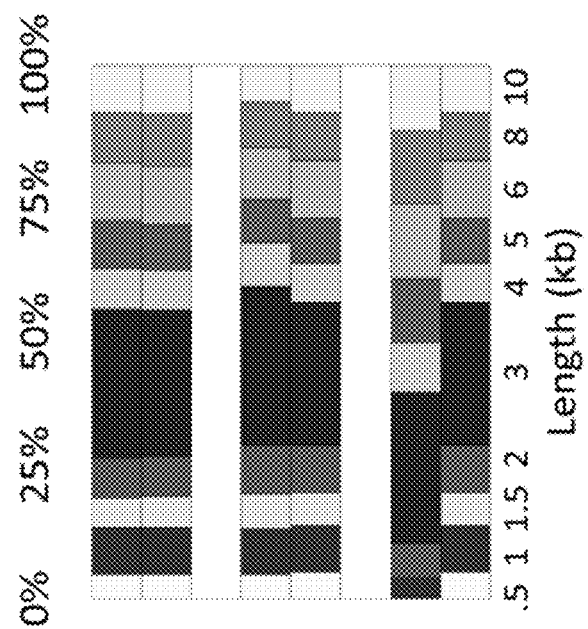
FIG. 4B shows exemplary results for unbiased (e.g., with respect to size or molecular weight), pre- and post-purification, of a DNA molecular weight ladder using isotachophoresis; comparisons to two solid phase column based nucleic acid purification methods are shown.
Figure 4A:
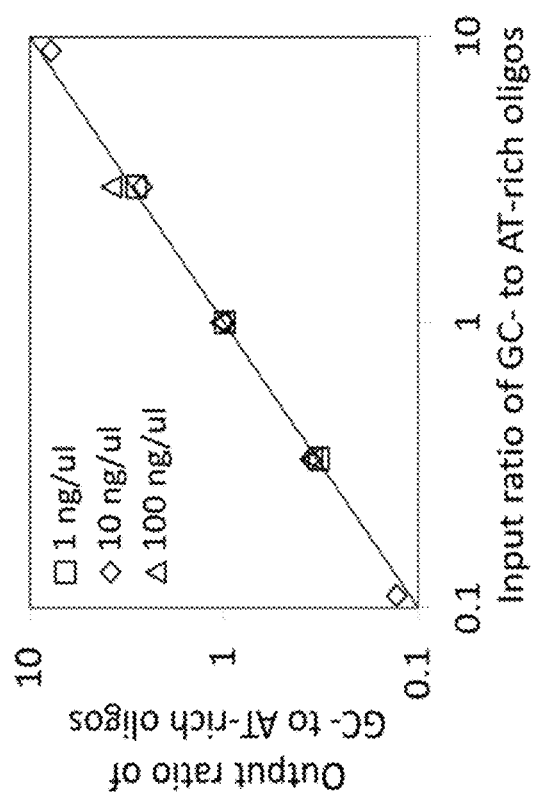
FIG. 4A shows exemplary results for unbiased (e.g., with respect to sequence) extractions of GC-rich and AT-rich synthetic DNA oligonucleotides mixed at sample concentration ratios using isotachophoresis.

Mixtures of synthetic 100 base labeled DNA oligonucleotides with 63% A-T content (37% G-C content, HEX label) and DNA oligonucleotides with 68% G-C content (FAM label) were prepared at three concentrations (1 ng/μL, square data points; 10 ng/μL, diamond data points; 100 ng/μL, triangle data points) and five concentration ratios (overall GC- to AT-rich ratio from 0.1 to 10). Ratios were calculated from fluorescence plate reader measurements obtained pre- and post-processing. FIG. 4A shows a comparison of the output GC- to AT-rich ratio versus the input GC- to AT-rich ratio for ITP processing, demonstrating a lack of bias in the ITP process.

A mixture of oligonucleotides from a 1 kb DNA ladder (New England Biosciences) was measured for length before and after processing, using integrated signals of electropherogram peaks from the Experion 12k DNA analysis kit (BioRad). Size distribution within the sample before and after processing was compared for on-device ITP (FIG. 4B, top), Qiagen QiaAmp column kit (FIG. 4B, middle), and Invitrogen PureLink column kit (FIG. 4B, bottom). The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. The sample was prepared in a leading electrolyte buffer (sample buffer) comprising 10 mM Tris with 5.6 mM HCl. For each comparison, the top row shows the size distribution in the recovered output fraction and the bottom row shows the initial size distribution in the sample.

Example 7—Off- or On-Chip Proteinase K Digestion of Cell Lysate Nucleic Acids

FIG. 25A shows an image of a single channel ITP chip loaded with nucleic acid (RNA extraction and proteolytic digest from human cells) stained with dye for visualization. On the left 2501 is an ITP band from sample processed off-chip prior to loading with 200 µg/mL proteinase K in sample buffer, while on the right 2502 is a sample not processed with proteinase K. The leading electrolyte buffer used for isotachophoresis comprised 100 mM Tris with 50 mM HCl. Trailing electrolyte was loaded into the trailing electrolyte reservoir and comprised 1.8M Tris with 1 M Caproic Acid and 1 M MOPS. The sample was prepared in a leading electrolyte buffer (sample buffer) comprising 10 mM Tris with 5.6 mM HCl. FIG. 25B shows an image of a single channel ITP chip loaded with nucleic acid (RNA extraction and proteolytic digest from human cells) stained with dye for visualization. On the left 2501 is an ITP band from sample processed on-chip 200 µg/mL proteinase K in leading electrolyte, while on the right 2502 is a sample not processed with proteinase K. In both cases, the sample processed with proteinase K exhibits a tighter ITP band, representing nucleic acids not associated with protein (higher effective mobility magnitude), while the sample not processed with proteinase K exhibits a smeared band, representing nucleic acid associated with variable amounts of protein (lower effective mobility magnitude).

Figure 26B:
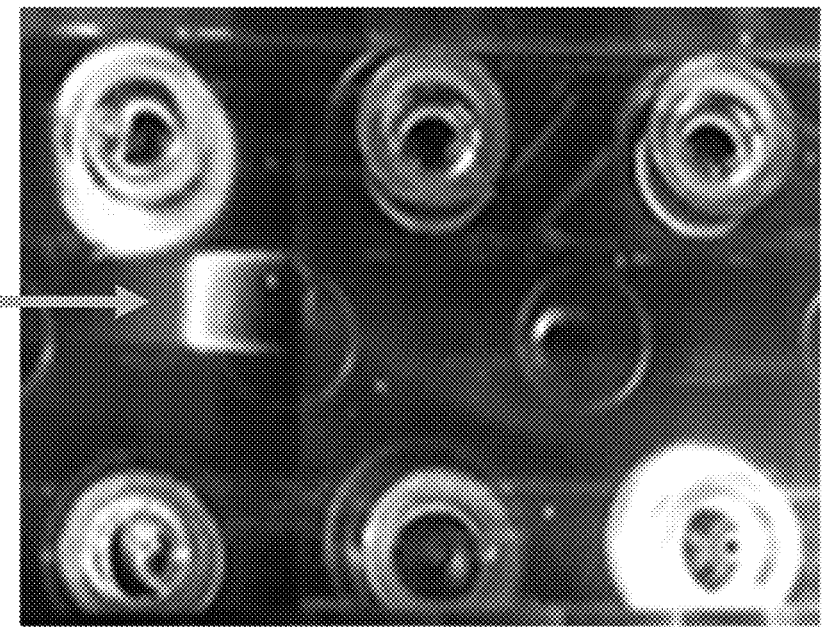
FIG. 26B shows an image of a total nucleic acid ITP band in a chip channel during purification.
Figure 26A:
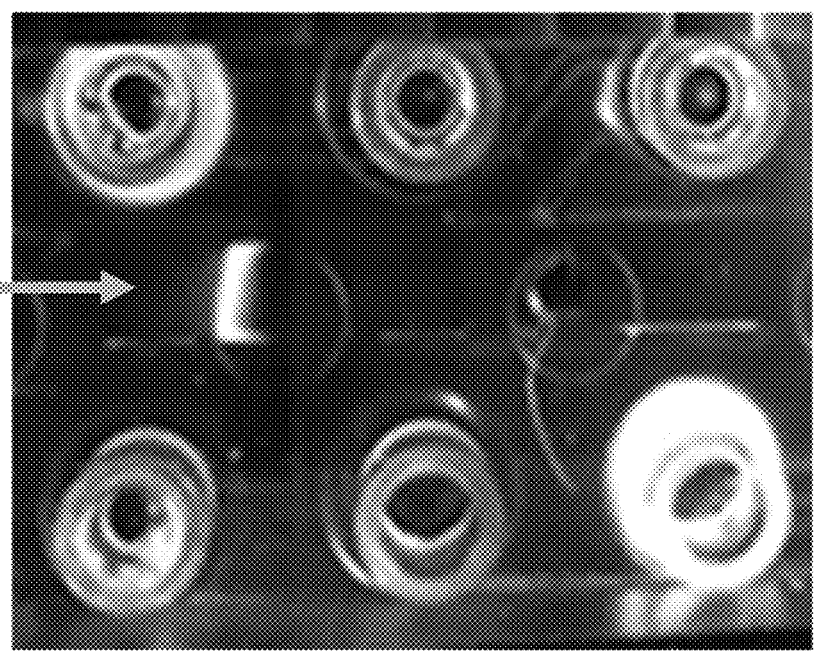
FIG. 26A shows an image of an RNA ITP band in a chip channel during purification.
Figure 26C:
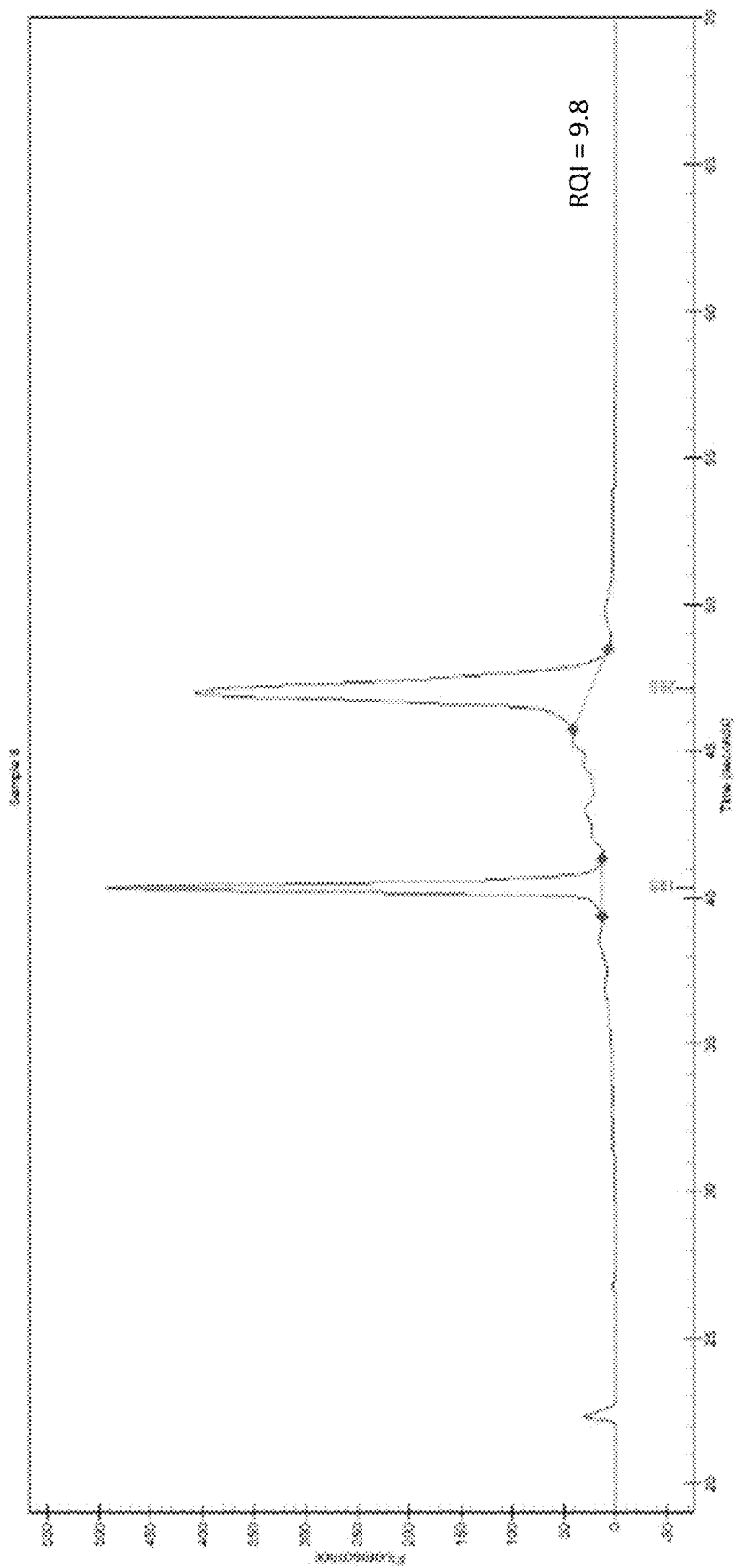
FIG. 26C shows a graph of an RNA quality electropherogram for the sample shown in FIG. 26A.
Figure 26D:
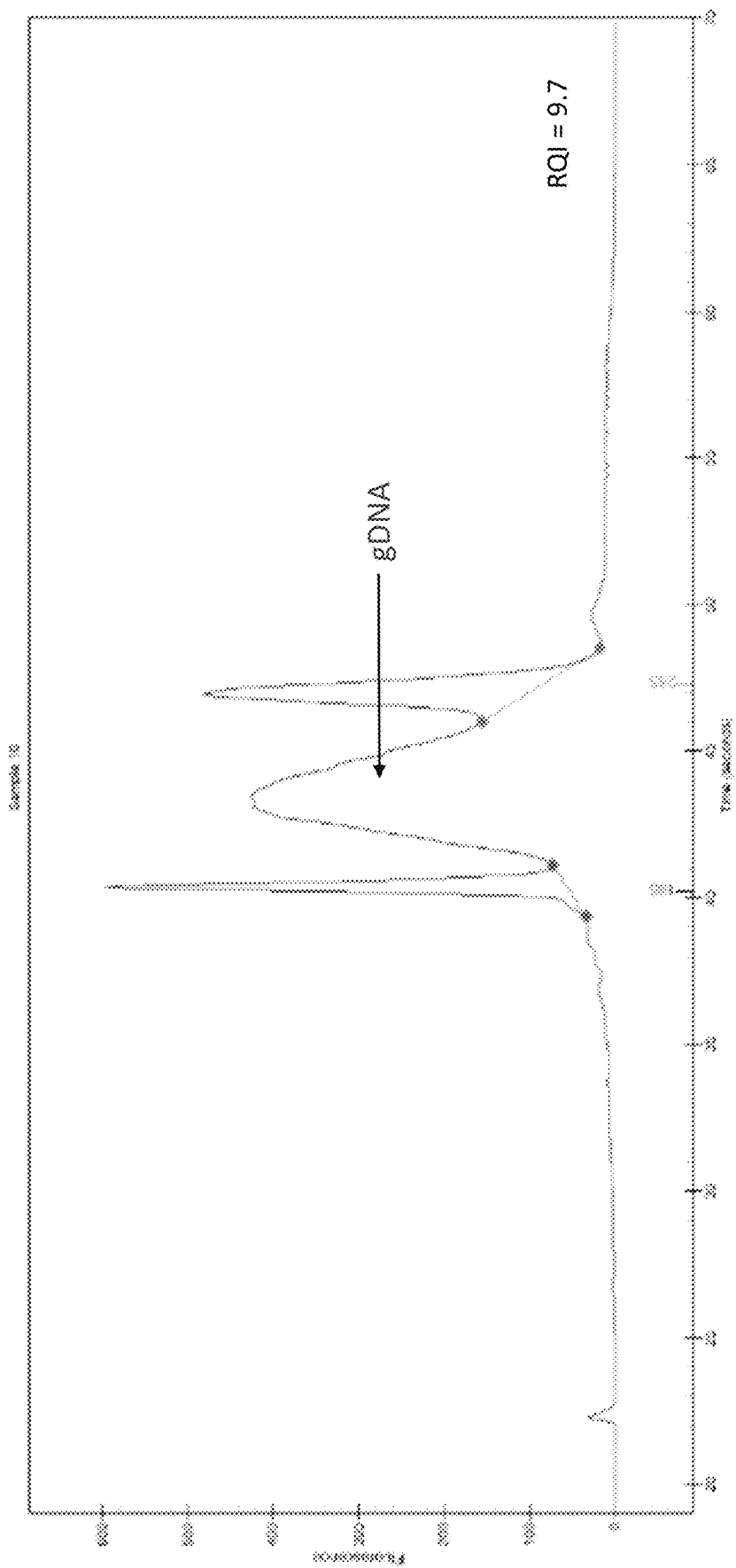
FIG. 26D shows a graph of an RNA quality electropherogram for the sample shown in FIG. 26B.

Example 8—RNA Extraction from Human Cells Using Off-Chip Lysis and On-Chip ITP Purification FIG. 26A shows an image of an RNA ITP band 2601 in a chip channel during extraction and purification of RNA from cell lysate (Jurkat cells) with DNA digested. FIG. 26B shows an image of a total nucleic acid ITP band 2602 in a chip channel during extraction and purification of RNA from cell lysate (Jurkat cells) without DNA digested. The leading electrolyte buffer used for isotachophoresis comprised 100 mM Tris with 50 mM HCl. Trailing electrolyte was loaded into the trailing electrolyte reservoir and comprised 1.8M Tris with 1 M Caproic Acid and 1 M MOPS. The sample was prepared in a leading electrolyte buffer (sample buffer) comprising 10 mM Tris with 5.6 mM HCl. FIG. 26C and FIG. 26D show graphs of RNA quality electropherograms (measured using the BioRad Experion) for the samples shown in FIG. 26A and FIG. 26B, respectively. Cell lysis and DNase digestion were performed in a buffered solution at pH 8 containing 7M urea, 2M thiourea, and a non-ionic surfactant as discussed herein. These results demonstrate the preparation of high quality RNA with or without DNA digestion.

Example 9—Extraction of Whole Lysed Blood Using ITP and 200 µl Chip Device

Figure 27A:
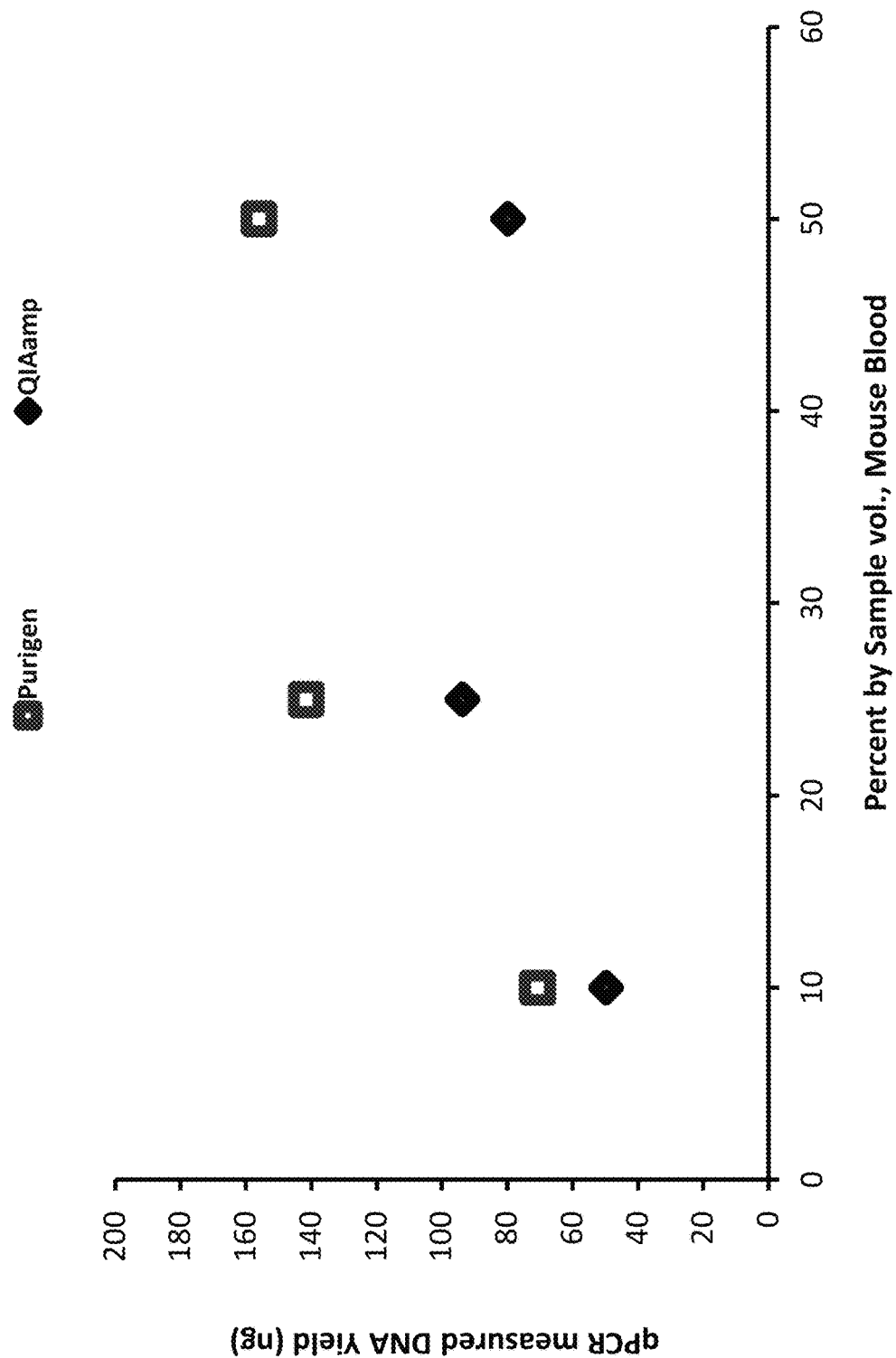
FIG. 27A shows results of DNA yield (ng) for ITP (square) compared to column (diamond, Qiagen QiaAmp) extraction of whole mouse blood as a function of percent by volume of whole blood in starting sample.
Figure 27B:
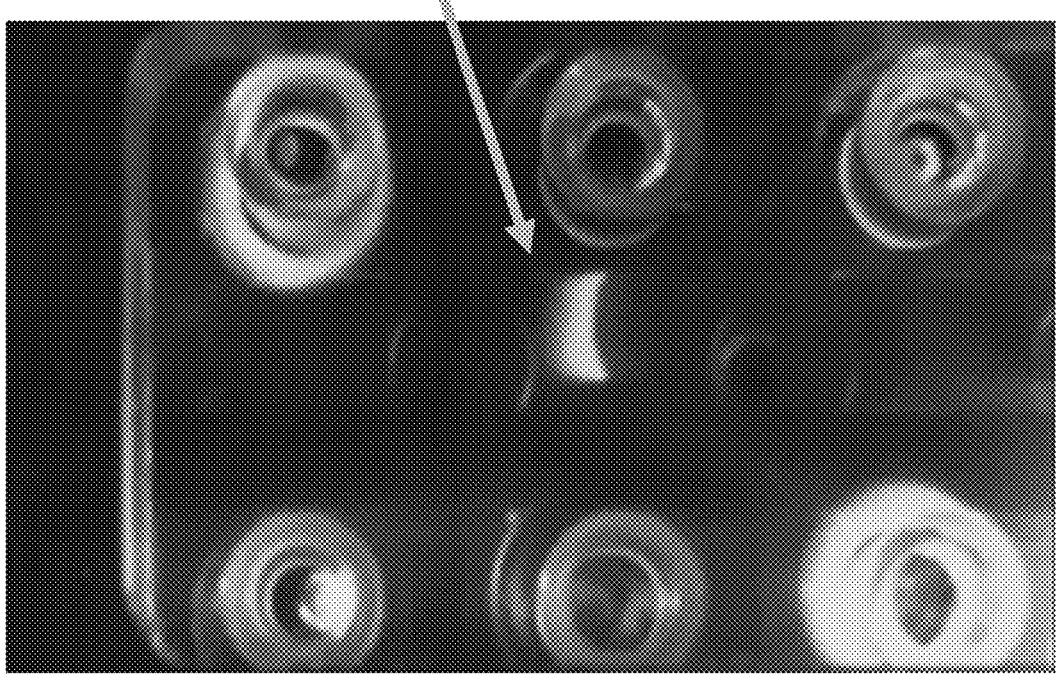
FIG. 27B shows an image of total nucleic acid in an ITP band during ITP purification of lysed whole mouse blood on a chip.

FIG. 27A shows results of DNA yield (ng) for ITP (square) compared to column (diamond, Qiagen QiaAmp) extraction of whole mouse blood as a function of percent by volume of whole blood in starting sample. FIG. 27B shows an image of total nucleic acid in an ITP band 2401 during ITP purification of lysed whole mouse blood on a chip. The leading electrolyte buffer used for isotachophoresis comprised 260 mM Tris with 130 mM HCl. Trailing electrolyte was loaded into the trailing electrolyte reservoir and comprised 2.1 M Tris with 0.5 M Caproic Acid and 0.7 M MOPS. The sample was prepared in a leading electrolyte buffer (sample buffer) comprising 10 mM Tris with 5.6 mM HCl.

Figure 27C:
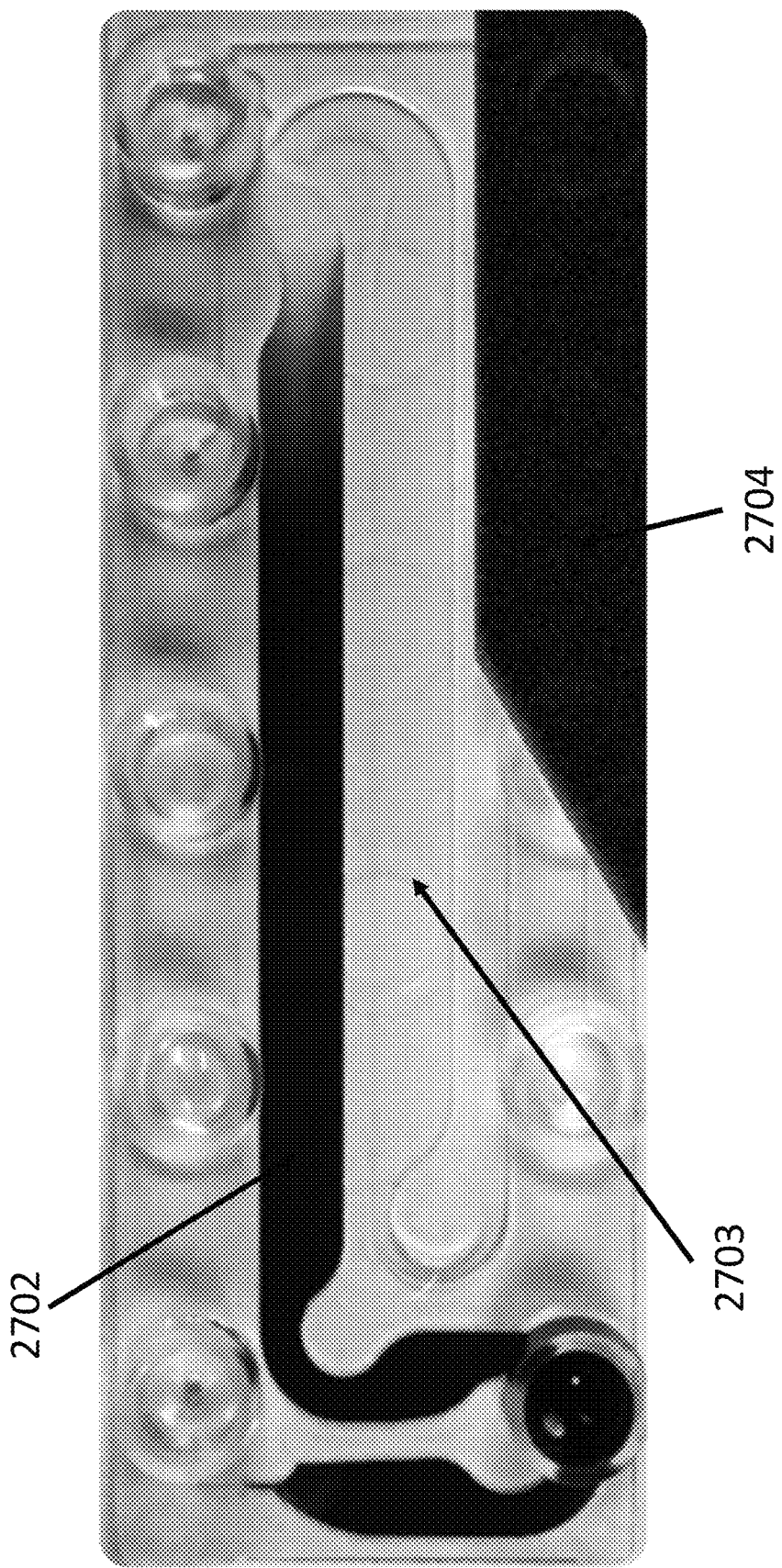
FIG. 27C and FIG. 27D show white light and fluorescence overlay images of ITP chip channels showing physical separation of heme in the sample/leading electrolyte channel from the elution channel and reservoir, before and after ITP purification of 50% by volume whole blood lysate. Nucleic acid is stained with green dye for visualization in elution well.
Figure 27D:
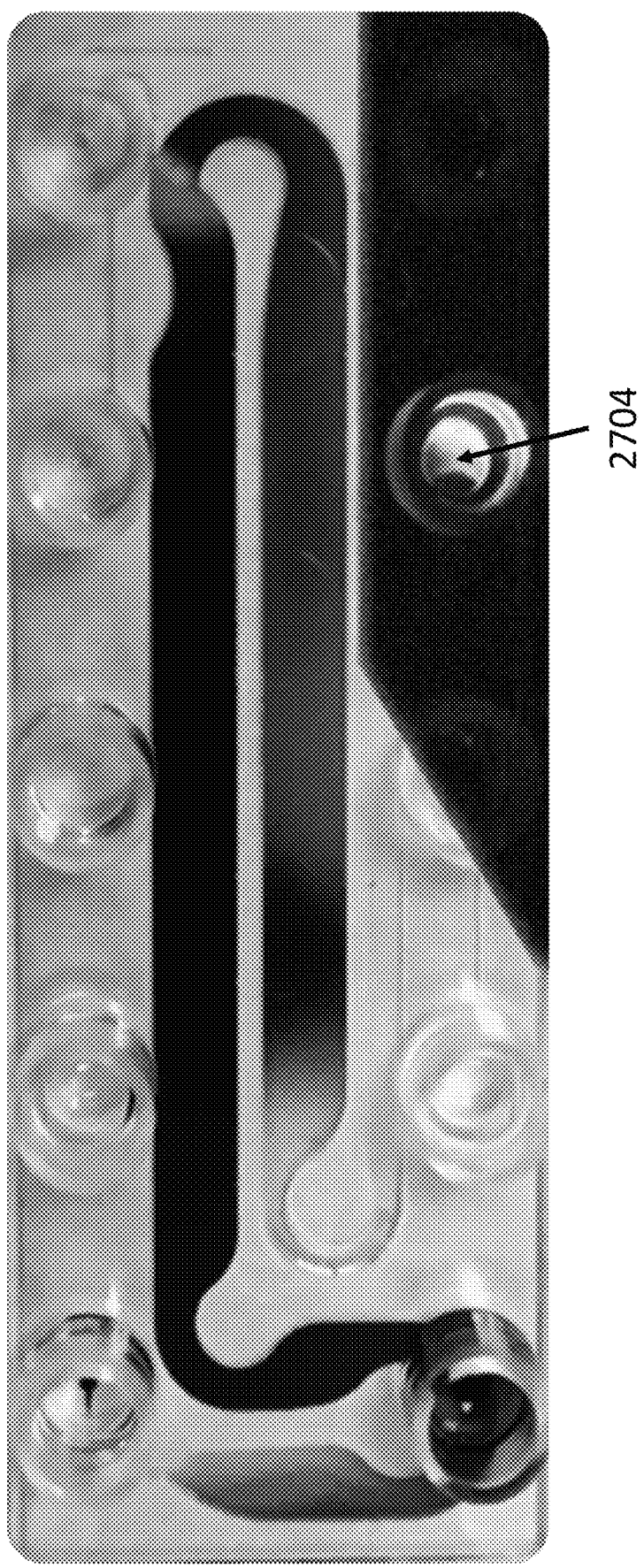
Figure 27E:
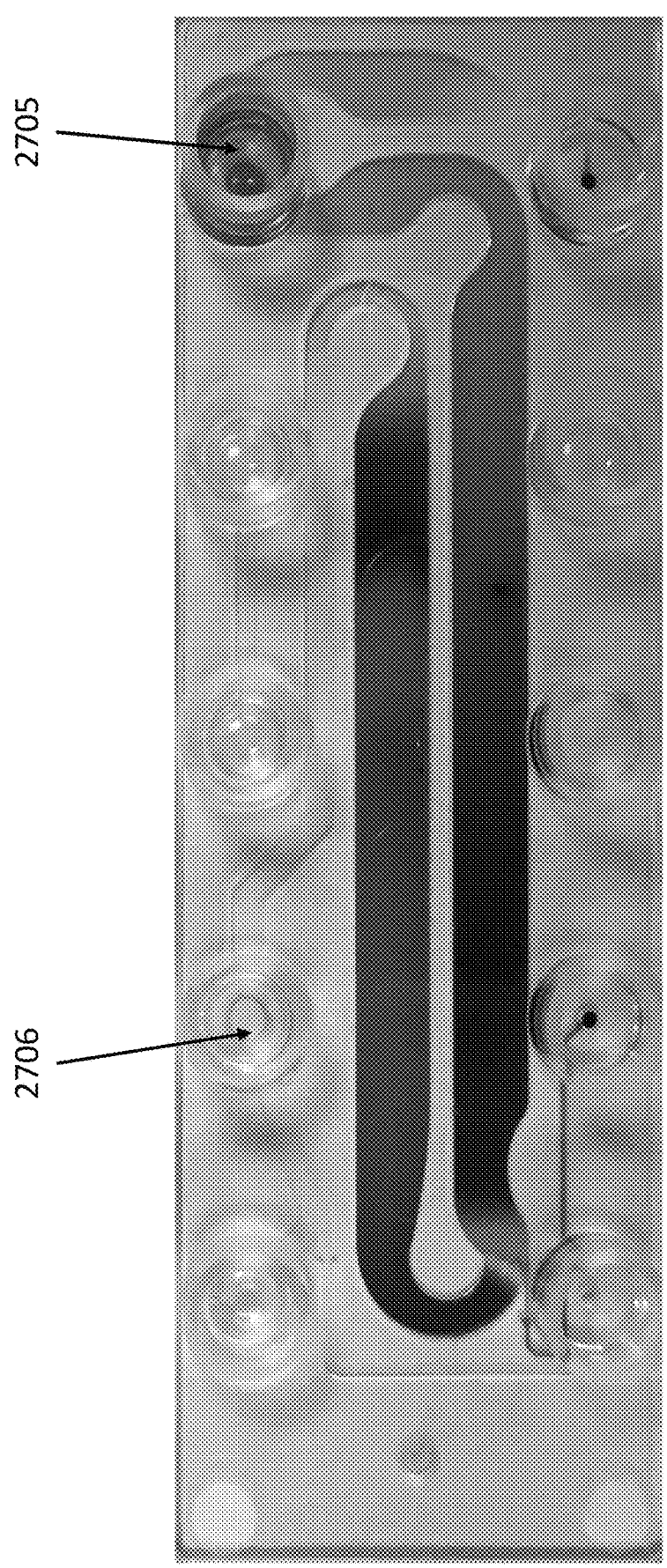
FIG. 27E shows an chip post ITP purification (50% by volume blood).
Figure 27F:
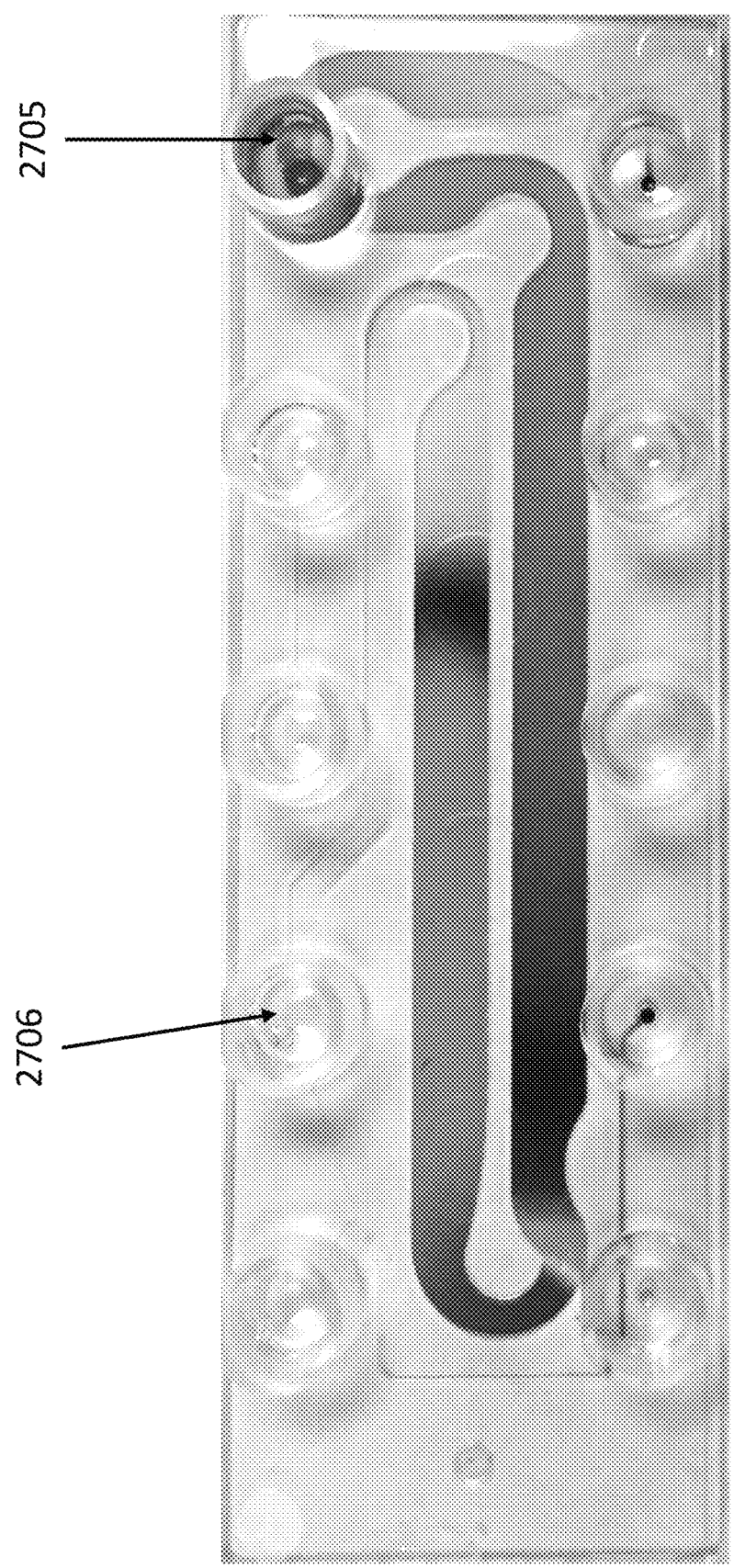
FIG. 27F shows an chip post ITP purification (25% by volume blood).

FIG. 27C and FIG. 27D show white light and fluorescence overlay images of ITP chip channels showing physical separation of heme from the blood sample in the sample channel and leading electrolyte (or separation) channel 2703 from the elution channel and reservoir 2704, before and after ITP purification of 50% by volume whole blood lysate 2702. The purified nucleic acid is stained with green dye for visualization in elution well. FIG. 27C shows the chip before ITP (blood lysate and ITP buffers loaded in chip; pure buffer and no DNA in elution well). FIG. 27D shows the chip after ITP (blood lysate and ITP buffers loaded in chip; pure buffer and DNA in elution well). FIG. 27E shows the chip post ITP purification, with a white light image of the chip channel showing physical separation of heme from the blood sample in the sample well 2705 and leading electrolyte (or separation) channel from the elution channel and reservoir 2706 in single channel chip device (50% by volume blood). FIG. 27F shows the chip post ITP purification, with a white light image of the chip channel showing physical separation of heme from the blood sample in the sample well 2705 and leading electrolyte (or separation) channel from the elution channel and reservoir 2706 in single channel chip device (25% by volume blood).

Figure 28:
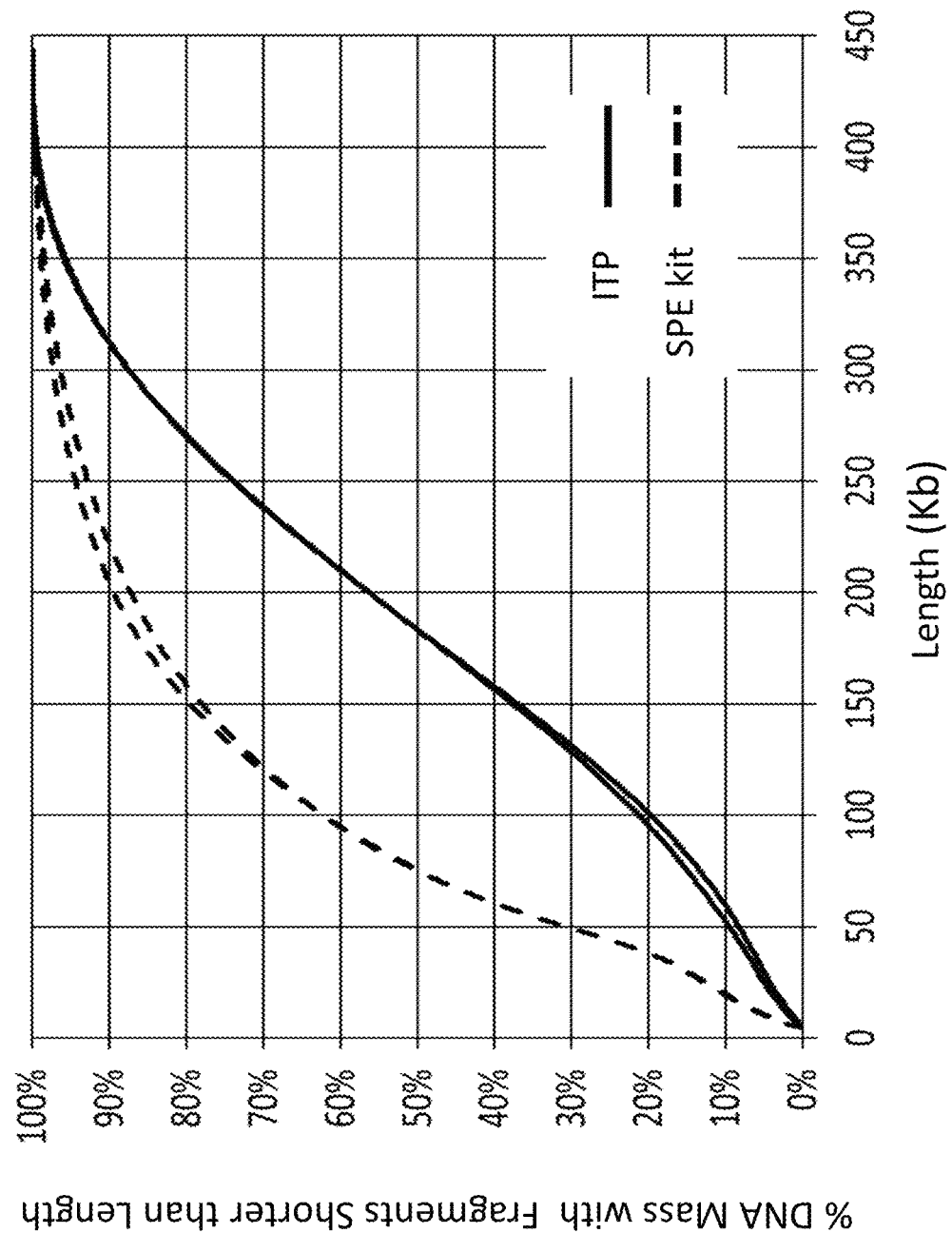
FIG. 28 shows results of high molecular weight DNA purification for ITP compared to solid phase extraction.

Example 10—Extraction of High Molecular Weight DNA from Cultured Human Cancer Cells Using Off-Chip Lysis and On-Chip ITP Purification FIG. 28 shows results of high molecular weight DNA purification for ITP (solid line) compared to solid phase extraction (SPE; dashed line, Qiagen MagAttract) of cultured human Jurkat cells as the percentage of DNA mass in the purified sample having fragments shorter than a given length (Kb). Cell lysis was performed off-chip in a buffered lysis solution containing 10 mM Tris with 5.6 mM HCl and 0.2% v/v IGEPAL CA-630. The buffered solution was configured to lyse the cells and reduce mechanical disruption of the DNA during lysis. Cell pellets were lysed in the lysis solution and mixed gently with inversion and slow-speed (automated pipettor), wide-bore tip pipetting (e.g. Rainin 200 µl wide bore tip) to aid in homogenization of the lysate. A final concentration of 500 µg/ml Proteinase K was added to the lysate and incubated for 20 min at 60° C. ITP was performed on the lysate with 88 mM Tris with 44 mM HCl as the leading electrolyte and 1.2 M Tris with 0.3 M caproic acid and 0.6 M MOPS as the trailing electrolyte. ITP-based purification led to 2 to 3 times greater mean DNA fragment lengths as compared to the bead-based PSE kit, in part due to reduced mechanical shearing of the DNA during isotachophoresis compared to SPE due to the lack of a solid phase component or high shear forces (e.g. from centrifugation) during the extraction process. The ITP purified DNA had an average DNA length of about 175 Kb (i.e. 50% of the DNA mass contained DNA fragments greater than about 175 Kb) compared to SPE purification which yielded DNA with an average length of about 75 Kb. More than 60% of the mass of the DNA extracted by ITP contained an average fragment length greater than 150 kB. ITP produced at least about three times as many DNA fragments with a size of at least 150 kB than the SPE method.

Example 11—Closing of Channels Using Mechanical Member

Figure 29A:
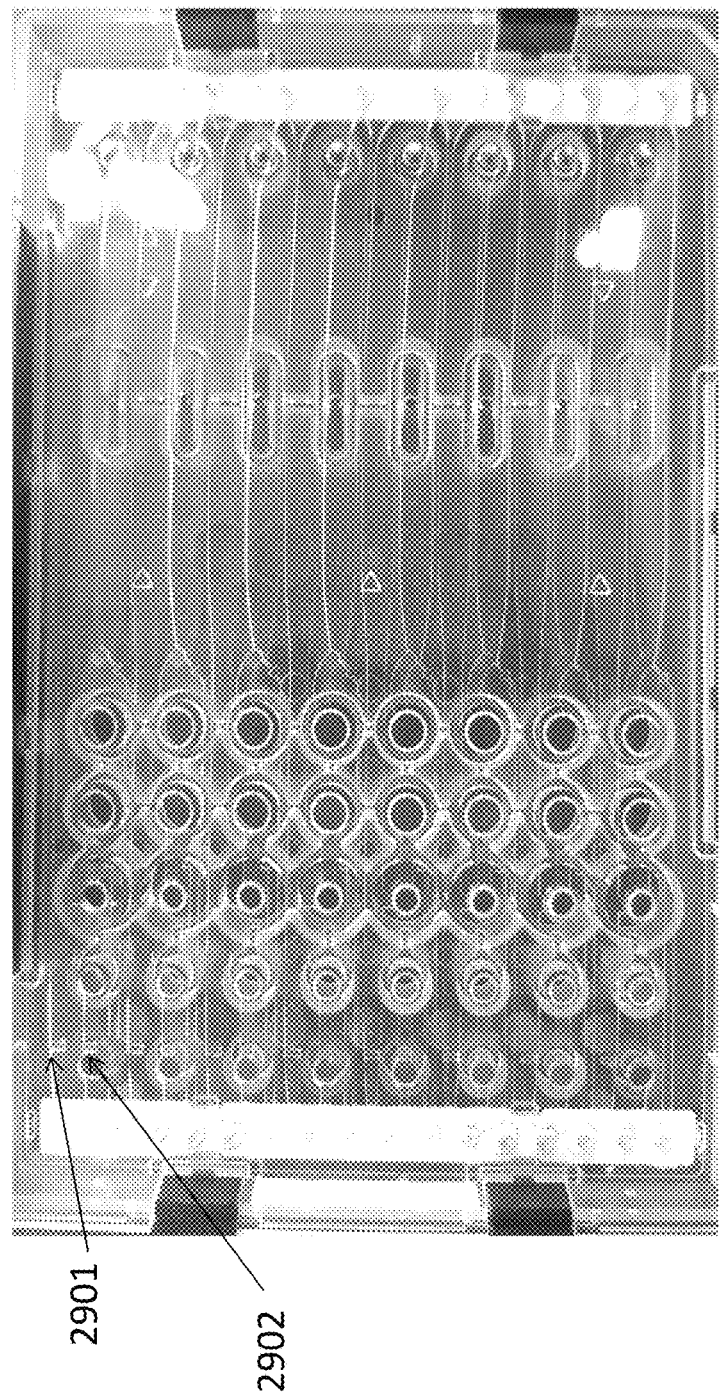
FIG. 29A shows a fluidic device comprising 8 closed channels.
Figure 29B:
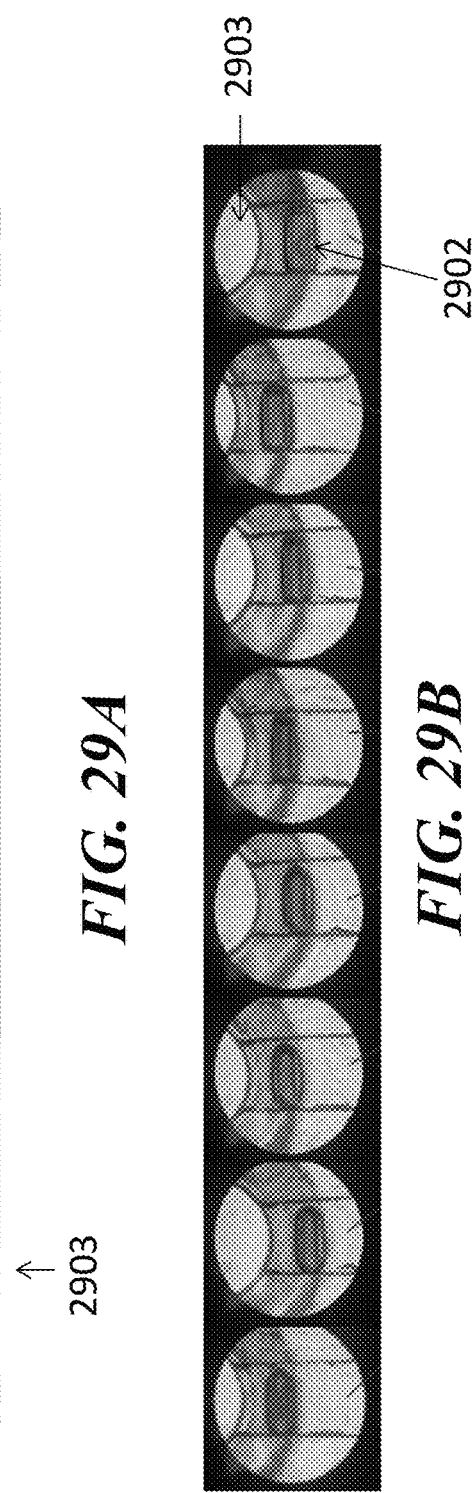
FIG. 29B shows a zoomed in microscopic view the second channel closure location adjacent the elution reservoir of each of the channels.
Figure 29D:
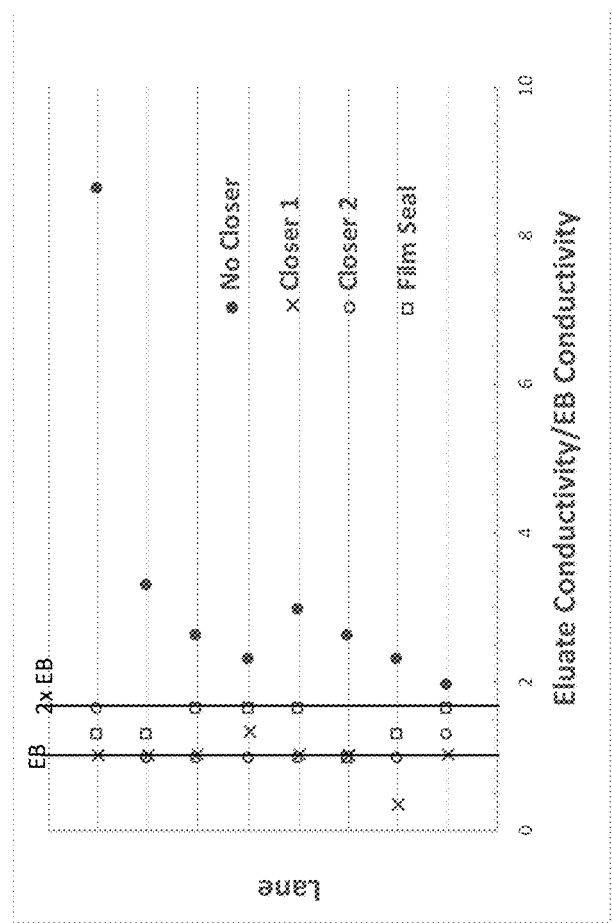
FIG. 29D shows the results of conductivity measurements of channel closure.
Figure 29C:
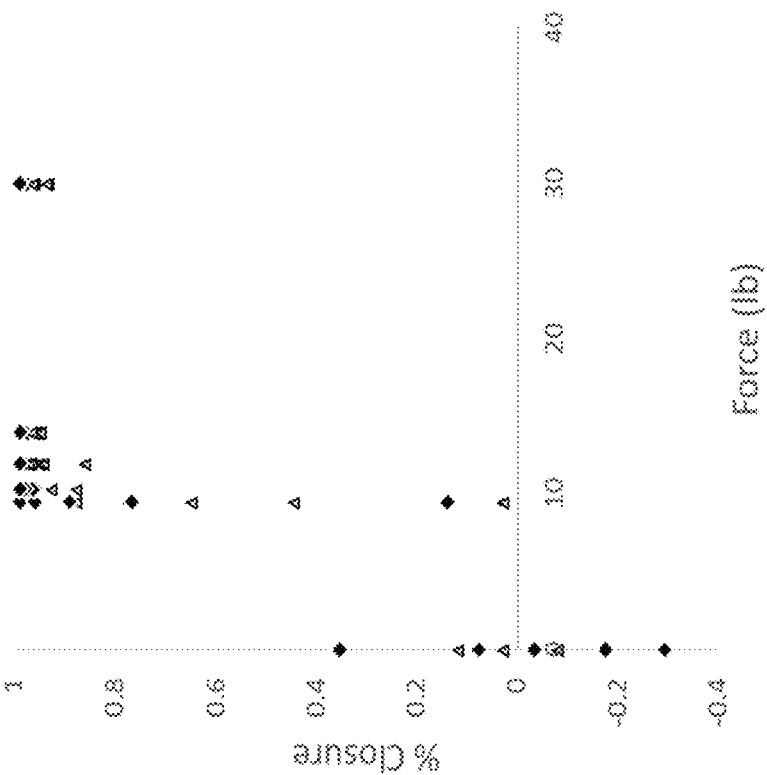
FIG. 29C shows the percent closure calculated as a function of force applied to the fluidic device.

FIG. 29A shows a fluidic device comprising 8 closed channels. Each channel was permanently closed at two locations 2902, 2902 as shown in FIG. 12B by applying a temperature of 150° C. and a pressure of 30 pounds (across all 16 locations; i.e. 1.875 pounds per tooth) to the device for 1 second with the comb-like mechanical member of FIG. 12A. FIG. 29B shows a zoomed in microscopic view the second channel closure location 2902 adjacent the elution reservoir 2903 of each of the channels. FIG. 29C shows the percent closure calculated as a function of force applied to the chips. The extent of channel closure was assessed without fluid loaded into the channel. Closure was measured by applying a constant pressure and measuring air flow rate through the channel. Five chips were assessed. Diamonds indicate closure data obtained from the first close location 2901 and triangles indicate closure data obtained from the second close location 2902. Without a force applied, the channels were open or mostly open. A force of 10 pounds across the device was sufficient close most of the channels while a force of 30 pounds across the device closed all or nearly all of the channels repeatedly. FIG. 29D shows the results of conductivity measurements with a conductivity meter to determine if channels are closed. The chip reservoirs and channels were loaded with ITP buffers as described in FIGS. 12A-12D or FIG. 15 (leading electrolyte, a high concentration of leading electrolyte for buffering, trailing electrolyte, elution buffer, a high concentration of elution buffer for buffering, and sample buffer without a biological sample). The channels were closed using the mechanical member and then the fluid in the elution reservoir 2903 was pipetted out of the reservoir and collected. The conductivity of the elution fluid was measured and compared to measurement of the conductivity of original (pre-loaded) elution buffer (same buffer initially loaded in the chip). It was expected that the conductivity of measured fluid would be the same as the original elution buffer if channel closure was sufficient to provide fluidic resistance at the first channel close location 2901 between the elution reservoir 2903 and the channel and at the second channel close location 2902 within the channel connecting the elution reservoir 2903 to the elution buffering reservoir (via the elution buffering channel; not shown). For a fully closed channel, the conductivity of the eluted volume (without performing ITP) can be equal to the conductivity of the elution buffer alone, indicating no transfer of fluids or ions during collection. Four situations were tested—without a closer (fully open channels), with the first close location 2901 closed (partially closed), with both locations 2901, 2902 closed (fully closed), or with every reservoir but the elution reservoir sealed with a film seal. In the film seal situation, the channels were not physically deformed by the mechanical member but were instead sealed with a film applied by the operator in order to increase resistance to fluid flow. Elution volumes from partially closed channels showed increased conductivity compared to fully closed channels. Sealing of the non-elution reservoirs with the film seal were increased compared to fully closed channels as well but remained generally less than the conductivity of a 2× elution buffer. These conductivity levels were, however, much lower than those obtained from eluates without channel closure.

FIG. 85 shows contrast images from fluorescence-based imaging of a fluorescently-dyed analyte material 8501 in the channel before (left side—analyte material 8502 clearly visible in 8 chip elution reservoirs) and after (right side—analyte material 8502 clearly less visible, as indicated by reflection 8503 in 8 individual chip elution reservoirs) pipetting out of the elution well following channel closing with the tooth-like member structure and mechanical actuator for closing the channels. The fluorescently-dyed analyte material 8501 in the channel did not move during the elution process, indicating that the channel closer prevented flow during the elution process.

FIG. 86 shows contrast images from fluorescence-based imaging of a fluorescently-dyed analyte material 8601 in the channel before (left side—analyte material 8602 clearly visible in 8 chip elution reservoirs) and after (right side—analyte material 8602 clearly less visible in 8 individual chip elution reservoirs, indicating it was removed) pipetting out of the elution well following channel closing with the PCR film membrane seal approach for closing the channels. The fluorescently-dyed analyte material 8601 in the channel did not move during the elution process, indicating that the channel closer prevented flow during the elution process.

Example 12—Closing of Channels Using Ridge-Like Mechanical Member

FIG. 87A shows conductivity data that was obtained by using a conductivity meter to measure the conductivity of eluted material (namely the conductivity of the ions contained in the eluted liquid volume) pipetted out of the elution reservoir from a chip. The non-elution wells were sealed using either a disposable PCR film (i.e. a membrane-enabled top seal to fluidic reservoirs of chip) or a ridge-like channel closer as shown in FIG. 54A. Sealing on the non-elution wells resulted in partial closure of the wells and higher conductivity than that of a 2× elution buffer. The conductivity levels of the eluate collected from the chip sealed with the ridge channel closer was lower-still compared to the PCR film seal, indicating a full or near-full closure of the channels had been attained. FIG. 87B shows contrast images from fluorescence-based imaging of a fluorescently-dyed analyte material 8701 in the elution reservoirs before (left side—material clearly visible in 8 chip elution reservoirs) and after (right side—material clearly less visible in 8 individual chip elution reservoirs) pipetting out of the elution well following channel closing with the ridge-like member structure and mechanical actuator for closing the channels.

Example 13—Closing of Channels Using Channel Closer with Rubber Sealing Member and Mechanical Actuator Table 2 shows conductivity data collected for eluted material recovered from a fluidic device channel closed with the device described in FIG. 58A. Each of the channels on an 8-channel fluidic chip were loaded with ITP buffers (5 buffer wells per channel) and sample (1 sample well per channel). The elution buffer was 10 mM Tris HCl pH 7.5 with 0.002% Tween 20. The channels were closed by applying a channel closer with a rubber sealing member and a mechanical actuator. A manual pipet was used to remove 50 ul of material from the 8 elution reservoirs following completion of ITP. The conductivity of each eluate was measured with a conductivity meter and compared to the conductivity of pure (unused/unloaded) elution buffer. It was expected that the conductivity of measured fluid would be the same as the original elution buffer if channel closure was sufficient to provide fluidic resistance at the channel closure locations. A partially-closed channel was expected to result in a conductivity ratio (measured/pure buffer) of between about 1 and about 2, with a preferred conductivity ratio value being within a range of about 1 to about 1.5. Channel closure with the rubber sealing member and mechanical actuator resulted in full closure in 6 of the 8 channels and partial closure in the other 2 channels.

TABLE 2

| Channel number | Load (g) | Conductivity Ratio (Eluted material/1X elution buffer) |
|---|---|---|
| 1 | 1324 | 1.2 |
| 2 | 1324 | 1 |
| 3 | 1324 | 1 |
| 4 | 1324 | 1 |
| 5 | 1324 | 1 |
| 6 | 1324 | 1 |
| 7 | 1324 | 1 |
| 8 | 1324 | 1.2 |

Example 14—Voltage Measurement and End-of-Run Triggering

Figure 30:
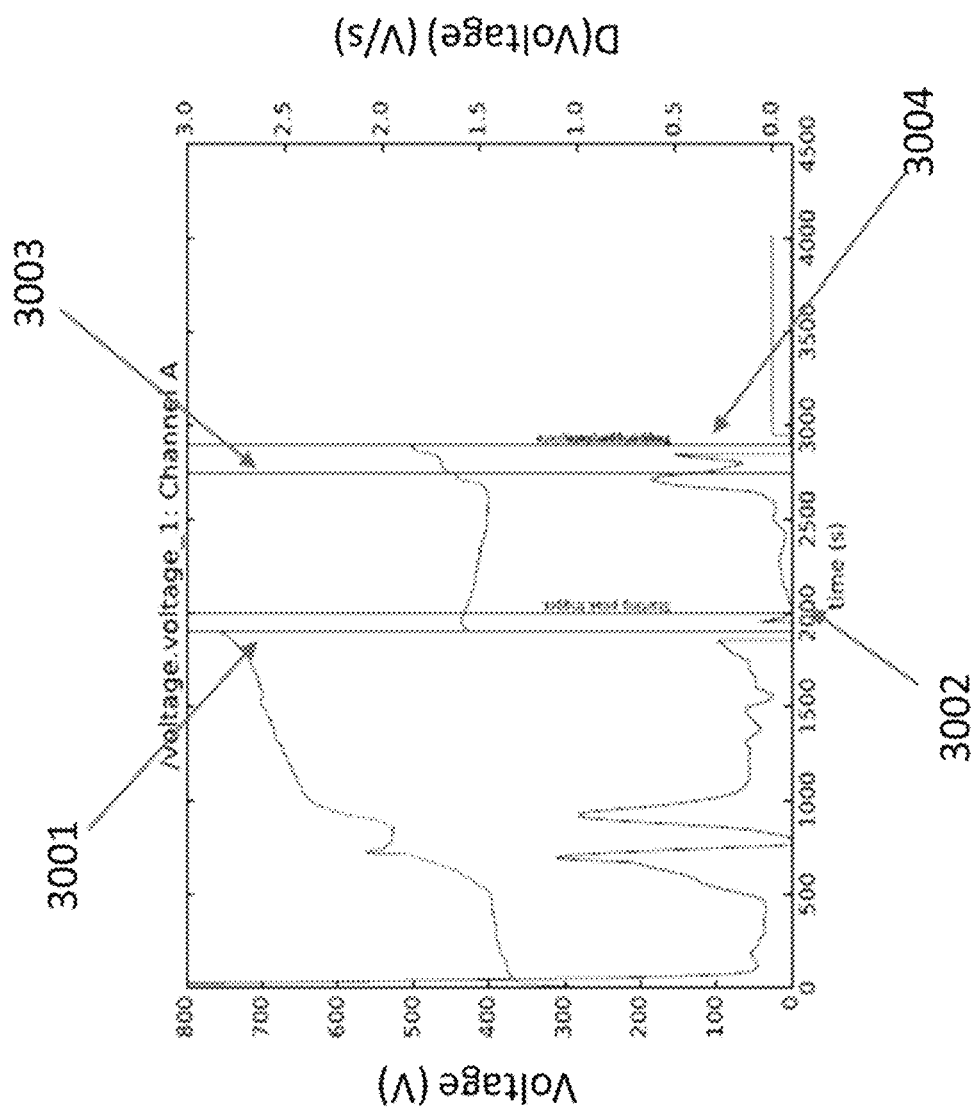
FIG. 30 a graph of voltage measurement and voltage derivative over time during an ITP run.

FIG. 30 shows an exemplary example using measurement of the driving voltage to trigger a reduction or removal of an electric current in one of the channels. A fluidic device comprising 8 channels was loaded with ITP buffers (leading electrolyte buffer comprising 88 mM Tris with 44 mM HCl, a high concentration of leading electrolyte for buffering, trailing electrolyte buffer comprising 1.2 M Tris with 0.3 M caproic acid and 0.6 M MOPS, an elution buffer comprising 10 mM Tris with 5.6 mM HCl, a high concentration of elution buffer for buffering) in each of the channels. A sample comprising 50,000 immortalized human cells lysed using the methods described herein was prepared and loaded into each of the channels. A pre-elution isotachophoresis separation was performed by driving 900 µA per channel through the channel for 1900 seconds. After 1900 seconds 3001, the current was reduced and 250 µA was applied to each channel to drive the nucleic acids into the elution reservoir. 100 seconds after starting isotachophoresis, signal processing using the voltage on the driving electrode as the data source was started 3002. The top line shown represents the voltage and the bottom line represents the derivative of the voltage. Two triggers were used to change the driving current (corresponding to triggers 1 and 4 described in FIG. 16, at locations C and D, respectively). Low-conductivity ions (e.g. sample ions or trailing electrolytes) entering the elution reservoir or channel can be detected by monitoring for peaks or maximums in the derivative of the voltage. The current was turned on at a first trigger point (trigger 1) 3001 to direct nucleic acids into the channel comprising elution buffer and signal processing 3002 was started shortly thereafter. A first increase was detected at trigger point 3 3003 as the nucleic acids entered the elution reservoir and a second increase was detected at trigger point 4 3004 as the trailing electrolytes began to enter the elution reservoir. The current was removed following detection of the second increase at trigger point 4 3004 so as to position or isolate the sample nucleic acids in the elution well.

Example 15—Temperature Sensing and End-of-Run Triggering

FIG. 21 shows exemplary temperature measurement results using an infra-red thermal sensor to trigger a reduction or elimination of an electric current in one of the channels. A fluidic device comprising 8 channels was loaded with ITP buffers (leading electrolyte buffer comprising 88 mM Tris with 44 mM HCl, a high concentration of leading electrolyte for buffering, trailing electrolyte buffer comprising 1.2 M Tris with 0.3 M caproic acid and 0.6 M MOPS, an elution buffer comprising 10 mM Tris with 5.6 mM HCl, a high concentration of elution buffer for buffering) in each of the channels. A sample comprising 50,000 immortalized human cells lysed using the methods described herein was prepared and loaded into each of the channels. A pre-elution isotachophoresis separation was performed by driving 900 µA per channel through the channel for 1900 seconds. After 1900 seconds, the current was reduced and 250 µA was applied to each channel to drive the nucleic acids into the elution reservoir. 100 seconds after starting isotachophoresis, signal processing using temperature data collected by a TMP007 infrared temperature sensor. The temperature was detected at location 2105 in the elution channel near the elution reservoir 2106, centered approximately 4.5 mm from the elution well 2106. The temperature sensor was place approximately 1 mm to 3 mm below the bottom surface of the fluidic channel. The temperature sensor may be centered approximately 4.5 mm from the elution reservoir 2106 (with edges at about 3.55 mm to about 5.45 mm from the elution reservoir). The temperature sensor was configured to detect temperature changes due to electrophoretic Joule heating in the channel. Electrophoretic joule heat dissipation per channel volume may be inversely proportional to conductivity at a constant current. During isotachophoresis, lower-conductivity ions (trailing electrolytes) may displace higher conductivity ions (leading electrolytes) as the ITP zone moves through the channel. The temperature sensor may sense the ITP zone moving past the detection location 2105, and the displacement of ions as the ITP zone moves, as a rise in temperature within the channel at the detection location.

The top line shows the temperature at the detection location 2105 and the bottom line shows the derivative of the temperature. The temperature was monitored in real-time for high derivatives in order to detect lower-conductivity buffer zones. The vertical lines indicate when key events occurred during monitoring. From left to right, the first line 2101 indicates the time at which the current was turned on and the second line 2102 indicates the start of signal processing shortly thereafter. The third line 2103 indicates the first detection of an increase in the derivative of the temperature, and the fourth line 2104 indicates the second detection of an increase in the derivative of the temperature, at which point the current was stopped and the voltage was disabled so as to land the voltage in the reservoir and position or isolate the nucleic acids in the elution reservoir.

Example 16—Temperature Sensing and End-of-Run Triggering

FIGS. 88A-88F show exemplary temperature measurement results using an infra-red thermal sensor to trigger a reduction or elimination of an electric current in one of the channels. FIG. 88A shows the temperature within the channel as monitored over time by an infrared sensor positioned as in FIG. 21. The vertical lines indicate when key events occurred during monitoring. Two temperature rises 8801 and 8802 were used to determine when to begin signal processing and when to end the run, respectively, as described in FIG. 21. FIG. 88B shows the first-order derivative values of the temperature data of FIG. 88A. The two peaks of first derivatives 8803 and 8804 correspond to events 8801 and 8802 in FIG. 88A. The identification of these two events was based on a peak detection algorithm. To evaluate the first-order derivatives, temperature data were collected as consecutive time groups within a time window. Within each time window, data were fitted by a low order polynomial function. The first-order derivatives were then calculated from the polynomial fit. To suppress noise in this signal, a general likelihood ratio test (GLRT) was used. The data was also fit to a null hypothesis of constant temperature. FIG. 88C shows the residual of the data minus the fit 8806 and the data minus the null hypothesis 8805, which were compared to produce a likelihood ratio. A function of this ratio 8807 was used to scale the derivative. The result was that, in regions in which the null hypothesis had a residual comparable to the line of best fit, the derivative was reduced to near zero. In regions where the null hypothesis was a poor fit compared to the best fit, the derivative was maintained. In order to detect the peak of first-order derivatives, an algorithm was used to track the maximum value of the derivative. When the current value declined below the pre-determined maximum value by a certain percentage, a peak was detected/recorded. The derivative peak value was configured to meet a pre-determined threshold in order to eliminate the possibilities of noise peaks being detected. The processed data were then fed to the triggering algorithm which actively searched for the occurrences of the two first-order derivative peaks based on the peak detection method described above. Once two peaks were successfully detected, the extraction process ended and the triggering algorithm stopped. As will be understood by one of ordinary skill in the art, voltage may be detected in addition to or as an alternative to the temperature using methods and algorithms similar to those described herein with regards to temperature alone.

FIG. 88D shows a block diagram of triggering process used. The nucleic acid extraction process began with a separation step (Step 8811). The instrument was configured to wait for a pre-determined amount of time (Step 8812) before triggering an elution step (Step 8813). The instrument was then instructed by the algorithm to wait for a second period of time (Step 8814) before starting signal processing to search for the first derivative peak of IR temperature signals (Step 8815). Once the first derivative peak was found, the algorithm began the search for the second derivative peak (Step 8816). Once the second derivative peak was detected, triggering was finished and the elution step was completed by ceasing voltage/current flow within the channel (Step 8817). The algorithm was configured to time out if no first or second derivative peak was detected (Steps 8818 and 8819).

FIG. 88E shows a successful triggering of the nucleic extraction process. An ITP concentrated band of nucleic acid 8822 was stopped by the triggering algorithm in elution reservoir 8821. The temperature trace and voltage trace both showed the typical two-step rises (8823 and 8824) near the end of the process as expected. FIG. 88F shows a failed triggering run. The majority of nucleic acid 8825 moved past the desired stop location (elution reservoir 8826) and before being stopped in a reservoir further downstream (on the right). The corresponding temperature and voltage traces showed no typical two-step rises. Only one rise step was properly presented in each trace. The triggering algorithm timed out after the first derivative peak was found and failed to trigger an end to the run, thereby resulting in the nucleic acid 8825 overshooting its target reservoir 8826.

Although a temperature trace was used in this example, the triggering algorithm may also rely on a voltage trace solely or voltage and temperature traces together to perform triggering.

Example 17—Slow Mobility Ion in Sample for Improved Passage Through a Capillary Barrier FIG. 89A shows a capillary barrier 8901 between sample (in this case, sample prepared in leading electrolyte) and leading electrolyte buffer, for example as shown in FIG. 10A. In some instances, such capillary barriers 8901 can trap nucleic acid during an (ITP-based) extraction process. To facilitate the passage of the nucleic acid past such a capillary barrier 8901, an ion with a slow magnitude of mobility was added into sample to disturb the accumulation of nucleic acids (e.g. into a tightly focused ITP band prior to reaching the capillary barrier 8901 which may impede passage of the band). This disturbance resulted in changes in the morphology of the nucleic acids and enabled the passage of the nucleic acids past the capillary barrier 8901 without loss of the nucleic acid sample. FIG. 89B compares the passage of a nucleic acid sample with the addition of a slow ion (14 mM 3-(N-morpholino)propanesulfonic acid (MOPS)) 8902 versus a control 8903 (i.e., same sample without the addition of a slow ion). The sample with slow ions passed the barrier successfully. In contrast, the control channel 8903 showed nucleic acid 8904 (stained so that it may be visualized in the channel during ITP) trapped at capillary barrier 8901. FIG. 89C demonstrates the nucleic acid morphology sometime later in the extraction process. Because of the trap of the nucleic acids caused by the capillary barrier in the control channel, the control sample 8903 comprises a longer "tail" 8905 of nucleic acids in the channel compared to the sample with added MOPS 8902, which may lead to loss of nucleic acids further downstream if a distinct ITP band does not form (or if sample remains captured near the capillary barrier) by the time the ITP process is stopped and the sample is eluted from the elution well as described herein.

Example 18—Shifted Liquid-Liquid Interface for Improved Passage Through a Capillary Barrier FIG. 89D shows the capillary barrier 8911 between leading electrolyte buffer and elution buffer. In some instances, capillary barrier 8911 can trap nucleic acid (NA) during the elution process (during ITP). To facilitate the passage, we adjusted the position of the fluid-to-fluid interface between the leading electrolyte buffer and the elution buffer by adjusting the liquid head heights in reservoirs as described in FIGS. 43 and 44. FIG. 89E shows examples of adjusting buffer interfaces 8912. We spiked in a fluorescence dye in elution buffer to visualize the interface. The upper lane 8910 shows an instance where the interface 8912 was moved to the right of barrier 8911, away from elution reservoir 8913. The lower lane 8920 shows an instance where the interface 8912 was moved to the left of the barrier 8911, toward elution reservoir 8913. When nucleic acid transitioned from leading electrolyte buffer to elution buffer, the volume of nucleic acid expanded to adapt to the change of ionic strength as described herein. When this expansion occurred before the passage of capillary barrier 8912 (e.g. at the location indicated in 8910), some nucleic was be trapped due to the limit of volume that the capillary barrier can allow to pass. However, when this expansion occurred after the passage of the capillary barrier 8912 (e.g. at the location indicated in 8920), NA can stay in compact shape and pass through without any loss. FIG. 89F shows how nucleic acid passage over the capillary barrier 8911 was facilitated or hampered by adjusting interface 8912 position. The upper lane 8910 had the buffer interface 8912 on the right of the capillary barrier 8911 and the lower lane 8920 had the interface 8912 on the left of the capillary barrier 8911. Some nucleic was trapped at the capillary barrier 8911 in upper lane 8910, whereas no nucleic was observed at the barrier 8911 in the lower lane 8920 but was instead found in the elution reservoir 8913.

Example 19—Simultaneous ITP in an 8-Channel Fluidic Device

FIG. 31A, FIG. 31B, FIG. 31C, and FIG. 31D show the results of simultaneously performing isotachophoresis in 8 channels of a fluidic device. DNA was extracted from cell culture lysate using a bench top controller device to automate isotachophoresis in a monolithic, 8-channel fluidic device. Leading electrolyte buffer containing 88 mM Tris with 44 mM HCl and 0.002% Tween 20 was loaded into the leading electrolyte reservoir of each channel. Trailing electrolyte comprising 1.2M Tris with 0.3 M Caproic Acid and 0.6 M MOPS with 0.002% Tween 20 was loaded into the trailing electrolyte reservoir of each channel. The sample for each channel was prepared in a second leading electrolyte buffer (e.g. sample buffer) comprising 10 mM Tris with 5.6 mM HCl with 0.002% Tween 20. Each sample comprised a cell lysate. The total number of human COLO 320 ccells per sample represented 100,000 diploid genome equivalents. Cells were pelleted and lysed off-chip in a lysis solution comprising 40 mM NaOH for 2 minutes and subsequently quenched at a 1:1 volume ratio with a buffered acidic solution to bring the final cell lysate sample to 10 mM Tris with 5.6 mM HCl and 20 mM NaCl at pH 8. Proteinase K was added to a final concentration of 400 µg/ml within the cell lysate sample volume. Four of the eight samples were treated with RNase A at a final concentration of 200 µg/ml and allowed to stand at room temperature for 2 minutes. All eight samples were then incubated for 10 minutes at 56° C. The lysed samples were then brought to room temperature and loaded into the separate eight sample reservoirs/channels on the microfluidic device, denoted by channels A through H, in preparation for isotachophoresis. The four samples that were not treated with RNase A were loaded into channels B, D, F and H. The four samples treated with RNase A were loaded into channels A, C, E, and G. Samples treated with RNase A contained additional buffering ions to enable optimal RNase activity, and therefore represented higher ionic strength or higher conductivity samples that, under fixed current (ITP conditions), resulted in different voltage data traces than the samples not treated with RNase. The independent electrical circuit control of channels A through H enabled voltage signal and feedback control for automated control and end-run triggering for each of the different channels of the device. FIG. 31A shows a micrograph of ITP bands with focused DNA 3101 in each of the 8 samples in the sample channel region of the device. The ITP band of DNA 3101 migrates within the channel in response to an applied electric field. The ITP band first travels away from the trailing electrolyte reservoir in the direction indicated by arrow 3102. The ITP band 3101 then traverses the 180° low-dispersion turn and continues through the channel towards the elution reservoir in the opposite direction (with respect to the chip) 3103 in response to the applied electric field. FIG. 31B shows independent voltage signal data at fixed currents for each of the 8 channels over time. FIG. 31C shows a micrograph of the same 8 ITP bands with focused DNA 3101 from the samples eluted in the elution reservoir by independently controlled end-of-run voltage based triggering (this image represents the end of the run with the electrical field automatically shut off). FIG. 31D is a magnified section of the voltage tracing (monitoring) used for triggering shown in FIG. 31B. The electric current of each channel was independently applied to the channel and the voltage of each channel was independently monitored in order to trigger a change (in this case cessation) in the electric field applied to each channel independently of every other channel.

Example 20—Off-Chip Lysis Efficiency

FIGS. 90A-90C show the lysis efficiency of three different cells lines lysed as described in FIG. 32A. FIG. 90A shows the lysis efficiency of COLO320 cells. The COLO320 cells were cultured in a mixture of suspended and adherent cells. FIG. 90B shows the lysis efficiency of GM24385 cells. The GM24385 cells were cultured in suspension. FIG. 90C shows the lysis efficiency of H2228 cells. The H2228 cells were cultured as adherent cells. In each of FIGS. 90A-90C, the cells were harvest and titrating amounts of cell inputs were lysed as described herein. FIGS. 90A-90C show scatterplots relating theoretical yield based on input cell number to observed yield as measured by the Qubit dsDNA assay. Cell inputs were corrected for ploidy (COLO320=2.27N; GM24385=2N1 H222=3.74N) and the theoretical yield was calculated based on an assumption of 6.6 pg of DNA per cell. FIG. 90A shows an $R^2$ value of 0.9407 for the COLO320 cells, FIG. 90B shows an $R^2$ value of 0.99997 for the GM24385 cells, and FIG. 90C shows an $R^2$ value of 0.98917 for the H2228 cells, indicating a strong linear relationship between cell input and yield (prior to ITP) across a range of cell types and sample amounts.

Example 21—Temperature Sensing and End-of-Run Triggering

FIGS. 91A-91B show exemplary temperature measurement results using an infra-red thermal sensor to trigger a reduction or elimination of an electric current in one of the channels. The chip was an 8-channel chip substantially similar to that shown in FIG. 38. FIG. 91A shows the ITP band 9101 successfully stopped at the end of the ITP run in a tight band within the elution reservoir 9102. FIG. 91B shows the temperature within each channel as monitored over time by an infrared sensor positioned as in FIG. 40. Arrow 9103 indicates the time at which the ITP band 9101 reached the infrared sensor location.

Example 22—Voltage and Temperature Sensing for End-of-Run Triggering

FIG. 92A shows a block diagram of sample channel to LE channel triggering process used. The nucleic acid extraction process began with a separation step (Step 9201). The instrument was then instructed by the algorithm to wait for a first period of time (Step 9202) before starting signal processing to search for the first derivative peak of the voltage signal at the capillary barrier between the sample channel and the LE channel (Step 9202). Once the first derivative peak was found (Step 9203), the algorithm began the search for the second derivative peak of the voltage signal at the channel narrowing after the capillary barrier within the LE channel. Alternatively, if no first peak derivative of the voltage signal was found, the instrument would time out after a second period of time (Step 9205) and the algorithm would begin searching for the second derivative peak of the voltage signal (Steps 9204, 9211).

FIG. 92B shows a trace of the voltage 9206, the derivative of the voltage 9207, and the measurement error 9208 at the first triggering location at the capillary barrier between the sample channel and the LE channel as a function of time.

FIG. 92C shows a block diagram of LE channel triggering process used. The instrument was instructed to search for the second derivative peak (Step 9204, 9211). The instrument was instructed by the algorithm to start signal processing to search for the second derivative peak at the narrowing after the capillary barrier within the LE channel (as shown in FIG. 40) (Step 9212). Once the second derivative peak was detected, the instrument was instructed to start searching for the first derivative peak of the temperature with the IR sensor within the elution branch of the channel (Step 9213, 9221). Alternatively, if no second peak derivative of the voltage signal was found, the instrument would time out after a third period of time (Step 9214) and the algorithm would begin searching for the first derivative peak of the temperature (Steps 9213, 9221).

FIG. 92D shows a trace of the voltage 9215, the derivative of the voltage 9216, and the measurement error 9217 at the second triggering location at the narrowing after the capillary barrier within the LE channel as a function of time.

FIG. 92E shows a block diagram of the elution triggering process used. The instrument was then instructed by the algorithm to wait for a fourth period of time before starting signal processing (Step 9213, 9221) to search for the first derivative peak of the temperature signal in the elution branch (Step 9222). Once the first derivative peak was found, the algorithm began the search for the second derivative peak of the temperature signal in the elution branch (Step 9223). Alternatively, if no first peak derivative of the temperature was found, the instrument would time out after a fifth period of time (Step 9224). Once the second derivative peak was detected, triggering was finished and the elution step was completed by ceasing voltage/current flow within the channel (Step 9225). The algorithm was configured to time out after a sixth period of time if no second derivative peak was detected (Step 9226).

FIG. 92F shows a trace of the voltage 9227, the derivative of the voltage 9228, and the measurement error 9229 at the temperature triggering location within the elution branch of the channel.

"A", "an", and "the", as used herein, can include plural referents unless expressly and unequivocally limited to one referent.

As used herein, the term "or" is used to refer to a nonexclusive or, such as "A or B" includes "A but not B," "B but not A," and "A and B," unless otherwise indicated. As used herein, the term "or" means "and/or" unless stated otherwise.

The term "about" as used herein, unless otherwise indicated, refers to a value that is no more than 10% above or below the value being modified by the term. For example, the term "about −20° C." means a range of from −22° C. to −18° C. As another example, "about 1 hour" means a range of from 54 minutes to 66 minutes.

The term "substantially" as used herein, unless otherwise indicated, refers to a value that is no more than 30% above or below the value being modified by the term. For example, the term "substantially −20° C." means a range of from −26° C. to −14° C.

The term "approximately" as used herein, unless otherwise indicated, refers to a value that is no more than 10% above or below the value being modified by the term. For example, the term "approximately −20° C." means a range of from −22° C. to −18° C. As another example, "approximately 1 hour" means a range of from 54 minutes to 66 minutes.

The term "substantially flat" as used herein, unless otherwise indicated, refers to surfaces that have their main extension in one plane in contrast to being shaped, for example a surface which is at least 70% linear.

The term "substantially parallel" as used herein, unless otherwise indicated, refers to a plane that largely extends in the same direction as the plane which is being modified by the term, for example a plane that is no more than 30° off axis from the plane parallel to the value being modified by the term. For example, the term "substantially parallel to the surface" means a plane which is within 30° of the plane parallel to the surface.

The term "substantially perpendicular" as used herein, unless otherwise indicated, refers to a plane that largely extends perpendicularly (i.e. along a plane that is 90° relative) to the plane which is being modified by the term, for example a plane that is no more than 30° off axis from the plane perpendicular to the value being modified by the term. For example, the term "substantially perpendicular to the surface" means a plane which is within 30° of the plane perpendicular to the surface.

The term "relatively aligned with" as used herein, unless otherwise indicated, refers to a value that large extends in the same direction as the value which is being modified by the term, for example along an axis that his not more than 30° off axis from the value being modified by the term. For example, the term "relatively aligned with the longitudinal axis" means an extending along an axis which is within 30° of the longitudinal axis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It can be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A fluidic device comprising a fluidic channel and disposed in said fluidic channel a three-dimensional capillary barrier that restricts flow of a liquid in said fluidic channel, wherein said three-dimensional capillary barrier comprises:
 a ramp protruding from a surface of said fluidic channel at a first angle;
 a plateau surface that is substantially parallel to a wall of said fluidic channel; and
 an arcuate cliff surface extending from said plateau surface to said surface of said fluidic channel and wherein said cliff surface intersects with said surface of said fluidic channel at a second angle that is 10 degrees or more steeper than said first angle.

2. A fluidic device comprising a fluidic channel and disposed in said fluidic channel a three-dimensional capillary barrier that restricts flow of a liquid in said fluidic channel, wherein said three-dimensional capillary barrier comprises:
(a) a first ramp protruding from a surface of said fluidic channel at a first angle that is less than 80 degrees;
(b) a plateau surface that is substantially parallel to a wall of said fluidic channel; and
(c) a second ramp extending from said plateau surface to said surface of said fluidic channel and wherein said second ramp intersects with said surface of said fluidic channel at a second angle that is less than 80 degrees.

3. The fluidic device of claim 1, wherein said first angle is no more than 60 degrees.

4. The fluidic device of claim 1, wherein said first angle is no more than 45 degrees.

5. The fluidic device of claim 1, wherein said first angle is no more than 30 degrees.

6. The fluidic device of claim 1, wherein said second angle is about 80 degrees to about 100 degrees.

7. The fluidic device of claim 1, wherein said second angle is about 90 degrees.

8. The fluidic device of claim 1, wherein at least one of said ramp, said cliff surface, and said plateau surface has a surface that comprises one or more grooves, ridges, indentations, steps, etchings, or protrusions.

9. The fluidic device of claim 1, wherein said fluidic channel further comprises a second three-dimensional capillary barrier that is spaced apart from said three-dimensional capillary barrier.

10. The fluidic device of claim 9, wherein said fluidic channel further comprises a first loading reservoir in fluid communication with said fluidic channel via an aperture in said fluidic channel, wherein said aperture is positioned between said three-dimensional capillary barrier and said second three-dimensional capillary barrier to permit said liquid entering said fluidic channel via said aperture to flow in one direction along said fluidic channel and arrest at said three-dimensional capillary barrier and to flow in another direction along said fluidic channel and arrest at said second three-dimensional capillary barrier.

11. The fluidic device of claim 10, wherein said liquid entering said fluidic channel via said aperture flows along a path to said three-dimensional capillary barrier or said second three-dimensional capillary barrier that is longer than a width of said fluidic channel.

12. The fluidic device of claim 10, wherein said liquid entering said fluidic channel via said aperture flows such that a meniscus of said liquid arrests at said three-dimensional capillary barrier or at said second three-dimensional capillary barrier, or at both.

13. The fluidic device of claim 9, wherein said fluidic device further comprises one or more branched fluidic circuits, wherein each of said one or more branched fluidic circuits comprises an isotachophoresis ("ITP") branch and an elution branch in communication with said ITP branch.

14. The fluidic device of claim 13, wherein said three-dimensional capillary barrier is configured and arranged to be breached by said liquid when a first burst pressure is applied to said one or more branched fluidic circuits and said second three-dimensional capillary barrier is configured and arranged to be breached by said liquid when a second burst pressure is applied to said one or more branched fluidic circuits.

15. The fluidic device of claim 14, wherein said first and said second burst pressures are about equal.

16. The fluidic device of claim 14, wherein said first burst pressure is greater than said second burst pressure.

17. The fluidic device of claim 9, wherein said second three-dimensional capillary barrier is a cliff capillary barrier, wherein said cliff capillary barrier comprises:
a second ramp protruding from said surface of said fluidic channel at a third angle;
a second plateau surface that is substantially parallel to said wall of said fluidic channel; and
a second arcuate cliff surface extending from said second plateau surface to said surface of said fluidic channel and wherein said second arcuate cliff surface intersects with said surface of said fluidic channel at a fourth angle that is 10 degrees or more steeper than said third angle.

18. The fluidic device of claim 9, wherein said second three-dimensional capillary barrier is a plateau capillary barrier, wherein said plateau capillary barrier comprises a first angled surface and a second angled surface, wherein the first and second angled surfaces are oblique to each other.

19. The fluidic device of claim 18, wherein said plateau capillary barrier is configured and arranged so that an air gap forms between said liquid after said liquid arrests at said plateau capillary barrier and a second liquid after said second liquid flows toward said plateau capillary barrier in another direction and arrests at said plateau capillary barrier opposite to said liquid.

20. The fluidic device of claim 1, further comprising a gas channel in fluid communication with said fluidic channel, and a pneumatic port in fluid communication with said gas channel, wherein the gas channel and pneumatic port are in fluid communication with the three-dimensional capillary barrier.

21. The fluidic device of claim 20, wherein the three-dimensional capillary barrier is disposed adjacent the gas channel.

22. The fluidic device of claim 1, wherein the three-dimensional capillary barrier spans the width of the fluidic channel.

23. The fluidic device of claim 1, further comprising a plurality of fluidic channels comprising capillary barriers.

24. The fluidic device of claim 1, wherein the fluidic channel has a width within a range of about 1 mm to about 3.8 mm, and a height within a range of about 0.1 mm to about 1.2 mm.

25. The fluidic device of claim 1, wherein the ramp of the three-dimensional capillary barrier is configured to gradually reduce the height of the fluidic channel from a first height within a range of about 50 µm to about 2 mm to a second height within a range of about 10 µm to about 30 µm.

26. The fluidic device of claim 1, wherein said second angle is 15 degrees or more steeper than said first angle.

27. The fluidic device of claim 1, wherein said second angle is 20 degrees or more steeper than said first angle.

* * * * *

UNITED STATES PATENT AND TRADEMARK OFFICE
CERTIFICATE OF CORRECTION

PATENT NO. : 11,987,789 B2
APPLICATION NO. : 17/230582
DATED : May 21, 2024
INVENTOR(S) : Marshall et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this
Twelfth Day of November, 2024

*Katherine Kelly Vidal*

Katherine Kelly Vidal
*Director of the United States Patent and Trademark Office*